United States Patent
Gordon-Kamm et al.

(10) Patent No.: US 9,765,352 B2
(45) Date of Patent: Sep. 19, 2017

(54) METHODS AND COMPOSITIONS FOR THE INTRODUCTION AND REGULATED EXPRESSION OF GENES IN PLANTS

(71) Applicants: PIONEER HI BRED INTERNATIONAL INC, Johnston, IA (US); E.I. DUPONT DE NEMOURS, Wilmington, DE (US)

(72) Inventors: William James Gordon-Kamm, Urbandale, IA (US); Theodore Mitchell Klein, Wilmington, DE (US); Keith S Lowe, Johnston, IA (US); Kevin E McBride, Davis, CA (US); Christopher Jay Scelonge, Ankeny, IA (US); Ning Wang, Johnston, IA (US)

(73) Assignees: E I DU PONT DE NEMOURS AND COMPANY, Wilmington, DE (US); PIONEER HI-BRED INTERNATIONAL, INC., Johnston, IA (US)

( * ) Notice: Subject to any disclaimer, the term of this patent is extended or adjusted under 35 U.S.C. 154(b) by 768 days.

(21) Appl. No.: 14/087,775

(22) Filed: Nov. 22, 2013

(65) Prior Publication Data
US 2014/0157453 A1    Jun. 5, 2014

Related U.S. Application Data

(63) Continuation of application No. 12/982,180, filed on Dec. 30, 2010, now abandoned.

(60) Provisional application No. 61/291,257, filed on Dec. 30, 2009.

(51) Int. Cl.
C12N 15/82 (2006.01)

(52) U.S. Cl.
CPC ..... *C12N 15/8241* (2013.01); *C12N 15/8213* (2013.01); *C12N 15/8216* (2013.01); *C12N 15/8262* (2013.01)

(58) Field of Classification Search
None
See application file for complete search history.

(56) References Cited

U.S. PATENT DOCUMENTS

| | | | |
|---|---|---|---|
| 5,451,513 A | 9/1995 | Maliga et al. | |
| 5,545,818 A | 8/1996 | McBride et al. | |
| 5,888,732 A | 3/1999 | Hartley et al. | |
| 6,093,874 A | 7/2000 | Jofuku et al. | |
| 6,143,557 A | 11/2000 | Hartley et al. | |
| 6,171,861 B1 | 1/2001 | Hartley et al. | |
| 6,270,969 B1 | 8/2001 | Hartley et al. | |
| 6,512,165 B1 | 1/2003 | Ross et al. | |
| 7,151,170 B1 | 12/2006 | Boutilier et al. | |
| 7,253,000 B2 | 8/2007 | Sivasankar et al. | |
| 7,256,322 B2 | 8/2007 | Lowe et al. | |
| 7,348,468 B1 | 3/2008 | Cahoon et al. | |
| 7,402,734 B2 | 7/2008 | Martinell et al. | |
| 7,414,172 B2 | 8/2008 | Pages et al. | |
| 7,491,813 B2 | 2/2009 | Wu et al. | |
| 7,579,529 B2 | 8/2009 | Gordon-Kamm et al. | |
| 7,595,434 B2 | 9/2009 | Fischer et al. | |
| 7,700,829 B2 | 4/2010 | Zuo et al. | |
| 7,816,580 B2 | 10/2010 | Zuo et al. | |
| 8,420,893 B2 | 4/2013 | Gordon-Kamm et al. | |
| 2003/0049835 A1 | 3/2003 | Helliwell et al. | |
| 2003/0082813 A1 | 5/2003 | Zuo et al. | |
| 2003/0135889 A1 | 7/2003 | Ross et al. | |
| 2004/0166563 A1* | 8/2004 | Lowe ................... | C07K 14/415 435/69.1 |
| 2004/0247620 A1 | 12/2004 | Julien | |
| 2005/0044595 A1 | 2/2005 | Arias et al. | |
| 2005/0257289 A1* | 11/2005 | Gordon-Kamm ........ | A01H 1/08 800/281 |
| 2006/0026716 A1* | 2/2006 | Sivasankar .......... | C07K 14/415 800/287 |
| 2007/0271628 A1 | 11/2007 | Lowe et al. | |
| 2009/0041331 A1 | 2/2009 | Prakash | |
| 2009/0094717 A1 | 4/2009 | Troukhan et al. | |
| 2009/0235391 A1 | 9/2009 | Allen et al. | |

FOREIGN PATENT DOCUMENTS

| | | |
|---|---|---|
| CN | 101445809 A | 6/2009 |
| EP | 1 033 405 A2 | 9/2000 |
| EP | 1 54 891 A1 | 11/2000 |
| EP | 1 057 891 A | 12/2000 |
| EP | 1 094 112 | 4/2001 |
| EP | 1 185 656 A1 | 3/2002 |

(Continued)

OTHER PUBLICATIONS

Zhang et al 2003 (Theoretical and Applied Genetics 107: p. 1157-1168). Of record in the parent case.*
Katzen 2007 (Expert Opinions in Drug Discovery 2:4 p. 571-589). Of record in the parent case.*
Written Opinion of the International Searching Authority—PCT/US2010/062531.
International Search Report—PCT/US2010/062531.
U.S. Appl. No. 13/790,641, filed Mar. 8, 2013.
U.S. Appl. No. 60/541,122, filed Feb. 2, 2004.
Written Opinion of the International Searching Authority—PCT/US2005/003135.
International Search Report—PCT/US2005/003135.

(Continued)

*Primary Examiner* — Matthew Keogh

(57) ABSTRACT

Compositions and methods are provided for the introduction and the regulated expression of genes in plants. Compositions include promoter constructs that provide a level of activity useful for the regulated expression of site-specific recombinases, while avoiding premature excision. Further provided are isolated polynucleotides encoding novel babyboom polypeptides, expression cassettes, and plants comprising the same. Methods for the introduction of genes into plants are provided, including methods for plastid transformation and methods for the transformation of tissues from mature seeds and leaves.

39 Claims, 17 Drawing Sheets

(56) References Cited

FOREIGN PATENT DOCUMENTS

| WO | 95/06722 A1 | 3/1995 |
| --- | --- | --- |
| WO | 98/07842 A | 2/1998 |
| WO | 99/15178 | 4/1999 |
| WO | 99/21574 | 5/1999 |
| WO | 99/41974 | 8/1999 |
| WO | 00/40694 A | 7/2000 |
| WO | 00/75330 | 12/2000 |
| WO | 03/001902 A2 | 1/2001 |
| WO | 01/23575 A2 | 4/2001 |
| WO | 02/059294 A1 | 8/2002 |
| WO | 02/097059 A2 | 12/2002 |
| WO | 03/002751 A | 1/2003 |
| WO | 02/063990 A2 | 7/2005 |
| WO | 2005/122750 A2 | 12/2005 |
| WO | 2007/092992 A1 | 8/2007 |
| WO | 2009/132057 A1 | 10/2009 |

OTHER PUBLICATIONS

Invitrogen Corporation, "Gateway® pDONR™ Vectors," User Manual, Version E, 2007, retrieved from http://wolfson.huji.ac.il/expression/gateway_pdonr_vectors.pdf, XP002627486.

Srinivasan, C., et al., "Heterologous expression of the Baby Boom AP2/ERF transcription factor enhances the regeneration capacity of tobacco (Nicotiana tabacum L.)," Planta, 2007, vol. 225, pp. 341-351.

Al-Abed, D., et al., "Split-seed: a new tool for maize researchers," Planta, 2006, vol. 223, pp. 1355-1360.

Boutilier, K., et al., "Ectopic Expression of Baby Boom Triggers a Conversation from Vegetative to Embryonic Growth," The Plant Cell, 2002, pp. 1737-1749, vol. 14.

Bowie, J.U., et al., "Deciphering the Message in Protein Sequences: Tolerance to Amino Acid Substitutions," Science, 1990, pp. 1306-1310, vol. 247.

Busk, P., et al., "Regulatory elements in vivo in the promoter of the abscisic acid responsive gene rab17 from maize," The Plant Journal, 1997, vol. 11(6), pp. 1285-1295.

El Ouakfaoui, et al., "Control of somatic embryogenesis and embryo development by AP2 transcription factors," Plant Mol Biol, published on-line 2010, 14 pages.

Feng, Q., et al., "Sequence and Analysis of Rice Chromosome 4," Nature, 2002, pp. 316-320, vol. 420.

Huang, X.-Q., et al., "High-frequency plant regeneration through callus initiation from mature embryos of maize (Zea mays L.)," Plant Cell Rep, 2004, vol. 22, pp. 793-800.

Kizis, D., et al., "Role of AP2/EREBP Transcription Factors in Gene Regulation During Abiotic Stress," FEBS Letters, 2001, pp. 187-189, vol. 498.

Marsch-Martinez, N., et al., "Bolita, an Arabidopsis AP2/ERF-Like Transcription Factor that Affects Cell Expansion and Proliferation/Differentiation Pathway," Plant Mol Biol., 2006, pp. 825-843, vol. 62.

McConnell, J.R., et al., "Role of Phabulosa and Phavoluta in determining Radial Patterning in Shoots," Nature, 2001 pp. 709-713, vol. 411.

Mizukami, Y., and Robert L. Fischer, "Plant Organ Size Control: Ainteguments Regulates Growth and Cell Numbers During Organogenesis," PNAS, 2000, pp. 942-947, vol. 97(2).

Morcillo, et al., "EgAP2-1, an Ainteguments-like (AIL) gene expressed in meristematic and proliferating tissues of embryos in oil palm," Planta, 2007, vol. 226, pp. 1353-1362.

Riechmann, J. L., et al., "The AP2/EREBP Family of Plant Transcription Factors," Biological Chemistry, 1998, pp. 633-646, vol. 379.

Sasakl, T., et al. "The Genome Sequence and Structure of Rice Chromosome 1," Nature, 2002, pp. 312-316, vol. 420.

Sato, S., et al., "Structural Analysis of Arabidopsis thaliana Chromosome 3. I. Sequence Features of the Regions of 4,504,864 bp Covered by Sixty P1 and TAC Clones," DNA Research, 2000, pp. 131-135, vol. 7.

Srinivasan, et al., "Heterologous expression of the Baby Boom AP2/ERF transcription factor enhances the regeneration capacity of tobacco (Nicotiana tabacum L.)," Planta, 2007, vol. 225, pp. 341-351.

Staub, J, et al., "Accumulation of D1 polypeptide in tobacco plastids is regulated via the untranslated region of the psbA mRNA," The EMBO Journal, 1993, vol. 12(2), pp. 601-606.

Svab, Z., et al., "Stable transformation of plastids in higher plants," Proc. Natl. Acad. Sci. USA, 1990, vol. 87, pp. 8526-8530.

Svab, Z, et al., "High-frequency plastid transformation in tobacco by selection for a chimeric aadA gene," Proc. Natl. Acad. Sci. USA, 1993, vol. 90, pp. 913-917.

Theologis, A., et al. "Sequence and Analysis of Chromosome 1 of the Plant Arabidopsis thaliana," Nature, 2000, pp. 816-820, vol. 408.

Töpfer, R., et al., "Uptake and Transient Expression of Chimeric Genes in Seed-Derived Embryos," The Plant Cell, 1989, vol. 1, pp. 133-139.

Vilardell, et al., "Gene sequence, developmental expression, and protein phosphorylation of RAB-17 in maize," Plant Molecular Biology, 1990, vol. 14, pp. 423-432.

Vilardell, et al., "Regulation of the maize rab17 gene promoter in transgenic heterologous systems," Plant Molecular Biology, 1991, vol. 17, pp. 985-993.

Wang, Andrew S., "Callus induction and plant generation from maize mature embryos," Plant Cell Reports, 1987, vol. 6, pp. 360-362.

GenBank Report for Accession No. AAD30633, Direct Submission on Oct. 30, 2002.

GenBank Report for Accession No. AAL47205, Direct Submission on May 31, 2002.

GenBank Report for Accession No. AAM33800, Direct Submission on Oct. 10, 2002.

GenBank Report for Accession No. AAM33801, Direct Submission on Oct. 10, 2002.

GenBank Report for Accession No. AAM33803, Direct Submission on Oct. 10, 2002.

GenBank Report for Accession No. AY062108, Direct Submission on Oct. 31, 2001.

GenBank Report for Accession No. AY062180, Direct Submission on Oct. 31, 2001.

GenBank Report for Accession No. BAB02492, Direct Submission on Feb. 14, 2004.

GenBank Report for Accession No. BAB89946, Direct Submission on Aug. 31, 2004.

GenBank Report for Accession No. CAE02944, Direct Submission on Apr. 16, 2005.

GenBank Report for Accession No. CAE05555, Direct Submission on Apr. 16, 2005.

GenBank Report for Accession No. CC603221, 2003.

GenBank Report for Accession No. CC667986, Jun. 20, 2003.

GenBank Report for Accession No. CL960366, Sep. 22, 2004.

GenBank Report for Accession No. F96549, Direct Submission on Mar. 31, 2001.

GenBank Report for Accession No. NP175530, Direct Submission on Feb. 23, 2005.

GenBank Report for Accession No. NP197245, Direct Submission on Feb. 23, 2005.

Genbank Accession No. XM_00245882; Jul. 13, 2009.

Genbank Accession No. AY899909; Nov. 17, 2010.

"Rice Genome Annotation Project; Funded by the NSF," http://rice.plantbiology.msu.edu/cgibin/ORG_infopage.cgi?orf=LOC_Os02g40070.1, 2011, pp. 1-3.

Gidoni, D., et al., "Embryonal Recombination and Germline Inheritance of Recombined FRT Loci Mediated by Constitutively Expressed FLP in Tobacco," Euphytica, 2001, pp. 145-156, vol. 121.

Nardmann, J., and W.Werr, "The Shoot Stem Cell Niche in Angiosperms: Expression Patterns of WUS Orthologues in Rice and Maize ImplyMajor Modifications in the Course of Mono- and Dicot Evolution," Mol. Biol. Evol., 2006, pp. 2492-2504, vol. 23(12).

Partial European Search Report, EP16167143,dated Aug. 8, 2016.

European Search Report—Application No. EP16167143—Date of completion of the search—Aug. 1, 2016, Letter from EP Agent date Nov. 11, 2016.

\* cited by examiner

|  | SEQ ID NO: |  |  |
|---|---|---|---|
| GmPLT3b | 70 | (221) | YEKELEEMKNMTRQEFVASLRRKSSGFSRGA |
| GmPLT3a | 71 | (217) | YEKELEEMKNMTRQEFVASLRRKSSGFSRGA |
| OsBBM | 14 | (353) | YEKELEEMKHMTRQEFVASLRRKSSGFSRGA |
| VvBBM | 6 | (278) | YEKEIEEMKHMTRQEYVASLRRKSSGFSRGA |
| GmBBM | 2 | (339) | YEKELEEMKHMTRQEYVASLRRKSSGFSRGA |
| ZmPLT3b | 72 | (210) | YEKELEEMKSMTRQEFIASLRRKSSGFSRGA |
| AtBBM | 22 | (280) | YEKEVEEMKHMTRQEYVASLRRKSSGFSRGA |
| OsPLT3 | 73 | (214) | YEKELEEMKHMTRQEFVASLRRKSSGFSRGA |
| ZmBBM | 10 | (343) | YEKELEDMKHMTRQEFVASLRRKSSGFSRGA |
| BnBBM2 | 26 | (280) | YEKEIEEMKHMTRQEYVASLRRKSSGFSRGA |
| BnBBM1 | 24 | (280) | YEKEVEEMKHMTRQEYVASLRRKSSGFSRGA |
| OsBBM1 | 16 | (238) | YEKELDEMKHMNRQEFVASLRRKSSGFSRGA |
| AtPLT3/AIL5 | 74 | (273) | YESELEEMKHMTRQEFVASLRRKSSGFSRGA |
| AtPLT2 | 75 | (260) | YEKEVEEMKNMTRQEFVASIRRKSSGFSRGA |
| SbPLT3b | 76 | (205) | YEKELEEMKSMTRQEFIASLRRKSSGFSRGA |
| OsAIL1 | 77 | (323) | YEKELEEMKHMTRQEFIAHLRRNSSGFSRGA |
| SbBBM | 4 | (347) | YEKELEDMKHMTRQEFVASLRRKSSGFSRGA |
| MtBBM | 8 | (329) | YEKEVEEMKHMTRQEYVASLRRKSSGFSRGA |
| SbBBM2 | 28 | (356) | YEKELEEMKHMTRQEYIAYLRRNSSGFSRGA |
| ZmBBM2 | 12 | (349) | YEKELEEMKHMTRQEYIAYLRRNSSGFSRGA |
| GmPLT2 | 78 | (234) | YEKELDEMKHMTRQEFVAAIRRKSSGFSRGA |
| OsBBM3 | 20 | (349) | YEKELEEMKHMTRQEYIAHLRRNSSGFSRGA |
| MtPLT3 | 79 | (229) | YEKEIDDMKNMTRQEFVASLRRKSSGFSRGA |
| ZmPLT3 | 80 | (197) | YEKEVEEMKNMTRQEFVASLRRKSSGFSRGA |
| OsPLT3b | 81 | (200) | YETELEEMKSMTRQEFIASLRRKSSGFSRGA |
| GmPLT1 | 82 | (239) | YEKELDEMKHMTRQEFVAAIRRKSSGFSRGA |
| AtPLT1 | 83 | (251) | YEKEVEEMKHMTRQEFVAAIRRKSSGFSRGA |
| OsBBM2 | 18 | (370) | YEKELDEMKHMTRQEYIAYLRRNSSGFSRGA |
| MtPLT1/2 | 84 | (233) | YEKEIDEMKHMTRQEFVASIRRKSSGFSRGA |
| ZmAIL1 | 85 | (341) | YEKELEEMKHMSRQEFIAHLRRNSSGFSRGA |
| GmAIL1 | 86 | (272) | YEKELEEMKHMTRQEFVANLRRKSSGFSRGA |
| SbPLT3 | 87 | (208) | YEKELEEMKTMTRQEFVASLRRKSSGFSRGA |
| GmAIL6 | 88 | (291) | YSKEVEEMKHVTKQEFIASLRRKSSGFSRGA |
| AtAIL6 | 89 | (323) | YSKEVEEMKHMTKQEFIASLRRKSSGFSRGA |
| MtAIL1 | 90 | (318) | YDKELEEMKHMTRQEFVANLRRKSSGFSRGA |
| SbAIL1 | 91 | (333) | YEKELEEMKHMSRQEFIAHLRRNSSGFSRGA |
| AtANT | 92 | (353) | YQKEIEDMKNMTRQEYVAHLRRKSSGFSRGA |
| SbANT | 93 | (353) | YQEELEEMKNMTRQEYVAHLRRKSSGFSRGA |
| GmAIL7 | 94 | (290) | YSKEVEEMKHVTKQEFIASLRRKSSGFSRGA |
| ZmANT | 67 | (372) | YREELEEMKNMTRQEYVAHLRRKSSGFSRGA |
| OsANT | 95 | (372) | YQEELEEMKNMSRQEYVAHLRRKSSGFSRGA |
| AtAIL7 | 96 | (243) | YSKELEEMNHMTKQEFIASLRRKSSGFSRGA |
| ZmANT2 | 97 | (354) | YRDELEEMKGMTRQEFVAHLRRRSSGFSRGA |
| MtANT | 98 | (380) | YQNQLEEMKNMTRQEYVAHLRRKSSGFSRGA |
| GmANT | 99 | (334) | YQVQLEEMKNMSRQEYVAHLRRKSSGFSRGA |
| AtAIL1 | 100 | (293) | YEKEIEELNNMNRQEFVAMLRRNSSGFSRGA |
| ZmANTr | 101 | (218) | YIREIQDMQNMNRRDVVASLRRKSSGFSRGA |
| AtWRI1 | 102 | (135) | YTKELEEMQRVTKEEYLASLRRQSSGFSRGV |
| AtAP2 | 103 | (191) | YDDDLKQMTNLTKEEFVHVLRRQSTGFPRGS |
| AtRAP2.7 | 104 | (213) | YEEDMKQVQNLSKEEFVHILRRQSTGFSRGS |
| Consensus | 48 |  | YEKELEEMK1MTRQE23A4LRRKSSGFSRGA |

```
              SEQ ID NO:
SbBBM            4      ( 378) SIYRGVTRHHQHGRWQARIGRVAGNKDLYLGTFSTQEEAA
OsBBM           13      ( 384) SIYRGVTRHHQHGRWQARIGRVAGNKDLYLGTFSTQEEAA
ZmBBM           10      ( 374) SIYRGVTRHHQHGRWQARIGRVAGNKDLYLGTFSTQEEAA
GmPLT3b         70      ( 252) SIYRGVTRHHQHGRWQARIGRVAGNKDLYLGTFSTQEEAA
GmPLT3a         71      ( 248) SIYRGVTRHHQHGRWQARIGRVAGNKDLYLGTFSTQEEAA
MtPLT3          79      ( 260) SIYRGVTRHHQHGRWQARIGRVAGNKDLYLGTFSTQEEAA
AtPLT3/AIL5     74      ( 304) SMYRGVTRHHQHGRWQARIGRVAGNKDLYLGTFSTQEEAA
SbBBM2          28      ( 387) SKYRGVTRHHQHGRWQARIGRVAGNKDLYLGTFSTEEEAA
OsBBM2          18      ( 401) SKYRGVTRHHQHGRWQARIGRVAGNKDLYLGTFSTEEEAA
ZmBBM2          12      ( 380) SKYRGVTRHHQHGRWQARIGRVAGNKDLYLGTFSTEEEAA
GmPLT2          78      ( 265) SMYRGVTRHHQHGRWQARIGRVAGNKDLYLGTFSTEEEAA
GmPLT1          82      ( 270) SMYRGVTRHHQHGRWQARIGRVAGNKDLYLGTFSTEEEAA
ZmPLT3b         72      ( 241) SIYRGVTRHHQHGRWQARIGRVAGNKDLYLGTFSTQEEAA
AtAIL1         100      ( 324) SVYRGVTRHHQHGRWQARIGRVAGNKDLYLGTFSTQEEAA
SbPLT3b         76      ( 236) SIYRGVTRHHQHGRWQARIGRVAGNKDLYLGTFSTQEEAA
OsPLT3b         81      ( 231) SIYRGVTRHHQHGRWQARIGRVAGNKDLYLGTFSTQEEAA
OsBBM1          16      ( 269) SIYRGVTRHHQHGRWQARIGRVAGNKDLYLGTFGTQEEAA
MtPLT1/2        84      ( 264) SMYRGVTRHHQHGRWQARIGRVAGNKDLYLGTFSTEEEAA
SbAIL1          91      ( 364) SMYRGVTRHHQHGRWQARIGRVAGNKDLYLGTFSTEEEAA
OsAIL1          77      ( 354) SMYRGVTRHHQHGRWQARIGRVAGNKDLYLGTFSTEEEAA
ZmAIL1          85      ( 372) SMYRGVTRHHQHGRWQARIGRVAGNKDLYLGTFSTEEEAA
AtPLT2          75      ( 291) SMYRGVTRHHQHGRWQARIGRVAGNKDLYLGTFSTEEEAA
AtPLT1          83      ( 282) SMYRGVTRHHQHGRWQARIGRVAGNKDLYLGTFSTEEEAA
OsBBM3          20      ( 380) SKYRGVTRHHQHGRWQARIGRVAGNKDIYLGTFSTEEEAA
VvBBM            6      ( 309) SIYRGVTRHHQHGRWQARIGRVAGNKDLYLGTFSTQEEAA
GmANT           99      ( 365) SIYRGVTRHHQHGRWQARIGRVAGNKDLYLGTFSTQEEAA
GmBBM            2      ( 370) SIYRGVTRHHQHGRWQARIGRVAGNKDLYLGTFSTQEEAA
MtBBM            8      ( 360) SIYRGVTRHHQHGRWQARIGRVAGNKDLYLGTFSTQEEAA
SbANT           93      ( 384) SMYRGVTRHHQHGRWQARIGRVSGNKDLYLGTFSTQEEAA
GmAIL1          86      ( 303) SVYRGVTRHHQHGRWQARIGRVAGNKDLYLGTFSTQEEAA
MtAIL1          90      ( 349) SVYRGVTRHHQHGRWQARIGRVAGNKDLYLGTFSTQEEAA
SbPLT3          87      ( 239) SIYRGVTRHHQHGRWQARIGRVAGNKDLYLGTFSTEEEAA
ZmPLT3          80      ( 228) SIYRGVTRHHQHGRWQARIGRVAGNKDLYLGTFSTEEEAA
AtBBM           22      ( 311) SIYRGVTRHHQHGRWQARIGRVAGNKDLYLGTFGTQEEAA
OsANT           95      ( 403) SIYRGVTRHHQHGRWQARIGRVSGNKDLYLGTFSTQEEAA
BnBBM2          26      ( 311) SIYRGVTRHHQHGRWQARIGRVAGNKDLYLGTFGTQEEAA
BnBBM1          24      ( 311) SIYRGVTRHHQHGRWQARIGRVAGNKDLYLGTFGTQEEAA
MtANT           98      ( 412) SMYRGVTRHHQHGRWQARIGRVAGNKDLYLGTFSTQEEAA
AtANT           92      ( 384) SIYRGVTRHHQHGRWQARIGRVAGNKDLYLGTFGTQEEAA
AtAIL6          89      ( 354) SIYRGVTRHHQQGRWQARIGRVAGNKDLYLGTFATEEEAA
ZmANT           67      ( 403) SIYRGVTRHHQHGRWQARIGRVSGNKDLYLGTFSTQEEAA
OsPLT3          73      ( 245) SIYRGVTRHHQHGRWQARIGRVAGNKDLYLGTFGTEEEAA
GmAIL7          94      ( 321) SIYRGVTRHHQQGRWQARIGRVAGNKDLYLGTFATEEEAA
GmAIL6          88      ( 322) SIYRGVTRHHQQGRWQARIGRVAGNKDLYLGTFATEEEAA
AtAIL7          96      ( 274) SIYRGVTRHHQQGRWQARIGRVAGNKDLYLGTFATEEEAA
ZmANT2          97      ( 385) SIYRGVTRHHQQGRWQSRIGRVAGNKDLYLGTFTTQEEAA
ZmANTr         101      ( 249) SIYRGVTKHHQHGRWQARIGRVAGNKDLYLGTFATEQEAA
AtWRI1         102      ( 166) SKYRGVARHHHNGRWEARIGRVFGNKYLYLGTYNTQEEAA
Consensus       49             S1YRGVTRHHQHGRWQARIGRVAGNKDLYLGTFST2EEAA
```

FIG. 2B

```
            SEQ ID NO:
SbBBM           4       ( 418)  EAYDIAAIKFRGLNAVTNFDMSR
OsBBM          14       ( 424)  EAYDIAAIKFRGLNAVTNFDMSR
ZmBBM          10       ( 414)  EAYDIAAIKFRGLNAVTNFDMSR
GmPLT3b        70       ( 292)  EAYDIAAIKFRGLNAVTNFDMSR
GmPLT3a        71       ( 288)  EAYDIAAIKFRGLNAVTNFDMSR
MtPLT3         79       ( 300)  EAYDIAAIKFRGLNAVTNFDMSR
AtPLT3/AIL5    74       ( 344)  EAYDIAAIKFRGLNAVTNFDISR
SbBBM2         28       ( 427)  EAYDIAAIKFRGLNAVTNFDMSR
OsBBM2         18       ( 441)  EAYDIAAIKFRGLNAVTNFDMSR
ZmBBM2         12       ( 420)  EAYDIAAIKFRGLNAVTNFDMSR
GmPLT2         78       ( 305)  EAYDIAAIKFRGLNAVTNFDMSR
GmPLT1         82       ( 310)  EAYDIAAIKFRGLNAVTNFDMSR
ZmPLT3b        72       ( 281)  EAYDIAAIKFRGLNAVTNFDMSR
AtAIL1        100       ( 364)  EAYDIAAIKFRGLNAVTNFDINR
SbPLT3b        76       ( 276)  EAYDIAAIKFRGLNAVTNFDMSR
OsPLT3b        81       ( 271)  EAYDIAAIKFRGLNAVTNFDMSR
OsBBM1         16       ( 309)  EAYDIAAIKFRGLNAVTNFDMSR
MtPLT1/2       84       ( 304)  EAYDIAAIKFRGLNAVTNFDMTR
SbAIL1         91       ( 404)  EAYDIAAIKFRGLNAVTNFDISK
OsAIL1         77       ( 394)  EAYDIAAIKFRGLNAVTNFDISK
ZmAIL1         85       ( 412)  EAYDIAAIKFRGLNAVTNFDISK
AtPLT2         75       ( 331)  EAYDIAAIKFRGLNAVTNFEINR
AtPLT1         83       ( 322)  EAYDIAAIKFRGLNAVTNFEINR
OsBBM3         20       ( 420)  EAYDIAAIKFRGLNAVTNFDMSR
VvBBM           6       ( 349)  EAYDIAAIKFRGLNAVTNFDMSR
GmANT          99       ( 405)  EAYDIAAIKFRGANAVTNFDISR
GmBBM           2       ( 410)  EAYDVAAIKFRGLSAVTNFDMSR
MtBBM           8       ( 400)  EAYDVAAIKFRGLSAVTNFDMSR
SbANT          93       ( 424)  EAYDIAAIKFRGLNAVTNFDITR
GmAIL1         86       ( 343)  EAYDIAAIKFRGTSAVTNFDISR
MtAIL1         90       ( 389)  EAYDIAAIKFRGTSAVTNFDISR
SbPLT3         87       ( 279)  EAYDIAAIKFRGLNAVTNFEISR
ZmPLT3         80       ( 268)  EAYDIAAIKFRGLNAVTNFEISR
AtBBM          22       ( 351)  EAYDIAAIKFRGLSAVTNFDMNR
OsANT          95       ( 443)  EAYDVAAIKFRGLNAVTNFDITR
BnBBM2         26       ( 351)  EAYDIAAIKFRGLTAVTNFDMNR
BnBBM1         24       ( 351)  EAYDIAAIKFRGLTAVTNFDMNR
MtANT          98       ( 452)  EAYDIAAIKFRGANAVTNFDIIK
AtANT          92       ( 424)  EAYDVAAIKFRGTNAVTNFDITR
AtAIL6         89       ( 394)  EAYDIAAIKFRGINAVTNFEMNR
ZmANT          67       ( 443)  EAYDVAAIKFRGLSAVTNFDITR
OsPLT3         73       ( 285)  EAYDIAAIKFRGLNAVTNFEIGR
GmAIL7         94       ( 361)  EAYDIAAIKFRGANAVTNFEMNR
GmAIL6         88       ( 362)  EAYDIAAIKFRGANAVTNFEMNR
AtAIL7         96       ( 314)  EAYDIAAIKFRGINAVTNFEMNR
ZmANT2         97       ( 425)  EAYDIAAIKFRGLNAVTNFDIAR
ZmANTr        101       ( 289)  EAYDIAALKFRGENAVTNFEPSR
AtWRI1        102       ( 206)  AAYDMAAIEYRGANAVTNFDISN
Consensus      49               EAYD3AAIKFRGLNAVTNF456R 1= I or M;  2= Q or E;  3= I or V;  4= D or E;  5=M or I;  6=S or N
```

FIG. 2B (continued)

|  | SEQ ID NO: |  |  |
|---|---|---|---|
| SbBBM | 4 | (276) | SIYRGVTRHRWTGRYEAHLWDNSCRREGQTRK |
| ZmBBM | 10 | (272) | SIYRGVTRHRWTGRYEAHLWDNSCRREGQTRK |
| VvBBM | 6 | (207) | SIYRGVTRHRWTGRYEAHLWDNSCRREGQTRK |
| GmBBM | 2 | (268) | SIYRGVTRHRWTGRYEAHLWDNSCRREGQTRK |
| OsBBM | 14 | (282) | SIYRGVTRHRWTGRYEAHLWDNSCRREGQTRK |
| MtBBM | 8 | (261) | SIYRGVTRHRWTGRYEAHLWDNSCRREGQTRK |
| SbBBM2 | 28 | (285) | SIYRGVTRHRWTGRYEAHLWDNSCRREGQSRK |
| OsBBM3 | 20 | (278) | SIYRGVTRHRWTGRYEAHLWDNSCRREGQSRK |
| OsBBM2 | 18 | (302) | SIYRGVTRHRWTGRYEAHLWDNSCRREGQSRK |
| ZmBBM2 | 12 | (278) | SIYRGVTRHRWTGRYEAHLWDNSCRREGQSRK |
| GmPLT3b | 70 | (150) | SIYRGVTRHRWTGRYEAHLWDNSCRREGQSRK |
| GmPLT3a | 71 | (146) | SIYRGVTRHRWTGRYEAHLWDNSCRREGQSRK |
| MtPLT3 | 79 | (161) | SIYRGVTRHRWTGRYEAHLWDNSCRREGQSRK |
| ZmANT | 67 | (301) | SQYRGVTRHRWTGRYEAHLWDNSCRKEGQTRK |
| GmAIL1 | 86 | (204) | SQYRGVTRHRWTGRYEAHLWDNSCRKEGQTRK |
| MtAIL1 | 90 | (250) | SQYRGVTRHRWTGRYEAHLWDNSCRKEGQTRK |
| SbANT | 93 | (285) | SQYRGVTRHRWTGRYEAHLWDNSCKKEGQTRK |
| OsANT | 95 | (304) | SQYRGVTRHRWTGRYEAHLWDNSCKKEGQTRK |
| GmANT | 99 | (267) | SQYRGVTRHRWTGRYEAHLWDNSCKKEGQTRK |
| GmAIL6 | 88 | (223) | SIYRGVTRHRWTGRYEAHLWDNSCRREGQARK |
| MtANT | 98 | (312) | SQYRGVTRHRWTGRYEAHLWDNSCKKEGQSRK |
| BnBBM2 | 26 | (209) | SIYRGVTRHRWTGRYEAHLWDNSCKREGQTRK |
| BnBBM1 | 24 | (209) | SIYRGVTRHRWTGRYEAHLWDNSCKREGQTRK |
| AtBBM | 22 | (209) | SIYRGVTRHRWTGRYEAHLWDNSCKREGQTRK |
| SbPLT3 | 87 | (140) | SIYRGVTRHRWTGRYEAHLWDNSCRREGQSRK |
| ZmPLT3 | 80 | (126) | SIYRGVTRHRWTGRYEAHLWDNSCRREGQSRK |
| GmPLT2 | 78 | (163) | SIYRGVTRHRWTGRYEAHLWDNSCRREGQSRK |
| GmPLT1 | 82 | (168) | SIYRGVTRHRWTGRYEAHLWDNSCRREGQSRK |
| OsPLT3 | 73 | (143) | SIYRGVTRHRWTGRYEAHLWDNSCRREGQSRK |
| GmAIL7 | 94 | (223) | SIYRGVTRHRWTGRYEAHLWDNSCRREGQARK |
| AtAIL6 | 89 | (253) | SIYRGVTRHRWTGRYEAHLWDNSCRREGQARK |
| AtPLT2 | 75 | (189) | SIYRGVTRHRWTGRYEAHLWDNSCRREGQSRK |
| OsPLT3b | 81 | (129) | SIYRGVTRHRWTGRYEAHLWDNSCRREGQSRK |
| AtPLT1 | 83 | (180) | SIYRGVTRHRWTGRYEAHLWDNSCRREGQSRK |
| AtPLT3/AIL5 | 74 | (202) | SIYRGVTRHRWTGRYEAHLWDNSCRREGQSRK |
| SbPLT3b | 76 | (134) | SIYRGVTRHRWTGRYEAHLWDNSCRREGQSRK |
| ZmPLT3b | 72 | (139) | SIYRGVTRHRWTGRYEAHLWDNSCRREGQSRK |
| ZmANT2 | 97 | (283) | SRYRGVTRHRWTGRYEAHLWDNSCRKDGQTRK |
| AtAIL7 | 96 | (172) | SIYRGVTRHRWTGRYEAHLWDNSCRREGQARK |
| MtPLT1/2 | 84 | (165) | SIYRGVTKHRWTGRYEAHLWDNSCRREGQSRK |
| SbAIL1 | 91 | (265) | SQFRGVTRHRWTGRYEAHLWDNTCRKEGQTRK |
| OsAIL1 | 77 | (252) | SQFRGVTRHRWTGRYEAHLWDNTCRKEGQTRK |
| ZmAIL1 | 85 | (270) | SQFRGVTRHRWTGRYEAHLWDNTCRKEGQTRK |
| OsBBM1 | 16 | (167) | SIYRGVTKHRWTGRYEAHLWDNSCRREGQTRK |
| AtAIL1 | 100 | (222) | SQYRGVTRHRWTGRYEAHLWDNSCKKEGQTRR |
| AtANT | 92 | (282) | SQYRGVTRHRWTGRYEAHLWDNSFKKEGHSRK |
| ZmANTr | 101 | (147) | SIYRGVTRHRWTGRYEAHLWDNTCRKEGQKRK |
| AtWRI1 | 102 | (64) | SIYRGVTRHRWTGRFEAHLWDKSSWNSIQNKK |
| Consensus | 50 |  | S0YRGVTRHRWTGRYEAHLWDNSCR1EGQ2RK |

FIG. 2C

```
          SEQ ID NO:
SbBBM       4      ( 308) GRQGGYDKEEKAARAYDLAALKYWGPTTTTNFPVNN
ZmBBM       10     ( 307) VYLGGYDKEEKAARAYDLAALKYWGATTTTNFPVSN
VvBBM       6      ( 242) VYLGGYDKEEKAARAYDLAALKYWGTTTTTNFPISN
GmBBM       2      ( 303) VYLGGYDKEEKAARAYDLAALKYWGTTTTTNFPISH
OsBBM       14     ( 317) VYLGGYDKEEKAARAYDLAALKYWGPTTTTNFPVNN
MtBBM       8      ( 293) GRQGGYDKEEKAARAYDLAALKYWGTTTTTNFPISH
SbBBM2      28     ( 320) VYLGGYDKEDKAARAYDLAALKYWGTTTTTNFPISN
OsBBM3      20     ( 313) VYLGGYDKEDKAARAYDLAALKYWGTTTTTNFPMSN
OsBBM2      18     ( 334) GRQGGYDKEDKAARAYDLAALKYWGTTTTTNFPISN
ZmBBM2      12     ( 313) VYLGGYDKEDKAARAYDLAALKYWGTTTTTNFPISN
GmPLT3b     70     ( 185) VYLGGYDKEDKAARAYDLAALKYWGPTTTTNFPISN
GmPLT3a     71     ( 181) VYLGGYDKEDKAARAYDLAALKYWGPTTTTNFPISN
MtPLT3      79     ( 193) GRQGGYDKEEKAARAYDLAALKYWGPTTTTNFPISN
ZmANT       67     ( 336) VYLGGYDVEEKAARAYDLAALKYWGTSTHVNFPVED
GmAIL1      86     ( 236) GRQGGYDKEEKAAKAYDLAALKYWGPTTHINFPLST
MtAIL1      90     ( 282) GRQGGYDKEEKAAKAYDLAALKYWGPTTHINFPLST
SbANT       93     ( 317) GRQGGYDMEEKAARAYDLAALKYWGPSTHINFPLED
OsANT       95     ( 336) GRQGGYDMEEKAARAYDLAALKYWGPSTHINFPLED
GmANT       99     ( 298) GRQGGYDMEEKAARAYDLAALKYWGPSTHINFSIEN
GmAIL6      88     ( 255) GRQGGYDKEEKAARAYDLAALKYWGPTATTNFPVSN
MtANT       98     ( 344) GRQGGYDMEEKAARAYDQAALKYWGPSTHINFPLEN
BnBBM2      26     ( 244) VYLGGYDKEEKAARAYDLAALKYWGTTTTTNFPMSE
BnBBM1      24     ( 244) VYLGGYDKEEKAARAYDLAALKYWGTTTTTNFPMSE
AtBBM       22     ( 244) VYLGGYDKEEKAARAYDLAALKYWGPTTTTNFPLSE
SbPLT3      87     ( 172) GRQGGYDKEEKAARAYDLAALKYWGSSTTTNFPVAE
ZmPLT3      80     ( 161) VYLGGYDKEEKAARAYDLAALKYWGSSTTTNFPVAE
GmPLT2      78     ( 198) VYLGGYDKEEKAARAYDLAALKYWGTSTTTNFPISN
GmPLT1      82     ( 203) VYLGGYDKEEKAARSYDLAALKYWGTSTTTNFPISN
OsPLT3      73     ( 178) VYLGGYDKEEKAARAYDLAALKYWGPSTTTNFPVAE
GmAIL7      94     ( 254) GRQGGYDKEEKAARSYDLAALKYWGPTATTNFPVSN
AtAIL6      89     ( 287) VYLGGYDKEDKAARAYDLAALKYWNATATTNFPITN
AtPLT2      75     ( 224) VYLGGYDKEEKAARAYDLAALKYWGPSTTNFPITN
OsPLT3b     81     ( 164) VYLGGYDKEEKAARAYDLAALKYWGPTTTTNFPVAN
AtPLT1      83     ( 215) VYLGGYDKEDKAARSYDLAALKYWGPSTTNFPITN
AtPLT3/AIL5 74     ( 237) VYLGGYDKEDKAARAYDLAALKYWGPTTTTNFPISN
SbPLT3b     76     ( 169) VYLGGYDKEEKAARAYDLAALKYWGATTTTNFPVSN
ZmPLT3b     72     ( 174) VYLGGYDKEEKAARAYDLAALKYWGPTTTTNFPVSN
ZmANT2      97     ( 318) VYLGGYDTEDKAARAYDLAALKYWGPATHVNFPVEN
AtAIL7      96     ( 207) VYLGGYDKEDRAARAYDLAALKYWGSTATTNFPVSS
MtPLT1/2    84     ( 197) GRQGGYDKEEKAARSYDLAALKYWGTSTTTNFPVSN
SbAIL1      91     ( 297) GRQGGYDREEKAARAYDLAALKYWGPSTHINFPLSH
OsAIL1      77     ( 287) VYLGGYDKEEKAARAYDLAALKYWGPTTHINFPLST
ZmAIL1      85     ( 305) VYLGGYDREEKAARAYDLAALKYWGPSTHINFPLSH
OsBBM1      16     ( 202) VYLGGYDKEEKAARAYDLAALKYWGTTTTTNFPVSN
AtAIL1      100    ( 257) VYLGGYDEEEKAARAYDLAALKYWGPTTHLNFPLSN
AtANT       92     ( 317) VYLGGYDMEEKAARAYDLAALKYWGPSTHTNFSAEN
ZmANTr      101    ( 182) VYLGGYDKEDKAARAYDIAALKYWGDNATTNFPREN
AtWRI1      102    (  99) VYLGAYDSEEAAAHTYDLAALKYWGPDTILNFPAET
Consensus   50              345GGYDKE6KAARAYDLAALKYWG72T89NFP*SN
0=I or Q; 1=R or K; 2= S or T; 3= V or G; 4= Y or R; 5=L or Q; 6=E or
D; 7= P or T; 8=T or H; 9=T or I; *=I, V, or L
```

FIG. 2C (continued)

```
            SEQ ID NO:
SbBBM2         28      ( 113)   AVEDSEPKLEDFLGGNSFVSEH
OsBBM2         18      ( 108)   AVEETEPKLEDFLGGNSFVSEQ
ZmBBM2         12      ( 110)   AVEDSEPKLEDFLGGNSFVSDQ
SbBBM           4      (  55)   SALVAEPKLEDFLGGISFSEQH
ZmBBM          10      (  56)   SALVAEPKLEDFLGGISFSEQH
OsBBM          14      (  61)   SALVAEPKLEDFLGGISFSEQQ
GmAIL6         88      (  77)   HVPPPPPKLEDFLGDSSAVMRY
MtBBM           8      ( 106)   NNQQAQPKLENFLGGHSFTDHQ
GmAIL7         94      (  75)   SVSHAPPKLEDFLGDSSAVMRY
MtAIL1         90      (  85)   NSNEEGPKLEDFLGCYSNQNQN
GmANT          99      (  97)   MVPTSSPKLEDFLGGATMGTHE
AtAIL6         89      (  71)   HSQNHIPKLEDFLGDSSSIVRY
VvBBM           6      ( 103)   NLENQEPKLENFLGCRSFADHE
GmBBM           2      ( 107)   QQQQQQPKLENFLGGHSFGEHE
ZmANT2         97      ( 106)   MVPSSPPKLEDFLGGGNGGGQE
BnBBM2         26      (  89)   NDEQDGPKLENFLGRTTTIYNT
BnBBM1         24      (  89)   NDEQDGPKLENFLGRTTTIYNT
OsPLT3         73      (  37)   AGAAPPPKLEDFLGGGCNGGSS
GmAIL1         86      (  50)   NSNEEGPKLEDFLGCYSNSPAK
AtBBM          22      (  91)   NNEQNGPKLENFLGRTTTIYNT
GmPLT2         78      (  54)   HSSNEIPKVADFLGVSKSENQS
MtPLT1/2       84      (  54)   HNSNEVPKVADFLGVCKSENHS
GmPLT3b        70      (  68)   SIFTGGPKFEDFLGSAATATT
SbPLT3         87      (  35)   AGAAPPPKLEDFLGGGVINGES
ZmPLT3         80      (  36)   AGAAPPPKLEDFLGGGVATGGP
GmPLT3a        71      (  64)   SIFTGAPKFEDFLGGSSATATA
GmPLT1         82      (  54)   HSSSEVPKVADFLGVSKSENES
AtPLT3/AIL5    74      (  95)   SVYPGGPKLENFLGGGASTTTT
AtAIL7         96      (  13)   HSQTQIPKLEDFLGDSFVRYSD
SbAIL1         91      (  72)   AAEANGPKLEDFMSVTCSSNNK
OsBBM1         16      (  47)   GEETAAPKLEDFLGMQVQQETA
AtPLT2         75      (  58)   GEGGEVPKVADFLGVSKSGDHH
ZmAIL1         85      (  76)   AAEAKGPKLEDFMSITCSNKSS
ZmANT          67      ( 123)   VVSSSSPKLEDFLGASASTAMA
OsAIL1         77      (  66)   HAEAKDPKLEDFMSVSYSNKSS
AtPLT1         83      (  52)   DEGGEVPKVADFLGVSKPDENQ
OsBBM3         20      ( 109)   DGVGEAPKLENFLDGNSFSDVH
MtANT          98      ( 110)   MSTTSAPKLENFLGNEAMGTPH
SbANT          93      ( 103)   QPDHHGPKLEDFLGAAAAQSQA
AtANT          92      ( 108)   HHQDSSPKVEDFFGTHHNNTSH
OsANT          95      ( 124)   VVSASPKLEDFLGAGPAMALS
MtPLT3         79      (  79)   SIFTGGHKFEDFLGSSVAPTRT
AtAIL1        100      (  41)   HHDEDVPKVEDLLSNSHQTEYP
OsPLT3b        81      (  42)   GPAEGAPKMEDFLGGLGGGGGA
ZmPLT3b        72      (  44)   AVEESPRTVEDFLGGVGGAGAP
SbPLT3b        76      (  45)   TVEESPKMVEDFLGGVGGAGAP
Consensus      51                      PK123FLG 1= L or V; 2= E or A; 3= D or N
```

FIG. 2D

```
           SEQ ID NO:
VvBBM         6       ( 377)  ILESSTLPIGGAAKRL
MtBBM         8       ( 428)  ILESSTLPIGGAAKRL
GmBBM         2       ( 438)  ILESTTLPIGGAAKRL
SbBBM2       28       ( 455)  ILESSTLPVGGAARRL
OsBBM2       18       ( 469)  ILESSTLPVGGAARRL
ZmBBM2       12       ( 448)  ILESSTLPVGGAARRL
AtPLT1       83       ( 350)  ILESSTLPIGGGAAKR
OsBBM3       20       ( 448)  ILDSSTLPVGGAARRL
GmPLT2       78       ( 333)  ILESNTLPIGGGAAKR
GmPLT1       82       ( 338)  ILESNTLPIGGGAAKR
MtPLT1/2     84       ( 332)  ILESNTLPIGGGAAKR
AtPLT2       75       ( 359)  ILESNTLPIGGGAAKR
BnBBM2       26       ( 379)  ILESPSLPIGSAAKRL
BnBBM1       24       ( 379)  ILESPSLPIGSAAKRL
SbBBM         4       ( 446)  ILDSSALPIGSAAKRL
ZmBBM        10       ( 442)  ILDSSALPIGSAAKRL
OsANT        95       ( 471)  ILESSTLLPGELARRK
AtAIL6       89       ( 421)  AIMKSALPIGGAAKRL
AtBBM        22       ( 379)  ILESPSLPIGSSAKRL
GmAIL7       94       ( 388)  AIMKSSLPVGGAAKRL
GmAIL6       88       ( 389)  AIMKSSLPVGGAAKRL
SbANT        93       ( 452)  IMASNTLLPGDLARRR
ZmANT        67       ( 471)  IMESSTLLPGEQVRRR
SbAIL1       91       ( 432)  ICASTHLIGGGDACRR
ZmAIL1       85       ( 440)  ICASTHLIGGGDACRR
OsBBM1       16       ( 337)  IIESSNLPIGTGTTRR
GmAIL1       86       ( 371)  ICSSSTLIAGDLAKRS
OsBBM        14       ( 452)  ILDSAALPVGTAAKRL
OsAIL1       77       ( 422)  ICSSTHLIGGDLACRR
GmANT        99       ( 433)  IMASSNLLAGELARRN
MtAIL1       90       ( 417)  ICSSSTLITGDLAKRS
GmPLT3b      70       ( 319)  SIANSTLPIGGLSGKN
GmPLT3a      71       ( 315)  SIANSTLPIGGLSGKN
AtANT        92       ( 452)  IMSSNTLLSGELARRN
AtAIL7       96       ( 341)  AVMNSSLPVGGAAAKR
SbPLT3b      76       ( 303)  SILNSDLPVGGGAAGR
OsPLT3b      81       ( 298)  SILNSDLPVGGGAATR
ZmANT2       97       ( 453)  IMESSTLLAVEEARKV
MtPLT3       79       ( 327)  SIANCSLPIGGLSNKN
ZmPLT3b      72       ( 308)  SILSSDLPVGGGASGR
OsPLT3       73       ( 312)  SIISSNLPIGSMAGNR
MtANT        98       ( 480)  IMASSNLLNIEQARRN
AtPLT3/AIL5  74       ( 371)  SIASCNLPVGGLMPKP
Consensus    52                     SSTLP1GG2A334
1=I or V; 2= A, L, or G; 3= K or R; 4= L or R
```

FIG. 2E

```
            SEQ ID NO:
AtBBM        22         ( 4)   MNNWLGFSLSPHDQNH
GmANT        99         (15)   NHNWLGFSLSPHMKME
BnBBM2       26         ( 2)   NNNWLGFSLSPYEQNH
BnBBM1       24         ( 2)   NNNWLGFSLSPYEQNH
VvBBM         6         ( 4)   MNNWLGFSLSPRELPP
OsBBM        14         ( 4)   MNNWLAFSLSPQDQLP
SbBBM         4         ( 4)   VNNWLAFSLSPQELPP
ZmBBM        10         ( 4)   VNNWLAFSLSPQELPP
MtANT        98         (16)   ENNWLGFSLSPQMNNI
OsBBM2       18         ( 4)   ANNWLGFSLSGQENPQ
ZmBBM2       12         ( 4)   ANNWLGFSLSGQDNPQ
SbBBM2       28         ( 5)   NNHWLGFSLSGQDNPQ
GmAIL1       86         ( 1)   MSNWLGFSLTPHLRID
MtAIL1       90         ( 1)   MSNWLGFSLTPHLRID
ZmANT2       97         ( 4)   GSNWLGFSLSPHTAME
GmAIL6       88         ( 4)   ATNWLSFSLSPMEMLR
GmPLT2       78         ( 2)   NNNWLSFPLSPTHSSL
GmPLT1       82         ( 2)   NNNWLSFPLSPTHSSL
MtPLT1/2     84         ( 2)   NNNWLSFPLSPSHSSL
GmAIL7       94         ( 5)   STNWLSFSLSPMDMLR
AtPLT1       83         ( 3)   SNNWLGFPLSPNNSSL
MtBBM         8         ( 3)   SMNLLGFSLSPQEQHP
AtPLT2       75         ( 3)   SNNWLAFPLSPTHSSL
ZmAIL1       85         ( 4)   NNGWLGFSLSPSAASR
OsBBM3       20         ( 4)   ADNWLGFSLSGQGNPQ
SbANT        93         (13)   ASSWLGFSLSPHMASA
OsANT        95         (20)   VGGWLGFSLSPHMATY
SbPLT3b      76         (10)   PHHWLSFSLSNNYHHG
OsPLT3b      81         (10)   PHHWLSFSLSNNYHHG
ZmPLT3b      72         (10)   PHHWLSFSLSNNYHHG
SbAIL1       91         ( 4)   NNGWLGFSLSPSAGRG
GmBBM         2         ( 3)   SMNLLGFSLSPQEHPS
AtPLT3/AIL5  74         (27)   HQNWLSFSLSNNNNNF
GmPLT3b      70         (13)   NNNSLAFSLSNHFPNP
GmPLT3a      71         ( 9)   NNNSLAFSLSNHFPNP
AtAIL1      100         ( 1)   MKKWLGFSLTPPLRIC
ZmANT        67         (23)   GGSWLGFSLSPHMAAT
OsPLT3       73         ( 8)   HYPWLNFSLAHHCEME
ZmPLT3       80         ( 7)   YHPWLNFSLAHHCDLE
SbPLT3       87         ( 6)   HYPWLNFSLAHHGDLE
OsAIL1       77         ( 4)   NSGWLGFSLSSSSARG
AtANT        92         (15)   TTNLLGFSLSSNMMKM
OsBBM1       16         ( 4)   ITNWLGFSSSSFSGAG
Consensus    53                   NWLXFSLSP
X=G or S
```

FIG. 2F

```
        SEQ ID NO:
MtBBM      8    ( 159)  NNSIGLSMIKTWLRNQPPPPE
BnBBM2    26    ( 130)  GGSLGLSMIKTWLRNQPVDNV
BnBBM1    24    ( 130)  GGSLGLSMIKTWLRNQPVDNV
SbBBM      4    ( 156)  SGSIGLSMIKNWLRSQPAPMQ
SbBBM2    28    ( 157)  SNTMELSMIKTWLRNNQVPQP
OsBBM     14    ( 156)  NGGIGLSMIKNWLRSQPAPQP
ZmBBM     10    ( 152)  GGGIGLSMIKNWLRSQPAPMQ
VvBBM      6    ( 131)  YISIGLSMIKTWLRNQPAPTH
ZmBBM2    12    ( 154)  SNTMELSMIKTWLRNNQVAQP
GmBBM      2    ( 164)  SSSIGLSMIKTWLRNQPPHSE
OsBBM3    20    ( 157)  GGTIELSMIKTWLRSNQSQQQ
OsBBM2    18    ( 154)  SNTMELSMIKTWLRNNGQVPA
OsBBM1    16    (  80)  SSVVGLSMIKNWLRSQPPPAV
AtBBM     22    ( 131)  GGSLGLSMIKTWLSNHSVANA
Consensus 54            1LSMIK2WLR
1= G or E; 2= T or N
```

FIG. 2G

```
          SEQ ID NO:
SbAIL1      91    ( 527)  AGVHQLPVFALWND
OsAIL1      77    ( 536)  TVHHQLPVFALWND
ZmAIL1      85    ( 529)  PGVHQLPMFALWND
ZmANT       67    ( 624)  VSIAHLPVFAAWTD
SbANT       93    ( 664)  VSIAHMPVFAAWTD
OsANT       95    ( 638)  VSIAHLPMFAAWTD
MtANT       98    ( 642)  LSLPQMPVFAAWTD
VvBBM        6    ( 629)  AVCHGTPTFTVWND
GmANT       99    ( 532)  ISLSHLPVFAAWTD
OsBBM       14    ( 681)  GVCHGAQLFSVWND
BnBBM2      26    ( 565)  GGGEVAPTFTVWND
BnBBM1      24    ( 565)  GGGEVAPTFTVWND
GmAIL1      86    ( 499)  GLVNQVPMFALWNE
MtAIL1      90    ( 561)  GLVNQVPMFALWNE
ZmANT2      97    ( 637)  VVVSHRPVFAAWAD
AtBBM       22    ( 570)  GGGEGAPTFSVWND
AtANT       92    ( 541)  LTLPQMPVFAAWAD
SbBBM        4    ( 689)  VGHGGAQLFSVWND
ZmBBM       10    ( 695)  VGHGGAQLFSVWND
GmPLT2      78    ( 540)  MQTSNGGVFTMWND
GmPLT1      82    ( 549)  MQTSNSGVFTMWND
GmPLT3b     70    (  92)  CAPPQLPQFSTDNN
GmPLT3a     71    (  88)  CAPPQLPQFSTDNN
MtPLT3      79    ( 105)  CAPTQLQQFSTDND
AtPLT2      75    ( 555)  QGSNPGGVFTMWNE
AtPLT1      83    ( 561)  QGSNPGGVFTMWNE
MtPLT1/2    84    ( 524)  ENMQTADLFTMWND
Consensus   55            PXFXXWND
X= any amino acid
```

FIG. 2H

```
SEQ ID NO:
GmANT      99    ( 210)  LQSLSLSMSPGSQSSC
AtANT      92    ( 194)  QQSLSLSMSPGSQSSC
GmPLT2     78    ( 120)  LQSLTLSMGSGKDSTC
GmPLT1     82    ( 121)  LQSLTLSMGSGKDSTC
MtPLT1/2   84    ( 122)  LQSLTLSMGSGKDSTC
MtANT      98    ( 250)  LHSLSLSMSPSSQSSC
MtBBM       8    ( 192)  VQTLSLSMTGSQSSS
GmBBM       2    ( 202)  QQTLSLSMSTGSQSST
VvBBM       6    ( 174)  AQTLSLSMSTGSHQTG
SbBBM2     28    ( 221)  SQSLALSMSTGSHLPM
OsBBM2     18    ( 234)  SQSLALSMSTGSHSHL
ZmBBM2     12    ( 214)  SQSLALSMSTGSHLPM
SbANT      93    ( 217)  HHALALSMSSGSLSSC
ZmBBM      10    ( 181)  AQGLSLSMNMAGTTQG
GmAIL1     86    ( 150)  FQSLSLTMSPSVQNGV
OsBBM      14    ( 177)  AQALSLSMNMAGTTTA
BnBBM2     26    ( 159)  AKGLSLSMNSSTSCDN
BnBBM1     24    ( 159)  AKGLSLSMNSSTSCDN
SbBBM       4    ( 185)  VQGLSLSMNMAGATQG
OsANT      95    ( 241)  LHPLTLSMSSAGSQSS
MtAIL1     90    ( 191)  FQSLNLTMSPCVQNGV
ZmANT      67    ( 231)  PHPLALSMSSGTGSQS
AtPLT1     83    ( 126)  LQSLTLSMGTTAGNNV
AtPLT2     75    ( 129)  LQSLTLSMGSTGAAAA
AtBBM      22    ( 160)  ARGLSLSMNSSTSDSN
OsBBM3     20    ( 220)  GQGLALSMSTGSVAAA
ZmANT2     97    ( 202)  TRPLSLSMMSPGTQLS
Consensus  56             LXLSM
X = S, T or A
```

FIG. 2I

```
SEQ ID NO:
SbBBM       4    ( 529)  GWCKQEQDHAVIAAAH
OsBBM      14    ( 534)  GWCKQEQDHAVIAAAH
ZmBBM      10    ( 531)  GWCKQEQDHAVIAAAH
SbBBM2     28    ( 536)  GWCKPEQDAAVAAAAH
OsBBM2     18    ( 560)  GWCKPEQDAAVAAAAH
ZmBBM2     12    ( 528)  GWCKPEQDAAAAAAHS
OsBBM3     20    ( 522)  GWCKPEQDAVIAAGHC
MtBBM       8    ( 522)  LWCKQEQDSDDHSTYT
VvBBM       6    ( 453)  VWCKQEQDPDGTHNFQ
OsBBM1     16    ( 416)  AWLKQEQDSSVVTAAQ
GmBBM       2    ( 527)  NWCKQEQDNSDASHSL
Consensus  57             WCKXEQD
X= Q or P
```

FIG. 2J

```
        SEQ ID NO:
OsBBM2     18    ( 529)   HHHGWPTIAFQQPPPLAVHYPY
SbBBM2     28    ( 508)   GHHAWPTIAFQQPSPLSVHYPY
ZmBBM2     12    ( 501)   GHHGWPTIAFQQPSPLSVHYPY
VvBBM       6    ( 425)   HHHGWPTVAFQQAQPFSMHYPY
SbBBM       4    ( 502)   YHGAWPTIAFQPSAATGLYHPY
ZmBBM      10    ( 500)   HGAAWPTIAFQPGAATTGLYHP
OsBBM      14    ( 502)   AAAAWPTIAFQAAAAPPPHAAG
Consensus  58                WPTIAFQ
```

FIG. 2K

```
        SEQ ID NO:
SbBBM       4    ( 572)   MHGLGSMDNASLEHSTGSNSVVYNG
ZmBBM      10    ( 577)   MHGLASIDSASLEHSTGSNSVVYNG
OsBBM      14    ( 576)   QHGLGSIDNASLEHSTGSNSVVYNG
VvBBM       6    ( 487)   LHNLMSMDSSSMDHSSGSNSVIYSG
MtBBM       8    ( 560)   LQNIMSMDSASMDNSSGSNSVVYGG
GmBBM       2    ( 567)   LHPMLSMDSASIDNSSSSNSVVYDG
Consensus  59                        SXGSNSVVYNG
X= S or T
```

FIG. 2L

```
        SEQ ID NO:
SbBBM2     28    (  78)   ETQDWNMRGLDY
ZmBBM2     12    (  75)   ETQDWNMRGLDY
OsBBM2     18    (  76)   EAQDWNMRGLDY
OsBBM3     20    (  74)   ETQDWAMRGLDY
SbBBM       4    (  43)   IPQDWSMRGSEL
OsBBM      14    (  49)   IPQDWSMRGSEL
ZmBBM      10    (  44)   IPQDWSMRGSEL
Consensus  60                QDWXMRG
X= S or N
```

```
           *        680         *        700         *        720         *        740         *        760         *
ZmBBM2  : GA-SS---------------------SSTYN-GGAG---------ASGGY-QGLGGSS-FLMSS-TVVAAADQGHSS-TANQGSTCSYGDDHQEGKLI----- : 626
SbBBM2  : GA-SS---------------------SAYNSGGGG---------ASGGYHQGLGGSSSFLMSS-TVVAGADQGHSSSTANQGSTCSYGDDHQEGKLI----- : 639
OsBBM2  : GA-SS---------------------STYN---G----------GGGGY-QGLG-GNAFLMAS-TVVA--DQGHSSTATNHGNTCSYGNEEQ-GKLI----- : 657
OsBBM3  : QQPAS---------------------SAYG--------------NGGGGGNAFMMMG-AVVAAADHGGGSSAYGGG--------DESGRLVV------- : 611
OsBBM1  : QQ-SD---------------------VPDYTG------------FVDAPSRSSDSYSFRYNGTNGFHGLPGGISYAMPVATAVDQGQGIHGYGED----- : 511
ZmBBM   : SAGGQAAAAAAMHGLASIDSASLEHSTGSNYYNGG-----------VGDSNGASAVSGGGYMMMSAAGATTTSAMVSHEQMHARAY----DEAKQAAQM-- : 654
SbBBM   : SAGQQ----AAMHGLGSMDNASLEHSTGSNYYNG------------VGDSNGSTVVSGG-YMMMSAATATATTAMVSHEQVHARAGGDHHDEAKQAAQM-- : 651
OsBBM   : SQAMQ-----QQHGLGSIDNASLEHSTGSNYYNS------------DNGG----GGGYIMAMSAVSATATAVASSHDHG--------GDGGKQVQM---- : 641
BnBBM1  : HQSSV---------------------SDDYTVCGNVVG------YGYQGF-AAY----------------NCDAYAASEFD-------------- : 524
BnBBM2  : HQSSV---------------------SDDYTVCGNVVG------YGYQGF-AAY----------------NCDAYAASEFD-------------- : 524
AtBBM   : HHSSY---------------------SDDYTVCGNVVS------YGYQGF-AIYG---------TSVNYDPFTAAEIA------------------ : 526
MtBBM   : MDNSS---------------------GSNYYGGGDHGG-------YGNGGY-MIM----AIANDGNQNPRSNNNFGESEIKGFGYENVFSTTTD    : 638
GmBBM   : IDNSS---------------------SSNYYDG-----------YGYGGGYNNMIMGTTTTVVANDGDQNPRSNHGFGDNEIKALGYESVYSSTTD   : 643
VvBBM   : MDHSS---------------------GSNYYSGGGAADGSAATGGSGSGSFQGVGYGNNIGF-YMYS---TVIAHEGGHG-QGNGGFGDSEVKAIGYDNMFS-STD : 579
                                                s               g     p                                         g

780         *        800         *        820         *
ZmBBM2  : -SQAAMVATAAGGDPYA-----------AARNGYQFS-QGSGSTVSIAR----ANGYANNWSSPSNNGMG- : 679
SbBBM2  : -SDAMVAATAAGGDPYA-----------AARSGYQFSSQGSGSTVSIAR----ANGYSNNWSSPSNGGMG- : 693
OsBBM2  : --SDAMAMASGAAG--------------GGYQLS-QGSASTVSIAR----ANGYSANWSSPSNGAMG- : 703
OsBBM3  : -SSGVVDPYAAMR---------------SAYELSQGSSSSSVSVAKA---ANGYPDNWSSPSN-GMG- : 658
OsBBM1  : -VAGIDTTHDLYG---------------SRNVYYLSEGSLLADVEKEG---DYGQSVGGNSWVLPTP-- : 559
ZmBBM   : -SESYLVNAENNGGG-------------RMSAWGTVVSAAAAAAASSNDNIAADVGHGGAQLSVWNDT : 709
SbBBM   : -SESYLVNAENYGGG-------------RMSAAWATVSAPPAASSNDN----MADVGHGGAQLSVWNDT : 703
OsBBM   : -SSSYLVGADAYGGGGA-----------GRMPSWAMIPASAPAATSSSD---MTGVCHG-AQLSVWNDT : 695
BnBBM1  : -SNAR---NHYYFAQ------------QQQTQQSPGGDFPAAMTNNVGSNMYYHGEGGGEVAPTSVWNDN : 579
BnBBM2  : -SNAR---NHYYFAQ------------QQQTQHSPGGDFPAAMTNNVGSNMYYHGEGGGEVAPTSVWNDN : 579
AtBBM   : -SNAR---NHYYYAQHQ----------QQQQIGQSPGGDFPVAISNNHSSNMYFHGEGGGEGAPTSVWNDT : 584
MtBBM   : PSHQAARNLYYQPQQ------------LSVDQG---SNWVPTAIPSLAPR-TTNVSLCP--PSLLHE- : 689
GmBBM   : PSHAH-ARNLYYLTQQQPSSVDAVKASAYDQGSACNTWVPTAIPSHAPRSSTSMALCHGATPSLLHE- : 710
VvBBM   : PSHAR---SLYYLSQQSSAG-MVKGSSAYDQGSGCNNWVPTAVPSLAPR-TNSLAVCHGTPTSVWNDT : 643
                                                                             f
```

METHODS AND COMPOSITIONS FOR THE INTRODUCTION AND REGULATED EXPRESSION OF GENES IN PLANTS

CROSS-REFERENCE TO RELATED APPLICATIONS

This application is a continuation of and claims the benefit of U.S. Ser. No. 12/982,180 filed Dec. 30, 2010, which claims the benefit of U.S. Provisional Application No. 61/291,257, filed on Dec. 30, 2009, the contents of which are hereby incorporated by reference in their entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 399843SEQLIST.TXT, created on Dec. 29, 2010, and having a size of 534 kilobytes and is filed concurrently with the specification. The sequence listing contained in this ASCII formatted document is part of the specification and is herein incorporated by reference in its entirety.

FIELD OF THE INVENTION

The present invention is drawn to the field of plant genetics and molecular biology. More particularly, the compositions and methods are directed to the introduction and regulated expression of genes in plants.

BACKGROUND OF THE INVENTION

Current transformation technology provides an opportunity to engineer plants with desired traits. Major advances in plant transformation have occurred over the last few years. However, most transformation methods rely on the introduction of polynucleotides into embryonic tissues that are rapidly proliferating. Methods that allow for the transformation of more mature tissues would save considerable time and money. Accordingly, methods are needed in the art to increase transformation efficiencies of plants and allow for the transformation of more mature tissues.

Further, it is often necessary to reduce the activity of a transgene because the transgene may negatively affect the growth or fertility of the plant. Recombination systems can be used to excise the transgene, wherein the expression of a site-specific recombinase is regulated by an inducible promoter. Often, these systems are associated with premature excision. Accordingly, methods are needed in the art to efficiently excise transgenes with limited premature excision.

BRIEF SUMMARY OF THE INVENTION

Compositions and methods are provided for the introduction and regulated expression of genes in plants. Compositions include promoter constructs useful for regulated induction of expression of an operably linked coding sequence. In particular embodiments, the promoter construct comprises a maize rab17 promoter or an active variant or fragment thereof and an attachment B (attB) site. The modified rab17 promoter constructs find use in methods for regulating the expression of various coding sequences, including site-specific recombinases, which can minimize the premature excision of polynucleotides of interest in plants.

Further provided are methods for the transformation of plastids, such as chloroplasts, that involve the introduction of a heterologous polynucleotide encoding a cell proliferation factor, such as a babyboom (BBM) polypeptide. Novel BBM sequences are provided, along with methods of introducing the sequences into plants and plants comprising the novel BBM sequences. Methods for preparing and transforming mature embryo explants and leaf tissues are also provided.

BRIEF DESCRIPTION OF THE FIGURES

FIGS. 2A-2M show the consensus motif sequences 1-10, 14, 15, and 19, respectively, discovered in the analysis described herein, along with the alignments of the regions of various polypeptides used to generate the consensus motifs.

FIGS. 4-1 through 4-3 show an alignment of the amino acid sequence of various BBM polypeptides: maize babyboom 2 (ZmBBM2; SEQ ID NO: 12), sorghum babyboom 2 (SbBBM2; SEQ ID NO: 28), rice babyboom 2 (OsBBM2; SEQ ID NO: 18), rice babyboom 3 (OsBBM3; SEQ ID NO: 20), rice babyboom 1 (OsBBM1; SEQ ID NO: 16), maize babyboom (ZmBBM; SEQ ID NO: 10), sorghum babyboom (SbBBM; SEQ ID NO: 4), rice babyboom (OsBBM; SEQ ID NO: 14), Brassica babyboom 1 (BnBBM1; SEQ ID NO: 24), Brassica babyboom 2 (BnBBM2; SEQ ID NO: 26), Arabidopsis babyboom (AtBBM; SEQ ID NO: 22), medicago babyboom (MtBBM; SEQ ID NO: 8), soybean babyboom (GmBBM; SEQ ID NO: 2), and grape babyboom (VvBBM; SEQ ID NO: 6).

DETAILED DESCRIPTION OF THE INVENTION

Figure 1:
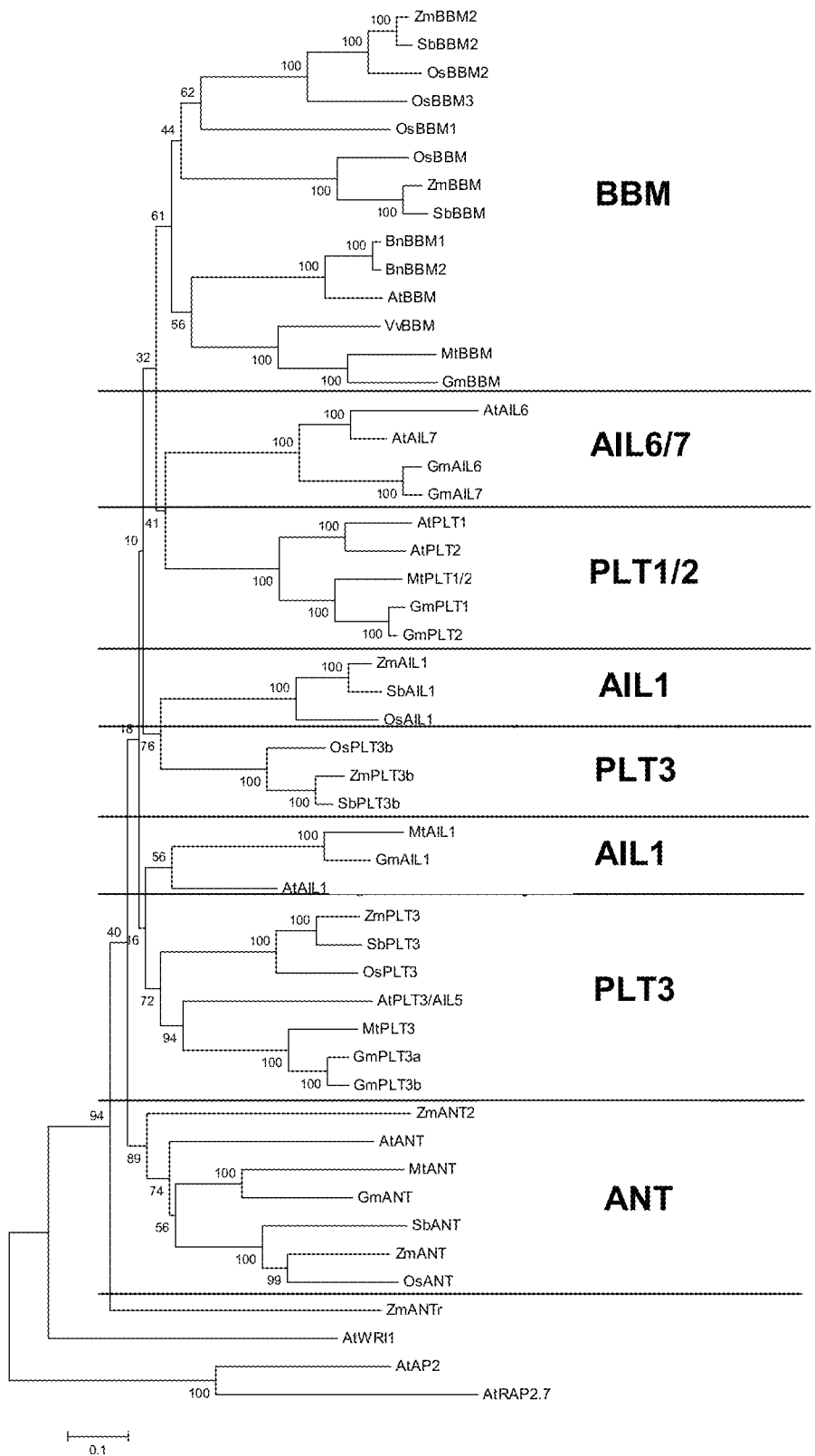
FIG. 1 provides a depiction of a phylogenetic analysis of 50 sequences with homology to maize babyboom (BBM).

The presently disclosed compositions and methods are useful for the introduction and the regulated expression of genes in plants. Compositions comprise promoter constructs that provide a level of activity useful for the regulated expression of various coding sequences, including site-specific recombinases. Further provided are compositions comprising novel babyboom (BBM) polynucleotide and polypeptide sequences and plants comprising the same. Methods for the introduction of genes into plants are provided, including methods for introducing novel BBM polynucleotides and polypeptides into plants, methods for the enhancement of plastid transformation, and methods for the transformation of tissues from mature seeds.

The expression cassette having the sequence set forth in SEQ ID NO: 45, which is comprised of the maize rab17 promoter, an attB site, and the coding sequence for the site-specific recombinase FLP, is capable of expressing FLP upon induction in such a manner as to reduce premature excision. Without being bound by any theory or mechanism of action, it is believed that the presence of the attB site modifies the activity of the promoter, allowing for a tightly regulated induction of expression of an operably linked coding sequence. Therefore, compositions include promoter constructs comprising a modified maize rab17 promoter or an active variant or fragment thereof. In some of these embodiments, the promoter construct comprises the maize rab17 promoter or an active variant or fragment thereof and an attB site or a variant or fragment thereof. In some of these embodiments, the maize rab17 promoter has the sequence set forth in SEQ ID NO: 29 or an active variant or fragment thereof.

As used herein, the term "promoter" includes reference to a region of DNA involved in the recognition and binding of RNA polymerase and other proteins to initiate transcription of a coding sequence. Promoters may be naturally occurring promoters, a variant or fragment thereof, or synthetically derived. A "promoter construct" is a polynucleotide comprising a promoter and optionally, sequences that are not necessary for transcription initiation or part of the coding sequence and are located in between the promoter and the coding sequence in an expression cassette. These intervening sequences can include modulators, restriction sites, sequences of the 5'-untranslated region (5'-UTR), which is the region of a transcript that is transcribed, but is not translated into a polypeptide, and recombination sites.

The promoter in the promoter constructs is the maize rab17 promoter or an active variant or fragment thereof. The maize rab17 (responsive to abscisic acid) gene (GenBank Accession No. X15994; Vilardell et al. (1990) *Plant Mol Biol* 14:423-432; Vilardell et al. (1991) *Plant Mol Biol* 17:985-993; each of which is herein incorporated in its entirety) is expressed in late embryos, but its expression can be induced by exposure to abscisic acid or water stress. The sequence of the maize rab17 promoter corresponds to nucleotides 1-558 of GenBank Accession No. X15994, which was disclosed in Vilardell et al. (1990) Plant Mol Biol 14:423-432 and is set forth in SEQ ID NO: 126. An alternative maize rab17 promoter was disclosed in U.S. Pat. Nos. 7,253,000 and 7,491,813, each of which is herein incorporated by reference in its entirety, and is set forth in SEQ ID NO: 29. The rab17 promoter contains 5 putative abscisic acid responsive elements (ABRE) (Busk et al. (1997) *Plant J* 11:1285-1295, which is herein incorporated by reference in its entirety). The putative ABRE elements can be found at about −208 to −203 (nucleotides 304 to 309 of SEQ ID NO: 29), −162 to −157 (nucleotides 348 to 353 of SEQ ID NO: 29), −147 to −142 (nucleotides 363 to 368 of SEQ ID NO: 29), −141 to −136 (nucleotides 369 to 374 of SEQ ID NO: 29), and −96 to −91 (nucleotides 414 to 419 of SEQ ID NO: 29) in the maize rab17 promoter. The rab17 promoter also contains drought-responsive elements (DRE), of which the core sequence is identical to the DRE (drought-responsive) and CRT (cold-response elements) elements in *Arabidopsis*. The drought-responsive elements are found at −213 to −206 (nucleotides 299 to 306 of SEQ ID NO: 29) and −190 to −185 (nucleotides 322 to 327 of SEQ ID NO: 29) of the maize rab17 promoter. The CAAT and TATAA box can be found from nucleotides 395 to 398 and 479 to 484 of SEQ ID NO: 29, respectively.

In some embodiments, the maize rab17 promoter that is part of the presently disclosed promoter constructs has the sequence set forth in SEQ ID NO: 29 or an active variant or fragment thereof. In other embodiments, the maize rab17 promoter that is part of the presently disclosed promoter constructs has the sequence set forth in SEQ ID NO: 125 or 126 or an active variant or fragment thereof.

In some embodiments of the methods and compositions, the promoter constructs comprise active variants or fragments of the maize rab17 promoter. An active variant or fragment of a maize rab17 promoter (e.g., SEQ ID NO: 29, 125, 126) is a polynucleotide variant or fragment that retains the ability to initiate transcription. In some embodiments, an active fragment of a maize rab17 promoter may comprise at least about 50, 100, 150, 200, 250, 300, 350, 400, 450, or 500 contiguous nucleotides of SEQ ID NO: 29, 125, or 126, or may have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 29, 125, or 126. In particular embodiments, an active variant or fragment of the maize rab17 promoter is one that is capable of initiating transcription in response to abscisic acid (ABA). In some of these embodiments, the promoter comprises at least one ABRE element. In particular embodiments, the promoter of the compositions and methods comprises from about −219 to about −102 of the maize rab17 promoter (corresponding to nucleotides 291 to 408 of SEQ ID NO: 29), which was shown to be sufficient to confer ABA responsiveness (Vilardell et al. (1991) *Plant Mol Biol* 17:985-993, which is herein incorporated by reference in its entirety).

In other embodiments, an active variant or fragment of the maize rab17 promoter is one that is capable of initiating transcription in response to dessication. In some of these embodiments, the promoter comprises at least one DRE element.

In particular embodiments, the active maize rab17 promoter fragment comprises from about −219 to about −80 of the maize rab17 promoter (nucleotides 291 to 430 of SEQ ID NO: 29), which comprises all of the putative DRE and ABRE elements.

Without being bound by any theory or mechanism of action, it is believed that a promoter construct (the sequence of which is set forth in SEQ ID NO: 30) comprising a maize rab17 promoter and a site-specific attachment B (attB) site has a modified level of activity in comparison to the promoter in the absence of the attB site due to the presence and/or the location of the attB site relative to the promoter. Therefore, it is believed the attB site functions as a modulator of the maize rab17 promoter. Accordingly, promoter constructs comprising a maize rab17 promoter or a fragment or variant thereof, and an attB site are provided, and in some of these embodiments, the attB site modifies the activity of the promoter. In other embodiments, the promoter construct comprises a maize rab17 promoter or a fragment or variant thereof and a modulator that modifies the activity of the rab17 promoter.

As used herein, a "modulator" refers to a polynucleotide that when present between a promoter and a coding sequence, serves to increase or decrease the activity of the promoter. Non-limiting examples of modulators include recombination sites, operators, and insulators.

Attachment sites are site-specific recombination sites found in viral and bacterial genomes that facilitate the integration or excision of the viral genome into and out of its host genome. Non-limiting examples of a viral and bacterial host system that utilize attachment sites is the lambda bacteriophage and *E. coli* system (Weisberg and Landy (1983) In Lambda II, eds. Hendrix et al. (Cold Spring Harbor Laboratory, Cold Spring Harbor, N.Y.) pp. 211-250). The modulator of the promoter constructs can be an *E. coli* attachment site B (attB) site. The attB site can be naturally occurring *E. coli* attB sites or an active variants or fragments thereof or a synthetically derived sequence. Synthetically derived attB sites and active variants and fragments of naturally occurring attB sites are those that are capable of recombining with a bacteriophage lambda attachment P site, a process that is catalyzed by the bacteriophage lambda Integrase (Int) and the *E. coli* Integration Host Factor (IHF) proteins (Landy (1989) *Ann Rev Biochem* 58: 913-949, which is herein incorporated by reference in its entirety). AttB sites typically have a length of about 25 nucleotides, with a core 15-base pair sequence that is involved in the actual crossover event. Alternatively, active variants and fragments of naturally occurring attB sites are those that are capable of modulating the activity of a promoter when present within a promoter construct. Non-limiting examples of attB sites that can be used include attB1 (SEQ ID NO: 31), attB2 (SEQ ID NO: 32), attB3 (SEQ ID NO: 33), and attB4 (SEQ ID NO: 34), and variants or fragments thereof. In some embodiments, the modulator is an active variant or fragment of an attB site that is capable of modulating (i.e., increasing, decreasing) the activity of a promoter, but is not capable of recombination with an attachment P site. Non-limiting examples of such active variants of an attB site include those having the sequence set forth in SEQ ID NO: 107, 108, or 109.

In some embodiments, the distance of the modulator from the promoter impacts the ability of the modulator to modify the activity of the promoter. The modulator may be contiguous with the promoter and/or the polynucleotide of interest. In other embodiments, a linker sequence separates the promoter sequence and the modulator. As used herein, a "linker sequence" is a nucleotide sequence that functions to link one functional sequence with another without otherwise contributing to the expression or translation of a polynucleotide of interest when present in a promoter construct. Accordingly, the actual sequence of the linker sequence can vary. The linker sequence can comprise plasmid sequences, restriction sites, and/or regions of the 5'-untranslated region (5'-UTR) of the gene from which the promoter is derived. The linker sequence separating the promoter and the modulator can have a length of about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 1000 nucleotides or greater. In certain embodiments, a linker sequence of about 133 nucleotides separates the promoter and the modulator. In some embodiments, the linker sequence comprises a fragment of the rab17 5'-UTR. The fragment of the 5'-UTR can be about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 nucleotides, or greater, in length. In certain embodiments, the promoter construct comprises a linker sequence separating the promoter and the modulator that comprises 95 nucleotides of the maize rab17 5'-UTR. In some of these embodiments, the 95 nucleotide sequence has the sequence set forth in SEQ ID NO: 35. In certain embodiments, the linker sequence between the promoter and modulator has the sequence set forth in SEQ ID NO: 36 or a variant or fragment thereof.

In some embodiments, the promoter construct comprises a linker sequence separating the modulator and the polynucleotide of interest. The length and sequence of this linker may also vary and can be about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 400, 500, 1000 nucleotides or greater in length. In certain embodiments, a linker sequence of about 61 nucleotides separates the modulator and the polynucleotide of interest. In certain embodiments, the linker sequence between the modulator and the polynucleotide of interest has the sequence set forth in SEQ ID NO: 37 or a variant or fragment thereof. In other embodiments, a linker sequence of about 25 nucleotides separates the modulator and the polynucleotide of interest. In certain embodiments, the linker sequence between the modulator and the polynucleotide of interest has the sequence set forth in SEQ ID NO: 123.

In certain embodiments, the promoter construct has the sequence set forth in SEQ ID NO: 30 or a variant or fragment thereof.

The promoter constructs can be operably linked to a polynucleotide of interest that encodes a polynucleotide or polypeptide within an expression cassette. "Operably linked" denotes a functional linkage between two or more elements. For example, an operable linkage between a polynucleotide of interest and a promoter is a functional link that allows for expression of the polynucleotide of interest. Operably linked elements may be contiguous or non-contiguous. The expression cassette can comprise other 5' or 3' regulatory elements necessary for expression.

Regulatory elements that can be included in the expression cassette 5' to the polynucleotide of interest include 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods or sequences known to enhance translation can also be utilized, for example, introns, and the like.

The expression cassette may also comprise a transcriptional and/or translational termination region functional in plants. The termination region may be native with the transcriptional initiation region (i.e., promoter), may be native with the operably linked polynucleotide of interest, may be native with the plant host, or may be derived from another source (i.e., foreign to the promoter, the polynucleotide of interest, the plant host, or any combination thereof). Convenient termination regions are available from the potato proteinase inhibitor (PinII) gene or the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639. In some embodiments, the pinII termination sequence has the sequence set forth in SEQ ID NO: 38 or an active variant or fragment thereof that is capable of terminating transcription and/or translation in a plant cell.

In certain embodiments, the expression cassette can comprise a recombination site, such as an attachment site 3' to the polynucleotide of interest. In some of these embodiments, the recombination site is a second attB site. In some of those embodiments wherein the promoter comprises a first attB site, the second attB site following the polynucleotide of interest and the modulator attB are non-identical. In some of those embodiments wherein the modulator attB site is attB1 (SEQ ID NO: 31), the second attB site 3' of the polynucleotide of interest can have the sequence set forth in SEQ ID NO: 31 (attB1), SEQ ID NO: 32 (attB2), SEQ ID NO: 33 (attB3), or SEQ ID NO: 34 (attB4), or an active variant or fragment thereof.

The recombination site 3' to the polynucleotide of interest can be 5' or 3' to the termination region when present. The recombination site can be contiguous with the polynucleotide of interest and/or the termination sequence, if present. In some embodiments, however, a linker sequence separates the polynucleotide of interest and the recombination site. The length of this linker sequence can vary, but in some embodiments, is about 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 nucleotides in length. In particular embodiments, the linker sequence separating the recombination site and the polynucleotide of interest is about 16 nucleotides. In certain embodiments, the recombination site and the polynucleotide of interest are separated by a linker sequence having the nucleotide sequence set forth in SEQ ID NO: 39, or a variant or fragment thereof. In other embodiments, the linker sequence separating the recombination site and the polynucleotide of interest is about 8 nucleotides. In certain embodiments, the recombination site and the polynucleotide of interest are separated by a linker sequence having the nucleotide sequence set forth in SEQ ID NO: 124, or a variant or fragment thereof.

In some of those embodiments wherein a termination region is present on the expression cassette and the expression cassette further comprises a recombination site 3' to the polynucleotide of interest, the termination region is 3' to the recombination site and a linker sequence separates the recombination site and the termination region. The length of this linker sequence can vary, but in some embodiments, is about 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 nucleotides in length. In particular embodiments, the linker sequence separating the recombination site and the termination region is about 14 nucleotides. In certain embodiments, the recombination site and the termination region are separated by a linker sequence having the nucleotide sequence set forth in SEQ ID NO: 40 or a variant or fragment thereof.

The expression cassettes comprise a presently disclosed promoter construct regulating the expression of a polynucleotide of interest. The polynucleotide of interest may be any polynucleotide that encodes a polynucleotide (e.g., antisense, siRNA) or encodes a polypeptide. Where appropriate, the polynucleotide(s) of interest may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In some embodiments, the polynucleotide of interest comprises a polynucleotide that encodes a site-specific recombinase. A site-specific recombinase, also referred to herein as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. The recombinase used in the methods and compositions can be a native recombinase or a biologically active fragment or variant of the recombinase. For reviews of site-specific recombinases and their recognition sites, see Sauer (1994) *Curr Op Biotechnol* 5:521-527; and Sadowski (1993) *FASEB* 7:760-767, each of which is herein incorporated by reference in its entirety.

Any recombinase system can be used in the methods and compositions. Non-limiting examples of site-specific recombinases include FLP, Cre, SSV1, lambda Int, phi C31 Int, HK022, R, Gin, Tn1721, CinH, ParA, Tn5053, Bxb1, TP907-1, U153, and other site-specific recombinases known in the art, including those described in Thomson and Ow (2006) *Genesis* 44:465-476, which is herein incorporated by reference in its entirety. Examples of site-specific recombination systems used in plants can be found in U.S. Pat. Nos. 5,929,301, 6,175,056, 6,331,661; and International Application Publication Nos. WO 99/25821, WO 99/25855, WO 99/25841, and WO 99/25840, the contents of each are herein incorporated by reference.

In some embodiments, the polynucleotide of interest encodes a recombinase from the Integrase or Resolvase families, including biologically active variants and fragments thereof. The Integrase family of recombinases has over one hundred members and includes, for example, FLP, Cre, lambda integrase, and R. For other members of the Integrase family, see, for example, Esposito et al. (1997) *Nucleic Acids Res* 25:3605-3614; and Abremski et al. (1992) *Protein Eng* 5:87-91; each of which are herein incorporated by reference in its entirety. Other recombination systems include, for example, the *Streptomycete* bacteriophage phi C31 (Kuhstoss et al. (1991) *J Mol Biol* 20:897-908); the SSV1 site-specific recombination system from *Sulfolobus shibatae* (Maskhelishvili et al. (1993) *Mol Gen Genet* 237: 334-342); and a retroviral integrase-based integration system (Tanaka et al. (1998) *Gene* 17:67-76). In some embodiments, the recombinase does not require cofactors or a supercoiled substrate. Such recombinases include Cre, FLP, or active variants or fragments thereof.

The FLP recombinase is a protein that catalyzes a site-specific reaction that is involved in amplifying the copy number of the two-micron plasmid of *S. cerevisiae* during DNA replication. FLP recombinase catalyzes site-specific recombination between two FRT sites. The FLP protein has been cloned and expressed (Cox (1993) *Proc Natl Acad Sci USA* 80:4223-4227, which is herein incorporated by reference in its entirety). The FLP recombinase for use in the methods and compositions may be derived from the genus *Saccharomyces*. In some embodiments, a recombinase polynucleotide modified to comprise more plant-preferred codons is used. A recombinant FLP enzyme encoded by a nucleotide sequence comprising maize preferred codons (FLPm) that catalyzes site-specific recombination events is known (the polynucleotide and polypeptide sequence of which is set forth in SEQ ID NO: 41 and 42, respectively; see, e.g., U.S. Pat. No. 5,929,301, which is herein incorporated by reference in its entirety). Additional functional variants and fragments of FLP are known (Buchholz et al.

(1998) *Nat Biotechnol* 16:657-662; Hartung et al. (1998) *J Biol Chem* 273:22884-22891; Saxena et al. (1997) *Biochim Biophys Acta* 1340:187-204; Hartley et al. (1980) *Nature* 286:860-864; Voziyanov et al. (2002) *Nucleic Acids Res* 30:1656-1663; Zhu & Sadowski (1995) *J Biol Chem* 270: 23044-23054; and U.S. Pat. No. 7,238,854, each of which is herein incorporated by reference in its entirety).

The bacteriophage recombinase Cre catalyzes site-specific recombination between two lox sites. The Cre recombinase is known (Guo et al. (1997) *Nature* 389:40-46; Abremski et al. (1984) *J Biol Chem* 259:1509-1514; Chen et al. (1996) *Somat Cell Mol Genet* 22:477-488; Shaikh et al. (1977) *J Biol Chem* 272:5695-5702; and, Buchholz et al. (1998) *Nat Biotechnol* 16:657-662, each of which is herein incorporated by reference in its entirety). Cre polynucleotide sequences may also be synthesized using plant-preferred codons, for example such sequences (moCre; the polynucleotide and polypeptide sequence of which is set forth in SEQ ID NO: 43 and 44, respectively) are described, for example, in International Application Publication No. WO 99/25840, which is herein incorporated by reference in its entirety. Variants of the Cre recombinase are known (see, for example U.S. Pat. No. 6,890,726; Rufer & Sauer (2002) *Nucleic Acids Res* 30:2764-2772; Wierzbicki et al. (1987) *J Mol Biol* 195:785-794; Petyuk et al. (2004) *J Biol Chem* 279:37040-37048; Hartung & Kisters-Woike (1998) *J Biol Chem* 273: 22884-22891; Santoro & Schultz (2002) *Proc Natl Acad Sci USA* 99:4185-4190; Koresawa et al. (2000) *J Biochem* (Tokyo) 127:367-372; and Vergunst et al. (2000) *Science* 290:979-982, each of which are herein incorporated by reference in its entirety).

In some embodiments, the polynucleotide of interest encodes a chimeric recombinase. A chimeric recombinase is a recombinant fusion protein which is capable of catalyzing site-specific recombination between recombination sites that originate from different recombination systems. For example, if the set of recombination sites comprises a FRT site and a LoxP site, a chimeric FLP/Cre recombinase or active variant or fragment thereof can be used, or both recombinases may be separately provided. Methods for the production and use of such chimeric recombinases or active variants or fragments thereof are described, for example, in International Application Publication No. WO 99/25840; and Shaikh & Sadowski (2000) *J Mol Biol* 302:27-48, each of which are herein incorporated by reference in its entirety.

In other embodiments, a variant recombinase is used. Methods for modifying the kinetics, cofactor interaction and requirements, expression, optimal conditions, and/or recognition site specificity, and screening for activity of recombinases and variants are known, see for example Miller et al. (1980) *Cell* 20:721-9; Lange-Gustafson and Nash (1984) *J Biol Chem* 259:12724-32; Christ et al. (1998) *J Mol Biol* 288:825-36; Lorbach et al. (2000) *J Mol Biol* 296:1175-81; Vergunst et al. (2000) *Science* 290:979-82; Dorgai et al. (1995) *J Mol Biol* 252:178-88; Dorgai et al. (1998) *J Mol Biol* 277:1059-70; Yagu et al. (1995) *J Mol Biol* 252:163-7; Sclimente et al. (2001) *Nucleic Acids Res* 29:5044-51; Santoro and Schultze (2002) *Proc Natl Acad Sci USA* 99:4185-90; Buchholz and Stewart (2001) *Nat Biotechnol* 19:1047-52; Voziyanov et al. (2002) *Nucleic Acids Res* 30:1656-63; Voziyanov et al. (2003) *J Mol Biol* 326:65-76; Klippel et al. (1988) *EMBO J* 7:3983-9; Arnold et al. (1999) *EMBO J* 18:1407-14; and International Application Publication Nos. WO 03/08045, WO 99/25840, and WO 99/25841; each of which is herein incorporated by reference in its entirety.

In particular embodiments, the expression cassette has the sequence set forth in SEQ ID NO: 45 or a variant or fragment thereof.

The expression cassette can be part of a vector that comprises multiple expression cassettes or multiple genes, such as a selectable marker gene. Selectable marker genes may be used to identify transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used.

In some embodiments, an expression cassette comprising a presently disclosed promoter construct can further comprise a polynucleotide encoding a cell proliferation factor. As used herein, a "cell proliferation factor" is a polypeptide or a polynucleotide capable of stimulating growth of a cell or tissue, including but not limited to promoting progression through the cell cycle, inhibiting cell death, such as apoptosis, stimulating cell division, and/or stimulating embryogenesis. The polynucleotides can fall into several categories, including but not limited to, cell cycle stimulatory polynucleotides, developmental polynucleotides, anti-apoptosis polynucleotides, hormone polynucleotides, or silencing constructs targeted against cell cycle repressors or pro-apoptotic factors. The following are provided as non-limiting examples of each category and are not considered a complete list of useful polynucleotides for each category: 1) cell cycle stimulatory polynucleotides including plant viral replicase genes such as RepA, cyclins, E2F, prolifera, cdc2 and cdc25; 2) developmental polynucleotides such as Lec1, Kn1 family, WUSCHEL, Zwille, BBM, Aintegumenta (ANT), FUS3, and members of the Knotted family, such as Kn1, STM, OSH1, and SbH1; 3) anti-apoptosis polynucleotides such as CED9, Bcl2, Bcl-X(L), Bcl-W, A1, McL-1, Mac1, Boo, and Bax-inhibitors; 4) hormone polynucleotides such as IPT, TZS, and CKI-1; and 5) silencing constructs targeted against cell cycle repressors, such as Rb, CK1, prohibitin, and wee1, or stimulators of apoptosis such as APAF-1, bad, bax, CED-4, and caspase-3, and repressors of plant developmental transitions, such as Pickle and WD polycomb genes including FIE and Medea. The polynucleotides can be silenced by any known method such as antisense, RNA interference, cosuppression, chimerplasty, or transposon insertion.

The cell proliferation factors can be introduced into cells through the introduction of a polynucleotide that encodes the proliferation factor. The use of the term "polynucleotide" is not intended to limit compositions to polynucleotides comprising DNA. Polynucleotides can comprise ribonucleotides and combinations of ribonucleotides and deoxyribonucleotides. Such deoxyribonucleotides and ribonucleotides include both naturally occurring molecules and synthetic analogues. The polynucleotides also encompass all forms of sequences including, but not limited to, single-, double-, or multi-stranded forms, hairpins, stem-and-loop structures, circular plasmids, and the like. The polynucleotide encoding the cell proliferation factor may be native to the cell or heterologous. A native polypeptide or polynucleotide comprises a naturally occurring amino acid sequence or nucleotide sequence. "Heterologous" in reference to a polypeptide or a nucleotide sequence is a polypeptide or a sequence that originates from a different species, or if from the same species, is substantially modified from its native form in composition and/or genomic locus by deliberate human intervention.

An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein or biologically active portion thereof is recombinantly produced, optimally culture medium represents less than about 30%, 20%, 10%, 5%, or 1% (by dry weight) of chemical precursors or non-protein-of-interest chemicals.

Any of a number of cell proliferation factors can be used. In certain embodiments, those cell proliferation factors that are capable of stimulating embryogenesis are used to enhance targeted polynucleotide modification. Such cell proliferation factors are referred to herein as embryogenesis-stimulating polypeptides and they include, but are not limited to, babyboom polypeptides.

In some embodiments, the cell proliferation factor is a member of the AP2/ERF family of proteins. The AP2/ERF family of proteins is a plant-specific class of putative transcription factors that regulate a wide variety of developmental processes and are characterized by the presence of an AP2 DNA binding domain that is predicted to form an amphipathic alpha helix that binds DNA (PFAM Accession PF00847). The AP2 domain was first identified in APETALA2, an *Arabidopsis* protein that regulates meristem identity, floral organ specification, seed coat development, and floral homeotic gene expression. The AP2/ERF proteins have been subdivided into distinct subfamilies based on the presence of conserved domains. Initially, the family was divided into two subfamilies based on the number of DNA binding domains, with the ERF subfamily having one DNA binding domain, and the AP2 subfamily having 2 DNA binding domains. As more sequences were identified, the family was subsequently subdivided into five subfamilies: AP2, DREB, ERF, RAV, and others. (Sakuma et al. (2002) *Biochem Biophys Res Comm* 290:998-1009).

Members of the APETALA2 (AP2) family of proteins function in a variety of biological events, including but not limited to, development, plant regeneration, cell division, embryogenesis, and cell proliferation (see, e.g., Riechmann and Meyerowitz (1998) *Biol Chem* 379:633-646; Saleh and Pagés (2003) *Genetika* 35:37-50 and Database of *Arabidopsis* Transcription Factors at daft.cbi.pku.edu.cn). The AP2 family includes, but is not limited to, AP2, ANT, Glossy15, AtBBM, BnBBM, and maize ODP2/BBM.

Provided herein is an analysis of fifty sequences with homology to a maize BBM sequence (also referred to as maize ODP2 or ZmODP2, the polynucleotide and amino acid sequence of the maize BBM is set forth in SEQ ID NO: 9 and 10, respectively; the polynucleotide and amino acid sequence of another ZmBBM is set forth in SEQ ID NO: 121 and 122, respectively). The analysis identified three motifs (motifs 4-6; set forth in SEQ ID NOs: 51-53), along with the AP2 domains (motifs 2 and 3; SEQ ID NOs: 49 and 50) and linker sequence that bridges the AP2 domains (motif 1; SEQ ID NO: 48), that are found in all of the BBM homologues. Thus, motifs 1-6 distinguish these BBM homologues from other AP2-domain containing proteins (e.g., WRI, AP2, and RAP2.7) and these BBM homologues comprise a subgroup of AP2 family of proteins referred to herein as the BBM/PLT subgroup. In some embodiments, the cell proliferation factor that is used in the methods and compositions is a member of the BBM/PLT group of AP2 domain-containing polypeptides. In these embodiments, the cell proliferation factor comprises two AP2 domains and motifs 4-6 (SEQ ID NOs: 51-53) or a fragment or variant thereof. In some of these embodiments, the AP2 domains have the sequence set forth in SEQ ID NOs: 49 and 50 or a fragment or variant thereof, and in particular embodiments, further comprises the linker sequence of SEQ ID NO: 48 or a fragment or variant thereof. In other embodiments, the cell proliferation factor comprises at least one of motifs 4-6 or a fragment or variant thereof, along with two AP2 domains, which in some embodiments have the sequence set forth in SEQ ID NO: 49 and/or 50 or a fragment or variant thereof, and in particular embodiments have the linker sequence of SEQ ID NO: 48 or a fragment or variant thereof. Based on the phylogenetic analysis provided herein, the subgroup of BBM/PLT polypeptides can be subdivided into the BBM, AIL6/7, PLT1/2, AIL1, PLT3, and ANT groups of polypeptides.

In some embodiments, the cell proliferation factor is a babyboom (BBM) polypeptide, which is a member of the AP2 family of transcription factors. The BBM protein from *Arabidopsis* (AtBBM) is preferentially expressed in the developing embryo and seeds and has been shown to play a central role in regulating embryo-specific pathways. Overexpression of AtBBM has been shown to induce spontaneous formation of somatic embryos and cotyledon-like structures on seedlings. See, Boutiler et al. (2002) *The Plant Cell* 14:1737-1749. The maize BBM protein also induces embryogenesis and promotes transformation (See, U.S. Pat. No. 7,579,529, which is herein incorporated by reference in its entirety). Thus, BBM polypeptides stimulate proliferation, induce embryogenesis, enhance the regenerative capacity of a plant, enhance transformation, and as demonstrated herein, enhance rates of targeted polynucleotide modification. As used herein "regeneration" refers to a morphogenic response that results in the production of new tissues, organs, embryos, whole plants or parts of whole plants that are derived from a single cell or a group of cells. Regeneration may proceed indirectly via a callus phase or directly, without an intervening callus phase. "Regenerative capacity" refers to the ability of a plant cell to undergo regeneration.

In some embodiments, the babyboom polypeptide comprises two AP2 domains and at least one of motifs 7 and 10 (set forth in SEQ ID NO: 54 and 57, respectively) or a variant or fragment thereof. In certain embodiments, the AP2 domains are motifs 3 and 2 (SEQ ID NOs: 50 and 49, respectively) or a fragment or variant thereof, and in particular embodiments, the babyboom polypeptide further comprises a linker sequence between AP2 domain 1 and 2 having motif 1 (SEQ ID NO: 48) or a fragment or variant thereof. In particular embodiments, the BBM polypeptide further comprises motifs 4-6 (SEQ ID NOs 51-53) or a fragment or variant thereof. The BBM polypeptide can further comprise motifs 8 and 9 (SEQ ID NOs: 55 and 56, respectively) or a fragment or variant thereof, and in some embodiments, motif 10 (SEQ ID NO: 57) or a variant or fragment thereof. In some of these embodiments, the BBM polypeptide also comprises at least one of motif 14 (set forth in SEQ ID NO: 58), motif 15 (set forth in SEQ ID NO: 59), and motif 19 (set forth in SEQ ID NO: 60), or variants or fragments thereof. The variant of a particular amino acid motif can be an amino acid sequence having at least about 40%, 50%, 60%, 70%, 75%, 80%, 85%, 90%, 95%, 96%, 97%, 98%, 99%, or greater sequence identity with the motif disclosed herein. Alternatively, variants of a particular amino acid motif can be an amino acid sequence that differs from the amino acid motif by 1, 2, 3, 4, 5, 6, 7, 8, 9, or 10 amino acids.

Non-limiting examples of babyboom polynucleotides and polypeptides that can be used in the methods and compositions include the *Arabidopsis thaliana* AtBBM (SEQ ID NOs: 21 and 22), *Brassica napus* BnBBM1 (SEQ ID NOs: 23 and 24), *Brassica napus* BnBBM2 (SEQ ID NOs: 25 and 26), *Medicago truncatula* MtBBM (SEQ ID NOs: 7 and 8), *Glycine max* GmBBM (SEQ ID NOs: 1 and 2), *Vitis vinifera* VvBBM (SEQ ID NOs: 5 and 6), *Zea mays* ZmBBM (SEQ ID NOs: 9 and 10 and genomic sequence set forth in SEQ ID NO: 68; or SEQ ID NOs: 121 and 122 and genomic sequence set forth in SEQ ID NO: 116) and ZmBBM2 (SEQ ID NOs: 11 and 12), *Oryza sativa* OsBBM (polynucleotide sequences set forth in SEQ ID NOs: 13 and 120; amino acid sequence set forth in SEQ ID NO: 14; and genomic sequence set forth in SEQ ID NO: 117), OsBBM1 (SEQ ID NOs: 15 and 16), OsBBM2 (SEQ ID NOs: 17 and 18), and OsBBM3 (SEQ ID NOs: 19 and 20), *Sorghum bicolor* SbBBM (SEQ ID NOs: 3 and 4 and genomic sequence set forth in SEQ ID NO: 69) and SbBBM2 (SEQ ID NOs: 27 and 28) or active fragments or variants thereof. In particular embodiments, the cell proliferation factor is a maize BBM polypeptide (SEQ ID NO: 10, 122, or 12) or a variant or fragment thereof, or is encoded by a maize BBM polynucleotide (SEQ ID NO: 9, 68, 121, 116, or 11) or a variant or fragment thereof.

Thus, in some embodiments, a polynucleotide encoding a cell proliferation factor has a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth in SEQ ID NO: 1, 3, 5, 7, 9, 11, 13, 15, 17, 19, 21, 23, 25, 27, 68, 116, 117, 120, 121, or 69 or the cell proliferation factor has an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth in SEQ ID NO: 2, 4, 6, 8, 10, 12, 14, 16, 18, 20, 22, 24, 26, 122, or 28. In some of these embodiments, the cell proliferation factor has at least one of motifs 7 and 10 (SEQ ID NO: 54 and 57, respectively) or a variant or fragment thereof at the corresponding amino acid residue positions in the babyboom polypeptide. In other embodiments, the cell proliferation factor further comprises at least one of motif 14 (set forth in SEQ ID NO: 58), motif 15 (set forth in SEQ ID NO: 59), and motif 19 (set forth in SEQ ID NO: 60) or a variant or fragment thereof at the corresponding amino acid residue positions in the babyboom polypeptide.

In other embodiments, other cell proliferation factors, such as, Lec1, Kn1 family, WUSCHEL (e.g., WUS1, the polynucleotide and amino acid sequence of which is set forth in SEQ ID NO: 61 and 62; WUS2, the polynucleotide and amino acid sequence of which is set forth in SEQ ID NO: 63 and 64; WUS2 alt, the polynucleotide and amino acid sequence of which is set forth in SEQ ID NO: 114 and 115; WUS3, the polynucleotide and amino acid sequence of which is set forth in SEQ ID NO: 105 and 106), Zwille, and Aintegumeta (ANT), may be used alone, or in combination with a babyboom polypeptide or other cell proliferation factor. See, for example, U.S. Application Publication No. 2003/0135889, International Application Publication No. WO 03/001902, and U.S. Pat. No. 6,512,165, each of which is herein incorporated by reference. When multiple cell proliferation factors are used, or when a babyboom polypeptide is used along with any of the abovementioned polypeptides, the polynucleotides encoding each of the factors can be present on the same expression cassette or on separate expression cassettes. When two or more factors are coded for by separate expression cassettes, the expression cassettes can be provided to the plant simultaneously or sequentially.

In some embodiments, polynucleotides or polypeptides having homology to a known babyboom polynucleotide or polypeptide and/or sharing conserved functional domains can be identified by screening sequence databases using programs such as BLAST. The databases can be queried using full length sequences, or with fragments including, but not limited to, conserved domains or motifs. In some embodiments, the sequences retrieved from the search can be further characterized by alignment programs to quickly identify and compare conserved functional domains, regions of highest homology, and nucleotide and/or amino differences between sequences, including insertions, deletions, or substitutions, including those programs described in more detail elsewhere herein. The retrieved sequences can also be evaluated using a computer program to analyze and output the phylogenetic relationship between the sequences.

In other embodiments, polynucleotides or polypeptides having homology to a known babyboom polynucleotide or polypeptide or one that has been disclosed herein and/or sharing conserved functional domains can be identified using standard nucleic acid hybridization techniques, such as those described in more detail elsewhere herein. Extensive guides on nucleic acid hybridization include Tijssen (1993) Laboratory Techniques in Biochemistry and Molecular Biology—Hybridization with Nucleic Acid Probes, Part I, Chapter 2 (Elsevier, N.Y.); Ausubel et al., eds. (1995) Current Protocols in Molecular Biology, Chapter 2 (Greene Publishing and Wiley-Interscience, NY); and, Sambrook et al. (1989) Molecular Cloning: A Laboratory Manual (2d ed., Cold Spring Harbor Laboratory Press, Plainview, N.Y.).

Compositions further comprise isolated BBM polynucleotides and isolated BBM polypeptides and variants and fragments thereof, expression cassettes comprising the same, and plants comprising the same. Compositions can comprise isolated polynucleotides encoding GmBBM (SEQ ID NO: 1), SbBBM (SEQ ID NO: 3), MtBBM (SEQ ID NO: 7), or OsBBM2 (SEQ ID NO: 17) or an active variant or fragment thereof. Isolated polypeptides include those having SEQ ID NO: 2, 4, 8, or 18 (GmBBM, SbBBM, MtBBM, or OsBBM2, respectively) or an active variant or fragment thereof. The percent identity of the novel BBM polypeptide sequences with those known in the art is presented in Table 1.

nucleotide having deletions at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides encoding polypeptides conservative variants include those sequences that, because of the degeneracy of the genetic code, encode the amino acid sequence the polypeptide (e.g., cell proliferation factor). Naturally occurring variants such as these can be identified with the use of well-known molecular biology techniques, such as, for example, with polymerase chain reaction (PCR) and hybridization techniques. Variant polynucleotides also include synthetically derived polynucleotides, such as those generated, for example, by using site-directed mutagenesis. Generally, variants of a particular will have at least about 40%, 45%, 50%, 55%, 60%, 65%, 70%, 75%, 80%, 85%, 90%, 91%,

TABLE 1

The percent sequence identity between each of 14 babyboom polypeptides.

|  | Zm BBM2 | Sb BBM2 | Os BBM2 | Os BBM3 | Os BBM1 | Zm BBM | Sb BBM | Os BBM | Bn BBM1 | Bn BBM2 | At BBM | Mt BBM | Gm BBM | Vv BBM |
|---|---|---|---|---|---|---|---|---|---|---|---|---|---|---|
| ZmBBM2 | 100 | | | | | | | | | | | | | |
| SbBBM2 | 92 | 100 | | | | | | | | | | | | |
| OsBBM2 | 79 | 77 | 100 | | | | | | | | | | | |
| OsBBM3 | 64 | 66 | 67 | 100 | | | | | | | | | | |
| OsBBM1 | 50 | 46 | 46 | 46 | 100 | | | | | | | | | |
| ZmBBM | 43 | 44 | 44 | 47 | 47 | 100 | | | | | | | | |
| SbBBM | 43 | 44 | 42 | 45 | 44 | 90 | 100 | | | | | | | |
| OsBBM | 44 | 44 | 45 | 46 | 49 | 69 | 70 | 100 | | | | | | |
| BnBBM1 | 42 | 41 | 42 | 41 | 40 | 45 | 42 | 43 | 100 | | | | | |
| BnBBM2 | 43 | 41 | 42 | 41 | 39 | 46 | 44 | 44 | 97 | 100 | | | | |
| AtBBM | 43 | 41 | 39 | 42 | 41 | 43 | 43 | 42 | 81 | 82 | 100 | | | |
| MtBBM | 41 | 40 | 40 | 41 | 43 | 42 | 43 | 41 | 47 | 47 | 47 | 100 | | |
| GmBBM | 45 | 44 | 42 | 45 | 44 | 41 | 42 | 44 | 46 | 46 | 43 | 68 | 100 | |
| VvBBM | 51 | 48 | 50 | 48 | 50 | 48 | 47 | 48 | 49 | 49 | 48 | 58 | 62 | 100 |

By "fragment" is intended a portion of the polynucleotide or a portion of an amino acid sequence and hence protein encoded thereby. Fragments of a polynucleotide may retain the biological activity of the native polynucleotide and, for example, have promoter activity (i.e., capable of initiating transcription), or are capable of stimulating proliferation, inducing embryogenesis, or modifying the regenerative capacity of a plant. In those embodiments wherein the polynucleotide encodes a polypeptide, fragments of the polynucleotide may encode protein fragments that retain the biological activity of the native protein. Alternatively, fragments of a polynucleotide that are useful as hybridization probes generally do not retain biological activity or encode fragment proteins that retain biological activity. Thus, fragments of a nucleotide sequence may range from at least about 20, 50, 100, 150, 200, 250, 300, 400, 500 nucleotides, or greater.

A fragment of a polynucleotide that encodes a biologically active portion of a cell proliferation factor, for example, will encode at least 15, 25, 30, 50, 100, 150, 200, 250, 300, 400, 500 contiguous amino acids, or up to the total number of amino acids present in the full-length cell proliferation factor. Fragments of a cell proliferation factor polynucleotide that are useful as hybridization probes or PCR primers generally need not encode a biologically active portion of a cell proliferation factor.

"Variants" is intended to mean substantially similar sequences. For polynucleotides, a variant comprises a poly- 92%, 93%, 94%, 95%, 96%, 97%, 98%, 99% or more sequence identity to that particular polynucleotide as determined by sequence alignment programs and parameters.

Variants of a particular polynucleotide that encodes a polypeptide can also be evaluated by comparison of the percent sequence identity between the polypeptide encoded by a variant polynucleotide and the polypeptide encoded by the particular polynucleotide. Percent sequence identity between any two polypeptides can be calculated using sequence alignment programs and parameters. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion of one or more amino acids at the N-terminal and/or C-terminal end of the native protein; deletion and/or addition of one or more amino acids at one or more internal sites in the native protein; and/or substitution of one or more amino acids at one or more sites in the native protein. Variant proteins retain the desired biological activity of the native protein. For example, variant cell proliferation factors stimulate proliferation and variant babyboom polypeptides are capable of stimulating proliferation, inducing embryogenesis, modifying the regenerative capacity of a plant, increasing the transformation efficiency in a plant, increasing or maintaining the yield in a plant under abiotic stress, producing asexually derived embryos in a plant, and/or enhancing rates of targeted polynucleotide modification. Such variants may result from, for example, genetic polymorphism or from human manipulation. Biologically active variants of a native cell proliferation factor will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters. A biologically active variant of a cell proliferation factor protein may differ from that protein by as few as 1-15 amino acid residues, as few as 1-10, such as 6-10, as few as 5, as few as 4, 3, 2, or even 1 amino acid residue.

In some embodiments, variants or fragments of the BBM polypeptide have amino acid residues valine, tyrosine, and leucine at the positions corresponding to positions 311, 312, and 313, respectively, of SEQ ID NO: 4 or variants or fragments of the BBM polynucleotide encodes a polypeptide having amino acid residues valine, tyrosine, and leucine at the positions corresponding to positions 311, 312, and 313, respectively, of SEQ ID NO: 4. In certain embodiments, variants or fragments of the BBM polypeptide have amino acid residues valine, tyrosine, and leucine at the positions corresponding to positions 337, 338, and 339, respectively, of SEQ ID NO: 18 or variants or fragments of the BBM polynucleotide encodes a polypeptide having amino acid residues valine, tyrosine, and leucine at the positions corresponding to positions 337, 338, and 339, respectively, of SEQ ID NO: 18. In other embodiments, variants or fragments of the BBM polypeptide have amino acid residues methionine, alanine, and serine at the positions corresponding to positions 1, 2, and 3, respectively, of SEQ ID NO: 8 or variants or fragments of the BBM polynucleotide encodes a polypeptide having amino acid residues methionine, alanine, and serine at the positions corresponding to positions 1, 2, and 3, respectively of SEQ ID NO: 8.

The babyboom polynucleotides and polypeptides can be introduced into a plant or plant cell in order to stimulate embryogenesis, modify the regenerative capacity of the plant, increase the transformation efficiency of the plant, increase or maintain the yield in the plant under abiotic stress, and/or to enhance targeted polynucleotide modification. The babyboom polynucleotide or polypeptide can be provided to a plant simultaneously with or prior to the introduction of a polynucleotide of interest in order to facilitate transformation of the plant with the polynucleotide of interest. Further, a haploid plant cell can be provided a novel babyboom polynucleotide or polypeptide to produce a haploid plant embryo (see U.S. Pat. No. 7,579,529, which is herein incorporated by reference in its entirety).

The cell proliferation factor polynucleotide can be operably linked to a promoter active in a plant. Various promoters can be used for the regulation of the expression of the cell proliferation factor. The promoter may be selected based on the desired outcome or expression pattern (for a review of plant promoters, see Potenza et al. (2004) In Vitro Cell Dev Biol 40:1-22).

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), the Agrobacterium nopaline synthase (NOS) promoter (Bevan et al. (1983) Nucl. Acids Res. 11:369-385), and the like. Other constitutive promoters are described in, for example, U.S. Pat. Nos. 5,608,149; 5,608,144; 5,604,121; 5,569,597; 5,466,785; 5,399,680; 5,268,463; 5,608,142; and 6,177,611.

In some embodiments, an inducible promoter can be used, such as from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) Neth. J. Plant Pathol. 89:245-254; Uknes et al. (1992) Plant Cell 4:645-656; and Van Loon (1985) Plant Mol. Virol. 4:111-116. See also WO 99/43819, herein incorporated by reference. Promoters that are expressed locally at or near the site of pathogen infection include, for example, Marineau et al. (1987) Plant Mol. Biol. 9:335-342; Matton et al. (1989) Mol Plant-Microbe Interact 2:325-331; Somsisch et al. (1986) Proc. Natl. Acad. Sci. USA 83:2427-2430; Somsisch et al. (1988) Mol. Gen. Genet. 2:93-98; and Yang (1996) Proc. Natl. Acad. Sci. USA 93:14972-14977. See also, Chen et al. (1996) Plant J. 10:955-966; Zhang et al. (1994) Proc. Natl. Acad. Sci. USA 91:2507-2511; Warner et al. (1993) Plant J. 3:191-201; Siebertz et al. (1989) Plant Cell 1:961-968; U.S. Pat. No. 5,750,386 (nematode-inducible); and the references cited therein. Additional promoters include the inducible promoter for the maize PRms gene, whose expression is induced by the pathogen Fusarium moniliforme (see, for example, Cordero et al. (1992) Physiol. Mol. Plant Path. 41:189-200). Wound-inducible promoters include potato proteinase inhibitor (pin II) gene (Ryan (1990) Ann. Rev. Phytopath. 28:425-449; Duan et al. (1996) Nat Biotechnol 14:494-498); wun1 and wun2, U.S. Pat. No. 5,428,148; win1 and win2 (Stanford et al. (1989) Mol. Gen. Genet. 215:200-208); systemin (McGurl et al. (1992) Science 225: 1570-1573); WIP1 (Rohmeier et al. (1993) Plant Mol. Biol. 22:783-792; Eckelkamp et al. (1993) FEBS Lett 323:73-76); MPI gene (Corderok et al. (1994) Plant J. 6:141-150); and the like, herein incorporated by reference. Another inducible promoter is the maize In2-2 promoter (deVeylder et al. (2007) Plant Cell Physiol 38:568-577, herein incorporated by reference).

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners (De Veylder et al. (1997) Plant Cell Physiol. 38:568-77), the maize GST promoter (GST-II-27, WO 93/01294), which is activated by hydrophobic electrophilic compounds that are used as pre-emergent herbicides, the PR-1 promoter (Cao et al. (2006) Plant Cell Reports 6:554-60), which is activated by BTH or benxo(1,2,3)thiaidazole-7-carbothioic acid s-methyl ester, the tobacco PR-la promoter (Ono et al. (2004) Biosci. Biotechnol. Biochem. 68:803-7), which is activated by salicylic acid, the copper inducible ACE1 promoter (Mett et al. (1993) PNAS 90:4567-4571), the ethanol-inducible promoter AlcA (Caddick et al. (1988) Nature Biotechnol 16:177-80), an estradiol-inducible promoter (Bruce et al. (2000) *Plant Cell* 12:65-79), the XVE estradiol-inducible promoter (Zao et al. (2000) *Plant J* 24:265-273), the VGE methoxyfenozide inducible promoter (Padidam et al. (2003) *Transgenic Res* 12:101-109), and the TGV dexamethasone-inducible promoter (Bohner et al. (1999) *Plant J* 19:87-95). Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237; Gatz et al. (1992) *Plant J* 2:397-404; and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Lam (1994) *Results Probl. Cell Differ.* 20:181-196; and Guevara-Garcia et al. (1993) *Plant J.* 4(3):495-505.

Leaf-preferred promoters are known in the art. See, for example, Yamamoto et al. (1997) *Plant J.* 12:255-265; Kwon et al. (1994) *Plant Physiol.* 105:357-67; Yamamoto et al. (1994) *Plant Cell Physiol.* 35:773-778; Gotor et al. (1993) *Plant J.* 3:509-18; Orozco et al. (1993) *Plant Mol. Biol.* 23:1129-1138; and Matsuoka et al. (1993) *Proc. Natl. Acad. Sci. USA* 90:9586-9590. In addition, promoter of cab and rubisco can also be used. See, for example, Simpson et al. (1958) *EMBO J* 4:2723-2729 and Timko et al. (1988) *Nature* 318:57-58.

Root-preferred promoters are known and can be selected from the many available. See, for example, Hire et al. (1992) *Plant Mol. Biol.* 20:207-218 (soybean root-specific glutamine synthase gene); Keller and Baumgartner (1991) *Plant Cell* 3:1051-1061 (root-specific control element in the GRP 1.8 gene of French bean); Sanger et al. (1990) *Plant Mol. Biol.* 14:433-443 (root-specific promoter of the mannopine synthase (MAS) gene of *Agrobacterium tumefaciens*); and Miao et al. (1991) *Plant Cell* 3:11-22 (full-length cDNA clone encoding cytosolic glutamine synthase (GS), which is expressed in roots and root nodules of soybean). See also Bogusz et al. (1990) *Plant Cell* 2:633-641, where two root-specific promoters isolated from hemoglobin genes from the nitrogen-fixing nonlegume *Parasponia andersonii* and the related non-nitrogen-fixing nonlegume *Trema tomentosa* are described. Leach and Aoyagi (1991) describe their analysis of the promoters of the highly expressed rolC and rolD root-inducing genes of *Agrobacterium rhizogenes* (see *Plant Sci* (Limerick) 79:69-76). Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue (see *EMBO J.* 8:343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29:759-772); and rolB promoter (Capana et al. (1994) *Plant Mol. Biol.* 25:681-691. See also U.S. Pat. Nos. 5,837,876; 5,750,386; 5,633,363; 5,459,252; 5,401,836; 5,110,732; and 5,023,179. Another root-preferred promoter includes the promoter of the phaseolin gene (Murai et al. (1983) *Science* 23:476-482 and Sengopta-Gopalen et al. (1988) *Proc. Natl. Acad. Sci. USA* 82:3320-3324.

Seed-preferred promoters include both those promoters active during seed development as well as promoters active during seed germination. See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase); (see WO 00/11177 and U.S. Pat. No. 6,225,529; herein incorporated by reference). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, nuc1, etc. See also WO 00/12733, where seed-preferred promoters from end1 and end2 genes are disclosed; herein incorporated by reference.

Where low-level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050), the core 35S CaMV promoter, and the like.

Other promoters of interest include the Rab16 promoter (Mundy et al. (1990) PNAS 87: 1406-1410), the *Brassica* LEA3-1 promoter (U.S. Application Publication No. US 2008/0244793), the HVA1s, Dhn8s, and Dhn4s from barley and the wsi18j, rab16Bj from rice (Xiao and Xue (2001) *Plant Cell Rep* 20:667-73), and D113 from cotton (Luo et al. (2008) *Plant Cell Rep* 27:707-717).

In some embodiments, the polynucleotide encoding a cell proliferation factor (e.g., babyboom polypeptide) is operably linked to a maize ubiquitin promoter or a maize oleosin promoter (e.g., SEQ ID NO: 65 or a variant or fragment thereof).

In some of those embodiments wherein the vector comprises a presently disclosed promoter construct operably linked to a polynucleotide encoding a site-specific recombinase and in some embodiments, a polynucleotide encoding a babyboom polypeptide, the vector can further comprise a polynucleotide encoding a Wuschel polypeptide (see International Application Publication No. WO 01/23575 and U.S. Pat. No. 7,256,322, each of which are herein incorporated by reference in its entirety). In certain embodiments, the polynucleotide encoding the Wuschel polypeptide has the sequence set forth in SEQ ID NO: 61, 63, 114, or 105 (WUS1, WUS2, WUS2 alt, or WUS3, respectively) or an active variant or fragment thereof. In particular embodiments, the Wuschel polypeptide has the sequence set forth in SEQ ID NO: 62, 64, 115, or 106 (WUS1, WUS2, WUS2 alt, or WUS3, respectively) or an active variant or fragment thereof. In some of these embodiments, the polynucleotide encoding a Wuschel polypeptide is operably linked to a promoter active in the plant, including but not limited to the maize In2-2 promoter or a nopaline synthase promoter. In some of these embodiments, the expression cassettes for the site-specific recombinase, the babyboom polypeptide, and the Wuschel polypeptide are all flanked by site-specific recombination sites that are directly repeated and are recognized by the site-specific recombinase whose expression is regulated by a presently disclosed promoter construct, such that expression of the site-specific recombinase results in the excision of the three expression cassettes.

In some embodiments, the vector comprises a promoter disclosed herein (maize Rab17 promoter with an attB1 site) operably linked to a site-specific recombinase (e.g., Cre, FLP); a second promoter operably linked to a cell proliferation factor (e.g., a babyboom polypeptide); and a third promoter operably linked to a polynucleotide of interest, such as those disclosed elsewhere herein (e.g., trait gene), or multiple polynucleotides of interest operably linked to one or more promoters; and in some embodiments, a fourth promoter operably linked to a WUS gene. In some of these embodiments, the expression cassettes for the site-specific recombinase, the cell proliferation factor, and the Wuschel polypeptide are all flanked by site-specific recombination sites that are directly repeated and are recognized by the site-specific recombinase, such that expression of the site-specific recombinase results in the excision of the three expression cassettes, leaving the polynucleotides of interest (e.g., trait genes) behind. In other embodiments, the polynucleotide of interest (e.g., trait gene) is introduced along with or following the vector comprising a presently disclosed promoter operably linked to a site-specific recombinase, and at least one cell proliferation factor (e.g., babyboom polypeptide, Wuschel polypeptide) operably linked to one or more promoters, wherein the polynucleotide of interest is present on a separate vector from the expression cassettes for the site-specific recombinase and cell proliferation factor(s). In some of these embodiments, the expression cassettes for the site-specific recombinase and cell proliferation factor(s) are flanked by recombination sites that are recognized by the site-specific recombinase. Expression of the cell proliferation factors facilitates the transformation of the polynucleotide of interest (e.g., trait gene) and expression of the site-specific recombinase results in the excision of the expression cassettes for the site-specific recombinase and cell proliferation factor(s).

The presently disclosed promoter constructs, expression cassettes, and vectors can be introduced into a host cell. By "host cell" is meant a cell, which comprises a heterologous nucleic acid sequence. Host cells may be prokaryotic cells such as *E. coli*, or eukaryotic cells such as yeast, insect, amphibian, or mammalian cells. In some examples, host cells are monocotyledonous or dicotyledonous plant cells. In particular embodiments, the monocotyledonous host cell is a maize host cell.

An intermediate host cell may be used, for example, to increase the copy number of the cloning vector and/or to mediate transformation of a different host cell. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein are available using *Bacillus* sp. and *Salmonella* (Palva et al. (1983) *Gene* 22:229-235); Mosbach et al. (1983) *Nature* 302:543-545).

Methods for expressing a polynucleotide of interest in a plant comprise introducing an expression cassette or vector. Alternatively, the method can comprise introducing a promoter construct, wherein the promoter construct is stably integrated into the genome of the plant and operably linked to a polynucleotide of interest.

"Introducing" is intended to mean presenting to the organism, such as a plant, or the cell the polynucleotide or polypeptide in such a manner that the sequence gains access to the interior of a cell of the organism or to the cell itself. The methods and compositions do not depend on a particular method for introducing a sequence into an organism or cell, only that the polynucleotide or polypeptide gains access to the interior of at least one cell of the organism. Methods for introducing polynucleotides or polypeptides into plants are known in the art including, but not limited to, stable transformation methods, transient transformation methods, virus-mediated methods, and sexual breeding.

"Stable transformation" is intended to mean that the nucleotide construct introduced into a plant integrates into a genome of the plant and is capable of being inherited by the progeny thereof "Transient transformation" is intended to mean that a polynucleotide is introduced into the plant and does not integrate into a genome of the plant or a polypeptide is introduced into a plant.

Protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci.*

USA 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Rep* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Rep* 12:250-255 and Christou and Ford (1995) *Annals of Botany* 75:407-413 (rice); Osjoda et al. (1996) *Nat Biotechnol* 14:745-750 (maize via *Agrobacterium tumefaciens*); all of which are herein incorporated by reference.

In specific embodiments, the sequences can be provided to a plant using a variety of transient transformation methods. Such transient transformation methods include, but are not limited to, the introduction of the polypeptide of interest directly into the plant or the introduction of a polynucleotide encoding the polypeptide of interest into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91:2176-2180 and Hush et al. (1994) *J Cell Sci* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide may be introduced into plants by contacting plants with a virus or viral nucleic acids. Generally, such methods involve incorporating a nucleotide construct within a viral DNA or RNA molecule. It is recognized that the cell proliferation factor may be initially synthesized as part of a viral polyprotein, which later may be processed by proteolysis in vivo or in vitro to produce the desired recombinant protein. Further, it is recognized that promoters also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Other methods of introducing polynucleotides into a plant can be used, including plastid transformation methods, and the methods for introducing polynucleotides into tissues from seedlings or mature seeds.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

In specific embodiments, methods are provided for the excision of a polynucleotide of interest from a target site in a plant, wherein the polynucleotide of interest is flanked by a first and a second recombination site that are recombinogenic with respect to one another and that are directly repeated. The method comprises introducing into the plant an expression cassette comprising a presently disclosed promoter construct (e.g., SEQ ID NO: 30 or a variant or fragment thereof) operably linked to a site-specific recombinase, expressing the recombinase, so that the recombinase recognizes and implements recombination at the recombination sites flanking the polynucleotide of interest, thereby excising the polynucleotide of interest. The expression cassette can comprise any of the linker sequences, attB sites, termination regions, etc., such as those described herein.

The terms "target site," and "target sequence," as used interchangeably herein, refer to a polynucleotide sequence present in a cell of an organism, such as a plant, that comprises at least one site-specific recombination site. The target site may be part of the organism's native genome or integrated therein or may be present on an episomal polynucleotide. The genomic target sequence may be on any region of any chromosome, and may or may not be in a region encoding a protein or RNA. The target site may be native to the cell or heterologous. In some embodiments, the heterologous target sequence may have been transgenically inserted into the organism's genome, and may be on any region of any chromosome, including an artificial or satellite chromosome, and may or may not be in a region encoding a protein or RNA. It is recognized that the cell or the organism may comprise multiple target sites, which may be located at one or multiple loci within or across chromosomes.

Alternative methods for excising a polynucleotide of interest from a target site in a plant include providing a plant comprising a target site comprising in operable linkage: a first site-specific recombination site, a first promoter, the polynucleotide of interest, a second promoter, a polynucleotide encoding a site-specific recombinase, and a second site-specific recombination site. The first and the second site-specific recombination sites are recombinogenic with respect to one another and directly repeated. The polynucleotide of interest and its operably linked promoter may precede or follow the polynucleotide encoding the site-specific recombinase and its operably linked promoter. The second promoter is one of the presently disclosed promoter constructs (e.g., SEQ ID NO: 30 or a variant or fragment thereof). The method comprises expressing the site-specific recombinase, whereby the site-specific recombinase recognizes and implements recombination at the first and the second site-specific recombination sites, thereby excising the polynucleotide of interest and the polynucleotide encoding the site-specific recombinase.

In some embodiments, the target site further comprises a third promoter operably linked to a polynucleotide encoding a Wuschel polypeptide. The three expression cassettes may be in any order, but in some embodiments, the target site comprises in operable linkage: the first site-specific recombination site, the third promoter, the polynucleotide encoding a Wuschel polypeptide, the first promoter, the polynucleotide of interest, the second promoter, the polynucleotide encoding the site-specific recombinase, and the second site-specific recombination site, wherein expression of the recombinase results in the excision of all three expression cassettes. The expression cassette can comprise any of the linker sequences, attB sites, termination regions, etc., such as those described herein.

Methods are provided to enhance the efficiency of plastid transformation, which include introducing into a plant cell a heterologous polynucleotide encoding a cell proliferation factor and expressing the heterologous polynucleotide before, during, or immediately following the transformation of the plastid of the plant cell with a polynucleotide of interest. The heterologous polynucleotide encoding a cell proliferation factor can be co-delivered with the polynucleotide of interest or the cell proliferation polynucleotide can first be introduced into the plant, followed by the introduction of the polynucleotide of interest.

As used herein, a "plastid" refers to an organelle present in plant cells that stores and manufactures chemical compounds used by the cell, such as starch, fatty acids, terpenes, and that has been derived from a proplastid. Thus, plastids of plants typically have the same genetic content. Plastids include chloroplasts, which are responsible for photosynthesis, amyloplasts, chromoplasts, statoliths, leucoplasts, elaioplasts, and proteinoplasts.

The plastid genome is circular and varies in size among plant species from about 120 to about 217 kilobase pairs (kb). The genome typically includes a large inverted repeat, which can contain up to about 76 kilobase pairs, but which is more typically in the range of about 20 to about 30 kilobase pairs. The inverted repeat present in the plastid genome of various organisms has been described (Palmer (1990) *Trends Genet* 6:115-120).

Transformation of plastids can result in a homoplasmic state, wherein essentially all of the plastids in a plant cell have the introduced DNA integrated into the plastid genome. This occurs through a selection process, whereby those cells that comprise a sufficient number of transformed plastids having an introduced selectable marker gene survive on the selection medium, and through the reproduction of the transformed plastid genomes. Plastids can be present in a plant cell at a very high copy number, with up to 50,000 copies per cell present for the chloroplast genome (Bendich (1987) *BioEssays* 6:279-282). Thus, through plastid transformation, plant cells can be engineered to maintain an introduced gene of interest at a very high copy number.

While plastid transformation is routine and relatively efficient in tobacco by bombardment of leaves, the application of plastid transformation technology in important crop species is not routine. For example, plastid transformation in maize and wheat has not been reported. Plastid transformation is possible in soybean, but the frequency of transformation with vectors carrying trait genes is low. Plastid transformation is possible in rice, but homoplasmic events have not been recovered.

The introduction and expression of polynucleotides encoding cell proliferation factors may be used to enhance the efficiency of plastid transformation. Any cell proliferation factor known in the art or described elsewhere herein may be used to enhance plastid transformation, including babyboom polypeptides. In certain embodiments, embryogenesis-stimulating polypeptides are used to enhance plastid transformation.

Methods are known in the art for introducing genes into the plastid genome. See, for example, Svab et al. (1990) *Proc. Natl. Acad. Sci. USA* 87: 8526-8530; Svab and Maliga (1993) *Proc. Natl. Acad. Sci. USA* 90: 913-917; Svab and Maliga (1993) *EMBO J.* 12: 601-606; and U.S. Pat. Nos. 5,451,513 and 5,545,818; each of which is herein incorporated by reference in its entirety.

One method involves the integration of a polynucleotide of interest into the plastid genome through homologous recombination. Such methods involve the introduction of a polynucleotide of interest flanked by regions of homology with regions of the plastid genome into a plant cell. Delivery of the polynucleotide of interest into the plant cell can be via any method of transformation known in the art, including those described elsewhere herein. These include, but are not limited to, particle gun delivery (Svab, Z. et al. (1990) *Proc Natl Acad Sci USA* 87:8526-8530; Svab and Maliga (1993) *Proc Natl Acad Sci USA* 90:913-917; and Staub and Maliga (1993) *EMBO J* 12:601-606; and U.S. Pat. Nos. 5,451,513 and 5,545,818; each of which is herein incorporated by reference in its entirety) and *Agrobacterium*-mediated transformation (U.S. Pat. No. 5,563,055 and U.S. Pat. No. 5,981,840). In some species, protoplasts can also be used for chloroplast transformation (O'Neill et al. (1993) *Plant J* 3:729-38; and Spoerlein et al. (1991) *Theor Appl Gen* 82:717-722; each of which is herein incorporated by reference in its entirety). Once the polynucleotide of interest flanked by the homologous regions enters the cell, the polynucleotide of interest will be integrated within the plastid genome.

The homologous regions flanking the polynucleotide of interest, and in some embodiments, its operably linked promoter, and in particular embodiments, the selectable marker gene as well, may vary in length. In some embodiments, the region of homology with the plastid genome is about 50, 75, 100, 200, 300, 400, 500, 600, 700, 800, 900, 1000 base pairs or greater in length. In most instances, the frequency of recombination and thus the frequency of obtaining plants having transformed plastids decreases with the decreasing size of the homologous regions. In those embodiments wherein the regions of homology are present in the inverted repeat regions of the plastid genome, two copies of the polynucleotide of interest are expected per transformed plastid.

In some embodiments, the polynucleotide of interest can be co-delivered with a selectable marker gene that is active in the plastid. The selectable marker gene and the polynucleotide of interest can be present on a single DNA construct or on separate constructs. A number of markers have been developed for use with plant cells, such as resistance to chloramphenicol, the aminoglycoside G418, hygromycin, or the like. Genes conferring resistance to kanamycin (NPTII or AphA6) have been used as a selectable marker for plastid transformation (Carrer et al. (1993) *Mol Gen Genetics* 241:49-56; and Huang et al. (2002) *Mol Gen Genomics* 268:19-27; each of which is herein incorporated by reference in its entirety). Other genes which encode a product involved in chloroplast metabolism may also be used as selectable markers.

Another example of a selectable marker gene for plastid transformation is a selectable marker gene that confers resistance to a substance which inhibits protein synthesis by the plastids, such that cells which have acquired the phenotype are selected for by contacting the cells with a substance which inhibits protein synthesis by the plastids. The plastid DNA encoding the nonlethal selectable phenotype may comprise 16S ribosomal DNA mutated to confer resistance to the effects of streptomycin, or to spectinomycin, or to both antibiotics simultaneously. Expression of heterologous genes that modify non-lethal antibiotics such as streptomycin or spectinomycin by phosphorylation, adenylation or acetylation also are suitable for the selection of plastid transformation events. Another non-limiting example of a gene that confers resistance to streptomycin and spectinomycin is the bacterial aadA gene that codes for streptomycin spectinomycin adenyltransferase (Svab et al. (1993) *Proc Natl Acad Sci USA* 90:913-917). The aadA gene product allows for continued growth and greening of cells in the presence of streptomycin or spectinomycin whose chloroplasts comprise the selectable marker gene product. Cells which do not contain the selectable marker gene product are bleached. Selection for the aadA gene marker is thus based on identification of plant cells which are not bleached by the presence of streptomycin or spectinomycin, in the plant growth medium.

Other examples of selectable marker genes are those that confer resistance to an herbicide, including a photosystem II herbicide, such as a triazine herbicide, specifically the triazine herbicide atrazine. This phenotype not only provides nonlethal selection, but also provides herbicide resistance. Genes that provide resistance to plant herbicides such as glyphosate, bromoxynil, or imidazolinone may find use as a selectable marker gene. Such genes have been reported (Stalker et al. (1985) *J Biol Chem* 260:4724-4728 (glyphosate resistant EPSP); Stalker et al. (1985) *J Biol Chem* 263:6310-6314 (bromoxynil resistant nitrilase gene); and Sathasivan et al. (1990) *Nucl Acids Res* 18:2188 (AHAS imidazolinone resistance gene); each of which is herein incorporated by reference in its entirety).

The selectable marker gene and/or the polynucleotide of interest can be placed under the regulatory control of a chloroplast 5' promoter and 3' transcription termination regions, such as the tobacco 16S rRNA promoter rrn region and rps16 3' termination region. Numerous additional promoter regions may also be used to drive expression of the selectable marker gene and/or the polynucleotide of interest, including various plastid promoters and bacterial promoters which have been shown to function in plant plastids. Further, if nuclear expression of the selectable marker gene and/or the polynucleotide of interest is not desired, plastid introns can be incorporated into the selectable marker gene and/or the polynucleotide of interest. Certain classes of plastid introns can not be correctly spliced out in the nucleus, thereby preventing expression of the selectable marker gene and/or the polynucleotide of interest within the nucleus. The polynucleotide of interest and/or the heterologous polynucleotide encoding the cell proliferation factor may be optimized for expression in the chloroplast to account for differences in codon usage between the plant nucleus and this organelle. In this manner, the polynucleotide may be synthesized using chloroplast-preferred codons. See, for example, U.S. Pat. No. 5,380,831, herein incorporated by reference.

An additional method of plastid transformation occurs through the transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91: 7301-7305, which is herein incorporated by reference in its entirety. In these methods, the heterologous polynucleotide encoding the cell proliferation factor is introduced into the cell and expressed prior to, during, or immediately after the expression of the plastid-directed RNA polymerase.

In order to select those cells having transformed plastids, following introduction of the chloroplast transformation vectors, the treated tissue is placed on tissue culture medium containing the appropriate selection agent. After a suitable period of incubation on selection medium, transformed cells can be identified and grown to a stage that allows regeneration of the whole plants. The regeneration processes are basically identical to those used for standard nuclear transformation events. Special care must be taken to ensure that selection and regeneration conditions promote the elimination of most wild-type chloroplast genomes. The status of the proportion of wild-type to transformed chloroplast genomes can be monitored by standard molecular techniques including Southern and PCR analysis.

For tobacco and a number of other species, leaves are a preferred target for plastid transformation. In some embodiments, one or more cell proliferation factors (e.g., babyboom polypeptides) can be used to trigger a tissue culture response from leaves of maize and other species. For boosting chloroplast transformation, polynucleotides encoding cell proliferation factors under the control of inducible promoters can be introduced into the species of interest by standard nuclear transformation protocols. Events that contain the transgene can be characterized for expression of the inducible embryogenesis-stimulating polypeptides. Then, the expression of the polynucleotide encoding the cell proliferation factor is induced, thereby stimulating an embryogenic tissue culture response. For example, leaves from plants transformed with the polynucleotide(s) encoding a cell proliferation factor under the control of the tetracycline-repressor system can be placed on medium containing appropriate concentrations of doxycyline for induction of expression. The leaves can be maintained on the induction medium to allow for cell division and the initiation of embryogenic callus to take place. The plastids of the leaves can be transformed with the polynucleotide of interest, and in certain embodiments, a selectable marker gene just prior to the induction of the polynucleotide(s) encoding cell proliferation factor, during induction, or immediately after induction. Alternatively, leaf tissue can be transformed using the methods disclosed elsewhere herein. After plastid transformation, the plastid transformation events can be selected by incubating the leaves on selection medium. Following selection, the leaves or plant cells are grown on medium that stimulates callus formation.

Methods are provided for the preparation and transformation of dried mature seeds, mature embryos, and mature embryo explants. A mature embryo explant is a tissue dissected from a mature embryo, which is an embryo that has an age of at least about 18 days after pollination. Methods for preparing a mature embryo comprise dissecting a mature embryo from a mature seed and methods for preparing a mature embryo explant further comprise preparing slices (e.g., longitudinal slices) of the mature embryo. The mature embryo explant comprises at least one of the following tissues: leaf primordia, mesocotyl, shoot apical meristem, and root primordia. In some embodiments, the mature embryo explant comprises leaf primordia, mesocotyl, and root primordia. In some of these embodiments, the mature embryo explant further comprises a shoot apical meristem. The slices may be prepared using any method or suitable apparatus known in the art, including slices prepared by hand with a scalpel. In certain embodiments, each mature embryo is sliced into about 3 to 4 thin sections using a scalpel. The use of a dissecting microscope can aid in slicing of the mature embryo.

The mature seed from which the mature embryo or mature embryo explant is derived can be a seed of any plant. In some embodiments, the mature seed is from a monocot. In particular embodiments, the mature seed is from maize, rice, *sorghum*, barley, wheat, oats, or millet. In certain embodiments, the mature seed is from a recalcitrant plant, such as an elite maize inbred. As used herein, a "recalcitrant tissue" or "recalcitrant plant" is a tissue or a plant that has a low rate of transformation using traditional methods of transformation, such as those disclosed elsewhere herein. In some embodiments, the recalcitrant tissue or plant is unable to be transformed in the absence of the cell proliferation factor. In other embodiments, the recalcitrant tissue or plant has a rate of successful transformation of less than about 20%, less than about 15%, less than about 10%, less than about 5%, less than about 1%, less than about 0.1%, less than about 0.01%, less than about 0.001%, or less.

The mature embryo or mature embryo explant can be prepared from a dried mature seed. The dried mature seed can comprise about 90%, 85%, 80%, 75%, 70%, 65%, 60%, 55%, 50%, 45%, 40%, 35%, 30%, 25%, 20%, 15%, 10%, 5%, 1%, 0.1% or less water than a mature seed that has not been dried. The dried mature seed can be imbibed with an aqueous solution for a sufficient period of time to allow the dried mature seed to soften so that the mature embryo may be dissected from the seed and in some embodiments, mature embryo explant slices prepared from the mature embryo. In some embodiments, the dried mature seed is imbibed in an aqueous solution for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 hours or greater. In certain embodiments, the aqueous solution is water. In certain embodiments, the dried mature seed is imbibed for a sufficient period of time to induce germination of the seed. A germinated seed is one in which the radical has emerged.

Mature embryos and mature embryo explants can be transformed with a polynucleotide of interest through the provision of a cell proliferation factor (e.g., babyboom polypeptide). A heterologous polynucleotide encoding the cell proliferation factor is introduced into the mature embryo explant prior to or at the same time as the introduction of the polynucleotide of interest. The heterologous polynucleotide encoding the cell proliferation factor and the polynucleotide of interest can be provided on the same expression cassette or on separate expression cassettes.

The polynucleotides can be introduced into the mature embryo explant using any method known in the art, including but not limited to, *Agrobacterium*-mediated transformation.

In some embodiments, transformed mature embryo explants can be identified. Any method can be used to identify a plant cell or tissue comprising the polynucleotide of interest. In some examples, plant cells or tissues comprising the polynucleotide of interest are identified using one or more of the following techniques, including but not limited to PCR methods, hybridization methods such as Southern or Northern blots, restriction digest analyses, or DNA sequencing. In some embodiments, the transformed mature embryo explants can be identified by incubating the leaf mature embryo explants under conditions to allow for growth of a callus. In some embodiments, those mature embryo explants that are able to grow into a callus with significant proliferation indicate those mature embryo explains that have been transformed. In other embodiments, the transformed mature embryo explants can be identified and selected for through the introduction and expression of a selectable marker gene into the mature embryo explant.

Methods are also provided herein for the transformation of leaf tissues, which can be a leaf base. A leaf base is the tissue of a leaf above the first leaf base node. The leaf tissue can be derived from any plant. In some embodiments, the leaf tissue is derived from a monocot. In particular embodiments, the leaf tissue is derived from maize, rice, *sorghum*, barley, wheat, oats, or millet. In certain embodiments, the leaf tissue is derived from a recalcitrant plant, such as an elite maize inbred.

The leaf base can be from a mature leaf or a leaf from a seedling. As used herein, a "seedling" refers to a germinated seed or germinated embryo, or a plantlet generated in an in vitro system (e.g., from callus). The seedlings can be prepared by germinating seeds or dissecting mature embryos from mature seeds for germination. In some embodiments, the mature embryos are dissected from dried mature seeds that have been imbibed with an aqueous solution, as described herein.

In some embodiments, the coleoptile is removed from the leaf tissue and the leaf fragment is split longitudinally, and then horizontal slices are made to cross-dissect the leaf fragment into leaf tissue pieces. In particular embodiments, the pieces of leaf tissue are about 1 to 2 mm in length.

The leaf tissue can be transformed with a polynucleotide of interest through the provision of a cell proliferation factor (e.g., babyboom polypeptide). The polynucleotides can be introduced into the leaf tissue using any method known in the art, including but not limited to, *Agrobacterium*-mediated transformation. A heterologous polynucleotide of interest encoding the cell proliferation factor is introduced into the leaf tissue prior to or at the same time as the introduction of the polynucleotide of interest. The heterologous polynucleotide encoding the cell proliferation factor is expressed. The heterologous polynucleotide encoding the cell proliferation factor and the polynucleotide of interest can be provided on the same expression cassette or on separate expression cassettes.

In some embodiments, transformed leaf tissues can be identified. Any method can be used to identify a plant cell or tissue comprising the polynucleotide of interest. In some examples, plant cells or tissues comprising the polynucleotide of interest are identified using one or more of the following techniques, including but not limited to PCR methods, hybridization methods such as Southern or Northern blots, restriction digest analyses, or DNA sequencing. In some embodiments, the transformed leaf tissues can be identified by incubating the leaf tissues under conditions to allow for growth of a callus. In some embodiments, those leaf tissues that are able to grow a callus with significant proliferation indicate those leaf tissues that have been transformed. In other embodiments, the transformed leaf tissue can be identified and selected for through the introduction and expression of a selectable marker gene into the leaf tissue.

The cells that have been transformed may be grown into plants in accordance with conventional ways. See, for example, McCormick et al. (1986) *Plant Cell Rep* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having a nucleotide construct, for example, an expression cassette, stably incorporated into their genome is provided. Thus, compositions of the invention include plant cells, plant tissues, plant parts, and plants comprising the presently disclosed polynucleotides, polypeptides, promoter constructs, expression cassettes, or vectors. Likewise, the methods of the invention can be performed in plant cells, plant tissues, plant parts, and plants.

In some embodiments, the activity and/or level of the cell proliferation factor (e.g., babyboom polypeptide, Wuschel) is reduced prior to regenerating a plant from a cell or tissue having the polynucleotide of interest. In some of these embodiments, the polynucleotide encoding the cell proliferation factor is excised prior to the regeneration of a plant. In certain embodiments, the promoter and other regulatory elements that are operably linked to the heterologous polynucleotide encoding the cell proliferation factor are excised along with the cell proliferation factor coding sequence. In certain embodiments, the polynucleotide encoding the cell proliferation factor is flanked by recombination sites and an appropriate site-specific recombinase is introduced into the mature embryo explant or callus grown therefrom to excise the polynucleotide encoding the cell proliferation factor prior to regeneration of the mature embryo explant or callus into a plant. In some of those embodiments wherein both a babyboom polypeptide and a Wuschel polypeptide are provided to the plant cell, both the polynucleotide encoding the babyboom polypeptide and the polynucleotide encoding the Wuschel polypeptide are excised. The two polynucleotides can be present on the same or different expression cassettes and, therefore, can be excised in one or two different excision reactions. In some of these embodiments, the polynucleotide encoding the site-specific recombinase for excising the babyboom and Wuschel polynucleotides can be located on the same expression cassette as the babyboom and Wuschel polynucleotides and all three polynucleotides can be excised through the activity of the site-specific recombinase.

In order to control the excision of the cell proliferation factor, the expression of the site-specific recombinase that is responsible for the excision can be controlled by a late embryo promoter or an inducible promoter. In some embodiments, the late embryo promoter is GZ (Uead et al. (1994) *Mol Cell Biol* 14:4350-4359), gamma-kafarin promoter (Mishra et al. (2008) *Mol Biol Rep* 35:81-88), Glb1 promoter (Liu et al. (1998) *Plant Cell Reports* 17:650-655), ZM-LEG1 (U.S. Pat. No. 7,211,712), EEP1 (U.S. Patent Application No. US 2007/0169226), B22E (Klemsdal et al. (1991) *Mol Gen Genet* 228:9-16), or EAP1 (U.S. Pat. No. 7,321,031). In some embodiments, the inducible promoter that regulates the expression of the site-specific recombinase is a heat-shock, light-induced promoter, a drought-inducible promoter, including but not limited to Hva1 (Straub et al. (1994) *Plant Mol Biol* 26:617-630), Dhn, and WSI18 (Xiao & Xue (2001) *Plant Cell Rep* 20:667-673). In other embodiments, expression of the site-specific recombinase is regulated by the maize rab17 promoter, or one of the presently disclosed promoter constructs (e.g., maize rab17 promoter and an attB site). In some embodiments, the site-specific recombinase that excises the polynucleotide encoding the cell proliferation factor is FLP or Cre.

Any plant species can be transformed, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena*), barley (*Hordeum*), *Arabidopsis*, switchgrass, vegetables, ornamentals, grasses, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

If the polynucleotide of interest is introduced into an organism, it may impart various changes in the organism, particularly plants, including, but not limited to, modification of the fatty acid composition in the plant, altering the amino acid content of the plant, altering pathogen resistance, and the like. These results can be achieved by providing expression of heterologous products, increased expression of endogenous products in plants, or suppressed expression of endogenous produces in plants.

General categories of polynucleotides of interest include, for example, those genes involved in information, such as zinc fingers, those involved in communication, such as kinases, those involved in biosynthetic pathways, and those involved in housekeeping, such as heat shock proteins. More specific categories of transgenes, for example, include sequences encoding important traits for agronomics, insect resistance, disease resistance, herbicide resistance, sterility, grain characteristics, oil, starch, carbohydrate, phytate, protein, nutrient, metabolism, digestibility, kernel size, sucrose loading, and commercial products.

Traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Protein modifications to alter amino acid levels are described in U.S. Pat. Nos. 5,703,049, 5,885,801, 5,885,802, and 5,990,389 and WO 98/20122, herein incorporated by reference.

Insect resistance genes may encode resistance to pests such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the S4 and/or Hra mutations in ALS), genes coding for resistance to herbicides that act to inhibit action of glutamine synthase, such as phosphinothricin or basta (e.g., the bar gene), genes providing resistance to glyphosate, such as GAT (glyphosate N-acetyltransferase; U.S. Pat. No. 6,395,485), EPSPS (enolpyruvylshikimate-3-phosphate synthase; U.S. Pat. Nos. 6,867,293, 5,188,642, 5,627,061), or GOX (glyphosate oxidoreductase; U.S. Pat. No. 5,463,175), or other such genes known in the art. The nptII gene encodes resistance to the antibiotics kanamycin and geneticin.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could, for example increase starch for ethanol production, or provide expression of proteins.

Reduction of the activity of specific genes (also known as gene silencing, or gene suppression) is desirable for several aspects of genetic engineering in plants. Many techniques for gene silencing are well known to one of skill in the art, including but not limited to antisense technology (see, e.g., Sheehy et al. (1988) *Proc. Natl. Acad. Sci. USA* 85:8805-8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan et al. (1994) *Bio/Technology* 12: 883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; Javier (2003) *Nature* 425:257-263; and, Montgomery et al. (1998) *Proc. Natl. Acad. Sci. USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; WO 02/00904; and WO 98/53083); ribozymes (Steinecke et al. (1992) *EMBO J.* 11:1525; U.S. Pat. No. 4,987,071; and, Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et at (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the babyboom polynucleotide. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire babyboom polynucleotide, or one or more portions thereof, may be used as a probe capable of specifically hybridizing to corresponding babyboom polynucleotide and messenger RNAs. To achieve specific hybridization under a variety of conditions, such probes include sequences that are unique among babyboom polynucleotide sequences and are optimally at least about 10 nucleotides in length, and most optimally at least about 20 nucleotides in length. Such probes may be used to amplify corresponding babyboom polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

The following examples are offered by way of illustration and not by way of limitation.

EXPERIMENTAL

Example 1. A Modified Rab17 Promoter for the Regulated Expression of Genes

Gateway™ technology (Invitrogen, Carlsbad, Calif.) was used to place Gateway™ recombination sites between a promoter and a coding sequence, and between the coding sequence and a terminator. The product of a Gateway™ reaction set up in this manner leaves attB sites in those locations.

The rab17 promoter was identified as a candidate for regulating the expression of FLP recombinase for excision of polynucleotides encoding cell proliferation factors in tissue culture. It was tested for FLP/FRT excision of cell proliferation factor genes in culture. The PHP31004 plasmid was constructed, which has the following operably linked components: Rab17 Pro-attB1::FLPm-attB2::PinII+Ubi Pro-FRT1::CFP::PinII+Ubi Pro::ZmBBM::PinII-FRT1::YFP::PinII+Ubi Pro::moPAT::PinII. The sequence of the expression cassette for the FLPm gene in the PHP31004 plasmid is provided in SEQ ID NO: 46.

After excision by the FLP recombinase, the PHP31004 plasmid has the following operably linked components: Rab17 Pro-attB1::FLPm-attB2::PinII+Ubi Pro-FRT1::YFP::PinII+Ubi Pro::moPAT::PinII.

A plasmid (PHP30642) lacking the attB sites, but comprising the FLPm gene was constructed. The PHP30642 has the following operably linked components: Rab17 pro::FLPm::Gz-W64A term+Ubi pro-FRT1::CFP::PinII+Ubi-Pro::ZmBBM::PinII-FRT1::YFP::PinII+Ubi Pro::moPAT::PinII The sequence of the expression cassette for the FLPm gene in the PHP30642 plasmid is provided in SEQ ID NO: 47.

After excision by the FLP recombinase, the PHP30642 plasmid has the following operably linked components: Rab17 pro::FLPm::Gz-W64A term+Ubi pro-FRT1::YFP::PinII+Ubi pro::moPAT::PinII The construct lacking the attB sites resulted in frequent premature excision of the cell proliferation factor genes.

Example 2. Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

A plasmid comprising the Zm-BBM (also referred to as Zm-ODP2) coding sequence (set forth in SEQ ID NO: 9) operably linked to a promoter is constructed. This could be a weak promoter such as nos, a tissue-specific promoter, such as globulin-1 or oleosin, an inducible promoter such as In2, or a strong promoter such as ubiquitin plus a plasmid containing the selectable marker gene phosphinothricin N-acetyltransferase (PAT; Wohlleben et al. (1988) *Gene* 70:25-37) that confers resistance to the herbicide bialaphos. The plasmid DNA containing the selectable marker gene PAT and the BBM plasmid are precipitated onto 1.1 μm (average diameter) tungsten pellets using a calcium chloride ($CaCl_2$) precipitation procedure by mixing 100 μl prepared tungsten particles in water, 10 μl (1 μg) DNA in Tris EDTA buffer (1 μg total DNA), 100 μl 2.5 M $CaCl_2$, and 10 μl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 μl 100% ethanol is added to the final tungsten particle pellet. For particle gun bombardment, the tungsten/DNA particles are briefly sonicated. 10 μl of the tungsten/DNA particles is spotted onto the center of each macro carrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000×

SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.).

Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2,4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 $OD_{550}$. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2,4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2,4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 µM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 3. Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI.

In one example, the BBM plasmid is precipitated onto gold particles with PEI, while the transgenic expression cassette (UBI::moPAT~GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 µl of the washed gold particle/EtOH mix was centrifuged and the EtOH discarded. The particles were washed once in 100 µl dd$H_2O$ to remove residual ethanol, 250 µl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 µl aliquots of 2.5 mM HEPES buffer, pH 7.1, with 1× pulse-sonication, and then a quick vortex before each centrifugation. The particles were then suspended in a final volume of 250 µl HEPES buffer. A 25 µl aliquot of the particles was added to fresh tubes before attaching DNA. To attach uncoated DNA, the particles were pulse-sonicated, then 1 µg of DNA (in 5 µl water) was added, followed by mixing by pipetting up and down a few times with a Pipetteman and incubated for 10 minutes. The particles were spun briefly (i.e. 10 seconds), the supernatant removed, and 60 µl EtOH added. The particles with PEI-precipitated DNA-1 were washed twice in 60 µl of EtOH. The particles were centrifuged, the supernatant discarded, and the particles were resuspended in 45 µl water. To attach the second DNA (DNA-2), precipitation using TFX-50 was used. The 45 µl of particles/DNA-1 suspension was briefly sonicated, and then 5 µl of 100 ng/µl of DNA-2 and 2.5 µl of TFX-50 were added. The solution was placed on a rotary shaker for 10 minutes, centrifuged at 10,000 g for 1 minute. The supernatant was removed, and the particles resuspended in 60 µl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI::RFP::pinII expression cassette, and DNA-2 contained a UBI::

CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI::BBM::pinII using PEI, then coated with UBI::moPAT~YFP using TFX-50, and then bombarded into scutellar cells on the surface of immature embryos. PEI-mediated precipitation results in a high frequency of transiently expressing cells on the surface of the immature embryo and extremely low frequencies of recovery of stable transformants (relative to the TFX-50 method). Thus, it is expected that the PEI-precipitated BBM cassette expresses transiently and stimulates a burst of embryogenic growth on the bombarded surface of the tissue (i.e. the scutellar surface), but this plasmid will not integrate. The PAT~GFP plasmid released from the $Ca^{++}$/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT~GFP/$Ca^{++}$ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI::moPAT~GFPm::pinII After co-cultivation, explants are allowed to recover on normal culture medium, and then are moved onto culture medium containing 3 mg/l bialaphos. After 6-8 weeks, it is expected that $GFP^+$, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT~GFPm::PinII It is expected that the cells receiving the RNA will immediately begin dividing more rapidly and a large portion of these will have integrated the agronomic gene. These events can further be validated as being transgenic clonal colonies because they will also express the PAT~GFP fusion protein (and thus will display green fluorescence under appropriate illumination). Plants regenerated from these embryos can then be screened for the presence of the polynucleotide of interest.

Example 4. Excision of Genes Encoding Cell Proliferation Factors a. Rab17::CRE

The following T-DNA was constructed: RB-Ubi pro-loxP::Rab17 pro-attB1::Cre-attB2::PinII+NOS::ZmWUS2::PinII+Ubi pro::ZmBBM::PinII-loxP::YFP::PinII+Ubi pro::moPAT::PinII-LB. As a control, a T-DNA containing Ubi pro::moPAT::PinII was constructed. These T-DNA are introduced into immature embryos (approximately 0.8-2.5 mm in length) of the maize inbred PHH5G using standard *Agrobacterium*-mediated transformation methods. Non-transformed immature embryos of this inbred swell and initiate a small volume of callus cells, but proliferation does not occur on media compositions typically used for maize tissue culture (for example, 605J media, which comprises 4.3 g/l MS salts, 0.6 g/l Shenk & Hildebrand vitamins, 100 mg/l calcium chloride, 275 mg/l ammonium sulfate, 275 mg/l ammonium sulfate, 240 mg/l potassium phosphate, 100 mg/l magnesium sulfate, 3.4 g/l potassium nitrate, 1.8 mg/l boric acid, 6 mg/l manganese sulfate, 0.15 mg/l sodium molybdate, 0.5 mg/l potassium iodide, 22 mg/l disodium EDTA, 17 mg/l ferrous sulfate, 3.4 mg/l silver nitrate, 1 g/l L-proline, 0.2 mg/l nicotinic acid, 0.4 mg/l thiamine, 0.2 mg/l pyridoxine, 0.8 mg/l glycine, 100 mg/l carbenicillin, 0.8 mg/l 2-4D, 1.2 mg/l dicamba, 0.3 g/l casein hydrosylate, 20 g/l sucrose, 0.6 g/l glucose, and 6 g/l TC agar, pH 5.8). Likewise, PHH5G immature embryos transformed with Ubi pro::moPAT::PinII alone do not produce healthy, growing callus, irrespective of whether bialaphos selection is provided. Thus, no transformed events were produced after introducing Ubi pro::moPAT::PinII alone (or with Ubi pro::moPAT::PinII+Ubi pro::YFP::PinII) In contrast, when the genes encoding cell proliferation factors (BBM and WUS2)+Ubi pro::moPAT::PinII were introduced into PHH5G immature embryos, vigorously-growing callus transformants were recovered from 45% of the treated embryos. To remove the genes encoding cell proliferation factors, the Rab17 promoter can be induced through exposure to either 20 mM abscisic acid (ABA), 20-30% sucrose, or desiccation. In this experiment, callus was placed on dry filter papers for three days to induce excision, and then transferred to regeneration medium. If callus was not treated to induce the expression of Cre recombinase, excision of the genes encoding cell proliferation factors did not occur and viable plantlets were not regenerated. However, for events that were taken through the desiccation treatment, Cre excision occurred in over 90% of single copy events (activating YFP) and subsequent regeneration was not inhibited. Transgenic plants were screened using combinations of PCR primers designed to detect the presence of the Ubi pro-loxP::YFP junction formed as a result of excision, and moPAT (not effected by excision), and the absence of Cre, WUS2 and BBM. Plants in which excision was complete were grown to maturity and were either selfed or out-crossed to wild-type plants. Transgenic progeny seed were readily identified through the yellow fluorescence phenotype and plants were easily tracked through either BASTA resistance or yellow fluorescence. PCR analysis in both the T1 and T2 generations indicated that only the excised locus was present in a single genomic copy and that no *Agrobacterium* plasmid backbone was present.

Both FLP and Cre recombinase have been successfully used to excise genes encoding cell proliferation factors before regeneration. The following two constructs represent examples of how the recombinases can be used for controlled excision:

PHP32371—FLP/FRT

RB-Ubi-FRT1::CFP::PinII-attB4+Rab17 Pro-attB1::FLP-attB2::PinII+Nos::ZmWUS2::PinII+Ubi::ZmBBM::PinII-FRT1::YFP::PinII+Ubi::moPAT::PinII-LB The T-DNA sequence of PHP32371 is set forth in SEQ ID NO: 110.

PHP35648—Cre/LoxP

RB-Ubi-LoxP::CFP::PinII-attB4+Rab17 Pro-attb1::Cre-attB2::PinII+Nos::ZmWUS2::PinII+Ubi::ZmBBM::PinII-LoxP::YFP::PinII+Ubi::MOPAT::PinII-LB The T-DNA sequence of PHP35648 is set forth in SEQ ID NO: 111.

For both recombinases, expression was controlled by the Rab17 promoter (Vilardell et al. (1991) *Plant Mol. Biol* 17:985-993) with the attb1 site.

For both constructs, transgenic callus events were readily recovered, and both constructs worked well for excision of the expression cassettes comprising genes encoding cell proliferation factors (see Table 2). Of the total number of calli exposed to the 3-day desiccation treatment, 61% (Cre) and 29% (FLP) of the resultant plants exhibited a normal wild-type phenotype. As confirmation of excision, PCR analysis in both the T1 and T2 generations indicated that only the excised locus was present in a single genomic copy and that no *Agrobacterium* plasmid backbone was present.

TABLE 2

Desiccation-induced excision of the recombinase, BBM & WUS expression cassettes prior to regeneration.

| | # of Callus events exposed to desiccation | # of events with normal T0 plant phenotype | # of T0 plantlets analyzed using PCR | # of single copy plants | # with a totally-excised DevGene package |
|---|---|---|---|---|---|
| PHP35648 | 180 | 110 (61%) | 168 | 94 (56%) | 81 (86%) |
| PHP32371 | 118 | 34 (29%) | 75 | 51 (68%) | 31 (61%) |

Additional constructs that utilize Cre/LoxP were generated.

PHP46446: RB-LoxP-Rab17 Pro-attB1::Cre-attB2::PinII+Nos::Zm-WUS2::PinII::GZ-W64A Term-attB2+Ubi::ZmBBM::PinII-LoxP-LB PHP48733: RB-LoxP-Rab17 Pro-attB1::Cre-attB2::PinII+Nos:ZmWUS2::PinII+Ubi::ZmBBM::PinII-LoxP-LB The T-DNA sequences of PHP46446 and PHP48733 is set forth in SEQ ID NO: 112 and 113, respectively.

Introduction of PHP35648, PHP48733, or PHP46446 into PHH5G immature maize embryos via *Agrobacterium* resulted in a transformation frequency of 46%, 67%, or 37%, respectively (see Table 3).

TABLE 3

Transformation of PHH5G immature maize embryos with maize BBM and WUS2 cell proliferation factors.

| Construct | No. of ears | No. of embryos | No. of callus events | Transformation frequency at callus level |
|---|---|---|---|---|
| PHP35648 | 14 | 589 | 268 | 45.5 |
| PHP48733 | 14 | 584 | 389 | 66.6 |
| PHP46446 | 14 | 547 | 203 | 37.1 |

The use of the PHP35648, PHP48733, PHP46446, and PHP32371 constructs (all of which comprised the Rab17 promoter (Vilardell et al. (1991) *Plant Mol. Biol* 17:985-993) with the attb1 site regulating the expression of the recombinase), did not result in frequent premature excision of the cell proliferation factor genes, similar to the results presented in Example 1 with the PHP31004 construct.

b. Tetracycline-Inducible CRE

A 35S promoter in which three tetracycline operator sequences (Top3) have been introduced in proximity to the TATA box (Gatz et al. (1992) *Plant J* 2:397-404) was operably linked to the CRE structural gene in the following T-DNA which also includes an expression cassette for the tetracycline repressor (TETR), BBM, WUS2, and moPAT, as follows:

RB-loxP-35S::Top3::CRE::PinII+Ubi pro::TETR::PinII+NOS::ZmWUS2::PinII+UBI::ZmBBM::PinII-loxP+UBI::moPAT::PinII-LB After *Agrobacterium*-mediated transformation of 12 DAP PH581 immature embryos, followed by 6 weeks of selection on 3 mg/l bialaphos, embryos into which the control T-DNA was introduced (RB-UBI::moPAT::PinII-LB) produced transformed events at a 1% frequency. In contrast, when the above T-DNA containing ZmBBM & ZmWUS2 was transformed into immature embryos harvested from the same PH581 ears, transgenic calli were recovered at a 15% frequency. Before regenerating plantlets, callus is moved onto medium containing 0.5 mg/l tetracycline for 1 week to induce CRE-mediated excision of CRE, WUS and BBM expression cassettes. Glufosinate ammonium-resistant plants are then readily regenerated.

Example 5. Control of BBM and WUS Expression with Regulated Promoters to Increase Transformation Frequencies a. OLE PRO::BBM In the inbred PH581 maize line, the introduction of UBI::ZmBBM+NOS:ZmWUS2 increased transformation frequencies from <1% in the control treatment (UBI PRO::moPAT::PinII alone) to 15%. However, such strong over-expression of BBM negatively affects the regeneration of plantlets. Therefore, an oleosin promoter having high levels of expression in callus, with little to no activity during vegetative growth was used to express BBM. When OLE::ZmBBM::PinII+NOS::ZmWUS2::PinII was introduced into PH581 on a first T-DNA and UBI PRO::moPAT::PinII was introduced into the same cells on a second T-DNA, callus transformants were recovered at a 25% frequency. Normal, fertile plants were regenerated and crossed to wild-type PH581. Ti progeny in which the cell proliferation gene locus had segregated away from the UBI PRO::moPAT::PinII locus were readily recovered.

b. Tetracycline-Inducible BBM and WUS2

A 35S promoter in which three tetracycline operator sequences have been introduced in proximity to the TATA box (Gatz et al. (1992) *Plant J* 2:397-404) is operably linked to both the BBM and WUS2 genes, and these expression cassettes are put into a T-DNA along with an expression cassette for the tetracycline repressor (TETR) as follows.

RB-35S-Top3::ZmBBM::PinII+35S-Top3::ZmWUS2::PinII+UBI::moPAT::PinII-LB

Following *Agrobacterium*-mediated transformation of Hi-II immature maize embryos, the embryos are transferred to selection medium 560R with 3 mg/l bialaphos+/−0.5 mg/l tetracycline. In the control treatment in which only the UBI::moPAT::PinII expression cassette is introduced, the transformation frequency is typically around 5-10%. For embryos in which the inducible BBM and WUS2 genes are introduced, transformation frequency is expected to be greatly increased upon the addition of tetracycline to the medium.

Example 6. Regulated Expression of BBM and WUS2 for Re-Transformation

Stable transgenic events in PHH5G are produced that express ZmBBM and ZmWUS2 in a regulated fashion, for example, having BBM and WUS2 under the control of the OLE and NOS promoters, respectively, or having them being driven by a tetracycline-inducible promoter. Immature embryos are then harvested and re-transformed using *Agrobacterium* to deliver UBI::moPAT::PinII PHH5G embryos not expressing BBM and WUS2 (i.e. wild-type control embryos) produce no transformation events. However, embryos expressing OLE PRO::ZmBBM::PinII and NOS PRO::ZmWUS2::PinII are expected to produce a much higher frequency of bialaphos-resistant events. Regulated expression of the genes encoding cell proliferation factors is expected to enhance the regeneration frequency of normal fertile plants, and the cell proliferation gene locus should readily segregate away from the newly-generated "trait" locus (represented here by the UBI::moPAT::PinII locus). Likewise, when the expression of tetracycline-inducible genes encoding cell proliferation factors are stimulated by the addition of 0.5 mg/l tetracycline, *Agrobacterium*-mediated transformation to deliver the RB-UBL:moPAT::PinII-LB T-DNA is expected to result in enhanced transformation frequencies.

Example 7. Two T-DNA Co-Transformation to Deliver Genes Encoding Cell Proliferation Factors and Trait Genes Separately An *Agrobacterium* was modified to contain two engineered plasmids, each containing a separate T-DNA. T-DNA-1 was PHP35648 (see Example 4 for description), and T-DNA-2 (PHP41877) contained RB-attB4-UBI::moPAT::PinII+UBI-FRT1::RFP::PinII-attB1+UBI::GAT::PinII-attB2-FRT87-attB3-LB (GAT=glyphosate-N-acetyltransferase) representing the T-DNA that will contain the desired stack of trait genes). *Agrobacterium*-mediated transformation of PHH5G immature maize embryos was followed by glyphosate selection. Only embryos that have integrated T-DNA-1 grew since growth in culture for PHH5G only occurred when the ZmWUS2 and ZmBBM genes were present. Only embryos containing T-DNA-2 were glyphosate-resistant and exhibited red fluorescence. Thus, only embryos that were co-transformed with both T-DNAs grew on glyphosate.

Example 8. Identification of BBM Motifs

Fifty genes from different plant species were identified through a homology search using the maize BBM amino acid sequence (SEQ ID NO: 10) queried against annotated protein sequences (see FIG. 1). The gene structure and sequences of these BBM homologs were manually inspected and compared with EST/cDNA alignments whenever possible. The fifty polypeptides are set forth in SEQ ID NOs: 2, 4, 6, 8, 10, 12, 14, 16, 18, 20, 22, 24, 26, 28, 67, and 70-104. To systematically identify possible motifs within the BBM homologs, protein sequences of these fifty homologs were submitted to the MEME web server, available on the world wide web at meme.nbcr.net/meme4_1/cgi-bin/meme.cgi, with the following specific parameters:

Number of different motifs: 20
Minimum motif width: 5
Maximum motif width: 300
Minimum number of sites: 5

Default values were applied for all other parameters. The raw results from MEME were manually compared with multiple sequence alignments generated by clustalw. Only those candidates showing good consensus with the sequence alignments were considered as motifs for further analysis.

Figure 3:
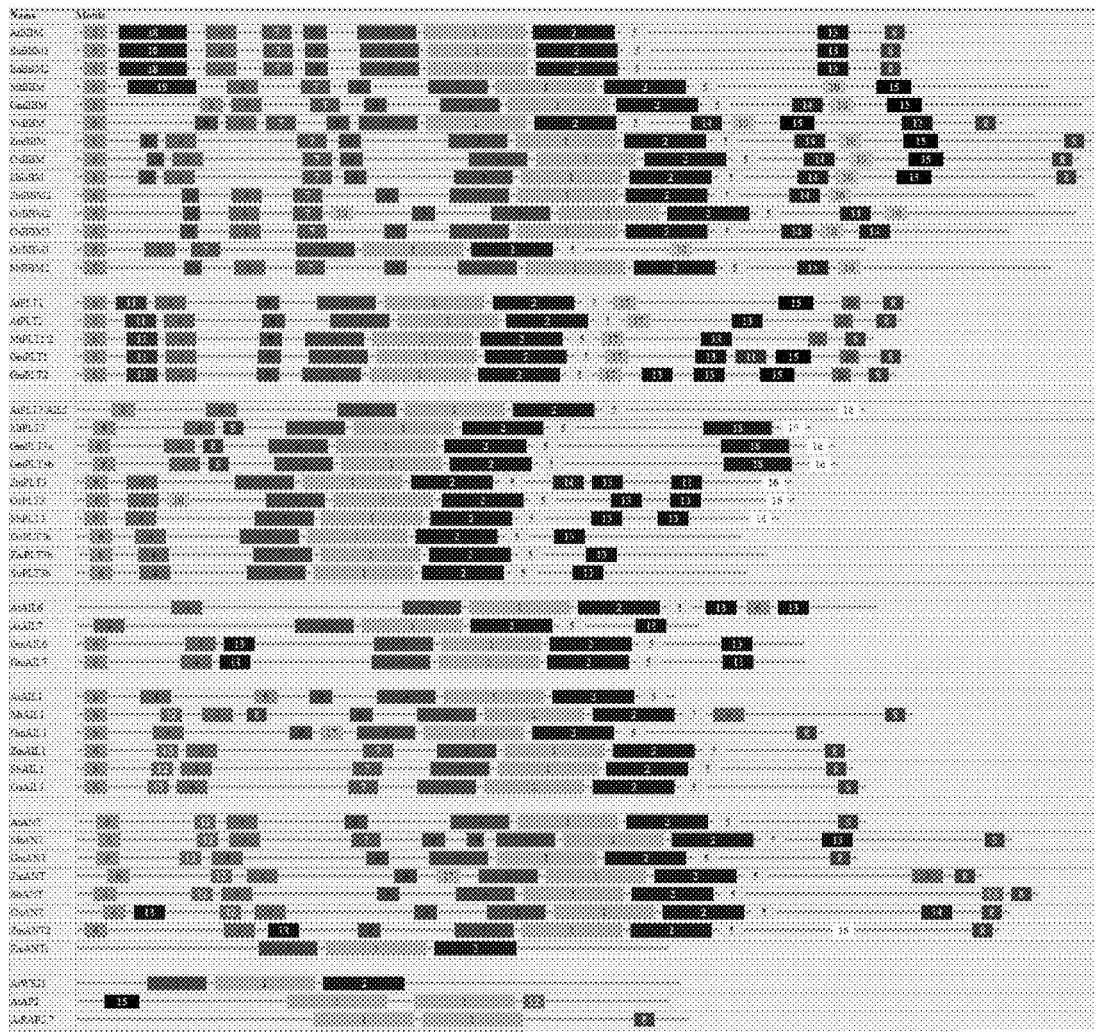
FIG. 3 depicts the motifs found within 50 sequences with homology to maize BBM (ZmBBM).

The fifty genes were subjected to a phylogenetic analysis and a total of six subgroups were identified, including BBM, PLT3, PLT1/2, AIL6/7, AIL1, and ANT (see FIG. 1). FIG. 3 depicts all 50 sequences with each of the motifs that were identified using the MEME web server. FIG. 2 provides the motif consensus sequences along with alignments of the various polypeptides used by the MEME web server to generate the consensus motif. With a few exceptions, motifs 1-6, as defined immediately hereinbelow, are present in all 50 genes. This includes motifs 1-3 (SEQ ID NOs 48-50, respectively), which represent the two AP2 domains and a sequence linking the two domains (linker sequence). Motif 4, with the consensus sequence of PK[L/V][E/A][D/N]FLG (SEQ ID NO: 51) is amino-terminal to the two AP2 domains. Motif 5 (SEQ ID NO: 52) flanks the two AP2 domains on the carboxy terminal end of the polypeptides. Near the amino terminus of the polypeptides is motif 6, with the consensus sequence of NWL[G/S]FSLSP (SEQ ID NO: 53).

There were motifs that were relatively specific for the BBM subgroup of the homologous sequences (referred to herein as BBM polypeptides). An alignment of the BBM polypeptides can be found in FIG. 4. Motif 7 is found in all BBM polypeptides at the amino terminus of the polypeptide and has the consensus sequence of [G/E]LSMIK[T/N]WLR (SEQ ID NO: 54). Another motif that is present in all of the BBM polypeptides except for the polypeptides from *Brassica* and from *Arabidopsis*, is Motif 10. Motif 10 has the consensus sequence of WCK[Q/P]EQD (SEQ ID NO: 57) and is located downstream of the AP2 domains.

There are three more motifs specific to the BBM group of polypeptides, including Motif 15 (SEQ ID NO: 59) which appears only in BBM orthologs, but not in the monocot BBM2 polypeptides; a monocot specific motif (Motif 19; SEQ ID NO: 60); and a general BBM specific motif (Motif 14; SEQ ID NO: 58), which appears in BBM homologs except for the *Brassica* and legume branch.

Figure 5:
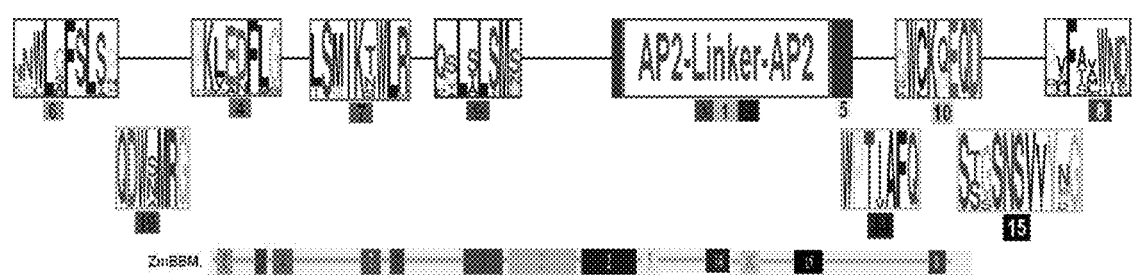
FIG. 5 provides a depiction of the motifs found in babyboom polypeptides.

FIG. 5 provides a summary of the motif structure of the BBM homologs. The amino terminal motifs 4 and 6 and the AP2 flanking motif 5 distinguish the BBM homologous sequences from other two AP2 domain-containing homologs, such as WRI, AP2, and RAP2.7. Therefore, motifs 1-6 can be considered as core BBM/PLT family motifs. Many subgroups of the BBM/PLT family (BBM, PLT1/2, AIL1, and ANT) also have a carboxy-terminal motif (motif 8; SEQ ID NO: 55) and the third amino terminal motif (motif 9; SEQ ID NO: 56).

The BBM polypeptides all have one additional motif (motif 7; SEQ ID NO: 54) in the amino terminus, and all but the *Brassica* and *Arabidopsis* BBM homologs have an AP2 downstream motif (motif 10; SEQ ID NO: 57). Some other BBM/PLT family members (e.g., monocot AIL1) may have a similar motif as motif 7, but none of them also have motif 9. Motif 10 appears only in BBM polypeptides. In summary, the MEME predicted motifs 1-10 can be regarded as BBM polypeptide motifs. All monocot BBM polypeptides (corn, *sorghum*, and rice) also have motif 14, 15, and 19 (see FIG. 3). Some dicot BBM polypeptides and the second monocot BBM group (BBM2) have one or two of these motifs, but none have all three motifs.

Example 9. Use of Maize BBM and WUS2 to Increase Transformation in Rice a. *Oryza sativa* L. ssp. *Indica*

Mature and immature Indica embryos were transformed using *Agrobacterium* with a T-DNA comprising the PHP46911 plasmid (control for immature embryos; see immediately hereinbelow for a description), the PHP32269 plasmid (control for mature embryos1; see immediately hereinbelow for a description), or PHP35648.
PHP46911: RB-CaMV35S::Hyg::Nos term+Ubi-FRT1::Zs-yellow1::PinII-FRT87-LB
PHP32269: RB-Ubi::PMI::PinII+Ubi::mo-PAT~Zs-yellow1::PinII-LB
(PMI=phosphomannose isomerase)

i. Immature Embryo Transformation

Immature embryos of proprietary Indica strain 851 G were transformed using the methods disclosed in International Application Publication No. WO/1995/06722 and Hiei and Komari (2006) *Plant Cell, Tissue and Organ Culture* 85:271-283, each of which is herein incorporated by reference in its entirety. Results are shown hereinbelow in Table 4.

TABLE 4

Transformation events in *Oryza sativa* L. ssp. *Indica* 851G immature embryos infected with *Agrobacterium* containing PHP35648.

| Embryo No. | No. of Pieces/Embryo | Total No. of Events/Embryo |
| --- | --- | --- |
| 1 | 2 | 1 (100%) |
| 2 | 3 | 1 (100%) |
| 3 | 6 | 3 (300%) |
| 4 | 2 | 2 (200%) |
| 5 | 3 | 3 (300%) |
| 6 | 3 | 2 (200%) |
| 7 | 6 | 2 (200%) |
| 8 | 7 | 2 (200%) |
| 9 | 11 | 6 (600%) |
| 10 | 3 | 3 (300%) |
| 11 | 5 | 3 (300%) |
| 12 | 3 | 3 (300%) |
| TOTAL | 54 | 31 (258%) |

In total, infection of 12 immature Indica embryos with *Agrobacterium* containing the PHP35648 plasmid resulted in 31 transformation events, a transformation frequency of 258% events/embryo. The 31 events were derived from 54 pieces of embryo, for a transformation frequency of 57% events/embryo pieces. On the other hand, the infection of nine embryos with *Agrobacterium* containing PHP46911 resulted in only one single transformation event and an overall transformation frequency of 11%.

ii. Mature Embryo Transformation

Mature embryos of Indica strains IRV95 and 851G were transformed using the following protocol. Healthy rice seeds were dehusked and soaked in 50 ml of sterile water with a drop of Tween 20 for 5 minutes. The seeds were sterilized with 75% ethanol for 2-3 minutes, followed by a soak in 50 ml sodium hypochlorite and a drop of Tween 20 for 15-20 minutes. The seeds were rinsed and then callus was initiated in callus induction medium (4.3 g/l MS salts, 10 ml/l B5 vitamins (100×), 2 mg/l 2,4-D, 500 mg/l L-proline, 30 g/l sucrose, 0.3 g/casein hydrolysate, 3 g/l Gelrite (added after bringing to volume with D-I $H_2O$ and adjusting pH to 5.8) under continuous light at 32° C. for 12 days.

Established callus was transformed using *Agrobacterium* by incubating the callus with the *Agrobacterium* for 10-15 minutes. The *Agrobacterium* solution was then decanted and 12-15 seeds were placed onto a filter paper disk that had been pre-moistened with 0.5 ml of AAM medium (50 ml/l AA macro elements (20×), 10 ml/l AA microelements (B5 microelements; 100×), 10 ml/l AA vitamins (B5 vitamins; 100×), 5 ml/l Fe-EDTA-B5 (200×), 1 mg/L 2,4-D, 100 ml/l amino acids, 68.5 g/l sucrose, 36 g/l glucose, 500 mg/l cas amino acid at pH 5.2) containing 50 µM acetosyringone. The seeds and pre-moistened filter papers were cultured in the dark at 21° C. for 72 hours in ACCM medium (4.3 g/l MS salts, 10 ml/l B5 vitamins (100×), 2 mg/l 2,4-D, 20 g/l sucrose, 10 g/l glucose, 0.5 g/l casein hydrolysate, 3 g/l Gelrite (added after bringing to volume with D-I $H_2O$ and adjusting pH to 5.2) containing 200 µM acetosyringone. The calli were washed and then transferred to resting ASM medium (100 ml/1580S major salts (10×), 10 ml/1580S minor salts (100×), 5 ml/1580S FeETDA-L (200×), 5 ml/l 580S vitamins (200×), 100 mg/l myo-inositol, 300 mg/l casein hydrolysate, 30 g/l maltose, 2 mg/l 2,4-D, 500 mg/l L-proline, 0.5 g/l MES buffer, 8 g/l agar (added after bringing to volume with D-I $H_2O$ and adjusting pH to 5.8) containing 250 mg/l carbenicillin for 15 days. Following the 15 day incubation, the calli were transferred to selection medium (100 ml/1580S major salts (10×), 10 ml/1580S minor salts (100×), 5 ml/1580S FeEDTA-L (200×), 5 ml/1580S vitamins (200×), 100 mg/l myo-inositol, 300 mg/l casein hydrolysate, 30 g/l sucrose, 2 mg/l 2,4-D, 500 mg/l L-proline, 0.5 g/l MES buffer, 8 g/l agar (added after bringing to volume with D-I $H_2O$ and adjusting pH to 5.8) with 200 mg/l carbenicillin and 2 mg/l bialaphos and subcultured every 15 days until transformation events arose.

The event was then dessicated on filter paper at 28° C. for 48 hours to excise the developmental genes. Dessicated events were identified based on the expression of Zs-yellow visualized under the microscope. The dessicated event was transferred to regeneration medium (100 ml/l N6 major salts (10×), 10 ml/l FeEDTA (100×), 10 ml/l B5 minor salts (100×), 10 ml/l B5 vitamins (100×), 1 mg/l 1-naphthalene acetic acid, 3 mg/l 6-benzyl amino purine, 30 g/L maltose, 0.3 g/l proline, 0.3 g/l vitamin assay casamino acids, 4 g/l agarose type 1, 30 mg/l glutamine (added after adjusting pH to 5.8 and sterilization) and grown at 32° C. under light. After 1-1.5 months, green shoots emerged from the callus and it was transferred to rooting medium (100 ml/l MS major salts (10×), 10 ml/l FeEDTA (100×), 10 ml/l MS minor salts (100×), 10 ml/l MS vitamins (100×), 2 mg/l indole-3-butyric acid, 15 g/l sucrose, 1 g/l vitamin assay casamino acids, 10×AA amino acid at pH 5.8). After another 15-20 days, the rooted plants are hardened in Y-medium (1.25 ml/l Stock A (9.14 g/100 ml ammonium nitrate (HI-MEDIA RM5657)), 1.25 ml/l Stock B (4.03 g/100 ml sodium hydrogen phosphate (HIMEDIA 58282)), 1.25 ml/l Stock C (7.14 g/100 ml potassium sulfate (HIMEDIA 29658-4B)), 1.25 ml/l Stock D (8.86 g/100 ml calcium chloride (HIMEDIA C5080)), 1.25 ml/l Stock E (3.234 g/100 ml magnesium sulfate (HIMEDIA RM683)), 1.25 ml/l Stock F (15 mg/100 ml magnesium chloride tetra hydrate (HIMEDIA 10149), 6.74 mg/100 ml ammonium molybdate (HIMEDIA 271974), 9.34 mg/100 ml boric acid (SIGMA 136768), 0.35 mg/100 ml zinc sulfate helpta hydrate (HI-MEDIA RM695), 0.31 mg/100 ml copper sulfate hepta hydrate (HIMEDIA C8027), 0.77 mg/100 ml ferric chloride hexa hydrate (SIGMA 236489), 119 mg/100 ml citric acid monohydrate (HIMEDIA C4540)) at pH 5.2.

Results are shown hereinbelow in Table 5.

TABLE 5

Transformation events in Oryza sativa L. ssp. Indica 851G and IRV95 mature embryo-derived callus.

| Seed No | Variety | Construct | No. of infected calli | No. of events | % of events | No. of events regenerated | % of regenerated events/infected calli |
|---|---|---|---|---|---|---|---|
| 1 | 851G | PHP35648 | 100 | 8 | 8.00% | 5 | 5.00% |
|   |       | PHP32269 | 50  | 1 | 2.00% | 0 | 0.00% |
| 2 | 851G | PHP35648 | 130 | 18 | 13.85% | N/A[a] | N/A |
|   |       | PHP32269 | 50  | 1 | 2.00% | N/A | N/A |
| 3 | IRV95 | PHP35648 | 128 | 20 | 15.63% | N/A | N/A |
|   |       | PHP32269 | 50  | 1 | 2.00% | N/A | N/A |

[a]N/A: data not available; calli are currently being dessicated, so no data on number or percentage of regenerated events are available b. *Nipponbare* Rice (cv. *Kitake*)

Callus was initiated from mature embryos of *Oryza sativa*, var. *Nipponbare*, cv. *Kitake*, and established callus was transformed using *Agrobacterium* strain LBA4404 containing UBI::ZmBBM::PinII and NOS PRO::ZmWUS2::PinII between the T-DNA borders. Callus culture medium for rice consisted of N6 salts, Eriksson's vitamins, 0.5 mg/l thiamine, 2 mg/lo 2,4-D, 2.1 g/l proline, 30 g/l sucrose, 300 mg/l casein hydrolysate, 100 mg/l myo-inositol, and 3 g/l gelrite at pH 5.8. Five days after Agro-infection, callus was observed under an epifluorescent dissecting microscope. For calli that were transformed with UBI::ZS-GREEN::PinII alone, all the visible fluorescent foci were single cells, with a few possible 2-4 cell foci. When callus was transformed with NOS::ZmWUS2::PinII+UBI::ZmBBM::PinII+UBI::ZS-GREEN::PinII and observed 5 days later, numerous rapidly-growing, green-fluorescent, multicellular colonies were present.

Example 10. The Rice, *Sorghum* and Grape BBM Genes Increase Transformation Frequency in Maize Growth assays were performed to test whether BBM genes from various species would stimulate growth in maize. For these experiments, 10-13 DAP embryos of the genotype PH581 were bombarded with a first plasmid containing a UBI PRO::moPAT~GFP::pinII expression cassette plus either a plasmid continuing 35S::GUS::pinII (control treatment) or a BBM gene driven by the ubiquitin promoter. To attach the DNAs to gold particles, a 25 µl aliquot of 0.6 µm particles (0.01 mg/µl) was added to fresh tubes before attaching DNA. To attach uncoated DNA, the particles were pulse-sonicated, then 500 ng of each DNA (in 5 µl water) was added, followed by mixing (pipetting up and down a few times with a Pipetteman). Then 2.5 µl of TFX-50 was added, and the solution was placed on a rotary shaker for 10 minutes. After centrifugation at 10,000 g for 1 minute, the supernatant was removed, and the particles were resuspended in 60 µl of EtOH, followed by a 10 minute incubation. The particles were spun briefly (i.e., 10 seconds), the supernatant removed, and 60 µl EtOH added. The solution was spotted onto macrocarriers and the gold particles onto which DNA had been attached were delivered into scutellar cells of 10-13 DAP immature embryos using a standard protocol for the DuPont PDS-1000 Helium Gun. After 4-5 weeks on culture medium, the embryos were examined and the number of GFP-expressing multicellular colonies were counted.

a. OsBBM

Based on the rice BBM genomic sequence (SEQ ID NO: 117), TIGR software was used to predict intron splicing and the resultant cDNA sequence (OsBBM (MOD1) is set forth in SEQ ID NO: 118). A plasmid containing an expression cassette for the rice BBM (MOD1) gene (UBI PRO::OsBBM (MOD1)::PinII) was co-delivered with UBI::moPAT~GFP::PinII into 13 DAP PH581 immature embryos using the particle gun. When the UBI PRO::moPAT~GFP::pinII cassette was introduced with 35S::GUS, few multicellular growing sectors were observed (see Tables 6-10). When UBI::ZmBBM::PinII was introduced along with UBI::moPAT~GFP::PinII, a stimulation of growth was observed as indicated by the total number of growing multicellular colonies observed as well as the number of embryos with multiple growing colonies. Despite many conserved amino acid motifs between the encoded maize protein and the protein encoded by the predicted OsBBM (MOD1) cDNA, when the rice expression cassette UBI::OsBBM (MOD1)::PinII, was introduced along with the moPAT~GFP cassette, no stimulation of growth was observed relative to the control treatment (35S::GUS) (see Tables 6 and 7). Based on a comparison of the maize and rice MOD1 amino acid sequences, and a more careful analysis of the rice genomic sequence, it was determined that the TIGR software failed to predict the splicing around a 9-bp exon that encodes the amino acids VYL in the first AP2 domain. Upon including this 9 bp exon in a re-synthesized rice cDNA (OsBBM (MOD2); set forth in SEQ ID NO: 120), and introducing this in the expression cassette UBI::OsBBM (MOD2)::PinII, a growth stimulation similar to that observed for the maize BBM gene was observed (Table 7, 8, 9 and 10).

TABLE 6

Number of green-fluorescent multicellular colonies six weeks after bombardment with UBI::moPAT~GFP plus the plasmid indicated in each treatment.

| TRT | GFP+ Colonies/Bombarded Embryo | | | | | | | | | | | Total Number of Multicellular Colonies |
|---|---|---|---|---|---|---|---|---|---|---|---|---|
|  | 0 | 1 | 2 | 3 | 4 | 5 | 6 | 7 | 8 | 9 | 10 |  |
| 35S::GUS | 44 |  |  |  |  |  |  |  |  |  |  | 0 |
| UBI::ZmBBM | 15 | 10 | 5 | 4 | 3 | 1 | 1 |  | 1 |  |  | 25 |
| UBI::OsBBM (MOD1) | 42 |  |  |  |  |  |  |  |  |  |  | 0 |
| OLE::ZmBBM | 14 | 16 | 6 | 1 |  |  |  |  |  |  |  | 14 |
| OLE::ZmANT | 44 |  |  |  |  |  |  |  |  |  |  | 0 |

TABLE 7

Number of green-fluorescent multicellular colonies five weeks after bombardment with UBI::moPAT~GFP plus the plasmid indicated in each treatment.

| TRT | GFP+ Colonies/Bombarded Embryo | | | | | | | | | Total Number of Multicellular Colonies |
|---|---|---|---|---|---|---|---|---|---|---|
|  | 0 | 1 | 2 | 3 | 4 | 5 | 6 | 7 | 8 |  |
| 35S::GUS | 70 | 5 | 0 | 3 |  |  |  |  |  | 8 |
| UBI::ZmBBM | 19 | 24 | 17 | 7 | 3 | 1 |  |  |  | 52 |
| UBI::OsBBM (MOD1) | 70 | 4 | 2 |  |  |  |  |  |  | 6 |
| UBI::OsBBM (MOD2) | 28 | 29 | 11 | 3 | 1 | 1 |  |  |  | 45 |
| OLE::ZmBBM | 28 | 24 | 11 | 9 | 2 | 1 | 2 |  |  | 49 |
| OLE::ZmANT | 55 | 16 | 1 | 1 | 1 |  |  |  |  | 19 |

TABLE 8

Number of green-fluorescent multicellular colonies five weeks after bombardment with UBI::moPAT~GFP plus the plasmid indicated in each treatment.

| Treatment | Number of GFP+ Colonies per Scored Embryo | | | | | | | Total Number of Multicellular Colonies |
|---|---|---|---|---|---|---|---|---|
|  | 0 | 1 | 2 | 3 | 4 | 5 | 6 |  |
| 35S::GUS | 70 | 5 | 0 | 3 | 0 | 0 | 0 | 8 |
| UBI::ZmBBM | 19 | 24 | 17 | 7 | 3 | 1 | 0 | 52 |
| UBI::OsBBM (MOD2) | 28 | 29 | 11 | 3 | 1 | 1 | 0 | 73 |
| OLE::ZmBBM | 28 | 24 | 11 | 9 | 2 | 1 | 2 | 49 |
| OLE::ZmANT | 55 | 16 | 1 | 1 | 1 | 0 | 0 | 19 |

TABLE 9

Number of green-fluorescent multicellular colonies five weeks after bombardment with UBI::moPAT~GFP plus the plasmid indicated in each treatment.

| Treatment | Number of GFP+ Colonies per Scored Embryo | | | | | | | Total Number of Multicellular Colonies |
|---|---|---|---|---|---|---|---|---|
|  | 0 | 1 | 2 | 3 | 4 | 5 | 6 |  |
| 35S::GUS | 61 | 6 | 1 | 0 | 0 | 0 | 0 | 7 |
| UBI::ZmBBM | 21 | 29 | 12 | 3 | 2 | 0 | 0 | 46 |
| UBI::OsBBM (MOD2) | 27 | 29 | 5 | 2 | 0 | 1 | 0 | 37 |
| UBI::VvBBM | 32 | 21 | 6 | 0 | 1 | 0 | 0 | 28 |
| UBI::ZmBBM (genomic) | 9 | 36 | 13 | 6 | 3 | 0 | 0 | 58 |

TABLE 10

Number of green-fluorescent multicellular colonies five weeks after bombardment with UBI::moPAT~GFP plus the plasmid indicated in each treatment.

| TRT | GFP+ Colonies/Scored Embryo | | | | | | | | | | | Total Number of Multicellular Colonies |
|---|---|---|---|---|---|---|---|---|---|---|---|---|
|  | 0 | 1 | 2 | 3 | 4 | 5 | 6 | 7 | 8 | 9 | 10 |  |
| 35S::GUS | 80 | 11 |  |  |  |  |  |  |  |  |  | 11 |
| UBI::ZmBBM | 43 | 28 | 13 | 5 | 2 |  |  |  |  |  |  | 48 |
| UBI::OsBBM (MOD2) | 45 | 32 | 11 | 3 |  |  |  |  |  |  |  | 46 |
| UBI::SbBBM (MOD1) | 81 | 10 |  |  |  |  |  |  |  |  |  | 10 | b. SbBBM

Based on the *sorghum* genomic BBM sequence (SEQ ID NO: 69), TIGR software was used to predict intron splicing and the resultant cDNA sequence (SbBBM (MOD1) is set forth in SEQ ID NO: 3). A plasmid containing an expression cassette for the *sorghum* BBM (MOD1) gene (UBI PRO:: SbBBM (MOD1)::PinII) was co-delivered with UBI::mo-PAT~GFP::PinII into 13 DAP PH581 immature embryos using the particle gun. When the UBI PRO::moPAT~GFP:: PinII cassette was introduced with 35S::GUS, few multicellular growing sectors were observed (see Table 10). Unlike UBI::ZmBBM and UBI::OsBBM (MOD2), which in this experiment produced a similar positive growth stimulation, UBI::SbBBM (MOD1)::PinII failed to simulate growth. Assuming there was some unknown defect in the SbBBM (MOD1) synthetic cDNA, the *sorghum* genomic BBM was cloned using PCR and sequenced to verify fidelity. In an earlier experiment, the maize genomic BBM (SEQ ID NO: 116) was placed behind the UBI promoter and when compared to the UBI::ZmBBM cDNA construct it produced a similar degree of growth stimulation (Table 9). Using the genomic *sorghum* clone [UBI::SbBBM (GEN)], a similar level of growth stimulation was also observed (Tables 11 and 12).

TABLE 11

Number of green-fluorescent multicellular colonies five weeks after bombardment with UBI.moPAT~GFP plus the plasmid indicated in each treatment.

| Treatment | GFP+ Colonies/Scored Embryo | | | | | | | | Total Number of Multicellular Colonies * |
|---|---|---|---|---|---|---|---|---|---|
| | 0 | 1 | 2 | 3 | 4 | 5 | 6 | 7 | 8 | |
| 35S::GUS | 57 | 3 | | | | | | | | 3 |
| UBI:VvBBM-NoVYL | 57 | 3 | | | | | | | | 3 |
| UBI:VvBBM | 36 | 15 | 4 | 1 | 1 | 1 | | | | 22 |
| UBI:SbBBM (Genomic) | 10 | 19 | 11 | 11 | 4 | 3 | 2 | | | 50 |
| UBI:ZmBBM | 12 | 18 | 8 | 10 | 4 | 3 | 1 | | 1 | 45 |

TABLE 12

Number of green-fluorescent multicellular colonies five weeks after bombardment with UBI::moPAT~GFP plus the plasmid indicated in each treatment.

| TRT | GFP+ Colonies/Scored Embryo | | | | | | Total Number of Multicellular Colonies |
|---|---|---|---|---|---|---|---|
| | 0 | 1 | 2 | 3 | 4 | 5 | |
| 35S::GUS | 60 | | | | | | 0 |
| UBI::ZmBBM | 19 | 18 | 11 | 7 | 4 | 1 | 41 |
| UBI::SbBBM (Genomic) | 20 | 15 | 14 | 6 | 5 | | 60 |
| UBI::VvBBM | 46 | 11 | 3 | | | | 14 |
| UBI::VvBBM-No VYL | 60 | | | | | | 0 | c. VvBBM

A nucleotide sequence was derived that provided good codon usage for maize, but expressed the amino acid sequence of a grape BBM (VvBBM; SEQ ID NO: 5). A plasmid containing an expression cassette for a synthetic grape BBM gene (UBI PRO::VvBBM::PinII) was co-delivered with UBI::moPAT~GFP::PinII into 10 DAP PH581 immature maize embryos using the particle gun. When the UBI PRO::moPAT~GFP::PinII cassette was introduced alone, no (Table 12) or very few (Tables 9 and 11) multicellular growing sectors were observed. When UBI:: VvBBM::PinII+UBI::moPAT~GFP::PinII were co-delivered, numerous RFP+ multicellular colonies were observed growing on the surface of bombarded embryo after 4 weeks. As with growth stimulation by the maize, rice and *sorghum* BBM genes, the growth stimulation imparted by the UBI:: VvBBM::PinII cassette was manifested by an increase in the overall number of multicellular colonies, and also an increase in the number of multicellular colonies growing on single embryos (see Tables 9, 11 and 12). When a construct comprising the VvBBM sequence, in which the 9-bp sequence encoding VYL in the AP2 domain was removed, was introduced into maize, there was no observed growth stimulation (Tables 11 and 12), similar to the observations made with the rice BBM gene lacking this same exon.

d. Maize ANT Gene

The following constructs were used for comparison: OLE PRO::ZmBBM::pinII, and OLE PRO::ZmANT::pinII The nucleotide and amino acid sequences of ZmANT are set forth in SEQ ID NOs: 66 and 67. Each of these plasmids was co-delivered with UBL:moPAT~GFP::pinII into 10 or 13 DAP PH581 immature embryos using the particle gun. When the UBI PRO::moPAT~GFP::pinII cassette was introduced alone, no (Table 6) or few multicellular growing sectors (Tables 7 and 8) were observed. When OLE:: ZmBBM::pinII+UBI::moPAT~GFP::pinII were co-delivered, a substantial increase in the number of embryos with GFP+ multicellular colonies were observed growing on the surface of each bombarded embryo after 5 weeks (i.e. relative to the control treatment). In addition, the number of embryos supporting multiple GFP+ colonies increased. Embryos co-bombarded with OLE::ZmANT::pinII+UBI:: moPAT::pinII appeared identical (Table 6, with no multicellular colonies in either treatment) or similar to the control treatment (FIGS. 6 and 7, with only a 2-fold increase in colony formation and numerous single GFP+ cells (indicating only transient expression but no division) and a reduced number of GFP+ colonies relative to the BBM treatment. In a second experiment with the same treatments (control with no BBM or ANT, Ole::BBM or Ole::ANT), out of 44 embryos shot per treatment, the control and ANT treatments produced no multicellular GFP+ colonies after 3 weeks while the BBM treatment produced 14 colonies.

Example 11. Expression of the Maize BBM and WUS Genes Improves Transformation in *Sorghum*

*Agrobacterium tumefaciens* LBA4404 and a super-binary vector constructed with pSB1 and pSB11 (Komari et al. (1996) *Plant J* 10:165-174; Thompson et al. (1987) *EMBO J* 6:2519-2523) can be used for *sorghum* transformation (Zhao (2006) In "*Agrobacterium* Protocols," vol. 1, Kan Wang, ed. Hamana Press, Totowa, N.J.; U.S. Pat. No. 6,369,298; and International Application Publication No. WO 98/49332). The super-binary vector contained a selectable marker gene, bar (Chalfie et al. (1994) *Science* 263: 802-805) and a visible marker gene, such as red fluorescent protein (RFP), yellow fluorescent protein (YFP), or intron-GFP (Jefferson et al. (1986) *Proc Natl Acad Sci USA* 83:8447-8451).

Minimal AB media included 50 ml/l Stock A, 50 ml/l Stock B, 5 g/l glucose, 9 g/l Phytagar. For the *Agrobacterium* strain used in this protocol, 50 mg/l spectinomycin is added after autoclaving. Stock A included 60 g/1K$_2$HPO$_4$, and 20 g/l NaH$_2$PO$_4$, pH 7.0. Stock B is 20 g/l NH$_4$Cl, 6 g/l MgSO$_4$ 7H$_2$O, 3 g/l KCl, 0.2 g/l CaCl$_2$, and 0.5 g/l FeSO$_4$H$_2$O. YP medium contained 5 g/l yeast extract, 10 g/l peptone, 5 g/l NaCl, and 15 g/l Bacto-agar. For the *Agrobacterium* stain used in this protocol, 50 mg/l spectinomycin was added after autoclaving.

PHI-T media included 4.3 g/l MS salts (GIBCO BRL catalog no. 11117-874), 0.5 mg/l nicotinic acid, 0.5 mg/l pyridoxine HCl, 1 mg/l thiamine HCl, 0.1 g/l myo-inositol, 1 g/l vitamin assay casamino acids, 1.5 mg/l 2,4-D, 68.5 g/l sucrose, 36 g/l glucose, pH 5.2. 100 µM acetosyringone is added before using.

PHI-I media included PHI-I with sucrose reduced to 20 g/l and glucose reduced to 10 g/l, 2,4-D increased to 2 mg/l, and with 0.5 g/l MES buffer, 0.7 g/l L-proline, 10 mg/l ascorbic acid, 100 µM acetosyringone and 8 g/l agar, pH 5.8 added.

PHI-U media included PHI-T without glucose and acetosyringone, and with 1.5 mg/l 2,4-D, 100 mg/l carbenicillin, and 5 mg/l PPT (glufosinate-HN4) added.

PHI-RF media included 4.3 g/L MS salts (GIBCO BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.49 µM cupric sulfate, 0.5 mg/L zeatin (Sigma Z-0164), 1 mg/L IAA, 26.4 µg/L ABA, 0.1 mg/L thidiazuron, 60 g/L sucrose, 3 mg/L bialaphos, 100 mg/L carbenicillin, and 8 g/L agar, pH 5.6.

PHI-Z media included 2.15 g/L MS salts, 2.5 ml/L MS vitamin mix, 20 g/L sucrose, and 3 g/L gelrite, pH 5.6

Suspension for immature embryo infection consisted of 100 µM acetosyringone in PHI-I medium (pre-warmed to room temperature). Bacteria were scraped off a working plate with a sterile bacteria loop and placed in PHI-I with 100 µM acetosyringone. The suspension was vigorously vortexed to break clumps and form a uniform suspension as determined by visual inspection. 1 ml of Agro-suspension was taken to measure optical density at 550 nm. The suspension was diluted with PHI-I plus 100 µM acetosyringone to 10$^9$ cfu/ml (OD at 0.7).

*Sorghum* plants were grown under greenhouse, growth chamber, or field conditions. Healthy *sorghum* plants were always important for a successful transformation. Immature panicles were harvested 9-13 days post-pollination depending on the growing conditions. The size of immature zygotic embryos used in transformation ranged from 0.8 to 2.5 mm in length. Immature kernels were removed from the panicles and sterilized with 50% bleach and 0.1% Tween-20 for 30 min. with vacuum, then the kernels were rinsed three times with sterile water. The kernels were kept in sterile water before isolating embryos. Embryos were aseptically dissected from each sterilized *sorghum* kernel and placed in a 2-ml microtube containing 2 ml PHI-I with 100 µM acetosyringone. Usually, about 100 embryos were placed in each tube.

PHI-I liquid medium was removed from the tube comprising the embryos with a 1 ml micropipettor and replaced with 1 ml of the *Agrobacterium* suspension. The tube was gently inverted a few times to mix well and incubated 5 minutes at room temperature. The *Agrobacterium* suspension was removed from the tube with a 1 ml micropipettor. The embryos were scraped from the tube using a sterile spatula. Immature embryos were transferred to a plate of PHI-T medium in a 100×15 mm Petri dish. The embryos were oriented with embryonic axis down on the surface of the medium. These embryos were incubated at 21-25° C. in the dark for 3 days. The embryos were transferred to PHI-U minus PPT with the same orientation and incubated at 28° C. in the dark for 4 days.

The embryos were transferred to PHI-U medium and incubated at 28° C. in the dark for 2-3 weeks and were subcultured every two to three weeks for about 10-20 weeks to obtain enough callus for regeneration into plants.

These calli were transferred to PHI-RF medium and incubated at 28° C. in the dark for approximately 2-3 weeks to develop shoots. When shoots formed, these cultures were moved to a lighted culture room under conditions of 16 hours light (270 µE m$^{-2}$ sec$^{-1}$) and 8 hours dark at 25° C. Shoots (about 3-5 cm tall) were transferred to plastic boxes (10×9×10 cm) containing PHI-Z medium. These shoots were cultured under the same light and temperature conditions for 3-5 days. Each box contained shoots derived from a single embryo. When the plantlets reached about 8-10 cm tall with healthy roots, these plantlets were transferred to pots with Universal Mix (Strong-Lite, Seneca, Ill. 61360) in the greenhouse.

Embryos were harvested from developing *sorghum* seed and transformed using *Agrobacterium*, delivering the PHP32371 T-DNA (see Example 4). As a control treatment, embryos were transformed with RB-Ubi::moPAT+Ubi:CFP-LB. Callus was selected on 3 mg/l bialaphos, and monitored for fluorescence to aid in identifying transgenic sectors. *Sorghum* transformation frequencies using Ubi:moPAT+Ubi:CFP averaged 0.5%. By comparison, in six experiments, a total of 393 embryos were transformed with PHP32371, producing an average transformation frequency of 18.3% (see Table 13). Callus from the first experiment (30 events from a starting total of 140 embryos) was used to test the desiccation-induced excision controlled by the Rab17 promoter, and subsequent plant regeneration. Twenty-one events were desiccated for three days on dry filter papers and then taken through the standard regeneration protocol. Fifteen of the 21 events produced a total of 81 plants, with multiple plants being regenerated for many of the individual events. Of these, 60% contained a single copy of the integrated DNA, and of the single copy events, 91% produced PCR results indicating complete excision of the genes encoding cell proliferation factors. From excised events, normal phenotype plants lacking FLP and WUS2 were readily regenerated.

TABLE 13

Transformation efficiencies after *Agrobacterium*-mediated transformation with PHP32371.

| Experiment ID | Number of Embryos | Number of Transformation Events | Transformation Frequency (%) |
|---|---|---|---|
| 1 | 140 | 30 | 21.4 |
| 2 | 40 | 3 | 7.5 |
| 3 | 60 | 8 | 13.3 |
| 4 | 40 | 7 | 17.5 |
| 5 | 61 | 12 | 19.7 |
| 6 | 52 | 12 | 23.1 |
| Average | | | 18.3 |

Example 12. Expression of the Maize BBM and WUS Genes Improves Transformation in Sugarcane A developmental gene binary vector with the ZmBBM/ZmWUS2 gene cassette was compared with a standard vector containing moPAT plus either DsRED or YFP without the ZmBBM/ZmWUS2 gene cassette for transformation frequency using two *Agrobacterium* strains, AGL1 and LBA4404, in CP89-2376 and CP01-1372 sugarcane cultivars. The developmental gene binary vector contains Ubi::LoxP::CFP+Rab17Pro-attB1::Cre-attB2::PinII+Nos::ZmWUS2::PinII+Ubi::ZmBBM::PinII-LoxP::YFP+Ubi::MOPAT::PinII The Lox cassette containing CFP::Cre::WUS::BBM can be excised by Cre recombinase controlled by the Rab17 promoter. Callus tissues of both CP89-2376 and CP01-1372 cultivars were induced and maintained on DBC3 medium. Tissues were infected with *Agrobacterium* containing the developmental gene binary vector in 10 mM MgSO4 plus 100 uM acetosyringone and then cocultivated with liquid DBC3(M5G) medium plus 100 uM acetosyringone on the filter paper in Petri dishes at 21° C. in the dark.

Three days after cocultivation, the tissues were transferred to DBC3 containing 100 mg/L cefotaxime and 150 mg/L timentin for AGL1, and DBC3 containing 100 mg/L carbenicillin for LBA4404, and incubated at 26° C. (±1° C.) in the dark or dim light for 3-7 days. Afterwards, the tissues were transferred to the same media as the previous step plus 3 or 5 mg/L bialaphos. After two months from the initiation of the experiment, transformation frequency was calculated by the number of tissues showing CFP expression divided by the number of explants infected by *Agrobacterium*. Table 14 demonstrated that AGL1 was even more efficient in transformation than LBA4404 in both CP89-2376 and CP01-1372. There was also a genotype difference in transformation frequency; CP89-2376 had much higher transformation frequencies than CP01-1372 using either of the *Agrobacterium* strains.

AGL1 containing the developmental gene vector was also used to test sugarcane germplasm screening in another set of experiments using 5 different cultivars (CP96-1252, CP01-1372, CP89-2376, CPCL97-2730 and HoCP85-845). Callus tissues of all 5 cultivars tested were induced and maintained on DBC3 medium and tissues were infected with AGL1 containing the developmental gene binary vector. The use of developmental genes dramatically increased transformation frequency in all 5 cultivars tested. Transformation frequencies in the most amenable cultivar, CP89-2376, using a standard binary vector averaged 116.7% (56/48) (Table 14). In contrast, an average transformation frequency in this cultivar from 5 experiments was >2,512.5% (>1,005 events/40 tissues infected) using the developmental gene binary vector. Similar results were obtained from the remaining 4 cultivars, CP96-1252, CP01-1372, CPCL97-2730 and HoCP85-845; transformation frequencies ranged from 62.5% to 187.5% in these 4 cultivars while no transgenic events were obtained using the standard vector without the BBM/WUS gene cassette from these cultivars.

TABLE 14

Transformation frequency in sugarcane using the developmental genes ZmBBM and ZmWUS2.

| Agrobacterium Strain | Binary Vector | Sugarcane Cultivar | | | | |
|---|---|---|---|---|---|---|
| | | CP96-1252 | CP01-1372 | CP89-2376 | CPCL97-2730 | HoCP85-845 |
| AGL1 | DG$^a$ | n.t.$^c$ | 37.5% (3/8) | n.t. | n.t. | n.t. |
| LBA4404 | DG | n.t. | 0% (0/8) | n.t. | n.t. | n.t. |
| AGL1 | DG | n.t. | >1,250.0% (>100/8) | >6,250.0% (>500/8) | n.t. | n.t. |
| LBA4404 | DG | n.t. | 12.5% (1/8) | >1,500% (>120/8) | n.t. | n.t. |
| AGL1 | DG | n.t. | n.t. | 687.5% (>55/8) | n.t. | n.t. |
| AGL1 | DG | n.t. | n.t. | >2,500% (>200/8) | 175.0% (14/8) | n.t. |
| AGL1 | DG | 150.0% (12/8) | 62.5% (5/8) | >625.0% (>50/8) | 62.5% (6/8) | n.t. |
| AGL1 | DG | n.t. | n.t. | >2,500% (>200/8) | n.t. | 187.5% (15/8) |
| AGL1 | Std$^b$ | 0% (0/8) | 0% (0/8) | 116.7% (56/48) | 0% (0/8) | 0% (0/8) |

Each transformation treatment had 8 pieces of callus tissues 0.4-0.5 cm in size.
DG$^a$: developmental gene vector with BBM/WUS gene cassette
Std$^b$: standard vector without BBM/WUS gene cassette
n.t.$^c$: not tested Transgenic callus tissues were desiccated on dry filter papers for three days to induce excision of the Lox cassette containing CFP::Cre::WUS::BBM by Cre recombinase driven by the Rab17 promoter. Excision was monitored by observing YFP expression on desiccated transgenic callus events by the presence of the UBI:loxP:YFP junction formed as a result of excision. Cre excision occurred at 83 of 87 transgenic events (95.4%) (Table 15). Plants from some transgenic events after excision are being regenerated on MSB plus 1 mg/L bialaphos and antibiotics.

TABLE 15

Excision efficiency of the BBM/WUS gene cassette in transgenic sugarcane events by desiccation.

| Sugarcane Cultivar | Agrobacterium Strain | Binary Vector | Excision Efficiency (%) |
|---|---|---|---|
| CP89-2376 | AGL1 | DG$^a$ | 93% (40/43) |
| CP89-2376 | LBA4404 | DG | 100% (25/25) |
| CP01-1372 | AGL1 | DG | 100% (13/13) |
| CP01-1372 | LBA4404 | DG | 0% (0/1) |
| CP89-2376 | AGL1 | DG | 100% (5/5) |
| Average | | | 95.4% (83/87) |

DG$^a$: developmental gene vector with BBM/WUS gene cassette

Example 13. Complementation of Separately Transformed BBM and WUS2 Genes

Nos::ZmWUS2::PinII and Rab17-attB1::CRE::PinII are integrated into the genome of an inbred maize plant. LoxP-UBI::BBM::PinII-LoxP+a trait gene operably linked to a promoter are re-transformed into the inbred as a single T-DNA. The BBM and WUS2 genes will complement each other, stimulating rapid growth only in the cells where both are present. BBM is then excised and normal fertile plants are regenerated. Later, the WUS2/CRE locus is segregated away from the genome.

Example 14. Transformation of Mature Dried Maize Seed

Cell proliferation factors can be used to increase transformation and/or recovery frequencies in recalcitrant plants and/or target tissues, such as mature seed.

A T-DNA containing an excisable construct comprising a maize BBM and a maize WUS gene was constructed: PHP38333: RB-Ubi-LoxP::CFP::PinII-attB4+Rab17 Pro-attb1::Cre-attB2::PinII+Nos::ZmWUS2::PinII+Ubi::ZmBBM::PinII-LoxP::YFP::PinII+Ubi::moPAT::PinII-LB As a control treatment, embryos were transformed with PHP32269: RB-Ubi::moPAT-YFP::PinII-LB.

The glycerol stock of a thymidine-auxotrophic mutant *Agrobacterium* strain LBA4404 with vector PHP38333, or the control vector were stored at −80° C. before use. A master plate was made by dipping an inoculation loop into a glycerol stock and streaking onto 12V solid medium with 50 mg/l thymidine in a 100×15 Petri dish (for PHP38333) or onto 12S solid medium with 50 mg/l spectinomycin (for the control plasmid). Plates were incubated (inverted) at 28° C. in the dark for 2-3 days to produce single colonies. Master plates were stored at 4° C. for up to 4 weeks and are used for initiating fresh culture for transformation. Several colonies were picked from the master plates and streaked onto 810F solid medium with 50 mg/l thymidine and incubated at 28° C., in the dark for 1 day and fresh *Agrobacterium* was used for transformation.

To make the *Agrobacterium* suspension, 20 ml of 700 liquid medium with 50 mg/l thymidine was added into a 50 ml snap cap tube. A stock solution of acetosyringone (AS) was added to achieve a final concentration of 200 uM and a stock solution of Silwet L-77 was added to achieve a final concentration of 0.04%. *Agrobacterium* was collected from a 1-day culture plate and suspended in the 700 liquid medium. The tube was vortexed until the *Agrobacterium* culture clumps were completely broken up and evenly dispersed throughout the solution. One ml of the suspension was transferred to a spectrophotometer tube and the OD of the suspension was adjusted to 0.7 at 550 nm by adding either more *Agrobacterium* or more of the same suspension medium.

Maize inbred line PHN46 was used as the initial genotype for transformation tests. Dry seeds were placed in a covered glass jar, in an 80% ethanol solution with stirring for 5 min. The ethanol was decanted and a 50% bleach solution with a few drops of the surfactant Tween-20 were added and seeds in the bleach solution were stirred for 30 min and washed three times with sterile water in a sterile flow hood. Surface sterilized seed were soaked in the sterile water for approximately 24 h at room temperature, which is sufficient to trigger germination. After 24 hours, the softened seeds were sterilized once again with a 50% bleach solution for 5 min, and then washed three times with sterile water in a sterile flow hood.

Mature embryos were dissected out of the softened and sterilized kernels. Each mature embryo was sliced into 3-4 thin sections by hand using a No. 10 surgical scalpel under the dissecting microscope. Each explant contained exposed leaf primordia, mesocotyl and root primordia regions. These regions on the embryo chips were the target area for T-DNA delivery during *Agrobacterium*-mediated transformation and contain cells that are culture responsive. Sliced explants were transferred into a 6-well culture plate containing 4 ml 700 liquid medium. About 45 explants were placed into each well for *Agrobacterium* infection.

Liquid medium in the 6-well plate was removed from the explants and replaced with 4 ml of prepared *Agrobacterium* suspension. The 6-well plate was transferred into a transparent polycarbonate desiccator container. The desiccator was covered and placed on a platform shaker rotating at a speed of 100 RPM and connected to an in-house vacuum system for 30 min. After infection, the *Agrobacterium* suspension was drawn off from the wells and the explants were transferred onto solid 7101 co-cultivation medium with 50 mg/l thymidine. The infected embryo explants on the solid medium were incubated at 21° C. in the dark for 3 days. The number of infected explants was recorded to later calculate transformation efficiencies.

To evaluate T-DNA delivery efficiency, both the control vector without genes encoding cell proliferation factors and the vector with the genes encoding cell proliferation factors were used to infect embryo explants. After 3d co-cultivation, all of the chips were transferred onto 605J medium for continuous culture. T-DNA delivery was evaluated around 5d after *Agrobacterium* infection. Transient expression of the color marker YFP (control vector) or CFP (test vector PHP38333) was a reliable indicator of the T-DNA delivery efficiency. In general, 30%-50% of the infected explants showed T-DNA delivery in the right target tissues or cells. Using an optimized infection medium and protocol, 70%-80% T-DNA delivery efficiency to the target area was achieved. Infected explants were sub-cultured to fresh medium every 3 weeks. After 6 weeks of culture, healthy, vigorously growing, embryogenic type I callus could be identified from those explants that had been infected with vector PHP38333 containing the genes encoding cell proliferation factors. These growing calli represented transformed events confirmed by the color marker (CFP) expression. Non-transformed tissues showed either no growth or very limited growth. Embryogenic type I calli were picked and transferred onto fresh culture medium to let the callus proliferate before plant regeneration (10-12 weeks). Transformation efficiency for PHP38333 at the callus level ranged from 12% to 20% calculated as the number events recovered per total number of infected explants (Table 16). Embryo explants that were infected with control vector PHP32269 also showed good T-DNA delivery based on transient YFP expression in the infected cells. However, these cells did not show significant proliferation and no healthy callus was formed during continuous culture.

TABLE 16

Transformation frequency of PHP38333 in PHN46 embryo chips.

| Experiment No. | Number of Chips infected | Number of CFP(+) Events | Transformation Frequency (%) |
|---|---|---|---|
| 1 | 137 | 23 | 16.8% |
| 2 | 134 | 19 | 14.2% |

TABLE 16-continued

Transformation frequency of PHP38333 in PHN46 embryo chips.

| Experiment No. | Number of Chips infected | Number of CFP(+) Events | Transformation Frequency (%) |
|---|---|---|---|
| 3 | 149 | 20 | 13.4% |
| 4 | 140 | 25 | 17.9% |
| 5 | 148 | 18 | 12.2% |
| 6 | 137 | 26 | 19.0% |
| 7 | 129 | 27 | 20.9% |
| 8 | 136 | 20 | 14.7% |
| 9 | 137 | 21 | 15.3% |
| 10 | 147 | 24 | 16.3% |
| Total | 1393 | 223 | 16.0% |

Transformed callus tissues were treated with either one of the following two desiccation methods to induce excision of the genes encoding cell proliferation factors before plant regeneration.

1) Desiccation by natural air exchange: Transformed callus tissues were transferred to an empty 60 mm×25 mm Petri dish containing a piece of autoclaved glass filter paper and covered with a lid but not sealed. Petri dishes with callus tissues were placed into a culture box with a loose cover. The box was kept at 28° C. in the dark for 3 days.

2) Desiccation in chambers containing a saturated salt solution: Transformed callus tissues were transferred to an empty 60 mm×25 mm Petri dish containing a piece of autoclaved glass filter paper and covered with a lid. The Petri dishes with callus tissues were placed into a container with a tight sealing cover. A glass jar containing saturated $(NH_4)_2SO_4$ salt solution without a cover was placed in the container. The container was kept at 28° C. in the dark for 3 days (as the moisture in the air inside the container was absorbed by the saturated salt solution, the callus tissue gradually lost water and experienced desiccation stress).

After 3 days of desiccation treatment, the callus tissues were transferred to 289L regeneration media for 2-3 weeks in the dark. When shoots formed with a length of about 1-2 cm, callus tissues with shoots were transferred to hormone-free 272V medium for further development of shoots and roots in the light culture room. When plantlets had formed well-developed shoots and roots, plant regeneration efficiency was evaluated. The plant regeneration frequency (number of callus producing plants out of total number of callus events for plant regeneration) varied from 45% to 75% among 10 initial experiments. At this stage, leaf samples were collected from the plantlets derived from each callus event for molecular analysis. Detailed PCR analyses were performed to determine the copy number of transgenes as well as to confirm that the genes encoding proliferation factors were excised and were not present in the regenerated transgenic plants.

Based on the molecular analysis of 316 T0 plants from 162 events, about 60% of the transgenic plants contain a single copy of the transgenes. These single-copy transgenic plants showed very efficient excision of the genes encoding cell proliferation factors from the desiccation-treatment-induction (see results in Table 17). In general, plants with complete excision of genes encoding cell proliferation factors displayed normal phenotype in the tube and also in later developmental stages in the greenhouse. In contrast, T0 plants in which excision did not occur (or where it was incomplete) displayed an abnormal phenotype, such as thickened roots.

Based on PCR analysis results, chimeric or incomplete excision T0 plants can be eliminated and only complete-excision (free of genes encoding cell proliferation factors) events were sent to the greenhouse.

TABLE 17

Analysis of T0 plants for excision of genes encoding cell proliferation factors.

| Number of Events/ T0 Plants | Single Copy | Complete Excision |
|---|---|---|
| 162 (Events) | 103 (63.6%) | 94 (91.3%) |
| 316 (Plants) | 189 (59.8%) | 173 (91.5%) |

Example 15. Transformation of Leaf Tissues a. Preparation of *Agrobacterium* and Maize Leaf Explants

*Agrobacterium* suspensions were prepared as described in Example 14. Pioneer maize inbred lines PHN46, PHR03 and PHEJW were used as the initial genotypes for transformation tests. Dry seed was sterilized and imbibed overnight as described above.

Sterilized seeds were placed onto 272V solid medium for direct germination. Alternatively, mature embryos were dissected from softened and sterilized seeds and placed onto 272V solid medium for faster germination. Plates with seeds or isolated embryos were placed in a culture box and incubated at 28° C. in the dark for 3-7 days. Shoot segments of about 2-3 cm long above the first leaf base node of the seedling were excised under sterile conditions. The coleoptile was removed and the leaf fragment was split longitudinally first, then cross-dissected into smaller segments (0.5 to 2 mm). Alternatively, the 2-3 cm-long segment above the first leaf base node of the seedling was simply diced with the scalpel to produce small leaf segments. Small leaf segments were transferred into a 6-well culture plate containing 4 ml of 700 liquid medium.

Liquid medium in the 6-well plate with leaf pieces were drawn off and replaced with 4 ml prepared *Agrobacterium* suspension. The 6-well plate was transferred into a transparent polycarbonate desiccator container. The desiccator was covered and placed on a platform of the shaker with a speed of 100 RPM and connected to an in-house vacuum system for 15 min. After infection, the *Agrobacterium* suspension was drawn off from the wells and the leaf tissues were transferred onto solid 7101 co-cultivation medium with 50 mg/l thymidine and were incubated at 21° C. in the dark for 3 days.

After 3d co-cultivation, all of the leaf tissues were transferred to 13152C culture medium. T-DNA delivery was evaluated about 5d after *Agrobacterium* infection. Transient expression of the color marker YFP (control vector) or CFP (test vector PHP38333) was a reliable indicator of the T-DNA delivery efficiency. 10%-25% of infected leaf segments showed multiple fluorescent cells along the cut edges or surface of leaf segments in all three inbred lines tested. Infected leaf tissues were sub-cultured every 2 weeks. After 6-8 weeks of culture, stable transformed callus events could be identified. The transgenic nature of these stable callus events was indicated by the expression of the fluorescent gene. Callus events with significant proliferation were subjected to desiccation treatment, and transferred onto regeneration medium for 2-4 weeks. Stable transgenic plantlets were regenerated from two tested maize inbreds, PHN46 and PHR03. Results from numerous experiments clearly demonstrated that stable transgenic plants could be produced form transformation of seedling tissue by using the vector that expresses the genes encoding cell proliferation factors. Leaf tissues infected with the control vector also showed good T-DNA delivery based on transient YFP expression, but the infected cells did not exhibit any subsequent proliferation and no stable callus events were identified from this treatment.

Example 16. The Utilization of Cell Proliferation Factors for Enhancing Chloroplast Transformation For tobacco and a number of other species, leaves are a preferred target for chloroplast transformation. Cell proliferation factors are used to trigger a tissue culture response from leaves of maize and other species. For boosting chloroplast transformation, cell proliferation factor genes under the control of inducible promoters are introduced into the species of interest by standard nuclear transformation protocols. Events that contain the transgene are characterized for expression of the inducible cell proliferation factor genes. For example, leaves of maize from plants transformed with the cell proliferation factor genes under the control of the tetracycline-repressor system are placed on medium containing appropriate concentrations of doxycyline. The doxycyline then activates the cell proliferation factor genes and thereby induces an embryogenic tissue culture response. The leaves are maintained on this medium for about 7-21 days during which time cell division and the initiation of embryogenic callus will take place. The leaves are bombarded with chloroplast transformation vectors carrying the aadA selectable marker gene and trait gene just prior to induction of the cell proliferation genes, during induction or just after induction. One to seven days after bombardment with the chloroplast transformation vector, the tissue is placed in petri plates containing agarose-solidified media supplemented with spectinomycin. The plates are then incubated at 28° C. in the light. The tissue is transferred to fresh medium every two weeks. After about 8 weeks of incubation, green callus is observed. This tissue can be further proliferated on 13152 medium (4.3 g/l MS salts, 0.25 g/l myo-inositol, 1.0 g/l casein hydrolysate, 1 mg/l thiamine, 1 mg/l 2,4-D, 30 g/l maltose, 0.69 g/l proline, 1.2 mg/l cupric sulfate, and 3.5 g/l phytagel, pH 5.8) and the tissue analyzed for the presence of the transgene using appropriate methods including PCR and Southern analysis.

In an alternative approach, expression cassettes containing the tetracycline-inducible BBM and WUS genes are co-bombarded along with the chloroplast transformation vectors carrying the aadA gene for selection. Either leaf explants or established green tissue callus are used as the target tissue for bombardment. Tetracycline or doxycycline at a concentration of 0.5 to 2.0 mg/l is added to the culture medium (13152) after particle bombardment. Expression of BBM and WUS in cells that have received DNA stimulate callus growth rates during the period while tetracycline (or doxycycline) is present in the medium. The accelerated growth that is stimulated by BBM & WUS will result in improved recovery of homoplastic transgenic events, and the nuclear-integrated BBM/WUS genes can be removed by outcrossing T0 plants to wild-type plants and selecting BBM/WUS null plants in the T1 generation.

In another variation on the particle gun approach for delivery of BBM and WUS, a UBI::BBM::PinII and a nos::WUS2::pinII are co-delivered along with the chloroplast transformation vectors.

In another alternative approach, the cell proliferation factor genes are delivered into leaf tissue by vacuum infiltration of an *Agrobacterium* solution. The cell proliferation factor genes are under the control of strong constitutive promoters such as ubi or act or viral promoters such as 35S (Gardner et al. (1981) *Nucl Acids Res* 9:2871-2888), MMV (Dey and Maiti (1999) *Plant Mol Riot* 40:771-782), or BSV (Shenk et al. (2001) *Plant Mol Biol* 47:399-412). The cell proliferation factor genes are carried on binary vectors that facilitate transfer from the bacteria to plant cells. Following vacuum infiltration, the tissue is incubated for an appropriate period of time to allow expression of the cell proliferation factor genes in the leaf tissue. Transient expression from the cell proliferation factor genes delivered by *Agrobacterium* is expected to provide a strong boost in cell division and tissue culture response. After vacuum infiltration with *Agrobacterium*, the tissue is bombarded with a chloroplast transformation vector carrying the aadA selectable marker gene. The tissue is then transferred to media containing spectinomycin and transgenic events selected. It is expected that the *Agrobacterium*-delivered cell proliferation factor genes will not be integrated into the nuclear genome of most of the events that are recovered.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A promoter construct comprising a promoter followed by a first attachment B (attB) site, wherein the promoter is selected from the group consisting of:
   a) a promoter comprising a nucleotide sequence having the sequence set forth in SEQ ID NO: 29; and
   b) a promoter comprising a nucleotide sequence having at least 95% sequence identity to the sequence set forth in SEQ ID NO: 29;
   wherein said first attB site has the nucleotide sequence set forth in SEQ ID NO: 31 and further wherein said first attB site decreases the activity of said promoter.

2. The promoter construct of claim 1, wherein said promoter comprises the sequence set forth in nucleotides 291-430 of SEQ ID NO: 29 or a sequence having at least 85% sequence identity to the sequence set forth in nucleotides 291-430 of SEQ ID NO: 29.

3. The promoter construct of claim 1, wherein said promoter construct further comprises a linker sequence that separates said promoter and said first attB site.

4. The promoter construct of claim 3, wherein said linker sequence that separates said promoter and said first attB site is about 133 nucleotides in length.

5. The promoter construct of claim 3, wherein said linker sequence that separates said promoter and said first attB site comprises nucleotides of a maize rab17 5' untranslated region (5'-UTR).

6. The promoter construct of claim 5, wherein said linker sequence that separates said promoter and said first attB site comprises the nucleotide sequence set forth in SEQ ID NO: 35.

7. The promoter construct of claim 3, wherein said linker sequence that separates said promoter and said first attB site has the sequence set forth in SEQ ID NO: 36 or a nucleotide sequence having at least 70% sequence identity to the sequence set forth in SEQ ID NO: 36.

8. An expression cassette comprising the promoter construct of claim 1 operably linked to a polynucleotide of interest.

9. The expression cassette of claim 8, wherein said polynucleotide of interest is a nucleotide sequence encoding a site-specific recombinase.

10. The expression cassette of claim 9, wherein said site-specific recombinase is selected from the group consisting of FLP, Cre, SSV1, lambda Int, phi C31 Int, HK022, R, Gin, Tn1721, CinH, ParA, Tn5053, Bxb1, TP907-1, and U153.

11. The expression cassette of claim 8, further comprising a polynucleotide encoding a babyboom polypeptide operably linked to a second promoter, wherein said second promoter is active in a plant.

12. The expression cassette of claim 11, wherein said babyboom polypeptide comprises at least two AP2 domains and at least one of the following amino acid sequences:
   a) the amino acid sequence set forth in SEQ ID NO: 54 or an amino acid sequence that differs from the amino acid sequence set forth in SEQ ID NO: 54 by one amino acid; and
   b) the amino acid sequence set forth in SEQ ID NO: 57 or an amino acid sequence that differs from the amino acid sequence set forth in SEQ ID NO: 57 by one amino acid.

13. The expression cassette of claim 11, wherein said polynucleotide encoding said babyboom polypeptide has a nucleotide sequence selected from the group consisting of:
   a) the nucleotide sequence set forth in SEQ ID NO: 13;
   b) a nucleotide sequence having at least 70% sequence identity to SEQ ID NO: 13;
   c) a nucleotide sequence encoding a polypeptide having the amino acid sequence set forth in SEQ ID NO: 14; and
   d) a nucleotide sequence encoding a polypeptide having an amino acid sequence having at least 70% sequence identity to the amino acid sequence set forth in SEQ ID NO: 14.

14. The expression cassette of claim 11, wherein said second promoter is a maize ubiquitin promoter or a maize oleosin promoter.

15. The expression cassette of claim 11, wherein said expression cassette further comprises a polynucleotide encoding a Wuschel polypeptide operably linked to a third promoter, wherein said third promoter is active in a plant.

16. The expression cassette of claim 15, wherein said polynucleotide encoding said Wuschel polypeptide has a nucleotide sequence selected from the group consisting of:
   a) the nucleotide sequence set forth in SEQ ID NO: 63; and
   b) a nucleotide sequence having at least 70% sequence identity to SEQ ID NO: 63;

c) a nucleotide sequence encoding a polypeptide having the amino acid sequence set forth in SEQ ID NO: 64; and d) a nucleotide sequence encoding a polypeptide having an amino acid sequence having at least 70% sequence identity to SEQ ID NO: 64.

17. The expression cassette of claim 15, wherein said third promoter is a maize In2-2 promoter or a nopaline synthase promoter.

18. A host cell comprising the expression cassette of claim 8.

19. A plant cell comprising the expression cassette of claim 8.

20. A transgenic seed of a plant comprising the plant cell of claim 19, wherein said seed comprises said expression cassette.

21. A plant cell comprising an expression cassette comprising a promoter construct according to claim 1 operably linked to a polynucleotide encoding a site-specific recombinase, wherein said plant cell further comprises a polynucleotide of interest flanked by a first and a second recombination site, wherein said first and second recombination sites are recombinogenic with respect to one another and are directly repeated, and wherein said site-specific recombinase can recognize and implement recombination at said first and said second recombination sites, thereby excising said polynucleotide of interest.

22. A method for expressing a polynucleotide of interest in a plant cell, said method comprising introducing into said plant cell an expression cassette, wherein said expression cassette is the expression cassette according to claim 8.

23. A method for excising a polynucleotide of interest from a target site in a plant cell, wherein said target site comprises a first site-specific recombination site, said polynucleotide of interest, and a second site-specific recombination site, wherein said first and said second site-specific recombination sites are recombinogenic with respect to one another and are directly repeated, said method comprising:
a) introducing into said plant cell an expression cassette comprising a first promoter operably linked to a polynucleotide encoding a site-specific recombinase, wherein said first promoter comprises the promoter construct of claim 1; and
b) expressing said polynucleotide encoding said site-specific recombinase, wherein said site-specific recombinase recognizes and implements recombination at said first and said second site-specific recombination sites, thereby excising said polynucleotide of interest.

24. The method of claim 23, wherein said target site comprises in operable linkage: said first recombination site, a second promoter, a polynucleotide sequence encoding a Wuschel polypeptide, a third promoter, a polynucleotide encoding a babyboom polypeptide, and said second recombination site, wherein said polynucleotide encoding said Wuschel polypeptide and its operably linked second promoter can follow or precede said polynucleotide encoding said babyboom polypeptide and its operably linked third promoter in the target site.

25. A method for excising a polynucleotide of interest from a target site in a plant cell, wherein said target site comprises in operable linkage: a first site-specific recombination site, a first promoter, said polynucleotide of interest, a second promoter, a polynucleotide encoding a site-specific recombinase, and a second site-specific recombination site; wherein said first and said second site-specific recombination sites are recombinogenic with respect to one another and are directly repeated; wherein said second promoter comprises the promoter construct of claim 1, wherein the polynucleotide of interest and its operably linked first promoter can follow or precede the polynucleotide encoding the site-specific recombinase and its operably linked second promoter in the target site; said method comprising expressing said polynucleotide encoding said site-specific recombinase; wherein said site-specific recombinase recognizes and implements recombination at said first and said second site-specific recombination sites, thereby excising said polynucleotide of interest and said polynucleotide encoding said site-specific recombinase.

26. The method of claim 25, wherein said first promoter is a maize ubiquitin promoter or a maize oleosin promoter.

27. The method of claim 25, wherein said target site further comprises a third promoter operably linked to a polynucleotide encoding a Wuschel polypeptide, wherein the target site comprises in operable linkage: said first site-specific recombination site, said third promoter, said polynucleotide encoding a Wuschel polypeptide, said first promoter, said polynucleotide of interest, said second promoter, said polynucleotide encoding said site-specific recombinase, and said second site-specific recombination site, wherein the polynucleotide encoding the Wuschel polypeptide and its operably linked third promoter, the polynucleotide of interest and its operably linked first promoter, and the polynucleotide encoding the site-specific recombinase and its operably linked second promoter can be in any order at the target site.

28. The method of claim 27, wherein the target site comprises in the following order: said first site-specific recombination site, said third promoter, said polynucleotide encoding a Wuschel polypeptide, said first promoter, said polynucleotide of interest, said second promoter, said polynucleotide encoding said site-specific recombinase, and said second site-specific recombination site.

29. The method of claim 25, wherein said site-specific recombinase is selected from the group consisting of FLP, Cre, SSV1, lambda Int, phi C31 Int, HK022, R, Gin, Tn1721, CinH, ParA, Tn5053, Bxb1, TP907-1, and U153.

30. The method of claim 25, wherein said polynucleotide of interest is a polynucleotide encoding a cell proliferation factor.

31. The method of claim 30, wherein said cell proliferation factor comprises a babyboom polypeptide.

32. The method of claim 31, wherein said babyboom polypeptide comprises at least two AP2 domains and at least one of the following amino acid sequences:
a) the amino acid sequence set forth in SEQ ID NO: 54 or an amino acid sequence that differs from the amino acid sequence set forth in SEQ ID NO: 54 by one amino acid; and
b) the amino acid sequence set forth in SEQ ID NO: 57 or an amino acid sequence that differs from the amino acid sequence set forth in SEQ ID NO: 57 by one amino acid.

33. The method of claim 31, wherein said polynucleotide encoding said babyboom polypeptide has a nucleotide sequence selected from the group consisting of:
a) the nucleotide sequence set forth in SEQ ID NO: 13;
b) a nucleotide sequence having at least 70% sequence identity to SEQ ID NO: 13;
c) a nucleotide sequence encoding a polypeptide having the amino acid sequence set forth in SEQ ID NO: 14; and d) a nucleotide sequence encoding a polypeptide having an amino acid sequence having at least 70% sequence identity to the amino acid sequence set forth in SEQ ID NO: 14.

34. The expression cassette of claim 13, further comprising a polynucleotide operably linked to a heterologous promoter for expression in a plant cell, wherein said polynucleotide sequence encodes a polypeptide having at least 75% sequence identity to the sequence set forth in SEQ ID NO: 14, wherein said amino acid sequence has amino acid residues valine, tyrosine, and leucine at the positions corresponding to positions 317, 318, and 319, respectively of SEQ ID NO: 14, wherein said polypeptide has BBM activity.

35. An expression cassette comprising the isolated polynucleotide of claim 34, wherein said polynucleotide is operably linked to a promoter that drives expression in a plant.

36. A plant comprising the expression cassette of claim 13, further comprising a second expression cassette comprising a heterologous polynucleotide operably linked to a second promoter that drives expression in the plant, wherein said polynucleotide sequence encodes a polypeptide having at least 75% sequence identity to the sequence set forth in SEQ ID NO: 14, wherein said amino acid sequence has amino acid residues valine, tyrosine, and leucine at the positions corresponding to positions 317, 318, and 319, respectively of SEQ ID NO: 14, wherein said polypeptide has BBM activity.

37. A method of increasing the activity of a polypeptide in a plant, comprising providing the construct of claim 34 to said plant,
wherein increasing the activity of said polypeptide produces a phenotype in the plant selected from the group consisting of:
a) produces asexually derived embryos in the plant;
b) modifies the regenerative capacity of the plant;
c) increases the transformation efficiency in the plant;
d) increases or maintains the yield in the plant under abiotic stress; and
e) induces embryogenesis.

38. A method of transforming a plant cell with the construct of claim 34.

39. The method of claim 38, wherein the plant cell is selected from the group consisting of: maize, soybean, sorghum, wheat, grape, rice, and sugarcane.

* * * * *

SEQUENCE LISTING

```
<160> NUMBER OF SEQ ID NOS: 126

<210> SEQ ID NO 1
<211> LENGTH: 2133
<212> TYPE: DNA
<213> ORGANISM: Glycine max
<220> FEATURE:
<221> NAME/KEY: CDS
<222> LOCATION: (1)...(2133)
```

```
<400> SEQUENCE: 1 atg ggg tct atg aat ttg tta ggt ttt tct ctc tct cct caa gaa cac         48
Met Gly Ser Met Asn Leu Leu Gly Phe Ser Leu Ser Pro Gln Glu His
 1               5                  10                  15 cct tct agt caa gat cac tct caa acg gca cct tct cgt ttt tgc ttc         96
Pro Ser Ser Gln Asp His Ser Gln Thr Ala Pro Ser Arg Phe Cys Phe
            20                  25                  30 aac cct gat gga atc tca agc act gat gta gca gga gac tgc ttt gat        144
Asn Pro Asp Gly Ile Ser Ser Thr Asp Val Ala Gly Asp Cys Phe Asp
        35                  40                  45 ctc act tct gac tca act cct cat tta ctc aac ctt ccc tct tac ggc        192
Leu Thr Ser Asp Ser Thr Pro His Leu Leu Asn Leu Pro Ser Tyr Gly
 50                  55                  60 ata tac gaa gct ttt cat agg agc aac aat att cac acc act caa gat        240
Ile Tyr Glu Ala Phe His Arg Ser Asn Asn Ile His Thr Thr Gln Asp
 65                  70                  75                  80 tgg aag gag aac tac aac agc caa aac ttg cta ttg gga act tca tgc        288
Trp Lys Glu Asn Tyr Asn Ser Gln Asn Leu Leu Leu Gly Thr Ser Cys
                85                  90                  95 agc aac caa aac atg aac cac aac cat cag caa caa caa caa caa cag        336
Ser Asn Gln Asn Met Asn His Asn His Gln Gln Gln Gln Gln Gln Gln
            100                 105                 110 cca aag ctt gaa aac ttc ctc ggt gga cac tca ttt ggt gaa cat gag        384
Pro Lys Leu Glu Asn Phe Leu Gly Gly His Ser Phe Gly Glu His Glu
        115                 120                 125 caa ccc tac ggt ggt aac tca gcc tct aca gaa tac atg ttc ccg gct        432
Gln Pro Tyr Gly Gly Asn Ser Ala Ser Thr Glu Tyr Met Phe Pro Ala
    130                 135                 140 cag ccg gta ttg gcc ggt ggc ggc ggt ggt agc aat agc agc aac            480
Gln Pro Val Leu Ala Gly Gly Gly Gly Gly Ser Asn Ser Ser Asn
145                 150                 155                 160 aca agc aac agt agc tcc ata ggg tta tcc atg ata aag aca tgg ttg        528
Thr Ser Asn Ser Ser Ser Ile Gly Leu Ser Met Ile Lys Thr Trp Leu
                165                 170                 175 agg aac caa cca cca cac tca gaa aac aac aat aac aac aac aat gaa        576
Arg Asn Gln Pro Pro His Ser Glu Asn Asn Asn Asn Asn Asn Asn Glu
            180                 185                 190 agt ggt ggc aat agt aga agc agt gtg cag cag act cta tca ctt tcc        624
Ser Gly Gly Asn Ser Arg Ser Ser Val Gln Gln Thr Leu Ser Leu Ser
        195                 200                 205 atg agt act ggt tca caa tca agc aca tca cta ccc ctt ctc act gct        672
Met Ser Thr Gly Ser Gln Ser Ser Thr Ser Leu Pro Leu Leu Thr Ala
    210                 215                 220 agt gtg gat aat gga gag agt tct tct gat aac aaa caa cca cat acc        720
Ser Val Asp Asn Gly Glu Ser Ser Ser Asp Asn Lys Gln Pro His Thr
225                 230                 235                 240 acg gct gca ctt gat aca acc caa acc gga gcc att gaa act gca ccc        768
Thr Ala Ala Leu Asp Thr Thr Gln Thr Gly Ala Ile Glu Thr Ala Pro
                245                 250                 255 aga aag tcc att gac act ttt gga cag aga act tct atc tac cgt ggt        816
Arg Lys Ser Ile Asp Thr Phe Gly Gln Arg Thr Ser Ile Tyr Arg Gly
            260                 265                 270 gta aca agg cat agg tgg acg ggg agg tat gag gct cac ctg tgg gat        864
Val Thr Arg His Arg Trp Thr Gly Arg Tyr Glu Ala His Leu Trp Asp
        275                 280                 285 aat agt tgt aga aga gag gga caa act cgc aaa gga agg caa gtt tac        912
Asn Ser Cys Arg Arg Glu Gly Gln Thr Arg Lys Gly Arg Gln Val Tyr
    290                 295                 300 ttg gga ggt tat gac aaa gaa gaa aag gca gct aga gcc tac gat ttg        960
Leu Gly Gly Tyr Asp Lys Glu Glu Lys Ala Ala Arg Ala Tyr Asp Leu
```

-continued

| | | |
|---|---|---|
| Leu Gly Gly Tyr Asp Lys Glu Glu Lys Ala Ala Arg Ala Tyr Asp Leu<br>305                        310                        315                        320 | |
| gca gca cta aaa tac tgg gga aca act acg aca aca aat ttt cca att<br>Ala Ala Leu Lys Tyr Trp Gly Thr Thr Thr Thr Thr Asn Phe Pro Ile<br>                        325                        330                        335 | 1008 |
| agc cac tat gag aaa gag ttg gaa gaa atg aag cac atg act agg caa<br>Ser His Tyr Glu Lys Glu Leu Glu Glu Met Lys His Met Thr Arg Gln<br>                     340                        345                        350 | 1056 |
| gag tac gtt gcg tca ttg aga agg aag agt agt ggg ttt tct cgc ggg<br>Glu Tyr Val Ala Ser Leu Arg Arg Lys Ser Ser Gly Phe Ser Arg Gly<br>                 355                        360                        365 | 1104 |
| gca tcc att tat cga ggt gtg acg aga cac cat caa cat gga aga tgg<br>Ala Ser Ile Tyr Arg Gly Val Thr Arg His His Gln His Gly Arg Trp<br>370                        375                        380 | 1152 |
| caa gcg agg att gga aga gtt gct ggc aac aag gat ctc tac ttg gga<br>Gln Ala Arg Ile Gly Arg Val Ala Gly Asn Lys Asp Leu Tyr Leu Gly<br>385                        390                        395                        400 | 1200 |
| act ttc agc acc caa gag gag gca gca gaa gca tat gat gta gca gca<br>Thr Phe Ser Thr Gln Glu Glu Ala Ala Glu Ala Tyr Asp Val Ala Ala<br>                     405                        410                        415 | 1248 |
| atc aaa ttc aga gga cta agt gct gtt aca aac ttt gac atg agc aga<br>Ile Lys Phe Arg Gly Leu Ser Ala Val Thr Asn Phe Asp Met Ser Arg<br>                420                        425                        430 | 1296 |
| tat gac gtg aaa agc ata ctt gag agc acc act ttg cca att ggt ggt<br>Tyr Asp Val Lys Ser Ile Leu Glu Ser Thr Thr Leu Pro Ile Gly Gly<br>                     435                        440                        445 | 1344 |
| gct gca aag cgt ttg aag gat atg gag cag gtg gaa ctg agg gtg gag<br>Ala Ala Lys Arg Leu Lys Asp Met Glu Gln Val Glu Leu Arg Val Glu<br>450                        455                        460 | 1392 |
| aat gtt cat aga gca gat caa gaa gat cat agt agc atc atg aac tct<br>Asn Val His Arg Ala Asp Gln Glu Asp His Ser Ser Ile Met Asn Ser<br>465                        470                        475                        480 | 1440 |
| cac tta act caa gga atc att aac aac tat gca gca gga gga aca aca<br>His Leu Thr Gln Gly Ile Ile Asn Asn Tyr Ala Ala Gly Gly Thr Thr<br>                     485                        490                        495 | 1488 |
| gcg act cat cat cat aac tgg cac aat gct ctt gca ttc cac caa cct<br>Ala Thr His His His Asn Trp His Asn Ala Leu Ala Phe His Gln Pro<br>                   500                        505                        510 | 1536 |
| caa cct tgc acc acc ata cac tac cct tat gga caa aga att aat tgg<br>Gln Pro Cys Thr Thr Ile His Tyr Pro Tyr Gly Gln Arg Ile Asn Trp<br>                515                        520                        525 | 1584 |
| tgc aag caa gaa caa gac aac tct gat gcc tct cac tct ttg tct tat<br>Cys Lys Gln Glu Gln Asp Asn Ser Asp Ala Ser His Ser Leu Ser Tyr<br>530                        535                        540 | 1632 |
| tca gat att cat caa cta cag cta ggg aac aat ggc aca cac aac ttc<br>Ser Asp Ile His Gln Leu Gln Leu Gly Asn Asn Gly Thr His Asn Phe<br>545                        550                        555                        560 | 1680 |
| ttt cac aca aat tca ggg ttg cac cct atg tta agc atg gat tct gct<br>Phe His Thr Asn Ser Gly Leu His Pro Met Leu Ser Met Asp Ser Ala<br>                     565                        570                        575 | 1728 |
| tcc att gac aat agc tct tca tct aac tct gtt gtt tat gat ggt tat<br>Ser Ile Asp Asn Ser Ser Ser Ser Asn Ser Val Val Tyr Asp Gly Tyr<br>                   580                        585                        590 | 1776 |
| gga ggt ggt ggg ggc tat aat gtg att cct atg ggg act act act<br>Gly Gly Gly Gly Gly Tyr Asn Val Ile Pro Met Gly Thr Thr Thr<br>              595                        600                        605 | 1824 |
| gtt gtt gca aat gat ggt gat caa aat cca aga agc aat cat ggt ttt<br>Val Val Ala Asn Asp Gly Asp Gln Asn Pro Arg Ser Asn His Gly Phe<br>610                        615                        620 | 1872 |

```
ggt gat aat gag ata aag gca ctt ggt tat gaa agt gtg tat ggt tct    1920
Gly Asp Asn Glu Ile Lys Ala Leu Gly Tyr Glu Ser Val Tyr Gly Ser
625                 630                 635                 640 aca act gat cct tat cat gca cat gca agg aac ttg tat tat ctt act    1968
Thr Thr Asp Pro Tyr His Ala His Ala Arg Asn Leu Tyr Tyr Leu Thr
                645                 650                 655 caa cag caa cca tct tct gtt gat gca gtg aag gct agt gca tat gat    2016
Gln Gln Gln Pro Ser Ser Val Asp Ala Val Lys Ala Ser Ala Tyr Asp
            660                 665                 670 caa gga tct gca tgc aat act tgg gtt cca act gct att cca act cat    2064
Gln Gly Ser Ala Cys Asn Thr Trp Val Pro Thr Ala Ile Pro Thr His
        675                 680                 685 gca cca agg tct agt act agt atg gct ctc tgc cat ggt gct acg ccc    2112
Ala Pro Arg Ser Ser Thr Ser Met Ala Leu Cys His Gly Ala Thr Pro
    690                 695                 700 ttc tct tta ttg cat gaa tag                                         2133
Phe Ser Leu Leu His Glu
705                 710
```

<210> SEQ ID NO 2
<211> LENGTH: 710
<212> TYPE: PRT
<213> ORGANISM: Glycine max

<400> SEQUENCE: 2

```
Met Gly Ser Met Asn Leu Leu Gly Phe Ser Leu Ser Pro Gln Glu His
1               5                   10                  15

Pro Ser Ser Gln Asp His Ser Gln Thr Ala Pro Ser Arg Phe Cys Phe
            20                  25                  30

Asn Pro Asp Gly Ile Ser Ser Thr Asp Val Ala Gly Asp Cys Phe Asp
        35                  40                  45

Leu Thr Ser Asp Ser Thr Pro His Leu Leu Asn Leu Pro Ser Tyr Gly
    50                  55                  60

Ile Tyr Glu Ala Phe His Arg Ser Asn Asn Ile His Thr Thr Gln Asp
65                  70                  75                  80

Trp Lys Glu Asn Tyr Asn Ser Gln Asn Leu Leu Leu Gly Thr Ser Cys
                85                  90                  95

Ser Asn Gln Asn Met Asn His Asn His Gln Gln Gln Gln Gln Gln Gln
            100                 105                 110

Pro Lys Leu Glu Asn Phe Leu Gly Gly His Ser Phe Gly Glu His Glu
        115                 120                 125

Gln Pro Tyr Gly Gly Asn Ser Ala Ser Thr Glu Tyr Met Phe Pro Ala
    130                 135                 140

Gln Pro Val Leu Ala Gly Gly Gly Gly Gly Ser Asn Ser Ser Asn
145                 150                 155                 160

Thr Ser Asn Ser Ser Ser Ile Gly Leu Ser Met Ile Lys Thr Trp Leu
                165                 170                 175

Arg Asn Gln Pro Pro His Ser Glu Asn Asn Asn Asn Asn Asn Asn Glu
            180                 185                 190

Ser Gly Gly Asn Ser Arg Ser Ser Val Gln Gln Thr Leu Ser Leu Ser
        195                 200                 205

Met Ser Thr Gly Ser Gln Ser Ser Thr Ser Leu Pro Leu Leu Thr Ala
    210                 215                 220

Ser Val Asp Asn Gly Glu Ser Ser Ser Asp Asn Lys Gln Pro His Thr
225                 230                 235                 240

Thr Ala Ala Leu Asp Thr Thr Gln Thr Gly Ala Ile Glu Thr Ala Pro
                245                 250                 255
```

-continued

```
Arg Lys Ser Ile Asp Thr Phe Gly Gln Arg Thr Ser Ile Tyr Arg Gly
            260                 265                 270

Val Thr Arg His Arg Trp Thr Gly Arg Tyr Glu Ala His Leu Trp Asp
            275                 280                 285

Asn Ser Cys Arg Arg Glu Gly Gln Thr Arg Lys Gly Arg Gln Val Tyr
            290                 295                 300

Leu Gly Gly Tyr Asp Lys Glu Glu Lys Ala Ala Arg Ala Tyr Asp Leu
305                 310                 315                 320

Ala Ala Leu Lys Tyr Trp Gly Thr Thr Thr Thr Asn Phe Pro Ile
                325                 330                 335

Ser His Tyr Glu Lys Glu Leu Glu Met Lys His Met Thr Arg Gln
            340                 345                 350

Glu Tyr Val Ala Ser Leu Arg Arg Lys Ser Ser Gly Phe Ser Arg Gly
            355                 360                 365

Ala Ser Ile Tyr Arg Gly Val Thr Arg His His Gln His Gly Arg Trp
            370                 375                 380

Gln Ala Arg Ile Gly Arg Val Ala Gly Asn Lys Asp Leu Tyr Leu Gly
385                 390                 395                 400

Thr Phe Ser Thr Gln Glu Glu Ala Ala Glu Ala Tyr Asp Val Ala Ala
                405                 410                 415

Ile Lys Phe Arg Gly Leu Ser Ala Val Thr Asn Phe Asp Met Ser Arg
            420                 425                 430

Tyr Asp Val Lys Ser Ile Leu Glu Ser Thr Thr Leu Pro Ile Gly Gly
            435                 440                 445

Ala Ala Lys Arg Leu Lys Asp Met Glu Gln Val Glu Leu Arg Val Glu
450                 455                 460

Asn Val His Arg Ala Asp Gln Glu Asp His Ser Ser Ile Met Asn Ser
465                 470                 475                 480

His Leu Thr Gln Gly Ile Ile Asn Asn Tyr Ala Ala Gly Gly Thr Thr
                485                 490                 495

Ala Thr His His His Asn Trp His Asn Ala Leu Ala Phe His Gln Pro
            500                 505                 510

Gln Pro Cys Thr Thr Ile His Tyr Pro Tyr Gly Gln Arg Ile Asn Trp
            515                 520                 525

Cys Lys Gln Glu Gln Asp Asn Ser Asp Ala Ser His Ser Leu Ser Tyr
            530                 535                 540

Ser Asp Ile His Gln Leu Gln Leu Gly Asn Asn Gly Thr His Asn Phe
545                 550                 555                 560

Phe His Thr Asn Ser Gly Leu His Pro Met Leu Ser Met Asp Ser Ala
                565                 570                 575

Ser Ile Asp Asn Ser Ser Ser Ser Asn Ser Val Val Tyr Asp Gly Tyr
            580                 585                 590

Gly Gly Gly Gly Gly Tyr Asn Val Ile Pro Met Gly Thr Thr Thr Thr
            595                 600                 605

Val Val Ala Asn Asp Gly Asp Gln Asn Pro Arg Ser Asn His Gly Phe
            610                 615                 620

Gly Asp Asn Glu Ile Lys Ala Leu Gly Tyr Glu Ser Val Tyr Gly Ser
625                 630                 635                 640

Thr Thr Asp Pro Tyr His Ala His Ala Arg Asn Leu Tyr Tyr Leu Thr
                645                 650                 655

Gln Gln Gln Pro Ser Ser Val Asp Ala Val Lys Ala Ser Ala Tyr Asp
            660                 665                 670
```

```
                Gln Gly Ser Ala Cys Asn Thr Trp Val Pro Thr Ala Ile Pro Thr His
                                675                 680                 685

Ala Pro Arg Ser Ser Thr Ser Met Ala Leu Cys His Gly Ala Thr Pro
                        690                 695                 700

Phe Ser Leu Leu His Glu
                705                 710

<210> SEQ ID NO 3
<211> LENGTH: 2112
<212> TYPE: DNA
<213> ORGANISM: Sorghum bicolor
<220> FEATURE:
<221> NAME/KEY: CDS
<222> LOCATION: (1)...(2112)

<400> SEQUENCE: 3 atg gct act gtg aac aac tgg ctc gct ttc tcc ctc tcc ccg cag gag        48
Met Ala Thr Val Asn Asn Trp Leu Ala Phe Ser Leu Ser Pro Gln Glu
  1               5                  10                  15 ctg ccg ccc acc cag acg gac tcc acc ctc atc tct gcc gcc acc acc        96
Leu Pro Pro Thr Gln Thr Asp Ser Thr Leu Ile Ser Ala Ala Thr Thr
             20                  25                  30 gac gat gtc tcc ggc gat gtc tgc ttc aac atc ccc caa gat tgg agc       144
Asp Asp Val Ser Gly Asp Val Cys Phe Asn Ile Pro Gln Asp Trp Ser
         35                  40                  45 atg agg gga tcc gag ctt tcg gcg ctc gtc gcc gag ccg aag ctg gag       192
Met Arg Gly Ser Glu Leu Ser Ala Leu Val Ala Glu Pro Lys Leu Glu
     50                  55                  60 gac ttc ctc ggc gga atc tcc ttc tcc gag cag cac cac aag gcc aac       240
Asp Phe Leu Gly Gly Ile Ser Phe Ser Glu Gln His His Lys Ala Asn
 65                  70                  75                  80 tgc aac atg atc ccc agc act agc agc aca gct tgc tac gcg agc tcg       288
Cys Asn Met Ile Pro Ser Thr Ser Ser Thr Ala Cys Tyr Ala Ser Ser
                 85                  90                  95 ggt gct acc gcc ggc tac cat cac cag ctg tac cac cag ccc acc agc       336
Gly Ala Thr Ala Gly Tyr His His Gln Leu Tyr His Gln Pro Thr Ser
            100                 105                 110 tcc gcg ctc cac ttc gct gac tcc gtc atg gtg gcc tcc tcg gcc ggc       384
Ser Ala Leu His Phe Ala Asp Ser Val Met Val Ala Ser Ser Ala Gly
        115                 120                 125 ggc gtc cac gac gga ggt gcc atg ctc agc gcg gcc agc gct aat ggt       432
Gly Val His Asp Gly Gly Ala Met Leu Ser Ala Ala Ser Ala Asn Gly
    130                 135                 140 agc gct ggc gct ggc gct gcc agt gcc aat ggc agc ggc agc atc ggg       480
Ser Ala Gly Ala Gly Ala Ala Ser Ala Asn Gly Ser Gly Ser Ile Gly
145                 150                 155                 160 ctg tcc atg atc aag aac tgg ctg cgg agc caa cca gct ccc atg cag       528
Leu Ser Met Ile Lys Asn Trp Leu Arg Ser Gln Pro Ala Pro Met Gln
                165                 170                 175 ccg agg gtg gcg gcg gct gag agc gtg cag ggg ctc tct ttg tcc atg       576
Pro Arg Val Ala Ala Ala Glu Ser Val Gln Gly Leu Ser Leu Ser Met
            180                 185                 190 aac atg gcg ggg gcg acg caa ggc gcc gct ggc atg cca ctt ctt gct       624
Asn Met Ala Gly Ala Thr Gln Gly Ala Ala Gly Met Pro Leu Leu Ala
        195                 200                 205 gga gag cgc ggc cgg gcg ccc gag agt gtc tcg acg tcg gca cag ggt       672
Gly Glu Arg Gly Arg Ala Pro Glu Ser Val Ser Thr Ser Ala Gln Gly
    210                 215                 220 gga gcc gtc gtc acg gct cca aag gag gat agc ggt ggc agc ggt gtt       720
Gly Ala Val Val Thr Ala Pro Lys Glu Asp Ser Gly Gly Ser Gly Val
225                 230                 235                 240
```

| | | | | | | | | | | | | | | | | |
|---|---|---|---|---|---|---|---|---|---|---|---|---|---|---|---|---|
| gcc | gcc | acc | ggc | gcc | cta | gta | gcc | gtg | agc | acg | gac | acg | ggt | ggc | agc | 768 |
| Ala | Ala | Thr | Gly | Ala | Leu | Val | Ala | Val | Ser | Thr | Asp | Thr | Gly | Gly | Ser | |
| | | | | 245 | | | | | 250 | | | | | 255 | | |
| ggc | gcg | tcg | gct | gac | aac | acg | gca | agg | aag | acg | gtg | gac | acg | ttc | ggg | 816 |
| Gly | Ala | Ser | Ala | Asp | Asn | Thr | Ala | Arg | Lys | Thr | Val | Asp | Thr | Phe | Gly | |
| | | | 260 | | | | | 265 | | | | | 270 | | | |
| cag | cgc | acg | tcg | att | tac | cgt | ggc | gtg | aca | agg | cat | aga | tgg | act | ggg | 864 |
| Gln | Arg | Thr | Ser | Ile | Tyr | Arg | Gly | Val | Thr | Arg | His | Arg | Trp | Thr | Gly | |
| | | 275 | | | | | 280 | | | | | 285 | | | | |
| aga | tat | gaa | gca | cat | ctg | tgg | gac | aac | agt | tgc | aga | agg | gaa | gga | caa | 912 |
| Arg | Tyr | Glu | Ala | His | Leu | Trp | Asp | Asn | Ser | Cys | Arg | Arg | Glu | Gly | Gln | |
| | 290 | | | | | 295 | | | | | 300 | | | | | |
| act | cgc | aag | ggt | cgt | caa | gtc | tat | tta | ggt | ggc | tat | gat | aaa | gag | gag | 960 |
| Thr | Arg | Lys | Gly | Arg | Gln | Val | Tyr | Leu | Gly | Gly | Tyr | Asp | Lys | Glu | Glu | |
| 305 | | | | | 310 | | | | | 315 | | | | | 320 | |
| aaa | gct | gct | agg | gct | tat | gat | ctg | gct | gct | ctt | aag | tac | tgg | ggt | ccc | 1008 |
| Lys | Ala | Ala | Arg | Ala | Tyr | Asp | Leu | Ala | Ala | Leu | Lys | Tyr | Trp | Gly | Pro | |
| | | | | 325 | | | | | 330 | | | | | 335 | | |
| acg | aca | aca | aca | aat | ttt | cca | gtg | aat | aac | tac | gaa | aag | gag | ctg | gag | 1056 |
| Thr | Thr | Thr | Thr | Asn | Phe | Pro | Val | Asn | Asn | Tyr | Glu | Lys | Glu | Leu | Glu | |
| | | | 340 | | | | | 345 | | | | | 350 | | | |
| gat | atg | aag | cac | atg | aca | agg | cag | gag | ttt | gta | gcg | tct | ctg | aga | agg | 1104 |
| Asp | Met | Lys | His | Met | Thr | Arg | Gln | Glu | Phe | Val | Ala | Ser | Leu | Arg | Arg | |
| | | 355 | | | | | 360 | | | | | 365 | | | | |
| aag | agc | agt | ggt | ttc | tcc | aga | ggt | gca | tcc | att | tac | agg | gga | gtg | act | 1152 |
| Lys | Ser | Ser | Gly | Phe | Ser | Arg | Gly | Ala | Ser | Ile | Tyr | Arg | Gly | Val | Thr | |
| | 370 | | | | | 375 | | | | | 380 | | | | | |
| agg | cat | cac | cag | cat | gga | aga | tgg | caa | gca | cgg | att | gga | cga | gtt | gca | 1200 |
| Arg | His | His | Gln | His | Gly | Arg | Trp | Gln | Ala | Arg | Ile | Gly | Arg | Val | Ala | |
| 385 | | | | | 390 | | | | | 395 | | | | | 400 | |
| ggg | aac | aag | gat | ctc | tac | ttg | ggc | acc | ttc | agc | acg | cag | gag | gag | gca | 1248 |
| Gly | Asn | Lys | Asp | Leu | Tyr | Leu | Gly | Thr | Phe | Ser | Thr | Gln | Glu | Glu | Ala | |
| | | | | 405 | | | | | 410 | | | | | 415 | | |
| gcg | gag | gca | tac | gac | att | gcg | gcg | atc | aag | ttc | cgc | ggc | ctc | aac | gcc | 1296 |
| Ala | Glu | Ala | Tyr | Asp | Ile | Ala | Ala | Ile | Lys | Phe | Arg | Gly | Leu | Asn | Ala | |
| | | | 420 | | | | | 425 | | | | | 430 | | | |
| gtc | aca | aac | ttc | gac | atg | agc | cgc | tac | gac | gtc | aag | agc | atc | ctg | gac | 1344 |
| Val | Thr | Asn | Phe | Asp | Met | Ser | Arg | Tyr | Asp | Val | Lys | Ser | Ile | Leu | Asp | |
| | | 435 | | | | | 440 | | | | | 445 | | | | |
| agc | agt | gcg | ctc | ccc | atc | ggc | agc | gcc | gcc | aag | cgt | ctc | aag | gag | gcc | 1392 |
| Ser | Ser | Ala | Leu | Pro | Ile | Gly | Ser | Ala | Ala | Lys | Arg | Leu | Lys | Glu | Ala | |
| | 450 | | | | | 455 | | | | | 460 | | | | | |
| gag | gcc | gcc | gcg | tcc | gca | cag | cac | cat | gcc | ggc | gtg | gtg | agc | tac | gac | 1440 |
| Glu | Ala | Ala | Ala | Ser | Ala | Gln | His | His | Ala | Gly | Val | Val | Ser | Tyr | Asp | |
| 465 | | | | | 470 | | | | | 475 | | | | | 480 | |
| gtc | ggc | cgc | ata | gcc | tca | cag | ctc | ggc | gac | ggc | ggc | gcc | ctg | gcg | gcg | 1488 |
| Val | Gly | Arg | Ile | Ala | Ser | Gln | Leu | Gly | Asp | Gly | Gly | Ala | Leu | Ala | Ala | |
| | | | | 485 | | | | | 490 | | | | | 495 | | |
| gcg | tac | ggc | gcg | cac | tac | cat | ggc | gcc | tgg | ccg | acc | atc | gcg | ttc | cag | 1536 |
| Ala | Tyr | Gly | Ala | His | Tyr | His | Gly | Ala | Trp | Pro | Thr | Ile | Ala | Phe | Gln | |
| | | | | 500 | | | | | 505 | | | | | 510 | | |
| ccg | agc | gcg | gcc | acg | ggc | ctg | tac | cac | ccg | tac | gcg | cag | ccg | atg | cgc | 1584 |
| Pro | Ser | Ala | Ala | Thr | Gly | Leu | Tyr | His | Pro | Tyr | Ala | Gln | Pro | Met | Arg | |
| | | | 515 | | | | | 520 | | | | | 525 | | | |
| ggg | tgg | tgc | aag | cag | gag | cag | gac | cac | gcg | gtg | atc | gcg | gcc | gcg | cac | 1632 |
| Gly | Trp | Cys | Lys | Gln | Glu | Gln | Asp | His | Ala | Val | Ile | Ala | Ala | Ala | His | |
| | | 530 | | | | | 535 | | | | | 540 | | | | |
| agc | ctg | cag | gag | ctc | cac | cac | ctg | aac | ctg | ggt | gct | gcc | gcc | ggc | gcg | 1680 |
| Ser | Leu | Gln | Glu | Leu | His | His | Leu | Asn | Leu | Gly | Ala | Ala | Ala | Gly | Ala | |

```
                  545                  550                  555                  560
cac gac ttc ttc tcg gcg ggg cag cag gcg gcg atg cac ggc ctg ggt           1728
His Asp Phe Phe Ser Ala Gly Gln Gln Ala Ala Met His Gly Leu Gly
                      565                  570                  575 agc atg gac aat gca tca ctc gag cac agc acc ggc tcc aac tcc gtc           1776
Ser Met Asp Asn Ala Ser Leu Glu His Ser Thr Gly Ser Asn Ser Val
            580                  585                  590 gtg tac aac ggt gtt ggt gat agc aac ggc agc acc gtc gtc ggc agt           1824
Val Tyr Asn Gly Val Gly Asp Ser Asn Gly Ser Thr Val Val Gly Ser
        595                  600                  605 ggt ggc tac atg atg cct atg agc gct gcc acg gcg acg gct acc acg           1872
Gly Gly Tyr Met Met Pro Met Ser Ala Ala Thr Ala Thr Ala Thr Thr
    610                  615                  620 gca atg gtg agc cac gag cag gtg cat gca cgg gca cag ggt gat cac           1920
Ala Met Val Ser His Glu Gln Val His Ala Arg Ala Gln Gly Asp His
625                  630                  635                  640 cac gac gaa gcc aag cag gct gct cag atg ggg tac gag agc tac ctg           1968
His Asp Glu Ala Lys Gln Ala Ala Gln Met Gly Tyr Glu Ser Tyr Leu
                      645                  650                  655 gtg aac gca gag aac tat ggc ggc ggg agg atg tct gcg gcc tgg gcg           2016
Val Asn Ala Glu Asn Tyr Gly Gly Gly Arg Met Ser Ala Ala Trp Ala
            660                  665                  670 act gtc tca gcg cca ccg gcg gca agc agc aac gat aac atg gcg gac           2064
Thr Val Ser Ala Pro Pro Ala Ala Ser Ser Asn Asp Asn Met Ala Asp
        675                  680                  685 gtc ggc cat ggc ggc gca cag ctc ttc agt gtc tgg aac gat act taa           2112
Val Gly His Gly Gly Ala Gln Leu Phe Ser Val Trp Asn Asp Thr
    690                  695                  700

<210> SEQ ID NO 4
<211> LENGTH: 703
<212> TYPE: PRT
<213> ORGANISM: Sorghum bicolor

<400> SEQUENCE: 4

Met Ala Thr Val Asn Asn Trp Leu Ala Phe Ser Leu Ser Pro Gln Glu
 1               5                  10                  15

Leu Pro Pro Thr Gln Thr Asp Ser Thr Leu Ile Ser Ala Ala Thr Thr
                20                  25                  30

Asp Asp Val Ser Gly Asp Val Cys Phe Asn Ile Pro Gln Asp Trp Ser
            35                  40                  45

Met Arg Gly Ser Glu Leu Ser Ala Leu Val Ala Glu Pro Lys Leu Glu
        50                  55                  60

Asp Phe Leu Gly Gly Ile Ser Phe Ser Glu Gln His His Lys Ala Asn
 65                  70                  75                  80

Cys Asn Met Ile Pro Ser Thr Ser Ser Thr Ala Cys Tyr Ala Ser Ser
                85                  90                  95

Gly Ala Thr Ala Gly Tyr His His Gln Leu Tyr His Gln Pro Thr Ser
            100                 105                 110

Ser Ala Leu His Phe Ala Asp Ser Val Met Val Ala Ser Ser Ala Gly
        115                 120                 125

Gly Val His Asp Gly Gly Ala Met Leu Ser Ala Ser Ala Asn Gly
    130                 135                 140

Ser Ala Gly Ala Gly Ala Ala Ser Ala Asn Gly Ser Gly Ser Ile Gly
145                 150                 155                 160

Leu Ser Met Ile Lys Asn Trp Leu Arg Ser Gln Pro Ala Pro Met Gln
                165                 170                 175
```

Pro Arg Val Ala Ala Glu Ser Val Gln Gly Leu Ser Leu Ser Met
            180                 185                 190

Asn Met Ala Gly Ala Thr Gln Ala Ala Gly Met Pro Leu Leu Ala
        195                 200                 205

Gly Glu Arg Gly Arg Ala Pro Glu Ser Val Ser Thr Ser Ala Gln Gly
210                 215                 220

Gly Ala Val Val Thr Ala Pro Lys Glu Asp Ser Gly Ser Gly Val
225                 230                 235                 240

Ala Ala Thr Gly Ala Leu Val Ala Val Ser Thr Asp Thr Gly Gly Ser
                245                 250                 255

Gly Ala Ser Ala Asp Asn Thr Ala Arg Lys Thr Val Asp Thr Phe Gly
        260                 265                 270

Gln Arg Thr Ser Ile Tyr Arg Gly Val Thr Arg His Arg Trp Thr Gly
        275                 280                 285

Arg Tyr Glu Ala His Leu Trp Asp Asn Ser Cys Arg Arg Glu Gly Gln
        290                 295                 300

Thr Arg Lys Gly Arg Gln Val Tyr Leu Gly Gly Tyr Asp Lys Glu Glu
305                 310                 315                 320

Lys Ala Ala Arg Ala Tyr Asp Leu Ala Ala Leu Lys Tyr Trp Gly Pro
                325                 330                 335

Thr Thr Thr Thr Asn Phe Pro Val Asn Asn Tyr Glu Lys Glu Leu Glu
                340                 345                 350

Asp Met Lys His Met Thr Arg Gln Glu Phe Val Ala Ser Leu Arg Arg
        355                 360                 365

Lys Ser Ser Gly Phe Ser Arg Gly Ala Ser Ile Tyr Arg Gly Val Thr
        370                 375                 380

Arg His His Gln His Gly Arg Trp Gln Ala Arg Ile Gly Arg Val Ala
385                 390                 395                 400

Gly Asn Lys Asp Leu Tyr Leu Gly Thr Phe Ser Thr Gln Glu Glu Ala
                405                 410                 415

Ala Glu Ala Tyr Asp Ile Ala Ala Ile Lys Phe Arg Gly Leu Asn Ala
                420                 425                 430

Val Thr Asn Phe Asp Met Ser Arg Tyr Asp Val Lys Ser Ile Leu Asp
        435                 440                 445

Ser Ser Ala Leu Pro Ile Gly Ser Ala Ala Lys Arg Leu Lys Glu Ala
450                 455                 460

Glu Ala Ala Ala Ser Ala Gln His His Ala Gly Val Val Ser Tyr Asp
465                 470                 475                 480

Val Gly Arg Ile Ala Ser Gln Leu Gly Asp Gly Gly Ala Leu Ala Ala
                485                 490                 495

Ala Tyr Gly Ala His Tyr His Gly Ala Trp Pro Thr Ile Ala Phe Gln
                500                 505                 510

Pro Ser Ala Ala Thr Gly Leu Tyr His Pro Tyr Ala Gln Pro Met Arg
        515                 520                 525

Gly Trp Cys Lys Gln Glu Gln Asp His Ala Val Ile Ala Ala Ala His
        530                 535                 540

Ser Leu Gln Glu Leu His His Leu Asn Leu Gly Ala Ala Ala Gly Ala
545                 550                 555                 560

His Asp Phe Phe Ser Ala Gly Gln Gln Ala Ala Met His Gly Leu Gly
                565                 570                 575

Ser Met Asp Asn Ala Ser Leu Glu His Ser Thr Gly Ser Asn Ser Val
        580                 585                 590

Val Tyr Asn Gly Val Gly Asp Ser Asn Gly Ser Thr Val Val Gly Ser

```
                  595                 600                 605
Gly Gly Tyr Met Met Pro Met Ser Ala Ala Thr Ala Thr Ala Thr Thr
            610                 615                 620

Ala Met Val Ser His Glu Gln Val His Ala Arg Ala Gln Gly Asp His
625                 630                 635                 640

His Asp Glu Ala Lys Gln Ala Ala Gln Met Gly Tyr Glu Ser Tyr Leu
                645                 650                 655

Val Asn Ala Glu Asn Tyr Gly Gly Arg Met Ser Ala Ala Trp Ala
            660                 665                 670

Thr Val Ser Ala Pro Pro Ala Ala Ser Ser Asn Asp Asn Met Ala Asp
            675                 680                 685

Val Gly His Gly Gly Ala Gln Leu Phe Ser Val Trp Asn Asp Thr
690                 695                 700

<210> SEQ ID NO 5
<211> LENGTH: 1932
<212> TYPE: DNA
<213> ORGANISM: Vitis vinifera
<220> FEATURE:
<221> NAME/KEY: CDS
<222> LOCATION: (1)...(1932)

<400> SEQUENCE: 5 atg gct tcc atg aac aac tgg ttg ggt ttc tct ttg tcc cct cga gaa     48
Met Ala Ser Met Asn Asn Trp Leu Gly Phe Ser Leu Ser Pro Arg Glu
1               5                   10                  15 ctt cca cca cag cct gaa aat cac tca cag aac agt gtc tct aga ctt    96
Leu Pro Pro Gln Pro Glu Asn His Ser Gln Asn Ser Val Ser Arg Leu
                20                  25                  30 ggt ttc aac tct gat gaa atc tct ggg act gat gtg tca ggt gag tgt   144
Gly Phe Asn Ser Asp Glu Ile Ser Gly Thr Asp Val Ser Gly Glu Cys
            35                  40                  45 ttt gat ctc act tca gat tcc act gct ccc tct ctc aac ctc cct ccc   192
Phe Asp Leu Thr Ser Asp Ser Thr Ala Pro Ser Leu Asn Leu Pro Pro
        50                  55                  60 cct ttt ggg ata ctt gaa gca ttc aac agg aat aat cag ccc caa gat   240
Pro Phe Gly Ile Leu Glu Ala Phe Asn Arg Asn Asn Gln Pro Gln Asp
65                  70                  75                  80 act aac tac aaa acc acc act tct gag ctc tcc atg ctc atg ggt agt   288
Thr Asn Tyr Lys Thr Thr Thr Ser Glu Leu Ser Met Leu Met Gly Ser
                85                  90                  95 tca tgc agt agt cat cat aac ctc gaa aac caa gaa ccc aaa ctt gaa   336
Ser Cys Ser Ser His His Asn Leu Glu Asn Gln Glu Pro Lys Leu Glu
            100                 105                 110 aat ttc ctg ggc tgc cgc tct ttt gct gat cat gag cag aaa ctt caa   384
Asn Phe Leu Gly Cys Arg Ser Phe Ala Asp His Glu Gln Lys Leu Gln
        115                 120                 125 ggg tac tac att tcc att ggt tta tcc atg atc aag aca tgg ctg cgg   432
Gly Tyr Tyr Ile Ser Ile Gly Leu Ser Met Ile Lys Thr Trp Leu Arg
130                 135                 140 aac caa cct gca ccc acc cat cag gat aac aac aag agt act gat act   480
Asn Gln Pro Ala Pro Thr His Gln Asp Asn Asn Lys Ser Thr Asp Thr
145                 150                 155                 160 ggg cct gtc ggt gga gcc gcc gct ggg aac cta ccc aat gca cag acc   528
Gly Pro Val Gly Gly Ala Ala Ala Gly Asn Leu Pro Asn Ala Gln Thr
                165                 170                 175 tta tcg ttg tcc atg agc acc ggc tcg cac cag acc ggt gcc att gaa   576
Leu Ser Leu Ser Met Ser Thr Gly Ser His Gln Thr Gly Ala Ile Glu
            180                 185                 190
```

```
acg gtg cca agg aag tcc att gat aca ttt gga cag agg aca tcc ata      624
Thr Val Pro Arg Lys Ser Ile Asp Thr Phe Gly Gln Arg Thr Ser Ile
        195                 200                 205 tac cgt ggt gta aca agg cat aga tgg acg ggt aga tat gag gct cat      672
Tyr Arg Gly Val Thr Arg His Arg Trp Thr Gly Arg Tyr Glu Ala His
210                 215                 220 cta tgg gac aac agt tgc aga aga gaa gga caa act cga aag gga agg      720
Leu Trp Asp Asn Ser Cys Arg Arg Glu Gly Gln Thr Arg Lys Gly Arg
225                 230                 235                 240 caa gtt tat tta ggt ggt tat gac aaa gaa gaa aag gca gct agg gct      768
Gln Val Tyr Leu Gly Gly Tyr Asp Lys Glu Glu Lys Ala Ala Arg Ala
            245                 250                 255 tac gat tta gca gca ctg aag tat tgg ggt acc acc acc aca aca aat      816
Tyr Asp Leu Ala Ala Leu Lys Tyr Trp Gly Thr Thr Thr Thr Thr Asn
            260                 265                 270 ttc cct att agc aac tat gaa aaa gag ata gag gag atg aag cac atg      864
Phe Pro Ile Ser Asn Tyr Glu Lys Glu Ile Glu Glu Met Lys His Met
            275                 280                 285 aca agg cag gag tac gta gca tct ctg cga agg aag agt agc ggg ttt      912
Thr Arg Gln Glu Tyr Val Ala Ser Leu Arg Arg Lys Ser Ser Gly Phe
290                 295                 300 tct cgt gga gca tcc ata tat aga gga gtg acc aga cac cat cag cat      960
Ser Arg Gly Ala Ser Ile Tyr Arg Gly Val Thr Arg His His Gln His
305                 310                 315                 320 ggg aga tgg cag gca agg att gga aga gtc gca ggc aac aaa gat ctt     1008
Gly Arg Trp Gln Ala Arg Ile Gly Arg Val Ala Gly Asn Lys Asp Leu
                325                 330                 335 tac ttg gga act ttc agc acc caa gag gaa gca gca gag gcc tat gac     1056
Tyr Leu Gly Thr Phe Ser Thr Gln Glu Glu Ala Ala Glu Ala Tyr Asp
                340                 345                 350 att gct gcc att aag ttt cga gga ttg aat gcg gtg acc aac ttt gat     1104
Ile Ala Ala Ile Lys Phe Arg Gly Leu Asn Ala Val Thr Asn Phe Asp
                355                 360                 365 atg agt aga tat gat gtt aat agc att cta gag agc agt acc ttg ccg     1152
Met Ser Arg Tyr Asp Val Asn Ser Ile Leu Glu Ser Ser Thr Leu Pro
370                 375                 380 att ggt gga gct gca aag cgg ttg aaa gat gct gag cag gct gaa atg     1200
Ile Gly Gly Ala Ala Lys Arg Leu Lys Asp Ala Glu Gln Ala Glu Met
385                 390                 395                 400 act ata gat gga cag agg aca gac gat gag atg agc tca cag ctg act     1248
Thr Ile Asp Gly Gln Arg Thr Asp Asp Glu Met Ser Ser Gln Leu Thr
                405                 410                 415 gat gga atc aac aac tat gga gca cac cac cat ggc tgg cct act gtt     1296
Asp Gly Ile Asn Asn Tyr Gly Ala His His His Gly Trp Pro Thr Val
                420                 425                 430 gca ttc caa caa gct cag cca ttt agc atg cac tac cct tat ggc cat     1344
Ala Phe Gln Gln Ala Gln Pro Phe Ser Met His Tyr Pro Tyr Gly His
                435                 440                 445 cag cag agg gct gtt tgg tgt aag caa gag caa gac cct gat ggc aca     1392
Gln Gln Arg Ala Val Trp Cys Lys Gln Glu Gln Asp Pro Asp Gly Thr
                450                 455                 460 cac aac ttt caa gat ctt cac caa cta caa ttg gga aac act cac aac     1440
His Asn Phe Gln Asp Leu His Gln Leu Gln Leu Gly Asn Thr His Asn
465                 470                 475                 480 ttc ttc cag cct aat gtt ctg cac aac ctc atg agc atg gac tct tct     1488
Phe Phe Gln Pro Asn Val Leu His Asn Leu Met Ser Met Asp Ser Ser
                485                 490                 495 tca atg gac cat agc tca ggc tcc aat tca gtc atc tat agc ggt ggt     1536
Ser Met Asp His Ser Ser Gly Ser Asn Ser Val Ile Tyr Ser Gly Gly
                500                 505                 510
```

```
gga gcc gct gat ggc agc gct gca act ggc ggc agt ggc agt ggg agc    1584
Gly Ala Ala Asp Gly Ser Ala Ala Thr Gly Gly Ser Gly Ser Gly Ser
            515                 520                 525 ttc caa ggg gta ggt tat ggg aac aac att ggc ttt gtg atg ccc ata    1632
Phe Gln Gly Val Gly Tyr Gly Asn Asn Ile Gly Phe Val Met Pro Ile
        530                 535                 540 agc acc gtc atc gct cat gaa ggc ggc cat ggc cag gga aat ggt ggc    1680
Ser Thr Val Ile Ala His Glu Gly Gly His Gly Gln Gly Asn Gly Gly
545                 550                 555                 560 ttt gga gat agc gaa gtg aag gcg att ggt tac gac aac atg ttt gga    1728
Phe Gly Asp Ser Glu Val Lys Ala Ile Gly Tyr Asp Asn Met Phe Gly
                565                 570                 575 tcg aca gat cct tac cat gct agg agc ttg tac tat ctt tca cag caa    1776
Ser Thr Asp Pro Tyr His Ala Arg Ser Leu Tyr Tyr Leu Ser Gln Gln
            580                 585                 590 tca tct gca ggc atg gtg aag ggc agt agt gca tat gat cag ggg tca    1824
Ser Ser Ala Gly Met Val Lys Gly Ser Ser Ala Tyr Asp Gln Gly Ser
        595                 600                 605 ggg tgt aac aac tgg gtt cca act gca gtt cca acc cta gct cca agg    1872
Gly Cys Asn Asn Trp Val Pro Thr Ala Val Pro Thr Leu Ala Pro Arg
610                 615                 620 act aac agc ttg gca gta tgc cat gga aca cct aca ttc aca gta tgg    1920
Thr Asn Ser Leu Ala Val Cys His Gly Thr Pro Thr Phe Thr Val Trp
625                 630                 635                 640 aat gat aca taa                                                    1932
Asn Asp Thr <210> SEQ ID NO 6
<211> LENGTH: 643
<212> TYPE: PRT
<213> ORGANISM: Vitis vinifera

<400> SEQUENCE: 6

Met Ala Ser Met Asn Asn Trp Leu Gly Phe Ser Leu Ser Pro Arg Glu
 1               5                  10                  15

Leu Pro Pro Gln Pro Glu Asn His Ser Gln Asn Ser Val Ser Arg Leu
            20                  25                  30

Gly Phe Asn Ser Asp Glu Ile Ser Gly Thr Asp Val Ser Gly Glu Cys
        35                  40                  45

Phe Asp Leu Thr Ser Asp Ser Thr Ala Pro Ser Leu Asn Leu Pro Pro
    50                  55                  60

Pro Phe Gly Ile Leu Glu Ala Phe Asn Arg Asn Asn Gln Pro Gln Asp
65                  70                  75                  80

Thr Asn Tyr Lys Thr Thr Thr Ser Glu Leu Ser Met Leu Met Gly Ser
                85                  90                  95

Ser Cys Ser Ser His His Asn Leu Glu Asn Gln Glu Pro Lys Leu Glu
            100                 105                 110

Asn Phe Leu Gly Cys Arg Ser Phe Ala Asp His Glu Gln Lys Leu Gln
        115                 120                 125

Gly Tyr Tyr Ile Ser Ile Gly Leu Ser Met Ile Lys Thr Trp Leu Arg
    130                 135                 140

Asn Gln Pro Ala Pro Thr His Gln Asp Asn Asn Lys Ser Thr Asp Thr
145                 150                 155                 160

Gly Pro Val Gly Gly Ala Ala Gly Asn Leu Pro Asn Ala Gln Thr
                165                 170                 175

Leu Ser Leu Ser Met Ser Thr Gly Ser His Gln Thr Gly Ala Ile Glu
            180                 185                 190
```

```
Thr Val Pro Arg Lys Ser Ile Asp Thr Phe Gly Gln Arg Thr Ser Ile
        195                 200                 205

Tyr Arg Gly Val Thr Arg His Arg Trp Thr Gly Arg Tyr Glu Ala His
        210                 215                 220

Leu Trp Asp Asn Ser Cys Arg Arg Glu Gly Gln Thr Arg Lys Gly Arg
225                 230                 235                 240

Gln Val Tyr Leu Gly Gly Tyr Asp Lys Glu Lys Ala Ala Arg Ala
                    245                 250                 255

Tyr Asp Leu Ala Ala Leu Lys Tyr Trp Gly Thr Thr Thr Thr Asn
                260                 265                 270

Phe Pro Ile Ser Asn Tyr Glu Lys Glu Ile Glu Met Lys His Met
                275                 280                 285

Thr Arg Gln Glu Tyr Val Ala Ser Leu Arg Arg Lys Ser Ser Gly Phe
        290                 295                 300

Ser Arg Gly Ala Ser Ile Tyr Arg Gly Val Thr Arg His His Gln His
305                 310                 315                 320

Gly Arg Trp Gln Ala Arg Ile Gly Arg Val Ala Gly Asn Lys Asp Leu
                    325                 330                 335

Tyr Leu Gly Thr Phe Ser Thr Gln Glu Glu Ala Ala Glu Ala Tyr Asp
                340                 345                 350

Ile Ala Ala Ile Lys Phe Arg Gly Leu Asn Ala Val Thr Asn Phe Asp
                355                 360                 365

Met Ser Arg Tyr Asp Val Asn Ser Ile Leu Glu Ser Ser Thr Leu Pro
        370                 375                 380

Ile Gly Gly Ala Ala Lys Arg Leu Lys Asp Ala Glu Gln Ala Glu Met
385                 390                 395                 400

Thr Ile Asp Gly Gln Arg Thr Asp Asp Glu Met Ser Ser Gln Leu Thr
                    405                 410                 415

Asp Gly Ile Asn Asn Tyr Gly Ala His His His Gly Trp Pro Thr Val
                420                 425                 430

Ala Phe Gln Gln Ala Gln Pro Phe Ser Met His Tyr Pro Tyr Gly His
        435                 440                 445

Gln Gln Arg Ala Val Trp Cys Lys Gln Glu Gln Asp Pro Asp Gly Thr
        450                 455                 460

His Asn Phe Gln Asp Leu His Gln Leu Gln Leu Gly Asn Thr His Asn
465                 470                 475                 480

Phe Phe Gln Pro Asn Val Leu His Asn Leu Met Ser Met Asp Ser Ser
                485                 490                 495

Ser Met Asp His Ser Ser Gly Ser Asn Ser Val Ile Tyr Ser Gly Gly
                500                 505                 510

Gly Ala Ala Asp Gly Ser Ala Ala Thr Gly Gly Ser Gly Ser Gly Ser
                515                 520                 525

Phe Gln Gly Val Gly Tyr Gly Asn Asn Ile Gly Phe Val Met Pro Ile
        530                 535                 540

Ser Thr Val Ile Ala His Glu Gly Gly His Gly Gln Gly Asn Gly Gly
545                 550                 555                 560

Phe Gly Asp Ser Glu Val Lys Ala Ile Gly Tyr Asp Asn Met Phe Gly
                565                 570                 575

Ser Thr Asp Pro Tyr His Ala Arg Ser Leu Tyr Tyr Leu Ser Gln Gln
                580                 585                 590

Ser Ser Ala Gly Met Val Lys Gly Ser Ser Ala Tyr Asp Gln Gly Ser
        595                 600                 605
```

```
Gly Cys Asn Asn Trp Val Pro Thr Ala Val Pro Thr Leu Ala Pro Arg
    610             615                 620

Thr Asn Ser Leu Ala Val Cys His Gly Thr Pro Thr Phe Thr Val Trp
625             630                 635                 640

Asn Asp Thr

<210> SEQ ID NO 7
<211> LENGTH: 2070
<212> TYPE: DNA
<213> ORGANISM: Medicago truncatula
<220> FEATURE:
<221> NAME/KEY: CDS
<222> LOCATION: (1)...(2070)

<400> SEQUENCE: 7 atg gcc tct atg aac ttg tta ggt ttc tct cta tct cca caa gaa caa      48
Met Ala Ser Met Asn Leu Leu Gly Phe Ser Leu Ser Pro Gln Glu Gln
 1               5                  10                  15 cat cca tca aca caa gat caa acg gtg gct tcc cgt ttt ggg ttc aac      96
His Pro Ser Thr Gln Asp Gln Thr Val Ala Ser Arg Phe Gly Phe Asn
            20                  25                  30 cct aat gaa atc tca ggc tct gat gtt caa gga gat cac tgc tat gat     144
Pro Asn Glu Ile Ser Gly Ser Asp Val Gln Gly Asp His Cys Tyr Asp
        35                  40                  45 ctc tct tct cac aca act cct cat cat tca ctc aac ctt tct cat cct     192
Leu Ser Ser His Thr Thr Pro His His Ser Leu Asn Leu Ser His Pro
 50                  55                  60 ttt tcc att tat gaa gct ttc cac aca aat aac aac att cac acc act     240
Phe Ser Ile Tyr Glu Ala Phe His Thr Asn Asn Asn Ile His Thr Thr
 65                  70                  75                  80 caa gat tgg aag gag aac tac aac aac caa aac cta cta ttg gga aca     288
Gln Asp Trp Lys Glu Asn Tyr Asn Asn Gln Asn Leu Leu Leu Gly Thr
                85                  90                  95 tca tgc atg aac caa aat gtg aac aac aac aac caa caa gca caa cca     336
Ser Cys Met Asn Gln Asn Val Asn Asn Asn Asn Gln Gln Ala Gln Pro
            100                 105                 110 aag cta gaa aac ttc ctc ggt gga cac tct ttc acc gac cat caa gaa     384
Lys Leu Glu Asn Phe Leu Gly Gly His Ser Phe Thr Asp His Gln Glu
        115                 120                 125 tac ggt ggt agc aac tca tac tct tca tta cac ctc cca cct cat cag     432
Tyr Gly Gly Ser Asn Ser Tyr Ser Ser Leu His Leu Pro Pro His Gln
130                 135                 140 ccg gaa gca tcc tgt ggc ggt ggt gat ggt agt aca agt aac aat aac     480
Pro Glu Ala Ser Cys Gly Gly Gly Asp Gly Ser Thr Ser Asn Asn Asn
145                 150                 155                 160 tca ata ggt tta tct atg ata aaa aca tgg ctc aga aac caa cca cca     528
Ser Ile Gly Leu Ser Met Ile Lys Thr Trp Leu Arg Asn Gln Pro Pro
                165                 170                 175 cca cca gaa aac aac aac aat aac aac aat gaa agt ggt gca cgt gtg     576
Pro Pro Glu Asn Asn Asn Asn Asn Asn Glu Ser Gly Ala Arg Val
            180                 185                 190 cag aca cta tca ctt tct atg agt act ggc tca cag tca agt tca tct     624
Gln Thr Leu Ser Leu Ser Met Ser Thr Gly Ser Gln Ser Ser Ser Ser
        195                 200                 205 gtg cct ctt ctc aat gca aat gtg atg agt ggt gag att tcc tca tcg     672
Val Pro Leu Leu Asn Ala Asn Val Met Ser Gly Glu Ile Ser Ser Ser
210                 215                 220 gaa aac aaa caa cca ccc aca act gca gtt gta ctt gat agc aac caa     720
Glu Asn Lys Gln Pro Pro Thr Thr Ala Val Val Leu Asp Ser Asn Gln
225                 230                 235                 240
```

```
aca agt gtc gtt gaa agt gct gtg cct aga aaa tcc gtt gat aca ttt      768
Thr Ser Val Val Glu Ser Ala Val Pro Arg Lys Ser Val Asp Thr Phe
            245                 250                 255 gga caa aga act tcc att tac cgt ggt gta aca agg cat aga tgg aca      816
Gly Gln Arg Thr Ser Ile Tyr Arg Gly Val Thr Arg His Arg Trp Thr
                260                 265                 270 ggg aga tat gaa gct cac ctt tgg gat aat agt tgt aga aga gag ggg      864
Gly Arg Tyr Glu Ala His Leu Trp Asp Asn Ser Cys Arg Arg Glu Gly
            275                 280                 285 cag act cgc aaa gga agg caa gtt tac ttg gga ggt tat gac aaa gaa      912
Gln Thr Arg Lys Gly Arg Gln Val Tyr Leu Gly Gly Tyr Asp Lys Glu
        290                 295                 300 gaa aaa gca gct aga gcc tat gat ttg gca gca cta aaa tat tgg gga      960
Glu Lys Ala Ala Arg Ala Tyr Asp Leu Ala Ala Leu Lys Tyr Trp Gly
305                 310                 315                 320 aca act act aca aca aat ttt cca att agc cat tat gaa aaa gaa gtg     1008
Thr Thr Thr Thr Thr Asn Phe Pro Ile Ser His Tyr Glu Lys Glu Val
                325                 330                 335 gaa gaa atg aag cat atg aca agg caa gag tac gtt gcg tca ttg aga     1056
Glu Glu Met Lys His Met Thr Arg Gln Glu Tyr Val Ala Ser Leu Arg
            340                 345                 350 agg aaa agt agt ggt ttt tca cga ggt gca tcc att tac cga gga gta     1104
Arg Lys Ser Ser Gly Phe Ser Arg Gly Ala Ser Ile Tyr Arg Gly Val
        355                 360                 365 aca aga cat cat caa cat ggt aga tgg caa gct agg att gga aga gtt     1152
Thr Arg His His Gln His Gly Arg Trp Gln Ala Arg Ile Gly Arg Val
    370                 375                 380 gca ggc aac aaa gat ctc tac cta gga act ttc agc act caa gaa gag     1200
Ala Gly Asn Lys Asp Leu Tyr Leu Gly Thr Phe Ser Thr Gln Glu Glu
385                 390                 395                 400 gca gca gag gca tat gat gtg gca gca ata aaa ttc aga gga ctg agt     1248
Ala Ala Glu Ala Tyr Asp Val Ala Ala Ile Lys Phe Arg Gly Leu Ser
                405                 410                 415 gca gtt aca aac ttt gac atg agc aga tat gat gtc aaa acc ata ctt     1296
Ala Val Thr Asn Phe Asp Met Ser Arg Tyr Asp Val Lys Thr Ile Leu
            420                 425                 430 gag agc agc aca tta cca att ggt ggt gct gca aag cgt tta aaa gac     1344
Glu Ser Ser Thr Leu Pro Ile Gly Gly Ala Ala Lys Arg Leu Lys Asp
        435                 440                 445 atg gag caa gtt gaa ttg aat cat gtg aat gtt gat att agc cat aga     1392
Met Glu Gln Val Glu Leu Asn His Val Asn Val Asp Ile Ser His Arg
    450                 455                 460 act gaa caa gat cat agc atc atc aac aac act tcc cat tta aca gaa     1440
Thr Glu Gln Asp His Ser Ile Ile Asn Asn Thr Ser His Leu Thr Glu
465                 470                 475                 480 caa gcc atc tat gca gca aca aat gca tct aat tgg cat gca ctt tca     1488
Gln Ala Ile Tyr Ala Ala Thr Asn Ala Ser Asn Trp His Ala Leu Ser
                485                 490                 495 ttc caa cat caa caa cca cat cat cat tac aat gcc aac aac atg cag     1536
Phe Gln His Gln Gln Pro His His His Tyr Asn Ala Asn Asn Met Gln
            500                 505                 510 tta cag aat tat cct tat gga act caa act caa aag ctt tgg tgc aaa     1584
Leu Gln Asn Tyr Pro Tyr Gly Thr Gln Thr Gln Lys Leu Trp Cys Lys
        515                 520                 525 caa gaa caa gat tct gat gat cat agt act tat act act gct act gat     1632
Gln Glu Gln Asp Ser Asp Asp His Ser Thr Tyr Thr Thr Ala Thr Asp
    530                 535                 540 att cat caa cta cag tta ggg aat aat aat aac aat act cac aat ttc     1680
Ile His Gln Leu Gln Leu Gly Asn Asn Asn Asn Asn Thr His Asn Phe
545                 550                 555                 560
```

```
ttt ggt tta caa aat atc atg agt atg gat tct gct tcc atg gat aat    1728
Phe Gly Leu Gln Asn Ile Met Ser Met Asp Ser Ala Ser Met Asp Asn
            565                 570                 575 agt tct gga tct aat tct gtt gtt tat ggt ggt gga gat cat ggt ggt    1776
Ser Ser Gly Ser Asn Ser Val Val Tyr Gly Gly Gly Asp His Gly Gly
        580                 585                 590 tat gga gga aat ggt gga tat atg att cca atg gct att gca aat gat    1824
Tyr Gly Gly Asn Gly Gly Tyr Met Ile Pro Met Ala Ile Ala Asn Asp
    595                 600                 605 ggt aac caa aat cca aga agc aac aac aat ttt ggt gag agt gag att    1872
Gly Asn Gln Asn Pro Arg Ser Asn Asn Asn Phe Gly Glu Ser Glu Ile
610                 615                 620 aaa gga ttt ggt tat gaa aat gtt ttt ggg act act act gat cct tat    1920
Lys Gly Phe Gly Tyr Glu Asn Val Phe Gly Thr Thr Thr Asp Pro Tyr
625                 630                 635                 640 cat gca cag gca gca agg aac ttg tac tat cag cca caa caa tta tct    1968
His Ala Gln Ala Ala Arg Asn Leu Tyr Tyr Gln Pro Gln Gln Leu Ser
            645                 650                 655 gtt gat caa gga tca aat tgg gtt cca act gct att cca aca ctt gct    2016
Val Asp Gln Gly Ser Asn Trp Val Pro Thr Ala Ile Pro Thr Leu Ala
        660                 665                 670 cca agg act acc aat gtc tct cta tgt cct cct ttc act ttg ttg cat    2064
Pro Arg Thr Thr Asn Val Ser Leu Cys Pro Pro Phe Thr Leu Leu His
    675                 680                 685 gaa tag                                                            2070
Glu

<210> SEQ ID NO 8
<211> LENGTH: 689
<212> TYPE: PRT
<213> ORGANISM: Medicago truncatula

<400> SEQUENCE: 8

Met Ala Ser Met Asn Leu Leu Gly Phe Ser Leu Ser Pro Gln Glu Gln
1               5                   10                  15

His Pro Ser Thr Gln Asp Gln Thr Val Ala Ser Arg Phe Gly Phe Asn
            20                  25                  30

Pro Asn Glu Ile Ser Gly Ser Asp Val Gln Gly Asp His Cys Tyr Asp
        35                  40                  45

Leu Ser Ser His Thr Thr Pro His His Ser Leu Asn Leu Ser His Pro
    50                  55                  60

Phe Ser Ile Tyr Glu Ala Phe His Thr Asn Asn Ile His Thr Thr
65                  70                  75                  80

Gln Asp Trp Lys Glu Asn Tyr Asn Asn Gln Asn Leu Leu Leu Gly Thr
                85                  90                  95

Ser Cys Met Asn Gln Asn Val Asn Asn Asn Gln Gln Ala Gln Pro
            100                 105                 110

Lys Leu Glu Asn Phe Leu Gly Gly His Ser Phe Thr Asp His Gln Glu
        115                 120                 125

Tyr Gly Gly Ser Asn Ser Tyr Ser Ser Leu His Leu Pro Pro His Gln
    130                 135                 140

Pro Glu Ala Ser Cys Gly Gly Asp Gly Ser Thr Ser Asn Asn Asn
145                 150                 155                 160

Ser Ile Gly Leu Ser Met Ile Lys Thr Trp Leu Arg Asn Gln Pro Pro
                165                 170                 175

Pro Pro Glu Asn Asn Asn Asn Asn Asn Glu Ser Gly Ala Arg Val
            180                 185                 190
```

```
Gln Thr Leu Ser Leu Ser Met Ser Thr Gly Ser Gln Ser Ser Ser
        195                 200                 205

Val Pro Leu Leu Asn Ala Asn Val Met Ser Gly Glu Ile Ser Ser Ser
    210                 215                 220

Glu Asn Lys Gln Pro Pro Thr Thr Ala Val Val Leu Asp Ser Asn Gln
225                 230                 235                 240

Thr Ser Val Val Glu Ser Ala Val Pro Arg Lys Ser Val Asp Thr Phe
                245                 250                 255

Gly Gln Arg Thr Ser Ile Tyr Arg Gly Val Thr Arg His Arg Trp Thr
            260                 265                 270

Gly Arg Tyr Glu Ala His Leu Trp Asp Asn Ser Cys Arg Arg Glu Gly
        275                 280                 285

Gln Thr Arg Lys Gly Arg Gln Val Tyr Leu Gly Gly Tyr Asp Lys Glu
    290                 295                 300

Glu Lys Ala Ala Arg Ala Tyr Asp Leu Ala Ala Leu Lys Tyr Trp Gly
305                 310                 315                 320

Thr Thr Thr Thr Thr Asn Phe Pro Ile Ser His Tyr Glu Lys Glu Val
                325                 330                 335

Glu Glu Met Lys His Met Thr Arg Gln Glu Tyr Val Ala Ser Leu Arg
            340                 345                 350

Arg Lys Ser Ser Gly Phe Ser Arg Gly Ala Ser Ile Tyr Arg Gly Val
        355                 360                 365

Thr Arg His His Gln His Gly Arg Trp Gln Ala Arg Ile Gly Arg Val
    370                 375                 380

Ala Gly Asn Lys Asp Leu Tyr Leu Gly Thr Phe Ser Thr Gln Glu Glu
385                 390                 395                 400

Ala Ala Glu Ala Tyr Asp Val Ala Ala Ile Lys Phe Arg Gly Leu Ser
                405                 410                 415

Ala Val Thr Asn Phe Asp Met Ser Arg Tyr Asp Val Lys Thr Ile Leu
            420                 425                 430

Glu Ser Ser Thr Leu Pro Ile Gly Gly Ala Ala Lys Arg Leu Lys Asp
        435                 440                 445

Met Glu Gln Val Glu Leu Asn His Val Asn Val Asp Ile Ser His Arg
    450                 455                 460

Thr Glu Gln Asp His Ser Ile Ile Asn Asn Thr Ser His Leu Thr Glu
465                 470                 475                 480

Gln Ala Ile Tyr Ala Ala Thr Asn Ala Ser Asn Trp His Ala Leu Ser
                485                 490                 495

Phe Gln His Gln Gln Pro His His His Tyr Asn Ala Asn Asn Met Gln
            500                 505                 510

Leu Gln Asn Tyr Pro Tyr Gly Thr Gln Thr Gln Lys Leu Trp Cys Lys
        515                 520                 525

Gln Glu Gln Asp Ser Asp Asp His Ser Thr Tyr Thr Thr Ala Thr Asp
    530                 535                 540

Ile His Gln Leu Gln Leu Gly Asn Asn Asn Asn Thr His Asn Phe
545                 550                 555                 560

Phe Gly Leu Gln Asn Ile Met Ser Met Asp Ser Ala Ser Met Asp Asn
                565                 570                 575

Ser Ser Gly Ser Asn Ser Val Val Tyr Gly Gly Asp His Gly Gly
            580                 585                 590

Tyr Gly Gly Asn Gly Gly Tyr Met Ile Pro Met Ala Ile Ala Asn Asp
        595                 600                 605
```

```
Gly Asn Gln Asn Pro Arg Ser Asn Asn Asn Phe Gly Glu Ser Glu Ile
        610                 615                 620

Lys Gly Phe Gly Tyr Glu Asn Val Phe Gly Thr Thr Thr Asp Pro Tyr
625                 630                 635                 640

His Ala Gln Ala Ala Arg Asn Leu Tyr Tyr Gln Pro Gln Gln Leu Ser
                645                 650                 655

Val Asp Gln Gly Ser Asn Trp Val Pro Thr Ala Ile Pro Thr Leu Ala
            660                 665                 670

Pro Arg Thr Thr Asn Val Ser Leu Cys Pro Pro Phe Thr Leu Leu His
        675                 680                 685

Glu

<210> SEQ ID NO 9
<211> LENGTH: 2130
<212> TYPE: DNA
<213> ORGANISM: Zea mays
<220> FEATURE:
<221> NAME/KEY: CDS
<222> LOCATION: (1)...(2130)

<400> SEQUENCE: 9 atg gcc act gtg aac aac tgg ctc gct ttc tcc ctc tcc ccg cag gag      48
Met Ala Thr Val Asn Asn Trp Leu Ala Phe Ser Leu Ser Pro Gln Glu
 1               5                  10                  15 ctg ccg ccc tcc cag acg acg gac tcc acg ctc atc tcg gcc gcc acc      96
Leu Pro Pro Ser Gln Thr Thr Asp Ser Thr Leu Ile Ser Ala Ala Thr
                20                  25                  30 gcc gac cat gtc tcc ggc gat gtc tgc ttc aac atc ccc caa gat tgg     144
Ala Asp His Val Ser Gly Asp Val Cys Phe Asn Ile Pro Gln Asp Trp
            35                  40                  45 agc atg agg gga tca gag ctt tcg gcg ctc gtc gcg gag ccg aag ctg     192
Ser Met Arg Gly Ser Glu Leu Ser Ala Leu Val Ala Glu Pro Lys Leu
        50                  55                  60 gag gac ttc ctc ggc ggc atc tcc ttc tcc gag cag cat cac aag tcc     240
Glu Asp Phe Leu Gly Gly Ile Ser Phe Ser Glu Gln His His Lys Ser
 65                 70                  75                  80 aac tgc aac ttg ata ccc agc act agc agc aca gtt tgc tac gcg agc     288
Asn Cys Asn Leu Ile Pro Ser Thr Ser Ser Thr Val Cys Tyr Ala Ser
                85                  90                  95 tca gct gct agc acc ggc tac cat cac cag ctg tac cag ccc acc agc     336
Ser Ala Ala Ser Thr Gly Tyr His His Gln Leu Tyr Gln Pro Thr Ser
                100                 105                 110 tcc gcg ctc cac ttc gcg gac tcc gtc atg gtg gcc tcc tcg gcc ggt     384
Ser Ala Leu His Phe Ala Asp Ser Val Met Val Ala Ser Ser Ala Gly
            115                 120                 125 gtc cac gac ggc ggt tcc atg ctc agc gcg gcc gcc gct aac ggt gtc     432
Val His Asp Gly Gly Ser Met Leu Ser Ala Ala Ala Ala Asn Gly Val
        130                 135                 140 gct ggc gct gcc agt gcc aac ggc ggc ggc atc ggg ctg tcc atg atc     480
Ala Gly Ala Ala Ser Ala Asn Gly Gly Gly Ile Gly Leu Ser Met Ile
145                 150                 155                 160 aag aac tgg ctg cgg agc caa ccg gcg ccc atg cag ccg agg gcg gcg     528
Lys Asn Trp Leu Arg Ser Gln Pro Ala Pro Met Gln Pro Arg Ala Ala
                165                 170                 175 gcg gct gag ggc gcg cag ggc ctc tct ttg tcc atg aac atg gcg ggg     576
Ala Ala Glu Gly Ala Gln Gly Leu Ser Leu Ser Met Asn Met Ala Gly
            180                 185                 190 acg acc caa ggc gct gct ggc atg cca ctt ctc gct gga gag cgc gca     624
Thr Thr Gln Gly Ala Ala Gly Met Pro Leu Leu Ala Gly Glu Arg Ala
        195                 200                 205
```

-continued

| | | |
|---|---|---|
| cgg gcg ccc gag agt gta tcg acg tca gca cag ggt ggt gcc gtc gtc<br>Arg Ala Pro Glu Ser Val Ser Thr Ser Ala Gln Gly Gly Ala Val Val<br>210                                  215                            220 | 672 |
| gtc acg gcg ccg aag gag gat agc ggt ggc agc ggt gtt gcc ggt gct<br>Val Thr Ala Pro Lys Glu Asp Ser Gly Gly Ser Gly Val Ala Gly Ala<br>225                             230                              235                        240 | 720 |
| cta gta gcc gtg agc acg gac acg ggt ggc agc ggc ggc gcg tcg gct<br>Leu Val Ala Val Ser Thr Asp Thr Gly Gly Ser Gly Gly Ala Ser Ala<br>                                 245                              250                        255 | 768 |
| gac aac acg gca agg aag acg gtg gac acg ttc ggg cag cgc acg tcg<br>Asp Asn Thr Ala Arg Lys Thr Val Asp Thr Phe Gly Gln Arg Thr Ser<br>                            260                              265                             270 | 816 |
| att tac cgt ggc gtg aca agg cat aga tgg act ggg aga tat gag gca<br>Ile Tyr Arg Gly Val Thr Arg His Arg Trp Thr Gly Arg Tyr Glu Ala<br>              275                            280                             285 | 864 |
| cat ctt tgg gat aac agt tgc aga agg gaa gga caa act cgt aag ggt<br>His Leu Trp Asp Asn Ser Cys Arg Arg Glu Gly Gln Thr Arg Lys Gly<br>              290                            295                             300 | 912 |
| cgt caa gtc tat tta ggt ggc tat gat aaa gag gag aaa gct gct agg<br>Arg Gln Val Tyr Leu Gly Gly Tyr Asp Lys Glu Glu Lys Ala Ala Arg<br>305                                310                              315                        320 | 960 |
| gct tat gat ctt gct gct ctg aag tac tgg ggt gcc aca aca aca aca<br>Ala Tyr Asp Leu Ala Ala Leu Lys Tyr Trp Gly Ala Thr Thr Thr Thr<br>                                325                              330                        335 | 1008 |
| aat ttt cca gtg agt aac tac gaa aag gag ctc gag gac atg aag cac<br>Asn Phe Pro Val Ser Asn Tyr Glu Lys Glu Leu Glu Asp Met Lys His<br>                                 340                             345                             350 | 1056 |
| atg aca agg cag gag ttt gta gcg tct ctg aga agg aag agc agt ggt<br>Met Thr Arg Gln Glu Phe Val Ala Ser Leu Arg Arg Lys Ser Ser Gly<br>              355                            360                             365 | 1104 |
| ttc tcc aga ggt gca tcc att tac agg gga gtg act agg cat cac caa<br>Phe Ser Arg Gly Ala Ser Ile Tyr Arg Gly Val Thr Arg His His Gln<br>              370                            375                             380 | 1152 |
| cat gga aga tgg caa gca cgg att gga cga gtt gca ggg aac aag gat<br>His Gly Arg Trp Gln Ala Arg Ile Gly Arg Val Ala Gly Asn Lys Asp<br>385                                390                              395                        400 | 1200 |
| ctt tac ttg ggc acc ttc agc acc cag gag gag gca gcg gag gcg tac<br>Leu Tyr Leu Gly Thr Phe Ser Thr Gln Glu Glu Ala Ala Glu Ala Tyr<br>                                 405                             410                             415 | 1248 |
| gac atc gcg gcg atc aag ttc cgc ggc ctc aac gcc gtc acc aac ttc<br>Asp Ile Ala Ala Ile Lys Phe Arg Gly Leu Asn Ala Val Thr Asn Phe<br>                            420                              425                             430 | 1296 |
| gac atg agc cgc tac gac gtg aag agc atc ctg gac agc agc gcc ctc<br>Asp Met Ser Arg Tyr Asp Val Lys Ser Ile Leu Asp Ser Ser Ala Leu<br>              435                            440                             445 | 1344 |
| ccc atc ggc agc gcc gcc aag cgt ctc aag gag gcc gag gcc gca gcg<br>Pro Ile Gly Ser Ala Ala Lys Arg Leu Lys Glu Ala Glu Ala Ala Ala<br>450                                455                              460 | 1392 |
| tcc gcg cag cac cac cac gcc ggc gtg gtg agc tac gac gtc ggc cgc<br>Ser Ala Gln His His His Ala Gly Val Val Ser Tyr Asp Val Gly Arg<br>465                                470                              475                        480 | 1440 |
| atc gcc tcg cag ctc ggc gac ggc gga gcc cta gcg gcg gcg tac ggc<br>Ile Ala Ser Gln Leu Gly Asp Gly Gly Ala Leu Ala Ala Ala Tyr Gly<br>                                 485                             490                             495 | 1488 |
| gcg cac tac cac ggc gcc gcc tgg ccg acc atc gcg ttc cag ccg ggc<br>Ala His Tyr His Gly Ala Ala Trp Pro Thr Ile Ala Phe Gln Pro Gly<br>                                 500                             505                             510 | 1536 |
| gcc gcc acc aca ggc ctg tac cac ccg tac gcg cag cag cca atg cgc<br>Ala Ala Thr Thr Gly Leu Tyr His Pro Tyr Ala Gln Gln Pro Met Arg | 1584 |

```
                515                 520                 525
ggc ggc ggg tgg tgc aag cag gag cag gac cac gcg gtg atc gcg gcc      1632
Gly Gly Gly Trp Cys Lys Gln Glu Gln Asp His Ala Val Ile Ala Ala
530                 535                 540 gcg cac agc ctg cag gac ctc cac cac ttg aac ctg ggc gcg gcc ggc      1680
Ala His Ser Leu Gln Asp Leu His His Leu Asn Leu Gly Ala Ala Gly
545                 550                 555                 560 gcg cac gac ttt ttc tcg gca ggg cag cag gcc gcc gcc gca gct gcg      1728
Ala His Asp Phe Phe Ser Ala Gly Gln Gln Ala Ala Ala Ala Ala Ala
                565                 570                 575 atg cac ggc ctg gct agc atc gac agt gcg tcg ctc gag cac agc acc      1776
Met His Gly Leu Ala Ser Ile Asp Ser Ala Ser Leu Glu His Ser Thr
580                 585                 590 ggc tcc aac tcc gtc gtc tac aac ggc ggg gtc ggc gat agc aac ggc      1824
Gly Ser Asn Ser Val Val Tyr Asn Gly Gly Val Gly Asp Ser Asn Gly
595                 600                 605 gcc agc gcc gtt ggc agc ggc ggt ggc tac atg atg ccg atg agc gct      1872
Ala Ser Ala Val Gly Ser Gly Gly Gly Tyr Met Met Pro Met Ser Ala
610                 615                 620 gcc gga gca acc act aca tcg gca atg gtg agc cac gag cag atg cat      1920
Ala Gly Ala Thr Thr Thr Ser Ala Met Val Ser His Glu Gln Met His
625                 630                 635                 640 gca cgg gcc tac gac gaa gcc aag cag gct gct cag atg ggg tac gag      1968
Ala Arg Ala Tyr Asp Glu Ala Lys Gln Ala Ala Gln Met Gly Tyr Glu
                645                 650                 655 agc tac ctg gtg aac gcg gag aac aat ggt ggc gga agg atg tct gca      2016
Ser Tyr Leu Val Asn Ala Glu Asn Asn Gly Gly Gly Arg Met Ser Ala
660                 665                 670 tgg ggg acc gtc gtc tct gca gcc gcg gcg gca gca gca agc agc aac      2064
Trp Gly Thr Val Val Ser Ala Ala Ala Ala Ala Ala Ser Ser Asn
675                 680                 685 gac aac att gcc gcc gac gtc ggc cat ggc ggc gcg cag ctc ttc agt      2112
Asp Asn Ile Ala Ala Asp Val Gly His Gly Gly Ala Gln Leu Phe Ser
690                 695                 700 gtc tgg aac gac act taa                                              2130
Val Trp Asn Asp Thr
705

<210> SEQ ID NO 10
<211> LENGTH: 709
<212> TYPE: PRT
<213> ORGANISM: Zea mays

<400> SEQUENCE: 10

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ser
65                  70                  75                  80

Asn Cys Asn Leu Ile Pro Ser Thr Ser Thr Val Cys Tyr Ala Ser
                85                  90                  95

Ser Ala Ala Ser Thr Gly Tyr His His Gln Leu Tyr Gln Pro Thr Ser
            100                 105                 110

Ser Ala Leu His Phe Ala Asp Ser Val Met Val Ala Ser Ser Ala Gly
```

```
            115                 120                 125
Val His Asp Gly Gly Ser Met Leu Ser Ala Ala Ala Asn Gly Val
130                 135                 140

Ala Gly Ala Ala Ser Ala Asn Gly Gly Gly Ile Gly Leu Ser Met Ile
145                 150                 155                 160

Lys Asn Trp Leu Arg Ser Gln Pro Ala Pro Met Gln Pro Arg Ala Ala
                165                 170                 175

Ala Ala Glu Gly Ala Gln Gly Leu Ser Leu Ser Met Asn Met Ala Gly
                180                 185                 190

Thr Thr Gln Gly Ala Ala Gly Met Pro Leu Leu Ala Gly Glu Arg Ala
                195                 200                 205

Arg Ala Pro Glu Ser Val Ser Thr Ser Ala Gln Gly Gly Ala Val Val
210                 215                 220

Val Thr Ala Pro Lys Glu Asp Ser Gly Gly Ser Gly Val Ala Gly Ala
225                 230                 235                 240

Leu Val Ala Val Ser Thr Asp Thr Gly Gly Ser Gly Gly Ala Ser Ala
                245                 250                 255

Asp Asn Thr Ala Arg Lys Thr Val Asp Thr Phe Gly Gln Arg Thr Ser
                260                 265                 270

Ile Tyr Arg Gly Val Thr Arg His Arg Trp Thr Gly Arg Tyr Glu Ala
                275                 280                 285

His Leu Trp Asp Asn Ser Cys Arg Arg Glu Gly Gln Thr Arg Lys Gly
                290                 295                 300

Arg Gln Val Tyr Leu Gly Gly Tyr Asp Lys Glu Glu Lys Ala Ala Arg
305                 310                 315                 320

Ala Tyr Asp Leu Ala Ala Leu Lys Tyr Trp Gly Ala Thr Thr Thr Thr
                325                 330                 335

Asn Phe Pro Val Ser Asn Tyr Glu Lys Glu Leu Glu Asp Met Lys His
                340                 345                 350

Met Thr Arg Gln Glu Phe Val Ala Ser Leu Arg Arg Lys Ser Ser Gly
                355                 360                 365

Phe Ser Arg Gly Ala Ser Ile Tyr Arg Gly Val Thr Arg His His Gln
370                 375                 380

His Gly Arg Trp Gln Ala Arg Ile Gly Arg Val Ala Gly Asn Lys Asp
385                 390                 395                 400

Leu Tyr Leu Gly Thr Phe Ser Thr Gln Glu Glu Ala Ala Glu Ala Tyr
                405                 410                 415

Asp Ile Ala Ala Ile Lys Phe Arg Gly Leu Asn Ala Val Thr Asn Phe
                420                 425                 430

Asp Met Ser Arg Tyr Asp Val Lys Ser Ile Leu Asp Ser Ser Ala Leu
                435                 440                 445

Pro Ile Gly Ser Ala Ala Lys Arg Leu Lys Glu Ala Glu Ala Ala Ala
                450                 455                 460

Ser Ala Gln His His His Ala Gly Val Val Ser Tyr Asp Val Gly Arg
465                 470                 475                 480

Ile Ala Ser Gln Leu Gly Asp Gly Gly Ala Leu Ala Ala Ala Tyr Gly
                485                 490                 495

Ala His Tyr His Gly Ala Ala Trp Pro Thr Ile Ala Phe Gln Pro Gly
                500                 505                 510

Ala Ala Thr Thr Gly Leu Tyr His Pro Tyr Ala Gln Gln Pro Met Arg
                515                 520                 525

Gly Gly Gly Trp Cys Lys Gln Glu Gln Asp His Ala Val Ile Ala Ala
530                 535                 540
```

```
Ala His Ser Leu Gln Asp Leu His His Leu Asn Leu Gly Ala Ala Gly
545                 550                 555                 560

Ala His Asp Phe Phe Ser Ala Gly Gln Gln Ala Ala Ala Ala Ala Ala
                565                 570                 575

Met His Gly Leu Ala Ser Ile Asp Ser Ala Ser Leu Glu His Ser Thr
            580                 585                 590

Gly Ser Asn Ser Val Val Tyr Asn Gly Gly Val Gly Asp Ser Asn Gly
        595                 600                 605

Ala Ser Ala Val Gly Ser Gly Gly Tyr Met Met Pro Met Ser Ala
    610                 615                 620

Ala Gly Ala Thr Thr Ser Ala Met Val Ser His Glu Gln Met His
625                 630                 635                 640

Ala Arg Ala Tyr Asp Glu Ala Lys Gln Ala Ala Gln Met Gly Tyr Glu
                645                 650                 655

Ser Tyr Leu Val Asn Ala Glu Asn Asn Gly Gly Gly Arg Met Ser Ala
            660                 665                 670

Trp Gly Thr Val Val Ser Ala Ala Ala Ala Ala Ala Ser Ser Asn
        675                 680                 685

Asp Asn Ile Ala Ala Asp Val Gly His Gly Gly Ala Gln Leu Phe Ser
690                 695                 700

Val Trp Asn Asp Thr
705

<210> SEQ ID NO 11
<211> LENGTH: 2040
<212> TYPE: DNA
<213> ORGANISM: Zea mays
<220> FEATURE:
<221> NAME/KEY: CDS
<222> LOCATION: (1)...(2040)

<400> SEQUENCE: 11 atg gct tca gcg aac aac tgg ctg ggc ttc tcg ctc tcg ggc cag gat     48
Met Ala Ser Ala Asn Asn Trp Leu Gly Phe Ser Leu Ser Gly Gln Asp
  1               5                  10                  15 aac ccg cag cct aac cag gat agc tcg cct gcc gcc ggt atc gac atc     96
Asn Pro Gln Pro Asn Gln Asp Ser Ser Pro Ala Ala Gly Ile Asp Ile
             20                  25                  30 tcc ggc gcc agc gac ttc tat ggc ctg ccc acg cag cag ggc tcc gac    144
Ser Gly Ala Ser Asp Phe Tyr Gly Leu Pro Thr Gln Gln Gly Ser Asp
         35                  40                  45 ggg cat ctc ggc gtg ccg ggc ctg cgg gac gat cac gct tct tat ggt    192
Gly His Leu Gly Val Pro Gly Leu Arg Asp Asp His Ala Ser Tyr Gly
     50                  55                  60 atc atg gag gcc tac aac agg gtt cct caa gaa acc caa gat tgg aac    240
Ile Met Glu Ala Tyr Asn Arg Val Pro Gln Glu Thr Gln Asp Trp Asn
 65                  70                  75                  80 atg agg ggc ttg gac tac aac ggc ggt ggc tcg gag ctc tcg atg ctt    288
Met Arg Gly Leu Asp Tyr Asn Gly Gly Gly Ser Glu Leu Ser Met Leu
                 85                  90                  95 gtg ggg tcc agc ggc ggc ggc ggg ggc aac ggc aag agg gcc gtg gaa    336
Val Gly Ser Ser Gly Gly Gly Gly Gly Asn Gly Lys Arg Ala Val Glu
            100                 105                 110 gac agc gag ccc aag ctc gaa gat ttc ctc ggc ggc aac tcg ttc gtc    384
Asp Ser Glu Pro Lys Leu Glu Asp Phe Leu Gly Gly Asn Ser Phe Val
        115                 120                 125 tcc gat caa gat cag tcc ggc ggt tac ctg ttc tct gga gtc ccg ata    432
Ser Asp Gln Asp Gln Ser Gly Gly Tyr Leu Phe Ser Gly Val Pro Ile
    130                 135                 140
```

```
                130             135             140
gcc agc agc gcc aat agc aac agc ggg agc aac acc atg gag ctc tcc      480
Ala Ser Ser Ala Asn Ser Asn Ser Gly Ser Asn Thr Met Glu Leu Ser
145                 150                 155                 160 atg atc aag acc tgg cta cgg aac aac cag gtg gcc cag ccc cag ccg      528
Met Ile Lys Thr Trp Leu Arg Asn Asn Gln Val Ala Gln Pro Gln Pro
                165                 170                 175 cca gct cca cat cag ccg cag cct gag gaa atg agc acc gac gcc agc      576
Pro Ala Pro His Gln Pro Gln Pro Glu Glu Met Ser Thr Asp Ala Ser
            180                 185                 190 ggc agc agc ttt gga tgc tcg gat tcg atg gga agg aac agc atg gtg      624
Gly Ser Ser Phe Gly Cys Ser Asp Ser Met Gly Arg Asn Ser Met Val
        195                 200                 205 gcg gct ggt ggg agc tcg cag agc ctg gcg ctc tcg atg agc acg ggc      672
Ala Ala Gly Gly Ser Ser Gln Ser Leu Ala Leu Ser Met Ser Thr Gly
    210                 215                 220 tcg cac ctg ccc atg gtt gtg ccc agc ggc gcc gcc agc gga gcg gcc      720
Ser His Leu Pro Met Val Val Pro Ser Gly Ala Ala Ser Gly Ala Ala
225                 230                 235                 240 tcg gag agc aca tcg tcg gag aac aag cga gcg agc ggt gcc atg gat      768
Ser Glu Ser Thr Ser Ser Glu Asn Lys Arg Ala Ser Gly Ala Met Asp
                245                 250                 255 tcg ccc ggc agc gcg gta gaa gcc gta ccg agg aag tcc atc gac acg      816
Ser Pro Gly Ser Ala Val Glu Ala Val Pro Arg Lys Ser Ile Asp Thr
            260                 265                 270 ttc ggg caa agg acc tct ata tat cga ggt gta aca agg cat aga tgg      864
Phe Gly Gln Arg Thr Ser Ile Tyr Arg Gly Val Thr Arg His Arg Trp
        275                 280                 285 aca ggg cgg tat gag gct cat cta tgg gat aat agt tgt aga agg gaa      912
Thr Gly Arg Tyr Glu Ala His Leu Trp Asp Asn Ser Cys Arg Arg Glu
    290                 295                 300 ggg cag agt cgc aag ggt agg caa gtt tac ctt ggt ggc tat gac aag      960
Gly Gln Ser Arg Lys Gly Arg Gln Val Tyr Leu Gly Gly Tyr Asp Lys
305                 310                 315                 320 gag gac aag gca gca agg gct tat gat ttg gca gct ctc aag tat tgg     1008
Glu Asp Lys Ala Ala Arg Ala Tyr Asp Leu Ala Ala Leu Lys Tyr Trp
                325                 330                 335 ggc act acg aca aca aca aat ttc cct ata agc aac tac gaa aag gag     1056
Gly Thr Thr Thr Thr Thr Asn Phe Pro Ile Ser Asn Tyr Glu Lys Glu
            340                 345                 350 cta gaa gaa atg aaa cat atg act aga cag gag tac att gca tac cta     1104
Leu Glu Glu Met Lys His Met Thr Arg Gln Glu Tyr Ile Ala Tyr Leu
        355                 360                 365 aga aga aat agc agt gga ttt tct cgt ggg gcg tca aag tat cgt gga     1152
Arg Arg Asn Ser Ser Gly Phe Ser Arg Gly Ala Ser Lys Tyr Arg Gly
    370                 375                 380 gta act aga cat cat cag cat ggg aga tgg caa gca agg ata ggg aga     1200
Val Thr Arg His His Gln His Gly Arg Trp Gln Ala Arg Ile Gly Arg
385                 390                 395                 400 gtt gca gga aac aag gat ctc tac ttg ggc aca ttc agc acc gag gag     1248
Val Ala Gly Asn Lys Asp Leu Tyr Leu Gly Thr Phe Ser Thr Glu Glu
                405                 410                 415 gag gcg gcg gag gcc tac gac atc gcc gcg atc aag ttc cgc ggt ctc     1296
Glu Ala Ala Glu Ala Tyr Asp Ile Ala Ala Ile Lys Phe Arg Gly Leu
            420                 425                 430 aac gcc gtc acc aac ttc gac atg agc cgc tac gac gtg aag agc atc     1344
Asn Ala Val Thr Asn Phe Asp Met Ser Arg Tyr Asp Val Lys Ser Ile
        435                 440                 445 ctc gag agc agc aca ctg cct gtc ggc ggt gcg gcc agg cgc ctc aag     1392
```

```
Leu Glu Ser Ser Thr Leu Pro Val Gly Gly Ala Ala Arg Arg Leu Lys
        450                 455                 460 gac gcc gtg gac cac gtg gag gcc ggc gcc acc atc tgg cgc gcc gac      1440
Asp Ala Val Asp His Val Glu Ala Gly Ala Thr Ile Trp Arg Ala Asp
465                 470                 475                 480 atg gac ggc gcc gtg atc tcc cag ctg gcc gaa gcc ggg atg ggc ggc      1488
Met Asp Gly Ala Val Ile Ser Gln Leu Ala Glu Ala Gly Met Gly Gly
                485                 490                 495 tac gcc tcg tac ggc cac cac ggc tgg ccg acc atc gcg ttc cag cag      1536
Tyr Ala Ser Tyr Gly His His Gly Trp Pro Thr Ile Ala Phe Gln Gln
            500                 505                 510 ccg tcg ccg ctc tcc gtc cac tac ccg tac ggc cag ccg tcc cgc ggg      1584
Pro Ser Pro Leu Ser Val His Tyr Pro Tyr Gly Gln Pro Ser Arg Gly
        515                 520                 525 tgg tgc aaa ccc gag cag gac gcg gcc gcc gcc gcg gcg cac agc ctg      1632
Trp Cys Lys Pro Glu Gln Asp Ala Ala Ala Ala Ala Ala His Ser Leu
530                 535                 540 cag gac ctc cag cag ctg cac ctc ggc agc gcg gcc cac aac ttc ttc      1680
Gln Asp Leu Gln Gln Leu His Leu Gly Ser Ala Ala His Asn Phe Phe
545                 550                 555                 560 cag gcg tcg tcg agc tcc aca gtc tac aac ggc ggc gcc ggc gcc agt      1728
Gln Ala Ser Ser Ser Ser Thr Val Tyr Asn Gly Gly Ala Gly Ala Ser
                565                 570                 575 ggt ggg tac cag ggc ctc ggt ggt ggc agc tct ttc ctc atg ccg tcg      1776
Gly Gly Tyr Gln Gly Leu Gly Gly Gly Ser Ser Phe Leu Met Pro Ser
            580                 585                 590 agc act gtc gtg gcg gcg gcc gac cag ggg cac agc agc acg gcc aac      1824
Ser Thr Val Val Ala Ala Ala Asp Gln Gly His Ser Ser Thr Ala Asn
        595                 600                 605 cag ggg agc acg tgc agc tac ggg gac gac cac cag gag ggg aag ctc      1872
Gln Gly Ser Thr Cys Ser Tyr Gly Asp Asp His Gln Glu Gly Lys Leu
610                 615                 620 atc ggt tac gac gcc gcc atg gtg gcg acc gca gct ggt gga gac ccg      1920
Ile Gly Tyr Asp Ala Ala Met Val Ala Thr Ala Ala Gly Gly Asp Pro
625                 630                 635                 640 tac gct gcg gcg agg aac ggg tac cag ttc tcg cag ggc tcg gga tcc      1968
Tyr Ala Ala Ala Arg Asn Gly Tyr Gln Phe Ser Gln Gly Ser Gly Ser
                645                 650                 655 acg gtg agc atc gcg agg gcg aac ggg tac gct aac aac tgg agc tct      2016
Thr Val Ser Ile Ala Arg Ala Asn Gly Tyr Ala Asn Asn Trp Ser Ser
            660                 665                 670 cct ttc aac aac ggc atg ggg tga                                      2040
Pro Phe Asn Asn Gly Met Gly
        675

<210> SEQ ID NO 12
<211> LENGTH: 679
<212> TYPE: PRT
<213> ORGANISM: Zea mays

<400> SEQUENCE: 12

Met Ala Ser Ala Asn Asn Trp Leu Gly Phe Ser Leu Ser Gly Gln Asp
1               5                   10                  15

Asn Pro Gln Pro Asn Gln Asp Ser Ser Pro Ala Ala Gly Ile Asp Ile
            20                  25                  30

Ser Gly Ala Ser Asp Phe Tyr Gly Leu Pro Thr Gln Gly Ser Asp
        35                  40                  45

Gly His Leu Gly Val Pro Gly Leu Arg Asp Asp His Ala Ser Tyr Gly
    50                  55                  60

Ile Met Glu Ala Tyr Asn Arg Val Pro Gln Glu Thr Gln Asp Trp Asn
```

-continued

```
            65                  70                  75                  80
Met Arg Gly Leu Asp Tyr Asn Gly Gly Ser Glu Leu Ser Met Leu
                85                  90                  95

Val Gly Ser Ser Gly Gly Gly Gly Asn Gly Lys Arg Ala Val Glu
            100                 105                 110

Asp Ser Glu Pro Lys Leu Glu Asp Phe Leu Gly Gly Asn Ser Phe Val
            115                 120                 125

Ser Asp Gln Asp Gln Ser Gly Gly Tyr Leu Phe Ser Gly Val Pro Ile
        130                 135                 140

Ala Ser Ser Ala Asn Ser Asn Ser Gly Ser Asn Thr Met Glu Leu Ser
145                 150                 155                 160

Met Ile Lys Thr Trp Leu Arg Asn Asn Gln Val Ala Gln Pro Gln Pro
                165                 170                 175

Pro Ala Pro His Gln Pro Gln Pro Glu Glu Met Ser Thr Asp Ala Ser
            180                 185                 190

Gly Ser Ser Phe Gly Cys Ser Asp Ser Met Gly Arg Asn Ser Met Val
            195                 200                 205

Ala Ala Gly Gly Ser Ser Gln Ser Leu Ala Leu Ser Met Ser Thr Gly
        210                 215                 220

Ser His Leu Pro Met Val Val Pro Ser Gly Ala Ala Ser Gly Ala Ala
225                 230                 235                 240

Ser Glu Ser Thr Ser Ser Glu Asn Lys Arg Ala Ser Gly Ala Met Asp
                245                 250                 255

Ser Pro Gly Ser Ala Val Glu Ala Val Pro Arg Lys Ser Ile Asp Thr
            260                 265                 270

Phe Gly Gln Arg Thr Ser Ile Tyr Arg Gly Val Thr Arg His Arg Trp
        275                 280                 285

Thr Gly Arg Tyr Glu Ala His Leu Trp Asp Asn Ser Cys Arg Arg Glu
        290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
            325                 330                 335

Gly Thr Thr Thr Thr Thr Asn Phe Pro Ile Ser Asn Tyr Glu Lys Glu
            340                 345                 350

Leu Glu Glu Met Lys His Met Thr Arg Gln Glu Tyr Ile Ala Tyr Leu
        355                 360                 365

Arg Arg Asn Ser Ser Gly Phe Ser Arg Gly Ala Ser Lys Tyr Arg Gly
        370                 375                 380

Val Thr Arg His His Gln His Gly Arg Trp Gln Ala Arg Ile Gly Arg
385                 390                 395                 400

Val Ala Gly Asn Lys Asp Leu Tyr Leu Gly Thr Phe Ser Thr Glu Glu
            405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
            435                 440                 445

Leu Glu Ser Ser Thr Leu Pro Val Gly Ala Ala Arg Arg Leu Lys
        450                 455                 460

Asp Ala Val Asp His Val Glu Ala Gly Ala Thr Ile Trp Arg Ala Asp
465                 470                 475                 480

Met Asp Gly Ala Val Ile Ser Gln Leu Ala Glu Ala Gly Met Gly Gly
            485                 490                 495
```

```
Tyr Ala Ser Tyr Gly His His Gly Trp Pro Thr Ile Ala Phe Gln Gln
            500                 505                 510

Pro Ser Pro Leu Ser Val His Tyr Pro Tyr Gly Gln Pro Ser Arg Gly
            515                 520                 525

Trp Cys Lys Pro Glu Gln Asp Ala Ala Ala Ala Ala His Ser Leu
            530                 535                 540

Gln Asp Leu Gln Gln Leu His Leu Gly Ser Ala Ala His Asn Phe Phe
545                 550                 555                 560

Gln Ala Ser Ser Ser Thr Val Tyr Asn Gly Gly Ala Gly Ala Ser
            565                 570                 575

Gly Gly Tyr Gln Gly Leu Gly Gly Ser Ser Phe Leu Met Pro Ser
            580                 585                 590

Ser Thr Val Val Ala Ala Asp Gln Gly His Ser Ser Thr Ala Asn
            595                 600                 605

Gln Gly Ser Thr Cys Ser Tyr Gly Asp Asp His Gln Glu Gly Lys Leu
            610                 615                 620

Ile Gly Tyr Asp Ala Ala Met Val Ala Thr Ala Ala Gly Gly Asp Pro
625                 630                 635                 640

Tyr Ala Ala Ala Arg Asn Gly Tyr Gln Phe Ser Gln Gly Ser Gly Ser
                    645                 650                 655

Thr Val Ser Ile Ala Arg Ala Asn Gly Tyr Ala Asn Asn Trp Ser Ser
                    660                 665                 670

Pro Phe Asn Asn Gly Met Gly
            675

<210> SEQ ID NO 13
<211> LENGTH: 2088
<212> TYPE: DNA
<213> ORGANISM: Oryza sativa
<220> FEATURE:
<221> NAME/KEY: CDS
<222> LOCATION: (1)...(2088)

<400> SEQUENCE: 13 atg gcc acc atg aac aac tgg ctg gcc ttc tcc ctc tcc ccg cag gat      48
Met Ala Thr Met Asn Asn Trp Leu Ala Phe Ser Leu Ser Pro Gln Asp
 1               5                  10                  15 cag ctc ccg ccg tct cag acc aac tcc act ctc atc tcc gcc gcc gcc      96
Gln Leu Pro Pro Ser Gln Thr Asn Ser Thr Leu Ile Ser Ala Ala Ala
                20                  25                  30 acc acc acc acc gcc ggc gac tcc tcc acc ggc gac gtc tgc ttc aac     144
Thr Thr Thr Thr Ala Gly Asp Ser Ser Thr Gly Asp Val Cys Phe Asn
            35                  40                  45 atc ccc caa gat tgg agc atg agg gga tcg gag ctc tcg gcg ctc gtc     192
Ile Pro Gln Asp Trp Ser Met Arg Gly Ser Glu Leu Ser Ala Leu Val
        50                  55                  60 gcc gag ccg aag ctg gag gac ttc ctc ggc ggc atc tcc ttc tcg gag     240
Ala Glu Pro Lys Leu Glu Asp Phe Leu Gly Gly Ile Ser Phe Ser Glu
 65                  70                  75                  80 cag cag cat cat cac ggc ggc aag ggc ggc gtg atc ccg agc agc gcc     288
Gln Gln His His His Gly Gly Lys Gly Gly Val Ile Pro Ser Ser Ala
                 85                  90                  95 gcc gct tgc tac gcg agc tcc ggc agc agc gtc ggc tac ctg tac cct     336
Ala Ala Cys Tyr Ala Ser Ser Gly Ser Ser Val Gly Tyr Leu Tyr Pro
            100                 105                 110 cct cca agc tca tcc tcg ctc cag ttc gcc gac tcc gtc atg gtg gcc     384
Pro Pro Ser Ser Ser Ser Leu Gln Phe Ala Asp Ser Val Met Val Ala
        115                 120                 125
```

| | | |
|---|---|---|
| acc tcc tcg ccc gtc gtc gcc cac gac ggc gtc agc ggc ggc ggc atg<br>Thr Ser Ser Pro Val Val Ala His Asp Gly Val Ser Gly Gly Gly Met<br>130                           135                          140 | 432 |
| gtg agc gcc gcc gcc gcc gcg gcg gcc agt ggc aac ggc ggc att ggc<br>Val Ser Ala Ala Ala Ala Ala Ala Ala Ser Gly Asn Gly Gly Ile Gly<br>145                   150                     155                     160 | 480 |
| ctg tcc atg atc aag aac tgg ctc cgg agc cag ccg gcg ccg cag ccg<br>Leu Ser Met Ile Lys Asn Trp Leu Arg Ser Gln Pro Ala Pro Gln Pro<br>                  165                     170                   175 | 528 |
| gcg cag gcg ctg tct ctg tcc atg aac atg gcg ggg acg acg acg gcg<br>Ala Gln Ala Leu Ser Leu Ser Met Asn Met Ala Gly Thr Thr Thr Ala<br>                180                     185                     190 | 576 |
| cag ggc ggc ggc gcc atg gcg ctc ctc gcc ggc gca ggg gag cga ggc<br>Gln Gly Gly Gly Ala Met Ala Leu Leu Ala Gly Ala Gly Glu Arg Gly<br>         195                     200                     205 | 624 |
| cgg acg acg ccc gcg tca gag agc ctg tcc acg tcg gcg cac gga gcg<br>Arg Thr Thr Pro Ala Ser Glu Ser Leu Ser Thr Ser Ala His Gly Ala<br>210                           215                          220 | 672 |
| acg acg gcg acg atg gct ggt ggt cgc aag gag att aac gag gaa ggc<br>Thr Thr Ala Thr Met Ala Gly Gly Arg Lys Glu Ile Asn Glu Glu Gly<br>225                         230                     235                   240 | 720 |
| agc ggc agc gcc ggc gcc gtg gtt gcc gtc ggc tcg gag tca ggc ggc<br>Ser Gly Ser Ala Gly Ala Val Val Ala Val Gly Ser Glu Ser Gly Gly<br>                     245                     250                   255 | 768 |
| agc ggc gcc gtg gtg gag gcc ggc gcg gcg gcg gcg gcg gcg agg aag<br>Ser Gly Ala Val Val Glu Ala Gly Ala Ala Ala Ala Ala Ala Arg Lys<br>                260                     265                     270 | 816 |
| tcc gtc gac acg ttc ggc cag aga aca tcg atc tac cgc ggc gtg aca<br>Ser Val Asp Thr Phe Gly Gln Arg Thr Ser Ile Tyr Arg Gly Val Thr<br>         275                     280                     285 | 864 |
| agg cat aga tgg aca ggg agg tat gag gct cat ctt tgg gac aac agc<br>Arg His Arg Trp Thr Gly Arg Tyr Glu Ala His Leu Trp Asp Asn Ser<br>290                           295                     300 | 912 |
| tgc aga aga gag ggc caa act cgc aag ggt cgt caa gtc tat cta ggt<br>Cys Arg Arg Glu Gly Gln Thr Arg Lys Gly Arg Gln Val Tyr Leu Gly<br>305                         310                     315                   320 | 960 |
| ggt tat gac aaa gag gaa aaa gct gct aga gct tat gat ttg gct gct<br>Gly Tyr Asp Lys Glu Glu Lys Ala Ala Arg Ala Tyr Asp Leu Ala Ala<br>                     325                     330                   335 | 1008 |
| ctc aaa tac tgg ggc ccg acg acg aca aat ttt ccg gta aat aac<br>Leu Lys Tyr Trp Gly Pro Thr Thr Thr Asn Phe Pro Val Asn Asn<br>340                           345                     350 | 1056 |
| tat gaa aag gag ctg gag gag atg aag cac atg aca agg cag gag ttc<br>Tyr Glu Lys Glu Leu Glu Glu Met Lys His Met Thr Arg Gln Glu Phe<br>                355                     360                     365 | 1104 |
| gta gcc tct ttg aga agg aag agc agt ggt ttc tcc aga ggt gca tcc<br>Val Ala Ser Leu Arg Arg Lys Ser Ser Gly Phe Ser Arg Gly Ala Ser<br>370                         375                     380 | 1152 |
| att tac cgt gga gta act agg cat cac cag cat ggg aga tgg caa gca<br>Ile Tyr Arg Gly Val Thr Arg His His Gln His Gly Arg Trp Gln Ala<br>385                       390                     395                   400 | 1200 |
| agg ata gga aga gtt gca ggg aac aag gac ctc tac ttg ggc acc ttc<br>Arg Ile Gly Arg Val Ala Gly Asn Lys Asp Leu Tyr Leu Gly Thr Phe<br>                     405                     410                   415 | 1248 |
| agc acg cag gag gag gcg gcg gag gcg tac gac atc gcg gcg atc aag<br>Ser Thr Gln Glu Glu Ala Ala Glu Ala Tyr Asp Ile Ala Ala Ile Lys<br>                420                     425                     430 | 1296 |
| ttc cgg ggg ctc aac gcc gtc acc aac ttc gac atg agc cgc tac gac<br>Phe Arg Gly Leu Asn Ala Val Thr Asn Phe Asp Met Ser Arg Tyr Asp<br>         435                     440                     445 | 1344 |

```
gtc aag agc atc ctc gac agc gct gcc ctc ccc gtc ggc acc gcc gcc    1392
Val Lys Ser Ile Leu Asp Ser Ala Ala Leu Pro Val Gly Thr Ala Ala
    450                 455                 460 aag cgc ctc aag gac gcc gag gcc gcc gcc tac gac gtc ggc cgc        1440
Lys Arg Leu Lys Asp Ala Glu Ala Ala Ala Tyr Asp Val Gly Arg
465                 470                 475                 480 atc gcc tcg cac ctc ggc ggc gac ggc gcc tac gcc gcg cat tac ggc    1488
Ile Ala Ser His Leu Gly Gly Asp Gly Ala Tyr Ala Ala His Tyr Gly
                485                 490                 495 cac cac cac cac tcg gcc gcc gcc gcc tgg ccg acc atc gcg ttc cag    1536
His His His His Ser Ala Ala Ala Ala Trp Pro Thr Ile Ala Phe Gln
            500                 505                 510 gcg gcg gcg gcg ccg ccg ccg cac gcc gcc ggg ctt tac cac ccg tac    1584
Ala Ala Ala Ala Pro Pro Pro His Ala Ala Gly Leu Tyr His Pro Tyr
        515                 520                 525 gcg cag ccg ctg cgt ggg tgg tgc aag cag gag cag gac cac gcc gtg    1632
Ala Gln Pro Leu Arg Gly Trp Cys Lys Gln Glu Gln Asp His Ala Val
    530                 535                 540 atc gcg gcg gcg cac agc ctg cag gat ctc cac cac ctc aac ctc ggc    1680
Ile Ala Ala Ala His Ser Leu Gln Asp Leu His His Leu Asn Leu Gly
545                 550                 555                 560 gcc gcc gcc gcc gcg cat gac ttc ttc tcg cag gcg atg cag cag cag    1728
Ala Ala Ala Ala Ala His Asp Phe Phe Ser Gln Ala Met Gln Gln Gln
                565                 570                 575 cac ggc ctc ggc agc atc gac aac gcg tcg ctc gag cac agc acc ggc    1776
His Gly Leu Gly Ser Ile Asp Asn Ala Ser Leu Glu His Ser Thr Gly
            580                 585                 590 tcc aac tcc gtc gtc tac aac ggc gac aat ggc ggc gga ggc ggc ggc    1824
Ser Asn Ser Val Val Tyr Asn Gly Asp Asn Gly Gly Gly Gly Gly Gly
        595                 600                 605 tac atc atg gcg ccg atg agc gcc gtg tcg gcc acg gcc acc gcg gtg    1872
Tyr Ile Met Ala Pro Met Ser Ala Val Ser Ala Thr Ala Thr Ala Val
    610                 615                 620 gcg agc agc cac gat cac ggc ggc gac ggc ggg aag cag gtg cag atg    1920
Ala Ser Ser His Asp His Gly Gly Asp Gly Gly Lys Gln Val Gln Met
625                 630                 635                 640 ggg tac gac agc tac ctc gtc ggc gca gac gcc tac ggc ggc ggc ggc    1968
Gly Tyr Asp Ser Tyr Leu Val Gly Ala Asp Ala Tyr Gly Gly Gly Gly
                645                 650                 655 gcc ggg agg atg cca tcc tgg gcg atg acg ccg gcg tcg gcg ccg gcc    2016
Ala Gly Arg Met Pro Ser Trp Ala Met Thr Pro Ala Ser Ala Pro Ala
            660                 665                 670 gcc acg agc agc agc gac atg acc gga gtc tgc cat ggc gca cag ctc    2064
Ala Thr Ser Ser Ser Asp Met Thr Gly Val Cys His Gly Ala Gln Leu
        675                 680                 685 ttc agc gtc tgg aac gac aca taa                                    2088
Phe Ser Val Trp Asn Asp Thr
    690                 695

<210> SEQ ID NO 14
<211> LENGTH: 695
<212> TYPE: PRT
<213> ORGANISM: Oryza sativa

<400> SEQUENCE: 14

Met Ala Thr Met Asn Asn Trp Leu Ala Phe Ser Leu Ser Pro Gln Asp
1               5                   10                  15

Gln Leu Pro Pro Ser Gln Thr Asn Ser Thr Leu Ile Ser Ala Ala Ala
            20                  25                  30
```

```
Thr Thr Thr Thr Ala Gly Asp Ser Thr Gly Asp Val Cys Phe Asn
             35                  40                  45

Ile Pro Gln Asp Trp Ser Met Arg Gly Ser Glu Leu Ser Ala Leu Val
 50                  55                  60

Ala Glu Pro Lys Leu Glu Asp Phe Leu Gly Gly Ile Ser Phe Ser Glu
 65                  70                  75                  80

Gln Gln His His His Gly Gly Lys Gly Gly Val Ile Pro Ser Ser Ala
                 85                  90                  95

Ala Ala Cys Tyr Ala Ser Ser Gly Ser Ser Val Gly Tyr Leu Tyr Pro
                100                 105                 110

Pro Pro Ser Ser Ser Ser Leu Gln Phe Ala Asp Ser Val Met Val Ala
             115                 120                 125

Thr Ser Ser Pro Val Val Ala His Asp Gly Val Ser Gly Gly Gly Met
 130                 135                 140

Val Ser Ala Ala Ala Ala Ala Ala Ser Gly Asn Gly Gly Ile Gly
145                 150                 155                 160

Leu Ser Met Ile Lys Asn Trp Leu Arg Ser Gln Pro Ala Pro Gln Pro
                 165                 170                 175

Ala Gln Ala Leu Ser Leu Ser Met Asn Met Ala Gly Thr Thr Thr Ala
             180                 185                 190

Gln Gly Gly Gly Ala Met Ala Leu Leu Ala Gly Ala Gly Glu Arg Gly
         195                 200                 205

Arg Thr Thr Pro Ala Ser Glu Ser Leu Ser Thr Ser Ala His Gly Ala
     210                 215                 220

Thr Thr Ala Thr Met Ala Gly Gly Arg Lys Glu Ile Asn Glu Glu Gly
225                 230                 235                 240

Ser Gly Ser Ala Gly Ala Val Val Ala Val Gly Ser Glu Ser Gly Gly
                 245                 250                 255

Ser Gly Ala Val Val Glu Ala Gly Ala Ala Ala Ala Ala Arg Lys
             260                 265                 270

Ser Val Asp Thr Phe Gly Gln Arg Thr Ser Ile Tyr Arg Gly Val Thr
         275                 280                 285

Arg His Arg Trp Thr Gly Arg Tyr Glu Ala His Leu Trp Asp Asn Ser
     290                 295                 300

Cys Arg Arg Glu Gly Gln Thr Arg Lys Gly Arg Gln Val Tyr Leu Gly
305                 310                 315                 320

Gly Tyr Asp Lys Glu Glu Lys Ala Ala Arg Ala Tyr Asp Leu Ala Ala
                 325                 330                 335

Leu Lys Tyr Trp Gly Pro Thr Thr Thr Asn Phe Pro Val Asn Asn
             340                 345                 350

Tyr Glu Lys Glu Leu Glu Glu Met Lys His Met Thr Arg Gln Glu Phe
         355                 360                 365

Val Ala Ser Leu Arg Arg Lys Ser Ser Gly Phe Ser Arg Gly Ala Ser
     370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                 405                 410                 415

Ser Thr Gln Glu Glu Ala Ala Glu Ala Tyr Asp Ile Ala Ala Ile Lys
             420                 425                 430

Phe Arg Gly Leu Asn Ala Val Thr Asn Phe Asp Met Ser Arg Tyr Asp
     435                 440                 445

Val Lys Ser Ile Leu Asp Ser Ala Ala Leu Pro Val Gly Thr Ala Ala
```

```
                450            455            460
Lys Arg Leu Lys Asp Ala Glu Ala Ala Ala Tyr Asp Val Gly Arg
465                 470                 475                 480

Ile Ala Ser His Leu Gly Gly Asp Gly Ala Tyr Ala Ala His Tyr Gly
                485                 490                 495

His His His His Ser Ala Ala Ala Trp Pro Thr Ile Ala Phe Gln
            500                 505                 510

Ala Ala Ala Ala Pro Pro His Ala Ala Gly Leu Tyr His Pro Tyr
            515                 520                 525

Ala Gln Pro Leu Arg Gly Trp Cys Lys Gln Glu Gln Asp His Ala Val
            530                 535                 540

Ile Ala Ala Ala His Ser Leu Gln Asp Leu His His Leu Asn Leu Gly
545                 550                 555                 560

Ala Ala Ala Ala Ala His Asp Phe Phe Ser Gln Ala Met Gln Gln Gln
                565                 570                 575

His Gly Leu Gly Ser Ile Asp Asn Ala Ser Leu Glu His Ser Thr Gly
            580                 585                 590

Ser Asn Ser Val Val Tyr Asn Gly Asp Asn Gly Gly Gly Gly Gly
                595                 600                 605

Tyr Ile Met Ala Pro Met Ser Ala Val Ser Ala Thr Ala Thr Ala Val
            610                 615                 620

Ala Ser Ser His Asp His Gly Gly Asp Gly Gly Lys Gln Val Gln Met
625                 630                 635                 640

Gly Tyr Asp Ser Tyr Leu Val Gly Ala Asp Tyr Gly Gly Gly Gly
                645                 650                 655

Ala Gly Arg Met Pro Ser Trp Ala Met Thr Pro Ala Ser Ala Pro Ala
                660                 665                 670

Ala Thr Ser Ser Ser Asp Met Thr Gly Val Cys His Gly Ala Gln Leu
            675                 680                 685

Phe Ser Val Trp Asn Asp Thr
            690                 695

<210> SEQ ID NO 15
<211> LENGTH: 1680
<212> TYPE: DNA
<213> ORGANISM: Oryza sativa
<220> FEATURE:
<221> NAME/KEY: CDS
<222> LOCATION: (1)...(1680)

<400> SEQUENCE: 15 atg gcc tcc atc acc aac tgg ctc ggc ttc tcc tcc tcc tcc ttc tcc      48
Met Ala Ser Ile Thr Asn Trp Leu Gly Phe Ser Ser Ser Ser Phe Ser
1               5                   10                  15 ggc gcc ggc gcc gac ccc gtc ctg ccc cac ccg ccg ctg caa gag tgg      96
Gly Ala Gly Ala Asp Pro Val Leu Pro His Pro Pro Leu Gln Glu Trp
            20                  25                  30 ggg agc gct tat gag ggc ggc ggc acg gtg gcg gcc gcc ggg ggg gag     144
Gly Ser Ala Tyr Glu Gly Gly Gly Thr Val Ala Ala Ala Gly Gly Glu
        35                  40                  45 gag acg gcg gcg ccg aag ctg gag gac ttc ctc ggc atg cag gtg cag     192
Glu Thr Ala Ala Pro Lys Leu Glu Asp Phe Leu Gly Met Gln Val Gln
    50                  55                  60 cag gag acg gcc gcc gcg gcg gcg ggg cac ggc cgt gga ggc agc tcg     240
Gln Glu Thr Ala Ala Ala Ala Ala Gly His Gly Arg Gly Gly Ser Ser
65                  70                  75                  80 tcg gtc gtt ggg ctg tcc atg atc aag aac tgg cta cgc agc cag ccg     288
```

```
Ser Val Val Gly Leu Ser Met Ile Lys Asn Trp Leu Arg Ser Gln Pro
                85                  90                  95 ccg ccc gcg gtg gtt ggg gga gaa gac gct atg atg gcg ctc gcg gtg      336
Pro Pro Ala Val Val Gly Gly Glu Asp Ala Met Met Ala Leu Ala Val
            100                 105                 110 tcg acg tcg gcg tcg ccg ccg gtg gac gcg acg gtg ccg gcc tgc att      384
Ser Thr Ser Ala Ser Pro Pro Val Asp Ala Thr Val Pro Ala Cys Ile
        115                 120                 125 tcg ccg gat ggg atg ggg tcg aag gcg gcc gac ggc ggc ggc gcg gcc      432
Ser Pro Asp Gly Met Gly Ser Lys Ala Ala Asp Gly Gly Gly Ala Ala
130                 135                 140 gag gcg gcg gcg gcg gcg gcg cag agg atg aag gcg gcc atg gac          480
Glu Ala Ala Ala Ala Ala Ala Gln Arg Met Lys Ala Ala Met Asp
145                 150                 155                 160 acg ttc ggg cag cgg acg tcc atc tac cgg ggt gtc acc aag cac agg      528
Thr Phe Gly Gln Arg Thr Ser Ile Tyr Arg Gly Val Thr Lys His Arg
                165                 170                 175 tgg aca gga agg tat gaa gcc cat ctt tgg gat aac agc tgc aga aga      576
Trp Thr Gly Arg Tyr Glu Ala His Leu Trp Asp Asn Ser Cys Arg Arg
            180                 185                 190 gaa ggt cag act cgc aaa ggc aga caa gta tat ctt gga gga tat gat      624
Glu Gly Gln Thr Arg Lys Gly Arg Gln Val Tyr Leu Gly Gly Tyr Asp
        195                 200                 205 aag gaa gaa aaa gct gct agg gct tat gat ttg gct gcc ctt aaa tac      672
Lys Glu Glu Lys Ala Ala Arg Ala Tyr Asp Leu Ala Ala Leu Lys Tyr
210                 215                 220 tgg ggc act aca acg acg acg aat ttt ccg gta agc aac tac gaa aaa      720
Trp Gly Thr Thr Thr Thr Thr Asn Phe Pro Val Ser Asn Tyr Glu Lys
225                 230                 235                 240 gag ttg gat gaa atg aag cac atg aat agg cag gaa ttt gtt gca tcc      768
Glu Leu Asp Glu Met Lys His Met Asn Arg Gln Glu Phe Val Ala Ser
                245                 250                 255 ctt aga aga aaa agc agt gga ttt tca cgt ggt gct tcc ata tat cgt      816
Leu Arg Arg Lys Ser Ser Gly Phe Ser Arg Gly Ala Ser Ile Tyr Arg
            260                 265                 270 ggt gtt aca aga cac cat cag cat gga agg tgg caa gca agg ata gga      864
Gly Val Thr Arg His His Gln His Gly Arg Trp Gln Ala Arg Ile Gly
        275                 280                 285 cgg gtg gca gga aac aag gat ctg tat ttg ggc aca ttt ggc acc caa      912
Arg Val Ala Gly Asn Lys Asp Leu Tyr Leu Gly Thr Phe Gly Thr Gln
290                 295                 300 gag gaa gct gca gag gca tat gat atc gct gca atc aaa ttc cgt ggt      960
Glu Glu Ala Ala Glu Ala Tyr Asp Ile Ala Ala Ile Lys Phe Arg Gly
305                 310                 315                 320 ctc aat gct gtg aca aac ttt gac atg agc cgg tac gat gtc aag agc     1008
Leu Asn Ala Val Thr Asn Phe Asp Met Ser Arg Tyr Asp Val Lys Ser
                325                 330                 335 atc att gaa agc agc aat ctc cca att ggt act gga acc acc cgg cga     1056
Ile Ile Glu Ser Ser Asn Leu Pro Ile Gly Thr Gly Thr Thr Arg Arg
            340                 345                 350 ttg aag gac tcc tct gat cac act gat aat gtc atg gac atc aat gtc     1104
Leu Lys Asp Ser Ser Asp His Thr Asp Asn Val Met Asp Ile Asn Val
        355                 360                 365 aat acc gaa ccc aat aat gtg gta tca tcc cac ttc acc aat ggg gtt     1152
Asn Thr Glu Pro Asn Asn Val Val Ser Ser His Phe Thr Asn Gly Val
370                 375                 380 ggc aac tat ggt tcg cag cat tat ggt tac aat gga tgg tcg cca att     1200
Gly Asn Tyr Gly Ser Gln His Tyr Gly Tyr Asn Gly Trp Ser Pro Ile
385                 390                 395                 400
```

```
agc atg cag ccg atc ccc tcg cag tac gcc aac ggc cag ccc agg gca    1248
Ser Met Gln Pro Ile Pro Ser Gln Tyr Ala Asn Gly Gln Pro Arg Ala
        405                 410                 415 tgg ttg aaa caa gag cag gac agc tct gtg gtt aca gcg gcg cag aac    1296
Trp Leu Lys Gln Glu Gln Asp Ser Ser Val Val Thr Ala Ala Gln Asn
            420                 425                 430 ctg cac aat cta cat cat ttt agt tcc ttg ggc tac acc cac aac ttc    1344
Leu His Asn Leu His His Phe Ser Ser Leu Gly Tyr Thr His Asn Phe
                435                 440                 445 ttc cag caa tct gat gtt cca gac gtc aca ggt ttc gtt gat gcg cct    1392
Phe Gln Gln Ser Asp Val Pro Asp Val Thr Gly Phe Val Asp Ala Pro
        450                 455                 460 tcg agg tcc agt gac tca tac tcc ttc agg tac aat gga aca aat ggc    1440
Ser Arg Ser Ser Asp Ser Tyr Ser Phe Arg Tyr Asn Gly Thr Asn Gly
465                 470                 475                 480 ttt cat ggt ctc ccg ggt gga atc agc tat gct atg ccg gtt gcg aca    1488
Phe His Gly Leu Pro Gly Gly Ile Ser Tyr Ala Met Pro Val Ala Thr
                485                 490                 495 gcg gtg gac caa ggt cag ggc atc cat ggc tat gga gaa gat ggt gtg    1536
Ala Val Asp Gln Gly Gln Gly Ile His Gly Tyr Gly Glu Asp Gly Val
            500                 505                 510 gca ggc att gac acc aca cat gac ctg tat ggc agc cgt aat gtg tac    1584
Ala Gly Ile Asp Thr Thr His Asp Leu Tyr Gly Ser Arg Asn Val Tyr
        515                 520                 525 tac ctt tcc gag ggt tcg ctt ctt gcc gat gtc gaa aaa gaa ggc gac    1632
Tyr Leu Ser Glu Gly Ser Leu Leu Ala Asp Val Glu Lys Glu Gly Asp
530                 535                 540 tat ggc caa tct gtg ggg ggc aac agc tgg gtt ttg ccg aca ccg tag    1680
Tyr Gly Gln Ser Val Gly Gly Asn Ser Trp Val Leu Pro Thr Pro
545                 550                 555

<210> SEQ ID NO 16
<211> LENGTH: 559
<212> TYPE: PRT
<213> ORGANISM: Oryza sativa

<400> SEQUENCE: 16

Met Ala Ser Ile Thr Asn Trp Leu Gly Phe Ser Ser Ser Ser Phe Ser
1               5                   10                  15

Gly Ala Gly Ala Asp Pro Val Leu Pro His Pro Pro Leu Gln Glu Trp
            20                  25                  30

Gly Ser Ala Tyr Glu Gly Gly Thr Val Ala Ala Gly Gly Glu
        35                  40                  45

Glu Thr Ala Ala Pro Lys Leu Glu Asp Phe Leu Gly Met Gln Val Gln
    50                  55                  60

Gln Glu Thr Ala Ala Ala Ala Gly His Gly Arg Gly Gly Ser Ser
65                  70                  75                  80

Ser Val Val Gly Leu Ser Met Ile Lys Asn Trp Leu Arg Ser Gln Pro
                85                  90                  95

Pro Pro Ala Val Val Gly Gly Glu Asp Ala Met Met Ala Leu Ala Val
            100                 105                 110

Ser Thr Ser Ala Ser Pro Pro Val Asp Ala Thr Val Pro Ala Cys Ile
        115                 120                 125

Ser Pro Asp Gly Met Gly Ser Lys Ala Ala Asp Gly Gly Ala Ala
    130                 135                 140

Glu Ala Ala Ala Ala Ala Ala Gln Arg Met Lys Ala Ala Met Asp
145                 150                 155                 160

Thr Phe Gly Gln Arg Thr Ser Ile Tyr Arg Gly Val Thr Lys His Arg
```

```
                    165                 170                 175
Trp Thr Gly Arg Tyr Glu Ala His Leu Trp Asp Asn Ser Cys Arg Arg
            180                 185                 190

Glu Gly Gln Thr Arg Lys Gly Arg Gln Val Tyr Leu Gly Gly Tyr Asp
            195                 200                 205

Lys Glu Glu Lys Ala Ala Arg Ala Tyr Asp Leu Ala Ala Leu Lys Tyr
            210                 215                 220

Trp Gly Thr Thr Thr Thr Asn Phe Pro Val Ser Asn Tyr Glu Lys
225                 230                 235                 240

Glu Leu Asp Glu Met Lys His Met Asn Arg Gln Glu Phe Val Ala Ser
                245                 250                 255

Leu Arg Arg Lys Ser Ser Gly Phe Ser Arg Gly Ala Ser Ile Tyr Arg
                260                 265                 270

Gly Val Thr Arg His His Gln His Gly Arg Trp Gln Ala Arg Ile Gly
                275                 280                 285

Arg Val Ala Gly Asn Lys Asp Leu Tyr Leu Gly Thr Phe Gly Thr Gln
            290                 295                 300

Glu Glu Ala Ala Glu Ala Tyr Asp Ile Ala Ala Ile Lys Phe Arg Gly
305                 310                 315                 320

Leu Asn Ala Val Thr Asn Phe Asp Met Ser Arg Tyr Asp Val Lys Ser
                325                 330                 335

Ile Ile Glu Ser Ser Asn Leu Pro Ile Gly Thr Gly Thr Thr Arg Arg
            340                 345                 350

Leu Lys Asp Ser Ser Asp His Thr Asp Asn Val Met Asp Ile Asn Val
            355                 360                 365

Asn Thr Glu Pro Asn Asn Val Val Ser Ser His Phe Thr Asn Gly Val
370                 375                 380

Gly Asn Tyr Gly Ser Gln His Tyr Gly Tyr Asn Gly Trp Ser Pro Ile
385                 390                 395                 400

Ser Met Gln Pro Ile Pro Ser Gln Tyr Ala Asn Gly Gln Pro Arg Ala
                405                 410                 415

Trp Leu Lys Gln Glu Gln Asp Ser Ser Val Val Thr Ala Ala Gln Asn
            420                 425                 430

Leu His Asn Leu His His Phe Ser Ser Leu Gly Tyr Thr His Asn Phe
            435                 440                 445

Phe Gln Gln Ser Asp Val Pro Asp Val Thr Gly Phe Val Asp Ala Pro
            450                 455                 460

Ser Arg Ser Ser Asp Ser Tyr Ser Phe Arg Tyr Asn Gly Thr Asn Gly
465                 470                 475                 480

Phe His Gly Leu Pro Gly Gly Ile Ser Tyr Ala Met Pro Val Ala Thr
                485                 490                 495

Ala Val Asp Gln Gly Gln Gly Ile His Gly Tyr Gly Glu Asp Gly Val
            500                 505                 510

Ala Gly Ile Asp Thr Thr His Asp Leu Tyr Gly Ser Arg Asn Val Tyr
            515                 520                 525

Tyr Leu Ser Glu Gly Ser Leu Leu Ala Asp Val Glu Lys Glu Gly Asp
            530                 535                 540

Tyr Gly Gln Ser Val Gly Gly Asn Ser Trp Val Leu Pro Thr Pro
545                 550                 555

<210> SEQ ID NO 17
<211> LENGTH: 2112
<212> TYPE: DNA
<213> ORGANISM: Oryza sativa
```

```
<220> FEATURE:
<221> NAME/KEY: CDS
<222> LOCATION: (1)...(2112)

<400> SEQUENCE: 17 atg gct tct gca aac aac tgg ctg ggc ttc tcg ctc tcc ggc caa gag      48
Met Ala Ser Ala Asn Asn Trp Leu Gly Phe Ser Leu Ser Gly Gln Glu
 1               5                  10                  15 aat ccg cag cct cac cag gat agc tcg cct ccg gca gcc atc gac gtc      96
Asn Pro Gln Pro His Gln Asp Ser Ser Pro Pro Ala Ala Ile Asp Val
             20                  25                  30 tcc ggc gcc ggc gac ttc tat ggc ctg ccg acg tcg cag ccg acg gcg     144
Ser Gly Ala Gly Asp Phe Tyr Gly Leu Pro Thr Ser Gln Pro Thr Ala
         35                  40                  45 gcc gac gcg cac ctc ggc gtg gcg ggg cat cat cac aac gcc tcg tat     192
Ala Asp Ala His Leu Gly Val Ala Gly His His His Asn Ala Ser Tyr
     50                  55                  60 ggc atc atg gag gcc ttc aat agg gga gct caa gag gca caa gat tgg     240
Gly Ile Met Glu Ala Phe Asn Arg Gly Ala Gln Glu Ala Gln Asp Trp
 65                  70                  75                  80 aac atg agg ggg ctg gac tac aac ggc ggc gcc tcg gag ctg tcg atg     288
Asn Met Arg Gly Leu Asp Tyr Asn Gly Gly Ala Ser Glu Leu Ser Met
                 85                  90                  95 ctc gtc ggc tcc agc ggc ggc aag agg gcg gcg gcg gtg gag gag acc     336
Leu Val Gly Ser Ser Gly Gly Lys Arg Ala Ala Ala Val Glu Glu Thr
            100                 105                 110 gag ccg aag ctg gag gac ttc ctc ggc ggc aac tcg ttc gtc tcc gag     384
Glu Pro Lys Leu Glu Asp Phe Leu Gly Gly Asn Ser Phe Val Ser Glu
        115                 120                 125 caa gat cat cac gcg gcg ggg ggc ttc ctc ttc tcc ggc gtc ccg atg     432
Gln Asp His His Ala Ala Gly Gly Phe Leu Phe Ser Gly Val Pro Met
    130                 135                 140 gcc agc agc acc aac agc aac agc ggg agc aac act atg gag ctc tcc     480
Ala Ser Ser Thr Asn Ser Asn Ser Gly Ser Asn Thr Met Glu Leu Ser
145                 150                 155                 160 atg atc aag acc tgg ctc cgg aac aac ggc cag gtg ccc gcc ggc cac     528
Met Ile Lys Thr Trp Leu Arg Asn Asn Gly Gln Val Pro Ala Gly His
                165                 170                 175 cag ccg cag cag cag cag ccg gcg gcc gcg gcc gcc gcg cag cag         576
Gln Pro Gln Gln Gln Gln Pro Ala Ala Ala Ala Ala Ala Gln Gln
            180                 185                 190 cag gcg cac gag gcg gcg gag atg agc acc gac gcg agc gcg agc agc     624
Gln Ala His Glu Ala Ala Glu Met Ser Thr Asp Ala Ser Ala Ser Ser
        195                 200                 205 ttc ggg tgc tcc tcc gac gcg atg ggg agg agt aac aac ggc ggc gcg     672
Phe Gly Cys Ser Ser Asp Ala Met Gly Arg Ser Asn Asn Gly Gly Ala
    210                 215                 220 gtc tcg gcg gcg gcc ggc ggg acg agc cag agc ctg gcg ctc tcg         720
Val Ser Ala Ala Ala Gly Gly Thr Ser Gln Ser Leu Ala Leu Ser
225                 230                 235                 240 atg agc acg ggc tcg cac tcg cac ctg cct atc gtc gtc gcc ggc ggc     768
Met Ser Thr Gly Ser His Ser His Leu Pro Ile Val Val Ala Gly Gly
                245                 250                 255 ggg aac gcc agc ggc gga gcg gcc gag agc aca tcg tcg gag aac aag     816
Gly Asn Ala Ser Gly Gly Ala Ala Glu Ser Thr Ser Ser Glu Asn Lys
            260                 265                 270 cgg gcc agc ggc gcc atg gat tcg ccg ggc ggt ggc gcg ata gag gcc     864
Arg Ala Ser Gly Ala Met Asp Ser Pro Gly Gly Gly Ala Ile Glu Ala
        275                 280                 285 gtg ccg agg aag tcc atc gac acg ttc ggg caa agg acc tcg ata tat     912
Val Pro Arg Lys Ser Ile Asp Thr Phe Gly Gln Arg Thr Ser Ile Tyr
```

```
Val Pro Arg Lys Ser Ile Asp Thr Phe Gly Gln Arg Thr Ser Ile Tyr
    290                 295                 300 cga ggt gta aca agg cat aga tgg aca ggg cga tat gag gct cat ctc    960
Arg Gly Val Thr Arg His Arg Trp Thr Gly Arg Tyr Glu Ala His Leu
305                 310                 315                 320 tgg gat aat agc tgt aga aga gaa ggg cag agt cgc aag ggt agg caa   1008
Trp Asp Asn Ser Cys Arg Arg Glu Gly Gln Ser Arg Lys Gly Arg Gln
                325                 330                 335 gtt tat ctt ggt ggc tat gac aag gag gat aaa gca gcg aga gct tat   1056
Val Tyr Leu Gly Gly Tyr Asp Lys Glu Asp Lys Ala Ala Arg Ala Tyr
            340                 345                 350 gat ttg gca gct ctg aag tat tgg ggc aca aca aca aca aat ttc       1104
Asp Leu Ala Ala Leu Lys Tyr Trp Gly Thr Thr Thr Thr Asn Phe
        355                 360                 365 cca ata agt aac tat gaa aaa gag cta gat gaa atg aaa cat atg acc   1152
Pro Ile Ser Asn Tyr Glu Lys Glu Leu Asp Glu Met Lys His Met Thr
    370                 375                 380 agg cag gag tat att gca tac cta aga agg aat agc agt gga ttt tct   1200
Arg Gln Glu Tyr Ile Ala Tyr Leu Arg Arg Asn Ser Ser Gly Phe Ser
385                 390                 395                 400 cgt ggt gca tcg aaa tat cgt ggt gta acc agg cac cat cag cat ggg   1248
Arg Gly Ala Ser Lys Tyr Arg Gly Val Thr Arg His His Gln His Gly
                405                 410                 415 aga tgg caa gca agg ata ggg agg gtt gca gga aac aag gac ctc tac   1296
Arg Trp Gln Ala Arg Ile Gly Arg Val Ala Gly Asn Lys Asp Leu Tyr
            420                 425                 430 tta ggc acc ttc agc acc gag gag gag gcg gcg gag gcg tac gac atc   1344
Leu Gly Thr Phe Ser Thr Glu Glu Glu Ala Ala Glu Ala Tyr Asp Ile
        435                 440                 445 gcg gcg atc aag ttc cgg ggg ctc aac gcc gtc acc aac ttt gac atg   1392
Ala Ala Ile Lys Phe Arg Gly Leu Asn Ala Val Thr Asn Phe Asp Met
    450                 455                 460 agc cgc tac gac gtc aag agc atc ctg gag agc agc acg ctg ccg gtg   1440
Ser Arg Tyr Asp Val Lys Ser Ile Leu Glu Ser Ser Thr Leu Pro Val
465                 470                 475                 480 ggc ggc gcg gcg agg cgg ctg aag gag gcg gcg gac cac gcg gag gcg   1488
Gly Gly Ala Ala Arg Arg Leu Lys Glu Ala Ala Asp His Ala Glu Ala
                485                 490                 495 gcc ggc gcc acc atc tgg cgc gcc gcc gac atg gac ggc gcc ggc gtc   1536
Ala Gly Ala Thr Ile Trp Arg Ala Ala Asp Met Asp Gly Ala Gly Val
            500                 505                 510 atc tcc ggc ctg gcc gac gtc ggg atg ggc gcc tac gcc gcc tcg tac   1584
Ile Ser Gly Leu Ala Asp Val Gly Met Gly Ala Tyr Ala Ala Ser Tyr
        515                 520                 525 cac cac cac cac cac cac ggc tgg ccg acc atc gcg ttc cag cag ccg   1632
His His His His His His Gly Trp Pro Thr Ile Ala Phe Gln Gln Pro
    530                 535                 540 ccg ccg ctc gcc gtg cac tac ccg tac ggc cag gcg ccg gcg gcg ccg   1680
Pro Pro Leu Ala Val His Tyr Pro Tyr Gly Gln Ala Pro Ala Ala Pro
545                 550                 555                 560 tcg cgc ggg tgg tgc aag ccc gag cag gac gcc gcc gtc gct gcc gcc   1728
Ser Arg Gly Trp Cys Lys Pro Glu Gln Asp Ala Ala Val Ala Ala Ala
                565                 570                 575 gcg cac agc ctc cag gac ctc cag cag ctg cac ctc ggc agc gcc gcc   1776
Ala His Ser Leu Gln Asp Leu Gln Gln Leu His Leu Gly Ser Ala Ala
            580                 585                 590 gcc cac aac ttc ttc cag gcg tcg tcg agc tcg acg gtc tac aac ggc   1824
Ala His Asn Phe Phe Gln Ala Ser Ser Ser Ser Thr Val Tyr Asn Gly
        595                 600                 605
```

```
ggc ggc ggc ggg tac cag ggc ctc ggt ggc aac gcc ttc ttg atg ccg    1872
Gly Gly Gly Gly Tyr Gln Gly Leu Gly Gly Asn Ala Phe Leu Met Pro
        610                 615                 620 gcg agc acc gtc gtg gcc gac cag ggg cac agc agc acg gcc acc aac    1920
Ala Ser Thr Val Val Ala Asp Gln Gly His Ser Ser Thr Ala Thr Asn
625                 630                 635                 640 cat gga aac acc tgc agc tac ggc aac gag gag cag ggg aag ctc atc    1968
His Gly Asn Thr Cys Ser Tyr Gly Asn Glu Glu Gln Gly Lys Leu Ile
                645                 650                 655 ggg tac gac gcc atg gcg atg gcg agc ggc gcc gcc ggc ggc ggg tac    2016
Gly Tyr Asp Ala Met Ala Met Ala Ser Gly Ala Ala Gly Gly Gly Tyr
            660                 665                 670 cag ctg tcg cag ggc tcg gcg tcg acg gtg agc atc gcg agg gcg aac    2064
Gln Leu Ser Gln Gly Ser Ala Ser Thr Val Ser Ile Ala Arg Ala Asn
        675                 680                 685 ggc tac tcg gcc aac tgg agc tcg cct ttc aat ggc gcc atg gga tga    2112
Gly Tyr Ser Ala Asn Trp Ser Ser Pro Phe Asn Gly Ala Met Gly
    690                 695                 700
```

<210> SEQ ID NO 18
<211> LENGTH: 703
<212> TYPE: PRT
<213> ORGANISM: Oryza sativa

<400> SEQUENCE: 18

```
Met Ala Ser Ala Asn Asn Trp Leu Gly Phe Ser Leu Ser Gly Gln Glu
1               5                   10                  15

Asn Pro Gln Pro His Gln Asp Ser Ser Pro Ala Ala Ile Asp Val
            20                  25                  30

Ser Gly Ala Gly Asp Phe Tyr Gly Leu Pro Thr Ser Gln Pro Thr Ala
        35                  40                  45

Ala Asp Ala His Leu Gly Val Ala Gly His His Asn Ala Ser Tyr
    50                  55                  60

Gly Ile Met Glu Ala Phe Asn Arg Gly Ala Gln Glu Ala Gln Asp Trp
65                  70                  75                  80

Asn Met Arg Gly Leu Asp Tyr Asn Gly Gly Ala Ser Glu Leu Ser Met
                85                  90                  95

Leu Val Gly Ser Ser Gly Gly Lys Arg Ala Ala Ala Val Glu Glu Thr
            100                 105                 110

Glu Pro Lys Leu Glu Asp Phe Leu Gly Gly Asn Ser Phe Val Ser Glu
        115                 120                 125

Gln Asp His His Ala Ala Gly Gly Phe Leu Phe Ser Gly Val Pro Met
    130                 135                 140

Ala Ser Ser Thr Asn Ser Asn Ser Gly Ser Asn Thr Met Glu Leu Ser
145                 150                 155                 160

Met Ile Lys Thr Trp Leu Arg Asn Asn Gly Gln Val Pro Ala Gly His
                165                 170                 175

Gln Pro Gln Gln Gln Gln Pro Ala Ala Ala Ala Ala Ala Gln Gln
            180                 185                 190

Gln Ala His Glu Ala Ala Glu Met Ser Thr Asp Ala Ser Ala Ser Ser
    195                 200                 205

Phe Gly Cys Ser Ser Asp Ala Met Gly Arg Ser Asn Asn Gly Gly Ala
    210                 215                 220

Val Ser Ala Ala Ala Gly Gly Thr Ser Ser Gln Ser Leu Ala Leu Ser
225                 230                 235                 240

Met Ser Thr Gly Ser His Ser His Leu Pro Ile Val Val Ala Gly Gly
                245                 250                 255
```

```
Gly Asn Ala Ser Gly Gly Ala Ala Glu Ser Thr Ser Ser Glu Asn Lys
            260                 265                 270

Arg Ala Ser Gly Ala Met Asp Ser Pro Gly Gly Ala Ile Glu Ala
        275                 280                 285

Val Pro Arg Lys Ser Ile Asp Thr Phe Gly Gln Arg Thr Ser Ile Tyr
    290                 295                 300

Arg Gly Val Thr Arg His Arg Trp Thr Gly Arg Tyr Glu Ala His Leu
305                 310                 315                 320

Trp Asp Asn Ser Cys Arg Arg Glu Gly Gln Ser Arg Lys Gly Arg Gln
                325                 330                 335

Val Tyr Leu Gly Gly Tyr Asp Lys Glu Asp Lys Ala Ala Arg Ala Tyr
            340                 345                 350

Asp Leu Ala Ala Leu Lys Tyr Trp Gly Thr Thr Thr Thr Asn Phe
        355                 360                 365

Pro Ile Ser Asn Tyr Glu Lys Glu Leu Asp Glu Met Lys His Met Thr
    370                 375                 380

Arg Gln Glu Tyr Ile Ala Tyr Leu Arg Arg Asn Ser Ser Gly Phe Ser
385                 390                 395                 400

Arg Gly Ala Ser Lys Tyr Arg Gly Val Thr Arg His His Gln His Gly
                405                 410                 415

Arg Trp Gln Ala Arg Ile Gly Arg Val Ala Gly Asn Lys Asp Leu Tyr
            420                 425                 430

Leu Gly Thr Phe Ser Thr Glu Glu Ala Ala Glu Ala Tyr Asp Ile
        435                 440                 445

Ala Ala Ile Lys Phe Arg Gly Leu Asn Ala Val Thr Asn Phe Asp Met
450                 455                 460

Ser Arg Tyr Asp Val Lys Ser Ile Leu Glu Ser Ser Thr Leu Pro Val
465                 470                 475                 480

Gly Gly Ala Ala Arg Arg Leu Lys Glu Ala Ala Asp His Ala Glu Ala
                485                 490                 495

Ala Gly Ala Thr Ile Trp Arg Ala Ala Asp Met Asp Gly Ala Gly Val
            500                 505                 510

Ile Ser Gly Leu Ala Asp Val Gly Met Gly Ala Tyr Ala Ala Ser Tyr
        515                 520                 525

His His His His His His Gly Trp Pro Thr Ile Ala Phe Gln Gln Pro
    530                 535                 540

Pro Pro Leu Ala Val His Tyr Pro Tyr Gly Gln Ala Pro Ala Ala Pro
545                 550                 555                 560

Ser Arg Gly Trp Cys Lys Pro Glu Gln Asp Ala Ala Val Ala Ala Ala
                565                 570                 575

Ala His Ser Leu Gln Asp Leu Gln Gln Leu His Leu Gly Ser Ala Ala
            580                 585                 590

Ala His Asn Phe Phe Gln Ala Ser Ser Ser Thr Val Tyr Asn Gly
        595                 600                 605

Gly Gly Gly Gly Tyr Gln Gly Leu Gly Gly Asn Ala Phe Leu Met Pro
    610                 615                 620

Ala Ser Thr Val Val Ala Asp Gln Gly His Ser Ser Thr Ala Thr Asn
625                 630                 635                 640

His Gly Asn Thr Cys Ser Tyr Gly Asn Glu Glu Gln Gly Lys Leu Ile
                645                 650                 655

Gly Tyr Asp Ala Met Ala Met Ser Gly Ala Ala Gly Gly Gly Tyr
            660                 665                 670
```

```
Gln Leu Ser Gln Gly Ser Ala Ser Thr Val Ser Ile Ala Arg Ala Asn
            675                 680                 685

Gly Tyr Ser Ala Asn Trp Ser Ser Pro Phe Asn Gly Ala Met Gly
    690                 695                 700

<210> SEQ ID NO 19
<211> LENGTH: 1977
<212> TYPE: DNA
<213> ORGANISM: Oryza sativa
<220> FEATURE:
<221> NAME/KEY: CDS
<222> LOCATION: (1)...(1977)

<400> SEQUENCE: 19 atg gct tct gca gat aac tgg cta ggc ttc tcg ctc tcc ggc caa ggc      48
Met Ala Ser Ala Asp Asn Trp Leu Gly Phe Ser Leu Ser Gly Gln Gly
 1               5                  10                  15 aac cca cag cat cac cag aac ggc tcg ccg tct gcc gcc ggc gac gcc      96
Asn Pro Gln His His Gln Asn Gly Ser Pro Ser Ala Ala Gly Asp Ala
             20                  25                  30 gcc atc gac atc tcc ggc tca ggc gac ttc tat ggt ctg cca acg ccg     144
Ala Ile Asp Ile Ser Gly Ser Gly Asp Phe Tyr Gly Leu Pro Thr Pro
         35                  40                  45 gac gca cac cac atc ggc atg gcg ggc gaa gac gcg ccc tat ggc gtc     192
Asp Ala His His Ile Gly Met Ala Gly Glu Asp Ala Pro Tyr Gly Val
     50                  55                  60 atg gat gct ttc aac aga ggc acc cat gaa acc caa gat tgg gcg atg     240
Met Asp Ala Phe Asn Arg Gly Thr His Glu Thr Gln Asp Trp Ala Met
 65                  70                  75                  80 agg ggt ttg gac tac ggc ggc ggc tcc tcc gac ctc tcg atg ctc gtc     288
Arg Gly Leu Asp Tyr Gly Gly Gly Ser Ser Asp Leu Ser Met Leu Val
                 85                  90                  95 ggc tcg agc ggc ggc ggg agg agg acg gtg gcc ggc gac ggc gtc ggc     336
Gly Ser Ser Gly Gly Gly Arg Arg Thr Val Ala Gly Asp Gly Val Gly
            100                 105                 110 gag gcg ccg aag ctg gag aac ttc ctc gac ggc aac tca ttc tcc gac     384
Glu Ala Pro Lys Leu Glu Asn Phe Leu Asp Gly Asn Ser Phe Ser Asp
        115                 120                 125 gtg cac ggc caa gcc gcc ggc ggg tac ctc tac tcc gga agc gct gtc     432
Val His Gly Gln Ala Ala Gly Gly Tyr Leu Tyr Ser Gly Ser Ala Val
    130                 135                 140 ggc ggc gcc ggt ggt tac agt aac ggc gga tgc ggc ggc gga acc ata     480
Gly Gly Ala Gly Gly Tyr Ser Asn Gly Gly Cys Gly Gly Gly Thr Ile
145                 150                 155                 160 gag ctg tcc atg atc aag acg tgg ctc cgg agc aac cag tcg cag cag     528
Glu Leu Ser Met Ile Lys Thr Trp Leu Arg Ser Asn Gln Ser Gln Gln
                165                 170                 175 cag cca tcg ccg ccg cag cac gct gat cag ggc atg agc acc gac gcc     576
Gln Pro Ser Pro Pro Gln His Ala Asp Gln Gly Met Ser Thr Asp Ala
            180                 185                 190 agc gcg agc agc tac gcg tgc tcc gac gtg ctg gtg ggg agc tgc ggc     624
Ser Ala Ser Ser Tyr Ala Cys Ser Asp Val Leu Val Gly Ser Cys Gly
        195                 200                 205 ggc ggc ggc gcc ggg ggc acg gcg agc tcg cat ggg cag ggc ctg gcg     672
Gly Gly Gly Ala Gly Gly Thr Ala Ser Ser His Gly Gln Gly Leu Ala
    210                 215                 220 ctg tcg atg agc acg ggg tcg gtg gcc gcc gga ggg ggc ggc gcc         720
Leu Ser Met Ser Thr Gly Ser Val Ala Ala Ala Gly Gly Gly Gly Ala
225                 230                 235                 240 gtc gtc gcg gcc gag agc tcg tcg tcg gag aac aag cgg gtg gat tcg     768
Val Val Ala Ala Glu Ser Ser Ser Ser Glu Asn Lys Arg Val Asp Ser
```

-continued

```
                    245                 250                 255
ccg ggc ggc gcc gtg gac ggc gcc gtc ccg agg aaa tcc atc gac acc        816
Pro Gly Gly Ala Val Asp Gly Ala Val Pro Arg Lys Ser Ile Asp Thr
            260                 265                 270 ttc ggg caa agg acg tct ata tac cga ggt gta aca agg cat aga tgg        864
Phe Gly Gln Arg Thr Ser Ile Tyr Arg Gly Val Thr Arg His Arg Trp
        275                 280                 285 aca gga aga tat gaa gct cat ctg tgg gat aat agc tgt agg aga gaa        912
Thr Gly Arg Tyr Glu Ala His Leu Trp Asp Asn Ser Cys Arg Arg Glu
    290                 295                 300 ggc caa agt cgc aag ggg aga cag gtt tat ttg ggc ggt tat gac aaa        960
Gly Gln Ser Arg Lys Gly Arg Gln Val Tyr Leu Gly Gly Tyr Asp Lys
305                 310                 315                 320 gaa gat aag gcg gct cgg gct tat gat ttg gca gct cta aaa tac tgg       1008
Glu Asp Lys Ala Ala Arg Ala Tyr Asp Leu Ala Ala Leu Lys Tyr Trp
                325                 330                 335 ggc acg acc aca aca aca aat ttc cca atg agt aat tat gaa aag gag       1056
Gly Thr Thr Thr Thr Thr Asn Phe Pro Met Ser Asn Tyr Glu Lys Glu
            340                 345                 350 cta gag gaa atg aaa cac atg acc agg cag gag tac att gca cat ctt       1104
Leu Glu Glu Met Lys His Met Thr Arg Gln Glu Tyr Ile Ala His Leu
        355                 360                 365 aga agg aat agc agt gga ttt tct cgt ggt gca tcc aaa tat cgt ggt       1152
Arg Arg Asn Ser Ser Gly Phe Ser Arg Gly Ala Ser Lys Tyr Arg Gly
    370                 375                 380 gtt act agg cat cat cag cat ggg aga tgg cag gca agg ata ggg cga       1200
Val Thr Arg His His Gln His Gly Arg Trp Gln Ala Arg Ile Gly Arg
385                 390                 395                 400 gtt gca ggc aac aag gat atc tac cta ggc acc ttc agc acc gag gag       1248
Val Ala Gly Asn Lys Asp Ile Tyr Leu Gly Thr Phe Ser Thr Glu Glu
                405                 410                 415 gag gcc gcc gag gcg tac gac atc gcc gcc atc aag ttc cgc ggg ctc       1296
Glu Ala Ala Glu Ala Tyr Asp Ile Ala Ala Ile Lys Phe Arg Gly Leu
            420                 425                 430 aac gcc gtc acc aac ttc gac atg agc cgg tac gac gtc aag agc atc       1344
Asn Ala Val Thr Asn Phe Asp Met Ser Arg Tyr Asp Val Lys Ser Ile
        435                 440                 445 ctg gac agc agc acg ctg ccg gtc ggc ggc gcg cgg cgg ctc aag            1392
Leu Asp Ser Ser Thr Leu Pro Val Gly Gly Ala Arg Arg Leu Lys
    450                 455                 460 gag gcg gag gtc gcc gcc gcc gcg ggc ggc ggc gtg atc gtc tcc            1440
Glu Ala Glu Val Ala Ala Ala Ala Gly Gly Gly Val Ile Val Ser
465                 470                 475                 480 cac ctg gcc gac ggc ggt gtg ggt ggg tac tac tac ggg tgc ggc ccg       1488
His Leu Ala Asp Gly Gly Val Gly Gly Tyr Tyr Tyr Gly Cys Gly Pro
                485                 490                 495 acc atc gcg ttc ggc ggc ggc cag cag ccg gcg ccg ctc gcc gtg            1536
Thr Ile Ala Phe Gly Gly Gly Gln Gln Pro Ala Pro Leu Ala Val
            500                 505                 510 cac tac ccg tcg tac ggc cag gcc agc ggg tgg tgc aag ccg gag cag       1584
His Tyr Pro Ser Tyr Gly Gln Ala Ser Gly Trp Cys Lys Pro Glu Gln
        515                 520                 525 gac gcg gtg atc gcg gcc ggg cac tgc gcg acg gac ctc cag cac ctg       1632
Asp Ala Val Ile Ala Ala Gly His Cys Ala Thr Asp Leu Gln His Leu
    530                 535                 540 cac ctc ggg agc ggc ggc gcc gcc acc cac aac ttc ttc cag cag           1680
His Leu Gly Ser Gly Gly Ala Ala Ala Thr His Asn Phe Phe Gln Gln
545                 550                 555                 560 ccg gcg tca agc tcg gcc gtc tac ggc aac ggc ggc ggc ggc ggc           1728
```

-continued

```
                Pro Ala Ser Ser Ser Ala Val Tyr Gly Asn Gly Gly Gly Gly Gly
                                565                 570                 575 aac gcg ttc atg atg ccg atg ggc gcc gtg gtg gcc gcc gcc gat cac      1776
Asn Ala Phe Met Met Pro Met Gly Ala Val Val Ala Ala Ala Asp His
            580                 585                 590 ggc ggg cag agc agc gcc tac ggc ggt ggc gac gag agc ggg agg ctc      1824
Gly Gly Gln Ser Ser Ala Tyr Gly Gly Gly Asp Glu Ser Gly Arg Leu
        595                 600                 605 gtc gtg ggg tac gac ggc gtc gtc gac ccg tac gcg gcc atg aga agc      1872
Val Val Gly Tyr Asp Gly Val Val Asp Pro Tyr Ala Ala Met Arg Ser
    610                 615                 620 gcg tac gag ctc tcg cag ggc tcg tcg tcg tcg gtg agc gtc gcg          1920
Ala Tyr Glu Leu Ser Gln Gly Ser Ser Ser Ser Val Ser Val Ala
625                 630                 635                 640 aag gcg gcg aac ggg tac ccg gac aac tgg agc tcg ccg ttc aac ggc      1968
Lys Ala Ala Asn Gly Tyr Pro Asp Asn Trp Ser Ser Pro Phe Asn Gly
            645                 650                 655 atg gga tga                                                           1977
Met Gly
```

<210> SEQ ID NO 20
<211> LENGTH: 658
<212> TYPE: PRT
<213> ORGANISM: Oryza sativa

<400> SEQUENCE: 20

```
Met Ala Ser Ala Asp Asn Trp Leu Gly Phe Ser Leu Ser Gly Gln Gly
 1               5                  10                  15

Asn Pro Gln His His Gln Asn Gly Ser Pro Ser Ala Ala Gly Asp Ala
            20                  25                  30

Ala Ile Asp Ile Ser Gly Ser Gly Asp Phe Tyr Gly Leu Pro Thr Pro
        35                  40                  45

Asp Ala His His Ile Gly Met Ala Gly Glu Asp Ala Pro Tyr Gly Val
    50                  55                  60

Met Asp Ala Phe Asn Arg Gly Thr His Glu Thr Gln Asp Trp Ala Met
65                  70                  75                  80

Arg Gly Leu Asp Tyr Gly Gly Gly Ser Ser Asp Leu Ser Met Leu Val
                85                  90                  95

Gly Ser Ser Gly Gly Gly Arg Arg Thr Val Ala Gly Asp Gly Val Gly
            100                 105                 110

Glu Ala Pro Lys Leu Glu Asn Phe Leu Asp Gly Asn Ser Phe Ser Asp
        115                 120                 125

Val His Gly Gln Ala Ala Gly Gly Tyr Leu Tyr Ser Gly Ser Ala Val
    130                 135                 140

Gly Gly Ala Gly Gly Tyr Ser Asn Gly Gly Cys Gly Gly Gly Thr Ile
145                 150                 155                 160

Glu Leu Ser Met Ile Lys Thr Trp Leu Arg Ser Asn Gln Ser Gln Gln
                165                 170                 175

Gln Pro Ser Pro Pro Gln His Ala Asp Gln Gly Met Ser Thr Asp Ala
            180                 185                 190

Ser Ala Ser Ser Tyr Ala Cys Ser Asp Val Leu Val Gly Ser Cys Gly
        195                 200                 205

Gly Gly Gly Ala Gly Gly Thr Ala Ser Ser His Gly Gln Gly Leu Ala
    210                 215                 220

Leu Ser Met Ser Thr Gly Ser Val Ala Ala Ala Gly Gly Gly Gly Ala
225                 230                 235                 240
```

```
Val Val Ala Ala Glu Ser Ser Ser Glu Asn Lys Arg Val Asp Ser
                245                 250                 255

Pro Gly Gly Ala Val Asp Gly Ala Val Pro Arg Lys Ser Ile Asp Thr
            260                 265                 270

Phe Gly Gln Arg Thr Ser Ile Tyr Arg Gly Val Thr Arg His Arg Trp
            275                 280                 285

Thr Gly Arg Tyr Glu Ala His Leu Trp Asp Asn Ser Cys Arg Arg Glu
            290                 295                 300

Gly Gln Ser Arg Lys Arg Gln Val Tyr Leu Gly Tyr Asp Lys
305                 310                 315                 320

Glu Asp Lys Ala Ala Arg Ala Tyr Asp Leu Ala Ala Leu Lys Tyr Trp
                325                 330                 335

Gly Thr Thr Thr Thr Asn Phe Pro Met Ser Asn Tyr Glu Lys Glu
            340                 345                 350

Leu Glu Glu Met Lys His Met Thr Arg Gln Glu Tyr Ile Ala His Leu
            355                 360                 365

Arg Arg Asn Ser Ser Gly Phe Ser Arg Gly Ala Ser Lys Tyr Arg Gly
370                 375                 380

Val Thr Arg His His Gln His Gly Arg Trp Gln Ala Arg Ile Gly Arg
385                 390                 395                 400

Val Ala Gly Asn Lys Asp Ile Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
            435                 440                 445

Leu Asp Ser Ser Thr Leu Pro Val Gly Gly Ala Arg Arg Leu Lys
450                 455                 460

Glu Ala Glu Val Ala Ala Ala Ala Gly Gly Val Ile Val Ser
465                 470                 475                 480

His Leu Ala Asp Gly Gly Val Gly Gly Tyr Tyr Gly Cys Gly Pro
                485                 490                 495

Thr Ile Ala Phe Gly Gly Gly Gln Gln Pro Ala Pro Leu Ala Val
            500                 505                 510

His Tyr Pro Ser Tyr Gly Gln Ala Ser Gly Trp Cys Lys Pro Glu Gln
            515                 520                 525

Asp Ala Val Ile Ala Ala Gly His Cys Ala Thr Asp Leu Gln His Leu
530                 535                 540

His Leu Gly Ser Gly Gly Ala Ala Thr His Asn Phe Phe Gln Gln
545                 550                 555                 560

Pro Ala Ser Ser Ser Ala Val Tyr Gly Asn Gly Gly Gly Gly Gly
                565                 570                 575

Asn Ala Phe Met Met Pro Met Gly Ala Val Val Ala Ala Ala Asp His
            580                 585                 590

Gly Gly Gln Ser Ser Ala Tyr Gly Gly Asp Glu Ser Gly Arg Leu
            595                 600                 605

Val Val Gly Tyr Asp Gly Val Val Asp Pro Tyr Ala Ala Met Arg Ser
610                 615                 620

Ala Tyr Glu Leu Ser Gln Gly Ser Ser Ser Ser Val Ser Val Ala
625                 630                 635                 640

Lys Ala Ala Asn Gly Tyr Pro Asp Asn Trp Ser Ser Pro Phe Asn Gly
                645                 650                 655

Met Gly
```

<210> SEQ ID NO 21
<211> LENGTH: 1755
<212> TYPE: DNA
<213> ORGANISM: Arabidopsis thaliana
<220> FEATURE:
<221> NAME/KEY: CDS
<222> LOCATION: (1)...(1755)

<400> SEQUENCE: 21

| | | | | | | | | | | | | | | | | |
|---|---|---|---|---|---|---|---|---|---|---|---|---|---|---|---|---|
| atg | aac | tcg | atg | aat | aac | tgg | tta | ggc | ttc | tct | ctc | tct | cct | cat | gat | 48 |
| Met | Asn | Ser | Met | Asn | Asn | Trp | Leu | Gly | Phe | Ser | Leu | Ser | Pro | His | Asp | |
| 1 | | | | 5 | | | | | 10 | | | | | 15 | | |
| caa | aat | cat | cac | cgt | acg | gat | gtt | gac | tcc | tcc | acc | acc | aga | acc | gcc | 96 |
| Gln | Asn | His | His | Arg | Thr | Asp | Val | Asp | Ser | Ser | Thr | Thr | Arg | Thr | Ala | |
| | | | 20 | | | | | 25 | | | | | 30 | | | |
| gta | gat | gtt | gcc | gga | ggg | tac | tgt | ttt | gat | ctg | gcc | gct | ccc | tcc | gat | 144 |
| Val | Asp | Val | Ala | Gly | Gly | Tyr | Cys | Phe | Asp | Leu | Ala | Ala | Pro | Ser | Asp | |
| | | | | 35 | | | | | 40 | | | | | 45 | | |
| gaa | tct | tct | gcc | gtt | caa | aca | tct | ttt | ctt | tct | cct | ttc | ggt | gtc | acc | 192 |
| Glu | Ser | Ser | Ala | Val | Gln | Thr | Ser | Phe | Leu | Ser | Pro | Phe | Gly | Val | Thr | |
| | 50 | | | | | 55 | | | | | 60 | | | | | |
| ctc | gaa | gct | ttc | acc | aga | gac | aat | aat | agt | cac | tcc | cga | gat | tgg | gac | 240 |
| Leu | Glu | Ala | Phe | Thr | Arg | Asp | Asn | Asn | Ser | His | Ser | Arg | Asp | Trp | Asp | |
| 65 | | | | | 70 | | | | | 75 | | | | | 80 | |
| atc | aat | ggt | ggt | gca | tgc | aat | aca | tta | acc | aat | aac | gaa | caa | aat | gga | 288 |
| Ile | Asn | Gly | Gly | Ala | Cys | Asn | Thr | Leu | Thr | Asn | Asn | Glu | Gln | Asn | Gly | |
| | | | | 85 | | | | | 90 | | | | | 95 | | |
| cca | aag | ctt | gag | aat | ttc | ctc | ggc | cgc | acc | acc | acg | att | tac | aat | acc | 336 |
| Pro | Lys | Leu | Glu | Asn | Phe | Leu | Gly | Arg | Thr | Thr | Thr | Ile | Tyr | Asn | Thr | |
| | | | 100 | | | | | 105 | | | | | 110 | | | |
| aac | gag | acc | gtt | gta | gat | gga | aat | ggc | gat | tgt | gga | gga | gga | gac | ggt | 384 |
| Asn | Glu | Thr | Val | Val | Asp | Gly | Asn | Gly | Asp | Cys | Gly | Gly | Gly | Asp | Gly | |
| | | | | 115 | | | | | 120 | | | | | 125 | | |
| ggt | ggc | ggc | ggc | tca | cta | ggc | ctt | tcg | atg | ata | aaa | aca | tgg | ctg | agt | 432 |
| Gly | Gly | Gly | Gly | Ser | Leu | Gly | Leu | Ser | Met | Ile | Lys | Thr | Trp | Leu | Ser | |
| | 130 | | | | | 135 | | | | | 140 | | | | | |
| aat | cat | tcg | gtt | gct | aat | gct | aat | cat | caa | gac | aat | ggt | aac | ggt | gca | 480 |
| Asn | His | Ser | Val | Ala | Asn | Ala | Asn | His | Gln | Asp | Asn | Gly | Asn | Gly | Ala | |
| 145 | | | | | 150 | | | | | 155 | | | | | 160 | |
| cga | ggc | ttg | tcc | ctc | tct | atg | aat | tca | tct | act | agt | gat | agc | aac | aac | 528 |
| Arg | Gly | Leu | Ser | Leu | Ser | Met | Asn | Ser | Ser | Thr | Ser | Asp | Ser | Asn | Asn | |
| | | | | 165 | | | | | 170 | | | | | 175 | | |
| tac | aac | aac | aat | gat | gat | gtc | gtc | caa | gag | aag | act | att | gtt | gat | gtc | 576 |
| Tyr | Asn | Asn | Asn | Asp | Asp | Val | Val | Gln | Glu | Lys | Thr | Ile | Val | Asp | Val | |
| | | | 180 | | | | | 185 | | | | | 190 | | | |
| gta | gaa | act | aca | ccg | aag | aaa | act | att | gag | agt | ttt | gga | caa | agg | acg | 624 |
| Val | Glu | Thr | Thr | Pro | Lys | Lys | Thr | Ile | Glu | Ser | Phe | Gly | Gln | Arg | Thr | |
| | | | | 195 | | | | | 200 | | | | | 205 | | |
| tct | ata | tac | cgc | ggt | gtt | aca | agg | cat | cgg | tgg | aca | ggt | aga | tac | gag | 672 |
| Ser | Ile | Tyr | Arg | Gly | Val | Thr | Arg | His | Arg | Trp | Thr | Gly | Arg | Tyr | Glu | |
| | 210 | | | | | 215 | | | | | 220 | | | | | |
| gca | cat | tta | tgg | gac | aat | agt | tgc | aaa | aga | gaa | ggc | cag | act | cgc | aaa | 720 |
| Ala | His | Leu | Trp | Asp | Asn | Ser | Cys | Lys | Arg | Glu | Gly | Gln | Thr | Arg | Lys | |
| 225 | | | | | 230 | | | | | 235 | | | | | 240 | |
| gga | aga | caa | gtt | tat | ctg | gga | ggt | tat | gac | aaa | gaa | gaa | aaa | gca | gct | 768 |
| Gly | Arg | Gln | Val | Tyr | Leu | Gly | Gly | Tyr | Asp | Lys | Glu | Glu | Lys | Ala | Ala | |
| | | | | 245 | | | | | 250 | | | | | 255 | | |
| agg | gct | tac | gat | tta | gcc | gca | cta | aag | tat | tgg | gga | ccc | acc | act | act | 816 |
| Arg | Ala | Tyr | Asp | Leu | Ala | Ala | Leu | Lys | Tyr | Trp | Gly | Pro | Thr | Thr | Thr | |
| | | | 260 | | | | | 265 | | | | | 270 | | | |

```
act aac ttc ccc ttg agt gaa tat gag aaa gag gta gaa gag atg aag      864
Thr Asn Phe Pro Leu Ser Glu Tyr Glu Lys Glu Val Glu Glu Met Lys
        275                 280                 285 cac atg acg agg caa gag tat gtt gcc tct ctg cgc aaa agt agt          912
His Met Thr Arg Gln Glu Tyr Val Ala Ser Leu Arg Arg Lys Ser Ser
    290                 295                 300 ggt ttc tct cgt ggt gca tcg att tat cga gga gta aca agg cat cac      960
Gly Phe Ser Arg Gly Ala Ser Ile Tyr Arg Gly Val Thr Arg His His
305                 310                 315                 320 caa cat gga agg tgg caa gct agg atc gga aga gtc gcc ggt aac aaa     1008
Gln His Gly Arg Trp Gln Ala Arg Ile Gly Arg Val Ala Gly Asn Lys
                325                 330                 335 gac ctc tac ttg gga act ttc ggc aca cag gaa gag gct gct gag gct     1056
Asp Leu Tyr Leu Gly Thr Phe Gly Thr Gln Glu Glu Ala Ala Glu Ala
            340                 345                 350 tat gac att gca gcc att aaa ttc aga gga tta agc gca gtg act aac     1104
Tyr Asp Ile Ala Ala Ile Lys Phe Arg Gly Leu Ser Ala Val Thr Asn
        355                 360                 365 ttc gac atg aac aga tac aat gtt aaa gca atc ctc gag agc ccg agt     1152
Phe Asp Met Asn Arg Tyr Asn Val Lys Ala Ile Leu Glu Ser Pro Ser
    370                 375                 380 cta cct att ggt agt tct gcg aaa cgt ctc aag gac gtt aac aat ccg     1200
Leu Pro Ile Gly Ser Ser Ala Lys Arg Leu Lys Asp Val Asn Asn Pro
385                 390                 395                 400 gtt cca gct atg atg att agt aat aac gtt tca gag agt gca aat aat     1248
Val Pro Ala Met Met Ile Ser Asn Asn Val Ser Glu Ser Ala Asn Asn
                405                 410                 415 gtt agc ggt tgg caa aac act gcg ttt cag cat cat cag gga atg gat     1296
Val Ser Gly Trp Gln Asn Thr Ala Phe Gln His His Gln Gly Met Asp
            420                 425                 430 ttg agc tta ttg cag caa cag cag gag agg tac gtt ggt tat tac aat     1344
Leu Ser Leu Leu Gln Gln Gln Gln Glu Arg Tyr Val Gly Tyr Tyr Asn
        435                 440                 445 gga gga aac ttg tct acc gag agt act agg gtt tgt ttc aaa caa gag     1392
Gly Gly Asn Leu Ser Thr Glu Ser Thr Arg Val Cys Phe Lys Gln Glu
    450                 455                 460 gag gaa caa caa cac ttc ttg aga aac tcg ccg agt cac atg act aat     1440
Glu Glu Gln Gln His Phe Leu Arg Asn Ser Pro Ser His Met Thr Asn
465                 470                 475                 480 gtt gat cat cat agc tcg acc tct gat gat tct gtt acc gtt tgt gga     1488
Val Asp His His Ser Ser Thr Ser Asp Asp Ser Val Thr Val Cys Gly
                485                 490                 495 aat gtt gtt agt tat ggt ggt tat caa gga ttc gca atc cct gtt gga     1536
Asn Val Val Ser Tyr Gly Gly Tyr Gln Gly Phe Ala Ile Pro Val Gly
            500                 505                 510 aca tcg gtt aat tac gat ccc ttt act gct gct gag att gct tac aac     1584
Thr Ser Val Asn Tyr Asp Pro Phe Thr Ala Ala Glu Ile Ala Tyr Asn
        515                 520                 525 gca aga aat cat tat tac tat gct cag cat cag caa caa cag cag att     1632
Ala Arg Asn His Tyr Tyr Tyr Ala Gln His Gln Gln Gln Gln Gln Ile
    530                 535                 540 cag cag tcg ccg gga gga gat ttt ccg gtg gcg att tcg aat aac cat     1680
Gln Gln Ser Pro Gly Gly Asp Phe Pro Val Ala Ile Ser Asn Asn His
545                 550                 555                 560 agc tct aac atg tac ttt cac ggg gaa ggt ggt gga gaa ggg gct cca     1728
Ser Ser Asn Met Tyr Phe His Gly Glu Gly Gly Gly Glu Gly Ala Pro
                565                 570                 575 acg ttt tca gtt tgg aac gac act tag                                 1755
Thr Phe Ser Val Trp Asn Asp Thr
```

-continued

580

<210> SEQ ID NO 22
<211> LENGTH: 584
<212> TYPE: PRT
<213> ORGANISM: Arabidopsis thaliana

<400> SEQUENCE: 22

```
Met Asn Ser Met Asn Asn Trp Leu Gly Phe Ser Leu Ser Pro His Asp
 1               5                  10                  15

Gln Asn His His Arg Thr Asp Val Asp Ser Ser Thr Thr Arg Thr Ala
            20                  25                  30

Val Asp Val Ala Gly Gly Tyr Cys Phe Asp Leu Ala Ala Pro Ser Asp
        35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Thr Leu Thr Asn Asn Glu Gln Asn Gly
                85                  90                  95

Pro Lys Leu Glu Asn Phe Leu Gly Arg Thr Thr Thr Ile Tyr Asn Thr
            100                 105                 110

Asn Glu Thr Val Val Asp Gly Asn Gly Asp Cys Gly Gly Gly Asp Gly
        115                 120                 125

Gly Gly Gly Gly Ser Leu Gly Leu Ser Met Ile Lys Thr Trp Leu Ser
    130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asp Asp Val Val Gln Glu Lys Thr Ile Val Asp Val
            180                 185                 190

Val Glu Thr Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
                245                 250                 255

Arg Ala Tyr Asp Leu Ala Ala Leu Lys Tyr Trp Gly Pro Thr Thr Thr
            260                 265                 270

Thr Asn Phe Pro Leu Ser Glu Tyr Glu Lys Glu Val Glu Glu Met Lys
        275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Ser Ala Val Thr Asn
        355                 360                 365
```

-continued

```
Phe Asp Met Asn Arg Tyr Asn Val Lys Ala Ile Leu Glu Ser Pro Ser
    370                 375                 380

Leu Pro Ile Gly Ser Ser Ala Lys Arg Leu Lys Asp Val Asn Pro
385                 390                 395                 400

Val Pro Ala Met Met Ile Ser Asn Asn Val Ser Glu Ser Ala Asn Asn
                405                 410                 415

Val Ser Gly Trp Gln Asn Thr Ala Phe Gln His His Gln Gly Met Asp
            420                 425                 430

Leu Ser Leu Leu Gln Gln Gln Gln Glu Arg Tyr Val Gly Tyr Tyr Asn
        435                 440                 445

Gly Gly Asn Leu Ser Thr Glu Ser Thr Arg Val Cys Phe Lys Gln Glu
450                 455                 460

Glu Glu Gln Gln His Phe Leu Arg Asn Ser Pro Ser His Met Thr Asn
465                 470                 475                 480

Val Asp His His Ser Ser Thr Ser Asp Asp Ser Val Thr Val Cys Gly
                485                 490                 495

Asn Val Val Ser Tyr Gly Gly Tyr Gln Gly Phe Ala Ile Pro Val Gly
            500                 505                 510

Thr Ser Val Asn Tyr Asp Pro Phe Thr Ala Ala Glu Ile Ala Tyr Asn
        515                 520                 525

Ala Arg Asn His Tyr Tyr Tyr Ala Gln His Gln Gln Gln Gln Gln Ile
    530                 535                 540

Gln Gln Ser Pro Gly Gly Asp Phe Pro Val Ala Ile Ser Asn Asn His
545                 550                 555                 560

Ser Ser Asn Met Tyr Phe His Gly Glu Gly Gly Gly Glu Gly Ala Pro
                565                 570                 575

Thr Phe Ser Val Trp Asn Asp Thr
                580
```

<210> SEQ ID NO 23
<211> LENGTH: 1740
<212> TYPE: DNA
<213> ORGANISM: Brassica napus
<220> FEATURE:
<221> NAME/KEY: CDS
<222> LOCATION: (1)...(1740)

<400> SEQUENCE: 23

```
atg aat aat aac tgg tta ggc ttt tct ctc tct cct tat gaa caa aat     48
Met Asn Asn Asn Trp Leu Gly Phe Ser Leu Ser Pro Tyr Glu Gln Asn
 1               5                  10                  15 cac cat cgt aag gac gtc tac tct tcc acc acc aca acc gtc gta gat     96
His His Arg Lys Asp Val Tyr Ser Ser Thr Thr Thr Thr Val Val Asp
                20                  25                  30 gtc gcc gga gag tac tgt tac gat ccg acc gct gcc tcc gat gag tct    144
Val Ala Gly Glu Tyr Cys Tyr Asp Pro Thr Ala Ala Ser Asp Glu Ser
            35                  40                  45 tca gcc atc caa aca tcg ttt cct tct ccc ttt ggt gtc gtc gtc gat    192
Ser Ala Ile Gln Thr Ser Phe Pro Ser Pro Phe Gly Val Val Val Asp
        50                  55                  60 gct ttc acc aga gac aac aat agt cac tcc cga gat tgg gac atc aat    240
Ala Phe Thr Arg Asp Asn Asn Ser His Ser Arg Asp Trp Asp Ile Asn
 65                  70                  75                  80 ggt tgt gca tgc aat aac atc cac aac gat gag caa gat gga cca aag    288
Gly Cys Ala Cys Asn Asn Ile His Asn Asp Glu Gln Asp Gly Pro Lys
                85                  90                  95 ctt gag aat ttc ctt ggc cgc acc acc acg att tac aac acc aac gaa    336
Leu Glu Asn Phe Leu Gly Arg Thr Thr Thr Ile Tyr Asn Thr Asn Glu
```

```
              100                 105                 110
aac gtt gga gat gga agt gga agt ggc tgt tat gga gga gac ggt       384
Asn Val Gly Asp Gly Ser Gly Ser Gly Cys Tyr Gly Gly Asp Gly
            115                 120                 125 ggt ggt ggc tca cta gga ctt tcg atg ata aag aca tgg ctg aga aat   432
Gly Gly Gly Ser Leu Gly Leu Ser Met Ile Lys Thr Trp Leu Arg Asn
130                 135                 140 caa ccc gtg gat aat gtt gat aat caa gaa aat ggc aat gct gca aaa   480
Gln Pro Val Asp Asn Val Asp Asn Gln Glu Asn Gly Asn Ala Ala Lys
145                 150                 155                 160 ggc ctg tcc ctc tca atg aac tca tct act tct tgt gat aac aac aac   528
Gly Leu Ser Leu Ser Met Asn Ser Ser Thr Ser Cys Asp Asn Asn Asn
                165                 170                 175 gac agc aat aac aac gtt gtt gcc caa ggg aag act att gat gat agc   576
Asp Ser Asn Asn Asn Val Val Ala Gln Gly Lys Thr Ile Asp Asp Ser
            180                 185                 190 gtt gaa gct aca ccg aag aaa act att gag agt ttt gga cag agg acg   624
Val Glu Ala Thr Pro Lys Lys Thr Ile Glu Ser Phe Gly Gln Arg Thr
            195                 200                 205 tct ata tac cgc ggt gtt aca agg cat cgg tgg aca gga aga tat gag   672
Ser Ile Tyr Arg Gly Val Thr Arg His Arg Trp Thr Gly Arg Tyr Glu
    210                 215                 220 gca cat tta tgg gat aat agt tgt aaa aga gaa ggc caa acg cgc aaa   720
Ala His Leu Trp Asp Asn Ser Cys Lys Arg Glu Gly Gln Thr Arg Lys
225                 230                 235                 240 gga aga caa gtt tat ttg gga ggt tat gac aaa gaa gaa aaa gca gct   768
Gly Arg Gln Val Tyr Leu Gly Gly Tyr Asp Lys Glu Glu Lys Ala Ala
                245                 250                 255 agg gct tat gat tta gcc gca ctc aag tat tgg gga acc acc act act   816
Arg Ala Tyr Asp Leu Ala Ala Leu Lys Tyr Trp Gly Thr Thr Thr Thr
            260                 265                 270 act aac ttc ccc atg agc gaa tat gaa aaa gag gta gaa gag atg aag   864
Thr Asn Phe Pro Met Ser Glu Tyr Glu Lys Glu Val Glu Glu Met Lys
            275                 280                 285 cac atg aca agg caa gag tat gtt gcc tca ctg cgc agg aaa agt agt   912
His Met Thr Arg Gln Glu Tyr Val Ala Ser Leu Arg Arg Lys Ser Ser
    290                 295                 300 ggt ttc tct cgt ggt gca tcg att tat cgt gga gta aca aga cat cac   960
Gly Phe Ser Arg Gly Ala Ser Ile Tyr Arg Gly Val Thr Arg His His
305                 310                 315                 320 caa cat gga aga tgg caa gct agg ata gga aga gtc gcc ggt aac aaa   1008
Gln His Gly Arg Trp Gln Ala Arg Ile Gly Arg Val Ala Gly Asn Lys
                325                 330                 335 gac ctc tac ttg gga act ttt ggc aca caa gaa gaa gct gca gag gca   1056
Asp Leu Tyr Leu Gly Thr Phe Gly Thr Gln Glu Glu Ala Ala Glu Ala
            340                 345                 350 tac gac att gcg gcc atc aaa ttc aga gga tta acc gca gtg act aac   1104
Tyr Asp Ile Ala Ala Ile Lys Phe Arg Gly Leu Thr Ala Val Thr Asn
            355                 360                 365 ttc gac atg aac aga tac aac gtt aaa gca atc ctc gaa agc cct agt   1152
Phe Asp Met Asn Arg Tyr Asn Val Lys Ala Ile Leu Glu Ser Pro Ser
    370                 375                 380 ctt cct att ggt agc gcc gca aaa cgt ctc aag gag gct aac cgt ccg   1200
Leu Pro Ile Gly Ser Ala Ala Lys Arg Leu Lys Glu Ala Asn Arg Pro
385                 390                 395                 400 gtt cca agt atg atg atg atc agt aat aac gtt tca gag agt gag aat   1248
Val Pro Ser Met Met Met Ile Ser Asn Asn Val Ser Glu Ser Glu Asn
                405                 410                 415 agt gct agc ggt tgg caa aac gct gcg gtt cag cat cat cag gga gta   1296
Ser Ala Ser Gly Trp Gln Asn Ala Ala Val Gln His His Gln Gly Val
```

```
Ser Ala Ser Gly Trp Gln Asn Ala Ala Val Gln His His Gln Gly Val
            420                 425                 430 gat ttg agc tta ttg cac caa cat caa gag agg tac aat ggt tat tat       1344
Asp Leu Ser Leu Leu His Gln His Gln Glu Arg Tyr Asn Gly Tyr Tyr
            435                 440                 445 tac aat gga gga aac ttg tct tcg gag agt gct agg gct tgt ttc aaa       1392
Tyr Asn Gly Gly Asn Leu Ser Ser Glu Ser Ala Arg Ala Cys Phe Lys
450                 455                 460 caa gag gat gat caa cac cat ttc ttg agc aac acg cag agc ctc atg       1440
Gln Glu Asp Asp Gln His His Phe Leu Ser Asn Thr Gln Ser Leu Met
465                 470                 475                 480 act aat atc gat cat caa agt tct gtt tcg gat gat tcg gtt act gtt       1488
Thr Asn Ile Asp His Gln Ser Ser Val Ser Asp Asp Ser Val Thr Val
                485                 490                 495 tgt gga aat gtt gtt ggt tat ggt ggt tat caa gga ttt gca gcc ccg       1536
Cys Gly Asn Val Val Gly Tyr Gly Gly Tyr Gln Gly Phe Ala Ala Pro
            500                 505                 510 gtt aac tgc gat gcc tac gct gct agt gag ttt gat tat aac gca aga       1584
Val Asn Cys Asp Ala Tyr Ala Ala Ser Glu Phe Asp Tyr Asn Ala Arg
        515                 520                 525 aac cat tat tac ttt gct cag cag cag cag acc cag cag tcg cca ggt       1632
Asn His Tyr Tyr Phe Ala Gln Gln Gln Gln Thr Gln Gln Ser Pro Gly
    530                 535                 540 gga gat ttt ccc gcg gca atg acg aat aat gtt ggc tct aat atg tat       1680
Gly Asp Phe Pro Ala Ala Met Thr Asn Asn Val Gly Ser Asn Met Tyr
545                 550                 555                 560 tac cat ggg gaa ggt ggt gga gaa gtt gct cca aca ttt aca gtt tgg       1728
Tyr His Gly Glu Gly Gly Gly Glu Val Ala Pro Thr Phe Thr Val Trp
                565                 570                 575 aac gac aat tag                                                        1740
Asn Asp Asn <210> SEQ ID NO 24
<211> LENGTH: 579
<212> TYPE: PRT
<213> ORGANISM: Brassica napus

<400> SEQUENCE: 24

Met Asn Asn Asn Trp Leu Gly Phe Ser Leu Ser Pro Tyr Glu Gln Asn
1               5                   10                  15

His His Arg Lys Asp Val Tyr Ser Ser Thr Thr Thr Val Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Val Asp
    50                  55                  60

Ala Phe Thr Arg Asp Asn Asn Ser His Ser Arg Asp Trp Asp Ile Asn
65                  70                  75                  80

Gly Cys Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Gly Ser Gly Ser Gly Cys Tyr Gly Gly Gly Asp Gly
        115                 120                 125

Gly Gly Gly Ser Leu Gly Leu Ser Met Ile Lys Thr Trp Leu Arg Asn
    130                 135                 140

Gln Pro Val Asp Asn Val Asp Asn Gln Glu Asn Gly Asn Ala Ala Lys
145                 150                 155                 160
```

-continued

```
Gly Leu Ser Leu Ser Met Asn Ser Ser Thr Ser Cys Asp Asn Asn Asn
                165                 170                 175

Asp Ser Asn Asn Asn Val Val Ala Gln Gly Lys Thr Ile Asp Asp Ser
            180                 185                 190

Val Glu Ala Thr Pro Lys Lys Thr Ile Glu Ser Phe Gly Gln Arg Thr
        195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Met Ser Glu Tyr Glu Lys Glu Val Glu Glu Met Lys
        275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Thr Ala Val Thr Asn
        355                 360                 365

Phe Asp Met Asn Arg Tyr Asn Val Lys Ala Ile Leu Glu Ser Pro Ser
    370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Ser Ala Ser Gly Trp Gln Asn Ala Ala Val Gln His His Gln Gly Val
            420                 425                 430

Asp Leu Ser Leu Leu His Gln His Gln Glu Arg Tyr Asn Gly Tyr Tyr
        435                 440                 445

Tyr Asn Gly Gly Asn Leu Ser Ser Glu Ser Ala Arg Ala Cys Phe Lys
    450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Ser Val Thr Val
                485                 490                 495

Cys Gly Asn Val Val Gly Tyr Gly Tyr Gln Gly Phe Ala Ala Pro
            500                 505                 510

Val Asn Cys Asp Ala Tyr Ala Ala Ser Glu Phe Asp Tyr Asn Ala Arg
        515                 520                 525

Asn His Tyr Tyr Phe Ala Gln Gln Gln Thr Gln Gln Ser Pro Gly
    530                 535                 540

Gly Asp Phe Pro Ala Ala Met Thr Asn Asn Val Gly Ser Asn Met Tyr
545                 550                 555                 560

Tyr His Gly Glu Gly Gly Glu Val Ala Pro Thr Phe Thr Val Trp
                565                 570                 575
```

Asn Asp Asn

<210> SEQ ID NO 25
<211> LENGTH: 1740
<212> TYPE: DNA
<213> ORGANISM: Brassica napus
<220> FEATURE:
<221> NAME/KEY: CDS
<222> LOCATION: (1)...(1740)

<400> SEQUENCE: 25

| | | | | | | | | | | | | | | | | |
|---|---|---|---|---|---|---|---|---|---|---|---|---|---|---|---|---|
| atg | aat | aat | aac | tgg | tta | ggc | ttt | tct | ctc | tct | cct | tat | gaa | caa | aat | 48 |
| Met | Asn | Asn | Asn | Trp | Leu | Gly | Phe | Ser | Leu | Ser | Pro | Tyr | Glu | Gln | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cac | cat | cgt | aag | gac | gtc | tgc | tct | tcc | acc | acc | aca | acc | gcc | gta | gat | 96 |
| His | His | Arg | Lys | Asp | Val | Cys | Ser | Ser | Thr | Thr | Thr | Thr | Ala | Val | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| gtc | gcc | gga | gag | tac | tgt | tac | gat | ccg | acc | gct | gcc | tcc | gat | gag | tct | 144 |
| Val | Ala | Gly | Glu | Tyr | Cys | Tyr | Asp | Pro | Thr | Ala | Ala | Ser | Asp | Glu | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| tca | gcc | atc | caa | aca | tcg | ttt | cct | tct | ccc | ttt | ggt | gtc | gtc | ctc | gat | 192 |
| Ser | Ala | Ile | Gln | Thr | Ser | Phe | Pro | Ser | Pro | Phe | Gly | Val | Val | Leu | Asp | |
| 50 | | | | | 55 | | | | | 60 | | | | | | |

| | | | | | | | | | | | | | | | | |
|---|---|---|---|---|---|---|---|---|---|---|---|---|---|---|---|---|
| gct | ttc | acc | aga | gac | aac | aat | agt | cac | tcc | cga | gat | tgg | gac | atc | aat | 240 |
| Ala | Phe | Thr | Arg | Asp | Asn | Asn | Ser | His | Ser | Arg | Asp | Trp | Asp | Ile | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggt | agt | gca | tgt | aat | aac | atc | cac | aat | gat | gag | caa | gat | gga | cca | aaa | 288 |
| Gly | Ser | Ala | Cys | Asn | Asn | Ile | His | Asn | Asp | Glu | Gln | Asp | Gly | Pro | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| ctt | gag | aat | ttc | ctt | ggc | cgc | acc | acc | acg | att | tac | aac | acc | aac | gaa | 336 |
| Leu | Glu | Asn | Phe | Leu | Gly | Arg | Thr | Thr | Thr | Ile | Tyr | Asn | Thr | Asn | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| aac | gtt | gga | gat | atc | gat | gga | agt | ggg | tgt | tat | gga | gga | gga | gac | ggt | 384 |
| Asn | Val | Gly | Asp | Ile | Asp | Gly | Ser | Gly | Cys | Tyr | Gly | Gly | Gly | Asp | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| ggt | ggt | ggc | tca | cta | gga | ctt | tcg | atg | ata | aag | aca | tgg | ctg | aga | aat | 432 |
| Gly | Gly | Gly | Ser | Leu | Gly | Leu | Ser | Met | Ile | Lys | Thr | Trp | Leu | Arg | Asn | |
| 130 | | | | | 135 | | | | | 140 | | | | | | |

| | | | | | | | | | | | | | | | | |
|---|---|---|---|---|---|---|---|---|---|---|---|---|---|---|---|---|
| caa | ccc | gtg | gat | aat | gtt | gat | aat | caa | gaa | aat | ggc | aat | ggt | gca | aaa | 480 |
| Gln | Pro | Val | Asp | Asn | Val | Asp | Asn | Gln | Glu | Asn | Gly | Asn | Gly | Ala | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | ctg | tcc | ctc | tca | atg | aac | tca | tct | act | tct | tgt | gat | aac | aac | aac | 528 |
| Gly | Leu | Ser | Leu | Ser | Met | Asn | Ser | Ser | Thr | Ser | Cys | Asp | Asn | Asn | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| tac | agc | agt | aac | aac | ctt | gtt | gcc | caa | ggg | aag | act | att | gat | gat | agc | 576 |
| Tyr | Ser | Ser | Asn | Asn | Leu | Val | Ala | Gln | Gly | Lys | Thr | Ile | Asp | Asp | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| gtt | gaa | gct | aca | ccg | aag | aaa | act | att | gag | agt | ttt | gga | cag | agg | acg | 624 |
| Val | Glu | Ala | Thr | Pro | Lys | Lys | Thr | Ile | Glu | Ser | Phe | Gly | Gln | Arg | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| tct | ata | tac | cgc | ggt | gtt | aca | agg | cat | cgg | tgg | aca | gga | aga | tat | gag | 672 |
| Ser | Ile | Tyr | Arg | Gly | Val | Thr | Arg | His | Arg | Trp | Thr | Gly | Arg | Tyr | Glu | |
| 210 | | | | | 215 | | | | | 220 | | | | | | |

| | | | | | | | | | | | | | | | | |
|---|---|---|---|---|---|---|---|---|---|---|---|---|---|---|---|---|
| gca | cat | tta | tgg | gat | aat | agt | tgt | aaa | cga | gaa | ggc | caa | acg | cgc | aaa | 720 |
| Ala | His | Leu | Trp | Asp | Asn | Ser | Cys | Lys | Arg | Glu | Gly | Gln | Thr | Arg | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gga | aga | caa | gtt | tat | ttg | gga | ggt | tat | gac | aaa | gaa | gaa | aaa | gca | gct | 768 |
| Gly | Arg | Gln | Val | Tyr | Leu | Gly | Gly | Tyr | Asp | Lys | Glu | Glu | Lys | Ala | Ala | |
| | | | | 245 | | | | | 250 | | | | | 255 | | |

| | | | | | | | | | | | | | | | | |
|---|---|---|---|---|---|---|---|---|---|---|---|---|---|---|---|---|
| agg | gct | tat | gat | tta | gcc | gca | ctc | aag | tat | tgg | gga | acc | acc | act | act | 816 |
| Arg | Ala | Tyr | Asp | Leu | Ala | Ala | Leu | Lys | Tyr | Trp | Gly | Thr | Thr | Thr | Thr | |

```
                      260                 265                 270
act aac ttc ccc atg agc gaa tat gag aaa gag ata gaa gag atg aag      864
Thr Asn Phe Pro Met Ser Glu Tyr Glu Lys Glu Ile Glu Glu Met Lys
            275                 280                 285 cac atg aca agg caa gag tat gtt gcc tca ctt cgc agg aaa agt agt      912
His Met Thr Arg Gln Glu Tyr Val Ala Ser Leu Arg Arg Lys Ser Ser
        290                 295                 300 ggt ttc tct cgt ggt gca tcg att tat cgt gga gta aca aga cat cac      960
Gly Phe Ser Arg Gly Ala Ser Ile Tyr Arg Gly Val Thr Arg His His
305                 310                 315                 320 caa cat gga aga tgg caa gct agg ata gga aga gtc gcc ggt aac aaa     1008
Gln His Gly Arg Trp Gln Ala Arg Ile Gly Arg Val Ala Gly Asn Lys
                325                 330                 335 gac ctc tac ttg gga act ttt ggc aca caa gaa gaa gct gca gag gca     1056
Asp Leu Tyr Leu Gly Thr Phe Gly Thr Gln Glu Glu Ala Ala Glu Ala
            340                 345                 350 tac gac att gcg gcc atc aaa ttc aga gga tta acc gca gtg act aac     1104
Tyr Asp Ile Ala Ala Ile Lys Phe Arg Gly Leu Thr Ala Val Thr Asn
        355                 360                 365 ttc gac atg aac aga tac aac gtt aaa gca atc ctc gaa agc cct agt     1152
Phe Asp Met Asn Arg Tyr Asn Val Lys Ala Ile Leu Glu Ser Pro Ser
370                 375                 380 ctt cct att ggt agc gcc gca aaa cgt ctc aag gag gct aac cgt ccg     1200
Leu Pro Ile Gly Ser Ala Ala Lys Arg Leu Lys Glu Ala Asn Arg Pro
                385                 390                 395                 400 gtt cca agt atg atg atg atc agt aat aac gtt tca gag agt gag aat     1248
Val Pro Ser Met Met Met Ile Ser Asn Asn Val Ser Glu Ser Glu Asn
            405                 410                 415 aat gct agc ggt tgg caa aac gct gcg gtt cag cat cat cag gga gta     1296
Asn Ala Ser Gly Trp Gln Asn Ala Ala Val Gln His His Gln Gly Val
        420                 425                 430 gat ttg agc tta ttg cag caa cat caa gag agg tac aat ggt tat tat     1344
Asp Leu Ser Leu Leu Gln Gln His Gln Glu Arg Tyr Asn Gly Tyr Tyr
435                 440                 445 tac aat gga gga aac ttg tct tcg gag agt gct agg gct tgt ttc aaa     1392
Tyr Asn Gly Gly Asn Leu Ser Ser Glu Ser Ala Arg Ala Cys Phe Lys
                450                 455                 460 caa gag gat gat caa cac cat ttc ttg agc aac acg cag agc ctc atg     1440
Gln Glu Asp Asp Gln His His Phe Leu Ser Asn Thr Gln Ser Leu Met
465                 470                 475                 480 act aat atc gat cat caa agt tct gtt tca gat gat tcg gtt act gtt     1488
Thr Asn Ile Asp His Gln Ser Ser Val Ser Asp Asp Ser Val Thr Val
            485                 490                 495 tgt gga aat gtt gtt ggt tat ggt ggt tat caa gga ttt gca gcc ccg     1536
Cys Gly Asn Val Val Gly Tyr Gly Gly Tyr Gln Gly Phe Ala Ala Pro
        500                 505                 510 gtt aac tgc gat gcc tac gct gct agt gag ttt gac tat aac gca aga     1584
Val Asn Cys Asp Ala Tyr Ala Ala Ser Glu Phe Asp Tyr Asn Ala Arg
515                 520                 525 aac cat tat tac ttt gct cag cag cag cag acc cag cat tcg cca gga     1632
Asn His Tyr Tyr Phe Ala Gln Gln Gln Gln Thr Gln His Ser Pro Gly
                530                 535                 540 gga gat ttt ccc gcg gca atg acg aat aat gtt ggc tct aat atg tat     1680
Gly Asp Phe Pro Ala Ala Met Thr Asn Asn Val Gly Ser Asn Met Tyr
545                 550                 555                 560 tac cat ggg gaa ggt ggt gga gaa gtt gct cca aca ttt aca gtt tgg     1728
Tyr His Gly Glu Gly Gly Gly Glu Val Ala Pro Thr Phe Thr Val Trp
            565                 570                 575 aac gac aat tag                                                    1740
```

-continued

Asn Asp Asn

<210> SEQ ID NO 26
<211> LENGTH: 579
<212> TYPE: PRT
<213> ORGANISM: Brassica napus

<400> SEQUENCE: 26

Met Asn Asn Asn Trp Leu Gly Phe Ser Leu Ser Pro Tyr Glu Gln Asn
1               5                   10                  15

His His Arg Lys Asp Val Cys Ser Thr Thr Thr Ala Val Asp
            20                  25                  30

Val Ala Gly Glu Tyr Cys Tyr Asp Pro Thr Ala Ala Ser Asp Glu Ser
            35                  40                  45

Ser Ala Ile Gln Thr Ser Phe Pro Ser Pro Phe Gly Val Val Leu Asp
        50                  55                  60

Ala Phe Thr Arg Asp Asn Asn Ser His Ser Arg Asp Trp Asp Ile Asn
65                  70                  75                  80

Gly Ser Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Ile Asp Gly Ser Gly Cys Tyr Gly Gly Asp Gly
            115                 120                 125

Gly Gly Gly Ser Leu Gly Leu Ser Met Ile Lys Thr Trp Leu Arg Asn
130                 135                 140

Gln Pro Val Asp Asn Val Asp Asn Gln Glu Asn Gly Asn Gly Ala Lys
145                 150                 155                 160

Gly Leu Ser Leu Ser Met Asn Ser Ser Thr Ser Cys Asp Asn Asn
                165                 170                 175

Tyr Ser Ser Asn Asn Leu Val Ala Gln Gly Lys Thr Ile Asp Asp Ser
            180                 185                 190

Val Glu Ala Thr Pro Lys Lys Thr Ile Glu Ser Phe Gly Gln Arg Thr
            195                 200                 205

Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Met Ser Glu Tyr Glu Lys Glu Ile Glu Glu Met Lys
        275                 280                 285

His Met Thr Arg Gln Glu Tyr Val Ala Ser Leu Arg Arg Lys Ser Ser
    290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Thr Ala Val Thr Asn
            355                 360                 365

```
                    Phe Asp Met Asn Arg Tyr Asn Val Lys Ala Ile Leu Glu Ser Pro Ser
                        370                 375                 380

Leu Pro Ile Gly Ser Ala Ala Lys Arg Leu Lys Glu Ala Asn Arg Pro
                    385                 390                 395                 400

Val Pro Ser Met Met Met Ile Ser Asn Asn Val Ser Glu Ser Glu Asn
                                    405                 410                 415

Asn Ala Ser Gly Trp Gln Asn Ala Ala Val Gln His Gln Gly Val
                                    420                 425                 430

Asp Leu Ser Leu Leu Gln Gln His Gln Glu Arg Tyr Asn Gly Tyr Tyr
                                435                 440                 445

Tyr Asn Gly Gly Asn Leu Ser Ser Glu Ser Ala Arg Ala Cys Phe Lys
                        450                 455                 460

Gln Glu Asp Asp Gln His His Phe Leu Ser Asn Thr Gln Ser Leu Met
                    465                 470                 475                 480

Thr Asn Ile Asp His Gln Ser Ser Val Ser Asp Ser Val Thr Val
                                    485                 490                 495

Cys Gly Asn Val Val Gly Tyr Gly Gly Tyr Gln Gly Phe Ala Ala Pro
                                    500                 505                 510

Val Asn Cys Asp Ala Tyr Ala Ala Ser Glu Phe Asp Tyr Asn Ala Arg
                                    515                 520                 525

Asn His Tyr Tyr Phe Ala Gln Gln Gln Thr Gln His Ser Pro Gly
                                530                 535                 540

Gly Asp Phe Pro Ala Ala Met Thr Asn Asn Val Gly Ser Asn Met Tyr
                    545                 550                 555                 560

Tyr His Gly Glu Gly Gly Gly Glu Val Ala Pro Thr Phe Thr Val Trp
                                    565                 570                 575

Asn Asp Asn

<210> SEQ ID NO 27
<211> LENGTH: 2082
<212> TYPE: DNA
<213> ORGANISM: Sorghum bicolor
<220> FEATURE:
<221> NAME/KEY: CDS
<222> LOCATION: (1)...(2082)

<400> SEQUENCE: 27 atg gct tcg acg aac aac cac tgg ctg ggt ttc tcg ctc tcg ggc cag      48
Met Ala Ser Thr Asn Asn His Trp Leu Gly Phe Ser Leu Ser Gly Gln
 1               5                  10                  15 gat aac ccg cag cct aat cat cag gac agc tcg cct gcc gcc gcc ggc      96
Asp Asn Pro Gln Pro Asn His Gln Asp Ser Ser Pro Ala Ala Ala Gly
             20                  25                  30 atc gac atc tcc ggc gcc agc gac ttc tat ggc ttg ccc acg cag cag     144
Ile Asp Ile Ser Gly Ala Ser Asp Phe Tyr Gly Leu Pro Thr Gln Gln
         35                  40                  45 ggc tcc gac ggg aat ctc ggc gtg ccg ggc ctg cgg gac gat cac gct     192
Gly Ser Asp Gly Asn Leu Gly Val Pro Gly Leu Arg Asp Asp His Ala
     50                  55                  60 tct tat ggc atc atg gag gcc ttc aac agg gtt cct caa gaa acc caa     240
Ser Tyr Gly Ile Met Glu Ala Phe Asn Arg Val Pro Gln Glu Thr Gln
 65                  70                  75                  80 gat tgg aac atg agg gga ttg gac tac aac ggc ggt ggc tcg gaa ctc     288
Asp Trp Asn Met Arg Gly Leu Asp Tyr Asn Gly Gly Gly Ser Glu Leu
                 85                  90                  95 tcg atg ctt gtg ggg tcc agc ggc ggc ggg ggc ggc ggc aag agg          336
Ser Met Leu Val Gly Ser Ser Gly Gly Gly Gly Gly Gly Lys Arg
            100                 105                 110
```

| | | | | | | | | | | | | | | | | |
|---|---|---|---|---|---|---|---|---|---|---|---|---|---|---|---|---|
| gcc | gtg | gaa | gac | agc | gag | ccc | aag | ctc | gaa | gat | ttc | ctc | ggc | ggc | aac | 384 |
| Ala | Val | Glu | Asp | Ser | Glu | Pro | Lys | Leu | Glu | Asp | Phe | Leu | Gly | Gly | Asn | |
| | | 115 | | | | 120 | | | | | 125 | | | | | |
| tcg | ttc | gtc | tcc | gag | cat | gat | cag | tcc | ggc | ggt | tac | ctg | ttc | tct | gga | 432 |
| Ser | Phe | Val | Ser | Glu | His | Asp | Gln | Ser | Gly | Gly | Tyr | Leu | Phe | Ser | Gly | |
| | 130 | | | | | 135 | | | | | 140 | | | | | |
| gtc | ccg | atg | gcc | agc | agc | acc | aac | agc | aac | agc | ggg | agc | aac | acc | atg | 480 |
| Val | Pro | Met | Ala | Ser | Ser | Thr | Asn | Ser | Asn | Ser | Gly | Ser | Asn | Thr | Met | |
| 145 | | | | | 150 | | | | | 155 | | | | | 160 | |
| gag | ctc | tcc | atg | atc | aag | acc | tgg | ctc | cgg | aac | aac | cag | gtg | ccc | cag | 528 |
| Glu | Leu | Ser | Met | Ile | Lys | Thr | Trp | Leu | Arg | Asn | Asn | Gln | Val | Pro | Gln | |
| | | | | 165 | | | | | 170 | | | | | 175 | | |
| ccg | cag | ccg | cca | gca | gct | ccg | cat | cag | gcg | ccg | cag | act | gag | gag | atg | 576 |
| Pro | Gln | Pro | Pro | Ala | Ala | Pro | His | Gln | Ala | Pro | Gln | Thr | Glu | Glu | Met | |
| | | | 180 | | | | | 185 | | | | | 190 | | | |
| agc | acc | gac | gcc | aac | gcc | agc | gcc | agc | agc | ttt | ggc | tgc | tcg | gat | tcg | 624 |
| Ser | Thr | Asp | Ala | Asn | Ala | Ser | Ala | Ser | Ser | Phe | Gly | Cys | Ser | Asp | Ser | |
| | | | | 195 | | | | | 200 | | | | | 205 | | |
| atg | ggg | agg | aac | ggc | acg | gtg | gcg | gct | gct | ggg | agc | tcc | cag | agc | ctg | 672 |
| Met | Gly | Arg | Asn | Gly | Thr | Val | Ala | Ala | Ala | Gly | Ser | Ser | Gln | Ser | Leu | |
| | | 210 | | | | | 215 | | | | | 220 | | | | |
| gcg | ctc | tcg | atg | agc | acg | ggc | tcg | cac | ctg | ccg | atg | gtt | gtg | gcc | ggc | 720 |
| Ala | Leu | Ser | Met | Ser | Thr | Gly | Ser | His | Leu | Pro | Met | Val | Val | Ala | Gly | |
| 225 | | | | | 230 | | | | | 235 | | | | | 240 | |
| ggc | ggc | gcc | agc | gga | gcg | gcc | tcg | gag | agc | acg | tca | tcg | gag | aac | aag | 768 |
| Gly | Gly | Ala | Ser | Gly | Ala | Ala | Ser | Glu | Ser | Thr | Ser | Ser | Glu | Asn | Lys | |
| | | | | 245 | | | | | 250 | | | | | 255 | | |
| cga | gcg | agc | ggc | gcc | atg | gat | tcg | ccc | ggc | agc | gcg | gta | gaa | gcc | gtc | 816 |
| Arg | Ala | Ser | Gly | Ala | Met | Asp | Ser | Pro | Gly | Ser | Ala | Val | Glu | Ala | Val | |
| | | | 260 | | | | | 265 | | | | | 270 | | | |
| ccg | agg | aag | tcc | atc | gac | acg | ttc | ggg | caa | agg | acc | tct | ata | tat | cga | 864 |
| Pro | Arg | Lys | Ser | Ile | Asp | Thr | Phe | Gly | Gln | Arg | Thr | Ser | Ile | Tyr | Arg | |
| | | 275 | | | | | 280 | | | | | 285 | | | | |
| ggt | gta | aca | aga | cat | aga | tgg | aca | ggg | cga | tat | gag | gct | cat | cta | tgg | 912 |
| Gly | Val | Thr | Arg | His | Arg | Trp | Thr | Gly | Arg | Tyr | Glu | Ala | His | Leu | Trp | |
| | 290 | | | | | 295 | | | | | 300 | | | | | |
| gat | aat | agt | tgt | aga | aga | gaa | ggg | cag | agt | cgc | aag | ggt | agg | caa | gtt | 960 |
| Asp | Asn | Ser | Cys | Arg | Arg | Glu | Gly | Gln | Ser | Arg | Lys | Gly | Arg | Gln | Val | |
| 305 | | | | | 310 | | | | | 315 | | | | | 320 | |
| tac | ctt | ggt | ggc | tat | gac | aag | gaa | gac | aag | gca | gca | agg | gct | tat | gat | 1008 |
| Tyr | Leu | Gly | Gly | Tyr | Asp | Lys | Glu | Asp | Lys | Ala | Ala | Arg | Ala | Tyr | Asp | |
| | | | | 325 | | | | | 330 | | | | | 335 | | |
| ttg | gca | gct | ctc | aag | tat | tgg | ggc | act | act | aca | aca | aca | aat | ttc | cct | 1056 |
| Leu | Ala | Ala | Leu | Lys | Tyr | Trp | Gly | Thr | Thr | Thr | Thr | Thr | Asn | Phe | Pro | |
| | | | 340 | | | | | 345 | | | | | 350 | | | |
| ata | agc | aac | tat | gaa | aag | gag | cta | gag | gaa | atg | aaa | cat | atg | act | agg | 1104 |
| Ile | Ser | Asn | Tyr | Glu | Lys | Glu | Leu | Glu | Glu | Met | Lys | His | Met | Thr | Arg | |
| | | 355 | | | | | 360 | | | | | 365 | | | | |
| cag | gag | tat | att | gca | tac | cta | aga | aga | aat | agc | agt | gga | ttt | tct | cgt | 1152 |
| Gln | Glu | Tyr | Ile | Ala | Tyr | Leu | Arg | Arg | Asn | Ser | Ser | Gly | Phe | Ser | Arg | |
| | 370 | | | | | 375 | | | | | 380 | | | | | |
| ggc | gca | tca | aaa | tat | cgt | gga | gta | act | aga | cat | cat | cag | cat | ggg | aga | 1200 |
| Gly | Ala | Ser | Lys | Tyr | Arg | Gly | Val | Thr | Arg | His | His | Gln | His | Gly | Arg | |
| 385 | | | | | 390 | | | | | 395 | | | | | 400 | |
| tgg | caa | gca | agg | ata | ggg | aga | gtt | gca | gga | aac | aag | gat | ctc | tac | ttg | 1248 |
| Trp | Gln | Ala | Arg | Ile | Gly | Arg | Val | Ala | Gly | Asn | Lys | Asp | Leu | Tyr | Leu | |
| | | | | 405 | | | | | 410 | | | | | 415 | | |
| ggc | aca | ttc | agc | acc | gag | gag | gag | gcg | gcg | gag | gcc | tac | gac | atc | gcc | 1296 |
| Gly | Thr | Phe | Ser | Thr | Glu | Glu | Glu | Ala | Ala | Glu | Ala | Tyr | Asp | Ile | Ala | |

```
                420             425             430
gcg atc aag ttc cgc ggt ctg aac gcc gtc acc aac ttc gac atg agc    1344
Ala Ile Lys Phe Arg Gly Leu Asn Ala Val Thr Asn Phe Asp Met Ser
        435                 440                 445 cgc tac gac gtc aag agc atc ctc gag agc agc acg ctg cct gtc ggc    1392
Arg Tyr Asp Val Lys Ser Ile Leu Glu Ser Ser Thr Leu Pro Val Gly
450                 455                 460 ggc gcg gcc agg cgc ctc aag gat gcc gtg gac cac gtg gag gcc ggc    1440
Gly Ala Ala Arg Arg Leu Lys Asp Ala Val Asp His Val Glu Ala Gly
465                 470                 475                 480 gcc acc atc tgg cgc gcc gac atg gac ggc ggc gtg atc tcc cag ctc    1488
Ala Thr Ile Trp Arg Ala Asp Met Asp Gly Gly Val Ile Ser Gln Leu
                485                 490                 495 gcc gaa gcc ggg atg ggc ggc tac gcc tcg tac ggg cac cac gcc tgg    1536
Ala Glu Ala Gly Met Gly Gly Tyr Ala Ser Tyr Gly His His Ala Trp
            500                 505                 510 ccg acc atc gcg ttc cag cag ccg tcg ccg ctc tcc gtc cac tac ccg    1584
Pro Thr Ile Ala Phe Gln Gln Pro Ser Pro Leu Ser Val His Tyr Pro
        515                 520                 525 tac ggg cag ccg ccg tcc cgc ggg tgg tgc aag ccc gag cag gac gcg    1632
Tyr Gly Gln Pro Pro Ser Arg Gly Trp Cys Lys Pro Glu Gln Asp Ala
530                 535                 540 gcc gtc gcc gcc gcc gcg cac agc ctg cag gac ctc cag cag ctg cac    1680
Ala Val Ala Ala Ala Ala His Ser Leu Gln Asp Leu Gln Gln Leu His
545                 550                 555                 560 ctc ggc agc gcg gca cac aac ttc ttc cag gcg tcg tcg agc tcg gca    1728
Leu Gly Ser Ala Ala His Asn Phe Phe Gln Ala Ser Ser Ser Ser Ala
                565                 570                 575 gtc tac aac agc ggc ggc ggc ggc gct agc ggc ggg tac cac cag ggc    1776
Val Tyr Asn Ser Gly Gly Gly Gly Ala Ser Gly Gly Tyr His Gln Gly
            580                 585                 590 ctc ggt ggc ggc agc agc tcc ttc ctc atg ccg tcg agc act gtc gtg    1824
Leu Gly Gly Gly Ser Ser Ser Phe Leu Met Pro Ser Ser Thr Val Val
        595                 600                 605 gcg ggg gcc gac cag ggg cac agc agc agc acg gcc aac cag ggg agc    1872
Ala Gly Ala Asp Gln Gly His Ser Ser Ser Thr Ala Asn Gln Gly Ser
610                 615                 620 acg tgc agc tac ggg gac gat cac cag gaa ggg aag ctc atc ggg tac    1920
Thr Cys Ser Tyr Gly Asp Asp His Gln Glu Gly Lys Leu Ile Gly Tyr
625                 630                 635                 640 gac gcc atg gtg gcg gcg acc gca gcc ggc ggg gac ccg tac gcc gcg    1968
Asp Ala Met Val Ala Ala Thr Ala Ala Gly Gly Asp Pro Tyr Ala Ala
                645                 650                 655 gcg agg agc ggg tac cag ttc tcg tcg cag ggc tcg gga tcc acg gtg    2016
Ala Arg Ser Gly Tyr Gln Phe Ser Ser Gln Gly Ser Gly Ser Thr Val
            660                 665                 670 agc atc gcg agg gcg aac ggg tac tct aac aac tgg agc tct cct ttc    2064
Ser Ile Ala Arg Ala Asn Gly Tyr Ser Asn Asn Trp Ser Ser Pro Phe
        675                 680                 685 aac ggc ggc atg ggg tga                                             2082
Asn Gly Gly Met Gly
        690

<210> SEQ ID NO 28
<211> LENGTH: 693
<212> TYPE: PRT
<213> ORGANISM: Sorghum bicolor

<400> SEQUENCE: 28

Met Ala Ser Thr Asn Asn His Trp Leu Gly Phe Ser Leu Ser Gly Gln
```

```
             1               5                  10                 15
           Asp Asn Pro Gln Pro Asn His Gln Asp Ser Pro Ala Ala Ala Gly
                         20                 25                 30

Ile Asp Ile Ser Gly Ala Ser Asp Phe Tyr Gly Leu Pro Thr Gln Gln
                         35                 40                 45

Gly Ser Asp Gly Asn Leu Gly Val Pro Gly Leu Arg Asp Asp His Ala
                     50                 55                 60

Ser Tyr Gly Ile Met Glu Ala Phe Asn Arg Val Pro Gln Glu Thr Gln
           65                 70                 75                 80

Asp Trp Asn Met Arg Gly Leu Asp Tyr Asn Gly Gly Ser Glu Leu
                              85                 90                 95

Ser Met Leu Val Gly Ser Ser Gly Gly Gly Gly Gly Lys Arg
                             100                105                110

Ala Val Glu Asp Ser Glu Pro Lys Leu Glu Asp Phe Leu Gly Gly Asn
                         115                120                125

Ser Phe Val Ser Glu His Asp Gln Ser Gly Gly Tyr Leu Phe Ser Gly
                         130                135                140

Val Pro Met Ala Ser Ser Thr Asn Ser Asn Ser Gly Ser Asn Thr Met
           145                150                155                160

Glu Leu Ser Met Ile Lys Thr Trp Leu Arg Asn Asn Gln Val Pro Gln
                             165                170                175

Pro Gln Pro Ala Ala Pro His Gln Ala Pro Gln Thr Glu Glu Met
                         180                185                190

Ser Thr Asp Ala Asn Ala Ser Ala Ser Ser Phe Gly Cys Ser Asp Ser
                         195                200                205

Met Gly Arg Asn Gly Thr Val Ala Ala Ala Gly Ser Ser Gln Ser Leu
                         210                215                220

Ala Leu Ser Met Ser Thr Gly Ser His Leu Pro Met Val Val Ala Gly
           225                230                235                240

Gly Gly Ala Ser Gly Ala Ala Ser Glu Ser Thr Ser Ser Glu Asn Lys
                         245                250                255

Arg Ala Ser Gly Ala Met Asp Ser Pro Gly Ser Ala Val Glu Ala Val
                         260                265                270

Pro Arg Lys Ser Ile Asp Thr Phe Gly Gln Arg Thr Ser Ile Tyr Arg
                         275                280                285

Gly Val Thr Arg His Arg Trp Thr Gly Arg Tyr Glu Ala His Leu Trp
                         290                295                300

Asp Asn Ser Cys Arg Arg Glu Gly Gln Ser Arg Lys Gly Arg Gln Val
           305                310                315                320

Tyr Leu Gly Gly Tyr Asp Lys Glu Asp Lys Ala Ala Arg Ala Tyr Asp
                             325                330                335

Leu Ala Ala Leu Lys Tyr Trp Gly Thr Thr Thr Thr Thr Asn Phe Pro
                         340                345                350

Ile Ser Asn Tyr Glu Lys Glu Leu Glu Met Lys His Met Thr Arg
                         355                360                365

Gln Glu Tyr Ile Ala Tyr Leu Arg Arg Asn Ser Ser Gly Phe Ser Arg
                         370                375                380

Gly Ala Ser Lys Tyr Arg Gly Val Thr Arg His His Gln His Gly Arg
           385                390                395                400

Trp Gln Ala Arg Ile Gly Arg Val Ala Gly Asn Lys Asp Leu Tyr Leu
                             405                410                415

Gly Thr Phe Ser Thr Glu Glu Glu Ala Ala Glu Ala Tyr Asp Ile Ala
                         420                425                430
```

```
Ala Ile Lys Phe Arg Gly Leu Asn Ala Val Thr Asn Phe Asp Met Ser
        435                 440                 445

Arg Tyr Asp Val Lys Ser Ile Leu Glu Ser Ser Thr Leu Pro Val Gly
    450                 455                 460

Gly Ala Ala Arg Arg Leu Lys Asp Ala Val Asp His Val Glu Ala Gly
465                 470                 475                 480

Ala Thr Ile Trp Arg Ala Asp Met Asp Gly Val Ile Ser Gln Leu
            485                 490                 495

Ala Glu Ala Gly Met Gly Gly Tyr Ala Ser Tyr Gly His His Ala Trp
            500                 505                 510

Pro Thr Ile Ala Phe Gln Gln Pro Ser Pro Leu Ser Val His Tyr Pro
            515                 520                 525

Tyr Gly Gln Pro Pro Ser Arg Gly Trp Cys Lys Pro Glu Gln Asp Ala
            530                 535                 540

Ala Val Ala Ala Ala His Ser Leu Gln Asp Leu Gln Gln Leu His
545                 550                 555                 560

Leu Gly Ser Ala Ala His Asn Phe Phe Gln Ala Ser Ser Ser Ala
                565                 570                 575

Val Tyr Asn Ser Gly Gly Gly Ala Ser Gly Gly Tyr His Gln Gly
            580                 585                 590

Leu Gly Gly Gly Ser Ser Ser Phe Leu Met Pro Ser Ser Thr Val Val
            595                 600                 605

Ala Gly Ala Asp Gln Gly His Ser Ser Ser Thr Ala Asn Gln Gly Ser
            610                 615                 620

Thr Cys Ser Tyr Gly Asp Asp His Gln Glu Gly Lys Leu Ile Gly Tyr
625                 630                 635                 640

Asp Ala Met Val Ala Ala Thr Ala Ala Gly Gly Asp Pro Tyr Ala Ala
                645                 650                 655

Ala Arg Ser Gly Tyr Gln Phe Ser Ser Gln Gly Ser Gly Ser Thr Val
                660                 665                 670

Ser Ile Ala Arg Ala Asn Gly Tyr Ser Asn Asn Trp Ser Ser Pro Phe
            675                 680                 685

Asn Gly Gly Met Gly
        690

<210> SEQ ID NO 29
<211> LENGTH: 508
<212> TYPE: DNA
<213> ORGANISM: Zea mays

<400> SEQUENCE: 29
ctatagtatt ttaaaattgc attaacaaac atgtcctaat tggtactcct gagatactat     60
accctcctgt tttaaaatag ttggcattat cgaattatca ttttactttt taatgttttc    120
tcttctttta atatatttta tgaatttttaa tgtattttaa aatgttatgc agttcgctct    180 ggactttttct gctgcgccta cacttgggtg tactgggcct aaattcagcc tgaccgaccg    240
cctgcattga ataatggatg agcaccggta aaatccgcgt acccaacttt cgagaagaac    300
cgagacgtgg cgggccgggc caccgacgca cggcaccagc gactgcacac gtcccgccgg    360
cgtacgtgta cgtgctgttc cctcactggc cgcccaatcc actcatgcat gcccacgtac    420 accccctgccg tggcgcgccc agatcctaat cctttcgccg ttctgcactt ctgctgccta    480
taaatggcgg catcgaccgt cacctgct                                        508
```

```
<210> SEQ ID NO 30
<211> LENGTH: 665
<212> TYPE: DNA
<213> ORGANISM: Artificial Sequence
<220> FEATURE:
<223> OTHER INFORMATION: Promoter construct comprising Zea mays Rab17
      promoter and attB1 site

<400> SEQUENCE: 30
ctatagtatt ttaaaattgc attaacaaac atgtcctaat tggtactcct gagatactat      60
accctcctgt tttaaaatag ttggcattat cgaattatca ttttactttt taatgttttc     120
tcttctttta atatatttta tgaattttaa tgtatttaa aatgttatgc agttcgctct      180
ggacttttct gctgcgccta cacttgggtg tactgggcct aaattcagcc tgaccgaccg     240
cctgcattga ataatggatg agcaccggta aaatccgcgt acccaacttt cgagaagaac     300
cgagacgtgg cgggccgggc caccgacgca cggcaccagc gactgcacac gtcccgccgg     360
cgtacgtgta cgtgctgttc cctcactggc cgcccaatcc actcatgcat gcccacgtac     420
acccctgccg tggcgcgccc agatcctaat cctttcgccg ttctgcactt ctgctgccta     480
taaatggcgg catcgaccgt cacctgcttc accaccggcg agccacatcg agaacacgat     540
cgagcacaca agcacgaaga ctcgtttagg agaaaccaca aaccaccaag ccgtgcaagc     600
accaagcttg gtcacccggt ccgggcctag aaggccagct tcaagtttgt acaaaaaagc     660
aggct                                                                 665

<210> SEQ ID NO 31
<211> LENGTH: 24
<212> TYPE: DNA
<213> ORGANISM: Artificial Sequence
<220> FEATURE:
<223> OTHER INFORMATION: attachment B1 site

<400> SEQUENCE: 31
caagtttgta caaaaaagca ggct                                             24

<210> SEQ ID NO 32
<211> LENGTH: 24
<212> TYPE: DNA
<213> ORGANISM: Artificial Sequence
<220> FEATURE:
<223> OTHER INFORMATION: attachment B2 site

<400> SEQUENCE: 32
acccagcttt cttgtacaaa gtgg                                             24

<210> SEQ ID NO 33
<211> LENGTH: 22
<212> TYPE: DNA
<213> ORGANISM: Artificial Sequence
<220> FEATURE:
<223> OTHER INFORMATION: attachment B3 site

<400> SEQUENCE: 33
acaactttgt ataataaagt tg                                               22

<210> SEQ ID NO 34
<211> LENGTH: 22
<212> TYPE: DNA
<213> ORGANISM: Artificial Sequence
<220> FEATURE:
<223> OTHER INFORMATION: attachment B4 site

<400> SEQUENCE: 34
```

```
acaactttgt atagaaaagt tg                                              22

<210> SEQ ID NO 35
<211> LENGTH: 95
<212> TYPE: DNA
<213> ORGANISM: Zea mays

<400> SEQUENCE: 35
tcaccaccgg cgagccacat cgagaacacg atcgagcaca caagcacgaa gactcgttta    60
ggagaaacca caaaccacca agccgtgcaa gcacc                               95

<210> SEQ ID NO 36
<211> LENGTH: 133
<212> TYPE: DNA
<213> ORGANISM: Artificial Sequence
<220> FEATURE:
<223> OTHER INFORMATION: Plasmid linker sequence

<400> SEQUENCE: 36
tcaccaccgg cgagccacat cgagaacacg atcgagcaca caagcacgaa gactcgttta    60
ggagaaacca caaaccacca agccgtgcaa gcaccaagct tggtcacccg gtccgggcct   120
agaaggccag ctt                                                      133

<210> SEQ ID NO 37
<211> LENGTH: 61
<212> TYPE: DNA
<213> ORGANISM: Artificial Sequence
<220> FEATURE:
<223> OTHER INFORMATION: Plasmid linker sequence

<400> SEQUENCE: 37
tcgaaggaga tagaaccaat tctctaagga aatacttaac catggtcgac tggatccaac    60
a                                                                    61

<210> SEQ ID NO 38
<211> LENGTH: 318
<212> TYPE: DNA
<213> ORGANISM: Artificial Sequence
<220> FEATURE:
<223> OTHER INFORMATION: PinII terminator

<400> SEQUENCE: 38
agacttgtcc atcttctgga ttggccaact taattaatgt atgaaataaa aggatgcaca    60
catagtgaca tgctaatcac tataatgtgg gcatcaaagt tgtgtgttat gtgtaattac   120
tagttatctg aataaaagag aaagagatca tccatatttc ttatcctaaa tgaatgtcac   180
gtgtctttat aattctttga tgaaccagat gcatttcatt aaccaaatcc atatacatat   240
aaatattaat catatataat taatatcaat tgggttagca aaacaaatct agtctaggtg   300
tgttttgcga attgcggc                                                 318

<210> SEQ ID NO 39
<211> LENGTH: 16
<212> TYPE: DNA
<213> ORGANISM: Artificial Sequence
<220> FEATURE:
<223> OTHER INFORMATION: Plasmid linker sequence

<400> SEQUENCE: 39
gtttcgagat atctag                                                    16
```

<210> SEQ ID NO 40
<211> LENGTH: 14
<212> TYPE: DNA
<213> ORGANISM: Artificial Sequence
<220> FEATURE:
<223> OTHER INFORMATION: Plasmid linker sequence

<400> SEQUENCE: 40
ccgttaacgg atcc                                                          14

<210> SEQ ID NO 41
<211> LENGTH: 1272
<212> TYPE: DNA
<213> ORGANISM: Artificial Sequence
<220> FEATURE:
<223> OTHER INFORMATION: Maize optimized FLP coding sequence
<220> FEATURE:
<221> NAME/KEY: CDS
<222> LOCATION: (1)...(1272)

<400> SEQUENCE: 41

```
atg ccc cag ttc gac atc ctc tgc aag acc ccc ccc aag gtg ctc gtg        48
Met Pro Gln Phe Asp Ile Leu Cys Lys Thr Pro Pro Lys Val Leu Val
  1               5                  10                  15 agg cag ttc gtg gag agg ttc gag agg ccc tcc ggc gag aag atc gcc        96
Arg Gln Phe Val Glu Arg Phe Glu Arg Pro Ser Gly Glu Lys Ile Ala
             20                  25                  30 ctc tgc gcc gcc gag ctc acc tac ctc tgc tgg atg atc acc cac aac       144
Leu Cys Ala Ala Glu Leu Thr Tyr Leu Cys Trp Met Ile Thr His Asn
         35                  40                  45 ggc acc gcc att aag agg gcc acc ttc atg tca tac aac acc atc atc       192
Gly Thr Ala Ile Lys Arg Ala Thr Phe Met Ser Tyr Asn Thr Ile Ile
     50                  55                  60 tcc aac tcc ctc tcc ttc gac atc gtg aac aag tcc ctc cag ttc aaa       240
Ser Asn Ser Leu Ser Phe Asp Ile Val Asn Lys Ser Leu Gln Phe Lys
 65                  70                  75                  80 tac aag acc cag aag gcc acc atc ctc gag gcc tcc ctc aag aag ctc       288
Tyr Lys Thr Gln Lys Ala Thr Ile Leu Glu Ala Ser Leu Lys Lys Leu
                 85                  90                  95 atc ccc gcc tgg gag ttc acc atc atc ccc tac tac ggc cag aag cac       336
Ile Pro Ala Trp Glu Phe Thr Ile Ile Pro Tyr Tyr Gly Gln Lys His
            100                 105                 110 cag tcc gac atc acc gac atc gtg tca tcc ctc cag ctt cag ttc gag       384
Gln Ser Asp Ile Thr Asp Ile Val Ser Ser Leu Gln Leu Gln Phe Glu
        115                 120                 125 tcc tcc gag gag gct gac aag ggc aac tcc cac tcc aag aag atg ctg       432
Ser Ser Glu Glu Ala Asp Lys Gly Asn Ser His Ser Lys Lys Met Leu
    130                 135                 140 aag gcc ctc ctc tcc gag ggc gag tcc atc tgg gag atc acc gag aag       480
Lys Ala Leu Leu Ser Glu Gly Glu Ser Ile Trp Glu Ile Thr Glu Lys
145                 150                 155                 160 atc ctc aac tcc ttc gag tac acc tcc agg ttc act aag acc aag acc       528
Ile Leu Asn Ser Phe Glu Tyr Thr Ser Arg Phe Thr Lys Thr Lys Thr
                165                 170                 175 ctc tac cag ttc ctc ttc ctc gcc acc ttc atc aac tgc ggc agg ttc       576
Leu Tyr Gln Phe Leu Phe Leu Ala Thr Phe Ile Asn Cys Gly Arg Phe
            180                 185                 190 tca gac atc aag aac gtg gac ccc aag tcc ttc aag ctc gtg cag aac       624
Ser Asp Ile Lys Asn Val Asp Pro Lys Ser Phe Lys Leu Val Gln Asn
        195                 200                 205 aag tac ctc ggc gtg atc atc cag tgc ctc gtg acc gag acc aag acc       672
Lys Tyr Leu Gly Val Ile Ile Gln Cys Leu Val Thr Glu Thr Lys Thr
```

| | | | | |
|---|---|---|---|---|
| tcc gtg tcc agg cac atc tac ttc ttc tcc gct cgc ggc agg atc gac | 720 |
| Ser Val Ser Arg His Ile Tyr Phe Phe Ser Ala Arg Gly Arg Ile Asp | |
| 225 230 235 240 | |

```
tcc gtg tcc agg cac atc tac ttc ttc tcc gct cgc ggc agg atc gac      720
Ser Val Ser Arg His Ile Tyr Phe Phe Ser Ala Arg Gly Arg Ile Asp
225                 230                 235                 240 ccc ctc gtg tac ctc gac gag ttc ctc agg aac tca gag ccc gtg ctc      768
Pro Leu Val Tyr Leu Asp Glu Phe Leu Arg Asn Ser Glu Pro Val Leu
                    245                 250                 255 aag agg gtg aac agg acc ggc aac tcc tcc aac aag cag gag tac          816
Lys Arg Val Asn Arg Thr Gly Asn Ser Ser Asn Lys Gln Glu Tyr
        260                 265                 270 cag ctc ctc aag gac aac ctc gtg agg tcc tac aac aag gcc ctc aag      864
Gln Leu Leu Lys Asp Asn Leu Val Arg Ser Tyr Asn Lys Ala Leu Lys
            275                 280                 285 aag aac gcc ccc tac tcc atc ttc gcc atc aag aac ggc ccc aag tcc      912
Lys Asn Ala Pro Tyr Ser Ile Phe Ala Ile Lys Asn Gly Pro Lys Ser
290                 295                 300 cac atc ggt agg cac ctc atg acc tcc ttc ctc tca atg aag ggc ctc      960
His Ile Gly Arg His Leu Met Thr Ser Phe Leu Ser Met Lys Gly Leu
305                 310                 315                 320 acc gag ctc acc aac gtg gtg ggc aac tgg tcc gac aag agg gcc tcc     1008
Thr Glu Leu Thr Asn Val Val Gly Asn Trp Ser Asp Lys Arg Ala Ser
                325                 330                 335 gcc gtg gcc agg acc acc tac acc cac cag atc acc gcc atc ccc gac     1056
Ala Val Ala Arg Thr Thr Tyr Thr His Gln Ile Thr Ala Ile Pro Asp
            340                 345                 350 cac tac ttc gcc ctc gtg tca agg tac tac gcc tac gac ccc atc tcc     1104
His Tyr Phe Ala Leu Val Ser Arg Tyr Tyr Ala Tyr Asp Pro Ile Ser
                355                 360                 365 aag gag atg atc gcc ctc aag gac gag act aac ccc atc gag gag tgg     1152
Lys Glu Met Ile Ala Leu Lys Asp Glu Thr Asn Pro Ile Glu Glu Trp
370                 375                 380 cag cac atc gag cag ctc aag ggc tcc gcc gag ggc tcc atc agg tac     1200
Gln His Ile Glu Gln Leu Lys Gly Ser Ala Glu Gly Ser Ile Arg Tyr
385                 390                 395                 400 ccc gcc tgg aac ggc atc atc tcc cag gag gtg ctc gac tac ctc tcc     1248
Pro Ala Trp Asn Gly Ile Ile Ser Gln Glu Val Leu Asp Tyr Leu Ser
                405                 410                 415 tcc tac atc aac agg agg atc tga                                     1272
Ser Tyr Ile Asn Arg Arg Ile
                420

<210> SEQ ID NO 42
<211> LENGTH: 423
<212> TYPE: PRT
<213> ORGANISM: Artificial Sequence
<220> FEATURE:
<223> OTHER INFORMATION: FLP

<400> SEQUENCE: 42

Met Pro Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
                20                  25                  30

Leu Cys Ala Ala Glu Leu Thr Tyr Leu Cys Trp Met Ile Thr His Asn
            35                  40                  45

Gly Thr Ala Ile Lys Arg Ala Thr Phe Met Ser Tyr Asn Thr Ile Ile
        50                  55                  60

Ser Asn Ser Leu Ser Phe Asp Ile Val Asn Lys Ser Leu Gln Phe Lys
65                  70                  75                  80
```

```
Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420

<210> SEQ ID NO 43
<211> LENGTH: 1032
<212> TYPE: DNA
<213> ORGANISM: Artificial Sequence
<220> FEATURE:
<223> OTHER INFORMATION: Maize optimized Cre coding sequence
<220> FEATURE:
<221> NAME/KEY: CDS
<222> LOCATION: (1)...(1032)

<400> SEQUENCE: 43
```

| | | |
|---|---|---|
| atg tcc aac ctg ctc acg gtt cac cag aac ctt ccg gct ctt cca gtg<br>Met Ser Asn Leu Leu Thr Val His Gln Asn Leu Pro Ala Leu Pro Val<br>1                         5                    10                 15 | 48 | |
| gac gcg acg tcc gat gaa gtc agg aag aac ctc atg gac atg ttc cgc<br>Asp Ala Thr Ser Asp Glu Val Arg Lys Asn Leu Met Asp Met Phe Arg<br>                  20                    25                    30 | 96 | |
| gac agg caa gcg ttc agc gag cac acc tgg aag atg ctg ctc tcc gtc<br>Asp Arg Gln Ala Phe Ser Glu His Thr Trp Lys Met Leu Leu Ser Val<br>        35                    40                    45 | 144 | |
| tgc cgc tcc tgg gct gca tgg tgc aag ctg aac aac agg aag tgg ttc<br>Cys Arg Ser Trp Ala Ala Trp Cys Lys Leu Asn Asn Arg Lys Trp Phe<br>     50                    55                    60 | 192 | |
| ccc gct gag ccc gag gac gtg agg gat tac ctt ctg tac ctg caa gct<br>Pro Ala Glu Pro Glu Asp Val Arg Asp Tyr Leu Leu Tyr Leu Gln Ala<br>65                        70                    75                 80 | 240 | |
| cgc ggg ctg gca gtg aag acc atc cag caa cac ctt gga caa ctg aac<br>Arg Gly Leu Ala Val Lys Thr Ile Gln Gln His Leu Gly Gln Leu Asn<br>                  85                    90                    95 | 288 | |
| atg ctt cac agg cgc tcc ggc ctc ccg cgc ccc agc gac tcg aac gcc<br>Met Leu His Arg Arg Ser Gly Leu Pro Arg Pro Ser Asp Ser Asn Ala<br>            100                    105                  110 | 336 | |
| gtg agc ctc gtc atg cgc cgc atc agg aag gaa aac gtc gat gcc ggc<br>Val Ser Leu Val Met Arg Arg Ile Arg Lys Glu Asn Val Asp Ala Gly<br>       115                    120                    125 | 384 | |
| gaa agg gca aag cag gcc ctc gcg ttc gag agg acc gat ttc gac cag<br>Glu Arg Ala Lys Gln Ala Leu Ala Phe Glu Arg Thr Asp Phe Asp Gln<br>    130                    135                    140 | 432 | |
| gtc cgc agc ctg atg gag aac agc gac agg tgc cag gac att agg aac<br>Val Arg Ser Leu Met Glu Asn Ser Asp Arg Cys Gln Asp Ile Arg Asn<br>145                      150                    155                160 | 480 | |
| ctg gcg ttc ctc gga att gca tac aac acg ctc ctc agg atc gcg gaa<br>Leu Ala Phe Leu Gly Ile Ala Tyr Asn Thr Leu Leu Arg Ile Ala Glu<br>                  165                    170                  175 | 528 | |
| att gcc cgc att cgc gtg aag gac att agc cgc acc gac ggc ggc agg<br>Ile Ala Arg Ile Arg Val Lys Asp Ile Ser Arg Thr Asp Gly Gly Arg<br>            180                    185                  190 | 576 | |
| atg ctt atc cac att ggc agg acc aag acg ctc gtt tcc acc gca ggc<br>Met Leu Ile His Ile Gly Arg Thr Lys Thr Leu Val Ser Thr Ala Gly<br>       195                    200                    205 | 624 | |
| gtc gaa aag gcc ctc agc ctc gga gtg acc aag ctc gtc gaa cgc tgg<br>Val Glu Lys Ala Leu Ser Leu Gly Val Thr Lys Leu Val Glu Arg Trp<br>    210                    215                    220 | 672 | |
| atc tcc gtg tcc ggc gtc gcg gac gac cca aac aac tac ctc ttc tgc<br>Ile Ser Val Ser Gly Val Ala Asp Asp Pro Asn Asn Tyr Leu Phe Cys<br>225                      230                    235                240 | 720 | |
| cgc gtc cgc aag aac ggg gtg gct gcc cct agc gcc acc agc caa ctc<br>Arg Val Arg Lys Asn Gly Val Ala Ala Pro Ser Ala Thr Ser Gln Leu<br>                  245                    250                  255 | 768 | |
| agc acg agg gcc ttg gaa ggt att ttc gag gcc acc cac cgc ctg atc<br>Ser Thr Arg Ala Leu Glu Gly Ile Phe Glu Ala Thr His Arg Leu Ile<br>            260                    265                  270 | 816 | |
| tac ggc gcg aag gat gac agc ggt caa cgc tac ctc gca tgg tcc ggg<br>Tyr Gly Ala Lys Asp Asp Ser Gly Gln Arg Tyr Leu Ala Trp Ser Gly<br>       275                    280                    285 | 864 | |
| cac tcc gcc cgc gtt gga gct gct agg gac atg gcc cgc gcc ggt gtt<br>His Ser Ala Arg Val Gly Ala Ala Arg Asp Met Ala Arg Ala Gly Val<br>    290                    295                    300 | 912 | |
| tcc atc ccc gaa atc atg cag gcg ggt gga tgg acg aac gtg aac att<br>Ser Ile Pro Glu Ile Met Gln Ala Gly Gly Trp Thr Asn Val Asn Ile<br>305                      310                    315                320 | 960 | |

```
gtc atg aac tac att cgc aac ctt gac agc gag acg ggc gca atg gtt    1008
Val Met Asn Tyr Ile Arg Asn Leu Asp Ser Glu Thr Gly Ala Met Val
            325                 330                 335 cgc ctc ctg gaa gat ggt gac tga                                    1032
Arg Leu Leu Glu Asp Gly Asp
            340
```

<210> SEQ ID NO 44
<211> LENGTH: 343
<212> TYPE: PRT
<213> ORGANISM: Artificial Sequence
<220> FEATURE:
<223> OTHER INFORMATION: Cre

<400> SEQUENCE: 44

```
Met Ser Asn Leu Leu Thr Val His Gln Asn Leu Pro Ala Leu Pro Val
 1               5                  10                  15

Asp Ala Thr Ser Asp Glu Val Arg Lys Asn Leu Met Asp Met Phe Arg
             20                  25                  30

Asp Arg Gln Ala Phe Ser Glu His Thr Trp Lys Met Leu Leu Ser Val
         35                  40                  45

Cys Arg Ser Trp Ala Ala Trp Cys Lys Leu Asn Asn Arg Lys Trp Phe
     50                  55                  60

Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
                 85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320
```

Val Met Asn Tyr Ile Arg Asn Leu Asp Ser Glu Thr Gly Ala Met Val
            325                 330                 335

Arg Leu Leu Glu Asp Gly Asp
            340

<210> SEQ ID NO 45
<211> LENGTH: 1198
<212> TYPE: DNA
<213> ORGANISM: Artificial Sequence
<220> FEATURE:
<223> OTHER INFORMATION: Expression cassette comprising Zea mays rab17
      promoter, attB1 site, and FLPm coding sequence

<400> SEQUENCE: 45
ctatagtatt ttaaaattgc attaacaaac atgtcctaat tggtactcct gagatactat      60
accctcctgt tttaaaatag ttggcattat cgaattatca ttttacttttt taatgttttc    120 tcttctttta atatatttta tgaatttttaa tgtattttaa aatgttatgc agttcgctct    180
ggacttttct gctgcgccta cacttgggtg tactgggcct aaattcagcc tgaccgaccg    240
cctgcattga ataatggatg agcaccggta aaatccgcgt acccaacttt cgagaagaac    300
cgagacgtgg cgggccgggc caccgacgca cggcaccagc gactgcacac gtcccgccgg    360
cgtacgtgta cgtgctgttc cctcactggc cgcccaatcc actcatgcat gcccacgtac    420
acccctgccg tggcgcgccc agatcctaat cctttcgccg ttctgcactt ctgctgccta    480
taaatggcgg catcgaccgt cacctgcttc accaccggcg agccacatcg agaacacgat    540
cgagcacaca agcacgaaga ctcgtttagg agaaaccaca aaccaccaag ccgtgcaagc    600
accaagcttg gtcacccggt ccgggcctag aaggccagct tcaagtttgt acaaaaaagc    660
aggcttcgaa ggagatagaa ccaattctct aaggaaatac ttaaccatgg tcgactggat    720
ccaacaatgc cccagttcga catcctctgc aagaccccc ccaaggtgct cgtgaggcag     780
ttcgtggaga ggttcgagag gccctccggc gagaagatcg ccctctgcgc cgccgagctc    840
acctacctct gctggatgat cacccacaac ggcaccgcca ttaagagggc caccttcatg    900
tcatacaaca ccatcatctc caactccctc tccttcgaca tcgtgaacaa gtccctccag    960
ttcaaataca gacccagaa ggccaccatc ctcgaggcct ccctcaagaa gctcatcccc     1020
gcctgggagt tcaccatcat cccctactac ggccagaagc accagtccga catcaccgac    1080
atcgtgtcat ccctccagct tcagttcgag tcctccgagg aggctgacaa gggcaactcc    1140
cactccaaga gatgctgaa ggccctcctc tccgagggcg agtccatctg ggagatca     1198

<210> SEQ ID NO 46
<211> LENGTH: 2370
<212> TYPE: DNA
<213> ORGANISM: Artificial Sequence
<220> FEATURE:
<223> OTHER INFORMATION: Plasmid PHP31004

<400> SEQUENCE: 46
ctatagtatt ttaaaattgc attaacaaac atgtcctaat tggtactcct gagatactat      60
accctcctgt tttaaaatag ttggcattat cgaattatca ttttacttttt taatgttttc    120 tcttctttta atatatttta tgaatttttaa tgtattttaa aatgttatgc agttcgctct    180
ggacttttct gctgcgccta cacttgggtg tactgggcct aaattcagcc tgaccgaccg    240
cctgcattga ataatggatg agcaccggta aaatccgcgt acccaacttt cgagaagaac    300
cgagacgtgg cgggccgggc caccgacgca cggcaccagc gactgcacac gtcccgccgg    360

```
cgtacgtgta cgtgctgttc cctcactggc cgcccaatcc actcatgcat gcccacgtac    420
acccctgccg tggcgcgccc agatcctaat cctttcgccg ttctgcactt ctgctgccta    480
taaatggcgg catcgaccgt cacctgcttc accaccggcg agccacatcg agaacacgat    540
cgagcacaca agcacgaaga ctcgtttagg agaaaccaca aaccaccaag ccgtgcaagc    600
accaagcttg gtcacccggt ccgggcctag aaggccagct tcaagtttgt acaaaaaagc    660
aggcttcgaa ggagatagaa ccaattctct aaggaaatac ttaaccatgg tcgactggat    720
ccaacaatgc cccagttcga catcctctgc aagaccccc ccaaggtgct cgtgaggcag    780
ttcgtggaga ggttcgagag gccctccggc gagaagatcg ccctctgcgc cgccgagctc    840
acctacctct gctggatgat cacccacaac ggcaccgcca ttaagagggc caccttcatg    900
tcatacaaca ccatcatctc caactccctc tccttcgaca tcgtgaacaa gtccctccag    960
ttcaaataca gacccagaa ggccaccatc ctcgaggcct ccctcaagaa gctcatcccc   1020
gcctgggagt tcaccatcat cccctactac ggccagaagc accagtccga catcaccgac   1080
atcgtgtcat ccctccagct tcagttcgag tcctccgagg aggctgacaa gggcaactcc   1140
cactccaaga agatgctgaa ggccctcctc tccgagggcg agtccatctg ggagatcacc   1200
gagaagatcc tcaactcctt cgagtacacc tccaggttca ctaagaccaa gaccctctac   1260
cagttcctct cctcgccac cttcatcaac tgcggcaggt tctcagacat caagaacgtg   1320 gacccccaagt ccttcaagct cgtgcagaac aagtacctcg gcgtgatcat ccagtgcctc   1380
gtgaccgaga ccaagaccctc cgtgtccagg cacatctact tcttctccgc tcgcggcagg   1440
atcgaccccc tcgtgtacct cgacgagttc ctcaggaact cagagccgt gctcaagagg   1500 gtgaacagga ccggcaactc ctcctccaac aagcaggagt accagctcct caaggacaac   1560
ctcgtgaggt cctacaacaa ggccctcaag aagaacgccc cctactccat cttcgccatc   1620
aagaacggcc ccaagtccca catcggtagg cacctcatga cctccttcct ctcaatgaag   1680
ggcctcaccg agctcaccaa cgtggtgggc aactggtccg acaagagggc ctccgccgtg   1740
gccaggacca cctacaccca ccagatcacc gccatccccg accactactt cgccctcgtg   1800
tcaaggtact acgcctacga ccccatctcc aaggagatga tcgccctcaa ggacgagact   1860
aaccccatcg aggagtggca gcacatcgag cagctcaagg gctccgccga gggctccatc   1920
aggtaccccg cctggaacgg catcatctcc caggaggtgc tcgactacct ctcctcctac   1980
atcaacagga ggatctgagt ttcgagatat ctagacccag ctttcttgta caaagtggcc   2040
gttaacggat ccagacttgt ccatcttctg gattggccaa cttaattaat gtatgaaata   2100
aaaggatgca cacatagtga catgctaatc actataatgt gggcatcaaa gttgtgtgtt   2160
atgtgtaatt actagttatc tgaataaaag agaaagagat catccatatt tcttatccta   2220
aatgaatgtc acgtgtcttt ataattcttt gatgaaccag atgcatttca ttaaccaaat   2280
ccatatacat ataaatatta atcatatata attaatatca attgggttag caaacaaat   2340 ctagtctagg tgtgttttgc gaattgcggc                                    2370
```

<210> SEQ ID NO 47
<211> LENGTH: 2383
<212> TYPE: DNA
<213> ORGANISM: Artificial Sequence
<220> FEATURE:
<223> OTHER INFORMATION: Plasmid PHP30642

<400> SEQUENCE: 47

```
ctatagtatt ttaaaattgc attaacaaac atgtcctaat tggtactcct gagatactat     60
```

-continued

```
accctcctgt tttaaaatag ttggcattat cgaattatca ttttactttt taatgttttc      120
tcttctttta atatatttta tgaattttaa tgtattttaa aatgttatgc agttcgctct      180
ggacttttct gctgcgccta cacttgggtg tactgggcct aaattcagcc tgaccgaccg      240
cctgcattga ataatggatg agcaccggta aaatccgcgt acccaactttt cgagaagaac     300
cgagacgtgg cgggccgggc caccgacgca cggcaccagc gactgcacac gtcccgccgg      360
cgtacgtgta cgtgctgttc cctcactggc cgcccaatcc actcatgcat gcccacgtac      420
accccctgccg tggcgcgccc agatcctaat cctttcgccg ttctgcactt ctgctgccta    480
taaatggcgg catcgaccgt cacctgcttc accaccggcg agccacatcg agaacacgat      540
cgagcacaca agcacgaaga ctcgtttagg agaaaccaca aaccaccaag ccgtgcaagc      600
accatggatc caacaatgcc ccagttcgac atcctctgca agaccccccc caaggtgctc     660
gtgaggcagt tcgtggagag gttcgagagg ccctccggcg agaagatcgc cctctgcgcc      720
gccgagctca cctacctctg ctggatgatc acccacaacg gcaccgccat taagagggcc     780
accttcatgt catacaacac catcatctcc aactccctct ccttcgacat cgtgaacaag      840
tccctccagt tcaaatacaa gacccagaag gccaccatcc tcgaggcctc cctcaagaag      900
ctcatccccg cctgggagtt caccatcatc ccctactacg gccagaagca ccagtccgac      960
atcaccgaca tcgtgtcatc cctccagctt cagttcgagt cctccgagga ggctgacaag     1020
ggcaactccc actccaagaa gatgctgaag gccctcctct ccgagggcga gtccatctgg     1080
gagatcaccg agaagatcct caactccttc gagtacacct ccaggttcac taagaccaag     1140
accctctacc agttcctctt cctcgccacc ttcatcaact gcggcaggtt ctcagacatc     1200
aagaacgtgg accccaagtc cttcaagctc gtgcagaaca agtacctcgg cgtgatcatc     1260
cagtgcctcg tgaccgagac caagacctcc gtgtccaggc acatctactt cttctccgct     1320
cgcggcagga tcgacccccct cgtgtacctc gacgagttcc tcaggaactc agagcccgtg   1380
ctcaagaggg tgaacaggac cggcaactcc tcctccaaca gcaggagta ccagctcctc      1440
aaggacaacc tcgtgaggtc ctacaacaag gccctcaaga agaacgcccc ctactccatc     1500
ttcgccatca agaacggccc caagtcccac atcggtaggc acctcatgac ctccttcctc    1560
tcaatgaagg gcctcaccga gctcaccaac gtggtgggca actggtccga caagagggcc     1620
tccgccgtgg ccaggaccac ctacacccac cagatcaccg ccatccccga ccactacttc     1680
gccctcgtgt caaggtacta cgcctacgac cccatctcca aggagatgat cgccctcaag     1740
gacgagacta accccatcga ggagtggcag cacatcgagc agctcaaggg ctccgccgag     1800
ggctccatca ggtaccccgc ctggaacggc atcatctccc aggaggtgct cgactacctc     1860
tcctcctaca tcaacaggag gatctgagtt ctagttcgaa tgtgagttga tccccggcgg    1920
tgtcccccac tgaagaaact atgtgctgta gtatagccgc tggctagcta gctagttgag    1980
tcatttagcg gcgatgattg agtaataatg tgtcacgcat caccatgcat gggtggcagt    2040
ctcagtgtga gcaatgacct gaatgaacaa ttgaaatgaa agaaaaaag tattgttcca     2100
aattaaacgt tttaaccttt taataggttt atacaataat tgatatatgt tttctgtata     2160
tgtctaattt gttatcatcc atttagatat agacgaaaaa aaatctaaga actaaaacaa    2220
atgctaattt gaaatgaagg gagtatatat tgggataatg tcgatgagat ccctcgtaat    2280
atcaccgaca tcacacgtgt ccagttaatg tatcagtgat acgtgtattc acatttgttg    2340
cgcgtaggcg tacccaacaa ttttgatcga ctatcagaaa gtc                      2383
```

```
<210> SEQ ID NO 48
<211> LENGTH: 31
<212> TYPE: PRT
<213> ORGANISM: Artificial Sequence
<220> FEATURE:
<223> OTHER INFORMATION: Consensus sequence motif 1
<220> FEATURE:
<221> NAME/KEY: VARIANT
<222> LOCATION: 10
<223> OTHER INFORMATION: Xaa = His or Asn
<220> FEATURE:
<221> NAME/KEY: VARIANT
<222> LOCATION: 16
<223> OTHER INFORMATION: Xaa = Phe or Tyr
<220> FEATURE:
<221> NAME/KEY: VARIANT
<222> LOCATION: 17
<223> OTHER INFORMATION: Xaa = Val or Ile
<220> FEATURE:
<221> NAME/KEY: VARIANT
<222> LOCATION: 19
<223> OTHER INFORMATION: Xaa = Ser or His

<400> SEQUENCE: 48

Tyr Glu Lys Glu Leu Glu Glu Met Lys Xaa Met Thr Arg Gln Glu Xaa
 1               5                  10                  15

Xaa Ala Xaa Leu Arg Arg Lys Ser Ser Gly Phe Ser Arg Gly Ala
            20                  25                  30

<210> SEQ ID NO 49
<211> LENGTH: 63
<212> TYPE: PRT
<213> ORGANISM: Artificial Sequence
<220> FEATURE:
<223> OTHER INFORMATION: Consensus sequence motif 2
<220> FEATURE:
<221> NAME/KEY: VARIANT
<222> LOCATION: 2
<223> OTHER INFORMATION: Xaa = Ile or Met
<220> FEATURE:
<221> NAME/KEY: VARIANT
<222> LOCATION: 36
<223> OTHER INFORMATION: Xaa = Gln or Glu
<220> FEATURE:
<221> NAME/KEY: VARIANT
<222> LOCATION: 45
<223> OTHER INFORMATION: Xaa = Ile or Val
<220> FEATURE:
<221> NAME/KEY: VARIANT
<222> LOCATION: 60
<223> OTHER INFORMATION: Xaa = Asp or Glu
<220> FEATURE:
<221> NAME/KEY: VARIANT
<222> LOCATION: 61
<223> OTHER INFORMATION: Xaa = Met or Ile
<220> FEATURE:
<221> NAME/KEY: VARIANT
<222> LOCATION: (62)...(62)
<223> OTHER INFORMATION: Xaa = Ser or Asn

<400> SEQUENCE: 49

Ser Xaa Tyr Arg Gly Val Thr Arg His His Gln His Gly Arg Trp Gln
 1               5                  10                  15

Ala Arg Ile Gly Arg Val Ala Gly Asn Lys Asp Leu Tyr Leu Gly Thr
            20                  25                  30

Phe Ser Thr Xaa Glu Glu Ala Ala Glu Ala Tyr Asp Xaa Ala Ala Ile
        35                  40                  45

Lys Phe Arg Gly Leu Asn Ala Val Thr Asn Phe Xaa Xaa Xaa Arg
 50                  55                  60
```

```
<210> SEQ ID NO 50
<211> LENGTH: 68
<212> TYPE: PRT
<213> ORGANISM: Artificial Sequence
<220> FEATURE:
<223> OTHER INFORMATION: Consensus sequence motif 3
<220> FEATURE:
<221> NAME/KEY: VARIANT
<222> LOCATION: 2
<223> OTHER INFORMATION: Xaa = Ile or Gln
<220> FEATURE:
<221> NAME/KEY: VARIANT
<222> LOCATION: 26
<223> OTHER INFORMATION: Xaa = Arg or Lys
<220> FEATURE:
<221> NAME/KEY: VARIANT
<222> LOCATION: 30, 59
<223> OTHER INFORMATION: Xaa = Ser or Thr
<220> FEATURE:
<221> NAME/KEY: VARIANT
<222> LOCATION: 33
<223> OTHER INFORMATION: Xaa = Val or Gly
<220> FEATURE:
<221> NAME/KEY: VARIANT
<222> LOCATION: 34
<223> OTHER INFORMATION: Xaa = Tyr or Arg
<220> FEATURE:
<221> NAME/KEY: VARIANT
<222> LOCATION: (35)...(35)
<223> OTHER INFORMATION: Xaa = Leu or Gln
<220> FEATURE:
<221> NAME/KEY: VARIANT
<222> LOCATION: (42)...(42)
<223> OTHER INFORMATION: Xaa = Glu or Asp
<220> FEATURE:
<221> NAME/KEY: VARIANT
<222> LOCATION: (58)...(58)
<223> OTHER INFORMATION: Xaa = Pro or Thr
<220> FEATURE:
<221> NAME/KEY: VARIANT
<222> LOCATION: (61)...(61)
<223> OTHER INFORMATION: Xaa = Thr or His
<220> FEATURE:
<221> NAME/KEY: VARIANT
<222> LOCATION: (62)...(62)
<223> OTHER INFORMATION: Xaa = Thr or Ile
<220> FEATURE:
<221> NAME/KEY: VARIANT
<222> LOCATION: (66)...(66)
<223> OTHER INFORMATION: Xaa = Ile, Val, or Leu

<400> SEQUENCE: 50

Ser Xaa Tyr Arg Gly Val Thr Arg His Arg Trp Thr Gly Arg Tyr Glu
 1               5                  10                  15

Ala His Leu Trp Asp Asn Ser Cys Arg Xaa Glu Gly Gln Xaa Arg Lys
                20                  25                  30

Xaa Xaa Xaa Gly Gly Tyr Asp Lys Glu Xaa Lys Ala Ala Arg Ala Tyr
            35                  40                  45

Asp Leu Ala Ala Leu Lys Tyr Trp Gly Xaa Xaa Thr Xaa Xaa Asn Phe
50                  55                  60

Pro Xaa Ser Asn
 65

<210> SEQ ID NO 51
<211> LENGTH: 8
<212> TYPE: PRT
<213> ORGANISM: Artificial Sequence
<220> FEATURE:
<223> OTHER INFORMATION: Consensus sequence motif 4
<220> FEATURE:
<221> NAME/KEY: VARIANT
<222> LOCATION: 3
<223> OTHER INFORMATION: Xaa = Leu or Val
```

```
<220> FEATURE:
<221> NAME/KEY: VARIANT
<222> LOCATION: 4
<223> OTHER INFORMATION: Xaa = Glu or Ala
<220> FEATURE:
<221> NAME/KEY: VARIANT
<222> LOCATION: 5
<223> OTHER INFORMATION: Xaa = Asp or Asn

<400> SEQUENCE: 51

Pro Lys Xaa Xaa Xaa Phe Leu Gly
  1               5

<210> SEQ ID NO 52
<211> LENGTH: 13
<212> TYPE: PRT
<213> ORGANISM: Artificial Sequence
<220> FEATURE:
<223> OTHER INFORMATION: Consensus sequence motif 5
<220> FEATURE:
<221> NAME/KEY: VARIANT
<222> LOCATION: 6
<223> OTHER INFORMATION: Xaa = Ile or Val
<220> FEATURE:
<221> NAME/KEY: VARIANT
<222> LOCATION: 9
<223> OTHER INFORMATION: Xaa = Ala or Leu
<220> FEATURE:
<221> NAME/KEY: VARIANT
<222> LOCATION: 11, 12
<223> OTHER INFORMATION: Xaa = Lys or Arg
<220> FEATURE:
<221> NAME/KEY: VARIANT
<222> LOCATION: 13
<223> OTHER INFORMATION: Xaa = Leu or Arg

<400> SEQUENCE: 52

Ser Ser Thr Leu Pro Xaa Gly Gly Xaa Ala Xaa Xaa Xaa
  1               5                  10

<210> SEQ ID NO 53
<211> LENGTH: 9
<212> TYPE: PRT
<213> ORGANISM: Artificial Sequence
<220> FEATURE:
<223> OTHER INFORMATION: Consensus sequence motif 6
<220> FEATURE:
<221> NAME/KEY: VARIANT
<222> LOCATION: 4
<223> OTHER INFORMATION: Xaa = Gly or Ser

<400> SEQUENCE: 53

Asn Trp Leu Xaa Phe Ser Leu Ser Pro
  1               5

<210> SEQ ID NO 54
<211> LENGTH: 10
<212> TYPE: PRT
<213> ORGANISM: Artificial Sequence
<220> FEATURE:
<223> OTHER INFORMATION: Consensus sequence motif 7
<220> FEATURE:
<221> NAME/KEY: VARIANT
<222> LOCATION: 1
<223> OTHER INFORMATION: Xaa = Gly or Glu
<220> FEATURE:
<221> NAME/KEY: VARIANT
<222> LOCATION: 7
<223> OTHER INFORMATION: Xaa = Thr or Asn

<400> SEQUENCE: 54

Xaa Leu Ser Met Ile Lys Xaa Trp Leu Arg
```

```
                1               5                   10
```

<210> SEQ ID NO 55
<211> LENGTH: 8
<212> TYPE: PRT
<213> ORGANISM: Artificial Sequence
<220> FEATURE:
<223> OTHER INFORMATION: Consensus sequence motif 8
<220> FEATURE:
<221> NAME/KEY: VARIANT
<222> LOCATION: 2, 4, 5
<223> OTHER INFORMATION: Xaa = Any Amino Acid

<400> SEQUENCE: 55

```
Pro Xaa Phe Xaa Xaa Trp Asn Asp
  1               5
```

<210> SEQ ID NO 56
<211> LENGTH: 5
<212> TYPE: PRT
<213> ORGANISM: Artificial Sequence
<220> FEATURE:
<223> OTHER INFORMATION: Consensus sequence motif 9
<220> FEATURE:
<221> NAME/KEY: VARIANT
<222> LOCATION: 2
<223> OTHER INFORMATION: Xaa = Ser, Thr, or Ala

<400> SEQUENCE: 56

```
Leu Xaa Leu Ser Met
  1               5
```

<210> SEQ ID NO 57
<211> LENGTH: 7
<212> TYPE: PRT
<213> ORGANISM: Artificial Sequence
<220> FEATURE:
<223> OTHER INFORMATION: Consensus sequence motif 10
<220> FEATURE:
<221> NAME/KEY: VARIANT
<222> LOCATION: 4
<223> OTHER INFORMATION: Xaa = Gln or Pro

<400> SEQUENCE: 57

```
Trp Cys Lys Xaa Glu Gln Asp
  1               5
```

<210> SEQ ID NO 58
<211> LENGTH: 7
<212> TYPE: PRT
<213> ORGANISM: Artificial Sequence
<220> FEATURE:
<223> OTHER INFORMATION: Consensus sequence motif 14

<400> SEQUENCE: 58

```
Trp Pro Thr Ile Ala Phe Gln
  1               5
```

<210> SEQ ID NO 59
<211> LENGTH: 11
<212> TYPE: PRT
<213> ORGANISM: Artificial Sequence
<220> FEATURE:
<223> OTHER INFORMATION: Consensus sequence motif 15
<220> FEATURE:
<221> NAME/KEY: VARIANT
<222> LOCATION: 2
<223> OTHER INFORMATION: Xaa = Ser or Thr

<400> SEQUENCE: 59

```
Ser Xaa Gly Ser Asn Ser Val Val Tyr Asn Gly
 1               5                  10

<210> SEQ ID NO 60
<211> LENGTH: 7
<212> TYPE: PRT
<213> ORGANISM: Artificial Sequence
<220> FEATURE:
<223> OTHER INFORMATION: Consensus sequence motif 19
<220> FEATURE:
<221> NAME/KEY: VARIANT
<222> LOCATION: 4
<223> OTHER INFORMATION: Xaa = Ser or Asn

<400> SEQUENCE: 60

Gln Asp Trp Xaa Met Arg Gly
 1               5

<210> SEQ ID NO 61
<211> LENGTH: 975
<212> TYPE: DNA
<213> ORGANISM: Zea mays
<220> FEATURE:
<221> NAME/KEY: CDS
<222> LOCATION: (1)...(975)

<400> SEQUENCE: 61 atg gag acg cca cag cag caa tcc gcc gcc gcc gcc gcc gcc gcc        48
Met Glu Thr Pro Gln Gln Gln Ser Ala Ala Ala Ala Ala Ala Ala
 1               5                  10                  15 cac ggg cag gac gac ggc ggg tcg ccg ccg atg tcg ccg gcc tcc gcc    96
His Gly Gln Asp Asp Gly Gly Ser Pro Pro Met Ser Pro Ala Ser Ala
                20                  25                  30 gcg gcg gcg gcg ctg gcg aac gcg cgg tgg aac ccg acc aag gag cag   144
Ala Ala Ala Ala Leu Ala Asn Ala Arg Trp Asn Pro Thr Lys Glu Gln
            35                  40                  45 gtg gcc gtg ctg gag ggg ctg tac gag cac ggc ctg cgc acc ccc agc   192
Val Ala Val Leu Glu Gly Leu Tyr Glu His Gly Leu Arg Thr Pro Ser
     50                  55                  60 gcg gag cag ata cag cag atc acg ggc agg ctg cgg gag cac ggc gcc   240
Ala Glu Gln Ile Gln Gln Ile Thr Gly Arg Leu Arg Glu His Gly Ala
 65                  70                  75                  80 atc gag ggc aag aac gtc ttc tac tgg ttc cag aac cac aag gcc cgc   288
Ile Glu Gly Lys Asn Val Phe Tyr Trp Phe Gln Asn His Lys Ala Arg
                 85                  90                  95 cag cgc cag agg cag aag cag gac agc ttc gcc tac ttc agc agg ctc   336
Gln Arg Gln Arg Gln Lys Gln Asp Ser Phe Ala Tyr Phe Ser Arg Leu
            100                 105                 110 ctc cgc cgg ccc ccg ctg ccc gtg ctc tcc atg ccc ccc gcg cca       384
Leu Arg Arg Pro Pro Leu Pro Val Leu Ser Met Pro Pro Ala Pro
        115                 120                 125 ccg tac cat cac gcc cgc gtc ccg gcg ccg ccc gcg ata ccg atg ccg   432
Pro Tyr His His Ala Arg Val Pro Ala Pro Ala Ile Pro Met Pro
    130                 135                 140 atg gcg ccg ccg ccg ccc gct gca tgc aac gac aac ggc ggc gcg cgt   480
Met Ala Pro Pro Pro Ala Ala Cys Asn Asp Asn Gly Gly Ala Arg
145                 150                 155                 160 gtg atc tac agg aac cca ttc tac gtg gct gcg ccg cag gcg ccc cct   528
Val Ile Tyr Arg Asn Pro Phe Tyr Val Ala Ala Pro Gln Ala Pro Pro
                165                 170                 175 gca aat gcc gcc tac tac tac cca cag cca cag cag cag cag cag cag   576
Ala Asn Ala Ala Tyr Tyr Tyr Pro Gln Pro Gln Gln Gln Gln Gln Gln
            180                 185                 190
```

```
cag gtg aca gtc atg tac cag tac ccg aga atg gag gta gcc ggc cag      624
Gln Val Thr Val Met Tyr Gln Tyr Pro Arg Met Glu Val Ala Gly Gln
            195                 200                 205 gac aag atg atg acc agg gcc gcg gcg cac cag cag cag cac aac          672
Asp Lys Met Met Thr Arg Ala Ala Ala His Gln Gln Gln Gln His Asn
210                 215                 220 ggc gcc ggg caa caa ccg gga cgc gcc ggc cac ccc agc cgc gag acg      720
Gly Ala Gly Gln Gln Pro Gly Arg Ala Gly His Pro Ser Arg Glu Thr
225                 230                 235                 240 ctc cag ctg ttc ccg ctc cag ccc acc ttc gtg ctg cgg cac gac aag      768
Leu Gln Leu Phe Pro Leu Gln Pro Thr Phe Val Leu Arg His Asp Lys
            245                 250                 255 ggg cgc gcc gcc aac ggc agt aat aac gac tcc ctg acg tcg acg tcg      816
Gly Arg Ala Ala Asn Gly Ser Asn Asn Asp Ser Leu Thr Ser Thr Ser
            260                 265                 270 acg gcg act gcg aca gcg aca gcg aca gcg tcc gct tcc atc              864
Thr Ala Thr Ala Thr Ala Thr Ala Thr Ala Ser Ala Ser Ile
            275                 280                 285 tcc gag gac tcg gat ggc ctg gag agc ggc agc tcc ggc aag ggc gtc      912
Ser Glu Asp Ser Asp Gly Leu Glu Ser Gly Ser Ser Gly Lys Gly Val
290                 295                 300 gag gag gcg ccc gcg ctg ccg ttc tat gac ttc ttc ggg ctc cag tcc      960
Glu Glu Ala Pro Ala Leu Pro Phe Tyr Asp Phe Phe Gly Leu Gln Ser
305                 310                 315                 320 tcc gga ggc cgc tga                                                  975
Ser Gly Gly Arg <210> SEQ ID NO 62
<211> LENGTH: 324
<212> TYPE: PRT
<213> ORGANISM: Zea mays

<400> SEQUENCE: 62

Met Glu Thr Pro Gln Gln Gln Ser Ala Ala Ala Ala Ala Ala
1               5                   10                  15

His Gly Gln Asp Asp Gly Gly Ser Pro Pro Met Ser Pro Ala Ser Ala
                20                  25                  30

Ala Ala Ala Ala Leu Ala Asn Ala Arg Trp Asn Pro Thr Lys Glu Gln
            35                  40                  45

Val Ala Val Leu Glu Gly Leu Tyr Glu His Gly Leu Arg Thr Pro Ser
        50                  55                  60

Ala Glu Gln Ile Gln Gln Ile Thr Gly Arg Leu Arg Glu His Gly Ala
65                  70                  75                  80

Ile Glu Gly Lys Asn Val Phe Tyr Trp Phe Gln Asn His Lys Ala Arg
                85                  90                  95

Gln Arg Gln Arg Gln Lys Gln Asp Ser Phe Ala Tyr Phe Ser Arg Leu
            100                 105                 110

Leu Arg Arg Pro Pro Pro Leu Pro Val Leu Ser Met Pro Ala Pro
        115                 120                 125

Pro Tyr His His Ala Arg Val Pro Ala Pro Ala Ile Pro Met Pro
    130                 135                 140

Met Ala Pro Pro Pro Ala Ala Cys Asn Asp Asn Gly Gly Ala Arg
145                 150                 155                 160

Val Ile Tyr Arg Asn Pro Phe Tyr Val Ala Pro Gln Ala Pro
                165                 170                 175

Ala Asn Ala Ala Tyr Tyr Tyr Pro Gln Pro Gln Gln Gln Gln
            180                 185                 190
```

```
Gln Val Thr Val Met Tyr Gln Tyr Pro Arg Met Glu Val Ala Gly Gln
            195                 200                 205

Asp Lys Met Met Thr Arg Ala Ala His Gln Gln Gln His Asn
    210                 215                 220

Gly Ala Gly Gln Gln Pro Gly Arg Ala Gly His Pro Ser Arg Glu Thr
225                 230                 235                 240

Leu Gln Leu Phe Pro Leu Gln Pro Thr Phe Val Leu Arg His Asp Lys
                245                 250                 255

Gly Arg Ala Ala Asn Gly Ser Asn Asn Asp Ser Leu Thr Ser Thr Ser
            260                 265                 270

Thr Ala Thr Ala Thr Ala Thr Ala Thr Ala Thr Ala Ser Ala Ser Ile
            275                 280                 285

Ser Glu Asp Ser Asp Gly Leu Glu Ser Gly Ser Ser Gly Lys Gly Val
            290                 295                 300

Glu Glu Ala Pro Ala Leu Pro Phe Tyr Asp Phe Phe Gly Leu Gln Ser
305                 310                 315                 320

Ser Gly Gly Arg
```

<210> SEQ ID NO 63
<211> LENGTH: 909
<212> TYPE: DNA
<213> ORGANISM: Zea mays
<220> FEATURE:
<221> NAME/KEY: CDS
<222> LOCATION: (1)...(909)

<400> SEQUENCE: 63

```
atg gcg gcc aat gcg ggc ggc ggt gga gcg gga gga ggc agc ggc agc      48
Met Ala Ala Asn Ala Gly Gly Gly Gly Ala Gly Gly Gly Ser Gly Ser
1               5                   10                  15 ggc agc gtg gct gcg ccg gcg gtg tgc cgc ccc agc ggc tcg cgg tgg      96
Gly Ser Val Ala Ala Pro Ala Val Cys Arg Pro Ser Gly Ser Arg Trp
                20                  25                  30 acg ccg acg ccg gag cag atc agg atg ctg aag gag ctc tac tac ggc     144
Thr Pro Thr Pro Glu Gln Ile Arg Met Leu Lys Glu Leu Tyr Tyr Gly
            35                  40                  45 tgc ggc atc cgg tcg ccc agc tcg gag cag atc cag cgc atc acc gcc     192
Cys Gly Ile Arg Ser Pro Ser Ser Glu Gln Ile Gln Arg Ile Thr Ala
        50                  55                  60 atg ctg cgg cag cac ggc aag atc gag ggc aag aac gtc ttc tac tgg     240
Met Leu Arg Gln His Gly Lys Ile Glu Gly Lys Asn Val Phe Tyr Trp
65                  70                  75                  80 ttc cag aac cac aag gcc cgc gag cgc cag aag cgc cgc ctc acc agc     288
Phe Gln Asn His Lys Ala Arg Glu Arg Gln Lys Arg Arg Leu Thr Ser
                85                  90                  95 ctc gac gtc aac gtg ccc gcc gcc ggc gcg gcc gac gcc acc acc agc     336
Leu Asp Val Asn Val Pro Ala Ala Gly Ala Ala Asp Ala Thr Thr Ser
            100                 105                 110 caa ctc ggc gtc ctc tcg ctg tcg tcg ccg ccg cct tca ggc gcg gcg     384
Gln Leu Gly Val Leu Ser Leu Ser Ser Pro Pro Pro Ser Gly Ala Ala
        115                 120                 125 cct ccc tcg ccc acc ctc ggc ttc tac gcc gcc ggc aat ggc ggc gga     432
Pro Pro Ser Pro Thr Leu Gly Phe Tyr Ala Ala Gly Asn Gly Gly Gly
130                 135                 140 tcg gct gtg ctg ctg gac acg agt tcc gac tgg ggc agc agc ggc gct     480
Ser Ala Val Leu Leu Asp Thr Ser Ser Asp Trp Gly Ser Ser Gly Ala
145                 150                 155                 160 gcc atg gcc acc gag aca tgc ttc ctg cag gac tac atg ggc gtg acg     528
Ala Met Ala Thr Glu Thr Cys Phe Leu Gln Asp Tyr Met Gly Val Thr
```

```
Ala Met Ala Thr Glu Thr Cys Phe Leu Gln Asp Tyr Met Gly Val Thr
                165                 170                 175 gac acg ggc agc tcg tcg cag tgg cca cgc ttc tcg tcg gac acg          576
Asp Thr Gly Ser Ser Ser Gln Trp Pro Arg Phe Ser Ser Ser Asp Thr
            180                 185                 190 ata atg gcg gcg gcc gcg gcg cgg gcg gcg acg acg cgg gcg ccc gag      624
Ile Met Ala Ala Ala Ala Ala Arg Ala Ala Thr Thr Arg Ala Pro Glu
        195                 200                 205 acg ctc cct ctc ttc ccg acc tgc ggc gac gac ggc ggc agc ggt agc      672
Thr Leu Pro Leu Phe Pro Thr Cys Gly Asp Asp Gly Gly Ser Gly Ser
    210                 215                 220 agc agc tac ttg ccg ttc tgg ggt gcc gcg tcc aca act gcc ggc gcc      720
Ser Ser Tyr Leu Pro Phe Trp Gly Ala Ala Ser Thr Thr Ala Gly Ala
225                 230                 235                 240 act tct tcc gtt gcg atc cag cag caa cac cag ctg cag gag cag tac      768
Thr Ser Ser Val Ala Ile Gln Gln Gln His Gln Leu Gln Glu Gln Tyr
                245                 250                 255 agc ttt tac agc aac agc aac agc acc cag ctg gcc ggc acc ggc aac      816
Ser Phe Tyr Ser Asn Ser Asn Ser Thr Gln Leu Ala Gly Thr Gly Asn
            260                 265                 270 caa gac gta tcg gca aca gca gca gcc gcc gcc ctg gag ctg agc          864
Gln Asp Val Ser Ala Thr Ala Ala Ala Ala Ala Leu Glu Leu Ser
        275                 280                 285 ctc agc tca tgg tgc tcc cct tac cct gct gca ggg agt atg tga          909
Leu Ser Ser Trp Cys Ser Pro Tyr Pro Ala Ala Gly Ser Met
    290                 295                 300

<210> SEQ ID NO 64
<211> LENGTH: 302
<212> TYPE: PRT
<213> ORGANISM: Zea mays

<400> SEQUENCE: 64

Met Ala Ala Asn Ala Gly Gly Gly Ala Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
        115                 120                 125

Pro Pro Ser Pro Thr Leu Gly Phe Tyr Ala Ala Gly Asn Gly Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Ser Asp Thr
            180                 185                 190
```

```
Ile Met Ala Ala Ala Ala Arg Ala Ala Thr Thr Arg Ala Pro Glu
            195                 200                 205

Thr Leu Pro Leu Phe Pro Thr Cys Gly Asp Asp Gly Ser Gly Ser
        210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
                260                 265                 270

Gln Asp Val Ser Ala Thr Ala Ala Ala Ala Ala Leu Glu Leu Ser
            275                 280                 285

Leu Ser Ser Trp Cys Ser Pro Tyr Pro Ala Ala Gly Ser Met
        290                 295                 300

<210> SEQ ID NO 65
<211> LENGTH: 961
<212> TYPE: DNA
<213> ORGANISM: Zea mays

<400> SEQUENCE: 65
gatccgattg actatctcat tcctccaaac ccaaacacct caaatatatc tgctatcggg     60
attggcattc ctgtatccct acgcccgtgt accccctgtt tagagaacct cccaaggtat   120
aagatggcga agattattgt tgtcttgtct ttcatcatat atcgagtctt tccctaggat   180
attattattg gcaatgagca ttacacggtt aatcgattga gagaacatgc atctcacctt   240
cagcaaataa ttacgataat ccatatttta cgcttcgtaa cttctcatga gtttcgatat   300
acaaatttgt tttctggaca ccctaccatt catcctcttc ggagaagaga ggaagtgtcc   360
tcaatttaaa tatgttgtca tgctgtagtt cttcacccaa tctcaacagg taccaagcac   420
attgtttcca caattatat tttagtcaca ataaatctat attattatta atatactaaa    480
actatactga cgctcagatg cttttactag ttcttgctag tatgtgatgt aggtctacgt   540
ggaccagaaa atagtgagac acggaagaca aaagaagtaa aagaggcccg gactacggcc   600
cacatgagat tcggccccgc cacctccggc aaccagcggc cgatccaacg gaagtgcgcg   660
cacacacaca acctcgtata tatcgccgcg cggaagcggc gcgaccgagg aagccttgtc   720
ctcgacaccc cctacacagg tgtcgcgctg cccccgacac gagtcccgca tgcgtcccac   780
gcggccgcgc cagatcccgc ctccgcgcgt tgccacgccc tctataaaca cccagctctc   840 cctcgcccctc atctacctca ctcgtagtcg tagctcaagc atcagcggca gcggcagcgg   900
caggagctct gggcagcgtg cgcacgtggg gtacctagct cgctctgcta gcctaccttca  960 a                                                                   961

<210> SEQ ID NO 66
<211> LENGTH: 1917
<212> TYPE: DNA
<213> ORGANISM: Zea mays
<220> FEATURE:
<221> NAME/KEY: CDS
<222> LOCATION: (1)...(1917)

<400> SEQUENCE: 66 atg acc agc aac agc agc cag aac atg agc agc tgc agc acc ggc gga    48
Met Thr Ser Asn Ser Ser Gln Asn Met Ser Ser Cys Ser Thr Gly Gly
1               5                   10                  15 agc gac gcg gcg gtc ggc ggc ggc agc tgg ctc ggc ttc tcg ctg tcg   96
```

```
                Ser Asp Ala Ala Val Gly Gly Gly Ser Trp Leu Gly Phe Ser Leu Ser
                                    20                  25                  30 cct cac atg gcg gcg acc atg gac ggc gcg gcc gac ggc gtt ccg gtg          144
Pro His Met Ala Ala Thr Met Asp Gly Ala Ala Asp Gly Val Pro Val
            35                  40                  45 cag cac cac cac cac gaa ggc ctc ttc tac cct ccc gtc gtc agc tcc          192
Gln His His His His Glu Gly Leu Phe Tyr Pro Pro Val Val Ser Ser
    50                  55                  60 tcg ccc gcg ccc ttc tgc tac gct ctc ggc ggc ggc caa gat ggc ctc          240
Ser Pro Ala Pro Phe Cys Tyr Ala Leu Gly Gly Gly Gln Asp Gly Leu
65                  70                  75                  80 gcc acg gcg gcc gcc aat ggt ggc ggg ggg ttc tac ccc ggg ctc tcc          288
Ala Thr Ala Ala Ala Asn Gly Gly Gly Gly Phe Tyr Pro Gly Leu Ser
                85                  90                  95 tct atg ccg ctc aag tcc gac ggc tcc cta tgc atc ctg gag gcc ctc          336
Ser Met Pro Leu Lys Ser Asp Gly Ser Leu Cys Ile Leu Glu Ala Leu
            100                 105                 110 cac agg agc gag caa gaa cgg cac ggg gtg gtg gtg tcg tcg tcg tcg          384
His Arg Ser Glu Gln Glu Arg His Gly Val Val Val Ser Ser Ser Ser
    115                 120                 125 ccc aaa ctg gag gat ttc ttg ggc gcg agc gcg agc acg gcg atg gcg          432
Pro Lys Leu Glu Asp Phe Leu Gly Ala Ser Ala Ser Thr Ala Met Ala
130                 135                 140 ctg agc ttg gac agc tcc agc ttc tac tac ggc tgc ggc cac ggc cac          480
Leu Ser Leu Asp Ser Ser Ser Phe Tyr Tyr Gly Cys Gly His Gly His
145                 150                 155                 160 ggc cac gac caa ggc ggg tac ctg cag cca atg cag tgc gcg gtg atg          528
Gly His Asp Gln Gly Gly Tyr Leu Gln Pro Met Gln Cys Ala Val Met
                165                 170                 175 ccc ggc tcg ggc ggg cac gac gtg tac ggc ggg ggg cac gcg cag atg          576
Pro Gly Ser Gly Gly His Asp Val Tyr Gly Gly Gly His Ala Gln Met
            180                 185                 190 gtg gac gag cag tcc gcc gcg gca atg gcg gcg agc tgg ttc tcc gcc          624
Val Asp Glu Gln Ser Ala Ala Ala Met Ala Ala Ser Trp Phe Ser Ala
    195                 200                 205 cgc ggc aat ggc ggc tac gac gtc gac ggc gcc ggc gcc ggc gcc atc          672
Arg Gly Asn Gly Gly Tyr Asp Val Asp Gly Ala Gly Ala Gly Ala Ile
210                 215                 220 gtg ccg ttg cag ggc cac ccg cac ccg ctc gcc ctc tcc atg agc tcc          720
Val Pro Leu Gln Gly His Pro His Pro Leu Ala Leu Ser Met Ser Ser
225                 230                 235                 240 ggg acg ggg tcc cag tcc agc agc gtc acc atg caa gtc ggc agc gcc          768
Gly Thr Gly Ser Gln Ser Ser Ser Val Thr Met Gln Val Gly Ser Ala
                245                 250                 255 cac gcc gac gcc gtc acc gag tac atc gcc atg gac ggg agc aag aag          816
His Ala Asp Ala Val Thr Glu Tyr Ile Ala Met Asp Gly Ser Lys Lys
            260                 265                 270 cgc ggc gcc ggc aac ggc gct agt gcc ggg cag aag cag ccc acc atc          864
Arg Gly Ala Gly Asn Gly Ala Ser Ala Gly Gln Lys Gln Pro Thr Ile
    275                 280                 285 cac cgc aag acc atc gac aca ttc ggg cag cgc acg tcg cag tac cgc          912
His Arg Lys Thr Ile Asp Thr Phe Gly Gln Arg Thr Ser Gln Tyr Arg
290                 295                 300 ggc gtc acc agg cat agg tgg acg ggg agg tat gag gcg cac ctc tgg          960
Gly Val Thr Arg His Arg Trp Thr Gly Arg Tyr Glu Ala His Leu Trp
305                 310                 315                 320 gac aac agc tgc agg aag gaa ggg cag acc cgg aaa ggc cgg caa gtt         1008
Asp Asn Ser Cys Arg Lys Glu Gly Gln Thr Arg Lys Gly Arg Gln Val
                325                 330                 335
```

-continued

| | |
|---|---|
| tat ctc ggc ggg tat gac gtg gag gag aag gcc gcg agg gca tat gac<br>Tyr Leu Gly Gly Tyr Asp Val Glu Glu Lys Ala Ala Arg Ala Tyr Asp<br>              340                     345                 350 | 1056 |
| ctg gcg gcg ctc aag tac tgg ggg acg tcc acg cac gtg aat ttc ccg<br>Leu Ala Ala Leu Lys Tyr Trp Gly Thr Ser Thr His Val Asn Phe Pro<br>        355                     360                     365 | 1104 |
| gtg gag gac tac agg gaa gag ctg gag gag atg aag aac atg acc aga<br>Val Glu Asp Tyr Arg Glu Glu Leu Glu Glu Met Lys Asn Met Thr Arg<br>     370                     375                     380 | 1152 |
| cag gag tac gtc gct cac ctg aga agg aaa agc agc ggc ttc tcg cgc<br>Gln Glu Tyr Val Ala His Leu Arg Arg Lys Ser Ser Gly Phe Ser Arg<br>385                     390                     395                 400 | 1200 |
| ggc gct tcg atc tac cgg gga gtc acc agg cat cac cag cac ggg cgg<br>Gly Ala Ser Ile Tyr Arg Gly Val Thr Arg His His Gln His Gly Arg<br>              405                     410                     415 | 1248 |
| tgg cag gcg cgc atc ggc cgc gtc tcg ggc aac aag gac ctc tac ctc<br>Trp Gln Ala Arg Ile Gly Arg Val Ser Gly Asn Lys Asp Leu Tyr Leu<br>            420                     425                     430 | 1296 |
| gga acg ttc agc acc cag gag gag gcg gcg gag gcg tac gac gtg gcc<br>Gly Thr Phe Ser Thr Gln Glu Glu Ala Ala Glu Ala Tyr Asp Val Ala<br>              435                     440                     445 | 1344 |
| gcg atc aag ttc cgc ggc ctc agc gcg gtc acc aac ttc gac atc acg<br>Ala Ile Lys Phe Arg Gly Leu Ser Ala Val Thr Asn Phe Asp Ile Thr<br>450                     455                     460 | 1392 |
| cgg tac gac gtg gac aag atc atg gag agc agc acg ctg ctc ccg ggc<br>Arg Tyr Asp Val Asp Lys Ile Met Glu Ser Ser Thr Leu Leu Pro Gly<br>465                     470                     475                 480 | 1440 |
| gag cag gtc cgg cgc agg aag gaa ggc gcc gac gcc gcg gtc tcg gag<br>Glu Gln Val Arg Arg Arg Lys Glu Gly Ala Asp Ala Ala Val Ser Glu<br>                485                     490                     495 | 1488 |
| gcc gcc gcc gcg ctg gtg cag gcc ggc aac tgc atg acg gac acc tgg<br>Ala Ala Ala Ala Leu Val Gln Ala Gly Asn Cys Met Thr Asp Thr Trp<br>                  500                     505                     510 | 1536 |
| aag atc cag gcg gcg ctg ccg gct gcc gcg cgg gcc gac gag cgc ggc<br>Lys Ile Gln Ala Ala Leu Pro Ala Ala Ala Arg Ala Asp Glu Arg Gly<br>            515                     520                     525 | 1584 |
| gcc ggc cag cag cag cgt cag gac ttg ctg tcg agc gag gcc ttc tcg<br>Ala Gly Gln Gln Gln Arg Gln Asp Leu Leu Ser Ser Glu Ala Phe Ser<br>     530                     535                     540 | 1632 |
| ctg ctc cac gac atc gtg tcc gtc gac gcc gct gct ggt aca ggg aca<br>Leu Leu His Asp Ile Val Ser Val Asp Ala Ala Ala Gly Thr Gly Thr<br>545                     550                     555                 560 | 1680 |
| ggg ggc atg tcg aac gcg tcc tcg ctg gcc ccc agc gtg agc aac<br>Gly Gly Met Ser Asn Ala Ser Ser Ser Leu Ala Pro Ser Val Ser Asn<br>              565                     570                     575 | 1728 |
| tcc cgg gag cag agc ccg gac cgg ggc ggc gcc agc ctc gcc atg ctc<br>Ser Arg Glu Gln Ser Pro Asp Arg Gly Gly Ala Ser Leu Ala Met Leu<br>            580                     585                     590 | 1776 |
| ttc gcc aag ccc gcc gcg gcg ccc aag ctg gct tgc ccg ctg ccg ctg<br>Phe Ala Lys Pro Ala Ala Ala Pro Lys Leu Ala Cys Pro Leu Pro Leu<br>              595                     600                     605 | 1824 |
| ggg tcc tgg gtg tcg ccg tcc gcg gtg tcc gcc agg ccg ccc ggc gtg<br>Gly Ser Trp Val Ser Pro Ser Ala Val Ser Ala Arg Pro Pro Gly Val<br>610                     615                     620 | 1872 |
| tca atc gcg cac ctg ccg gtg ttc gcc gcg tgg acc gac gca tga<br>Ser Ile Ala His Leu Pro Val Phe Ala Ala Trp Thr Asp Ala<br>625                     630                     635 | 1917 |

<210> SEQ ID NO 67
<211> LENGTH: 638

<212> TYPE: PRT
<213> ORGANISM: Zea mays

<400> SEQUENCE: 67

```
Met Thr Ser Asn Ser Ser Gln Asn Met Ser Ser Cys Ser Thr Gly Gly
1               5                   10                  15

Ser Asp Ala Ala Val Gly Gly Ser Trp Leu Gly Phe Ser Leu Ser
            20                  25                  30

Pro His Met Ala Ala Thr Met Asp Gly Ala Ala Asp Gly Val Pro Val
            35                  40                  45

Gln His His His His Glu Gly Leu Phe Tyr Pro Pro Val Val Ser Ser
            50                  55                  60

Ser Pro Ala Pro Phe Cys Tyr Ala Leu Gly Gly Gln Asp Gly Leu
65                  70                  75                  80

Ala Thr Ala Ala Ala Asn Gly Gly Gly Phe Tyr Pro Gly Leu Ser
                85                  90                  95

Ser Met Pro Leu Lys Ser Asp Gly Ser Leu Cys Ile Leu Glu Ala Leu
                100                 105                 110

His Arg Ser Glu Gln Glu Arg His Gly Val Val Ser Ser Ser Ser
            115                 120                 125

Pro Lys Leu Glu Asp Phe Leu Gly Ala Ser Ala Ser Thr Ala Met Ala
130                 135                 140

Leu Ser Leu Asp Ser Ser Ser Phe Tyr Tyr Gly Cys Gly His Gly His
145                 150                 155                 160

Gly His Asp Gln Gly Gly Tyr Leu Gln Pro Met Gln Cys Ala Val Met
                165                 170                 175

Pro Gly Ser Gly Gly His Asp Val Tyr Gly Gly His Ala Gln Met
                180                 185                 190

Val Asp Glu Gln Ser Ala Ala Ala Met Ala Ala Ser Trp Phe Ser Ala
            195                 200                 205

Arg Gly Asn Gly Gly Tyr Asp Val Asp Gly Ala Gly Ala Ile
            210                 215                 220

Val Pro Leu Gln Gly His Pro His Pro Leu Ala Leu Ser Met Ser Ser
225                 230                 235                 240

Gly Thr Gly Ser Gln Ser Ser Ser Val Thr Met Gln Val Gly Ser Ala
                245                 250                 255

His Ala Asp Ala Val Thr Glu Tyr Ile Ala Met Asp Gly Ser Lys Lys
            260                 265                 270

Arg Gly Ala Gly Asn Gly Ala Ser Ala Gly Gln Lys Gln Pro Thr Ile
            275                 280                 285

His Arg Lys Thr Ile Asp Thr Phe Gly Gln Arg Thr Ser Gln Tyr Arg
            290                 295                 300

Gly Val Thr Arg His Arg Trp Thr Gly Arg Tyr Glu Ala His Leu Trp
305                 310                 315                 320

Asp Asn Ser Cys Arg Lys Glu Gly Gln Thr Arg Lys Gly Arg Gln Val
                325                 330                 335

Tyr Leu Gly Gly Tyr Asp Val Glu Glu Lys Ala Ala Arg Ala Tyr Asp
            340                 345                 350

Leu Ala Ala Leu Lys Tyr Trp Gly Thr Ser Thr His Val Asn Phe Pro
            355                 360                 365

Val Glu Asp Tyr Arg Glu Glu Leu Glu Glu Met Lys Asn Met Thr Arg
            370                 375                 380

Gln Glu Tyr Val Ala His Leu Arg Arg Lys Ser Ser Gly Phe Ser Arg
385                 390                 395                 400
```

```
Gly Ala Ser Ile Tyr Arg Gly Val Thr Arg His His Gln His Gly Arg
            405                 410                 415

Trp Gln Ala Arg Ile Gly Arg Val Ser Gly Asn Lys Asp Leu Tyr Leu
        420                 425                 430

Gly Thr Phe Ser Thr Gln Glu Glu Ala Glu Ala Tyr Asp Val Ala
            435                 440                 445

Ala Ile Lys Phe Arg Gly Leu Ser Ala Val Thr Asn Phe Asp Ile Thr
    450                 455                 460

Arg Tyr Asp Val Asp Lys Ile Met Glu Ser Ser Thr Leu Leu Pro Gly
465                 470                 475                 480

Glu Gln Val Arg Arg Lys Glu Gly Ala Asp Ala Val Ser Glu
                485                 490                 495

Ala Ala Ala Ala Leu Val Gln Ala Gly Asn Cys Met Thr Asp Thr Trp
            500                 505                 510

Lys Ile Gln Ala Ala Leu Pro Ala Ala Arg Ala Asp Glu Arg Gly
        515                 520                 525

Ala Gly Gln Gln Gln Arg Gln Asp Leu Leu Ser Ser Glu Ala Phe Ser
    530                 535                 540

Leu Leu His Asp Ile Val Ser Val Asp Ala Ala Ala Gly Thr Gly Thr
545                 550                 555                 560

Gly Gly Met Ser Asn Ala Ser Ser Ser Leu Ala Pro Ser Val Ser Asn
            565                 570                 575

Ser Arg Glu Gln Ser Pro Asp Arg Gly Gly Ala Ser Leu Ala Met Leu
        580                 585                 590

Phe Ala Lys Pro Ala Ala Ala Pro Lys Leu Ala Cys Pro Leu Pro Leu
            595                 600                 605

Gly Ser Trp Val Ser Pro Ser Ala Val Ser Ala Arg Pro Pro Gly Val
    610                 615                 620

Ser Ile Ala His Leu Pro Val Phe Ala Ala Trp Thr Asp Ala
625                 630                 635

<210> SEQ ID NO 68
<211> LENGTH: 2260
<212> TYPE: DNA
<213> ORGANISM: Zea mays

<400> SEQUENCE: 68
cttccctaac ctttgcactg tccaaaatgg cttcctgatc ccctcacttc ctcgaatcaa      60
tctaagaaga aactcaagcc gcaaccatta ggggcagatt aattgctgca ctttcagata     120
atcaaccatg ccactgtga caactggct cgctttctcc ctctcccgc aggagctgcc       180 gccctcccag acgacggact ccacactcat ctcggccgcc accgccacc atgtctccgg     240 cgatgtctgc ttcaacatcc cccaagattg agcatgagg ggatcagagc tttcggcgct     300
cgtcgcggag ccgaagctgg aggacttcct cggcggcatc tccttctccg agcagcatca     360
caaggccaac tgcaacatga tacccagcac tagcagcaca gtttgctacg cgagctcagg     420
tgctagcacc ggctaccatc accagctgta ccaccagccc accagctcag cgctccactt     480
cgcggactcc gtaatggtgg cctcctcggc cggtgtccac gacggcggtg ccatgctcag     540
cgcggccgcc gctaacggtg tcgctggcgc tgccagtgcc aacggcggcg catcgggct      600 gtccatgatt aagaactggc tgcggagcca accggcgccc atgcagccga ggtggcggc     660 ggctgagggc gcgcagggggc tctctttgtc catgaacatg gcggggacga cccaaggcgc    720
tgctggcatg ccacttctcg ctggagagcg cgcacgggcg cccgagagtg tatcgacgtc    780
```

```
agcacagggt ggagccgtcg tcgtcacggc gccgaaggag gatagcggtg gcagcggtgt      840
tgccggcgct ctagtagccg tgagcacgga cacgggtggc agcggcggcg cgtcggctga      900
caacacggca aggaagacgg tggacacgtt cgggcagcgc acgtcgattt accgtggcgt      960
gacaaggcat agatggactg ggagatatga ggcacatctt tgggataaca gttgcagaag     1020
ggaagggcaa actcgtaagg gtcgtcaagt ctatttaggt ggctatgata agaggagaa      1080 agctgctagg gcttatgatc ttgctgctct gaagtactgg ggtgccacaa caacaacaaa     1140
ttttccagtg agtaactacg aaaaggagct cgaggacatg aagcacatga caaggcagga     1200
gtttgtagcg tctctgagaa ggaagagcag tggtttctcc agaggtgcat ccatttacag     1260
gggagtgact aggcatcacc aacatggaag atggcaagca cggattggac gagttgcagg     1320
gaacaaggat ctttacttgg gcaccttcag cacccaggag gaggcagcgg aggcgtacga     1380
catcgcggcg atcaagttcc gcggcctcaa cgccgtcacc aacttcgaca tgagccgcta     1440
cgacgtgaag agcatcctgg acagcagcgc cctccccatc ggcagcgccg ccaagcgcct     1500
caaggaggcc gaggccgcag cgtccgcgca gcaccaccac gccggcgtgg tgagctacga     1560
cgtcggccgc atcgcctcgc agctcggcga cggcggagcc ctggcggcgg cgtacgcgc      1620 gcactaccac ggcgccgcct ggccgaccat cgcgttccag ccgggcgccg ccagcacagg     1680
cctgtaccac ccgtacgcgc agcagccaat gcgcggcggc gggtggtgca agcaggagca     1740
ggaccacgcg gtgatcgcgg ccgcgcacag cctgcaggac ctccaccacc tgaacctggg     1800
cgcggccggc gcgcacgact ttttctcggc agggcagcag gccgccgccg ctgcgatgca     1860
cggcctgggt agcatcgaca gtgcgtcgct cgagcacagc accggctcca actccgtcgt     1920
ctacaacggc ggggtcggcg acagcaacgg cgccagcgcc gtcggcggca gtggcggtgg     1980
ctacatgatg ccgatgagcg ctgccggagc aaccactaca tcggcaatgg tgagccacga     2040
gcaggtgcat gcacgggcct acgacgaagc caagcaggct gctcagatgg ggtacgagag     2100
ctacctggtg aacgcggaga caatggtgg cggaaggatg tctgcatggg ggactgtcgt      2160
gtctgcagcc gcggcggcag cagcaagcag caacgacaac atggccgccg acgtcggcca     2220
tggcggcgcg cagctcttca gtgtctggaa cgacacttaa                           2260
```

<210> SEQ ID NO 69
<211> LENGTH: 3766
<212> TYPE: DNA
<213> ORGANISM: Sorghum bicolor

<400> SEQUENCE: 69

```
atggctactg tgaacaactg gctcgctttc tccctctccc cgcaggagct gccgcccacc       60
cagacggact ccaccctcat ctctgccgcc accaccgacg atgtctccgg cgatgtctgc      120
ttcaacatcc cccaaggtat gcatctatcg atcgatatat gtacgtacag tgcgcatata      180
tatatatatc tgcagtttgt ggtacgaata ctgattgaag ctagcatgaa atgtcgtttg      240
ttctttcaga ttggagcatg aggggatccg agctttcggc gctcgtcgcc gagccgaagc      300
tggaggactt cctcggcgga atctccttct ccgagcagca ccacaaggcc aactgcaaca      360
tgatccccag cactagcagc acagcttgct acgcgagctc gggtgctacc gccggctacc      420
atcaccagct gtaccaccag cccaccagct ccgcgctcca cttcgctgac tccgtcatgg      480
tggcctcctc ggccggcggc gtccacgacg gaggtgccat gctcagcgcg ccagcgcta      540 atggtagcgc tggcgctggc gctgccagtg ccaatggcag cggcagcatc gggctgtcca      600
```

```
tgatcaagaa ctggctgcgg agccaaccag ctcccatgca gccgagggtg gcggcggctg      660
agagcgtgca ggggctctct ttgtccatga acatggcggg ggcgacgcaa ggcgccgctg      720
gcatgccact tcttgctgga gagcgcggcc gggcgcccga gagtgtctcg acgtcggcac      780
agggtggagc cgtcgtcacg gctccaaagg aggatagcgg tggcagcggt gttgccgcca      840
ccggcgccct agtagccgtg agcacggaca cgggtggcag cggcgcgtcg gctgacaaca      900
cggcaaggaa gacggtggac acgttcgggc agcgcacgtc gatttaccgt ggcgtgacaa      960
ggtaataagg gtccggtatt acaatgaatc gtcacttcgt cagagaacta aactagcaca     1020
aatcagcaat gaatcaagta atatcatgaa atttagaaaa gccgttagca atgcaaggag     1080
ctatcattat agatttgatt gcatctagac agttctgaat taaatgagta gggcaatgtg     1140
tagcctttga tgatctcgct gattattagg agtgccattt gtattggcta tgattgtggt     1200
atatacagca gtagacaatt aacaaaaggc taccactttc gaattatttt aggcatagat     1260
ggactgggag atatgaagca catctgtggg acaacagttg cagaagggaa ggacaaactc     1320
gcaagggtcg tcaaggtacc aatataatgc aatcaccgt atttaaatat atatgctttt      1380
ctgtaattaa gtttatactt tcacaaaact gacattactt cgcattatca tttttggatt     1440
gtcgtcgtca tgattggcgg gattgaaatg aactattgaa tctacagtct atttaggtaa     1500
gcgatttcac ttggttatta atttgggacc aactacttaa tccagtttgt ttttcccta      1560 taaccattat ttttcatct gtgttctcaa ctcttacttt tccatcttgt tccactgata      1620
ggtggctatg ataagagga gaaagctgct agggcttatg atctggctgc tcttaagtac      1680
tggggtccca cgacaacaac aaattttcca gtatgtatat gtagaatgca gttttacttc     1740
actgaagatc ataccttgc tatgtctcaa atgccgttca ttagttagtg gatctgaagt      1800
gaaggttctg taatttttgt taactatgta cattgctgga attgtactta aagtcatttg     1860 ttttgtata tctaggtgaa taactacgaa aaggagctgg aggatatgaa gcacatgaca      1920
aggcaggagt ttgtagcgtc tctgagaagg tcggtcgaac agcattgatt aatcaatgcc     1980
aactctattg aataaacatc tactctgtta attgttaaag tttgagagaa agatctgcat     2040
gttagatctt aatagaccac tgtatatgaa tgcaggaaga gcagtggttt ctccagaggt     2100
gcatccattt acaggggagt gactaggtat gaattcatat aatggcgtca acaaacacac     2160
atacactttg attgaggagg cgaatgcacg catggattga atgtgaatgg tgttttactt     2220
gaactatgta attataggca tcaccagcat ggaagatggc aagcacggat tggacgagtt     2280
gcagggaaca aggatctcta cttgggcacc ttcagtaagt atcagagatg ttttctcatt     2340
gtatatagag gagtacttct atatgtatat atacattcag ttattcacca cacaaaagca     2400
aattgcagtc aactaataac aatctcaacg caatgagaag caagtgttac agctgatagt     2460
acacatttgt agaccttctg catatggatg ttatatatga tgactattaa aaatgtgacc     2520
attgcatcaa gtcatgcaaa gttgcattgc agtagtacat acattactta gtgcatgctc     2580
ctcaagtggc tttttcaaac ctgatcccat gtctggcgct attgttgtct cccattcacc     2640
cgtgcatcag gtcaaaatag tactatgcct caataagaaa cacatgagca tgcactggca     2700
gcagcagact aatcaagttc tatcatttac taataaacta attaggctac agcatccaaa     2760
agattctacc cattaagcca caactgttca tgcatgcatt cataaaccag gataccacca     2820
tgcatgcgtg caccgtgttc gtgcttggaa tattgagctg agccgagtgc acccttgcgt     2880
ggatgcaggc acgcaggagg aggcagcgga ggcatacgac attgcggcga tcaagttccg     2940
cggcctcaac gccgtcacaa acttcgacat gagccgctac gacgtcaaga gcatcctgga     3000
```

```
cagcagtgcg ctccccatcg gcagcgccgc caagcgtctc aaggaggccg aggccgccgc   3060
gtccgcacag caccatgccg gcgtggtgag ctacgacgtc ggccgcatag cctcacagct   3120
cggcgacggc ggcgccctgg cggcggcgta cggcgcgcac taccatggcg cctggccgac   3180
catcgcgttc cagccgagcg cggccacggg cctgtaccac ccgtacgcgc agccgatgcg   3240
cgggtggtgc aagcaggagc aggaccacgc ggtgatcgcg gccgcgcaca gcctgcagga   3300
gctccaccac ctgaacctgg gtgctgccgc cggcgcgcac gacttcttct cggcggggca   3360
gcaggcggcg atgcacggcc tgggtagcat ggacaatgca tcactcgagc acagcaccgg   3420
ctccaactcc gtcgtgtaca acggtgttgg tgatagcaac ggcagcaccg tcgtcggcag   3480
tggtggctac atgatgccta tgagcgctgc cacggcgacg gctaccacgg caatggtgag   3540
ccacgagcag gtgcatgcac gggcacaggg tgatcaccac gacgaagcca agcaggctgc   3600
tcagatgggg tacgagagct acctggtgaa cgcagagaac tatggcggcg ggaggatgtc   3660
tgcggcctgg gcgactgtct cagcgccacc ggcggcaagc agcaacgata acatggcgga   3720
cgtcggccat ggcggcgcac agctcttcag tgtctggaac gatact                 3766
```

```

<210> SEQ ID NO 70
<211> LENGTH: 530
<212> TYPE: PRT
<213> ORGANISM: Glycine max

<400> SEQUENCE: 70

Met Asp Ser Ser Ser Ser Ser Pro Pro Asn Ser Thr Asn Asn Asn Ser
1               5                   10                  15

Leu Ala Phe Ser Leu Ser Asn His Phe Pro Asn Pro Ser Ser Ser Pro
            20                  25                  30

Leu Ser Leu Phe His Ser Phe Thr Tyr Pro Ser Leu Ser Leu Thr Gly
        35                  40                  45

Ser Asn Thr Val Asp Ala Pro Pro Glu Pro Thr Ala Gly Ala Gly Pro
    50                  55                  60

Thr Asn Leu Ser Ile Phe Thr Gly Gly Pro Lys Phe Glu Asp Phe Leu
65                  70                  75                  80

Gly Gly Ser Ala Ala Thr Ala Thr Thr Val Ala Cys Ala Pro Pro Gln
                85                  90                  95

Leu Pro Gln Phe Ser Thr Asp Asn Asn Asn His Leu Tyr Asp Ser Glu
            100                 105                 110

Leu Lys Ser Thr Ile Ala Ala Cys Phe Pro Arg Ala Leu Ala Ala Glu
        115                 120                 125

Gln Ser Thr Glu Pro Gln Lys Pro Ser Pro Lys Lys Thr Val Asp Thr
    130                 135                 140

Phe Gly Gln Arg Thr Ser Ile Tyr Arg Gly Val Thr Arg His Arg Trp
145                 150                 155                 160

Thr Gly Arg Tyr Glu Ala His Leu Trp Asp Asn Ser Cys Arg Arg Glu
                165                 170                 175

Gly Gln Ser Arg Lys Gly Arg Gln Val Tyr Leu Gly Gly Tyr Asp Lys
            180                 185                 190

Glu Asp Lys Ala Ala Arg Ala Tyr Asp Leu Ala Ala Leu Lys Tyr Trp
        195                 200                 205

Gly Pro Thr Thr Thr Thr Asn Phe Pro Ile Ser Asn Tyr Glu Lys Glu
    210                 215                 220

Leu Glu Glu Met Lys Asn Met Thr Arg Gln Glu Phe Val Ala Ser Leu
225                 230                 235                 240
```

```
Arg Arg Lys Ser Ser Gly Phe Ser Arg Gly Ala Ser Ile Tyr Arg Gly
                245                 250                 255

Val Thr Arg His His Gln His Gly Arg Trp Gln Ala Arg Ile Gly Arg
        260                 265                 270

Val Ala Gly Asn Lys Asp Leu Tyr Leu Gly Thr Phe Ser Thr Gln Glu
            275                 280                 285

Glu Ala Ala Glu Ala Tyr Asp Ile Ala Ala Ile Lys Phe Arg Gly Leu
290                 295                 300

Asn Ala Val Thr Asn Phe Asp Met Ser Arg Tyr Asp Val Lys Ser Ile
305                 310                 315                 320

Ala Asn Ser Thr Leu Pro Ile Gly Gly Leu Ser Gly Lys Asn Lys Asn
                325                 330                 335

Ser Thr Asp Ser Ala Ser Glu Ser Lys Ser His Glu Pro Ser Gln Ser
                340                 345                 350

Asp Gly Asp Pro Ser Ser Ala Ser Ser Val Thr Phe Ala Ser Gln Gln
            355                 360                 365

Gln Pro Ser Ser Ser Asn Leu Ser Phe Ala Ile Pro Ile Lys Gln Asp
    370                 375                 380

Pro Ser Asp Tyr Trp Ser Ile Leu Gly Tyr His Asn Thr Pro Leu Asp
385                 390                 395                 400

Asn Ser Gly Ile Arg Asn Thr Thr Ser Thr Val Thr Thr Thr Thr Phe
                405                 410                 415

Pro Ser Ser Asn Asn Gly Thr Ala Ser Ser Leu Thr Pro Phe Asn Met
            420                 425                 430

Glu Phe Ser Ser Ala Pro Ser Ser Thr Gly Ser Asp Asn Asn Ala Ala
        435                 440                 445

Phe Phe Ser Gly Gly Gly Ile Phe Val Gln Gln Gln Thr Ser His Gly
    450                 455                 460

His Gly Asn Ala Ser Ser Gly Ser Ser Ser Ser Leu Ser Cys Ser
465                 470                 475                 480

Ile Pro Phe Ala Thr Pro Ile Phe Ser Leu Asn Ser Asn Thr Ser Tyr
                485                 490                 495

Glu Ser Ser Ala Gly Tyr Gly Asn Trp Ile Gly Pro Thr Leu His Thr
            500                 505                 510

Phe Gln Ser His Ala Lys Pro Ser Leu Phe Gln Thr Pro Ile Phe Gly
        515                 520                 525

Met Glu
530

<210> SEQ ID NO 71
<211> LENGTH: 528
<212> TYPE: PRT
<213> ORGANISM: Glycine max

<400> SEQUENCE: 71

Met Asp Ser Cys Ser Ser Pro Pro Asn Asn Ser Leu Ala Phe Ser
 1               5                  10                  15

Leu Ser Asn His Phe Pro Asn Pro Ser Ser Pro Leu Ser Leu Phe
                20                  25                  30

His Ser Phe Thr Tyr Pro Ser Leu Ser Leu Thr Gly Ser His Thr Ala
            35                  40                  45

Asp Ala Pro Pro Glu Pro Ile Ala Gly Gly Ala Thr Asn Leu Ser
50                  55                  60

Ile Phe Thr Gly Ala Pro Lys Phe Glu Asp Phe Leu Gly Gly Ser Ser
```

-continued

```
                65                  70                  75                  80
Ala Thr Ala Thr Ala Thr Thr Cys Ala Pro Pro Gln Leu Pro Gln Phe
                        85                  90                  95

Ser Thr Asp Asn Asn Asn His Leu Tyr Asp Ser Glu Leu Lys Thr Thr
            100                 105                 110

Ile Ala Ala Cys Phe Pro Arg Ala Phe Ala Ala Glu Pro Thr Thr Glu
            115                 120                 125

Pro Gln Lys Pro Ser Pro Lys Lys Thr Val Asp Thr Phe Gly Gln Arg
    130                 135                 140

Thr Ser Ile Tyr Arg Gly Val Thr Arg His Arg Trp Thr Gly Arg Tyr
145                 150                 155                 160

Glu Ala His Leu Trp Asp Asn Ser Cys Arg Arg Glu Gly Gln Ser Arg
                165                 170                 175

Lys Gly Arg Gln Val Tyr Leu Gly Gly Tyr Asp Lys Glu Asp Lys Ala
            180                 185                 190

Ala Arg Ala Tyr Asp Leu Ala Ala Leu Lys Tyr Trp Gly Pro Thr Thr
            195                 200                 205

Thr Thr Asn Phe Pro Ile Ser Asn Tyr Glu Lys Glu Leu Glu Glu Met
    210                 215                 220

Lys Asn Met Thr Arg Gln Glu Phe Val Ala Ser Leu Arg Arg Lys Ser
225                 230                 235                 240

Ser Gly Phe Ser Arg Gly Ala Ser Ile Tyr Arg Gly Val Thr Arg His
                245                 250                 255

His Gln His Gly Arg Trp Gln Ala Arg Ile Gly Arg Val Ala Gly Asn
            260                 265                 270

Lys Asp Leu Tyr Leu Gly Thr Phe Ser Thr Gln Glu Glu Ala Ala Glu
            275                 280                 285

Ala Tyr Asp Ile Ala Ala Ile Lys Phe Arg Gly Leu Asn Ala Val Thr
    290                 295                 300

Asn Phe Asp Met Ser Arg Tyr Asp Val Lys Ser Ile Ala Asn Ser Thr
305                 310                 315                 320

Leu Pro Ile Gly Gly Leu Ser Gly Lys Asn Lys Asn Ser Thr Asp Ser
                325                 330                 335

Ala Ser Glu Ser Lys Ser His Glu Ala Ser Arg Ser Asp Glu Arg Asp
            340                 345                 350

Pro Ser Ala Ala Ser Ser Val Thr Phe Ala Ser Gln Gln Gln Pro Ser
            355                 360                 365

Ser Ser Thr Leu Ser Phe Ala Ile Pro Ile Lys Gln Asp Pro Ser Asp
    370                 375                 380

Tyr Trp Ser Ile Leu Gly Tyr His Asn Ser Pro Leu Asp Asn Thr Gly
385                 390                 395                 400

Ile Arg Asn Thr Thr Ser Val Thr Ala Thr Ser Phe Pro Ser Ser Asn
                405                 410                 415

Asn Gly Thr Thr Ser Ser Leu Thr Pro Phe His Met Glu Phe Ser Asn
            420                 425                 430

Ala Pro Thr Ser Thr Gly Ser Asp Asn Asp Ala Ala Phe Phe Ser Gly
            435                 440                 445

Gly Gly Ile Phe Val Gln Gln Ser Gly His Gly Asn Gly His Gly
    450                 455                 460

Ser Gly Ser Ser Gly Ser Ser Ser Ser Leu Ser Cys Ser Ile Pro
465                 470                 475                 480

Phe Ala Thr Pro Ile Phe Ser Leu Asn Ser Asn Thr Ser Tyr Glu Asn
                485                 490                 495
```

Ser Ala Gly Tyr Gly Asn Trp Ile Gly Pro Thr Leu His Thr Phe Gln
                500                 505                 510

Ser His Ala Lys Pro Ser Leu Phe Gln Thr Pro Ile Phe Gly Met Glu
            515                 520                 525

<210> SEQ ID NO 72
<211> LENGTH: 488
<212> TYPE: PRT
<213> ORGANISM: Zea mays

<400> SEQUENCE: 72

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
                20                  25                  30

Ser Ser Gly Thr Pro Leu Gly Asp Glu Gln Gly Ala Val Glu Glu Ser
            35                  40                  45

Pro Arg Thr Val Glu Asp Phe Leu Gly Val Gly Gly Ala Gly Ala
        50                  55                  60

Pro Pro Gln Pro Ala Ala Ala Ala Asp Gln Asp His Gln Leu Val Cys
65                  70                  75                  80

Gly Glu Leu Gly Ser Ile Thr Ala Arg Phe Leu Arg His Tyr Pro Ala
                85                  90                  95

Ala Pro Ala Gly Thr Thr Val Glu Asn Pro Gly Ala Val Thr Val Ala
                100                 105                 110

Ala Met Ser Ser Thr Asp Val Ala Gly Ala Glu Ser Asp Gln Ala Arg
            115                 120                 125

Arg Pro Ala Glu Thr Phe Gly Gln Arg Thr Ser Ile Tyr Arg Gly Val
        130                 135                 140

Thr Arg His Arg Trp Thr Gly Arg Tyr Glu Ala His Leu Trp Asp Asn
145                 150                 155                 160

Ser Cys Arg Arg Glu Gly Gln Ser Arg Lys Gly Arg Gln Val Tyr Leu
                165                 170                 175

Gly Gly Tyr Asp Lys Glu Glu Lys Ala Ala Arg Ala Tyr Asp Leu Ala
                180                 185                 190

Ala Leu Lys Tyr Trp Gly Pro Thr Thr Thr Thr Asn Phe Pro Val Ser
            195                 200                 205

Asn Tyr Glu Lys Glu Leu Glu Glu Met Lys Ser Met Thr Arg Gln Glu
        210                 215                 220

Phe Ile Ala Ser Leu Arg Arg Lys Ser Ser Gly Phe Ser Arg Gly Ala
225                 230                 235                 240

Ser Ile Tyr Arg Gly Val Thr Arg His His Gln His Gly Arg Trp Gln
                245                 250                 255

Ala Arg Ile Gly Arg Val Ala Gly Asn Lys Asp Leu Tyr Leu Gly Thr
                260                 265                 270

Phe Ser Thr Gln Glu Glu Ala Ala Glu Ala Tyr Asp Ile Ala Ala Ile
            275                 280                 285

Lys Phe Arg Gly Leu Asn Ala Val Thr Asn Phe Asp Met Ser Arg Tyr
        290                 295                 300

Asp Val Glu Ser Ile Leu Ser Ser Asp Leu Pro Val Gly Gly Gly Ala
305                 310                 315                 320

Ser Gly Arg Ala Pro Ala Lys Phe Pro Leu Asp Ser Leu Gln Pro Gly
                325                 330                 335

Ser Ala Ala Ala Met Met Leu Ala Gly Ala Ala Ala Ala Ser Gln Ala

```
                    340                 345                 350
Thr Met Pro Pro Ser Glu Lys Asp Tyr Trp Ser Leu Leu Ala Leu His
            355                 360                 365

Tyr Gln Gln Gln Glu Gln Glu Arg Gln Phe Pro Ala Ser Ala Tyr
    370                 375                 380

Glu Ala Tyr Gly Ser Gly Val Asn Val Asp Phe Thr Met Gly Thr
385                 390                 395                 400

Ser Ser Gly Asn Asn Asn Asn Thr Gly Ser Gly Val Met Trp Gly
                405                 410                 415

Ala Thr Thr Gly Ala Val Val Val Gly Gln Gln Asp Ser Ser Gly Lys
            420                 425                 430

Gln Gly Asn Gly Tyr Ala Ser Asn Ile Pro Tyr Ala Ala Ala Met
            435                 440                 445

Val Ser Gly Ser Ala Gly Tyr Glu Gly Ser Thr Gly Asp Asn Gly Thr
    450                 455                 460

Trp Val Thr Thr Thr Ser Ser Asn Thr Gly Thr Ala Pro His Tyr
465                 470                 475                 480

Tyr Asn Tyr Leu Phe Gly Met Glu
                485

<210> SEQ ID NO 73
<211> LENGTH: 495
<212> TYPE: PRT
<213> ORGANISM: Oryza sativa

<400> SEQUENCE: 73

Met Asp Met Asp Thr Ser His His Tyr Pro Trp Leu Asn Phe Ser Leu
 1               5                  10                  15

Ala His His Cys Glu Met Glu Glu Glu Arg Gly Ala Ala Ala Glu
                20                  25                  30

Leu Ala Ala Ile Ala Gly Ala Ala Pro Pro Lys Leu Glu Asp Phe
            35                  40                  45

Leu Gly Gly Gly Cys Asn Gly Gly Ser Ser Gly Gly Ala Cys Pro Pro
 50                  55                  60

Val Gln Thr Thr Ala Pro Thr Ala Ala Glu Leu Tyr Glu Ser Glu Leu
 65                  70                  75                  80

Lys Phe Leu Ala Ala Gly Phe Gln Leu Ser Gly Ala Ala Gly Ala Ala
                85                  90                  95

Pro Pro Val Pro Ala Leu Leu Pro Ala Ala Leu Glu Gln Thr Asp
            100                 105                 110

Glu Thr Lys Gln Leu Ala Leu Pro Gln Ala Ala Val Ala Pro Pro
            115                 120                 125

Pro Glu Gln Lys Lys Ala Val Asp Ser Phe Gly Gln Arg Thr Ser Ile
    130                 135                 140

Tyr Arg Gly Val Thr Arg His Arg Trp Thr Gly Arg Tyr Glu Ala His
145                 150                 155                 160

Leu Trp Asp Asn Ser Cys Arg Arg Glu Gly Gln Ser Arg Lys Gly Arg
                165                 170                 175

Gln Val Tyr Leu Gly Gly Tyr Asp Lys Glu Glu Lys Ala Ala Arg Ala
            180                 185                 190

Tyr Asp Leu Ala Ala Leu Lys Tyr Trp Gly Pro Ser Thr Thr Thr Asn
        195                 200                 205

Phe Pro Val Ala Glu Tyr Glu Lys Glu Leu Glu Glu Met Lys His Met
    210                 215                 220
```

Thr Arg Gln Glu Phe Val Ala Ser Leu Arg Arg Lys Ser Ser Gly Phe
225                 230                 235                 240

Ser Arg Gly Ala Ser Ile Tyr Arg Gly Val Thr Arg His His Gln His
            245                 250                 255

Gly Arg Trp Gln Ala Arg Ile Gly Arg Val Ala Gly Asn Lys Asp Leu
        260                 265                 270

Tyr Leu Gly Thr Phe Gly Thr Glu Glu Ala Ala Glu Ala Tyr Asp
    275                 280                 285

Ile Ala Ala Ile Lys Phe Arg Gly Leu Asn Ala Val Thr Asn Phe Glu
290                 295                 300

Ile Gly Arg Tyr Asn Val Glu Ser Ile Ile Ser Ser Asn Leu Pro Ile
305                 310                 315                 320

Gly Ser Met Ala Gly Asn Arg Ser Thr Lys Ala Gly Leu Glu Leu Ala
                325                 330                 335

Pro Ser Ser Ala Asp Ala Ile Ala Ala Thr Glu Ala Asn His Thr
            340                 345                 350

Gly Val Ala Pro Pro Ser Thr Leu Ala Phe Thr Ala Leu Pro Met Lys
        355                 360                 365

Tyr Asp Gln Ala Asp Tyr Leu Ser Tyr Leu Ala Leu Gln His His Gln
370                 375                 380

Gln Gly Asn Leu Gln Gly Leu Gly Phe Gly Leu Tyr Ser Ser Gly Val
385                 390                 395                 400

Asn Leu Asp Phe Ala Asn Ala Asn Gly Asn Gly Ala Met Ser Asn Cys
                405                 410                 415

Tyr Thr Asn Val Ser Leu His Glu Gln Gln Gln His Gln His Gln
            420                 425                 430

His Gln Gln Glu Gln Gln Gln Asp Gln Asp Asp Gln Ser Gln Ser
        435                 440                 445

Ser Asn Asn Ser Cys Gly Ser Ile Pro Phe Ala Thr Pro Ile Ala Phe
450                 455                 460

Ser Gly Ser Tyr Glu Ser Ser Met Thr Ala Ala Gly Thr Phe Gly Tyr
465                 470                 475                 480

Tyr Pro Asn Val Ala Ala Phe Gln Thr Pro Ile Phe Gly Met Glu
                485                 490                 495

<210> SEQ ID NO 74
<211> LENGTH: 558
<212> TYPE: PRT
<213> ORGANISM: Arabidopsis thaliana

<400> SEQUENCE: 74

Met Lys Asn Asn Asn Lys Ser Ser Ser Ser Ser Tyr Asp Ser
1               5                   10                  15

Ser Leu Ser Pro Ser Ser Ser Ser Ser His Gln Asn Trp Leu Ser
            20                  25                  30

Phe Ser Leu Ser Asn Asn Asn Asn Phe Asn Ser Ser Ser Asn Pro
        35                  40                  45

Asn Leu Thr Ser Ser Thr Ser Asp His His His Pro His Pro Ser His
    50                  55                  60

Leu Ser Leu Phe Gln Ala Phe Ser Thr Pro Val Glu Arg Gln Asp
65                  70                  75                  80

Gly Ser Pro Gly Val Ser Pro Ser Asp Ala Thr Ala Val Leu Ser Val
                85                  90                  95

Tyr Pro Gly Gly Pro Lys Leu Glu Asn Phe Leu Gly Gly Gly Ala Ser
            100                 105                 110

```
Thr Thr Thr Thr Arg Pro Met Gln Gln Val Gln Ser Leu Gly Gly Val
            115                 120                 125

Val Phe Ser Ser Asp Leu Gln Pro Pro Leu His Pro Pro Ser Ala Ala
    130                 135                 140

Glu Ile Tyr Asp Ser Glu Leu Lys Ser Ile Ala Ala Ser Phe Leu Gly
145                 150                 155                 160

Asn Tyr Ser Gly Gly His Ser Ser Glu Val Ser Ser Val His Lys Gln
                165                 170                 175

Gln Pro Asn Pro Leu Ala Val Ser Glu Ala Ser Pro Thr Pro Lys Lys
            180                 185                 190

Asn Val Glu Ser Phe Gly Gln Arg Thr Ser Ile Tyr Arg Gly Val Thr
        195                 200                 205

Arg His Arg Trp Thr Gly Arg Tyr Glu Ala His Leu Trp Asp Asn Ser
    210                 215                 220

Cys Arg Arg Glu Gly Gln Ser Arg Lys Gly Arg Gln Val Tyr Leu Gly
225                 230                 235                 240

Gly Tyr Asp Lys Glu Asp Lys Ala Ala Arg Ala Tyr Asp Leu Ala Ala
                245                 250                 255

Leu Lys Tyr Trp Gly Pro Thr Thr Thr Thr Asn Phe Pro Ile Ser Asn
            260                 265                 270

Tyr Glu Ser Glu Leu Glu Glu Met Lys His Met Thr Arg Gln Glu Phe
        275                 280                 285

Val Ala Ser Leu Arg Arg Lys Ser Ser Gly Phe Ser Arg Gly Ala Ser
    290                 295                 300

Met Tyr Arg Gly Val Thr Arg His His Gln His Gly Arg Trp Gln Ala
305                 310                 315                 320

Arg Ile Gly Arg Val Ala Gly Asn Lys Asp Leu Tyr Leu Gly Thr Phe
                325                 330                 335

Ser Thr Gln Glu Glu Ala Ala Glu Ala Tyr Asp Ile Ala Ala Ile Lys
            340                 345                 350

Phe Arg Gly Leu Asn Ala Val Thr Asn Phe Asp Ile Ser Arg Tyr Asp
        355                 360                 365

Val Lys Ser Ile Ala Ser Cys Asn Leu Pro Val Gly Gly Leu Met Pro
    370                 375                 380

Lys Pro Ser Pro Ala Thr Ala Ala Ala Asp Lys Thr Val Asp Leu Ser
385                 390                 395                 400

Pro Ser Asp Ser Pro Ser Leu Thr Thr Pro Ser Leu Thr Phe Asn Val
                405                 410                 415

Ala Thr Pro Val Asn Asp His Gly Gly Thr Phe Tyr His Thr Gly Ile
            420                 425                 430

Pro Ile Lys Pro Asp Pro Ala Asp His Tyr Trp Ser Asn Ile Phe Gly
        435                 440                 445

Phe Gln Ala Asn Pro Lys Ala Glu Met Arg Pro Leu Ala Asn Phe Gly
    450                 455                 460

Ser Asp Leu His Asn Pro Ser Pro Gly Tyr Ala Ile Met Pro Val Met
465                 470                 475                 480

Gln Glu Gly Glu Asn Asn Phe Gly Gly Ser Phe Val Gly Ser Asp Gly
                485                 490                 495

Tyr Asn Asn His Ser Ala Ala Ser Asn Pro Val Ser Ala Ile Pro Leu
            500                 505                 510

Ser Ser Thr Thr Met Ser Asn Gly Asn Glu Gly Tyr Gly Gly Asn
        515                 520                 525
```

```
Ile Asn Trp Ile Asn Asn Ile Ser Ser Ser Tyr Gln Thr Ala Lys
    530             535                 540

Ser Asn Leu Ser Val Leu His Thr Pro Val Phe Gly Leu Glu
545             550             555

<210> SEQ ID NO 75
<211> LENGTH: 568
<212> TYPE: PRT
<213> ORGANISM: Arabidopsis thaliana

<400> SEQUENCE: 75

Met Asn Ser Asn Asn Trp Leu Ala Phe Pro Leu Ser Pro Thr His Ser
  1               5                  10                  15

Ser Leu Pro Pro His Ile His Ser Ser Gln Asn Ser His Phe Asn Leu
             20                  25                  30

Gly Leu Val Asn Asp Asn Ile Asp Asn Pro Phe Gln Asn Gln Gly Trp
         35                  40                  45

Asn Met Ile Asn Pro His Gly Gly Gly Glu Gly Gly Glu Val Pro
     50                  55                  60

Lys Val Ala Asp Phe Leu Gly Val Ser Lys Ser Gly Asp His His Thr
 65                  70                  75                  80

Asp His Asn Leu Val Pro Tyr Asn Asp Ile His Gln Thr Asn Ala Ser
                 85                  90                  95

Asp Tyr Tyr Phe Gln Thr Asn Ser Leu Leu Pro Thr Val Thr Cys
            100                 105                 110

Ala Ser Asn Ala Pro Asn Asn Tyr Glu Leu Gln Glu Ser Ala His Asn
        115                 120                 125

Leu Gln Ser Leu Thr Leu Ser Met Gly Ser Thr Gly Ala Ala Ala
    130                 135                 140

Glu Val Ala Thr Val Lys Ala Ser Pro Ala Glu Thr Ser Ala Asp Asn
145                 150                 155                 160

Ser Ser Ser Thr Thr Asn Thr Ser Gly Gly Ala Ile Val Glu Ala Thr
                165                 170                 175

Pro Arg Arg Thr Leu Glu Thr Phe Gly Gln Arg Thr Ser Ile Tyr Arg
            180                 185                 190

Gly Val Thr Arg His Arg Trp Thr Gly Arg Tyr Glu Ala His Leu Trp
        195                 200                 205

Asp Asn Ser Cys Arg Arg Glu Gly Gln Ser Arg Lys Gly Arg Gln Val
    210                 215                 220

Tyr Leu Gly Gly Tyr Asp Lys Glu Glu Lys Ala Ala Arg Ala Tyr Asp
225                 230                 235                 240

Leu Ala Ala Leu Lys Tyr Trp Gly Pro Ser Thr Thr Asn Phe Pro
                245                 250                 255

Ile Thr Asn Tyr Glu Lys Glu Val Glu Met Lys Asn Met Thr Arg
            260                 265                 270

Gln Glu Phe Val Ala Ser Ile Arg Arg Lys Ser Ser Gly Phe Ser Arg
        275                 280                 285

Gly Ala Ser Met Tyr Arg Gly Val Thr Arg His His Gln His Gly Arg
    290                 295                 300

Trp Gln Ala Arg Ile Gly Arg Val Ala Gly Asn Lys Asp Leu Tyr Leu
305                 310                 315                 320

Gly Thr Phe Ser Thr Glu Glu Ala Ala Glu Ala Tyr Asp Ile Ala
                325                 330                 335

Ala Ile Lys Phe Arg Gly Leu Asn Ala Val Thr Asn Phe Glu Ile Asn
            340                 345                 350
```

-continued

Arg Tyr Asp Val Lys Ala Ile Leu Glu Ser Asn Thr Leu Pro Ile Gly
            355                 360                 365

Gly Gly Ala Ala Lys Arg Leu Lys Glu Ala Gln Ala Leu Glu Ser Ser
370                 375                 380

Arg Lys Arg Glu Glu Met Ile Ala Leu Gly Ser Asn Phe His Gln Tyr
385                 390                 395                 400

Gly Ala Ala Ser Gly Ser Ser Val Ala Ser Ser Ser Arg Leu Gln
            405                 410                 415

Leu Gln Pro Tyr Pro Leu Ser Ile Gln Gln Pro Phe Glu His Leu His
            420                 425                 430

His His Gln Pro Leu Leu Thr Leu Gln Asn Asn Asn Asp Ile Ser Gln
            435                 440                 445

Tyr His Asp Ser Phe Ser Tyr Ile Gln Thr Gln Leu His Leu His Gln
            450                 455                 460

Gln Gln Thr Asn Asn Tyr Leu Gln Ser Ser His Thr Ser Gln Leu
465                 470                 475                 480

Tyr Asn Ala Tyr Leu Gln Ser Asn Pro Gly Leu Leu His Gly Phe Val
            485                 490                 495

Ser Asp Asn Asn Thr Ser Gly Phe Leu Gly Asn Asn Gly Ile Gly
            500                 505                 510

Ile Gly Ser Ser Thr Val Gly Ser Ser Ala Glu Glu Phe Pro
            515                 520                 525

Ala Val Lys Val Asp Tyr Asp Met Pro Pro Ser Gly Gly Ala Thr Gly
            530                 535                 540

Tyr Gly Gly Trp Asn Gly Glu Ser Ala Gln Gly Ser Asn Pro Gly
545                 550                 555                 560

Gly Val Phe Thr Met Trp Asn Glu
            565

<210> SEQ ID NO 76
<211> LENGTH: 474
<212> TYPE: PRT
<213> ORGANISM: Sorghum bicolor

<400> SEQUENCE: 76

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Ser Ala Ala Pro Leu Gly Asp Glu Gln Gly Thr Val Glu Glu
        35                  40                  45

Ser Pro Lys Met Val Glu Asp Phe Leu Gly Val Gly Gly Ala Gly
    50                  55                  60

Ala Pro Pro Ala Ala Ala Thr Ala Ala Glu Asp His Gln Leu Val Cys
65                  70                  75                  80

Gly Glu Leu Gly Ser Ile Thr Ala Gly Phe Leu Arg His Tyr Pro Ala
                85                  90                  95

Pro Gly Thr Thr Val Glu Asn Pro Gly Ala Val Thr Val Ala Ala Met
            100                 105                 110

Ser Thr Asp Val Ala Glu Ser Asp Gln Ala Arg Arg Pro Ala Glu Thr
        115                 120                 125

Phe Gly Gln Arg Thr Ser Ile Tyr Arg Gly Val Thr Arg His Arg Trp
    130                 135                 140

Thr Gly Arg Tyr Glu Ala His Leu Trp Asp Asn Ser Cys Arg Arg Glu

```
                145                 150                 155                 160
        Gly Gln Ser Arg Lys Gly Arg Gln Val Tyr Leu Gly Tyr Asp Lys
                        165                 170                 175

Glu Glu Lys Ala Ala Arg Ala Tyr Asp Leu Ala Ala Leu Lys Tyr Trp
                    180                 185                 190

Gly Ala Thr Thr Thr Asn Phe Pro Val Ser Asn Tyr Glu Lys Glu
                    195                 200                 205

Leu Glu Glu Met Lys Ser Met Thr Arg Gln Phe Ile Ala Ser Leu
            210                 215                 220

Arg Arg Lys Ser Ser Gly Phe Ser Arg Gly Ala Ser Ile Tyr Arg Gly
        225                 230                 235                 240

Val Thr Arg His His Gln His Gly Arg Trp Gln Ala Arg Ile Gly Arg
                        245                 250                 255

Val Ala Gly Asn Lys Asp Leu Tyr Leu Gly Thr Phe Ser Thr Gln Glu
                    260                 265                 270

Glu Ala Ala Glu Ala Tyr Asp Ile Ala Ala Ile Lys Phe Arg Gly Leu
                    275                 280                 285

Asn Ala Val Thr Asn Phe Asp Met Ser Arg Tyr Asp Val Asp Ser Ile
            290                 295                 300

Leu Asn Ser Asp Leu Pro Val Gly Gly Ala Ala Gly Arg Ala Ser
        305                 310                 315                 320

Lys Phe Pro Leu Asp Ser Leu Gln Pro Gly Ser Ala Ala Met Ile
                        325                 330                 335

Ala Gly Ala Ala Ser Gln Ala Met Pro Pro Ser Glu Lys Asp Tyr Trp
                    340                 345                 350

Ser Leu Leu Ala Leu His Tyr Gln Gln Gln Gln Gln Gln Gln Phe
                    355                 360                 365

Pro Ala Ser Ala Tyr Glu Ala Tyr Gly Ser Gly Val Asn Val Asp Phe
                    370                 375                 380

Thr Met Gly Thr Ser Ser His Ser Ser Ser Asn Thr Gly Ser Gly Val
        385                 390                 395                 400

Met Trp Gly Thr Thr Thr Gly Ala Met Gly Gln Gln Asp Ser Ser Ser
                        405                 410                 415

Ser Lys Gln Gly Asn Gly Tyr Ala Ser Asn Ile Pro Tyr Ala Ala Ala
                    420                 425                 430

Ala Ala Ala Met Val Ser Gly Ser Ala Gly Tyr Glu Gly Ser Thr Gly
                    435                 440                 445

Asn Asn Gly Thr Trp Val Thr Ser Ser Thr Thr Ser Thr Ala Pro
        450                 455                 460

Gln Tyr Tyr Asn Tyr Leu Phe Gly Met Glu
        465                 470

<210> SEQ ID NO 77
<211> LENGTH: 549
<212> TYPE: PRT
<213> ORGANISM: Oryza sativa

<400> SEQUENCE: 77

Met Asp Met Asn Ser Gly Trp Leu Gly Phe Ser Leu Ser Ser Ser
  1                5                  10                 15

Ala Arg Gly Tyr Gly Asp Gly Cys Gly Glu Gly Asn Gly Gly Asp
                20                  25                  30

Gly Asp Gly Ser Cys Ser Ser Pro Val Ala Ala Ser Pro Leu Val Ala
            35                  40                  45
```

```
Met Pro Leu His Ser Asp Gly Ser Val His Tyr Asp Ala Pro Asp Trp
     50                  55                  60

Arg His Ala Glu Ala Lys Asp Pro Lys Leu Glu Asp Phe Met Ser Val
 65                  70                  75                  80

Ser Tyr Ser Asn Lys Ser Ser Ser Asn Leu Tyr Gly Ser Ser Ser Ser
                 85                  90                  95

Ser Ser Cys Gly His Ala Asp Gln Ile Lys Tyr His His Val His Asp
            100                 105                 110

Val Gln Ala Phe Ser Thr Pro Tyr Phe Tyr Gly His Gly Gly Ser Gly
            115                 120                 125

Val Gly Ile Asp Ile Asn Met Asn Ala Pro Pro Ala Gly Cys Thr Gly
145 130                 135                 140

Val Leu Pro Asp His Arg Pro Pro Pro Gln Gln Asp His Ile Phe
145                 150                 155                 160

Leu Pro Pro His Gly Gln Tyr Phe Leu Gly Pro Pro Asn Pro Met Ala
                165                 170                 175

Pro Ala Pro Met Tyr Asn Ala Gly Gly Gly Gly Gly Val Val Asp
            180                 185                 190

Gly Ser Met Ser Ile Ser Gly Ile Lys Ser Trp Leu Arg Gln Ala Met
            195                 200                 205

Tyr Val Pro Glu Arg Ser Ala Ala Leu Ser Leu Ser Val Pro Ala
            210                 215                 220

Ala Pro Pro Ser Glu Ala Pro Leu Pro Pro Ala Ala Met Pro Val Val
225                 230                 235                 240

Arg Lys Pro Ala Gln Thr Phe Gly Gln Arg Thr Ser Gln Phe Arg Gly
                245                 250                 255

Val Thr Arg His Arg Trp Thr Gly Arg Tyr Glu Ala His Leu Trp Asp
            260                 265                 270

Asn Thr Cys Arg Lys Glu Gly Gln Thr Arg Lys Gly Arg Gln Val Tyr
            275                 280                 285

Leu Gly Gly Tyr Asp Lys Glu Glu Lys Ala Ala Arg Ala Tyr Asp Leu
            290                 295                 300

Ala Ala Leu Lys Tyr Trp Gly Pro Thr His Ile Asn Phe Pro Leu
305                 310                 315                 320

Ser Thr Tyr Glu Lys Glu Leu Glu Glu Met Lys His Met Thr Arg Gln
                325                 330                 335

Glu Phe Ile Ala His Leu Arg Arg Asn Ser Ser Gly Phe Ser Arg Gly
            340                 345                 350

Ala Ser Met Tyr Arg Gly Val Thr Arg His His Gln His Gly Arg Trp
            355                 360                 365

Gln Ala Arg Ile Gly Arg Val Ala Gly Asn Lys Asp Leu Tyr Leu Gly
            370                 375                 380

Thr Phe Ser Thr Gln Glu Glu Ala Ala Glu Ala Tyr Asp Ile Ala Ala
385                 390                 395                 400

Ile Lys Phe Arg Gly Leu Asn Ala Val Thr Asn Phe Asp Ile Ser Lys
                405                 410                 415

Tyr Asp Val Lys Arg Ile Cys Ser Ser Thr His Leu Ile Gly Gly Asp
            420                 425                 430

Leu Ala Cys Arg Arg Ser Pro Thr Arg Met Leu Pro Pro Asp Ala Pro
            435                 440                 445

Ala Gly Ala Ala Gly Val Asp Val Val Ala Pro Gly Asp His Gln
450                 455                 460

Gln Ile Ser Ala Gly Gly Gly Gly Ala Ser Asp Asn Ser Asp Thr Ala
```

```
                465                 470                 475                 480
        Ser Asp Gly His Arg Gly Ala His Leu Leu His Gly Leu Gln Tyr Ala
                        485                 490                 495

His Ala Met Lys Phe Glu Ala Gly Ser Ser Gly Gly Gly Gly
                    500                 505                 510

Asp Gly Ala Thr Thr Asn Trp Met Ala Ala Ala Ala Ala Arg
                    515                 520                 525

Pro Val Ala Gly Ile Pro Thr Thr Val His His Gln Leu Pro Val Phe
                    530                 535                 540

Ala Leu Trp Asn Asp
        545

<210> SEQ ID NO 78
<211> LENGTH: 553
<212> TYPE: PRT
<213> ORGANISM: Glycine max

<400> SEQUENCE: 78

Met Asn Asn Asn Trp Leu Ser Phe Pro Leu Ser Pro Thr His Ser Ser
 1               5                  10                  15

Leu Pro Ala His Asp Leu Gln Ala Thr Gln Tyr His Gln Phe Ser Leu
            20                  25                  30

Gly Leu Val Asn Glu Asn Met Asp Asn Pro Phe Gln Asn His Asp Trp
        35                  40                  45

Asn Leu Ile Asn Thr His Ser Ser Asn Glu Ile Pro Lys Val Ala Asp
     50                  55                  60

Phe Leu Gly Val Ser Lys Ser Glu Asn Gln Ser Asp Leu Ala Ala Leu
 65                  70                  75                  80

Asn Glu Ile His Ser Asn Asp Ser Asp Tyr Leu Phe Thr Asn Asn Ser
                85                  90                  95

Leu Val Pro Met Gln Asn Pro Val Leu Asp Thr Pro Ser Asn Glu Tyr
            100                 105                 110

Gln Glu Asn Ala Asn Ser Asn Leu Gln Ser Leu Thr Leu Ser Met Gly
        115                 120                 125

Ser Gly Lys Asp Ser Thr Cys Glu Thr Ser Gly Glu Asn Ser Thr Asn
    130                 135                 140

Thr Thr Val Glu Val Ala Pro Arg Arg Thr Leu Asp Thr Phe Gly Gln
145                 150                 155                 160

Arg Thr Ser Ile Tyr Arg Gly Val Thr Arg His Arg Trp Thr Gly Arg
                165                 170                 175

Tyr Glu Ala His Leu Trp Asp Asn Ser Cys Arg Arg Glu Gly Gln Ser
            180                 185                 190

Arg Lys Gly Arg Gln Val Tyr Leu Gly Gly Tyr Asp Lys Glu Glu Lys
        195                 200                 205

Ala Ala Arg Ala Tyr Asp Leu Ala Ala Leu Lys Tyr Trp Gly Thr Ser
    210                 215                 220

Thr Thr Thr Asn Phe Pro Ile Ser Asn Tyr Glu Lys Glu Leu Asp Glu
225                 230                 235                 240

Met Lys His Met Thr Arg Gln Glu Phe Val Ala Ala Ile Arg Arg Lys
                245                 250                 255

Ser Ser Gly Phe Ser Arg Gly Ala Ser Met Tyr Arg Gly Val Thr Arg
            260                 265                 270

His His Gln His Gly Arg Trp Gln Ala Arg Ile Gly Arg Val Ala Gly
        275                 280                 285
```

-continued

```
Asn Lys Asp Leu Tyr Leu Gly Thr Phe Ser Thr Glu Glu Ala Ala
    290                 295                 300

Glu Ala Tyr Asp Ile Ala Ala Ile Lys Phe Arg Gly Leu Asn Ala Val
305                 310                 315                 320

Thr Asn Phe Asp Met Ser Arg Tyr Asp Val Lys Ala Ile Leu Glu Ser
                325                 330                 335

Asn Thr Leu Pro Ile Gly Gly Ala Ala Lys Arg Leu Lys Glu Ala
            340                 345                 350

Gln Ala Leu Glu Ser Ser Arg Lys Arg Glu Glu Met Ile Ala Leu Gly
                355                 360                 365

Ser Ser Ser Thr Phe Gln Tyr Gly Thr Ser Ala Ser Ser Ser Arg Leu
370                 375                 380

His Ala Tyr Pro Leu Met Gln His His Gln Phe Glu Gln Pro Gln
385                 390                 395                 400

Pro Leu Leu Thr Leu Gln Asn His Asp Ile Ser Ser His Phe Ser
                405                 410                 415

His Gln Gln Asp Pro Leu His His Gln Gly Tyr Ile Thr Gln Leu
                420                 425                 430

Gln Leu His Gln Gln Ser Gly Ala Ser Ser Tyr Ser Phe Gln Asn Asn
                435                 440                 445

Ala Gln Phe Tyr Asn Gly Tyr Leu Gln Asn His Pro Ala Leu Leu Gln
450                 455                 460

Gly Met Met Asn Met Gly Ser Ser Ser Ser Ser Ser Val Leu Glu
465                 470                 475                 480

Asn Asn Asn Ser Asn Asn Asn Asn Val Gly Gly Phe Val Gly
                485                 490                 495

Ser Gly Phe Gly Met Ala Ser Asn Ala Thr Ala Gly Asn Thr Val Gly
                500                 505                 510

Thr Ala Glu Glu Leu Gly Leu Val Lys Val Asp Tyr Asp Met Pro Ala
            515                 520                 525

Gly Gly Tyr Gly Gly Trp Ser Ala Ala Asp Ser Met Gln Thr Ser Asn
530                 535                 540

Gly Gly Val Phe Thr Met Trp Asn Asp
545                 550

<210> SEQ ID NO 79
<211> LENGTH: 509
<212> TYPE: PRT
<213> ORGANISM: Medicago truncatula

<400> SEQUENCE: 79

Met Asp Lys Ser Ser Ser Ser Pro Pro Thr Asn Thr Asn Asn Thr Ser
  1               5                  10                  15

Leu Ala Phe Ser Leu Ser Asn Asn Asn Phe Pro Asn Pro Ser His Ser
                20                  25                  30

Ser Ser Ser His Leu Ser Leu Phe His Ser Phe Thr Pro Tyr Pro Ser
            35                  40                  45

Ser Ile Ile Pro Pro Ser Leu Thr Leu Thr Gly Ser Asn Asn Pro Val
    50                  55                  60

Glu Ala Ser Pro Glu Ala Thr Asp Gly Thr Thr Asn Leu Ser Ile
65                  70                  75                  80

Phe Thr Gly Gly His Lys Phe Glu Asp Phe Leu Gly Ser Ser Val Ala
                85                  90                  95

Pro Thr Arg Thr Ala Ala Ala Thr Cys Ala Pro Thr Gln Leu Gln Gln
            100                 105                 110
```

```
Phe Ser Thr Asp Asn Asp Val Tyr Asn Ser Glu Leu Lys Lys Thr Ile
            115                 120                 125

Ala Ala Cys Phe Pro Gly Gly Tyr Pro Thr Glu Pro Asn Ser Glu Pro
130                 135                 140

Gln Lys Pro Ser Pro Lys Lys Thr Val Asp Thr Phe Gly Gln Arg Thr
145                 150                 155                 160

Ser Ile Tyr Arg Gly Val Thr Arg His Arg Trp Thr Gly Arg Tyr Glu
                165                 170                 175

Ala His Leu Trp Asp Asn Ser Cys Arg Arg Glu Gly Gln Ser Arg Lys
            180                 185                 190

Gly Arg Gln Gly Gly Tyr Asp Lys Glu Glu Lys Ala Ala Arg Ala Tyr
        195                 200                 205

Asp Leu Ala Ala Leu Lys Tyr Trp Gly Pro Thr Thr Thr Thr Asn Phe
    210                 215                 220

Pro Ile Ser Asn Tyr Glu Lys Glu Ile Asp Asp Met Lys Asn Met Thr
225                 230                 235                 240

Arg Gln Glu Phe Val Ala Ser Leu Arg Arg Lys Ser Ser Gly Phe Ser
                245                 250                 255

Arg Gly Ala Ser Ile Tyr Arg Gly Val Thr Arg His His Gln His Gly
            260                 265                 270

Arg Trp Gln Ala Arg Ile Gly Arg Val Ala Gly Asn Lys Asp Leu Tyr
        275                 280                 285

Leu Gly Thr Phe Ser Thr Gln Glu Glu Ala Ala Glu Ala Tyr Asp Ile
    290                 295                 300

Ala Ala Ile Lys Phe Arg Gly Leu Asn Ala Val Thr Asn Phe Asp Met
305                 310                 315                 320

Ser Arg Tyr Asp Val Lys Ser Ile Ala Asn Cys Ser Leu Pro Ile Gly
                325                 330                 335

Gly Leu Ser Asn Lys Asn Asn Lys Asn Ser Thr Asp Cys Val Ser Glu
            340                 345                 350

Thr Lys Ile Asn Glu Pro Ile Gln Ser Asp Glu Ile Asp His Pro Ser
        355                 360                 365

Ser Thr Ser Ser Ala Thr Thr Leu Ser Phe Ala Leu Pro Ile Lys Gln
    370                 375                 380

Asp Pro Ser Thr Asp Tyr Trp Ser Asn Ile Leu Gly Phe His Asn Asn
385                 390                 395                 400

Pro Ser Ala Val Thr Thr Thr Ile Pro Phe Asn Met Asp Phe Ser
                405                 410                 415

Ala His Val Pro Ser Asn Thr Asn Ser Asp Asn Pro His Asn Ala Ala
            420                 425                 430

Phe Phe Ser Gly Ser Gly Ile Phe Val Gln Gln Asn Met Asn Gly
        435                 440                 445

Ser Ser Gly Ser Asn Ser Ser Ser Ser Ser Ala Ser Thr Ser Ser
    450                 455                 460

Ile Pro Phe Ala Thr Pro Ile Phe Ser Leu Asn Ser Asn Ser Ser Ser
465                 470                 475                 480

Tyr Gly Asn Gly Asn Asn Trp Ile Gly His Thr Phe Gln Thr His Ala
                485                 490                 495

Lys Pro Ser Leu Phe Gln Thr Pro Ile Phe Gly Met Glu
            500                 505

<210> SEQ ID NO 80
<211> LENGTH: 492
```

```
<212> TYPE: PRT
<213> ORGANISM: Zea mays

<400> SEQUENCE: 80

Met Asp Thr Ser His His Tyr His Pro Trp Leu Asn Phe Ser Leu Ala
1               5                   10                  15

His His Cys Asp Leu Glu Glu Glu Arg Gly Ala Ala Ala Glu Leu
            20                  25                  30

Ala Ala Ile Ala Gly Ala Ala Pro Pro Lys Leu Glu Asp Phe Leu
        35                  40                  45

Gly Gly Gly Val Ala Thr Gly Gly Pro Glu Ala Val Ala Pro Ala Glu
    50                  55                  60

Met Tyr Asp Ser Asp Leu Lys Phe Ile Ala Ala Ala Gly Phe Leu Gly
65                  70                  75                  80

Gly Ser Ala Ala Ala Ala Thr Ser Pro Leu Ser Ser Leu Asp Gln
                85                  90                  95

Ala Gly Ser Lys Leu Ala Leu Pro Ala Ala Ala Ala Pro Ala Pro
            100                 105                 110

Glu Gln Arg Lys Ala Val Asp Ser Phe Gly Gln Arg Thr Ser Ile Tyr
            115                 120                 125

Arg Gly Val Thr Arg His Arg Trp Thr Gly Arg Tyr Glu Ala His Leu
    130                 135                 140

Trp Asp Asn Ser Cys Arg Arg Glu Gly Gln Ser Arg Lys Gly Arg Gln
145                 150                 155                 160

Val Tyr Leu Gly Gly Tyr Asp Lys Glu Glu Lys Ala Ala Arg Ala Tyr
                165                 170                 175

Asp Leu Ala Ala Leu Lys Tyr Trp Gly Ser Ser Thr Thr Thr Asn Phe
            180                 185                 190

Pro Val Ala Glu Tyr Glu Lys Glu Val Glu Glu Met Lys Asn Met Thr
            195                 200                 205

Arg Gln Glu Phe Val Ala Ser Leu Arg Arg Lys Ser Ser Gly Phe Ser
    210                 215                 220

Arg Gly Ala Ser Ile Tyr Arg Gly Val Thr Arg His His Gln His Gly
225                 230                 235                 240

Arg Trp Gln Ala Arg Ile Gly Arg Val Ala Gly Asn Lys Asp Leu Tyr
                245                 250                 255

Leu Gly Thr Phe Ser Thr Glu Glu Glu Ala Ala Glu Ala Tyr Asp Ile
            260                 265                 270

Ala Ala Ile Lys Phe Arg Gly Leu Asn Ala Val Thr Asn Phe Glu Ile
        275                 280                 285

Ser Arg Tyr Asn Val Glu Thr Ile Met Ser Ser Asn Leu Pro Val Ala
290                 295                 300

Ser Met Ser Ser Ser Ala Ala Ala Ala Gly Gly Arg Ser Ser Lys
305                 310                 315                 320

Ala Leu Glu Ser Pro Pro Ser Gly Ser Leu Asp Gly Gly Gly Met
                325                 330                 335

Pro Val Val Glu Ala Ser Thr Ala Pro Pro Leu Phe Ile Pro Val Lys
            340                 345                 350

Tyr Asp Gln Gln Gln Glu Tyr Leu Ser Met Leu Ala Leu Gln Gln
            355                 360                 365

His His Gln Gln Gln Gln Ala Gly Asn Leu Leu Gln Gly Pro Leu Val
    370                 375                 380

Gly Phe Gly Gly Leu Tyr Ser Ser Gly Val Asn Leu Asp Phe Ala Asn
385                 390                 395                 400
```

```
Ser His Gly Thr Ala Ala Pro Ser Ser Met Ala His His Cys Tyr Ala
            405                 410                 415

Asn Gly Thr Ala Ser Ala Ser His Glu His Gln His Gln Met Gln Gln
        420                 425                 430

Gly Gly Glu Asn Glu Thr Gln Pro Gln Pro Gln Ser Ser Ser Ser
        435                 440                 445

Cys Ser Ser Leu Pro Phe Ala Thr Pro Val Ala Phe Asn Gly Ser Tyr
450                 455                 460

Glu Ser Ser Ile Thr Ala Ala Gly Pro Phe Gly Tyr Ser Tyr Pro Asn
465                 470                 475                 480

Val Ala Ala Phe Gln Thr Pro Ile Tyr Gly Met Glu
                485                 490

<210> SEQ ID NO 81
<211> LENGTH: 469
<212> TYPE: PRT
<213> ORGANISM: Oryza sativa

<400> SEQUENCE: 81

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Leu Ser Thr
                20                  25                  30

Thr Ser Ala Pro Pro Leu Gly Glu Glu Gly Pro Ala Glu Gly Ala Pro
            35                  40                  45

Lys Met Glu Asp Phe Leu Gly Gly Leu Gly Gly Gly Gly Gly Ala Val
    50                  55                  60

Ala Ala Ala Pro Ala Ala Ala Pro Glu Asp Gln Leu Ser Cys Gly Glu
65                  70                  75                  80

Leu Gly Ser Ile Ala Ala Gly Phe Leu Arg Arg Tyr Pro Ala Pro Glu
                85                  90                  95

Asn Ala Gly Gly Val Thr Ile Ala Met Ala Thr Asp Ala Ala Ala Glu
            100                 105                 110

Leu Ala Asp Pro Ala Arg Arg Thr Ala Glu Thr Phe Gly Gln Arg Thr
        115                 120                 125

Ser Ile Tyr Arg Gly Val Thr Arg His Arg Trp Thr Gly Arg Tyr Glu
    130                 135                 140

Ala His Leu Trp Asp Asn Ser Cys Arg Arg Glu Gly Gln Ser Arg Lys
145                 150                 155                 160

Gly Arg Gln Val Tyr Leu Gly Gly Tyr Asp Lys Glu Glu Lys Ala Ala
                165                 170                 175

Arg Ala Tyr Asp Leu Ala Ala Leu Lys Tyr Trp Gly Pro Thr Thr Thr
            180                 185                 190

Thr Asn Phe Pro Val Ala Asn Tyr Glu Thr Glu Leu Glu Glu Met Lys
        195                 200                 205

Ser Met Thr Arg Gln Glu Phe Ile Ala Ser Leu Arg Arg Lys Ser Ser
    210                 215                 220

Gly Phe Ser Arg Gly Ala Ser Ile Tyr Arg Gly Val Thr Arg His His
225                 230                 235                 240

Gln His Gly Arg Trp Gln Ala Arg Ile Gly Arg Val Ala Gly Asn Lys
                245                 250                 255

Asp Leu Tyr Leu Gly Thr Phe Ser Thr Gln Glu Glu Ala Ala Glu Ala
            260                 265                 270

Tyr Asp Ile Ala Ala Ile Lys Phe Arg Gly Leu Asn Ala Val Thr Asn
```

```
                    275                 280                 285

Phe Asp Met Ser Arg Tyr Asp Val Asp Ser Ile Leu Asn Ser Asp Leu
290                 295                 300

Pro Val Gly Gly Gly Ala Ala Thr Arg Ala Ser Lys Phe Pro Ser Asp
305                 310                 315                 320

Pro Ser Leu Pro Leu Pro Ser Pro Ala Met Pro Pro Ser Glu Lys Asp
                    325                 330                 335

Tyr Trp Ser Leu Leu Ala Leu His Tyr His His Gln Gln Gln Gln
                340                 345                 350

Gln Gln Gln Gln Phe Pro Ala Ser Ala Phe Asp Thr Tyr Gly Cys Ser
            355                 360                 365

Ser Gly Val Asn Val Asp Phe Thr Met Gly Thr Ser Ser His Ser Gly
370                 375                 380

Ser Asn Ser Asn Ser Ser Ser Ser Ala Ile Trp Gly Thr Ala Ala
385                 390                 395                 400

Gly Ala Ala Met Gly Arg Gln Gln Asn Gly Ser Ser Asn Lys Gln
                405                 410                 415

Ser Asn Ser Tyr Ser Gly Asn Asn Ile Pro Tyr Ala Ala Ala Ala
                420                 425                 430

Met Thr Ser Gly Ser Ala Leu Tyr Gly Gly Ser Thr Gly Ser Asn Gly
            435                 440                 445

Thr Trp Val Ala Ser Asn Thr Ser Thr Ala Pro His Phe Tyr Asn Tyr
450                 455                 460

Leu Phe Gly Met Glu
465

<210> SEQ ID NO 82
<211> LENGTH: 562
<212> TYPE: PRT
<213> ORGANISM: Glycine max

<400> SEQUENCE: 82

Met Asn Asn Asn Trp Leu Ser Phe Pro Leu Ser Pro Thr His Ser Ser
1               5                   10                  15

Leu Pro Ala His Asp Leu Gln Ala Thr Gln Tyr His Gln Phe Ser Leu
                20                  25                  30

Gly Leu Val Asn Glu Asn Met Glu Asn Pro Phe Gln Asn His Asp Trp
            35                  40                  45

Ser Leu Ile Asn Thr His Ser Ser Glu Val Pro Lys Val Ala Asp
50                  55                  60

Phe Leu Gly Val Ser Lys Ser Glu Asn Glu Ser Asp Leu Ala Ala Ser
65                  70                  75                  80

Leu Asn Glu Ile Gln Ser Asn Asp Ser Asp Tyr Leu Phe Thr Asn Asn
                85                  90                  95

Ser Leu Val Pro Met Gln Asn Pro Ala Val Asp Thr Pro Ser Asn Glu
            100                 105                 110

Tyr Gln Glu Asn Ala Asn Ser Ser Leu Gln Ser Leu Thr Leu Ser Met
        115                 120                 125

Gly Ser Gly Lys Asp Ser Thr Cys Glu Thr Ser Gly Asp Asn Ser Thr
130                 135                 140

Asn Thr Thr Thr Thr Thr Val Glu Ala Ala Pro Arg Arg Thr Leu
145                 150                 155                 160

Asp Thr Phe Gly Gln Arg Thr Ser Ile Tyr Arg Gly Val Thr Arg His
                165                 170                 175
```

-continued

Arg Trp Thr Gly Arg Tyr Glu Ala His Leu Trp Asp Asn Ser Cys Arg
            180                 185                 190

Arg Glu Gly Gln Ser Arg Lys Gly Arg Gln Val Tyr Leu Gly Gly Tyr
        195                 200                 205

Asp Lys Glu Glu Lys Ala Ala Arg Ser Tyr Asp Leu Ala Ala Leu Lys
        210                 215                 220

Tyr Trp Gly Thr Ser Thr Thr Asn Phe Pro Ile Ser Asn Tyr Glu
225                 230                 235                 240

Lys Glu Leu Asp Glu Met Lys His Met Thr Arg Gln Glu Phe Val Ala
                245                 250                 255

Ala Ile Arg Arg Lys Ser Ser Gly Phe Ser Arg Gly Ala Ser Met Tyr
            260                 265                 270

Arg Gly Val Thr Arg His His Gln His Gly Arg Trp Gln Ala Arg Ile
            275                 280                 285

Gly Arg Val Ala Gly Asn Lys Asp Leu Tyr Leu Gly Thr Phe Ser Thr
        290                 295                 300

Glu Glu Glu Ala Ala Glu Ala Tyr Asp Ile Ala Ala Ile Lys Phe Arg
305                 310                 315                 320

Gly Leu Asn Ala Val Thr Asn Phe Asp Met Ser Arg Tyr Asp Val Lys
            325                 330                 335

Ala Ile Leu Glu Ser Asn Thr Leu Pro Ile Gly Gly Ala Ala Lys
            340                 345                 350

Arg Leu Lys Glu Ala Gln Ala Leu Glu Ser Ser Arg Lys Arg Glu Glu
        355                 360                 365

Met Ile Ala Leu Gly Ser Ser Thr Phe Gln Tyr Gly Thr Thr Ser Ser
370                 375                 380

Asn Ser Arg Leu His Ala Tyr Pro Leu Met Gln His His Gln Phe
385                 390                 395                 400

Glu Gln Pro Gln Pro Leu Leu Thr Leu Gln Asn His Asp Ile Ser Ser
                405                 410                 415

His Phe Ser His Gln Asp Pro Leu His Gly Tyr Ile Gln Thr
            420                 425                 430

Gln Leu Gln Leu His Gln Gln Ser Gly Gly Ser Ser Ser Tyr Ser
        435                 440                 445

Phe Gln Asn Asn Asn Ile Asn Asn Ala Gln Phe Tyr Asn Gly Tyr Asn
450                 455                 460

Leu Gln Asn His Pro Ala Leu Leu Gln Gly Met Ile Asn Met Gly Ser
465                 470                 475                 480

Ser Ser Ser Ser Val Leu Glu Asn Asn Ser Asn Asn Asn
                485                 490                 495

Val Gly Gly Phe Val Gly Ser Gly Phe Gly Met Ala Ser Asn Ala Thr
            500                 505                 510

Ser Gly Asn Thr Val Gly Thr Ala Glu Glu Leu Gly Leu Val Lys Val
        515                 520                 525

Asp Tyr Asp Met Pro Thr Gly Tyr Gly Gly Trp Ser Ala Ala
            530                 535                 540

Ala Ala Glu Ser Met Gln Thr Ser Asn Ser Gly Val Phe Thr Met Trp
545                 550                 555                 560

Asn Asp

<210> SEQ ID NO 83
<211> LENGTH: 574
<212> TYPE: PRT
<213> ORGANISM: Arabidopsis thaliana

<400> SEQUENCE: 83

```
Met Asn Ser Asn Asn Trp Leu Gly Phe Pro Leu Ser Pro Asn Asn Ser
1               5                   10                  15

Ser Leu Pro Pro His Glu Tyr Asn Leu Gly Leu Val Ser Asp His Met
            20                  25                  30

Asp Asn Pro Phe Gln Thr Gln Glu Trp Asn Met Ile Asn Pro His Gly
        35                  40                  45

Gly Gly Gly Asp Glu Gly Gly Glu Val Pro Lys Val Ala Asp Phe Leu
    50                  55                  60

Gly Val Ser Lys Pro Asp Glu Asn Gln Ser Asn His Leu Val Ala Tyr
65                  70                  75                  80

Asn Asp Ser Asp Tyr Tyr Phe His Thr Asn Ser Leu Met Pro Ser Val
                85                  90                  95

Gln Ser Asn Asp Val Val Ala Ala Cys Asp Ser Asn Thr Pro Asn
            100                 105                 110     Asn

Asn Ser Ser Tyr His Glu Leu Gln Glu Ser Ala His Asn Leu Gln Ser
        115                 120                 125

Leu Thr Leu Ser Met Gly Thr Thr Ala Gly Asn Asn Val Val Asp Lys
    130                 135                 140

Ala Ser Pro Ser Glu Thr Thr Gly Asp Asn Ala Ser Gly Gly Ala Leu
145                 150                 155                 160

Ala Val Val Glu Thr Ala Thr Pro Arg Arg Ala Leu Asp Thr Phe Gly
                165                 170                 175

Gln Arg Thr Ser Ile Tyr Arg Gly Val Thr Arg His Arg Trp Thr Gly
            180                 185                 190

Arg Tyr Glu Ala His Leu Trp Asp Asn Ser Cys Arg Arg Glu Gly Gln
        195                 200                 205

Ser Arg Lys Gly Arg Gln Val Tyr Leu Gly Gly Tyr Asp Lys Glu Asp
    210                 215                 220

Lys Ala Ala Arg Ser Tyr Asp Leu Ala Ala Leu Lys Tyr Trp Gly Pro
225                 230                 235                 240

Ser Thr Thr Thr Asn Phe Pro Ile Thr Asn Tyr Glu Lys Glu Val Glu
                245                 250                 255

Glu Met Lys His Met Thr Arg Gln Glu Phe Val Ala Ala Ile Arg Arg
            260                 265                 270

Lys Ser Ser Gly Phe Ser Arg Gly Ala Ser Met Tyr Arg Gly Val Thr
        275                 280                 285

Arg His His Gln His Gly Arg Trp Gln Ala Arg Ile Gly Arg Val Ala
    290                 295                 300

Gly Asn Lys Asp Leu Tyr Leu Gly Thr Phe Ser Thr Glu Glu Glu Ala
305                 310                 315                 320

Ala Glu Ala Tyr Asp Ile Ala Ala Ile Lys Phe Arg Gly Leu Asn Ala
                325                 330                 335

Val Thr Asn Phe Glu Ile Asn Arg Tyr Asp Val Lys Ala Ile Leu Glu
            340                 345                 350

Ser Ser Thr Leu Pro Ile Gly Gly Ala Ala Lys Arg Leu Lys Glu
        355                 360                 365

Ala Gln Ala Leu Glu Ser Ser Arg Lys Arg Glu Ala Glu Met Ile Ala
    370                 375                 380

Leu Gly Ser Ser Phe Gln Tyr Gly Gly Ser Ser Thr Gly Ser Gly
385                 390                 395                 400

Ser Thr Ser Ser Arg Leu Gln Leu Gln Pro Tyr Pro Leu Ser Ile Gln
```

```
                        405                 410                 415
Gln Pro Leu Glu Pro Phe Leu Ser Leu Gln Asn Asn Asp Ile Ser His
                420                 425                 430

Tyr Asn Asn Asn Ala His Asp Ser Ser Phe Asn His His Ser
            435                 440                 445

Tyr Ile Gln Thr Gln Leu His Leu His Gln Gln Thr Asn Asn Tyr Leu
        450                 455                 460

Gln Gln Gln Ser Ser Gln Asn Ser Gln Gln Leu Tyr Asn Ala Tyr Leu
465                 470                 475                 480

His Ser Asn Pro Ala Leu Leu His Gly Leu Val Ser Thr Ser Ile Val
                485                 490                 495

Asp Asn Asn Asn Asn Gly Gly Ser Ser Gly Ser Tyr Asn Thr Ala
            500                 505                 510

Ala Phe Leu Gly Asn His Gly Ile Gly Ile Gly Ser Ser Ser Thr Val
        515                 520                 525

Gly Ser Thr Glu Glu Phe Pro Thr Val Lys Thr Asp Tyr Asp Met Pro
530                 535                 540

Ser Ser Asp Gly Thr Gly Gly Tyr Ser Gly Trp Thr Ser Glu Ser Val
545                 550                 555                 560

Gln Gly Ser Asn Pro Gly Gly Val Phe Thr Met Trp Asn Glu
                565                 570

<210> SEQ ID NO 84
<211> LENGTH: 543
<212> TYPE: PRT
<213> ORGANISM: Medicago truncatula

<400> SEQUENCE: 84

Met Asn Asn Asn Trp Leu Ser Phe Pro Leu Ser Pro Ser His Ser Ser
1               5                   10                  15

Leu Pro Ser Asn Asp Leu Gln Ala Thr Gln Tyr His His Phe Pro Leu
            20                  25                  30

Gly Leu Val Asn Asp Asn Met Glu Asn Pro Phe Gln Asn His Asp Trp
        35                  40                  45

Asn Leu Met Asn Thr His Asn Ser Asn Glu Val Pro Lys Val Ala Asp
    50                  55                  60

Phe Leu Gly Val Cys Lys Ser Glu Asn His Ser Asp Leu Ala Thr Pro
65                  70                  75                  80

Asn Glu Ile Gln Ser Asn Asp Ser Asp Tyr Leu Phe Thr Asn Asn Asn
                85                  90                  95

Thr Leu Met Pro Met Gln Asn Gln Met Val Thr Thr Cys Thr Asn Glu
            100                 105                 110

Tyr Gln Glu Lys Ala Ser Asn Ser Asn Leu Gln Ser Leu Thr Leu Ser
        115                 120                 125

Met Gly Ser Gly Lys Asp Ser Thr Cys Glu Thr Ser Gly Glu Asn Ser
130                 135                 140

Thr Asn Thr Val Glu Val Ala Val Pro Lys Arg Thr Ser Glu Thr Phe
145                 150                 155                 160

Gly Gln Arg Thr Ser Ile Tyr Arg Gly Val Thr Lys His Arg Trp Thr
                165                 170                 175

Gly Arg Tyr Glu Ala His Leu Trp Asp Asn Ser Cys Arg Arg Glu Gly
            180                 185                 190

Gln Ser Arg Lys Gly Arg Gln Gly Gly Tyr Asp Lys Glu Glu Lys Ala
        195                 200                 205
```

Ala Arg Ser Tyr Asp Leu Ala Ala Leu Lys Tyr Trp Gly Thr Ser Thr
    210                 215                 220

Thr Thr Asn Phe Pro Val Ser Asn Tyr Glu Lys Glu Ile Asp Glu Met
225                 230                 235                 240

Lys His Met Thr Arg Gln Glu Phe Val Ala Ser Ile Arg Arg Lys Ser
                245                 250                 255

Ser Gly Phe Ser Arg Gly Ala Ser Met Tyr Arg Gly Val Thr Arg His
            260                 265                 270

His Gln His Gly Arg Trp Gln Ala Arg Ile Gly Arg Val Ala Gly Asn
        275                 280                 285

Lys Asp Leu Tyr Leu Gly Thr Phe Ser Thr Glu Glu Ala Ala Glu
290                 295                 300

Ala Tyr Asp Ile Ala Ala Ile Lys Phe Arg Gly Leu Asn Ala Val Thr
305                 310                 315                 320

Asn Phe Asp Met Thr Arg Tyr Asp Val Lys Ala Ile Leu Glu Ser Asn
                325                 330                 335

Thr Leu Pro Ile Gly Gly Ala Ala Lys Arg Leu Lys Glu Ala Gln
            340                 345                 350

Ala Leu Glu Thr Ser Arg Lys Arg Glu Glu Met Leu Ala Leu Asn Ser
        355                 360                 365

Ser Ser Phe Gln Tyr Gly Thr Ser Ser Ser Asn Thr Arg Leu Gln
370                 375                 380

Pro Tyr Pro Leu Met Gln Tyr His His Gln Phe Glu Gln Pro Gln Pro
385                 390                 395                 400

Leu Leu Thr Leu Gln Asn Asn His Glu Ser Leu Asn Ser Gln Gln Phe
                405                 410                 415

Ser Gln His Gln Gly Gly Gly Tyr Phe Gln Thr Gln Leu Glu Leu Cys
            420                 425                 430

Gln Gln Gln Asn Gln Gln Pro Ser Gln Asn Ser Asn Ile Gly Ser Phe
        435                 440                 445

Tyr Asn Gly Tyr Tyr Gln Asn His Pro Gly Leu Phe Gln Met Asn Asn
450                 455                 460

Ile Gly Ser Ser Ser Ser Ser Val Met Gly Asn Asn Gly Gly
465                 470                 475                 480

Ser Ser Gly Ile Tyr Ser Asn Ser Gly Gly Leu Ile Ser Asn Asn Ala
            485                 490                 495

Val Glu Glu Phe Val Pro Val Lys Val Asp Tyr Asp Met Gln Gly Asp
        500                 505                 510

Gly Ser Gly Phe Gly Gly Trp Ser Ala Ala Gly Glu Asn Met Gln Thr
    515                 520                 525

Ala Asp Leu Phe Thr Met Trp Asn Asp Tyr Glu Thr Arg Glu Asn
530                 535                 540

<210> SEQ ID NO 85
<211> LENGTH: 543
<212> TYPE: PRT
<213> ORGANISM: Zea mays

<400> SEQUENCE: 85

Met Asp Met Asn Asn Gly Trp Leu Gly Phe Ser Leu Ser Pro Ser Ala
  1               5                  10                  15

Ala Ser Arg Gly Gly Tyr Gly Tyr Gly Asp Gly Gly Gly Ala Ser
             20                  25                  30

Ala Ser Ala Cys Gly Asp Gly Glu Gly Ser Cys Pro Ser Pro Ala Ala
         35                  40                  45

```
Ala Ala Ser Pro Leu Pro Leu Val Ala Met Pro Leu Asp Asp Ser Leu
         50                  55                  60

His Tyr Ser Ser Ala Pro Asp Trp Arg His Gly Ala Ala Glu Ala Lys
 65                  70                  75                  80

Gly Pro Lys Leu Glu Asp Phe Met Ser Ile Thr Cys Ser Asn Lys Ser
                 85                  90                  95

Ser Gly Arg Ser Leu Tyr Asp Ser Cys Gly His His Asp Asp Glu Gln
            100                 105                 110

Ala Ser Lys Tyr His Glu Val His Gly Ile His Pro Leu Ser Cys Gly
        115                 120                 125

Ser Tyr Tyr His Gly Cys Ile Ser Ser Gly Gly Gly Gly Gly Gly Gly
    130                 135                 140

Ile Gly Leu Gly Ile Asn Met Asn Ala Pro Pro Cys Thr Gly Gly Phe
145                 150                 155                 160

Pro Asp His Gln His His Gln Phe Val Pro Ser Ser His His Gly Gln
                165                 170                 175

Tyr Phe Leu Gly Ala Pro Ala Ala Ser Ala Gly Pro Pro Ala Gly Ala
            180                 185                 190

Ala Met Pro Met Tyr Asn Ala Gly Gly Gly Ser Val Val Gly Gly Ser
        195                 200                 205

Met Ser Ile Ser Gly Ile Lys Ser Trp Leu Arg Glu Ala Met Tyr Val
    210                 215                 220

Pro Pro Glu Arg Pro Ala Ala Ala Leu Ser Leu Ala Val Thr Asp
225                 230                 235                 240

Asp Val Pro Pro Ala Glu Pro Pro Gln Leu Leu Pro Ala Pro Leu Pro
                245                 250                 255

Val His Arg Lys Pro Ala Gln Thr Phe Gly Gln Arg Thr Ser Gln Phe
            260                 265                 270

Arg Gly Val Thr Arg His Arg Trp Thr Gly Arg Tyr Glu Ala His Leu
        275                 280                 285

Trp Asp Asn Thr Cys Arg Lys Glu Gly Gln Thr Arg Lys Gly Arg Gln
    290                 295                 300

Val Tyr Leu Gly Gly Tyr Asp Arg Glu Glu Lys Ala Ala Arg Ala Tyr
305                 310                 315                 320

Asp Leu Ala Ala Leu Lys Tyr Trp Gly Pro Ser Thr His Ile Asn Phe
                325                 330                 335

Pro Leu Ser His Tyr Glu Lys Glu Leu Glu Glu Met Lys His Met Ser
            340                 345                 350

Arg Gln Glu Phe Ile Ala His Leu Arg Arg Asn Ser Ser Gly Phe Ser
        355                 360                 365

Arg Gly Ala Ser Met Tyr Arg Gly Val Thr Arg His His Gln His Gly
    370                 375                 380

Arg Trp Gln Ala Arg Ile Gly Arg Val Ala Gly Asn Lys Asp Leu Tyr
385                 390                 395                 400

Leu Gly Thr Phe Ser Thr Gln Glu Glu Ala Ala Glu Ala Tyr Asp Ile
                405                 410                 415

Ala Ala Ile Lys Phe Arg Gly Leu Asn Ala Val Thr Asn Phe Asp Ile
            420                 425                 430

Ser Lys Tyr Asp Val Lys Arg Ile Cys Ala Ser Thr His Leu Ile Gly
        435                 440                 445

Gly Gly Asp Ala Cys Arg Arg Ser Pro Thr Arg Pro Pro Asp Ala Ala
    450                 455                 460
```

```
Pro Ala Leu Ala Gly Gly Ala Asp Arg Ser Ser Asp Ala Pro Gly Asp
465                 470                 475                 480

Gln Ala Ala Ser Asp Asn Ser Asp Thr Ser Asp Gly His Arg Gly Ala
            485                 490                 495

His Leu Leu His Gly Leu Gln Tyr Gly His Pro Met Lys Leu Glu Ala
            500                 505                 510

Gly Glu Gly Ser Ser Trp Met Ala Ala Ala Ala Ala Arg Pro Val
            515                 520                 525

Pro Gly Val His Gln Leu Pro Met Phe Ala Leu Trp Asn Asp Cys
530                 535                 540

<210> SEQ ID NO 86
<211> LENGTH: 512
<212> TYPE: PRT
<213> ORGANISM: Glycine max

<400> SEQUENCE: 86

Met Ser Asn Trp Leu Gly Phe Ser Leu Thr Pro His Leu Arg Ile Asp
1               5                   10                  15

Glu Glu Phe Glu Arg Glu Asn Gln Glu Arg Gly Gly Gly Ile Ile Leu
            20                  25                  30

Phe Glu Lys Lys Thr Lys Trp Arg Tyr Asp Ser Ala Ile Gly Gly
        35                  40                  45

Gly Asn Ser Asn Glu Glu Gly Pro Lys Leu Glu Asp Phe Leu Gly Cys
    50                  55                  60

Tyr Ser Asn Ser Pro Ala Lys Val Phe Cys Gln Asp Ser Gln Pro Asp
65                  70                  75                  80

Gln Asn Gln Ser Gln Asn Asn Val Ser Lys Ile Asn Ile Glu Thr Gly
                85                  90                  95

Asp Asn Leu Thr Asn Pro Ser Ser Leu Leu His Ser Phe His Ala Tyr
            100                 105                 110

Asn Asp Asn Ser His Ala Leu Ile Pro Thr Asn Gly Met Tyr Lys Ser
        115                 120                 125

Trp Leu Ala Gln Thr Gln Phe Ser Ser Asp Gly Lys Pro Ser Asn Glu
    130                 135                 140

Ala Asn Gly Cys Asn Phe Gln Ser Leu Ser Leu Thr Met Ser Pro Ser
145                 150                 155                 160

Val Gln Asn Gly Val Gly Ala Ile Ser Ser Val Gln Val Asn Glu Asp
                165                 170                 175

Ser Arg Lys Arg Val Met Ala Lys Ser His Ala Arg Glu Pro Val Pro
            180                 185                 190

Arg Lys Ser Ile Asp Thr Phe Gly Gln Arg Thr Ser Gln Tyr Arg Gly
        195                 200                 205

Val Thr Arg His Arg Trp Thr Gly Arg Tyr Glu Ala His Leu Trp Asp
    210                 215                 220

Asn Ser Cys Arg Lys Glu Gly Gln Thr Arg Lys Gly Arg Gln Gly Gly
225                 230                 235                 240

Tyr Asp Lys Glu Glu Lys Ala Ala Lys Ala Tyr Asp Leu Ala Ala Leu
                245                 250                 255

Lys Tyr Trp Gly Pro Thr Thr His Ile Asn Phe Pro Leu Ser Thr Tyr
            260                 265                 270

Glu Lys Glu Leu Glu Glu Met Lys His Met Thr Arg Gln Glu Phe Val
        275                 280                 285

Ala Asn Leu Arg Arg Lys Ser Ser Gly Phe Ser Arg Gly Ala Ser Val
    290                 295                 300
```

Tyr Arg Gly Val Thr Arg His His Gln His Gly Arg Trp Gln Ala Arg
305                 310                 315                 320

Ile Gly Arg Val Ala Gly Asn Lys Asp Leu Tyr Leu Gly Thr Phe Ser
            325                 330                 335

Thr Gln Glu Glu Ala Ala Glu Ala Tyr Asp Ile Ala Ala Ile Lys Phe
        340                 345                 350

Arg Gly Thr Ser Ala Val Thr Asn Phe Asp Ile Ser Arg Tyr Asp Val
    355                 360                 365

Lys Arg Ile Cys Ser Ser Thr Leu Ile Ala Gly Asp Leu Ala Lys
370                 375                 380

Arg Ser Pro Lys Glu Ser Pro Ala Pro Pro Leu Ala Ile Thr
385                 390                 395                 400

Asp Gly Glu His Ser Asp Glu Leu Ser Asn Met Met Trp Asn Ala Asn
                405                 410                 415

Asn Ser Asp Glu Gln Ala Gln Asn Glu Ser Gly Gly Ala Glu Phe Asn
            420                 425                 430

Asn Asn Val Thr Glu Ser Ser Ser Gln Gln Val Ser Pro Ser Ser
        435                 440                 445

Asn Lys Asp Ala Leu Asn Pro Gln Ser Pro Asn Glu Phe Gly Val Ser
450                 455                 460

Gly Ala Asp Tyr Gly His Gly Tyr Phe Thr Leu Asp Gly Pro Lys Tyr
465                 470                 475                 480

Asp Asp Gly Asn Asn Glu Asn Asp His Met Ser Thr Asn Arg Leu Gly
                485                 490                 495

Asn Leu Gly Leu Val Asn Gln Val Pro Met Phe Ala Leu Trp Asn Glu
            500                 505                 510

<210> SEQ ID NO 87
<211> LENGTH: 485
<212> TYPE: PRT
<213> ORGANISM: Sorghum bicolor

<400> SEQUENCE: 87

Met Asp Thr Ser His His Tyr Pro Trp Leu Asn Phe Ser Leu Ala His
1               5                   10                  15

His Gly Asp Leu Glu Glu Glu Arg Gly Ala Ala Glu Leu Ala
            20                  25                  30

Ala Ile Ala Gly Ala Ala Pro Pro Lys Leu Glu Asp Phe Leu Gly
        35                  40                  45

Gly Gly Val Ile Asn Gly Glu Ser Ala Arg Ser Gly Gly Val Pro
    50                  55                  60

Val Ala Ala Pro Glu Val Ser Ala Pro Ala Glu Met Tyr Asp Ser Asp
65                  70                  75                  80

Leu Lys Phe Ile Ala Ala Ala Gly Phe Leu Gly Gly Ser Ala Ala
                85                  90                  95

Gly Pro Val Ala Thr Ser Pro Leu Ser Ser Leu Asp Gln Ala Asp Pro
            100                 105                 110

Lys Leu Ala Leu Pro Ala Ala Ala Ala Pro Ala Pro Glu Gln
        115                 120                 125

Arg Lys Ala Val Asp Ser Phe Gly Gln Arg Thr Ser Ile Tyr Arg Gly
    130                 135                 140

Val Thr Arg His Arg Trp Thr Gly Arg Tyr Glu Ala His Leu Trp Asp
145                 150                 155                 160

Asn Ser Cys Arg Arg Glu Gly Gln Ser Arg Lys Gly Arg Gln Gly Gly

```
                165                 170                 175
Tyr Asp Lys Glu Glu Lys Ala Ala Arg Ala Tyr Asp Leu Ala Ala Leu
                180                 185                 190

Lys Tyr Trp Gly Ser Ser Thr Thr Thr Asn Phe Pro Val Ala Glu Tyr
            195                 200                 205

Glu Lys Glu Leu Glu Glu Met Lys Thr Met Thr Arg Gln Glu Phe Val
        210                 215                 220

Ala Ser Leu Arg Arg Lys Ser Ser Gly Phe Ser Arg Gly Ala Ser Ile
225                 230                 235                 240

Tyr Arg Gly Val Thr Arg His His Gln His Gly Arg Trp Gln Ala Arg
                245                 250                 255

Ile Gly Arg Val Ala Gly Asn Lys Asp Leu Tyr Leu Gly Thr Phe Ser
            260                 265                 270

Thr Glu Glu Glu Ala Ala Glu Ala Tyr Asp Ile Ala Ala Ile Lys Phe
        275                 280                 285

Arg Gly Leu Asn Ala Val Thr Asn Phe Glu Ile Ser Arg Tyr Asn Val
    290                 295                 300

Glu Ser Ile Met Asn Ser Asn Ile Pro Met Gly Ser Met Ser Ala Gly
305                 310                 315                 320

Gly Arg Ser Asn Lys Ala Leu Glu Ser Pro Pro Ser Gly Ser Pro Asp
                325                 330                 335

Ala Met Pro Val Glu Ala Ser Thr Ala Pro Leu Phe Ala Ala Leu Pro
            340                 345                 350

Val Lys Tyr Asp Gln Gln Gln Gln Asp Tyr Leu Ser Met Leu Ala Leu
        355                 360                 365

Gln His His Gln Gln Gly Asn Leu Gln Gly Leu Gly Phe Gly Leu Tyr
    370                 375                 380

Ser Ser Gly Val Asn Leu Asp Phe Ala Asn Ser His Ser Thr Ala Ser
385                 390                 395                 400

Ser Met Thr His Cys Tyr Val Asn Gly Gly Thr Val Ser Ser His Glu
                405                 410                 415

Gln His Gln His His Gln Gln Leu Gln Asp His Gln Gln Gln Gly Glu
            420                 425                 430

Ser Glu Thr Gln Gln Ser Ser Asn Ser Cys Ser Ser Leu Pro Phe Ala
        435                 440                 445

Thr Pro Ile Ala Phe Asn Gly Ser Tyr Glu Ser Met Thr Ala Ala
    450                 455                 460

Gly Pro Phe Gly Tyr Ser Tyr Pro Asn Val Ala Ala Phe Gln Thr Pro
465                 470                 475                 480

Ile Tyr Gly Met Glu
                485

<210> SEQ ID NO 88
<211> LENGTH: 507
<212> TYPE: PRT
<213> ORGANISM: Glycine max

<400> SEQUENCE: 88

Met Ala Arg Ala Thr Asn Trp Leu Ser Phe Ser Leu Ser Pro Met Glu
1               5                   10                  15

Met Leu Arg Thr Ser Glu Pro Gln Phe Leu Gln Tyr Asp Ala Ala Ser
            20                  25                  30

Ala Thr Ser Ser His His Tyr Tyr Leu Asp Asn Leu Thr Asn Gly
        35                  40                  45
```

-continued

```
Trp Gly Asn Gly Ser Leu Lys Phe Glu Gln Asn Leu Asn His Ser Asp
 50                  55                  60
Val Ser Phe Val Glu Ser Ser Gln Ser Val Gly His Val Pro Pro
 65                  70                  75                  80
Pro Pro Pro Lys Leu Glu Asp Phe Leu Gly Asp Ser Ser Ala Val Met
                 85                  90                  95
Arg Tyr Ser Asp Ser Gln Thr Glu Thr Gln Asp Ser Ser Leu Thr His
                100                 105                 110
Ile Tyr Asp His His His His His His His Gly Ser Thr Ser
             115                 120                 125
Tyr Phe Gly Gly Asp Gln Gln Asp Leu Lys Ala Ile Thr Gly Phe Gln
130                 135                 140
Ala Phe Ser Thr Asn Ser Gly Ser Glu Val Asp Asp Ser Ala Ser Ile
145                 150                 155                 160
Gly Lys Ala Gln Ala Ser Glu Phe Gly Thr His Ser Ile Glu Ser Ser
                165                 170                 175
Gly Asn Glu Phe Ala Ala Phe Ser Gly Gly Thr Thr Gly Thr Leu Ser
                180                 185                 190
Leu Ala Val Ala Leu Ser Ser Glu Lys Ala Val Val Ala Ala Glu Ser
195                 200                 205
Asn Ser Ser Lys Lys Ile Val Asp Thr Phe Gly Gln Arg Thr Ser Ile
210                 215                 220
Tyr Arg Gly Val Thr Arg His Arg Trp Thr Gly Arg Tyr Glu Ala His
225                 230                 235                 240
Leu Trp Asp Asn Ser Cys Arg Arg Glu Gly Gln Ala Arg Lys Gly Arg
                245                 250                 255
Gln Gly Gly Tyr Asp Lys Glu Glu Lys Ala Ala Arg Ala Tyr Asp Leu
                260                 265                 270
Ala Ala Leu Lys Tyr Trp Gly Pro Thr Ala Thr Asn Phe Pro Val
                275                 280                 285
Ser Asn Tyr Ser Lys Glu Val Glu Glu Met Lys His Val Thr Lys Gln
290                 295                 300
Glu Phe Ile Ala Ser Leu Arg Arg Lys Ser Ser Gly Phe Ser Arg Gly
305                 310                 315                 320
Ala Ser Ile Tyr Arg Gly Val Thr Arg His His Gln Gln Gly Arg Trp
                325                 330                 335
Gln Ala Arg Ile Gly Arg Val Ala Gly Asn Lys Asp Leu Tyr Leu Gly
                340                 345                 350
Thr Phe Ala Thr Glu Glu Glu Ala Ala Glu Ala Tyr Asp Ile Ala Ala
                355                 360                 365
Ile Lys Phe Arg Gly Ala Asn Ala Val Thr Asn Phe Glu Met Asn Arg
370                 375                 380
Tyr Asp Val Glu Ala Ile Met Lys Ser Ser Leu Pro Val Gly Gly Ala
385                 390                 395                 400
Ala Lys Arg Leu Arg Leu Ser Leu Glu Ser Glu Gln Lys Ala Pro Pro
                405                 410                 415
Val Asn Ser Ser Ser Gln Gln Gln Asn Pro Gln Cys Gly Asn Val Ser
                420                 425                 430
Gly Ser Ile Asn Phe Ser Ala Ile His Gln Pro Ile Ala Ser Ile Pro
                435                 440                 445
Cys Gly Ile Pro Phe Asp Ser Thr Thr Ala Tyr Tyr Pro His Asn Leu
450                 455                 460
Phe Gln His Phe His Pro Thr Asn Ala Gly Ala Ala Ala Ser Ala Val
```

```
                465                 470                 475                 480
Thr Ser Asn Ala Thr Ala Leu Thr Ala Leu Pro Ala Ser Ala Ala
                    485                 490                 495
Thr Glu Phe Phe Ile Trp Pro His Gln Ser Tyr
                500                 505

<210> SEQ ID NO 89
<211> LENGTH: 569
<212> TYPE: PRT
<213> ORGANISM: Arabidopsis thaliana

<400> SEQUENCE: 89

Met Glu Met Leu Arg Ser Ser Asp Gln Ser Gln Phe Val Ser Tyr Asp
 1               5                  10                  15

Ala Ser Ser Ala Ala Ser Ser Pro Tyr Leu Leu Asp Asn Phe Tyr
                20                  25                  30

Gly Trp Ser Asn Gln Lys Pro Gln Glu Phe Phe Lys Glu Glu Ala Gln
        35                  40                  45

Leu Ala Ala Ala Ala Ser Met Ala Asp Ser Thr Ile Leu Thr Thr Phe
    50                  55                  60

Val Asp Pro Gln Ser His His Ser Gln Asn His Ile Pro Lys Leu Glu
65                  70                  75                  80

Asp Phe Leu Gly Asp Ser Ser Ser Ile Val Arg Tyr Ser Asp Asn Ser
                85                  90                  95

Gln Thr Asp Thr Gln Asp Ser Ser Leu Thr Gln Ile Tyr Asp Pro Arg
            100                 105                 110

His His His Asn Gln Thr Gly Phe Tyr Ser Asp His His Asp Phe Lys
        115                 120                 125

Thr Met Ala Gly Phe Gln Ser Ala Phe Ser Thr Asn Ser Gly Ser Glu
   130                 135                 140

Val Asp Asp Ser Ala Ser Ile Gly Arg Thr His Leu Ala Gly Asp Tyr
145                 150                 155                 160

Leu Gly His Val Val Glu Ser Ser Gly Pro Glu Leu Gly Phe His Gly
                165                 170                 175

Gly Ser Thr Gly Ala Leu Ser Leu Gly Val Asn Val Asn Asn Asn Thr
            180                 185                 190

Asn His Arg Asn Asp Asn Asp Asn His Tyr Arg Gly Asn Asn Asn Gly
        195                 200                 205

Glu Arg Ile Asn Asn Asn Asn Asn Asp Asn Glu Lys Thr Asp Ser
    210                 215                 220

Glu Lys Glu Lys Ala Val Val Ala Val Glu Thr Ser Asp Cys Ser Asn
225                 230                 235                 240

Lys Lys Ile Ala Asp Thr Phe Gly Gln Arg Thr Ser Ile Tyr Arg Gly
                245                 250                 255

Val Thr Arg His Arg Trp Thr Gly Arg Tyr Glu Ala His Leu Trp Asp
            260                 265                 270

Asn Ser Cys Arg Arg Glu Gly Gln Ala Arg Lys Gly Arg Gln Val Tyr
        275                 280                 285

Leu Gly Gly Tyr Asp Lys Glu Asp Lys Ala Ala Arg Ala Tyr Asp Leu
    290                 295                 300

Ala Ala Leu Lys Tyr Trp Asn Ala Thr Ala Thr Thr Asn Phe Pro Ile
305                 310                 315                 320

Thr Asn Tyr Ser Lys Glu Val Glu Glu Met Lys His Met Thr Lys Gln
                325                 330                 335
```

```
Glu Phe Ile Ala Ser Leu Arg Arg Lys Ser Gly Phe Ser Arg Gly
            340                 345                 350

Ala Ser Ile Tyr Arg Gly Val Thr Arg His His Gln Gln Gly Arg Trp
            355                 360                 365

Gln Ala Arg Ile Gly Arg Val Ala Gly Asn Lys Asp Leu Tyr Leu Gly
            370                 375                 380

Thr Phe Ala Thr Glu Glu Ala Ala Glu Ala Tyr Asp Ile Ala Ala
385                 390                 395                 400

Ile Lys Phe Arg Gly Ile Asn Ala Val Thr Asn Phe Glu Met Asn Arg
                405                 410                 415

Tyr Asp Val Glu Ala Ile Met Lys Ser Ala Leu Pro Ile Gly Gly Ala
            420                 425                 430

Ala Lys Arg Leu Lys Leu Ser Leu Glu Ala Ala Ser Ser Glu Gln
            435                 440                 445

Lys Pro Ile Leu Gly His His Gln Leu His His Phe Gln Gln Gln Gln
    450                 455                 460

Gln Gln Gln Gln Leu Gln Leu Gln Ser Ser Pro Asn His Ser Ser Ile
465                 470                 475                 480

Asn Phe Ala Leu Cys Pro Asn Ser Ala Val Gln Ser Gln Gln Ile Ile
                485                 490                 495

Pro Cys Gly Ile Pro Phe Glu Ala Ala Ala Leu Tyr His His His Gln
            500                 505                 510

Gln Gln Gln Gln His Gln Gln Gln Gln Gln Asn Phe Phe Gln
            515                 520                 525

His Phe Pro Ala Asn Ala Ala Ser Asp Ser Thr Gly Ser Asn Asn Asn
530                 535                 540

Ser Asn Val Gln Gly Thr Met Gly Leu Met Ala Pro Asn Pro Ala Glu
545                 550                 555                 560

Phe Phe Leu Trp Pro Asn Gln Ser Tyr
                565

<210> SEQ ID NO 90
<211> LENGTH: 574
<212> TYPE: PRT
<213> ORGANISM: Medicago truncatula

<400> SEQUENCE: 90

Met Ser Asn Trp Leu Gly Phe Ser Leu Thr Pro His Leu Arg Ile Asp
1               5                   10                  15

Glu Glu Phe Gly Thr Glu Asn Gln Asn Gln Asn His Val Ala
            20                  25                  30

Glu Gly Ser Glu Ile Gly Arg Asn Tyr Val Thr Pro Ser Ser His Pro
            35                  40                  45

His Pro His His Leu Ser Ile Met Pro Leu Arg Ser Asp Gly Ser Leu
    50                  55                  60

Cys Val Ser Asp Ser Phe Thr Pro Gln Glu Trp Arg Tyr Glu Asn Ala
65                  70                  75                  80

Ile Thr Asp Gly Asn Ser Asn Glu Glu Gly Pro Lys Leu Glu Asp Phe
                85                  90                  95

Leu Gly Cys Tyr Ser Asn Gln Asn Gln Asn Ser Thr Thr Thr Ser Thr
            100                 105                 110

Met Ser Lys Ile Asn Val Asn Val Ser Pro Ser Phe Cys Thr Asn Asn
            115                 120                 125

Asn Pro Glu Ile Asp Thr Arg Glu Asn Leu Thr Asn Gln Ser Leu Ile
130                 135                 140
```

```
His Ser Phe His Ala Tyr Asn Asp His Ser Asn Asn His His Ala
145                 150                 155                 160

Leu Ile His Asp Asn Ser Met Tyr Lys Ser Trp Met Thr Gln Thr Gln
                165                 170                 175

Phe Ser Ser Glu Gly Lys Thr Thr Ser Ser Asp Gly Asn Gly Phe Gln
            180                 185                 190

Ser Leu Asn Leu Thr Met Ser Pro Cys Val Gln Asn Gly Val Gly Gly
                195                 200                 205

Gly Val Gly Ser Ala Ile Ser Asn Val Gln Val Asn Glu Asp Pro Arg
210                 215                 220

Lys Arg Ser Leu Ser Lys Ser Asn Ala Arg Glu Pro Val Pro Arg Lys
225                 230                 235                 240

Ser Ile Asp Thr Phe Gly Gln Arg Thr Ser Gln Tyr Arg Gly Val Thr
                245                 250                 255

Arg His Arg Trp Thr Gly Arg Tyr Glu Ala His Leu Trp Asp Asn Ser
                260                 265                 270

Cys Arg Lys Glu Gly Gln Thr Arg Lys Gly Arg Gln Gly Gly Tyr Asp
            275                 280                 285

Lys Glu Glu Lys Ala Ala Lys Ala Tyr Asp Leu Ala Ala Leu Lys Tyr
290                 295                 300

Trp Gly Pro Thr Thr His Ile Asn Phe Pro Leu Ser Thr Tyr Asp Lys
305                 310                 315                 320

Glu Leu Glu Glu Met Lys His Met Thr Arg Gln Glu Phe Val Ala Asn
                325                 330                 335

Leu Arg Arg Lys Ser Ser Gly Phe Ser Arg Gly Ala Ser Val Tyr Arg
                340                 345                 350

Gly Val Thr Arg His His Gln His Gly Arg Trp Gln Ala Arg Ile Gly
                355                 360                 365

Arg Val Ala Gly Asn Lys Asp Leu Tyr Leu Gly Thr Phe Ser Thr Gln
370                 375                 380

Glu Glu Ala Ala Glu Ala Tyr Asp Ile Ala Ala Ile Lys Phe Arg Gly
385                 390                 395                 400

Thr Ser Ala Val Thr Asn Phe Asp Ile Ser Arg Tyr Asp Val Lys Arg
                405                 410                 415

Ile Cys Ser Ser Ser Thr Leu Ile Thr Gly Asp Leu Ala Lys Arg Ser
            420                 425                 430

Pro Lys Asp Ser Thr Pro Pro Ala Thr Thr Ala Glu Asp Phe Asn Ser
            435                 440                 445

Cys Gly Ser Ser Ser Thr Leu Ser Gln Pro Pro Leu Thr Ile Thr
            450                 455                 460

Asp Gly Glu Gln His Ser Asp Glu Leu Ser Asn Met Val Trp Asn Ser
465                 470                 475                 480

Asn Asn Asp Glu Gln Lys Pro Gln Asn Gly Thr Asn Ile Thr Glu Ser
                485                 490                 495

Ser Gln His Gly Ser Pro Ser Asn Lys Asn Glu Met Asn Pro Gln Ser
            500                 505                 510

Pro Lys Cys Ser Leu Gly Leu Pro Asn Glu Phe Gly Val Ser Gly Ala
            515                 520                 525

Asp Tyr Gly His Gly Tyr Phe Thr Leu His Gly Pro Lys Phe Asp Asp
            530                 535                 540

Gly Ser Asn Glu Asn Asp His Met Asn Asn Asn Arg Leu Gly Asn Leu
545                 550                 555                 560
```

```
Gly Leu Val Asn Gln Val Pro Met Phe Ala Leu Trp Asn Glu
                565                 570
```

<210> SEQ ID NO 91
<211> LENGTH: 541
<212> TYPE: PRT
<213> ORGANISM: Sorghum bicolor

<400> SEQUENCE: 91

```
Met Asp Met Asn Asn Gly Trp Leu Gly Phe Ser Leu Ser Pro Ser Ala
 1               5                  10                  15

Gly Arg Gly Gly Tyr Gly Asp Gly Ala Ser Ala Ser Gly Asp Gly
                20                  25                  30

Gly Asp Gly Ser Cys Ser Ser Pro Ala Ala Ala Ser Pro Val Pro
                35                  40                  45

Leu Val Ala Met Pro Leu Gln Pro Asp Gly Ser Leu His Tyr Thr Ser
            50                  55                  60

Ala Pro Asp Trp Arg His Gly Ala Ala Glu Ala Asn Gly Pro Lys Leu
65                  70                  75                  80

Glu Asp Phe Met Ser Val Thr Cys Ser Ser Asn Asn Lys Arg Ser Ser
                85                  90                  95

Ser Ser Ser Ser Phe Tyr Asp Arg Cys Ser His Ala Glu Gln Ala Asn
                100                 105                 110

Lys Tyr His Glu Val His Asp Leu Gln Pro Leu Ser Cys Gly Ser Tyr
                115                 120                 125

Tyr His Gly Ser Ser Gly Gly Gly Asn Gly Ile Ala Leu Gly Ile
            130                 135                 140

Asn Met Asn Ala Pro Pro Cys Ser Gly Gly Phe Pro Asp His His
145                 150                 155                 160

His His His Gln Phe Val Ser Ser His His Gly Gln Tyr Phe Leu Gly
                165                 170                 175

Ala Pro Leu Asn Ala Ser Pro Pro Gly Ala Val Pro Met Tyr Ser Ala
            180                 185                 190

Gly Gly Gly Gly Val Gly Gly Ser Met Ser Ile Ser Gly Ile Lys Ser
            195                 200                 205

Trp Leu Arg Glu Ala Met Tyr Val Pro Pro Glu Arg Pro Val Ala Ala
210                 215                 220

Ala Ala Ala Leu Ser Leu Ala Val Thr Asp Asp Val Gly Ala Glu Pro
225                 230                 235                 240

Pro Gln Leu Leu Pro Ala Ala Pro Met Pro Pro Val His Arg Lys Pro
                245                 250                 255

Ala Gln Thr Phe Gly Gln Arg Thr Ser Gln Phe Arg Gly Val Thr Arg
            260                 265                 270

His Arg Trp Thr Gly Arg Tyr Glu Ala His Leu Trp Asp Asn Thr Cys
            275                 280                 285

Arg Lys Glu Gly Gln Thr Arg Lys Gly Arg Gln Gly Gly Tyr Asp Arg
290                 295                 300

Glu Glu Lys Ala Ala Arg Ala Tyr Asp Leu Ala Ala Leu Lys Tyr Trp
305                 310                 315                 320

Gly Pro Ser Thr His Ile Asn Phe Pro Leu Ser His Tyr Glu Lys Glu
                325                 330                 335

Leu Glu Glu Met Lys His Met Ser Arg Gln Glu Phe Ile Ala His Leu
                340                 345                 350

Arg Arg Asn Ser Ser Gly Phe Ser Arg Gly Ala Ser Met Tyr Arg Gly
            355                 360                 365
```

-continued

```
Val Thr Arg His His Gln His Gly Arg Trp Gln Ala Arg Ile Gly Arg
    370                 375                 380

Val Ala Gly Asn Lys Asp Leu Tyr Leu Gly Thr Phe Ser Thr Gln Glu
385                 390                 395                 400

Glu Ala Ala Glu Ala Tyr Asp Ile Ala Ala Ile Lys Phe Arg Gly Leu
                405                 410                 415

Asn Ala Val Thr Asn Phe Asp Ile Ser Lys Tyr Asp Val Lys Arg Ile
                420                 425                 430

Cys Ala Ser Thr His Leu Ile Gly Gly Gly Asp Ala Cys Arg Arg Ser
                435                 440                 445

Pro Thr Gln Pro Pro Asp Ala Pro Ala Leu Ala Ile Asp Ala Ala Gly
    450                 455                 460

Ala Asp Arg Ser Ser Asp Ala Pro Gly Gly Asp Gln Ala Val Ser
465                 470                 475                 480

Asp Asn Ser Asp Thr Ser Ala Gly His Arg Gly Ala His Leu Leu His
                485                 490                 495

Gly Leu Gln Tyr Gly His Pro Met Lys Leu Glu Ala Gly Glu Gly Ser
                500                 505                 510

Ser Trp Met Ala Ala Thr Ala Ala Ala Arg Pro Val Ala Gly
                515                 520                 525

Val His Gln Leu Pro Val Phe Ala Leu Trp Asn Asp Cys
    530                 535                 540
```

<210> SEQ ID NO 92
<211> LENGTH: 555
<212> TYPE: PRT
<213> ORGANISM: Arabidopsis thaliana

<400> SEQUENCE: 92

```
Met Lys Ser Phe Cys Asp Asn Asp Asn Asn His Ser Asn Thr Thr
1               5                   10                  15

Asn Leu Leu Gly Phe Ser Leu Ser Ser Asn Met Met Lys Met Gly Gly
                20                  25                  30

Arg Gly Gly Arg Glu Ala Ile Tyr Ser Ser Ser Thr Ser Ser Ala Ala
            35                  40                  45

Thr Ser Ser Ser Ser Val Pro Pro Gln Leu Val Val Gly Asp Asn Thr
    50                  55                  60

Ser Asn Phe Gly Val Cys Tyr Gly Ser Asn Pro Asn Gly Gly Ile Tyr
65                  70                  75                  80

Ser His Met Ser Val Met Pro Leu Arg Ser Asp Gly Ser Leu Cys Leu
                85                  90                  95

Met Glu Ala Leu Asn Arg Ser Ser His Ser Asn His Gln Asp Ser
                100                 105                 110

Ser Pro Lys Val Glu Asp Phe Phe Gly Thr His His Asn Asn Thr Ser
    115                 120                 125

His Lys Glu Ala Met Asp Leu Ser Leu Asp Ser Leu Phe Tyr Asn Thr
            130                 135                 140

Thr His Glu Pro Asn Thr Thr Thr Asn Phe Gln Glu Phe Phe Ser Phe
145                 150                 155                 160

Pro Gln Thr Arg Asn His Glu Glu Glu Thr Arg Asn Tyr Gly Asn Asp
                165                 170                 175

Pro Ser Leu Thr His Gly Gly Ser Phe Asn Val Gly Val Tyr Gly Glu
                180                 185                 190

Phe Gln Gln Ser Leu Ser Leu Ser Met Ser Pro Gly Ser Gln Ser Ser
```

```
                195                 200                 205
Cys Ile Thr Gly Ser His His His Gln Gln Asn Gln Asn Gln Asn His
    210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Lys Lys Lys Arg Gly
            245                 250                 255

Gln Glu Asp Val Val Val Gly Gln Lys Gln Ile Val His Arg Lys
            260                 265                 270

Ser Ile Asp Thr Phe Gly Gln Arg Thr Ser Gln Tyr Arg Gly Val Thr
    275                 280                 285

Arg His Arg Trp Thr Gly Arg Tyr Glu Ala His Leu Trp Asp Asn Ser
    290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Gln Lys Glu Ile Glu Asp Met Lys Asn Met Thr Arg Gln Glu Tyr
    355                 360                 365

Val Ala His Leu Arg Arg Lys Ser Ser Gly Phe Ser Arg Gly Ala Ser
    370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
            420                 425                 430

Phe Arg Gly Thr Asn Ala Val Thr Asn Phe Asp Ile Thr Arg Tyr Asp
    435                 440                 445

Val Asp Arg Ile Met Ser Ser Asn Thr Leu Leu Ser Gly Glu Leu Ala
450                 455                 460

Arg Arg Asn Asn Asn Ser Ile Val Val Arg Asn Thr Glu Asp Gln Thr
465                 470                 475                 480

Ala Leu Asn Ala Val Val Glu Gly Gly Ser Asn Lys Glu Val Ser Thr
                485                 490                 495

Pro Glu Arg Leu Leu Ser Phe Pro Ala Ile Phe Ala Leu Pro Gln Val
            500                 505                 510

Asn Gln Lys Met Phe Gly Ser Asn Met Gly Gly Asn Met Ser Pro Trp
    515                 520                 525

Thr Ser Asn Pro Asn Ala Glu Leu Lys Thr Val Ala Leu Thr Leu Pro
    530                 535                 540

Gln Met Pro Val Phe Ala Ala Trp Ala Asp Ser
545                 550                 555

<210> SEQ ID NO 93
<211> LENGTH: 678
<212> TYPE: PRT
<213> ORGANISM: Sorghum bicolor

<400> SEQUENCE: 93

Met Thr Asn Asn Asn Gly Asn Gly Thr Asn Ala Ala Ala Ser Ser Trp
1               5                   10                  15
```

```
Leu Gly Phe Ser Leu Ser Pro His Met Ala Ser Ala Met Asp Glu His
             20                  25                  30

His His Val Gln Gln Gln Gln His His His His Ser Leu Phe
         35                  40                  45

Phe Pro Ser Val Thr Ala Ala Ala Ala Ala Tyr Gly Leu Gly Gly
         50                  55                  60

Ser Asp Gly Gly Val Ala Thr Ser Ala Ser Pro Tyr Tyr Thr Pro Gln
 65              70                  75                      80

Leu Ala Ser Met Pro Leu Lys Ser Asp Gly Ser Leu Cys Ile Met Glu
                 85                  90                  95

Ala Leu Arg Arg Ser Asp Gln Pro Asp His His Gly Pro Lys Leu Glu
             100                 105                 110

Asp Phe Leu Gly Ala Ala Ala Ala Gln Ser Gln Ala Met Ala Leu Ser
         115                 120                 125

Leu Gln Asp Asn Pro Ala Ala Ala Ser Ser Phe Tyr Tyr Tyr Gly
         130                 135                 140

Asn Gly Gly Gly Gly Ser Gly His Gln His His Gly Gly Phe Leu
145                 150                 155                 160

Gln Pro Cys Ala Asp Leu Tyr Gly Gly Pro Ser Glu Ala Ser Leu Val
                 165                 170                 175

Ala Asp Asp Asp Glu Ala Ala Ala Ala Thr Ala Met Ala Ser Trp
                 180                 185                 190

Val Ala Ala Arg Ala Gly Glu Ser Gly Gly Val Leu Ser Ala Ala Ala
             195                 200                 205

Ala Ala Ala Gly His Gln His His His Ala Leu Ala Leu Ser Met
210                 215                 220

Ser Ser Gly Ser Leu Ser Ser Cys Val Thr Ala His Pro Gly Ala Ala
225                 230                 235                 240

Ala Ala Asp Tyr Gly Val Val Ala Thr Ala Ser Ala Ser Leu Asp
                 245                 250                 255

Gly Gly Arg Lys Arg Gly Gly Ala Ala Gly Gln Lys Gln Pro Val His
             260                 265                 270

His Arg Lys Ser Ile Asp Thr Phe Gly Gln Arg Thr Ser Gln Tyr Arg
             275                 280                 285

Gly Val Thr Arg His Arg Trp Thr Gly Arg Tyr Glu Ala His Leu Trp
         290                 295                 300

Asp Asn Ser Cys Lys Lys Glu Gly Gln Thr Arg Lys Gly Arg Gln Gly
305                 310                 315                 320

Gly Tyr Asp Met Glu Glu Lys Ala Ala Arg Ala Tyr Asp Leu Ala Ala
                 325                 330                 335

Leu Lys Tyr Trp Gly Pro Ser Thr His Ile Asn Phe Pro Leu Glu Asp
             340                 345                 350

Tyr Gln Glu Glu Leu Glu Glu Met Lys Asn Met Thr Arg Gln Glu Tyr
             355                 360                 365

Val Ala His Leu Arg Arg Lys Ser Ser Gly Phe Ser Arg Gly Ala Ser
         370                 375                 380

Met Tyr Arg Gly Val Thr Arg His His Gln His Gly Arg Trp Gln Ala
385                 390                 395                 400

Arg Ile Gly Arg Val Ser Gly Asn Lys Asp Leu Tyr Leu Gly Thr Phe
                 405                 410                 415

Ser Thr Gln Glu Glu Ala Ala Glu Ala Tyr Asp Ile Ala Ala Ile Lys
             420                 425                 430

Phe Arg Gly Leu Asn Ala Val Thr Asn Phe Asp Ile Thr Arg Tyr Asp
```

```
            435                 440                 445
Val Asp Lys Ile Met Ala Ser Asn Thr Leu Leu Pro Gly Asp Leu Ala
450                 455                 460

Arg Arg Arg Lys Asp Asp Pro Ala Ala Val Ile Ala Gly Ala Asp
465                 470                 475                 480

Ala Ser Asn Gly Gly Val Thr Thr Ala Ala Ala Ala Ala Leu
                485                 490                 495

Val Gln Gln Ala Ala Ala Ala Ala Ala Gly Ala Gly Gly Asn His
                500                 505                 510

Ser Ala Ser Ser Ser Glu Thr Trp Ile Lys Val Ala Ala Ala Ala
                515                 520                 525

Leu Gln Ala Ala Gly Ala Ala Pro Arg Asp Gly Asn His His His
                530                 535                 540

His His Asp Val Leu Ser Gly Glu Ala Phe Ser Val Leu His Asp Leu
545                 550                 555                 560

Val Val Thr Ala Ala Asp Gly Gly Asn Gly Asn Gly Asn Gly His
                565                 570                 575

His His His His Val His Asn Ser Ala Ala Thr Ala Gln His Met Ser
                580                 585                 590

Met Ser Ser Ala Ser Ser Leu Val Thr Ser Leu Gly Asn Ser Arg Glu
                595                 600                 605

Gly Ser Pro Asp Arg Gly Gly Leu Ser Met Leu Phe Ser Lys Pro
                610                 615                 620

Pro Ala Pro Ala Pro Ala Ala Ser Ala His Ala Ala Asn Lys Pro Met
625                 630                 635                 640

Ser Pro Leu Met Pro Leu Gly Ser Trp Ala Ser Thr Ala Ala Ser
                645                 650                 655

Ala Arg Ala Ala Ala Ala Val Ser Ile Ala His Met Pro Val Phe
                660                 665                 670

Ala Ala Trp Thr Asp Ala
                675

<210> SEQ ID NO 94
<211> LENGTH: 509
<212> TYPE: PRT
<213> ORGANISM: Glycine max

<400> SEQUENCE: 94

Met Ala Arg Ala Ser Thr Asn Trp Leu Ser Phe Ser Leu Ser Pro Met
1               5                   10                  15

Asp Met Leu Arg Thr Pro Glu Pro Gln Phe Val Gln Tyr Asp Ala Ala
                20                  25                  30

Ser Asp Thr Ser Ser His His Tyr Tyr Leu Asp Asn Leu Tyr Thr Asn
                35                  40                  45

Gly Trp Gly Asn Gly Ser Leu Lys Phe Glu Gln Asn Leu Asn His Ser
            50                  55                  60

Asp Val Ser Phe Val Gln Ser Ser Gln Ser Val Ser His Ala Pro
65                  70                  75                  80

Pro Lys Leu Glu Asp Phe Leu Gly Asp Ser Ser Ala Val Met Arg Tyr
                85                  90                  95

Ser Asp Ser Gln Thr Glu Thr Gln Asp Ser Ser Leu Thr His Ile Tyr
                100                 105                 110

Asp His His His His His His Gly Ser Ser Ala Tyr Phe Gly Gly
                115                 120                 125
```

```
Asp His Gln Asp Leu Lys Ala Ile Thr Gly Phe Gln Ala Phe Ser Thr
    130                 135                 140

Asn Ser Gly Ser Glu Val Asp Asp Ser Ala Ser Ile Gly Lys Ala Gln
145                 150                 155                 160

Gly Ser Glu Phe Gly Thr His Ser Ile Glu Ser Ser Val Asn Glu Phe
                165                 170                 175

Ala Ala Phe Ser Gly Thr Asn Thr Gly Thr Leu Ser Leu Ala
                180                 185                 190

Val Ala Gln Ser Ser Glu Lys Ala Val Ala Ala Ala Glu Ser Asp
                195                 200                 205

Arg Ser Lys Lys Val Val Asp Thr Phe Gly Arg Thr Ser Ile Tyr
210                 215                 220

Arg Gly Val Thr Arg His Arg Trp Thr Gly Arg Tyr Glu Ala His Leu
225                 230                 235                 240

Trp Asp Asn Ser Cys Arg Arg Glu Gly Gln Ala Arg Lys Gly Arg Gln
                245                 250                 255

Gly Gly Tyr Asp Lys Glu Glu Lys Ala Ala Arg Ser Tyr Asp Leu Ala
                260                 265                 270

Ala Leu Lys Tyr Trp Gly Pro Thr Ala Thr Thr Asn Phe Pro Val Ser
            275                 280                 285

Asn Tyr Ser Lys Glu Val Glu Glu Met Lys His Val Thr Lys Gln Glu
        290                 295                 300

Phe Ile Ala Ser Leu Arg Arg Lys Ser Ser Gly Phe Ser Arg Gly Ala
305                 310                 315                 320

Ser Ile Tyr Arg Gly Val Thr Arg His His Gln Gln Gly Arg Trp Gln
                325                 330                 335

Ala Arg Ile Gly Arg Val Ala Gly Asn Lys Asp Leu Tyr Leu Gly Thr
                340                 345                 350

Phe Ala Thr Glu Glu Glu Ala Ala Glu Ala Tyr Asp Ile Ala Ala Ile
            355                 360                 365

Lys Phe Arg Gly Ala Asn Ala Val Thr Asn Phe Glu Met Asn Arg Tyr
    370                 375                 380

Asp Val Glu Ala Ile Met Lys Ser Ser Leu Pro Val Gly Gly Ala Ala
385                 390                 395                 400

Lys Arg Leu Lys Leu Ser Leu Glu Ser Glu Gln Lys Ala Leu Pro Val
                405                 410                 415

Ser Ser Ser Ser Ser Ser Gln Gln Gln Asn Pro Gln Cys Gly Asn
                420                 425                 430

Val Ser Ala Ser Ile Asn Phe Ser Ile His Gln Pro Ile Ala Ser
            435                 440                 445

Ile Pro Cys Gly Ile Pro Phe Asp Ser Thr Thr Ala Tyr Tyr His His
    450                 455                 460

Asn Leu Phe Gln His Phe His Pro Thr Asn Ala Gly Thr Ala Ala Ser
465                 470                 475                 480

Ala Val Thr Ser Ala Asn Ala Asn Ala Leu Thr Ala Leu Pro Pro Thr
                485                 490                 495

Ala Ala Ala Glu Phe Phe Ile Trp Pro His Gln Ser Tyr
                500                 505
```

<210> SEQ ID NO 95
<211> LENGTH: 652
<212> TYPE: PRT
<213> ORGANISM: Oryza sativa

<400> SEQUENCE: 95

```
Met Ala Ser Gly Asn Ser Ser Ser Gly Ser Met Ala Ala Thr
 1               5                  10                 15

Ala Gly Gly Val Gly Gly Trp Leu Gly Phe Ser Leu Ser Pro His Met
             20              25              30

Ala Thr Tyr Cys Ala Gly Val Asp Asp Val Gly His His His
         35                  40                  45

His His Val His Gln His Gln Gln His Gly Gly Gly Leu Phe Tyr
     50              55              60

Asn Pro Ala Ala Val Ala Ser Ser Phe Tyr Tyr Gly Gly Gly His Asp
 65              70              75                  80

Ala Val Val Thr Ser Ala Ala Gly Gly Ser Tyr Tyr Gly Ala Gly
                 85              90                  95

Phe Ser Ser Met Pro Leu Lys Ser Asp Gly Ser Leu Cys Ile Met Glu
             100             105             110

Ala Leu Arg Gly Gly Asp Gln Glu Gln Gln Gly Val Val Ser Ala
         115             120             125

Ser Pro Lys Leu Glu Asp Phe Leu Gly Ala Gly Pro Ala Met Ala Leu
     130             135             140

Ser Leu Asp Asn Ser Ala Phe Tyr Tyr Gly Gly His Gly His His Gln
145             150             155             160

Gly His Ala Gln Asp Gly Gly Ala Val Gly Gly Asp Pro His His Gly
             165             170             175

Gly Gly Gly Phe Leu Gln Cys Ala Val Ile Pro Gly Ala Gly Ala Gly
             180             185             190

His Asp Ala Ala Leu Val His Asp Gln Ser Ala Ala Val Ala Ala
         195             200             205

Gly Trp Ala Ala Met His Gly Gly Gly Tyr Asp Ile Ala Asn Ala Ala
     210             215             220

Ala Asp Asp Val Cys Ala Ala Gly Pro Ile Ile Pro Thr Gly His
225             230             235             240

Leu His Pro Leu Thr Leu Ser Met Ser Ser Ala Gly Ser Gln Ser Ser
             245             250             255

Cys Val Thr Val Gln Ala Ala Ala Gly Glu Pro Tyr Met Ala Met
             260             265             270

Asp Ala Val Ser Lys Lys Arg Gly Gly Ala Asp Arg Ala Gly Gln Lys
         275             280             285

Gln Pro Val His Arg Lys Ser Ile Asp Thr Phe Gly Gln Arg Thr Ser
     290             295             300

Gln Tyr Arg Gly Val Thr Arg His Arg Trp Thr Gly Arg Tyr Glu Ala
305             310             315             320

His Leu Trp Asp Asn Ser Cys Lys Lys Glu Gly Gln Thr Arg Lys Gly
             325             330             335

Arg Gln Gly Gly Tyr Asp Met Glu Glu Lys Ala Ala Arg Ala Tyr Asp
             340             345             350

Leu Ala Ala Leu Lys Tyr Trp Gly Pro Ser Thr His Ile Asn Phe Pro
         355             360             365

Leu Glu Asp Tyr Gln Glu Glu Leu Glu Glu Met Lys Asn Met Ser Arg
     370             375             380

Gln Glu Tyr Val Ala His Leu Arg Arg Lys Ser Ser Gly Phe Ser Arg
385             390             395             400

Gly Ala Ser Ile Tyr Arg Gly Val Thr Arg His His Gln His Gly Arg
             405             410             415
```

```
Trp Gln Ala Arg Ile Gly Arg Val Ser Gly Asn Lys Asp Leu Tyr Leu
                420                 425                 430

Gly Thr Phe Ser Thr Gln Glu Glu Ala Glu Ala Tyr Asp Val Ala
            435                 440                 445

Ala Ile Lys Phe Arg Gly Leu Asn Ala Val Thr Asn Phe Asp Ile Thr
450                 455                 460

Arg Tyr Asp Val Asp Lys Ile Leu Glu Ser Ser Thr Leu Leu Pro Gly
465                 470                 475                 480

Glu Leu Ala Arg Arg Lys Gly Lys Val Gly Asp Gly Gly Ala Ala
                485                 490                 495

Ala Val Ala Asp Ala Ala Ala Leu Val Gln Ala Gly Asn Val Ala
            500                 505                 510

Glu Trp Lys Met Ala Thr Ala Ala Leu Pro Ala Ala Arg Thr
            515                 520                 525

Glu Gln Gln Gln His Gly His Gly Gly His Gln His His Asp Leu
            530                 535                 540

Leu Pro Ser Asp Ala Phe Ser Val Leu Gln Asp Ile Val Ser Thr Val
545                 550                 555                 560

Asp Ala Ala Gly Ala Pro Pro Arg Ala Pro His Met Ser Met Ala Ala
                565                 570                 575

Thr Ser Leu Gly Asn Ser Arg Glu Gln Ser Pro Asp Arg Gly Val Gly
            580                 585                 590

Gly Gly Gly Gly Gly Val Leu Ala Thr Leu Phe Ala Lys Pro Ala
                595                 600                 605

Ala Ala Ser Lys Leu Tyr Ser Pro Val Pro Leu Asn Thr Trp Ala Ser
610                 615                 620

Pro Ser Pro Ala Val Ser Ser Val Pro Ala Arg Ala Gly Val Ser Ile
625                 630                 635                 640

Ala His Leu Pro Met Phe Ala Ala Trp Thr Asp Ala
                645                 650

<210> SEQ ID NO 96
<211> LENGTH: 440
<212> TYPE: PRT
<213> ORGANISM: Arabidopsis thaliana

<400> SEQUENCE: 96

Met Ala Asp Ser Thr Thr Leu Ser Thr Phe Phe Asp His Ser Gln Thr
1               5                   10                  15

Gln Ile Pro Lys Leu Glu Asp Phe Leu Gly Asp Ser Phe Val Arg Tyr
                20                  25                  30

Ser Asp Asn Gln Thr Glu Thr Gln Asp Ser Ser Ser Leu Thr Pro Phe
            35                  40                  45

Tyr Asp Pro Arg His Arg Thr Val Ala Glu Gly Val Thr Gly Phe Phe
50                  55                  60

Ser Asp His His Gln Pro Asp Phe Lys Thr Ile Asn Ser Gly Pro Glu
65                  70                  75                  80

Ile Phe Asp Asp Ser Thr Thr Ser Asn Ile Gly Gly Thr His Leu Ser
                85                  90                  95

Ser His Val Val Glu Ser Ser Thr Ala Lys Leu Gly Phe Asn Gly
            100                 105                 110

Asp Cys Thr Thr Thr Gly Gly Val Leu Ser Leu Gly Val Asn Asn Thr
            115                 120                 125

Ser Asp Gln Pro Leu Ser Cys Asn Asn Gly Glu Arg Gly Gly Asn Ser
130                 135                 140
```

-continued

```
Asn Lys Lys Lys Thr Val Ser Lys Lys Glu Thr Ser Asp Asp Ser Lys
145                 150                 155                 160

Lys Lys Ile Val Glu Thr Leu Gly Gln Arg Thr Ser Ile Tyr Arg Gly
            165                 170                 175

Val Thr Arg His Arg Trp Thr Gly Arg Tyr Glu Ala His Leu Trp Asp
        180                 185                 190

Asn Ser Cys Arg Arg Glu Gly Gln Ala Arg Lys Gly Arg Gln Val Tyr
            195                 200                 205

Leu Gly Gly Tyr Asp Lys Glu Asp Arg Ala Ala Arg Ala Tyr Asp Leu
        210                 215                 220

Ala Ala Leu Lys Tyr Trp Gly Ser Thr Ala Thr Thr Asn Phe Pro Val
225                 230                 235                 240

Ser Ser Tyr Ser Lys Glu Leu Glu Glu Met Asn His Met Thr Lys Gln
            245                 250                 255

Glu Phe Ile Ala Ser Leu Arg Arg Lys Ser Ser Gly Phe Ser Arg Gly
        260                 265                 270

Ala Ser Ile Tyr Arg Gly Val Thr Arg His His Gln Gln Gly Arg Trp
            275                 280                 285

Gln Ala Arg Ile Gly Arg Val Ala Gly Asn Lys Asp Leu Tyr Leu Gly
        290                 295                 300

Thr Phe Ala Thr Glu Glu Glu Ala Ala Glu Ala Tyr Asp Ile Ala Ala
305                 310                 315                 320

Ile Lys Phe Arg Gly Ile Asn Ala Val Thr Asn Phe Glu Met Asn Arg
            325                 330                 335

Tyr Asp Ile Glu Ala Val Met Asn Ser Ser Leu Pro Val Gly Gly Ala
        340                 345                 350

Ala Ala Lys Arg His Lys Leu Lys Leu Ala Leu Glu Ser Pro Ser Ser
            355                 360                 365

Ser Ser Ser Asp His Asn Leu Gln Gln Gln Gln Leu Leu Pro Ser Ser
        370                 375                 380

Ser Pro Ser Asp Gln Asn Pro Asn Ser Ile Pro Cys Gly Ile Pro Phe
385                 390                 395                 400

Glu Pro Ser Val Leu Tyr Tyr His Gln Asn Phe Phe Gln His Tyr Pro
            405                 410                 415

Leu Val Ser Asp Ser Thr Ile Gln Ala Pro Met Asn Gln Ala Glu Phe
        420                 425                 430

Phe Leu Trp Pro Asn Gln Ser Tyr
        435                 440

<210> SEQ ID NO 97
<211> LENGTH: 651
<212> TYPE: PRT
<213> ORGANISM: Zea mays

<400> SEQUENCE: 97

Met Ala Asn Gly Ser Asn Trp Leu Gly Phe Ser Leu Ser Pro His Thr
1               5                   10                  15

Ala Met Glu Val Pro Ser Val Ser Glu Pro Ala Ser Thr His His Ala
            20                  25                  30

Pro Pro Pro Pro Ser Ser Ser Thr Ile Ser Ser Ser Ser Thr Asn
        35                  40                  45

Asn Thr Ile Ser Ser Asn Phe Leu Phe Ser Pro Met Ala Ser Pro Tyr
    50                  55                  60

Pro Gly Tyr Tyr Cys Val Gly Gly Ala Tyr Gly Asp Gly Thr Ser Ala
```

-continued

```
                65                  70                  75                  80
Ala Gly Val Tyr Tyr Ser His Leu Pro Ala Met Pro Asn Lys Ser Asp
                    85                  90                  95

Asp Gly Thr Leu Cys Asn Met Glu Gly Met Val Pro Ser Ser Pro Pro
                100                 105                 110

Lys Leu Glu Asp Phe Leu Gly Gly Asn Gly Gly Gly Gln Glu Thr
            115                 120                 125

Ala Thr Tyr Tyr Ser His Gln Gln Gln Gly Gln Glu Glu Gly Ala Ser
        130                 135                 140

Arg Asp Tyr Arg Gln Tyr His Tyr Gln His Gln Gln Leu Val Pro Tyr
145                 150                 155                 160

Asn Phe Gln Pro Leu Thr Glu Ala Glu Met Leu Gln Glu Gly Ala Ala
                165                 170                 175

Pro Met Glu Glu Ala Met Ala Ala Ala Lys Asn Phe Leu Leu Ala Ser
                180                 185                 190

Tyr Gly Ala Cys Tyr Ser Asn Glu Glu Thr Arg Pro Leu Ser Leu Ser
            195                 200                 205

Met Met Ser Pro Gly Thr Gln Leu Ser Ser Cys Val Ser Ala Ala Pro
        210                 215                 220

Gln Gln Gln His Gln Met Ala Ala Thr Val Ala Thr Ala Ala Thr Ala
225                 230                 235                 240

Ala Ala Ala Leu Gly Arg Ser Asn Gly Asp Gly Glu Gln Cys Val Gly
                245                 250                 255

Arg Lys Arg Ser Thr Gly Lys Gly Gly His Lys Gln Thr Val His Arg
            260                 265                 270

Lys Ser Ile Asp Thr Phe Gly Gln Arg Thr Ser Arg Tyr Arg Gly Val
        275                 280                 285

Thr Arg His Arg Trp Thr Gly Arg Tyr Glu Ala His Leu Trp Asp Asn
290                 295                 300

Ser Cys Arg Lys Asp Gly Gln Thr Arg Lys Gly Arg Gln Val Tyr Leu
305                 310                 315                 320

Gly Gly Tyr Asp Thr Glu Asp Lys Ala Ala Arg Ala Tyr Asp Leu Ala
                325                 330                 335

Ala Leu Lys Tyr Trp Gly Pro Ala Thr His Val Asn Phe Pro Val Glu
            340                 345                 350

Asn Tyr Arg Asp Glu Leu Glu Glu Met Lys Gly Met Thr Arg Gln Glu
        355                 360                 365

Phe Val Ala His Leu Arg Arg Arg Ser Ser Gly Phe Ser Arg Gly Ala
370                 375                 380

Ser Ile Tyr Arg Gly Val Thr Arg His His Gln Gln Gly Arg Trp Gln
385                 390                 395                 400

Ser Arg Ile Gly Arg Val Ala Gly Asn Lys Asp Leu Tyr Leu Gly Thr
                405                 410                 415

Phe Thr Thr Gln Glu Glu Ala Ala Glu Ala Tyr Asp Ile Ala Ala Ile
            420                 425                 430

Lys Phe Arg Gly Leu Asn Ala Val Thr Asn Phe Asp Ile Ala Arg Tyr
        435                 440                 445

Asp Val Asp Lys Ile Met Glu Ser Ser Thr Leu Leu Ala Val Glu Glu
450                 455                 460

Ala Arg Lys Val Lys Ala Val Glu Ala Ala Ser Ser Ala Pro Met Thr
465                 470                 475                 480

His Thr His Ser Gly Gly Lys Glu Gln Leu Asn Ala Thr Thr Ala Glu
            485                 490                 495
```

```
Glu Thr Ser Ser Ala Gly Trp Arg Met Val Leu His Gly Ser Pro His
            500                 505                 510

Gln Leu Glu Ala Ala Arg Cys Pro Glu Ala Ala Asp Leu Gln Ser Ala
            515                 520                 525

Ile Met Asn Asn Asp Ser His Pro Arg Pro Ser Leu His Gly Ile Ala
530                 535                 540

Gly Leu Asp Ile Glu Cys Ala Val His Asp His His Asp His Leu Asp
545                 550                 555                 560

Val Pro Ala Gly Ser Arg Thr Thr Ala Ala Gly Ser Ile Asn Phe Ser
                565                 570                 575

Asn Ser Ser Ser Gln Val Thr Ser Leu Gly Asn Ser Arg Glu Gly Ser
            580                 585                 590

Pro Glu Arg Leu Gly Leu Ala Met Met Tyr Gly Lys Gln Pro Ser Ser
            595                 600                 605

Ala Val Ser Leu Ala Ala Thr Met Ser Pro Trp Thr Pro Val Ala Ala
            610                 615                 620

Gln Thr Val Ala His Val Leu Lys Gln Gln Pro Asn Val Val Val Ser
625                 630                 635                 640

His Arg Pro Val Phe Ala Ala Trp Ala Asp Ala
                645                 650
```

<210> SEQ ID NO 98
<211> LENGTH: 656
<212> TYPE: PRT
<213> ORGANISM: Medicago truncatula

<400> SEQUENCE: 98

```
Met Lys Arg Met Glu Asn Asn Asp Asp Ser Val Asp Ile Asn Asn Glu
1               5                   10                  15

Asn Asn Trp Leu Gly Phe Ser Leu Ser Pro Gln Met Asn Asn Ile Gly
            20                  25                  30

Val Ser Ser His Thr His His His Ser Leu Pro Ser Ala Thr Ala Thr
            35                  40                  45

Ala Ser Glu Val Val Pro Leu Gln Ala Ser Phe Tyr His Ser Ser Pro
    50                  55                  60

Leu Ser Asn Phe Cys Tyr Ser Tyr Gly Leu Glu His Glu Asn Ala Gly
65                  70                  75                  80

Leu Tyr Ser Leu Leu Pro Ile Met Pro Leu Lys Ser Asp Gly Ser Leu
                85                  90                  95

Phe Glu Met Glu Ala Leu Ser Arg Ser Gln Thr Gln Ala Met Ser Thr
            100                 105                 110

Thr Ser Ala Pro Lys Leu Glu Asn Phe Leu Gly Asn Glu Ala Met Gly
            115                 120                 125

Thr Pro His Tyr Ala Cys Ser Ser Thr Val Thr Glu Thr Met Pro Leu
            130                 135                 140

Ser Leu Asp Ser Met Phe Gln Asn Gln Ile Gln Asn Met Asn Met
145                 150                 155                 160

Asn Asn Gln Gln His Leu Ser Tyr Tyr Asn Ser Thr Leu Arg Asn His
                165                 170                 175

Glu Leu Met Leu Glu Gly Ser Lys Gln Ser Gln Thr Ser Ser Gly Asn
            180                 185                 190

Phe His Gln Ser Asn Met Gly Glu Asp His Gly Leu Ser Gly Leu Lys
            195                 200                 205

Asn Trp Val Leu Arg Asn Phe Pro Ala Ser His Gly His Asp Gln Ser
```

-continued

```
            210                 215                 220
Lys Met Ile Val Pro Val Glu Glu Asn Glu Gly Glu Cys Gly Ser
225                 230                 235                 240

Asn Ile Gly Ser Met Ala Tyr Gly Asp Leu His Ser Leu Ser Leu Ser
                245                 250                 255

Met Ser Pro Ser Ser Gln Ser Ser Cys Val Thr Thr Ser Gln Asn Met
                260                 265                 270

Ser Ser Ala Val Val Glu Asn Ser Val Ala Met Asp Thr Lys Lys Arg
                275                 280                 285

Gly Ser Glu Lys Phe Glu Gln Lys Gln Ile Val His Arg Lys Ser Ile
                290                 295                 300

Asp Thr Phe Gly Gln Arg Thr Ser Gln Tyr Arg Gly Val Thr Arg His
305                 310                 315                 320

Arg Trp Thr Gly Arg Tyr Glu Ala His Leu Trp Asp Asn Ser Cys Lys
                325                 330                 335

Lys Glu Gly Gln Ser Arg Lys Gly Arg Gln Gly Gly Tyr Asp Met Glu
                340                 345                 350

Glu Lys Ala Ala Arg Ala Tyr Asp Gln Ala Ala Leu Lys Tyr Trp Gly
                355                 360                 365

Pro Ser Thr His Ile Asn Phe Pro Leu Glu Asn Tyr Gln Asn Gln Leu
                370                 375                 380

Glu Glu Met Lys Asn Met Thr Arg Gln Glu Tyr Val Ala His Leu Arg
385                 390                 395                 400

Arg Lys Ser Ser Gly Phe Ser Arg Gly Ala Ser Met Tyr Arg Gly Val
                405                 410                 415

Thr Ser Arg His His Gln His Gly Arg Trp Gln Ala Arg Ile Gly Arg
                420                 425                 430

Val Ala Gly Asn Lys Asp Leu Tyr Leu Gly Thr Phe Ser Thr Gln Glu
                435                 440                 445

Glu Ala Ala Glu Ala Tyr Asp Ile Ala Ala Ile Lys Phe Arg Gly Ala
                450                 455                 460

Asn Ala Val Thr Asn Phe Asp Ile Ile Lys Tyr Asp Val Glu Lys Ile
465                 470                 475                 480

Met Ala Ser Ser Asn Leu Leu Asn Ile Glu Gln Ala Arg Arg Asn Lys
                485                 490                 495

Glu Val Val Asp Ile Ser Ser Thr Gln Tyr Ile Asp Gln Asn Lys Pro
                500                 505                 510

Ser Ser Ala Tyr Asp Asn Asn Ser Thr Gln Glu Ala Ile Ser Met Gln
                515                 520                 525

Lys Ser Met Val Leu Tyr Gln Ser Ser Gln His Gln Gln Leu Gln Gln
                530                 535                 540

Asn Gln Pro Arg Phe Glu Asn Glu Arg Thr His Gln Thr Phe Ser Ser
545                 550                 555                 560

Val Ser Leu Asp Asn Met Phe His Gln Glu Val Val Glu Glu Ala Ser
                565                 570                 575

Lys Met Arg Thr His Val Ser Asn Ala Ser Ser Leu Ala Thr Ser Leu
                580                 585                 590

Ser Ser Ser Arg Glu Gly Thr Pro Asp Arg Thr Ser Leu Gln Asn Leu
                595                 600                 605

Ser Gly Ile Met Pro Thr Ala Ser Lys Leu Leu Val Thr Ser Ala
                610                 615                 620

Pro Asn Ser Asn Leu Asn Ser Trp Asp Pro Ser Gln His Leu Arg Pro
625                 630                 635                 640
```

Ser Leu Ser Leu Pro Gln Met Pro Val Phe Ala Ala Trp Thr Asp Ala
            645                 650                 655

<210> SEQ ID NO 99
<211> LENGTH: 546
<212> TYPE: PRT
<213> ORGANISM: Glycine max

<400> SEQUENCE: 99

Met Lys Arg Met Asn Glu Ser Asn Asn Thr Asp Asp Gly Asn Asn His
1               5                   10                  15

Asn Trp Leu Gly Phe Ser Leu Ser Pro His Met Lys Met Glu Val Thr
            20                  25                  30

Ser Ala Ala Thr Val Ser Asp Asn Asn Val Pro Thr Thr Phe Tyr Met
            35                  40                  45

Ser Pro Ser His Met Ser Asn Ser Gly Met Cys Tyr Ser Val Gly Glu
        50                  55                  60

Asn Gly Asn Phe His Ser Pro Leu Thr Val Met Pro Leu Lys Ser Asp
65                  70                  75                  80

Gly Ser Leu Gly Ile Leu Glu Ala Leu Asn Arg Ser Gln Thr Gln Val
                85                  90                  95

Met Val Pro Thr Ser Pro Lys Leu Glu Asp Phe Leu Gly Gly Ala
            100                 105                 110

Thr Met Gly Thr His Glu Tyr Gly Asn His Glu Arg Gly Leu Ser Leu
            115                 120                 125

Asp Ser Ile Tyr Tyr Asn Ser Gln Asn Ala Glu Ala Gln Pro Asn Arg
130                 135                 140

Asn Leu Leu Ser His Pro Phe Arg Gln Gln Gly His Ala Pro Ser Glu
145                 150                 155                 160

Glu Glu Ala Thr Lys Glu Thr His Val Ser Val Met Pro Gln Met Thr
                165                 170                 175

Gly Gly Gly Leu Gln Asn Trp Ile Leu Glu Gln Gln Met Asn Cys Gly
            180                 185                 190

Ile Trp Asn Glu Arg Ser Gly Val Ser Val Gly Thr Val Gly Cys Gly
            195                 200                 205

Glu Leu Gln Ser Leu Ser Leu Ser Met Ser Pro Gly Ser Gln Ser Ser
210                 215                 220

Cys Val Thr Ala Pro Ser Gly Thr Asp Ser Val Ala Val Asp Ala Lys
225                 230                 235                 240

Lys Arg Gly His Ala Lys Leu Gly Gln Lys Gln Pro Val His Arg Lys
                245                 250                 255

Ser Ile Asp Thr Phe Gly Gln Arg Thr Ser Gln Tyr Arg Gly Val Thr
            260                 265                 270

Arg His Arg Trp Thr Gly Arg Tyr Glu Ala His Leu Trp Asp Asn Ser
        275                 280                 285

Cys Lys Lys Glu Gly Gln Thr Arg Lys Gly Arg Gln Gly Gly Tyr Asp
290                 295                 300

Met Glu Glu Lys Ala Ala Arg Ala Tyr Asp Leu Ala Ala Leu Lys Tyr
305                 310                 315                 320

Trp Gly Pro Ser Thr His Ile Asn Phe Ser Ile Glu Asn Tyr Gln Val
                325                 330                 335

Gln Leu Glu Glu Met Lys Asn Met Ser Arg Gln Glu Tyr Val Ala His
            340                 345                 350

Leu Arg Arg Lys Ser Ser Gly Phe Ser Arg Gly Ala Ser Ile Tyr Arg

```
                355                 360                 365
Gly Val Thr Arg His His Gln His Gly Arg Trp Gln Ala Arg Ile Gly
        370                 375                 380

Arg Val Ala Gly Asn Lys Asp Leu Tyr Leu Gly Thr Phe Ser Thr Gln
385                 390                 395                 400

Glu Glu Ala Ala Glu Ala Tyr Asp Ile Ala Ile Lys Phe Arg Gly
                405                 410                 415

Ala Asn Ala Val Thr Asn Phe Asp Ile Ser Arg Tyr Asp Val Glu Arg
                420                 425                 430

Ile Met Ala Ser Ser Asn Leu Leu Ala Gly Glu Leu Ala Arg Arg Asn
                435                 440                 445

Lys Asp Asn Asp Pro Arg Asn Glu Ala Ile Asp Tyr Asn Lys Ser Val
        450                 455                 460

Phe Lys Gln Glu Thr Thr Met Lys Met Ile Arg Ser Gly Arg Cys Leu
465                 470                 475                 480

Ser Ser Ser Arg Glu Ala Ser Pro Glu Lys Met Gly Pro Ser Leu Leu
                485                 490                 495

Phe Pro Lys Pro Pro Met Glu Thr Lys Ile Val Asn Pro Ile Gly
                500                 505                 510

Thr Ser Val Thr Ser Trp Leu Pro Ser Pro Thr Val Gln Met Arg Pro
                515                 520                 525

Ser Pro Ala Ile Ser Leu Ser His Leu Pro Val Phe Ala Ala Trp Thr
        530                 535                 540

Asp Thr
545

<210> SEQ ID NO 100
<211> LENGTH: 415
<212> TYPE: PRT
<213> ORGANISM: Arabidopsis thaliana

<400> SEQUENCE: 100

Met Lys Lys Trp Leu Gly Phe Ser Leu Thr Pro Pro Leu Arg Ile Cys
1               5                   10                  15

Asn Ser Glu Glu Glu Leu Arg His Asp Gly Ser Asp Val Trp Arg
            20                  25                  30

Tyr Asp Ile Asn Phe Asp His His His Asp Glu Asp Val Pro Lys
                35                  40                  45

Val Glu Asp Leu Leu Ser Asn Ser His Gln Thr Glu Tyr Pro Ile Asn
    50                  55                  60

His Asn Gln Thr Asn Val Asn Cys Thr Thr Val Val Asn Arg Leu Asn
65                  70                  75                  80

Pro Pro Gly Tyr Leu Leu His Asp Gln Thr Val Val Thr Pro His Tyr
                85                  90                  95

Pro Asn Leu Asp Pro Asn Leu Ser Asn Asp Tyr Gly Gly Phe Glu Arg
            100                 105                 110

Val Gly Ser Val Ser Val Phe Lys Ser Trp Leu Glu Gln Gly Thr Pro
        115                 120                 125

Ala Phe Pro Leu Ser Ser His Tyr Val Thr Glu Glu Ala Gly Thr Ser
130                 135                 140

Asn Asn Ile Ser His Phe Ser Asn Glu Glu Thr Gly Tyr Asn Thr Asn
145                 150                 155                 160

Gly Ser Met Leu Ser Leu Ala Leu Ser His Gly Ala Cys Ser Asp Leu
                165                 170                 175
```

Ile Asn Glu Ser Asn Val Ser Ala Arg Val Glu Pro Val Lys Val
                180                 185                 190

Asp Glu Lys Arg Lys Arg Leu Val Val Lys Pro Gln Val Lys Glu Ser
            195                 200                 205

Val Pro Arg Lys Ser Val Asp Ser Tyr Gly Gln Arg Thr Ser Gln Tyr
210                 215                 220

Arg Gly Val Thr Arg His Arg Trp Thr Gly Arg Tyr Glu Ala His Leu
225                 230                 235                 240

Trp Asp Asn Ser Cys Lys Lys Glu Gly Gln Thr Arg Arg Gly Arg Gln
                245                 250                 255

Val Tyr Leu Gly Gly Tyr Asp Glu Glu Glu Lys Ala Ala Arg Ala Tyr
            260                 265                 270

Asp Leu Ala Ala Leu Lys Tyr Trp Gly Pro Thr Thr His Leu Asn Phe
275                 280                 285

Pro Leu Ser Asn Tyr Glu Lys Glu Ile Glu Glu Leu Asn Asn Met Asn
            290                 295                 300

Arg Gln Glu Phe Val Ala Met Leu Arg Arg Asn Ser Ser Gly Phe Ser
305                 310                 315                 320

Arg Gly Ala Ser Val Tyr Arg Gly Val Thr Arg His His Gln His Gly
                325                 330                 335

Arg Trp Gln Ala Arg Ile Gly Arg Val Ala Gly Asn Lys Asp Leu Tyr
            340                 345                 350

Leu Gly Thr Phe Ser Thr Gln Glu Glu Ala Ala Glu Ala Tyr Asp Ile
355                 360                 365

Ala Ala Ile Lys Phe Arg Gly Leu Asn Ala Val Thr Asn Phe Asp Ile
            370                 375                 380

Asn Arg Tyr Asp Val Lys Arg Ile Cys Ser Ser Ser Thr Ile Val Asp
385                 390                 395                 400

Ser Asp Gln Ala Lys His Ser Pro Thr Ser Ser Gly Ala Gly His
                405                 410                 415

<210> SEQ ID NO 101
<211> LENGTH: 428
<212> TYPE: PRT
<213> ORGANISM: Zea mays

<400> SEQUENCE: 101

Met Ser Pro Pro Thr Asn Gly Ala Ile Ser Leu Ala Tyr Ala Pro Ser
1               5                   10                  15

Met Met Leu Gly Ala Gly Ala Leu Thr Asn Pro Pro Leu Leu Pro Phe
            20                  25                  30

Asp Gly Phe Thr Asp Glu Asp Phe Leu Ala Ser Ala Asp Ala Ala Leu
        35                  40                  45

Leu Gly Glu Ala Gly Thr Asp Gln Thr Leu Leu Leu Pro Ser Cys
    50                  55                  60

Pro Gly Ala Asn Cys Cys Gly Gly Ser Ser Asp Gln Gly Leu Gly
65                  70                  75                  80

Ala Leu Ala Cys Glu Val Thr Thr Ala Gly Ser Phe Ser Leu Leu Gly
                85                  90                  95

Gln Pro Ala Pro Gly Gln Val Ser Trp Glu Val Thr Thr Ala Val Ala
            100                 105                 110

Ala Asp Arg Asn Thr Phe Ser Arg Ala Arg Asp Pro Ala Pro Ser Pro
        115                 120                 125

Pro Pro Ser Pro Ala Leu Pro Leu Val Gln Thr Thr Ser Gln Ser Gln
    130                 135                 140

```
Arg Thr Ser Ile Tyr Arg Gly Val Thr Arg His Arg Trp Thr Gly Arg
145                 150                 155                 160

Tyr Glu Ala His Leu Trp Asp Asn Thr Cys Arg Lys Glu Gly Gln Lys
                165                 170                 175

Arg Lys Gly Arg Gln Val Tyr Leu Gly Gly Tyr Asp Lys Glu Asp Lys
            180                 185                 190

Ala Ala Arg Ala Tyr Asp Ile Ala Ala Leu Lys Tyr Trp Gly Asp Asn
            195                 200                 205

Ala Thr Thr Asn Phe Pro Arg Glu Asn Tyr Ile Arg Glu Ile Gln Asp
210                 215                 220

Met Gln Asn Met Asn Arg Arg Asp Val Val Ala Ser Leu Arg Arg Lys
225                 230                 235                 240

Ser Ser Gly Phe Ser Arg Gly Ala Ser Ile Tyr Arg Gly Val Thr Lys
                245                 250                 255

His His Gln His Gly Arg Trp Gln Ala Arg Ile Gly Arg Val Ala Gly
                260                 265                 270

Asn Lys Asp Leu Tyr Leu Gly Thr Phe Ala Thr Glu Gln Glu Ala Ala
            275                 280                 285

Glu Ala Tyr Asp Ile Ala Ala Leu Lys Phe Arg Gly Glu Asn Ala Val
            290                 295                 300

Thr Asn Phe Glu Pro Ser Arg Tyr Asn Leu Leu Ala Ile Ala Gln Arg
305                 310                 315                 320

Asp Ile Pro Ile Leu Gly Arg Lys Leu Ile Gln Lys Pro Ala Pro Glu
                325                 330                 335

Ala Glu Asp Gln Ala Ala Leu Ser Arg Ser Phe Ser Gln Ser Gln
            340                 345                 350

Gln Ser Ser Asn Ser Leu Pro Pro Tyr Phe Leu Thr Asn Leu Leu Gln
            355                 360                 365

Pro Leu Pro Ser Gln His Ser Leu Ala Gln Ala Leu Pro Ser Tyr Asn
            370                 375                 380

Asn Leu Gly Phe Gly Glu Pro Ser Leu Tyr Trp Pro Cys Pro Cys Gly
385                 390                 395                 400

Asp Pro Gly Glu Gln Lys Val Gln Leu Gly Ser Lys Leu Glu Ile Val
                405                 410                 415

Asp Gly Leu Val Gln Leu Ala Asn Ser Ala Ala Asn
            420                 425

<210> SEQ ID NO 102
<211> LENGTH: 438
<212> TYPE: PRT
<213> ORGANISM: Arabidopsis thaliana

<400> SEQUENCE: 102

Met Lys Lys Arg Leu Thr Thr Ser Thr Cys Ser Ser Ser Pro Ser Ser
1               5                   10                  15

Ser Val Ser Ser Ser Thr Thr Ser Ser Pro Ile Gln Ser Glu Ala
            20                  25                  30

Pro Arg Pro Lys Arg Ala Lys Arg Ala Lys Lys Ser Ser Pro Ser Gly
            35                  40                  45

Asp Lys Ser His Asn Pro Thr Ser Pro Ala Ser Thr Arg Arg Ser Ser
        50                  55                  60

Ile Tyr Arg Gly Val Thr Arg His Arg Trp Thr Gly Arg Phe Glu Ala
65                  70                  75                  80

His Leu Trp Asp Lys Ser Ser Trp Asn Ser Ile Gln Asn Lys Lys Gly
```

```
                    85                  90                  95
Lys Gln Val Tyr Leu Gly Ala Tyr Asp Ser Glu Glu Ala Ala His
                100                 105                 110

Thr Tyr Asp Leu Ala Ala Leu Lys Tyr Trp Gly Pro Asp Thr Ile Leu
                115                 120                 125

Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
                180                 185                 190

Leu Tyr Leu Gly Thr Tyr Asn Thr Gln Glu Ala Ala Ala Tyr
                195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
                260                 265                 270

Val Lys Gln Gln Tyr Val Glu Glu Pro Gln Glu Glu Glu Lys
                275                 280                 285

Glu Glu Glu Lys Ala Glu Gln Gln Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
                340                 345                 350

Asn Glu Asn Pro Ile Glu Tyr Pro Glu Leu Phe Asn Glu Leu Ala Phe
                355                 360                 365

Glu Asp Asn Ile Asp Phe Met Phe Asp Gly Lys His Glu Cys Leu
    370                 375                 380

Asn Leu Glu Asn Leu Asp Cys Cys Val Val Gly Arg Glu Ser Pro
385                 390                 395                 400

Ser Ser Ser Ser Pro Leu Ser Cys Leu Ser Thr Asp Ser Ala Ser Ser
                405                 410                 415

Thr Thr Thr Thr Thr Thr Ser Val Ser Cys Asn Tyr Leu Phe Gln Gly
                420                 425                 430

Leu Phe Val Gly Ser Glu
                435

<210> SEQ ID NO 103
<211> LENGTH: 432
<212> TYPE: PRT
<213> ORGANISM: Arabidopsis thaliana

<400> SEQUENCE: 103

Met Trp Asp Leu Asn Asp Ala Pro His Gln Thr Gln Arg Glu Glu Glu
  1               5                  10                  15
```

-continued

```
Ser Glu Glu Phe Cys Tyr Ser Ser Pro Ser Lys Arg Val Gly Ser Phe
             20                  25                  30

Ser Asn Ser Ser Ser Ala Val Val Ile Glu Asp Gly Ser Asp Asp
         35                  40                  45

Asp Glu Leu Asn Arg Val Arg Pro Asn Asn Pro Leu Val Thr His Gln
     50                  55                  60

Phe Phe Pro Glu Met Asp Ser Asn Gly Gly Val Ala Ser Gly Phe
 65              70                  75                  80

Pro Arg Ala His Trp Phe Gly Val Lys Phe Cys Gln Ser Asp Leu Ala
                 85                  90                  95

Thr Gly Ser Ser Ala Gly Lys Ala Thr Asn Val Ala Ala Ala Val Val
             100                 105                 110

Glu Pro Ala Gln Pro Leu Lys Lys Ser Arg Arg Gly Pro Arg Ser Arg
         115                 120                 125

Ser Ser Gln Tyr Arg Gly Val Thr Phe Tyr Arg Arg Thr Gly Arg Trp
     130                 135                 140

Glu Ser His Ile Trp Asp Cys Gly Lys Gln Val Tyr Leu Gly Gly Phe
145                 150                 155                 160

Asp Thr Ala His Ala Ala Arg Ala Tyr Asp Arg Ala Ala Ile Lys
                 165                 170                 175

Phe Arg Gly Val Glu Ala Asp Ile Asn Phe Asn Ile Asp Asp Tyr Asp
                 180                 185                 190

Asp Asp Leu Lys Gln Met Thr Asn Leu Thr Lys Glu Glu Phe Val His
         195                 200                 205

Val Leu Arg Arg Gln Ser Thr Gly Phe Pro Arg Gly Ser Ser Lys Tyr
 210                 215                 220

Arg Gly Val Thr Leu His Lys Cys Gly Arg Trp Glu Ala Arg Met Gly
225                 230                 235                 240

Gln Phe Leu Gly Lys Lys Tyr Val Tyr Leu Gly Leu Phe Asp Thr Glu
                 245                 250                 255

Val Glu Ala Ala Arg Ala Tyr Asp Lys Ala Ala Ile Lys Cys Asn Gly
             260                 265                 270

Lys Asp Ala Val Thr Asn Phe Asp Pro Ser Ile Tyr Asp Glu Glu Leu
         275                 280                 285

Asn Ala Glu Ser Ser Gly Asn Pro Thr Thr Pro Gln Asp His Asn Leu
 290                 295                 300

Asp Leu Ser Leu Gly Asn Ser Ala Asn Ser Lys His Lys Ser Gln Asp
305                 310                 315                 320

Met Arg Leu Arg Met Asn Gln Gln Gln Asp Ser Leu His Ser Asn
                 325                 330                 335

Glu Val Leu Gly Leu Gly Gln Thr Gly Met Leu Asn His Thr Pro Asn
             340                 345                 350

Ser Asn His Gln Phe Pro Gly Ser Ser Asn Ile Gly Ser Gly Gly Gly
         355                 360                 365

Phe Ser Leu Phe Pro Ala Ala Glu Asn His Arg Phe Asp Gly Arg Ala
 370                 375                 380

Ser Thr Asn Gln Val Leu Thr Asn Ala Ala Ser Ser Gly Phe Ser
385                 390                 395                 400

Pro His His His Asn Gln Ile Phe Asn Ser Thr Ser Thr Pro His Gln
                 405                 410                 415

Asn Trp Leu Gln Thr Asn Gly Phe Gln Pro Pro Leu Met Arg Pro Ser
         420                 425                 430
```

```
<210> SEQ ID NO 104
<211> LENGTH: 449
<212> TYPE: PRT
<213> ORGANISM: Arabidopsis thaliana

<400> SEQUENCE: 104

Met Leu Asp Leu Asn Leu Asn Ala Asp Ser Pro Glu Ser Thr Gln Tyr
 1               5                  10                  15

Gly Gly Asp Ser Tyr Leu Asp Arg Gln Thr Ser Asp Asn Ser Ala Gly
                20                  25                  30

Asn Arg Val Glu Glu Ser Gly Thr Ser Thr Ser Ser Val Ile Asn Ala
            35                  40                  45

Asp Gly Asp Glu Asp Ser Cys Ser Thr Arg Ala Phe Thr Leu Ser Phe
        50                  55                  60

Asp Ile Leu Lys Val Gly Ser Ser Ser Gly Gly Asp Glu Ser Pro Ala
 65                  70                  75                  80

Ala Ser Ala Ser Val Thr Lys Glu Phe Phe Pro Val Ser Gly Asp Cys
                85                  90                  95

Gly His Leu Arg Asp Val Glu Gly Ser Ser Ser Arg Asn Trp Ile
            100                 105                 110

Asp Leu Ser Phe Asp Arg Ile Gly Asp Gly Glu Thr Lys Leu Val Thr
        115                 120                 125

Pro Val Pro Thr Pro Ala Pro Val Pro Ala Gln Val Lys Lys Ser Arg
    130                 135                 140

Arg Gly Pro Arg Ser Arg Ser Ser Gln Tyr Arg Gly Val Thr Phe Tyr
145                 150                 155                 160

Arg Arg Thr Gly Arg Trp Glu Ser His Ile Trp Asp Cys Gly Lys Gln
                165                 170                 175

Val Tyr Leu Gly Gly Phe Asp Thr Ala His Ala Ala Arg Ala Tyr
            180                 185                 190

Asp Arg Ala Ala Ile Lys Phe Arg Gly Val Asp Ala Asp Ile Asn Phe
        195                 200                 205

Thr Leu Gly Asp Tyr Glu Glu Asp Met Lys Gln Val Gln Asn Leu Ser
    210                 215                 220

Lys Glu Glu Phe Val His Ile Leu Arg Arg Gln Ser Thr Gly Phe Ser
225                 230                 235                 240

Arg Gly Ser Ser Lys Tyr Arg Gly Val Thr Leu His Lys Cys Gly Arg
                245                 250                 255

Trp Glu Ala Arg Met Gly Gln Phe Leu Gly Lys Lys Ala Tyr Asp Lys
            260                 265                 270

Ala Ala Ile Asn Thr Asn Gly Arg Glu Ala Val Thr Asn Phe Glu Met
        275                 280                 285

Ser Ser Tyr Gln Asn Glu Ile Asn Ser Glu Ser Asn Asn Ser Glu Ile
    290                 295                 300

Asp Leu Asn Leu Gly Ile Ser Leu Ser Thr Gly Asn Ala Pro Lys Gln
305                 310                 315                 320

Asn Gly Arg Leu Phe His Phe Pro Ser Asn Thr Tyr Glu Thr Gln Arg
                325                 330                 335

Gly Val Ser Leu Arg Ile Asp Asn Glu Tyr Met Gly Lys Pro Val Asn
            340                 345                 350

Thr Pro Leu Pro Tyr Gly Ser Ser Asp His Arg Leu Tyr Trp Asn Gly
        355                 360                 365

Ala Cys Pro Ser Tyr Asn Asn Pro Ala Glu Gly Arg Ala Thr Glu Lys
    370                 375                 380
```

Arg Ser Glu Ala Glu Gly Met Met Ser Asn Trp Gly Trp Gln Arg Pro
385                 390                 395                 400

Gly Gln Thr Ser Ala Val Arg Pro Gln Pro Gly Pro Gln Pro Pro
            405                 410                 415

Pro Leu Phe Ser Val Ala Ala Ala Ser Ser Gly Phe Ser His Phe Arg
        420                 425                 430

Pro Gln Pro Pro Asn Asp Asn Ala Thr Arg Gly Tyr Phe Tyr Pro His
        435                 440                 445

Pro

<210> SEQ ID NO 105
<211> LENGTH: 663
<212> TYPE: DNA
<213> ORGANISM: Zea mays
<220> FEATURE:
<221> NAME/KEY: CDS
<222> LOCATION: (1)...(663)

<400> SEQUENCE: 105

| | |
|---|---:|
| atg gag gcg ctg agc ggg cgg gta ggc gtc aag tgc ggg cgg tgg aac<br>Met Glu Ala Leu Ser Gly Arg Val Gly Val Lys Cys Gly Arg Trp Asn<br>1               5                   10                  15 | 48 |
| cct acg gcg gag cag gtg aag gtc ctg acg gag ctc ttc cgc gcg ggg<br>Pro Thr Ala Glu Gln Val Lys Val Leu Thr Glu Leu Phe Arg Ala Gly<br>            20                  25                  30 | 96 |
| ctg cgg acg ccc agc acg gag cag atc cag cgc atc tcc acc cac ctc<br>Leu Arg Thr Pro Ser Thr Glu Gln Ile Gln Arg Ile Ser Thr His Leu<br>        35                  40                  45 | 144 |
| agc gcc ttc ggc aag gtg gag agc aag aac gtc ttc tac tgg ttc cag<br>Ser Ala Phe Gly Lys Val Glu Ser Lys Asn Val Phe Tyr Trp Phe Gln<br>    50                  55                  60 | 192 |
| aac cac aag gcc cgc gag cgc cac cac cac aag aag cgc cgc cgc ggc<br>Asn His Lys Ala Arg Glu Arg His His His Lys Lys Arg Arg Arg Gly<br>65                  70                  75                  80 | 240 |
| gcg tcg tcg tcc tcc ccc gac agc ggc agc ggc agg gga agc aac aac<br>Ala Ser Ser Ser Ser Pro Asp Ser Gly Ser Gly Arg Gly Ser Asn Asn<br>                85                  90                  95 | 288 |
| gag gaa gac ggc cgt ggt gcc gcc tcg cag tcg cac gac gcc gac gcc<br>Glu Glu Asp Gly Arg Gly Ala Ala Ser Gln Ser His Asp Ala Asp Ala<br>            100                 105                 110 | 336 |
| gac gcc gac ctc gtg ctg caa ccg cca gag agc aag cgg gag gcc aga<br>Asp Ala Asp Leu Val Leu Gln Pro Pro Glu Ser Lys Arg Glu Ala Arg<br>        115                 120                 125 | 384 |
| agc tat ggc cac cat cac cgg ctc gtg aca tgc tac gtc agg gac gtg<br>Ser Tyr Gly His His His Arg Leu Val Thr Cys Tyr Val Arg Asp Val<br>    130                 135                 140 | 432 |
| gtg gag cag cag gag gcg tcg ccg tcg tgg gag cgg ccg acg agg gag<br>Val Glu Gln Gln Glu Ala Ser Pro Ser Trp Glu Arg Pro Thr Arg Glu<br>145                 150                 155                 160 | 480 |
| gtg gag acg cta gag ctc ttc ccc ctc aag tcg tac ggc gac ctc gag<br>Val Glu Thr Leu Glu Leu Phe Pro Leu Lys Ser Tyr Gly Asp Leu Glu<br>                165                 170                 175 | 528 |
| gcg gcg gag aag gtc cgg tcg tac gtc aga ggc atc gcc gcc acc agc<br>Ala Ala Glu Lys Val Arg Ser Tyr Val Arg Gly Ile Ala Ala Thr Ser<br>            180                 185                 190 | 576 |
| gag cag tgc agg gag ttg tcc ttc ttc gac gtc tcc gcc ggc cgg gat<br>Glu Gln Cys Arg Glu Leu Ser Phe Phe Asp Val Ser Ala Gly Arg Asp<br>        195                 200                 205 | 624 |
| ccg ccg ctc gag ctc agg ctc tgc agc ttc ggt ccc tag<br>Pro Pro Leu Glu Leu Arg Leu Cys Ser Phe Gly Pro | 663 |

<210> SEQ ID NO 106
<211> LENGTH: 220
<212> TYPE: PRT
<213> ORGANISM: Zea mays

<400> SEQUENCE: 106

Met Glu Ala Leu Ser Gly Arg Val Gly Val Lys Cys Gly Arg Trp Asn
1               5                   10                  15

Pro Thr Ala Glu Gln Val Lys Val Leu Thr Glu Leu Phe Arg Ala Gly
            20                  25                  30

Leu Arg Thr Pro Ser Thr Glu Gln Ile Gln Arg Ile Ser Thr His Leu
        35                  40                  45

Ser Ala Phe Gly Lys Val Glu Ser Lys Asn Val Phe Tyr Trp Phe Gln
    50                  55                  60

Asn His Lys Ala Arg Glu Arg His His Lys Lys Arg Arg Gly
65                  70                  75                  80

Ala Ser Ser Ser Pro Asp Ser Gly Ser Arg Gly Ser Asn Asn
                85                  90                  95

Glu Glu Asp Gly Arg Gly Ala Ala Ser Gln Ser His Asp Ala Asp Ala
            100                 105                 110

Asp Ala Asp Leu Val Leu Gln Pro Pro Glu Ser Lys Arg Glu Ala Arg
        115                 120                 125

Ser Tyr Gly His His His Arg Leu Val Thr Cys Tyr Val Arg Asp Val
    130                 135                 140

Val Glu Gln Gln Glu Ala Ser Pro Ser Trp Glu Arg Pro Thr Arg Glu
145                 150                 155                 160

Val Glu Thr Leu Glu Leu Phe Pro Leu Lys Ser Tyr Gly Asp Leu Glu
                165                 170                 175

Ala Ala Glu Lys Val Arg Ser Tyr Val Arg Gly Ile Ala Ala Thr Ser
            180                 185                 190

Glu Gln Cys Arg Glu Leu Ser Phe Phe Asp Val Ser Ala Gly Arg Asp
        195                 200                 205

Pro Pro Leu Glu Leu Arg Leu Cys Ser Phe Gly Pro
    210                 215                 220

<210> SEQ ID NO 107
<211> LENGTH: 24
<212> TYPE: DNA
<213> ORGANISM: Artificial Sequence
<220> FEATURE:
<223> OTHER INFORMATION: attB1 variant

<400> SEQUENCE: 107
caagttcgta caaaaaagca ggct                                          24

<210> SEQ ID NO 108
<211> LENGTH: 23
<212> TYPE: DNA
<213> ORGANISM: Artificial Sequence
<220> FEATURE:
<223> OTHER INFORMATION: attB1 variant

<400> SEQUENCE: 108
caagtttgta caaaaaggac tct                                           23

<210> SEQ ID NO 109
<211> LENGTH: 24

```
<212> TYPE: DNA
<213> ORGANISM: Artificial Sequence
<220> FEATURE:
<223> OTHER INFORMATION: attB1 variant

<400> SEQUENCE: 109
caagtgcata caaaaaggac tgct                                            24

<210> SEQ ID NO 110
<211> LENGTH: 17747
<212> TYPE: DNA
<213> ORGANISM: Artificial Sequence
<220> FEATURE:
<223> OTHER INFORMATION: PHP32371
<220> FEATURE:
<221> NAME/KEY: misc_feature
<222> LOCATION: (4310)...(4817)
<223> OTHER INFORMATION: Rab17 promoter
<220> FEATURE:
<221> NAME/KEY: misc_feature
<222> LOCATION: (4818)...(4912)
<223> OTHER INFORMATION: Rab17 5' UTR
<220> FEATURE:
<221> NAME/KEY: misc_feature
<222> LOCATION: (4951)...(4974)
<223> OTHER INFORMATION: attB1
<220> FEATURE:
<221> NAME/KEY: misc_feature
<222> LOCATION: (5036)...(6496)
<223> OTHER INFORMATION: FLP
<220> FEATURE:
<221> NAME/KEY: misc_feature
<222> LOCATION: (6513)...(6536)
<223> OTHER INFORMATION: attB2
<220> FEATURE:
<221> NAME/KEY: misc_feature
<222> LOCATION: (6551)...(6868)
<223> OTHER INFORMATION: PinII term

<400> SEQUENCE: 110
gtttacccgc caatatatcc tgtcaaacac tgatagttta aactgaaggc gggaaacgac     60
aatctgatca tgagcggaga attaagggag tcacgttatg accccgccg atgacgcggg     120 acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacca gagctggtca cctttgtcca ccaagatgga actgcggccg    300
ctcattaatt aagtcaggcg cgcctctagt tgaagacacg ttcatgtctt catcgtaaga    360
agacactcag tagtcttcgg ccagaatggc catctggatt cagcaggcct agaaggccat    420
ttaaatcctg aggatctggt cttcctaagg acccgggata tcgctatcaa ctttgtatag    480
aaaagttggg ccgaattcga gctcggtacg gccagaatgg cccggaccgg gttaccgaat    540
tcgagctcgt accctgggat ccggtgcgg gcctcttcgc tattacgcca gctggcgaaa    600
gggggatgtg ctgcaaggcg attaagttgg gtaacgccag ggttttccca gtcacgacgt    660
tgtaaaacga cggccagtgc caagctcaga tcagcttgca tgcctgcagt gcagcgtgac    720
ccggtcgtgc ccctctctag agataatgag cattgcatgt ctaagttata aaaaattacc    780
acatattttt tttgtcacac ttgtttgaag tgcagtttat ctatctttat acatatattt    840
aaactttact ctacgaataa tataatctat agtactacaa taatatcagt gttttagaga    900
atcatataaa tgaacagtta gacatggtct aaaggacaat tgagtatttt gacaacagga    960
ctctacagtt ttatcttttt agtgtgcatg tgttctcctt tttttttgca aatagcttca   1020
cctatataat acttcatcca ttttattagt acatccattt agggtttagg gttaatggtt   1080
```

```
tttatagact aattttttta gtacatctat tttattctat tttagcctct aaattaagaa      1140
aactaaaact ctattttagt tttttttattt aataatttag atataaaata gaataaaata      1200
aagtgactaa aaattaaaca aatacccttt aagaaattaa aaaaactaag gaaacatttt      1260
tcttgtttcg agtagataat gccagcctgt taaacgccgt cgacgagtct aacggacacc      1320
aaccagcgaa ccagcagcgt cgcgtcgggc aagcgaagc agacggcacg gcatctctgt       1380
cgctgcctct ggaccctct cgagagttcc gctccaccgt tggacttgct ccgctgtcgg       1440
catccagaaa ttgcgtggcg gagcggcaga cgtgagccgg cacggcaggc ggcctcctcc      1500
tcctctcacg gcacggcagc tacggggat tcctttccca ccgctccttc gctttcccctt     1560 cctcgcccgc cgtaataaat agacaccccc tccacaccct ctttcccaa cctcgtgttg      1620 ttcggagcgc acacacac aaccagatct cccccaaatc cacccgtcgg cacctccgct       1680
tcaaggtacg ccgctcgtcc tcccccccc cccctctcta ccttctctag atcggcgttc       1740
cggtccatgg ttagggcccg gtagttctac ttctgttcat gtttgtgtta gatccgtgtt     1800
tgtgttagat ccgtgctgct agcgttcgta cacgatgcg acctgtacgt cagacacgtt     1860
ctgattgcta acttgccagt gttttctcttt ggggaatcct gggatggctc tagccgttcc     1920
gcagacggga tcgatttcat gattttttt gtttcgttgc ataggggttg gtttgccctt       1980
ttcctttatt tcaatatatg ccgtgcactt gtttgtcggg tcatcttttc atgctttttt      2040
ttgtcttggt tgtgatgatg tggtctggtt gggcggtcgt tctagatcgg agtagaattc     2100
tgtttcaaac tacctggtgg atttattaat tttggatctg tatgtgtgtg ccatacatat      2160
tcatagttac gaattgaaga tgatggatgg aaatatcgat ctaggatagg tatacatgtt     2220
gatgcgggtt ttactgatgc atatacagag atgctttttg ttcgcttggt tgtgatgatg    2280
tggtgtggtt gggcggtcgt tcattcgttc tagatcggag tagaatactg tttcaaacta    2340
cctggtgtat ttattaattt tggaactgta tgtgtgtgtc atacatcttc atagttacga    2400
gtttaagatg gatggaaata tcgatctagg ataggtatac atgttgatgt gggttttact    2460
gatgcatata catgatggca tatgcagcat ctattcatat gctctaacct tgagtaccta    2520
tctattataa taaacaagta tgttttataa ttatttgat cttgatatac ttggatgatg    2580
gcatatgcag cagctatatg tggattttttt tagccctgcc ttcatacgct atttatttgc    2640
ttggtactgt ttcttttgtc gatgctcacc ctgttgtttg gtgttacttc tgcaggtcga    2700
ctctagagga tccaccatgg ctagcgaagt tcctattccg aagttcctat tctctagaaa    2760
gtataggaac ttcagatctg ccctgtccaa caagttcatc ggcgacgaca tgaagatgac    2820
ctaccacatg gacggctgcg tgaacggcca ctacttcacc gtgaagggcg agggcagcgg    2880
caagccctac gagggcaccc agaccctcca cttcaaggtg accatggcca acggcggccc    2940
cctggccttc tccttcgaca tcctgtccac cgtgttcatg tacggcaacc gctgcttcac    3000
cgcctacccc accagcatgc ccgactactt caagcaggcc ttccccgacg gcatgtccta    3060
cgagagaacc ttcacctacg aggacggcgg cgtggccacc gccagctggg agatcagcct    3120
gaagggcaac tgcttcgagc acaagtccac cttccacggc gtgaacttcc ccgccgacgg    3180
ccccgtgatg gccaagaaga ccaccggctg ggaccctcc ttcgagaaga tgaccgtgtg     3240
cgacggcatc ttgaagggcg acgtgaccgc cttcctgatg ctgcagggcg cggcaacta    3300 cagatgccag ttccacaccct cctacaagac caagaagccc gtgaccatgc ccccaaccca   3360
cgtggtggag caccgcatcg ccagaaccga cctggacaag ggcggcaaca cgtgcagct    3420 gaccgagcac gccgtggccc acatcacctc cgtggtgccc ttctgaagcg ccgcaaccct   3480
```

-continued

```
agacttgtcc atcttctgga ttggccaact taattaatgt atgaaataaa aggatgcaca    3540
catagtgaca tgctaatcac tataatgtgg gcatcaaagt tgtgtgttat gtgtaattac    3600
tagttatctg aataaaagag aaagagatca tccatatttc ttatcctaaa tgaatgtcac    3660
gtgtctttat aattctttga tgaaccagat gcatttcatt aaccaaatcc atatacatat    3720
aaatattaat catatataat taatatcaat tgggttagca aaacaaatct agtctaggtg    3780
tgttttgcga attcgtaatc atggtcatag ctgtttcctg tgtgaaattg ttatccgctc    3840
acaattccac acaacatacg agccggaagc ataaagtgta aagcctgggg tgcctaatga    3900
gtgagctaac tcacattaat tgcgttgcgc tcactgcccg ctttccagtc gggaaacctg    3960
tcgtgccagc tgcattaatg aatcggccaa cgcgcgggga gaggcggttt gcgtattggg    4020
cgctcttccg atccgatatc gatgggccct ggccgaagct tggtcacccg gtccgggcct    4080
agaaggccag cttcaagttt gtacaaaaaa gcaggctccg ccagaatgg cccggaccgg     4140
gttaccgaat tcgagctcgg taccctggga tccgatatcg atgggccctg gccgaagctg    4200
ggatatcgct atcaactttg tatagaaaag ttgggccgaa ttcgagctcg gtacggccag    4260
aatggcccgg accgggttac cgaattcgag ctcggtaccc tggggatccc tatagtattt    4320
taaaattgca ttaacaaaca tgtcctaatt ggtactcctg agatactata ccctcctgtt    4380
ttaaaatagt tggcattatc gaattatcat tttacttttt aatgttttct cttcttttaa    4440
tatattttat gaattttaat gtattttaaa atgttatgca gttcgctctg acttttctg     4500
ctgcgcctac acttgggtgt actgggccta aattcagcct gaccgaccgc ctgcattgaa    4560
taatggatga gcaccggtaa aatccgcgta cccaactttc gagaagaacc gagacgtggc    4620
gggccgggcc accgacgcac ggcaccagcg actgcacacg tcccgccggc gtacgtgtac    4680
gtgctgttcc ctcactggcc gcccaatcca ctcatgcatg cccacgtaca cccctgccgt    4740
ggcgcgccca gatcctaatc ctttcgccgt tctgcacttc tgctgcctat aaatggcggc    4800
atcgaccgtc acctgcttca ccaccggcga gccacatcga gaacacgatc gagcacacaa    4860
gcacgaagac tcgtttagga gaaccacaa accaccaagc cgtgcaagca ccaagcttgg    4920
tcacccggtc cgggcctaga aggccagctt caagtttgta caaaaaagca ggcttcgaag    4980
gagatagaac caattctcta aggaaatact taaccatggt cgactggatc caacaatgcc    5040
ccagttcgac atcctctgca agaccccccc caaggtgctc gtgaggcagt tcgtggagag    5100
gttcgagagg ccctccggcg agaagatcgc cctctgcgcc gccgagctca cctacctctg    5160
ctggatgatc acccacaacg gcaccgccat taagagggcc accttcatgt catacaacac    5220
catcatctcc aactccctct ccttcgacat cgtgaacaag tccctccagt tcaaatacaa    5280
gacccagaag gccaccatcc tcgaggcctc cctcaagaag ctcatccccg cctgggagtt    5340
caccatcatc ccctactacg gccagaagca ccagtccgac atcaccgaca tcgtgtcatc    5400
cctccagctt cagttcgagt cctccgagga ggctgacaag ggcaactccc actccaagaa    5460
gatgctgaag gccctcctct ccgagggcga gtccatctgg gagatcaccg agaagatcct    5520
caactccttc gagtacacct ccaggttcac taagaccaag accctctacc agttcctctt    5580
cctcgccacc ttcatcaact gcggcaggtt ctcagacatc aagaacgtgg accccaagtc    5640
cttcaagctc gtgcagaaca agtacctagg tttgtttctg cttctacctt tgatatatat    5700
ataataatta tcattaatta gtagtaatat aatatttcaa atatttttt caaaataaaa     5760
gaatgtagta tatagcaatt gcttttctgt agtttataag tgtgtatatt ttaatttata    5820
```

| | |
|---|---|
| acttttctaa tatatgacca aaacatggtg atgcctaggt gtcatcatcc agtgcctcgt | 5880 |
| gaccgagacc aagacctccg tgtccaggca catctacttc ttctccgctc gcggcaggat | 5940 |
| cgaccccctc gtgtacctcg acgagttcct caggaactca gagcccgtgc tcaagagggt | 6000 |
| gaacaggacc ggcaactcct cctccaacaa gcaggagtac cagctcctca aggacaacct | 6060 |
| cgtgaggtcc tacaacaagg ccctcaagaa gaacgccccc tactccatct tcgccatcaa | 6120 |
| gaacggcccc aagtcccaca tcggtaggca cctcatgacc tccttcctct caatgaaggg | 6180 |
| cctcaccgag ctcaccaacg tggtgggcaa ctggtccgac aagagggcct ccgccgtggc | 6240 |
| caggaccacc tacacccacc agatcaccgc catccccgac cactacttcg ccctcgtgtc | 6300 |
| aaggtactac gcctacgacc ccatctccaa ggagatgatc gccctcaagg acgagactaa | 6360 |
| ccccatcgag gagtggcagc acatcgagca gctcaagggc tccgccgagg gctccatcag | 6420 |
| gtaccccgcc tggaacggca tcatctccca ggaggtgctc gactacctct cctcctacat | 6480 |
| caacaggagg atctgagttt cgagatatct agacccagct ttcttgtaca agtggccgt | 6540 |
| taacggatcc agacttgtcc atcttctgga ttggccaact taattaatgt atgaaataaa | 6600 |
| aggatgcaca catagtgaca tgctaatcac tataatgtgg gcatcaaagt tgtgtgttat | 6660 |
| gtgtaattac tagttatctg aataaaagag aaagagatca tccatatttc ttatcctaaa | 6720 |
| tgaatgtcac gtgtctttat aattctttga tgaaccagat gcatttcatt aaccaaatcc | 6780 |
| atatacatat aaatattaat catatataat taatatcaat tgggttagca aaacaaatct | 6840 |
| agtctaggtg tgttttgcga attgcggcaa gcttgcggcc gccccagctt ggtcacccgg | 6900 |
| tccgggccta gaaggccgat ctcccgggca cccagctttc ttgtacaaag tggccgttaa | 6960 |
| cggatcggcc agaatggccc ggaccggggtt accgaattcg agctcggtac cctgggatcg | 7020 |
| accgaagctg accgaagctt gcggccgcac actgatagtt taaactgaag gcgggaaacg | 7080 |
| acaatctgat catgagcgga gaattaaggg agtcacgtta tgaccccgcc gatgacgcg | 7140 |
| ggacaagccg ttttacgttt ggaactgaca gaaccgcaac gattgaagga gccactcagc | 7200 |
| cgcgggtttc tggagtttaa tgagctaagc acatacgtca gaaaccatta ttgcgcgttc | 7260 |
| aaaagtcgcc taaggtcact atcagctagc aaatatttct tgtcaaaaat gctccactga | 7320 |
| cgttccataa attcccctcg gtatccaatt agagtctcat attcactctc ccgggggatc | 7380 |
| tcgactctag aggatcgctc aggaaggccg ctgagataga ggcatggcgg ccaatgcggg | 7440 |
| cggcggtgga gcgggaggag gcagcggcag cggcagcgtg gctgcgccgg cggtgtgccg | 7500 |
| ccccagcggc tcgcggtgga cgccgacgcc ggagcagatc aggatgctga aggagctcta | 7560 |
| ctacggctgc ggcatccggt cgcccagctc ggagcagatc cagcgcatca ccgccatgct | 7620 |
| gcggcagcac ggcaagatcg agggcaagaa cgtcttctac tggttccaga ccacaaggc | 7680 |
| ccgcgagcgc cagaagcgcc gcctcaccag cctcgacgtc aacgtgcccg ccgccggcgc | 7740 |
| ggccgacgcc accaccagcc aactcggcgt cctctcgctg tcgtcgccgc gccttcagg | 7800 |
| cgcggcgcct ccctcgccca ccctcggctt ctacgccgcc gcaatggcg gcggatcggc | 7860 |
| tgtgctgctg acacgagtt ccgactgggg cagcagcggc gctgccatgg ccaccgagac | 7920 |
| atgcttcctg caggactaca tgggcgtgac ggacacgggc agctcgtcgc agtggccacg | 7980 |
| cttctcgtcg tcggacacga taatggcggc ggccgcggcg cgggcggcga cgacgcgggc | 8040 |
| gcccgagacg ctccctctct tcccgacctg cggcgacgac ggcggcagcg gtagcagcag | 8100 |
| ctacttgccg ttctgggggtg ccgcgtccac aactgccggc gccacttctt ccgttgcgat | 8160 |
| ccagcagcaa caccagctgc aggagcagta cagcttttac agcaacagca acagcaccca | 8220 |

```
gctggccggc accggcaacc aagacgtatc ggcaacagca gcagcagccg ccgccctgga    8280
gctgagcctc agctcatggt gctcccctta ccctgctgca gggagtatgt gagagcaacg    8340
cgagctgcca ctgctcttca ctgatgtctc tggaatggaa ggaggaggaa gtgagcatag    8400
cgttggtgcg ttgctgtcaa gggcgaattg taccacatgg ttaacctaga cttgtccatc    8460
ttctggattg gccaacttaa ttaatgtatg aaataaaagg atgcacacat agtgacatgc    8520
taatcactat aatgtgggca tcaaagttgt gtgttatgtg taattactag ttatctgaat    8580
aaaagagaaa gagatcatcc atatttctta tcctaaatga atgtcacgtg tctttataat    8640
tctttgatga accagatgca tttcattaac caaatccata tacatataaa tattaatcat    8700
atataattaa tatcaattgg gttagcaaaa caaatctagt ctaggtgtgt tttgcgaatt    8760
gcggccgcca ccgcgtggga gctcgaattc cggtcagctt gcatgcctgc agtgcagcgt    8820
gacccggtcg tgcccctctc tagagataat gagcattgca tgtctaagtt ataaaaaatt    8880
accacatatt tttttgtca cacttgtttg aagtgcagtt tatctatctt tatacatata    8940
tttaaacttt actctacgaa taatataatc tatagtacta caataatatc agtgttttag    9000
agaatcatat aaatgaacag ttagacatgg tctaaaggac aattgagtat tttgacaaca    9060
ggactctaca gttttatctt tttagtgtgc atgtgttctc cttttttttt gcaaatagct    9120
tcacctatat aatacttcat ccattttatt agtacatcca tttagggttt agggttaatg    9180
gtttttatag actaattttt ttagtacatc tattttattc tattttagcc tctaaattaa    9240
gaaaactaaa actctatttt agttttttta tttaataatt tagatataaa atagaataaa    9300
ataaagtgac taaaaattaa acaaataccc tttaagaaat taaaaaaact aaggaaacat    9360
ttttcttgtt tcgagtagat aatgccagcc tgttaaacgc cgtcgacgag tctaacggac    9420
accaaccagc gaaccagcag cgtcgcgtcg ggccaagcga agcagacggc acggcatctc    9480
tgtcgctgcc tctggacccc tctcgagagt tccgctccac cgttggactt gctccgctgt    9540
cggcatccag aaattgcgtg gcggagcggc agacgtgagc cggcacggca ggcggcctcc    9600
tcctcctctc acggcaccgg cagctacggg ggattccttt cccaccgctc cttcgctttc    9660
ccttcctcgc ccgccgtaat aaatagacac cccctccaca ccctctttcc caacctcgt    9720 gttgttcgga gcgcacacac acacaaccag atctccccca aatccacccg tcggcacctc    9780
cgcttcaagg tacgccgctc gtcctccccc cccccctct ctaccttctc tagatcggcg    9840
ttccggtcca tgcatggtta gggcccggta gttctacttc tgttcatgtt tgtgttagat    9900
ccgtgtttgt gttagatccg tgctgctagc gttcgtacac ggatgcgacc tgtacgtcag    9960
acacgttctg attgctaact tgccagtgtt tctctttggg gaatcctggg atggctctag   10020
ccgttccgca gacgggatcg atttcatgat ttttttgtt tcgttgcata gggtttggtt   10080
tgcccttttc ctttatttca atatatgccg tgcacttgtt tgtcgggtca tcttttcatg   10140 ctttttttg tcttggttgt gatgatgtgg tctggttggg cggtcgttct agatcggagt   10200
agaattctgt ttcaaactac ctggtggatt tattaattt ggatctgtat gtgtgtgcca   10260
tacatattca tagttacgaa ttgaagatga tggatggaaa tatcgatcta ggataggtat   10320
acatgttgat gcgggtttta ctgatgcata tacagagatg cttttttgttc gcttggttgt   10380 gatgatgtgg tgtggttggg cggtcgttca ttcgttctag atcggagtag aatactgttt   10440
caaactacct ggtgtattta ttaattttgg aactgtatgt gtgtgtcata catcttcata   10500
gttacgagtt taagatggat ggaaatatcg atctaggata ggtatacatg ttgatgtggg   10560
```

| | |
|---|---|
| ttttactgat gcatatacat gatggcatat gcagcatcta ttcatatgct ctaaccttga | 10620 |
| gtacctatct attataataa acaagtatgt tttataatta ttttgatctt gatatacttg | 10680 |
| gatgatggca tatgcagcag ctatatgtgg atttttttag ccctgccttc atacgctatt | 10740 |
| tatttgcttg gtactgtttc ttttgtcgat gctcaccctg ttgtttggtg ttacttctgc | 10800 |
| aggtcgactc tagaggatcc atggccactg tgaacaactg gctcgctttc tccctctccc | 10860 |
| cgcaggagct gccgccctcc cagacgacgg actccacact catctcggcc gccaccgccg | 10920 |
| accatgtctc cggcgatgtc tgcttcaaca tcccccaaga ttggagcatg aggggatcag | 10980 |
| agctttcggc gctcgtcgcg gagccgaagc tggaggactt cctcggcggc atctccttct | 11040 |
| ccgagcagca tcacaaggcc aactgcaaca tgatacccag cactagcagc acagtttgct | 11100 |
| acgcgagctc aggtgctagc accggctacc atcaccagct gtaccaccag cccaccagct | 11160 |
| cagcgctcca cttcgcggac tccgtaatgg tggcctcctc ggccggtgtc cacgacggcg | 11220 |
| gtgccatgct cagcgcggcc gccgctaacg gtgtcgctgg cgctgccagt gccaacggcg | 11280 |
| gcggcatcgg gctgtccatg attaagaact ggctgcggag ccaaccggcg cccatgcagc | 11340 |
| cgagggtggc ggcggctgag ggcgcgcagg ggctctcttt gtccatgaac atggcgggga | 11400 |
| cgacccaagg cgctgctggc atgccacttc tcgctggaga gcgcgcacgg gcgcccgaga | 11460 |
| gtgtatcgac gtcagcacag ggtggagccg tcgtcgtcac ggcgccgaag gaggatagcg | 11520 |
| gtggcagcgg tgttgccggc gctctagtag ccgtgagcac ggacacgggt ggcagcggcg | 11580 |
| gcgcgtcggc tgacaacacg gcaaggaaga cggtggacac gttcgggcag cgcacgtcga | 11640 |
| tttaccgtgg cgtgacaagg catagatgga ctgggagata tgaggcacat ctttgggata | 11700 |
| acagttgcag aagggaaggg caaactcgta agggtcgtca agtctattta ggtggctatg | 11760 |
| ataaagagga gaaagctgct agggcttatg atcttgctgc tctgaagtac tggggtgcca | 11820 |
| caacaacaac aaattttcca gtgagtaact acgaaaagga gctcgaggac atgaagcaca | 11880 |
| tgacaaggca ggagttttgta gcgtctctga aaggaagag cagtggtttc tccagaggtg | 11940 |
| catccatttta caggggagtg actaggcatc accaacatgg aagatggcaa gcacggattg | 12000 |
| gacgagttgc agggaacaag gatctttact tgggcacctt cagcacccag gaggaggcag | 12060 |
| cggaggcgta cgacatcgcg gcgatcaagt tccgcggcct caacgccgtc accaacttcg | 12120 |
| acatgagccg ctacgacgtg aagagcatcc tggacagcag cgccctcccc atcggcagcg | 12180 |
| ccgccaagcg cctcaaggag gccgaggccg cagcgtccgc gcagcaccac cacgccggcg | 12240 |
| tggtgagcta cgacgtcggc cgcatcgcct cgcagctcgg cgacggcgga gccctggcgg | 12300 |
| cggcgtacgg cgcgcactac cacggcgccg cctggccgac catcgcgttc cagccgggcg | 12360 |
| ccgccagcac aggcctgtac cacccgtacg cgcagcagcc aatgcgcggc ggcgggtggt | 12420 |
| gcaagcagga gcaggaccac gcggtgatcg cggccgcgca cagcctgcag gacctccacc | 12480 |
| acctgaacct gggcgcggcc ggcgcgcacg actttttctc ggcagggcag caggccgccg | 12540 |
| ccgctgcgat gcacggcctg ggtagcatcg acagtgcgtc gctcgagcac agcaccggct | 12600 |
| ccaactccgt cgtctacaac ggcggggtcg gcgacagcaa cggcgccagc gccgtcggcg | 12660 |
| gcagtggcgg tggctacatg atgccgatga gcgctgccgg agcaaccact acatcggcaa | 12720 |
| tggtgagcca cgagcaggtg catgcacggg cctacgacga agccaagcag gctgctcaga | 12780 |
| tggggtacga gagctacctg gtgaacgcgg agaacaatgg tggcggaagg atgtctgcat | 12840 |
| gggggactgt cgtgtctgca gccgcggcgg cagcagcaag cagcaacgac aacatggccg | 12900 |
| ccgacgtcgg ccatggcggc gcgcagctct tcagtgtctg gaacgacact taagcgtacg | 12960 |

```
tgccggcctg gctctccgaa agggcgaatt ccagcacact ggcggccgtt actagaccca    13020
acctagactt gtccatcttc tggattggcc aacttaatta atgtatgaaa taaaaggatg    13080
cacacatagt gacatgctaa tcactataat gtgggcatca agttgtgtg ttatgtgtaa     13140 ttactagtta tctgaataaa agagaaagag atcatccata tttcttatcc taaatgaatg    13200
tcacgtgtct ttataattct tgatgaacc agatgcattt cattaaccaa atccatatac     13260
atataaatat taatcatata taattaatat caattgggtt agcaaaacaa atctagtcta    13320
ggtgtgtttt gcgaatgcgg ccgccaccgc ggtggagctc gaattccggt cgatccgata    13380
tcgatgggcc ctggccgaag ctaattcctg cagtgcagcg tgacccggtc gtgcccctct    13440
ctagtggatc tgagcttcta gcgaagttcc tattccgaag ttcctattct ctagaaagta    13500
taggaacttc agatctgccc acagcaagca cggcctgaag gaggagatga ccatgaagta    13560
ccacatggag ggctgcgtga acggccacaa gttcgtgatc accggcgagg gcatcggcta    13620 cccttcaag ggcaagcaga ccatcaacct gtgcgtgatc gagggcggcc cctgcccctt     13680
cagcgaggac atcctgagcg ccggcttcaa gtacggcgac cggatcttca ccgagtaccc    13740
ccaggacatc gtggactact tcaagaacag ctgccccgcc ggctacacct ggggccggag    13800
cttcctgttc gaggacggcg ccgtgtgcat ctgtaacgtg gacatcaccg tgagcgtgaa    13860
ggagaactgc atctaccaca agagcatctt caacggcgtg aacttccccg ccgacggccc    13920
cgtgatgaag aagatgacca ccaactggga ggccagctgc gagaagatca tgcccgtgcc    13980
taagcagggc atcctgaagg gcgacgtgag catgtacctg ctgctgaagg acggcggccg    14040
gtaccggtgc cagttcgaca ccgtgtacaa ggccaagagc gtgcccagca gatgccga     14100 gtggcacttc atccagcaca agctgctgcg ggaggaccgg agcgacgcca agaaccagaa    14160
gtggcagctg accgagcacg ccatcgcctt ccccagcgcc ctggcctgaa gcggccgcaa    14220
cctagacttg tccatcttct ggattggcca acttaattaa tgtatgaaat aaaaggatgc    14280
acacatagtg acatgctaat cactataatg tgggcatcaa agttgtgtgt tatgtgtaat    14340
tactagttat ctgaataaaa gagaaagaga tcatccatat ttcttatcct aaatgaatgt    14400
cacgtgtctt tataattctt tgatgaacca gatgcatttc attaaccaaa tccatataca    14460
tataaatatt aatcatatat aattaatatc aattgggtta gcaaaacaaa tctagtctag    14520
gtgtgttttg cgaattagct tggtcacccg gtccgggcct agaaggccag cttgcggccg    14580
ccccgggcaa ctttattata caaagttgat agatatcgga ccgattaaac tttaattcgg    14640
tccgaagctt gcatgcctgc agtgcagcgt gacccggtcg tgcccctctc tagagataat    14700
gagcattgca tgtctaagtt ataaaaaatt accacatatt ttttttgtca cacttgtttg    14760
aagtgcagtt tatctatctt tatacatata tttaacttt actctacgaa taatataatc     14820
tatagtacta caataatatc agtgttttag agaatcatat aaatgaacag ttagacatgg    14880
tctaaaggac aattgagtat tttgacaaca ggactctaca gttttatctt tttagtgtgc    14940
atgtgttctc cttttttttt gcaaatagct tcacctatat aatacttcat ccattttatt    15000
agtacatcca tttagggttt agggttaatg gtttttatag actaattttt ttagtacatc    15060
tattttattc tattttagcc tctaaattaa gaaaactaaa actctatttt agttttttta    15120
tttaataatt tagatataaa atagaataaa ataaagtgac taaaaattaa acaaataccc    15180
tttaagaaat taaaaaaact aaggaaacat ttttcttgtt tcgagtagat aatgccagcc    15240
tgttaaacgc cgtcgacgag tctaacggac accaaccagc gaaccagcag cgtcgcgtcg    15300
```

```
ggccaagcga agcagacggc acggcatctc tgtcgctgcc tctggacccc tctcgagagt   15360
tccgctccac cgttggactt gctccgctgt cggcatccag aaattgcgtg cggagcggc    15420
agacgtgagc cggcacggca ggcggcctcc tcctcctctc acggcaccgg cagctacggg   15480
ggattccttt cccaccgctc cttcgctttc ccttcctcgc ccgccgtaat aaatagacac   15540
cccctccaca ccctctttcc ccaacctcgt gttgttcgga gcgcacacac acacaaccag   15600
atctccccca aatccacccg tcggcacctc cgcttcaagg tacgccgctc gtcctccccc   15660
cccccctct ctaccttctc tagatcggcg ttccggtcca tgcatggtta gggcccggta    15720
gttctacttc tgttcatgtt tgtgttagat ccgtgtttgt gttagatccg tgctgctagc   15780
gttcgtacac ggatgcgacc tgtacgtcag acacgttctg attgctaact tgccagtgtt   15840
tctcttggg gaatcctggg atggctctag ccgttccgca gacgggatcg atttcatgat    15900
ttttttgtt tcgttgcata gggtttggtt tgcccttttc ctttatttca atatatgccg    15960
tgcacttgtt tgtcgggtca tcttttcatg cttttttttg tcttggttgt gatgatgtgg   16020
tctggttggg cggtcgttct agatcggagt agaattctgt ttcaaactac ctggtggatt   16080
tattaatttt ggatctgtat gtgtgtgcca tacatattca tagttacgaa ttgaagatga   16140
tggatggaaa tatcgatcta ggataggtat acatgttgat gcgggtttta ctgatgcata   16200
tacagagatg cttttttgttc gcttggttgt gatgatgtgg tgtggttggg cggtcgttca   16260
ttcgttctag atcggagtag aatactgttt caaactacct ggtgtattta ttaattttgg   16320
aactgtatgt gtgtgtcata catcttcata gttacgagtt taagatggat ggaaatatcg   16380
atctaggata ggtatacatg ttgatgtggg ttttactgat gcatatacat gatggcatat   16440
gcagcatcta ttcatatgct ctaaccttga gtacctatct attataataa acaagtatgt   16500
tttataatta ttttgatctt gatatacttg gatgatggca tatgcagcag ctatatgtgg   16560
attttttag ccctgccttc atacgctatt tatttgcttg gtactgtttc ttttgtcgat    16620
gctcaccctg ttgtttggtg ttacttctgc aggtcgactt taacttagcc taggatccac   16680
acgacaccat gtcccccgag cgccgccccg tcgagatccg cccggccacc gccgccgaca   16740
tggccgccgt gtgcgacatc gtgaaccact acatcgagac ctccaccgtg aacttccgca   16800
ccgagccgca gaccccgcag gagtggatcg acgacctgga gcgcctccag gaccgctacc   16860
cgtggctcgt ggccgaggtg gagggcgtgg tggccggcat cgcctacgcc ggcccgtgga   16920
aggcccgcaa cgcctacgac tggaccgtgg agtccaccgt gtacgtgtcc caccgccacc   16980
agcgcctcgg cctcggctcc accctctaca cccacctcct caagagcatg gaggcccagg   17040
gcttcaagtc cgtggtggcc gtgatcggcc tcccgaacga cccgtccgtg cgcctccacg   17100
aggccctcgg ctacaccgcc cgcggcaccc tccgcgccgc cggctacaag cacggcggct   17160
ggcacgacgt cggcttctgg cagcgcgact tcgagctgcc ggccccgccg cgcccggtgc   17220
gcccggtgac gcagatctga gtcgaaacct agacttgtcc atcttctgga ttggccaact   17280
taattaatgt atgaaataaa aggatgcaca catagtgaca tgctaatcac tataatgtgg   17340
gcatcaaagt tgtgtgttat gtgtaattac tagttatctg aataaaagag aaagagatca   17400
tccatatttc ttatcctaaa tgaatgtcac gtgtctttat aattctttga tgaaccagat   17460
gcatttcatt aaccaaatcc atatacatat aaatattaat catatataat taatatcaat   17520
tgggttagca aaacaaatct agtctaggtg tgttttgcga attgcggccg ccaccgcggt   17580
ggagctcgaa ttcattccga ttaatcgtgg cctcttgctc ttcaggatga agagctatgt   17640
ttaaacgtgc aagcgctact agacaattca gtacattaaa aacgtccgca atgtgttatt   17700
```
aagttgtcta agcgtcaatt tgtttacacc acaatatatc ctgccac       17747

<210> SEQ ID NO 111
<211> LENGTH: 17373
<212> TYPE: DNA
<213> ORGANISM: Artificial Sequence
<220> FEATURE:
<223> OTHER INFORMATION: PHP35648
<220> FEATURE:
<221> NAME/KEY: misc_feature
<222> LOCATION: (4301)...(4808)
<223> OTHER INFORMATION: Rab17 promoter
<220> FEATURE:
<221> NAME/KEY: misc_feature
<222> LOCATION: (4809)...(4903)
<223> OTHER INFORMATION: Rab17 5' UTR
<220> FEATURE:
<221> NAME/KEY: misc_feature
<222> LOCATION: (4942)...(4965)
<223> OTHER INFORMATION: attB1
<220> FEATURE:
<221> NAME/KEY: misc_feature
<222> LOCATION: (4991)...(6208)
<223> OTHER INFORMATION: Cre
<220> FEATURE:
<221> NAME/KEY: misc_feature
<222> LOCATION: (6217)...(6240)
<223> OTHER INFORMATION: attB2
<220> FEATURE:
<221> NAME/KEY: misc_feature
<222> LOCATION: (6255)...(6572)
<223> OTHER INFORMATION: PinII term

<400> SEQUENCE: 111
gtttacccgc caatatatcc tgtcaaacac tgatagttta aactgaaggc gggaaacgac    60
aatctgatca tgagcggaga attaagggag tcacgttatg accccgccg atgacgcggg    120 acaagccgtt ttacgtttgg aactgacaga accgcaacgt tgaaggagcc actcagcaag    180
ctggtacgat tgtaatacga ctcactatag ggcgaattga gcgctgttta acgctcttc    240 aactggaaga gcggttacca gagctggtca cctttgtcca ccaagatgga actgcggccg    300
ctcattaatt aagtcaggcg cgcctctagt tgaagacacg ttcatgtctt catcgtaaga    360
agacactcag tagtcttcgg ccagaatggc catctggatt cagcaggcct agaaggccat    420
ttaaatcctg aggatctggt cttcctaagg acccgggata tcgctatcaa ctttgtatag    480
aaaagttggg ccgaattcga gctcggtacg gccagaatgg cccggaccgg ttaccgaat    540 tcgagctcgg taccctggga tccggtgcgg gcctcttcgc tattacgcca gctggcgaaa    600
gggggatgtg ctgcaaggcg attaagttgg gtaacgccag ggttttccca gtcacgacgt    660
tgtaaaacga cggccagtgc caagctcaga tcagcttgca tgcctgcagt gcagcgtgac    720
ccggtcgtgc ccctctctag agataatgag cattgcatgt ctaagttata aaaaattacc    780
acatattttt tttgtcacac ttgtttgaag tgcagtttat ctatctttat acatatattt    840
aaactttact ctacgaataa tataatctat agtactacaa taatatcagt gttttagaga    900
atcatataaa tgaacagtta gacatggtct aaaggacaat tgagtatttt gacaacagga    960
ctctacagtt ttatcttttt agtgtgcatg tgttctcctt ttttttttgca aatagcttca    1020 cctatataat acttcatcca ttttattagt acatccattt agggtttagg gttaatggtt    1080
tttatagact aattttttta gtacatctat tttattctat tttagcctct aaattaagaa    1140
aactaaaact ctattttagt ttttttattt ataatttag atataaaata gaataaaata    1200
aagtgactaa aaattaaaca aatacccttt aagaaattaa aaaaactaag gaaacatttt    1260

```
tcttgtttcg agtagataat gccagcctgt taaacgccgt cgacgagtct aacggacacc    1320
aaccagcgaa ccagcagcgt cgcgtcgggc caagcgaagc agacggcacg gcatctctgt    1380
cgctgcctct ggacccctct cgagagttcc gctccaccgt tggacttgct ccgctgtcgg    1440
catccagaaa ttgcgtggcg gagcggcaga cgtgagccgg cacggcaggc ggcctcctcc    1500
tcctctcacg gcacggcagc tacgggggat tcctttccca ccgctccttc gctttccctt    1560
cctcgcccgc cgtaataaat agacaccccc tccacaccct ctttcccaa cctcgtgttg    1620 ttcggagcgc acacacacac aaccagatct cccccaaatc cacccgtcgg cacctccgct    1680
tcaaggtacg ccgctcgtcc tccccccccc ccctctcta ccttctctag atcggcgttc    1740
cggtccatgg ttagggcccg gtagttctac ttctgttcat gtttgtgtta gatccgtgtt    1800
tgtgttagat ccgtgctgct agcgttcgta cacggatgcg acctgtacgt cagacacgtt    1860
ctgattgcta acttgccagt gtttctcttt ggggaatcct gggatggctc tagccgttcc    1920
gcagacggga tcgatttcat gatttttttt gtttcgttgc atagggtttg gtttgccctt    1980
ttcctttatt tcaatatatg ccgtgcactt gtttgtcggg tcatcttttc atgcttttt     2040 ttgtcttggt tgtgatgatg tggtctggtt gggcggtcgt tctagatcgg agtagaattc    2100
tgtttcaaac tacctggtgg atttattaat tttggatctg tatgtgtgtg ccatacatat    2160
tcatagttac gaattgaaga tgatggatgg aaatatcgat ctaggatagg tatacatgtt    2220
gatgcgggtt ttactgatgc atatacagag atgcttttg ttcgcttggt tgtgatgatg     2280
tggtgtggtt gggcggtcgt tcattcgttc tagatcggag tagaatactg tttcaaacta    2340
cctggtgtat ttattaattt tggaactgta tgtgtgtgtc atacatcttc atagttacga    2400
gtttaagatg gatggaaata tcgatctagg ataggtatac atgttgatgt gggttttact    2460
gatgcatata catgatggca tatgcagcat ctattcatat gctctaacct tgagtaccta    2520
tctattataa taaacaagta tgttttataa ttatttttgat cttgatatac ttggatgatg    2580
gcatatgcag cagctatatg tggattttt tagccctgcc ttcatacgct atttatttgc     2640
ttggtactgt ttcttttgtc gatgctcacc ctgttgtttg gtgttacttc tgcaggtcga    2700
ctctagagga tccaccatgg ctagcataac ttcgtatagc atacattata cgaagttatc    2760
cagatctgcc ctgtccaaca agttcatcgg cgacgacatg aagatgacct accacatgga    2820
cggctgcgtg aacggccact acttcaccgt gaagggcgag ggcagcggca agccctacga    2880
gggcacccag acctccacct tcaaggtgac catggccaac ggcggccccc tggccttctc    2940
cttcgacatc ctgtccaccg tgttcatgta cggcaaccgc tgcttcaccg cctaccccac    3000
cagcatgccc gactacttca gcaggccttt ccccgacggc atgtcctacg agagaacctt    3060
cacctacgag gacggcggcg tggccaccgc cagctgggag atcagcctga agggcaactg    3120
cttcgagcac aagtccacct tccacggcgt gaacttcccc gccgacggcc ccgtgatggc    3180
caagaagacc accggctggg acccctcctt cgagaagatg accgtgtgcg acggcatctt    3240
gaagggcgac gtgaccgcct tcctgatgct gcagggcggc ggcaactaca gatgccagtt    3300
ccacacctcc tacaagacca agaagcccgt gaccatgccc cccaaccacg tggtggagca    3360
ccgcatcgcc agaaccgacc tggacaaggg cggcaacagc gtgcagctga ccgagcacgc    3420
cgtggcccac atcacctccg tggtgccctt ctgaagcggc cgcaacctag acttgtccat    3480
cttctggatt ggccaactta attaatgtat gaaataaaag gatgcacaca tagtgacatg    3540
ctaatcacta taatgtgggc atcaaagttg tgtgttatgt gtaattacta gttatctgaa    3600
taaaagagaa agagatcatc catatttctt atcctaaatg aatgtcacgt gtctttataa    3660
```

```
ttctttgatg aaccagatgc atttcattaa ccaaatccat atacatataa atattaatca    3720
tatataatta atatcaattg ggttagcaaa acaaatctag tctaggtgtg ttttgcgaat    3780
tcgtaatcat ggtcatagct gtttcctgtg tgaaattgtt atccgctcac aattccacac    3840
aacatacgag ccggaagcat aaagtgtaaa gcctggggtg cctaatgagt gagctaactc    3900
acattaattg cgttgcgctc actgcccgct ttccagtcgg gaaacctgtc gtgccagctg    3960
cattaatgaa tcggccaacg cgcgggggaga ggcggtttgc gtattgggcg ctcttccgct   4020
gatccgatat cgatgggccc tggccgaagc ttggtcaccc ggtccgggcc tagaaggcca    4080
gcttcaagtt tgtacaaaaa agcaggctcc ggccagaatg gcccgaccg ggttaccgaa     4140
ttcgagctcg gtaccctggg atccgatatc gatgggccct ggccgaagct gggatatcgc    4200
tatcaacttt gtatagaaaa gttgggccga attcgagctc ggtacggcca gaatggcccg    4260
gaccgggtta ccgaattcga gctcggtacc ctggggatcc ctatagtatt ttaaaattgc    4320
attaacaaac atgtcctaat tggtactcct gagatactat accctcctgt tttaaaatag    4380
ttggcattat cgaattatca ttttactttt taatgttttc tcttctttta atatatttta    4440
tgaatttttaa tgtattttaa aatgttatgc agttcgctct ggacttttct gctgcgccta   4500
cacttgggtg tactgggcct aaattcagcc tgaccgaccg cctgcattga ataatggatg    4560
agcaccggta aaatccgcgt acccaacttt cgagaagaac cgagacgtgg cgggccgggc    4620
caccgacgca cggcaccagc gactgcacac gtcccgccgg cgtacgtgta cgtgctgttc    4680
cctcactggc cgcccaatcc actcatgcat gcccacgtac accctgccg tggcgcgccc     4740
agatcctaat cctttcgccg ttctgcactt ctgctgccta taaatggcgg catcgaccgt    4800
cacctgcttc accaccggcg agccacatcg agaacgat cgagcacaca agcacgaaga     4860
ctcgtttagg agaaaccaca aaccaccaag ccgtgcaagc accaagcttg gtcacccggt    4920
ccgggcctag aaggccagct tcaagtttgt acaaaaaagc aggcttcgaa ggagatagaa    4980
ccgatccacc atgtccaacc tgctcacggt tcaccagaac cttccggctc ttccagtgga    5040
cgcgacgtcc gatgaagtca ggaagaacct catggacatg ttccgcgaca ggcaagcgtt    5100
cagcgagcac acctggaaga tgctgctctc cgtctgccgc tcctgggctg catggtgcaa    5160
gctgaacaac aggaagtggt tccccgctga gcccgaggac gtgagggatt accttctgta    5220
cctgcaagcg cgaggtttgt ttctgcttct accttgata tatatataat aattatcatt     5280
aattagtagt aatataatat ttcaaatatt tttttcaaaa taaagaatg tagtatatag     5340
caattgcttt tctgtagttt ataagtgtgt atattttaat ttataacttt tctaatatat    5400
gaccaaaaca tggtgatgcc taggtctggc agtgaagacc atccagcaac accttggaca    5460
actgaacatg cttcacaggc gctccggcct cccgcgcccc agcgactcga acgccgtgag    5520
cctcgtcatg cgccgcatca ggaaggaaaa cgtcgatgcc ggcgaaaggg caaagcaggc    5580
cctcgcgttc gagaggaccg atttcgacca ggtccgcagc ctgatggaga acagcgacag    5640
gtgccaggac attaggaacc tggcgttcct cggaattgca tacaacacgc tcctcaggat    5700
cgcggaaatt gcccgcattc gcgtgaagga cattagccgc accgacgcg gcaggatgct     5760
tatccacatt ggcaggacca agacgctcgt ttccaccgca ggcgtcgaaa aggccctcag    5820
cctcggagtg accaagctcg tcgaacgctg gatctccgtg tccggcgtcg cggacgaccc    5880
aaacaactac ctcttctgcc gcgtccgcaa gaacggggtg gctgcccta gcgccaccag     5940
ccaactcagc acgagggcct tggaaggtat tttcgaggcc acccaccgcc tgatctacgg    6000
```

```
cgcgaaggat gacagcggtc aacgctacct cgcatggtcc gggcactccg cccgcgttgg    6060
agctgctagg gacatggccc gcgccggtgt ttccatcccc gaaatcatgc aggcgggtgg    6120
atggacgaac gtgaacattg tcatgaacta cattcgcaac cttgacagcg agacgggcgc    6180
aatggttcgc ctcctggaag atggtgactg agctagaccc agcttttctt g tacaaagtgg    6240 ccgttaacgg atccagactt gtccatcttc tggattggcc aacttaatta atgtatgaaa    6300
taaaaggatg cacacatagt gacatgctaa tcactataat gtgggcatca agttgtgtg    6360 ttatgtgtaa ttactagtta tctgaataaa agagaaagag atcatccata tttcttatcc    6420
taaatgaatg tcacgtgtct ttataattct ttgatgaacc agatgcattt cattaaccaa    6480
atccatatac atataaatat taatcatata taattaatat caattgggtt agcaaaacaa    6540
atctagtcta ggtgtgtttt gcgaattgcg gcaagcttgc ggccgcccca gcttggtcac    6600
ccggtccggg cctagaaggc cgatctcccg ggcacccagc tttcttgtac aaagtggccg    6660
ttaacggatc ggccagaatg gcccggaccg ggttaccgaa ttcgagctcg gtaccctggg    6720
atcgaccgaa gctgaccgaa gcttgcgccg cacactgat agtttaaact gaaggcggga    6780
aacgacaatc tgatcatgag cggagaatta agggagtcac gttatgaccc ccgccgatga    6840
cgcgggacaa gccgttttac gtttggaact gacagaaccg caacgattga aggagccact    6900
cagccgcggg tttctggagt ttaatgagct aagcacatac gtcagaaacc attattgcgc    6960
gttcaaaagt cgcctaaggt cactatcagc tagcaaatat ttcttgtcaa aaatgctcca    7020
ctgacgttcc ataaattccc ctcggtatcc aattagagtc tcatattcac tctcccgggg    7080
gatctcgact ctagaggatc gctcaggaag gccgctgaga tagaggcatg gcggccaatg    7140
cgggcggcgg tggagcggga ggaggcagcg gcagcggcag cgtggctgcg ccggcggtgt    7200
gccgccccag cggctcgcgg tggacgccga cgccggagca gatcaggatg ctgaaggagc    7260
tctactacgg ctgcggcatc cggtcgccca gctcggagca gatccagcgc atcaccgcca    7320
tgctgcggca gcacgcaag atcgagggca agaacgtctt ctactggttc cagaaccaca    7380
aggcccgcga gcgccagaag cgccgcctca ccagcctcga cgtcaacgtg cccgccgccg    7440
gcgcggccga cgccaccacc agccaactcg gcgtcctctc gctgtcgtcg ccgccgcctt    7500
caggcgcggc gcctccctcg cccaccctcg gcttctacgc cgccggcaat ggcggcggat    7560
cggctgtgct gctggacacg agttccgact ggggcagcag cggcgctgcc atggccaccg    7620
agacatgctt cctgcaggac tacatgggcg tgacggacac gggcagctcg tcgcagtggc    7680
cacgcttctc gtcgtcggac acgataatgg cggcggccgc ggcgcgggcg cgacgacgc    7740 gggcgcccga gacgctccct ctcttcccga cctgcggcga cgacggcggc agcggtagca    7800
gcagctactt gccgttctgg ggtgccgcgt ccacaactgc cggcgccact tcttccgttg    7860
cgatccagca gcaacaccag ctgcaggagc agtacagctt ttacagcaac agcaacagca    7920
cccagctggc cggcaccggc aaccaagacg tatcggcaac agcagcagca gccgccgccc    7980
tggagctgag cctcagctca tggtgctccc cttaccctgc tgcagggagt atgtgagagc    8040
aacgcgagct gccactgctc ttcactgatg tctctggaat ggaaggagga ggaagtgagc    8100
atagcgttgg tgcgttgctg tcaagggcga attgtaccac atggttaacc tagacttgtc    8160
catcttctgg attggccaac ttaattaatg tatgaaataa aaggatgcac acatagtgac    8220
atgctaatca ctataatgtg gcatcaaag ttgtgtgtta tgtgtaatta ctagttatct    8280
gaataaaaga gaaagagatc atccatattt cttatcctaa atgaatgtca cgtgtcttta    8340
taattctttg atgaaccaga tgcatttcat taaccaaatc catatacata taaatattaa    8400
```

```
tcatatataa ttaatatcaa ttgggttagc aaaacaaatc tagtctaggt gtgttttgcg      8460
aattgcggcc gccaccgcgg tggagctcga attccggtca gcttgcatgc ctgcagtgca      8520
gcgtgacccg tcgtgccccc tctctagaga taatgagcat tgcatgtcta agttataaaa      8580
aattaccaca tattttttt gtcacacttg tttgaagtgc agtttatcta tctttataca      8640
tatatttaaa ctttactcta cgaataatat aatctatagt actacaataa tatcagtgtt      8700
ttagagaatc atataaatga acagttagac atggtctaaa ggacaattga gtattttgac      8760
aacaggactc tacagtttta tcttttagt gtgcatgtgt tctccttttt ttttgcaaat      8820
agcttcacct atataatact tcatccattt tattagtaca tccatttagg gtttagggtt      8880
aatggttttt atagactaat ttttttagta catctatttt attctatttt agcctctaaa      8940
ttaagaaaac taaaactcta ttttagtttt tttatttaat aatttagata taaaatagaa      9000
taaaataaag tgactaaaaa ttaaacaaat acccttaag aaattaaaaa aactaaggaa      9060
acatttttct tgtttcgagt agataatgcc agcctgttaa acgccgtcga cgagtctaac      9120
ggacaccaac cagcgaacca gcagcgtcgc gtcgggccaa gcgaagcaga cggcacggca      9180
tctctgtcgc tgcctctgga cccctctcga gagttccgct ccaccgttgg acttgctccg      9240
ctgtcggcat ccagaaattg cgtggcggag cggcagacgt gagccggcac ggcaggcggc      9300
ctcctcctcc tctcacggca ccggcagcta cggggattc ctttcccacc gctccttcgc      9360
tttcccttcc tcgcccgccg taataaatag acaccccctc cacaccctct ttccccaacc      9420
tcgtgttgtt cggagcgcac acacacacaa ccagatctcc cccaaatcca cccgtcggca      9480
cctccgcttc aaggtacgcc gctcgtcctc cccccccccc ctctctacct tctctagatc      9540
ggcgttccgg tccatgcatg gttagggccc ggtagttcta cttctgttca tgtttgtgtt      9600
agatccgtgt ttgtgttaga tccgtgctgc tagcgttcgt acacggatgc gacctgtacg      9660
tcagacacgt tctgattgct aacttgccag tgtttctctt tggggaatcc tgggatggct      9720
ctagccgttc cgcagacggg atcgatttca tgattttttt tgtttcgttg catagggttt      9780
ggtttgccct tttcctttat ttcaatatat gccgtgcact tgtttgtcgg gtcatctttt      9840
catgcttttt tttgtcttgg ttgtgatgat gtggtctggt tgggcggtcg ttctagatcg      9900
gagtagaatt ctgtttcaaa ctacctggtg gatttattaa ttttggatct gtatgtgtgt      9960
gccatacata ttcatagtta cgaattgaag atgatggatg gaaatatcga tctaggatag     10020
gtatacatgt tgatgcgggt tttactgatg catatacaga gatgcttttt gttcgcttgg     10080
ttgtgatgat gtggtgtggt tgggcggtcg ttcattcgtt ctagatcgga gtagaatact     10140
gtttcaaact acctggtgta tttattaatt ttggaactgt atgtgtgtgt catacatctt     10200
catagttacg agtttaagat ggatggaaat atcgatctag gataggtata catgttgatg     10260
tgggttttac tgatgcatat acatgatggc atatgcagca tctattcata tgctctaacc     10320
ttgagtacct atctattata ataaacaagt atgttttata attattttga tcttgatata     10380
cttggatgat ggcatatgca gcagctatat gtggattttt ttagccctgc cttcatacgc     10440
tatttatttg cttggtactg tttctttgt cgatgctcac cctgttgttt ggtgttactt     10500
ctgcaggtcg actctagagg atccatgcc actgtgaaca actggctcgc tttctccctc     10560
tccccgcagg agctgccgcc ctcccagacg acggactcca cactcatctc ggccgccacc     10620
gccgaccatg tctccggcga tgtctgcttc aacatccccc aagattggag catgagggga     10680
tcagagcttt cggcgctcgt cgcggagccg aagctggagg acttcctcgg cggcatctcc     10740
```

```
ttctccgagc agcatcacaa ggccaactgc aacatgatac ccagcactag cagcacagtt    10800
tgctacgcga gctcaggtgc tagcaccggc taccatcacc agctgtacca ccagcccacc    10860
agctcagcgc tccacttcgc ggactccgta atggtggcct cctcggccgg tgtccacgac    10920
ggcggtgcca tgctcagcgc ggccgccgct aacggtgtcg ctggcgctgc cagtgccaac    10980
ggcggcggca tcgggctgtc catgattaag aactggctgc ggagccaacc ggcgcccatg    11040
cagccgaggg tggcggcggc tgagggcgcg caggggctct ctttgtccat gaacatggcg    11100
gggacgaccc aaggcgctgc tggcatgcca cttctcgctg gagagcgcgc acgggcgccc    11160
gagagtgtat cgacgtcagc acagggtgga gccgtcgtcg tcacggcgcc gaaggaggat    11220
agcggtggca gcggtgttgc cggcgctcta gtagccgtga gcacggacac gggtggcagc    11280
ggcggcgcgt cggctgacaa cacggcaagg aagacggtgg acacgttcgg gcagcgcacg    11340
tcgatttacc gtggcgtgac aaggcataga tggactggga gatatgaggc acatctttgg    11400
gataacagtt gcagaaggga agggcaaact cgtaagggtc gtcaagtcta tttaggtggc    11460
tatgataaag aggagaaagc tgctagggct tatgatcttg ctgctctgaa gtactgggt    11520 gccacaacaa caacaaattt tccagtgagt aactacgaaa aggagctcga ggacatgaag    11580
cacatgacaa ggcaggagtt tgtagcgtct ctgagaagga agagcagtgg tttctccaga    11640
ggtgcatcca tttacagggg agtgactagg catcaccaac atggaagatg caagcacgg    11700 attggacgag ttgcagggaa caaggatctt tacttgggca ccttcagcac ccaggaggag    11760
gcagcggagg cgtacgacat cgcggcgatc aagttccgcg gcctcaacgc cgtcaccaac    11820
ttcgacatga ccgctacga cgtgaagagc atcctggaca gcagcgccct ccccatcggc    11880
agcgccgcca agcgcctcaa ggaggccgag gccgcagcgt ccgcgcagca ccaccacgcc    11940
ggcgtggtga gctacgacgt cggccgcatc gcctcgcagc tcggcgacgg cggagccctg    12000
gcggcggcgt acggcgcgca ctaccacggc gccgcctggc cgaccatcgc gttccagccg    12060
ggcgccgcca gcacaggcct gtaccacccg tacgcgcagc agccaatgcg cggcggcggg    12120
tggtgcaagc aggagcagga ccacgcggtg atcgcggccg cgcacagcct gcaggacctc    12180
caccacctga acctgggcgc ggccggcgcg cacgactttt tctcggcagg gcagcaggcc    12240
gccgccgctg cgatgcacgg cctgggtagc atcgacagtg cgtcgctcga gcacagcacc    12300
ggctccaact ccgtcgtcta caacggcggg gtcggcgaca gcaacggcgc cagcgccgtc    12360
ggcggcagtg gcggtggcta catgatgccg atgagcgctg ccggagcaac cactacatcg    12420
gcaatggtga gccacgagca ggtgcatgca cgggcctacg acgaagccaa gcaggctgct    12480
cagatggggt acgagagcta cctggtgaac gcggagaaca atggtggcgg aaggatgtct    12540
gcatggggga ctgtcgtgtc tgcagccgcg cggcagcag caagcagcaa cgacaacatg    12600
gccgccgacg tcggccatgg cggcgcgcag ctcttcagtg tctggaacga cacttaagcg    12660
tacgtgccgg cctggctctc cgaaagggcg aattccagca cactggcggc cgttactaga    12720
cccaacctag acttgtccat cttctggatt ggccaactta attaatgtat gaaataaaag    12780
gatgcacaca tagtgacatg ctaatcacta taatgtgggc atcaaagttg tgtgttatgt    12840
gtaattacta gttatctgaa taaaagagaa agagatcatc catatttctt atcctaaatg    12900
aatgtcacgt gtctttataa ttctttgatg aaccagatgc atttcattaa ccaaatccat    12960
atacatataa atattaatca tatataatta atatcaattg ggttagcaaa acaaatctag    13020
tctaggtgtg ttttgcgaat gcggccgcca ccgcggtgga gctcgaattc cggtcgatcc    13080
gatgatcctg agcttctagc ataacttcgt atagcataca ttatacgaag ttatccagat    13140
```

```
ctgcccacag caagcacggc ctgaaggagg agatgaccat gaagtaccac atggagggct    13200
gcgtgaacgg ccacaagttc gtgatcaccg gcgagggcat cggctacccc ttcaagggca    13260
agcagaccat caacctgtgc gtgatcgagg gcggccccct gcccttcagc gaggacatcc    13320
tgagcgccgg cttcaagtac ggcgaccgga tcttcaccga gtaccccag acatcgtgg     13380 actacttcaa gaacagctgc cccgccggct acacctgggg ccggagcttc ctgttcgagg    13440
acggcgccgt gtgcatctgt aacgtggaca tcaccgtgag cgtgaaggag aactgcatct    13500
accacaagag catcttcaac ggcgtgaact tccccgccga cggccccgtg atgaagaaga    13560
tgaccaccaa ctgggaggcc agctgcgaga agatcatgcc cgtgcctaag cagggcatcc    13620
tgaagggcga cgtgagcatg tacctgctgc tgaaggacgg cggccggtac cggtgccagt    13680
tcgacaccgt gtacaaggcc aagagcgtgc ccagcaagat gcccgagtgg cacttcatcc    13740
agcacaagct gctgcgggag gaccggagcg acgccaagaa ccagaagtgg cagctgaccg    13800
agcacgccat cgccttcccc agcgccctgg cctgaagcgg ccgcaaccta gacttgtcca    13860
tcttctggat tggccaactt aattaatgta tgaaataaaa ggatgcacac atagtgacat    13920
gctaatcact ataatgtggg catcaaagtt gtgtgttatg tgtaattact agttatctga    13980
ataaaagaga aagagatcat ccatatttct tatcctaaat gaatgtcacg tgtctttata    14040
attctttgat gaaccagatg catttcatta accaaatcca tatacatata aatattaatc    14100
atatataatt aatatcaatt gggttagcaa aacaaatcta gtctaggtgt gttttgcgaa    14160
ttagcttggt cacccggtcc gggcctagaa ggccagcttg cggccgcccc gggcaacttt    14220
attatacaaa gttgatagat atcggaccga ttaaacttta attcggtccg aagcttgcat    14280
gcctgcagtg cagcgtgacc cggtcgtgcc cctctctaga gataatgagc attgcatgtc    14340
taagttataa aaaattacca catattttt ttgtcacact tgtttgaagt gcagtttatc    14400
tatctttata catatattta aacttactc tacgaataat ataatctata gtactacaat    14460
aatatcagtg ttttagagaa tcatataaat gaacagttag acatggtcta aaggacaatt    14520
gagtattttg acaacaggac tctacagttt tatctttta gtgtgcatgt gttctccttt    14580 tttttttgcaa atagcttcac ctatataata cttcatccat tttattagta catccattta    14640
gggtttaggg ttaatggttt ttatagacta attttttag tacatctatt ttattctatt    14700
ttagcctcta aattaagaaa actaaaactc tattttagtt tttttattta ataatttaga    14760
tataaaatag aataaaataa agtgactaaa aattaaacaa atacccttta agaaattaaa    14820
aaaactaagg aaacattttt cttgtttcga gtagataatg ccagcctgtt aaacgccgtc    14880
gacgagtcta acggacacca accagcgaac cagcagcgtc gcgtcgggcc aagcgaagca    14940
gacggcacgg catctctgtc gctgcctctg gaccctctc gagagttccg ctccaccgtt    15000
ggacttgctc cgctgtcggc atccagaaat tgcgtggcgg agcggcagac gtgagccggc    15060
acggcaggcg gcctcctcct cctctcacgg caccggcagc tacgggggat tcctttccca    15120
ccgctccttc gctttccctt cctcgcccgc cgtaataaat agacacccc tccacaccct    15180 ctttccccaa cctcgtgttg ttcggagcgc acacacacac aaccagatct cccccaaatc    15240
cacccgtcgg cacctccgct tcaaggtacg ccgctcgtcc tccccccccc cctctctac    15300 cttctctaga tcggcgttcc ggtccatgca tggttagggc ccggtagttc tacttctgtt    15360
catgtttgtg ttagatccgt gtttgtgtta gatccgtgct gctagcgttc gtacacggat    15420
gcgacctgta cgtcagacac gttctgattg ctaacttgcc agtgtttctc tttggggaat    15480
```

-continued

```
cctgggatgg ctctagccgt tccgcagacg ggatcgattt catgattttt tttgtttcgt    15540
tgcatagggt ttggtttgcc cttttccttt atttcaatat atgccgtgca cttgtttgtc    15600
gggtcatctt ttcatgcttt ttttttgtctt ggttgtgatg atgtggtctg gttgggcggt   15660
cgttctagat cggagtagaa ttctgtttca aactacctgg tggatttatt aattttggat    15720
ctgtatgtgt gtgccataca tattcatagt tacgaattga agatgatgga tggaaatatc   15780
gatctaggat aggtatacat gttgatgcgg gttttactga tgcatataca gagatgcttt    15840
ttgttcgctt ggttgtgatg atgtggtgtg gttgggcggt cgttcattcg ttctagatcg    15900
gagtagaata ctgtttcaaa ctacctggtg tatttattaa ttttggaact gtatgtgtgt    15960
gtcatacatc ttcatagtta cgagtttaag atggatggaa atatcgatct aggataggta    16020
tacatgttga tgtgggtttt actgatgcat atacatgatg gcatatgcag catctattca    16080
tatgctctaa ccttgagtac ctatctatta taataaacaa gtatgtttta taattatttt    16140
gatcttgata tacttggatg atggcatatg cagcagctat atgtggattt ttttagccct    16200
gccttcatac gctatttatt tgcttggtac tgtttctttt gtcgatgctc accctgttgt    16260
ttggtgttac ttctgcaggt cgactttaac ttagcctagg atccacacga caccatgtcc    16320
cccgagcgcc gccccgtcga gatccgcccg gccaccgccg ccgacatggc cgccgtgtgc    16380
gacatcgtga accactacat cgagacctcc accgtgaact tccgcaccga gccgcagacc    16440
ccgcaggagt ggatcgacga cctggagcgc ctccaggacc gctacccgtg gctcgtggcc    16500
gaggtggagg gcgtggtggc cggcatcgcc tacgccggcc cgtggaaggc ccgcaacgcc    16560
tacgactgga ccgtggagtc caccgtgtac gtgtcccacc gccaccagcg cctcggcctc    16620
ggctccaccc tctacaccca cctcctcaag agcatggagg cccagggctt caagtccgtg    16680
gtggccgtga tcgcctcccc gaacgacccg tccgtgcgcc tccacgaggc cctcggctac    16740 accgccgcg caccctccg cgccgccggc tacaagcacg gcggctggca cgacgtcggc    16800
ttctggcagc gcgacttcga gctgccggcc ccgccgcgcc cggtgcgccc ggtgacgcag    16860
atctgagtcg aaacctagac ttgtccatct tctggattgg ccaacttaat taatgtatga    16920
aataaaagga tgcacacata gtgacatgct aatcactata atgtgggcat caaagttgtg    16980
tgttatgtgt aattactagt tatctgaata aaagagaaag agatcatcca tatttcttat    17040
cctaaatgaa tgtcacgtgt ctttataatt ctttgatgaa ccagatgcat ttcattaacc    17100
aaatccatat acatataaat attaatcata tataattaat atcaattggg ttagcaaaac    17160
aaatctagtc taggtgtgtt ttgcgaattg cggccgccac cgcggtggag ctcgaattca    17220
ttccgattaa tcgtggcctc ttgctcttca ggatgaagag ctatgtttaa acgtgcaagc    17280
gctactagac aattcagtac attaaaaacg tccgcaatgt gttattaagt tgtctaagcg    17340
tcaatttgtt tacaccacaa tatatcctgc cac                                 17373
```

<210> SEQ ID NO 112
<211> LENGTH: 11111
<212> TYPE: DNA
<213> ORGANISM: Artificial Sequence
<220> FEATURE:
<223> OTHER INFORMATION: PHP46446
<220> FEATURE:
<221> NAME/KEY: misc_feature
<222> LOCATION: (1249)...(1756)
<223> OTHER INFORMATION: Rab17 promoter
<220> FEATURE:
<221> NAME/KEY: misc_feature
<222> LOCATION: (1757)...(1851)
<223> OTHER INFORMATION: Rab17 5' UTR

```
<220> FEATURE:
<221> NAME/KEY: misc_feature
<222> LOCATION: (1890)...(1913)
<223> OTHER INFORMATION: attB1
<220> FEATURE:
<221> NAME/KEY: misc_feature
<222> LOCATION: (1939)...(3156)
<223> OTHER INFORMATION: Cre
<220> FEATURE:
<221> NAME/KEY: misc_feature
<222> LOCATION: (3165)...(3188)
<223> OTHER INFORMATION: attB2
<220> FEATURE:
<221> NAME/KEY: misc_feature
<222> LOCATION: (3203)...(3520)
<223> OTHER INFORMATION: PinII term

<400> SEQUENCE: 112
```

| | | | | | |
|---|---|---|---|---|---|
| gtttacccgc | caatatatcc | tgtcaaacac | tgatagttta | aactgaaggc | gggaaacgac      60 |
| aatctgatca | tgagcggaga | attaagggag | tcacgttatg | accccgccg | atgacgcggg     120 |
| acaagccgtt | ttacgtttgg | aactgacaga | accgcaacgt | tgaaggagcc | actcagcaag     180 |
| ctggtacgat | tgtaatacga | ctcactatag | ggcgaattga | gcgctgttta | aacgctcttc     240 |
| aactggaaga | gcggttacta | ccggctggat | ggcggggcct | tgatcgtgca | ccgccggcgt     300 |
| ccggactaac | taactagtcg | agctagttac | cctatgaggt | gacatgaagc | gctcacggtt     360 |
| actatgacgg | ttagcttcac | gactgttggt | ggcagtagcg | tacgacttag | ctatagttcc     420 |
| ggacttaccg | ggcccaccgg | tggtaccgag | ctcgttttaaa | cgctcttcaa | ctggaagagc     480 |
| ggttaccaga | gctggtcacc | tttgtccacc | aagatggaac | tggcgcggct | aatttaaatc     540 |
| ctgaggatat | cgctatcaac | tttgtataga | aaagttgggc | cgaattcgag | ctcggtacgg     600 |
| ccagaatggc | ccggaccggg | ttaccgaatt | cgagctcggt | accctgggat | ccgatatcga     660 |
| tgggccctgg | ccgaagcttg | gtcacccggt | ccggcctag | aaggccagct | tcaagtttgt     720 |
| acaaaaaagc | aggctccggc | cagaatggcc | cggaccgggt | taccgaattc | gagctcggta     780 |
| ccctgggatc | cgatatcgat | gggccctggc | cgaagcttgg | tcacccggtc | cgggcctaga     840 |
| aggccgatct | cccgggcacc | cagctttctt | gtacaaagtg | gccgttaacg | gatcggccag     900 |
| aatggcccgg | accgggttac | cgaattcgag | ctcggtaccc | tgggatccga | tatcgatggg     960 |
| ccctggccga | agcttggtca | cccggtccgg | cctagaagg | ccagcttcgg | ccgccccggg    1020 |
| caactttatt | atacaaagtt | gatagataaa | tcctgaggat | ctggtcttcc | taaggacccg    1080 |
| ggatatcgga | ccgattaaac | tttaattcgg | tccgacctgg | tggcgccgct | agcgtatacg    1140 |
| aagttcctat | tccgaagttc | ctattctcca | gaaagtatag | gaacttctgt | acaataactt    1200 |
| cgtatagcat | acattatacg | aagttatgcc | cgggctggta | tttcaaaact | atagtatttt    1260 |
| aaaattgcat | taacaaacat | gtcctaattg | gtactcctga | gatactatac | cctcctgttt    1320 |
| taaaatagtt | ggcattatcg | aattatcatt | ttactcttta | atgttttctc | ttcttttaat    1380 |
| atatttatg | aatttaatg | tattttaaaa | tgttatgcag | ttcgctctgg | acttttctgc    1440 |
| tgcgcctaca | cttgggtgta | ctgggcctaa | attcagcctg | accgaccgcc | tgcattgaat    1500 |
| aatggatgag | caccggtaaa | atccgcgtac | ccaactttcg | agaagaaccg | agacgtggcg    1560 |
| ggccgggcca | ccgacgcacg | gcaccagcga | ctgcacacgt | cccgccggcg | tacgtgtacg    1620 |
| tgctgttccc | tcactggccg | cccaatccac | tcatgcatgc | ccacgtacac | ccctgccgtg    1680 |
| gcgcgcccag | atcctaatcc | tttcgccgtt | ctgcacttct | gctgcctata | aatgcggca    1740 |
| tcgaccgtca | cctgcttcac | caccggcgag | ccacatcgag | aacacgatcg | agcacacaag    1800 |

```
cacgaagact cgtttaggag aaaccacaaa ccaccaagcc gtgcaagcac caagcttggt    1860
cacccggtcc gggcctagaa ggccagcttc aagtttgtac aaaaaagcag cttcgaagg    1920 agatagaacc gatccaccat gtccaacctg ctcacggttc accagaacct tccggctctt    1980
ccagtggacg cgacgtccga tgaagtcagg aagaacctca tggacatgtt ccgcgacagg    2040
caagcgttca gcgagcacac ctggaagatg ctgctctccg tctgccgctc ctgggctgca    2100
tggtgcaagc tgaacaacag gaagtggttc cccgctgagc ccgaggacgt gagggattac    2160
cttctgtacc tgcaagcgcg aggtttgttt ctgcttctac ctttgatata tatataataa    2220
ttatcattaa ttagtagtaa tataatattt caaatatttt tttcaaaata aagaatgta    2280 gtatatagca attgcttttc tgtagtttat aagtgtgtat atttaattt ataacttttc    2340 taatatatga ccaaaacatg gtgatgccta ggtctggcag tgaagaccat ccagcaacac    2400
cttggacaac tgaacatgct tcacaggcgc tccggcctcc cgcgcccag cgactcgaac    2460 gccgtgagcc tcgtcatgcg ccgcatcagg aaggaaaacg tcgatgccgg cgaaagggca    2520
aagcaggccc tcgcgttcga gaggaccgat ttcgaccagg tccgcagcct gatggagaac    2580
agcgacaggt gccaggacat taggaacctg gcgttcctcg gaattgcata caacacgctc    2640
ctcaggatcg cggaaattgc ccgcattcgc gtgaaggaca ttagccgcac cgacggcggc    2700
aggatgctta ccacattgg caggaccaag acgctcgttt ccaccgcagg cgtcgaaaag    2760
gccctcagcc tcgagtgac caagctcgtc gaacgctgga tctccgtgtc cggcgtcgcg    2820
gacgacccaa acaactacct cttctgccgc gtccgcaaga cgggggtggc tgccctagc    2880 gccaccagcc aactcagcac gagggccttg aaggtatttt cgaggccac ccaccgcctg    2940 atctacggcg cgaaggatga cagcggtcaa cgctacctcg catggtccgg gcactccgcc    3000
cgcgttggag ctgctaggga catggcccgc gccggtgttt ccatcccga aatcatgcag    3060 gcgggtggat ggacgaacgt gaacattgtc atgaactaca ttcgcaacct tgacagcgag    3120
acgggcgcaa tggttcgcct cctggaagat ggtgactgag ctagacccag ctttcttgta    3180
caaagtggcc gttaacggat ccagacttgt ccatcttctg gattggccaa cttaattaat    3240
gtatgaaata aaaggatgca cacatagtga catgctaatc actataatgt gggcatcaaa    3300
gttgtgtgtt atgtgtaatt actagttatc tgaataaaag agaaagagat catccatatt    3360
tcttatccta aatgaatgtc acgtgtcttt ataattcttt gatgaaccag atgcatttca    3420
ttaaccaaat ccatatacat ataaatatta atcatatata attaatatca attgggttag    3480
caaaacaaat ctagtctagg tgtgttttgc gaattgcggc aagcttcggc cgccccagct    3540
tggtcacccg gtccgggcct agaaggccga tctcccgggc acccagcttt cttgtacaaa    3600
gtggccgtta acggatcggc cagaatggcc cggaccgggt taccgaattc gagctcggta    3660
ccctgggatc gaccgaagct gaccgaagct tgcggccgca cactgatagt ttaaactgaa    3720
ggcgggaaac gacaatctga tcatgagcgg agaattaagg gagtcacgtt atgaccccg    3780 ccgatgacgc gggacaagcc gttttacgtt tggaactgac agaaccgcaa cgttgaagga    3840
gccactcagc cgcgggtttc tggagtttaa tgagctaagc acatacgtca gaaaccatta    3900
ttgcgcgttc aaaagtcgcc taaggtcact atcagctagc aaatatttct tgtcaaaaat    3960
gctccactga cgttccataa attcccctcg gtatccaatt agagtctcat attcactctc    4020 ccggggatc tcgactctag aggatcgctc aggaaggccg ctgagataga ggcatggcgg    4080
ccaatgcggg cggcggtgga gcgggaggag gcagcggcag cggcagcgtg gctgcgccgg    4140
cggtgtgccg ccccagcggc tcgcggtgga cgccgacgcc ggagcagatc aggatgctga    4200
```

```
aggagctcta ctacggctgc ggcatccggt cgcccagctc ggagcagatc cagcgcatca    4260
ccgccatgct gcggcagcac ggcaagatcg agggcaagaa cgtcttctac tggttccaga    4320
accacaaggc ccgcgagcgc cagaagcgcc gcctcaccag cctcgacgtc aacgtgcccg    4380
ccgccggcgc ggccgacgcc accaccagcc aactcggcgt cctctcgctg tcgtcgccgc    4440
cgccttcagg cgcggcgcct ccctcgccca ccctcggctt ctacgccgcc ggcaatggcg    4500
gcggatcggc tgtgctgctg gacacgagtt ccgactgggg cagcagcggc gctgccatgg    4560
ccaccgagac atgcttcctg caggactaca tgggcgtgac ggacacgggc agctcgtcgc    4620
agtggccacg cttctcgtcg tcggacacga taatggcggc ggccgcggcg cgggcggcga    4680
cgacgcgggc gcccgagacg ctccctctct cccgacctg cggcgacgac ggcggcagcg    4740
gtagcagcag ctacttgccg ttctggggtg ccgcgtccac aactgccggc gccacttctt    4800
ccgttgcgat ccagcagcaa caccagctgc aggagcagta cagcttttac agcaacagca    4860
acagcaccca gctggccggc accggcaacc aagacgtatc ggcaacagca gcagcagccg    4920
ccgccctgga gctgagcctc agctcatggt gctcccctta ccctgctgca gggagtatgt    4980
gagagcaacg cgagctgcca ctgctcttca ctgatgtctc tggaatggaa ggaggaggaa    5040
gtgagcatag cgttggtgcg ttgctgtcaa gggcgaattc acatggttaa cctagacttg    5100
tccatcttct ggattggcca acttaattaa tgtatgaaat aaaaggatgc acacatagtg    5160
acatgctaat cactataatg tgggcatcaa agttgtgtgt tatgtgtaat tactagttat    5220
ctgaataaaa gagaaagaga tcatccatat ttcttatcct aaatgaatgt cacgtgtctt    5280
tataattctt tgatgaacca gatgcatttc attaaccaaa tccatataca tataaatatt    5340
aatcatatat aattaatatc aattgggtta gcaaaacaaa tctagtctag gtgtgttttg    5400
cgaatgcggc cgcgactcta gatcataatc agccatacca cattcgaatg tgagttgatc    5460
cccggcggtg tcccccactg aagaaactat gtgctgtagt atagccgctg cccgctggct    5520
agctagctag ttgagtcatt tagcggcgat gattgagtaa taatgtgtca cgcatcacca    5580
tgcatgggtg gcagtgtcag tgtgagcaat gacctgaatg aacaattgaa atgaaaagaa    5640
aaaagtattg ttccaaatta aacgttttaa ccttttaata ggtttataca ataattgata    5700
tatgttttct gtatatgtct aatttgttat catccattta gatatagaca aaaaaaatct    5760
aagaactaaa acaaatgcta atttgaaatg aagggagtat atattgggat aatgtcgatg    5820
agatccctcg taatatcacc gacatcacac gtgtccagtt aatgtatcag tgatacgtgt    5880
attcacattt gttgcgcgta ggcgtaccca acaattttga tcgactatca gaaagtcaac    5940
ggaagcgagt cgacctcgag ggggggcccg gtaccaagat atcaaccgcg gaaagatcta    6000
agcatgcaag gcccaagtc gacctgcaga agcttcggtc cgggcctaga aggccgatct    6060
cccgggcacc cagctttctt gtacaaagtg gccgttaacg gatcggccag aatggcccgg    6120
accgggttac cgaattcgag ctcggtaccc tgggatcgac cgaagcttgc atgcctgcag    6180
tgcagcgtga cccggtcgtg cccctctcta gagataatga gcattgcatg tctaagttat    6240
aaaaaattac cacatatttt ttttgtcaca cttgtttgaa gtgcagttta tctatcttta    6300
tacatatatt taaactttac tctacgaata tataatctcta tagtactaca ataatatcag    6360
tgttttagag aatcatataa atgaacagtt agacatggtc taaggacaa ttgagtattt    6420 tgacaacagg actctacagt tttatctttt tagtgtgcat gtgttctcct tttttttttgc    6480 aaatagcttc acctatataa tacttcatcc attttattag tacatccatt tagggtttag    6540
```

```
ggttaatggt tttttatagac taattttttt agtacatcta ttttattcta ttttagcctc    6600
taaattaaga aaactaaaac tctattttag ttttttttatt taataattta gatataaaat    6660
agaataaaat aaagtgacta aaaattaaac aaatacccctt taagaaatta aaaaaactaa    6720
ggaaacattt ttcttgtttc gagtagataa tgccagcctg ttaaacgccg tcgacgagtc    6780
taacggacac caaccagcga accagcagcg tcgcgtcggg ccaagcgaag cagacggcac    6840
ggcatctctg tcgctgcctc tggaccccctc tcgagagttc cgctccaccg ttggacttgc    6900
tccgctgtcg gcatccagaa attgcgtggc ggagcggcag acgtgagccg gcacggcagg    6960
cggcctcctc ctcctctcac ggcaccggca gctacggggg attcctttcc caccgctcct    7020
tcgctttccc ttcctcgccc gccgtaataa atagacaccc cctccacacc ctctttcccc    7080
aacctcgtgt tgttcggagc gcacacacac acaaccagat ctcccccaaa tccacccgtc    7140
ggcacctccg cttcaaggta cgccgctcgt cctcccccccc ccccctctct accttctcta    7200
gatcggcgtt ccggtccatg catggttagg gcccggtagt tctacttctg ttcatgtttg    7260
tgttagatcc gtgtttgtgt tagatccgtg ctgctagcgt tcgtacacgg atgcgacctg    7320
tacgtcagac acgttctgat tgctaacttg ccagtgtttc tctttgggga atcctgggat    7380
ggctctagcc gttccgcaga cgggatcgat ttcatgattt tttttgtttc gttgcatagg    7440
gtttggtttg ccctttttcct ttatttcaat atatgccgtg cacttgtttg tcgggtcatc    7500
ttttcatgct ttttttttgtc ttggttgtga tgatgtggtc tggttgggcg gtcgttctag    7560
atcggagtag aattctgttt caaactacct ggtggattta ttaattttgg atctgtatgt    7620
gtgtgccata catattcata gttacgaatt gaagatgatg gatggaaata tcgatctagg    7680
ataggtatac atgttgatgc gggttttact gatgcatata cagagatgct ttttgttcgc    7740
ttggttgtga tgatgtggtg tggttgggcg gtcgttcatt cgttctagat cggagtagaa    7800
tactgtttca aactacctgg tgtatttatt aattttggaa ctgtatgtgt gtgtcataca    7860
tcttcatagt tacgagttta agatggatgg aaatatcgat ctaggatagg tatacatgtt    7920
gatgtgggtt ttactgatgc atatacatga tggcatatgc agcatctatt catatgctct    7980
aaccttgagt acctatctat tataataaac aagtatgttt taatttatt ttgatcttga    8040
tatacttgga tgatggcata tgcagcagct atatgtggat tttttttagcc ctgccttcat    8100
acgctattta tttgcttggt actgtttctt ttgtcgatgc tcaccctgtt gtttggtgtt    8160
acttctgcag gtcgactcta gaggatccat ggccactgtg aacaactggc tcgctttctc    8220
cctctccccg caggagctgc cgccctccca gacgacggac tccacactca tctcggccgc    8280
caccgccgac catgtctccg gcgatgtctg cttcaacatc ccccaagatt ggagcatgag    8340
gggatcagag ctttcggcgc tcgtcgcgga gccgaagctg gaggacttcc tcggcggcat    8400
ctccttctcc gagcagcatc acaaggccaa ctgcaacatg atacccagca ctagcagcac    8460
agtttgctac gcgagctcag gtgctagcac cggctaccat caccagctgt accaccagcc    8520
caccagctca gcgctccact tcgcggactc cgtaatggtg gcctcctcgg ccggtgtcca    8580
cgacggcggt gccatgctca gcgcggccgc cgctaacggt gtcgctggcg ctgccagtgc    8640
caacggcggc ggcatcgggc tgtccatgat taagaactgg ctgcggagcc aaccggcgcc    8700
catgcagccg agggtggcgg cggctgaggg cgcgcagggg ctctctttgt ccatgaacat    8760
ggcggggacg acccaaggcg ctgctggcat gccacttctc gctggagagc gcgcacgggc    8820
gcccgagagt gtatcgacgt cagcacaggg tggagccgtc gtcgtcacgg cgccgaagga    8880
ggatagcggt ggcagcggtg ttgccggcgc tctagtagcc gtgagcacgg acacgggtgg    8940
```

```
cagcggcggc gcgtcggctg acaacacggc aaggaagacg gtggacacgt tcgggcagcg    9000
cacgtcgatt taccgtggcg tgacaaggca tagatggact gggagatatg aggcacatct    9060
ttgggataac agttgcagaa gggaagggca aactcgtaag ggtcgtcaag tctatttagg    9120
tggctatgat aaagaggaga aagctgctag ggcttatgat cttgctgctc tgaagtactg    9180
gggtgccaca acaacaacaa attttccagt gagtaactac gaaaaggagc tcgaggacat    9240
gaagcacatg acaaggcagg agtttgtagc gtctctgaga aggaagagca gtggtttctc    9300
cagaggtgca tccatttaca ggggagtgac taggcatcac caacatggaa gatggcaagc    9360
acggattgga cgagttgcag ggaacaagga tctttacttg ggcaccttca gcacccagga    9420
ggaggcagcg gaggcgtacg acatcgcggc gatcaagttc cgcggcctca acgccgtcac    9480
caacttcgac atgagccgct acgacgtgaa gagcatcctg gacagcagcg ccctccccat    9540
cggcagcgcc gccaagcgcc tcaaggaggc cgaggccgca gcgtccgcgc agcaccacca    9600
cgccggcgtg gtgagctacg acgtcggccg catcgcctcg cagctcggcg acggcggagc    9660
cctggcggcg gcgtacggcg cgcactacca cggcgccgcc tggccgacca tcgcgttcca    9720
gccgggcgcc gccagcacag gcctgtacca cccgtacgcg cagcagccaa tgcgcggcgg    9780
cgggtggtgc aagcaggagc aggaccacgc ggtgatcgcg gccgcgcaca gcctgcagga    9840
cctccaccac ctgaacctgg gcgcggccgg cgcgcacgac ttttctcgg cagggcagca    9900
ggccgccgcc gctgcgatgc acggcctggg tagcatcgac agtgcgtcgc tcgagcacag    9960
caccggctcc aactccgtcg tctacaacgg cggggtcggc gacagcaacg gcgccagcgc    10020
cgtcggcggc agtggcggtg gctacatgat gccgatgagc gctgccggag caaccactac    10080
atcggcaatg gtgagccacg agcaggtgca tgcacgggcc tacgacgaag ccaagcaggc    10140
tgctcagatg gggtacgaga gctacctggt gaacgcggag aacaatggtg gcggaaggat    10200
gtctgcatgg gggactgtcg tgtctgcagc cgcggcggca gcagcaagca gcaacgacaa    10260
catggccgcc gacgtcggcc atggcggcgc gcagctcttc agtgtctgga acgacactta    10320
agcgtacgtg ccggcctggc tctccgaaag ggcgaattcc agcacactgg cggccgttac    10380
tagacccaac ctagacttgt ccatcttctg gattggccaa cttaattaat gtatgaaata    10440
aaaggatgca cacatagtga catgctaatc actataatgt gggcatcaaa gttgtgtgtt    10500
atgtgtaatt actagttatc tgaataaaag agaaagagat catccatatt tcttatccta    10560
aatgaatgtc acgtgtcttt ataattcttt gatgaaccag atgcatttca ttaaccaaat    10620
ccatatacat ataaatatta atcatatata attaatatca attgggttag caaaacaaat    10680
ctagtctagg tgtgttttgc gaattagctt ggtcacccgg tccgggccta gaaggccagc    10740
ttcggccgcc ccgggcaact ttattataca aagttgatag atcgaataac ttcgtatagc    10800
atacattata cgaagttatc ctgagctgat tccgatgact tcgtaggttc ctagctcaag    10860
ccgctcgtgt ccaagcgtca cttacgatta gctaatgatt acggcatcta ggaccgacta    10920
gctaactaac tagtacgtag aattgtagaa ttaattcatt ccgattaatc gtggcctctt    10980
gctcttcagg atgaagagct atgtttaaac gtgcaagcgc tactagacaa ttcagtacat    11040
taaaaacgtc cgcaatgtgt tattaagttg tctaagcgtc aatttgttta caccacaata    11100
tatcctgcca c                                                         11111
```

<210> SEQ ID NO 113
<211> LENGTH: 10477
<212> TYPE: DNA

<213> ORGANISM: Artificial Sequence
<220> FEATURE:
<223> OTHER INFORMATION: PHP48733
<220> FEATURE:
<221> NAME/KEY: misc_feature
<222> LOCATION: (1306)...(1813)
<223> OTHER INFORMATION: Rab17 promoter
<220> FEATURE:
<221> NAME/KEY: misc_feature
<222> LOCATION: (1814)...(1908)
<223> OTHER INFORMATION: Rab17 5' UTR
<220> FEATURE:
<221> NAME/KEY: misc_feature
<222> LOCATION: (1947)...(1970)
<223> OTHER INFORMATION: attB1
<220> FEATURE:
<221> NAME/KEY: misc_feature
<222> LOCATION: (1996)...(3213)
<223> OTHER INFORMATION: Cre
<220> FEATURE:
<221> NAME/KEY: misc_feature
<222> LOCATION: (3222)...(3245)
<223> OTHER INFORMATION: attB2
<220> FEATURE:
<221> NAME/KEY: misc_feature
<222> LOCATION: (3260)...(3577)
<223> OTHER INFORMATION: PinII term

<400> SEQUENCE: 113

```
gtttacccgc caatatatcc tgtcaaacac tgatagttta aactgaaggc gggaaacgac      60
aatctgatca tgagcggaga attaagggag tcacgttatg accccgccg atgacgcggg     120
acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacta ccggctggat ggcgggcct tgatcgtgca ccgccggcgt     300
ccggactaac taactagtcg agctagttac cctatgaggt gacatgaagc gctcacggtt    360
actatgacgg ttagcttcac gactgttggt ggcagtagcg tacgacttag ctatagttcc    420
ggacttaccg ggcccaccgg tggtaccgag ctcgtttaaa cgctcttcaa ctggaagagc    480
ggttaccaga gctggtcacc tttgtccacc aagatggaac tggcgcggct aatttaaatc    540
ctgaggatat cgctatcaac tttgtataga aaagttgggc cgaattcgag ctcggtacgg    600
ccagaatggc ccggaccggg ttaccgaatt cgagctcggt accctgggat ccgatatcga    660
tgggccctgg ccgaagcttg gtcacccggt ccgggcctag aaggccagct tcaagtttgt    720
acaaaaaagc aggctccggc cagaatggcc cggaccgggt taccgaattc gagctcggta    780
ccctgggatc cgatatcgat gggccctggc cgaagcttgg tcacccggtc cgggcctaga    840
aggccgatct cccgggcacc cagctttctt gtacaaagtg gccgttaacg gatcggccag    900
aatggcccgg accggttac cgaattcgag ctcggtaccc tgggatccga tatcgatggg    960
ccctggccga agcttggtca cccggtccgg gcctagaagg ccagcttcgg ccgccccggg   1020
caactttatt atacaaagtt gatagataaa tcctgaggat ctggtcttcc taaggacccg   1080
ggatatcgga ccgattaaac tttaattcgg tccgacctgg tggcgccgct agcataactt   1140
cgtatagcat acattatacg aagttatcca tatctgaccg gcttaccgaa tgcgtgctcg   1200
ctaccctggg atgcgatttc gatggcccct ggccgaagct ggcatatcgc tatgaccggg   1260
ttagccaatt cgacctcgct accctgggga tgctacgtaa cgcgtctata gtattttaaa   1320
attgcattaa caaacatgtc ctaattggta ctcctgagat actataccct cctgttttaa   1380
aatagttggc attatcgaat tatcatttta ctttttaatg ttttctcttc ttttaatata   1440
ttttatgaat tttaatgtat tttaaaatgt tatgcagttc gctctggact tttctgctgc   1500
```

```
gcctacactt gggtgtactg ggcctaaatt cagcctgacc gaccgcctgc attgaataat  1560
ggatgagcac cggtaaaatc cgcgtaccca actttcgaga agaaccgaga cgtggcgggc  1620
cgggccaccg acgcacggca ccagcgactg cacacgtccc gccggcgtac gtgtacgtgc  1680
tgttccctca ctggccgccc aatccactca tgcatgccca cgtacacccc tgccgtggcg  1740
cgcccagatc ctaatccttt cgccgttctg cacttctgct gcctataaat ggcggcatcg  1800
accgtcacct gcttcaccac cggcgagcca catcgagaac acgatcgagc acacaagcac  1860
gaagactcgt ttaggagaaa ccacaaacca ccaagccgtg caagcaccag gcttgggcac  1920
ccgctccggg cttagaaggc cagcttcaag tttgtacaaa aaagcaggct tcgaaggaga  1980
tagaaccgat ccaccatgtc caacctgctc acggttcacc agaaccttcc ggctcttcca  2040
gtggacgcga cgtccgatga agtcaggaag aacctcatgg acatgttccg cgacaggcaa  2100
gcgttcagcg agcacacctg gaagatgctg ctctccgtct gccgctcctg ggctgcatgg  2160
tgcaagctga acaacaggaa gtggttcccc gctgagcccg aggacgtgag ggattacctt  2220
ctgtacctgc aagcgcgagg tttgtttctg cttctacctt tgatatatat ataataatta  2280
tcattaatta gtagtaatat aatatttcaa atatttttt caaaataaaa gaatgtagta  2340
tatagcaatt gcttttctgt agtttataag tgtgtatatt ttaatttata acttttctaa  2400
tatatgacca aaacatggtg atgcctaggt ctggcagtga agaccatcca gcaacacctt  2460
ggacaactga acatgcttca caggcgctcc ggcctcccgc gccccagcga ctcgaacgcc  2520
gtgagcctcg tcatgcgccg catcaggaag gaaaacgtcg atgccggcga aagggcaaag  2580
caggccctcg cgttcgagag gaccgatttc gaccaggtcc gcagcctgat ggagaacagc  2640
gacaggtgcc aggacattag gaacctggcg ttcctcggaa ttgcatacaa cacgctcctc  2700
aggatcgcgg aaattgcccg cattcgcgtg aaggacatta gccgcaccga cggcggcagg  2760
atgcttatcc acattggcag gaccaagacg ctcgtttcca ccgcaggcgt cgaaaaggcc  2820
ctcagcctcg gagtgaccaa gctcgtcgaa cgctggatct ccgtgtccgg cgtcgcggac  2880
gacccaaaca actacctctt ctgccgcgtc cgcaagaacg gggtggctgc ccctagcgcc  2940
accagccaac tcagcacgag ggccttggaa ggtattttcg aggccaccca ccgcctgatc  3000
tacggcgcga aggatgacag cggtcaacgc tacctcgcat ggtccgggca ctccgcccgc  3060
gttggagctg ctagggacat ggcccgcgcc ggtgtttcca tccccgaaat catgcaggcg  3120
ggtggatgga cgaacgtgaa cattgtcatg aactacattc gcaaccttga cagcgagacg  3180
ggcgcaatgg ttcgcctcct ggaagatggt gactgagcta gacccagctt tcttgtacaa  3240
agtggccgtt aacggatgca gacttgtcca tcttctggat tggccaactt aattaatgta  3300
tgaaataaaa ggatgcacac atagtgacat gctaatcact ataatgtggg catcaaagtt  3360
gtgtgttatg tgtaattact agttatctga ataaagaga aagagatcat ccatatttct  3420
tatcctaaat gaatgtcacg tgtctttata attctttgat gaaccagatg catttcatta  3480
accaaatcca tatacatata aatattaatc atatataatt aatatcaatt gggttagcaa  3540
aacaaatcta gtctaggtgt gttttgcgaa ttgcggcaag gttgcgcccg ccccagcttg  3600
gtcagccgct ccgggcttag aaggccgatc tcgcgggcac ccagctttct tctacaaagt  3660
ggccgtttac ggatcggcta gaatgtcccg caccggctta ccgatttgca cctcgctacc  3720
ctgggttcga ccgaagctga ccgatgcttg cgccgctcg cgaggccggc cacactgata  3780
gtttaaactg aaggcgggaa acgacaatct gatcatgagc ggagaattaa gggagtcacg  3840
```

| | |
|---|---|
| ttatgacccc cgccgatgac gcgggacaag ccgttttacg tttggaactg acagaaccgc | 3900 |
| aacgattgaa ggagccactc agccgcgggt ttctggagtt taatgagcta agcacatacg | 3960 |
| tcagaaacca ttattgcgcg ttcaaaagtc gcctaaggtc actatcagct agcaaatatt | 4020 |
| tcttgtcaaa aatgctccac tgacgttcca taaattcccc tcggtatcca attagagtct | 4080 |
| catattcact ctcccggcgg atctcgactc tagaggatcg ctcaggaagg ccgctgagat | 4140 |
| agagccatgg cggccaatgc gggcggcggt ggagcgggag gaggcagcgg cagcggcagc | 4200 |
| gtggctgcgc cggcggtgtg ccgccccagc ggctcgcggt ggacgccgac gccggagcag | 4260 |
| atcaggatgc tgaaggagct ctactacggc tgcggcatcc ggtcgcccag ctcggagcag | 4320 |
| atccagcgca tcaccgccat gctgcggcag cacggcaaga tcgagggcaa gaacgtcttc | 4380 |
| tactggttcc agaaccacaa ggccgcgag cgccagaagc gccgcctcac cagcctcgac | 4440 |
| gtcaacgtgc ccgccgccgg cgcggccgac gccaccacca gccaactcgg cgtcctctcg | 4500 |
| ctgtcgtcgc cgccgccttc aggcgcggcg cctccctcgc ccaccctcgg cttctacgcc | 4560 |
| gccggcaatg gcgcggatc ggctgtgctg ctggacacga gttccgactg gggcagcagc | 4620 |
| ggcgctgcta tggccaccga gacatgcttc ctgcaggact acatgggcgt gacggacacg | 4680 |
| ggcagctcgt cgcagtggcc acgcttctcg tcgtcggaca cgataatggc ggcggccgcg | 4740 |
| gcgcgggcgg cgacgacgcg ggcgcccgag acgctccctc tcttcccgac ctgcggcgac | 4800 |
| gacggcggca gcgtagcag cagctacttg ccgttctggg gtgccgcgtc cacaactgcc | 4860 |
| ggcgccactt cttccgttgc gatccaacag caacaccagc tgcaggagca gtacagcttt | 4920 |
| tacagcaaca gcaacagcac ccagctggcc ggcaccggca accaagacgt atcggcaaca | 4980 |
| gcagcagcag ccgccgccct ggagctgagc ctcagctcat ggtgctcccc ttaccctgct | 5040 |
| gcagggagta tgtgagagca acgcgagctg ccactgctct tcactgatgt ctctggaatg | 5100 |
| gaaggaggag gaagtgagca tagcgttggt gcgttgctgt caagggcgaa ttgtaccaca | 5160 |
| tggttaacct agacttgtcc atcttctgga ttggccaact taattaatgt atgaaataaa | 5220 |
| aggatgcaca catagtgaca tgctaatcac tataatgtgg gcatcaaagt tgtgtgttat | 5280 |
| gtgtaattac tagttatctg aataaaagag aaagagatca tccatatttc ttatcctaaa | 5340 |
| tgaatgtcac gtgtctttat aattctttga tgaaccagat gcatttcatt aaccaaatcc | 5400 |
| atatacatat aaatattaat catatataat taatatcaat tgggttagca aaacaaatct | 5460 |
| agtctaggtg tgttttgcgg gtaccattta aattgcgccc gccacggccg tggaggtcgt | 5520 |
| attccggtca gcttgcatcc ctgcagtgca gcgtgacccg gtcgtgcccc tctctagaga | 5580 |
| taatgagcat tgcatgtcta agttataaaa aattaccaca tattttttt gtcacacttg | 5640 |
| tttgaagtgc agtttatcta tctttataca tatatttaaa ctttactcta cgaataatat | 5700 |
| aatctatagt actacaataa tatcagtgtt ttagagaatc atataaatga acagttagac | 5760 |
| atggtctaaa ggacaattga gtattttgac aacaggactc tacagtttta tcttttagt | 5820 |
| gtgcatgtgt tctcctttt ttttgcaaat agcttcacct atataatact tcatccattt | 5880 |
| tattagtaca tccatttagg gtttagggtt aatggttttt atagactaat tttttagta | 5940 |
| catctatttt attctatttt agcctctaaa ttaagaaaac taaaactcta ttttagttttt | 6000 |
| tttatttaat aatttagata taaatagaa taaaataaag tgactaaaaa ttaaacaaat | 6060 |
| acccttttaag aaattaaaaa aactaaggaa acatttttct tgtttcgagt agataatgcc | 6120 |
| agcctgttaa acgccgtcga cgagtctaac ggacaccaac cagcgaacca gcagcgtcgc | 6180 |
| gtcgggccaa gcgaagcaga cggcacggca tctctgtcgc tgcctctgga cccctctcga | 6240 |

| | |
|---|---|
| gagttccgct ccaccgttgg acttgctccg ctgtcggcat ccagaaattg cgtggcggag | 6300 |
| cggcagacgt gagccggcac ggcaggcggc ctcctcctcc tctcacggca ccggcagcta | 6360 |
| cgggggattc ctttcccacc gctccttcgc tttcccttcc tcgcccgccg taataaatag | 6420 |
| acacccccte cacaccctct ttccccaacc tcgtgttgtt cggagcgcac acacacacaa | 6480 |
| ccagatctcc cccaaatcca cccgtcggca cctccgcttc aaggtacgcc gctcgtcctc | 6540 |
| cccccccccc ctctctacct tctctagatc ggcgttccgg tccatgcatg gttagggccc | 6600 |
| ggtagttcta cttctgttca tgtttgtgtt agatccgtgt tgtgttaga tccgtgctgc | 6660 |
| tagcgttcgt acacggatgc gacctgtacg tcagacacgt tctgattgct aacttgccag | 6720 |
| tgtttctctt tggggaatcc tgggatggct ctagccgttc cgcagacggg atcgatttca | 6780 |
| tgatttttt tgtttcgttg catagggttt ggtttgccct tttcctttat ttcaatatat | 6840 |
| gccgtgcact tgtttgtcgg gtcatctttt catgcttttt tttgtcttgg ttgtgatgat | 6900 |
| gtggtctggt tgggcggtcg ttctagatcg gagtagaatt ctgtttcaaa ctacctggtg | 6960 |
| gatttattaa ttttggatct gtatgtgtgt gccatacata ttcatagtta cgaattgaag | 7020 |
| atgatggatg gaaatatcga tctaggatag gtatacatgt tgatgcgggt tttactgatg | 7080 |
| catatacaga gatgcttttt gttcgcttgg ttgtgatgat gtggtgtggt tgggcggtcg | 7140 |
| ttcattcgtt ctagatcgga gtagaatact gtttcaaact acctggtgta tttattaatt | 7200 |
| ttggaactgt atgtgtgtgt catacatctt catagttacg agtttaagat ggatggaaat | 7260 |
| atcgatctag dataggtata catgttgatg tgggttttac tgatgcatat acatgatggc | 7320 |
| atatgcagca tctattcata tgctctaacc ttgagtacct atctattata ataaacaagt | 7380 |
| atgtttata attattttga tcttgatata cttggatgat ggcatatgca gcagctatat | 7440 |
| gtggatttt ttagccctgc cttcatacgc tatttatttg cttggtactg tttcttttgt | 7500 |
| cgatgctcac cctgttgttt ggtgttactt ctgcaggtcg actctagagg atccatggcc | 7560 |
| actgtgaaca actggctcgc tttctccctc tccccgcagg agctgccgcc ctcccagacg | 7620 |
| acggactcca cactcatctc ggccgccacc gccgaccatg tctccggcga tgtctgcttc | 7680 |
| aacatccccc aagattggag catgagggga tcagagcttt cggcgctcgt cgcggagccg | 7740 |
| aagctggagg acttcctcgg cggcatctcc ttctccgagc agcatcacaa ggccaactgc | 7800 |
| aacatgatac ccagcactag cagcacagtt tgctacgcga gctcaggtgc tagcaccggc | 7860 |
| taccatcacc agctgtacca ccagcccacc agctcagcgc tccacttcgc ggactccgta | 7920 |
| atggtggctt cctcggccgg tgtccacgac ggcggtgcca tgctcagcgc ggccgccgct | 7980 |
| aacggtgtcg ctggcgctgc cagtgccaac ggcggcggca tcgggctgtc catgattaag | 8040 |
| aactggctgc ggagccaacc ggcgcccatg cagccgaggg tggcggcggc tgagggcgcg | 8100 |
| cagggctct ctttgtccat gaacatggcg gggacgaccc aaggcgctgc tggcatgcca | 8160 |
| cttctcgctg gagagcgcgc acgggcgccc gagagtgtat cgacgtcagc acagggtgga | 8220 |
| gccgtcgtcg tcacggcgcc gaaggaggat agcggtggca gcggtgttgc cggcgctcta | 8280 |
| gtagccgtga gcacggacac gggtggcagc ggcggcgcgt cggctgacaa cacggcaagg | 8340 |
| aagacggtgg acacgttcgg gcagcgcacg tcgatttacc gtggcgtgac aaggcataga | 8400 |
| tggactggga gatatgaggc acatctttgg gataacagtt gcagaaggga agggcaaact | 8460 |
| cgtaagggtc gtcaagtcta tttaggtggc tatgataaag aggagaaagc tgctagggct | 8520 |
| tatgatcttg ctgctctgaa gtactggggt gccacaacaa caacaaattt tccagtgagt | 8580 |

| | |
|---|---|
| aactacgaaa aggagctcga ggacatgaag cacatgacaa ggcaggagtt tgtagcgtct | 8640 |
| ctgagaagga agagcagtgg tttctccaga ggtgcatcca tttacagggg agtgactagg | 8700 |
| catcaccaac atggaagatg gcaagcacgg attggacgag ttgcagggaa caaggatctt | 8760 |
| tacttgggca ccttcagcac ccaggaggag gcagcgagg cgtacgacat cgcggcgatc | 8820 |
| aagttccgcg gcctcaacgc cgtcaccaac ttcgacatga gccgctacga cgtgaagagc | 8880 |
| atcctggaca gcagcgccct ccccatcggc agcgccgcca agcgcctcaa ggaggccgag | 8940 |
| gccgcagcgt ccgcgcagca ccaccacgcc ggcgtggtga gctacgacgt cggccgcatc | 9000 |
| gcctcgcagc tcggcgacgg cggagccctg gcggcggcgt acggcgcgca ctaccacggc | 9060 |
| gccgcctggc cgaccatcgc gttccagccg gcgccgcca gcacaggcct gtaccacccg | 9120 |
| tacgcgcagc agccaatgcg cggcggcggg tggtgcaagc aggagcagga ccacgcggtg | 9180 |
| atcgcggccg cgcacagcct gcaggacctc caccacctga acctgggcgc ggccggcgcg | 9240 |
| cacgactttt tctcggcagg gcagcaggcc gccgccgctg cgatgcacgg cctgggtagc | 9300 |
| atcgacagtg cgtcgctcga gcacagcacc ggctccaact ccgtcgtcta caacggcggg | 9360 |
| gtcggcgaca gcaacggcgc cagcgccgtc ggcggcagtg gcggtggcta catgatgccg | 9420 |
| atgagcgctg ccggagcaac cactacatcg gcaatggtga ccacgagca ggtgcatgca | 9480 |
| cgggcctacg acgaagccaa gcaggctgct cagatggggt acgagagcta cctggtgaac | 9540 |
| gcggagaaca atggtggcgg aaggatgtct gcatggggga ctgtcgtgtc tgcagccgcg | 9600 |
| gcggcagcag caagcagcaa cgacaacatg gccgccgacg tcgggcatgg cggcgcgcag | 9660 |
| ctcttcagtg tctggaacga cacttaagcg tacgtgccgg cctggctctc cgaaagggcg | 9720 |
| tattccagca cactggcggc cgttactaga cccaacctag acttgtccat cttctggatt | 9780 |
| ggccaactta attaatgtat gaaataaaag gatgcacaca tagtgacatg ctaatcacta | 9840 |
| taatgtgggc atcaaagttg tgtgttatgt gtaattacta gttatctgaa taaaagagaa | 9900 |
| agagatcatc catatttctt atcctaaatg aatgtcacgt gtctttataa ttctttgatg | 9960 |
| aaccagatgc atttcattaa ccaaatccat atacatataa atattaatca tatataatta | 10020 |
| atatcaattg ggttagcaaa acaaatctag tctaggtgtg ttttgcgaat tagcttggtc | 10080 |
| acccggtccg ggcctagaag gccagcttcg gccgccccgg gcaactttat tatacaaagt | 10140 |
| tgatagatcg aataacttcg tatagcatac attatacgaa gttatcctga gctgattccg | 10200 |
| atgacttcgt aggttcctag ctcaagccgc tcgtgtccaa gcgtcactta cgattagcta | 10260 |
| atgattacgg catctaggac cgactagcta actaactagt acgtagaatt gtagaattaa | 10320 |
| ttcattccga ttaatcgtgg cctcttgctc ttcaggatga agagctatgt ttaaacgtgc | 10380 |
| aagcgctact agacaattca gtacattaaa aacgtccgca atgtgttatt aagttgtcta | 10440 |
| agcgtcaatt tgtttacacc acaatatatc ctgccac | 10477 |

<210> SEQ ID NO 114
<211> LENGTH: 978
<212> TYPE: DNA
<213> ORGANISM: Zea mays
<220> FEATURE:
<221> NAME/KEY: CDS
<222> LOCATION: (1)...(978)

<400> SEQUENCE: 114

| | |
|---|---|
| atg gcg gcc aat gcg ggc ggc ggt gga gcg gga gga ggc agc ggc agc<br>Met Ala Ala Asn Ala Gly Gly Gly Gly Ala Gly Gly Gly Ser Gly Ser<br>1               5                   10               15 | 48 |

| | | |
|---|---|---|
| ggc agc gtg gct gcg ccg gcg gtg tgc cgc ccc agc ggc tcg cgg tgg<br>Gly Ser Val Ala Ala Pro Ala Val Cys Arg Pro Ser Gly Ser Arg Trp<br>20 25 30 | 96 | |
| acg ccg acg ccg gag cag atc agg atg ctg aag gag ctc tac tac ggc<br>Thr Pro Thr Pro Glu Gln Ile Arg Met Leu Lys Glu Leu Tyr Tyr Gly<br>35 40 45 | 144 | |
| tgc ggc atc cgg tcg ccc agc tcg gag cag atc cag cgc atc acc gcc<br>Cys Gly Ile Arg Ser Pro Ser Ser Glu Gln Ile Gln Arg Ile Thr Ala<br>50 55 60 | 192 | |
| atg ctg cgg cag cac ggc aag atc gag ggc aag aac gtc ttc tac tgg<br>Met Leu Arg Gln His Gly Lys Ile Glu Gly Lys Asn Val Phe Tyr Trp<br>65 70 75 80 | 240 | |
| ttc cag aac cac aag gcc cgc gag cgc cag aag cgc cgc ctc acc agc<br>Phe Gln Asn His Lys Ala Arg Glu Arg Gln Lys Arg Arg Leu Thr Ser<br>85 90 95 | 288 | |
| ctc gac gtc aac gtg ccc gcc gcc ggc gcg gcc gac gcc acc acc agc<br>Leu Asp Val Asn Val Pro Ala Ala Gly Ala Ala Asp Ala Thr Thr Ser<br>100 105 110 | 336 | |
| caa ctc ggc gtc ctc tcg ctg tcg tcg ccg cct tca ggc gcg gcg cct<br>Gln Leu Gly Val Leu Ser Leu Ser Ser Pro Pro Ser Gly Ala Ala Pro<br>115 120 125 | 384 | |
| ccc tcg ccc acc ctc ggc ttc tac gcc gcc gga aat ggc ggc gga tcg<br>Pro Ser Pro Thr Leu Gly Phe Tyr Ala Ala Gly Asn Gly Gly Gly Ser<br>130 135 140 | 432 | |
| gct ggg ctg ctg gac acg agt tcc gac tgg ggc agc agc ggc gct gct<br>Ala Gly Leu Leu Asp Thr Ser Ser Asp Trp Gly Ser Ser Gly Ala Ala<br>145 150 155 160 | 480 | |
| atg gcc acc gag aca tgc ttc ctg cag gac tac atg ggc gtg acg gac<br>Met Ala Thr Glu Thr Cys Phe Leu Gln Asp Tyr Met Gly Val Thr Asp<br>165 170 175 | 528 | |
| acg ggc agc tcg tcg cag tgg cca tgc ttc tcg tcg tcg gac acg ata<br>Thr Gly Ser Ser Ser Gln Trp Pro Cys Phe Ser Ser Ser Asp Thr Ile<br>180 185 190 | 576 | |
| atg gcg gcg gcg gcg gcc gcg gcg cgg gtg gcg acg acg cgg gcg ccc<br>Met Ala Ala Ala Ala Ala Ala Arg Val Ala Thr Thr Arg Ala Pro<br>195 200 205 | 624 | |
| gag aca ctc cct ctc ttc ccg acc tgc ggc gac gac gac gac gac gac<br>Glu Thr Leu Pro Leu Phe Pro Thr Cys Gly Asp Asp Asp Asp Asp Asp<br>210 215 220 | 672 | |
| agc cag ccc ccg ccg cgg ccg cgg cac gca gtc cca gtc ccg gca ggc<br>Ser Gln Pro Pro Pro Arg Pro Arg His Ala Val Pro Val Pro Ala Gly<br>225 230 235 240 | 720 | |
| gag acc atc cgc ggc ggc ggc agc agc agc agc tac ttg ccg ttc<br>Glu Thr Ile Arg Gly Gly Gly Ser Ser Ser Ser Tyr Leu Pro Phe<br>245 250 255 | 768 | |
| tgg ggt gcc ggt gcc gcg tcc aca act gcc ggc gcc act tct tcc gtt<br>Trp Gly Ala Gly Ala Ala Ser Thr Thr Ala Gly Ala Thr Ser Ser Val<br>260 265 270 | 816 | |
| gcg atc cag cag caa cac cag ctg cag gag cag tac agc ttt tac agc<br>Ala Ile Gln Gln Gln His Gln Leu Gln Glu Gln Tyr Ser Phe Tyr Ser<br>275 280 285 | 864 | |
| aac agc acc cag ctg gcc ggc acc ggc agc caa gac gta tcg gct tca<br>Asn Ser Thr Gln Leu Ala Gly Thr Gly Ser Gln Asp Val Ser Ala Ser<br>290 295 300 | 912 | |
| gcg gcc gcc ctg gag ctg agc ctc agc tca tgg tgc tcc cct tac cct<br>Ala Ala Ala Leu Glu Leu Ser Leu Ser Ser Trp Cys Ser Pro Tyr Pro<br>305 310 315 320 | 960 | |
| gct gca ggg agc atg tga<br>Ala Ala Gly Ser Met<br>325 | 978 | |

<210> SEQ ID NO 115
<211> LENGTH: 325
<212> TYPE: PRT
<213> ORGANISM: Zea mays

<400> SEQUENCE: 115

Met Ala Asn Ala Gly Gly Gly Ala Gly Gly Ser Gly Ser
1               5                   10                  15

Gly Ser Val Ala Ala Pro Ala Val Cys Arg Pro Ser Gly Ser Arg Trp
                20                  25                  30

Thr Pro Thr Pro Glu Gln Ile Arg Met Leu Lys Glu Leu Tyr Tyr Gly
            35                  40                  45

Cys Gly Ile Arg Ser Pro Ser Ser Glu Gln Ile Gln Arg Ile Thr Ala
        50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Pro Ser Gly Ala Ala Pro
        115                 120                 125

Pro Ser Pro Thr Leu Gly Phe Tyr Ala Ala Gly Asn Gly Gly Gly Ser
    130                 135                 140

Ala Gly Leu Leu Asp Thr Ser Ser Asp Trp Gly Ser Ser Gly Ala Ala
145                 150                 155                 160

Met Ala Thr Glu Thr Cys Phe Leu Gln Asp Tyr Met Gly Val Thr Asp
                165                 170                 175

Thr Gly Ser Ser Ser Gln Trp Pro Cys Phe Ser Ser Ser Asp Thr Ile
            180                 185                 190

Met Ala Ala Ala Ala Ala Ala Arg Val Ala Thr Thr Arg Ala Pro
        195                 200                 205

Glu Thr Leu Pro Leu Phe Pro Thr Cys Gly Asp Asp Asp Asp Asp
    210                 215                 220

Ser Gln Pro Pro Pro Arg Pro Arg His Ala Val Pro Val Pro Ala Gly
225                 230                 235                 240

Glu Thr Ile Arg Gly Gly Gly Gly Ser Ser Ser Tyr Leu Pro Phe
                245                 250                 255

Trp Gly Ala Gly Ala Ser Thr Thr Ala Gly Ala Thr Ser Ser Val
            260                 265                 270

Ala Ile Gln Gln Gln His Gln Leu Gln Glu Gln Tyr Ser Phe Tyr Ser
        275                 280                 285

Asn Ser Thr Gln Leu Ala Gly Thr Gly Ser Gln Asp Val Ser Ala Ser
    290                 295                 300

Ala Ala Ala Leu Glu Leu Ser Leu Ser Trp Cys Ser Pro Tyr Pro
305                 310                 315                 320

Ala Ala Gly Ser Met
            325

<210> SEQ ID NO 116
<211> LENGTH: 3727
<212> TYPE: DNA
<213> ORGANISM: Zea mays

<400> SEQUENCE: 116

```
atggccactg tgaacaactg gctcgctttc tccctctccc cgcaggagct gccgccctcc      60
cagacgacgg actccacact catctcggcc gccaccgccg accatgtctc cggcgatgtc     120
tgcttcaaca tcccccaaga ttggagcatg aggggatcag agctttcggc gctcgtcgcg     180
gagccgaagc tggaggactt cctcggcggc atctccttct ccgagcagca tcacaaggcc     240
aactgcaaca tgatacccag cactagcagc acagtttgct acgcgagctc aggtgctagc     300
accggctacc atcaccagct gtaccaccag cccaccagct cagcgctcca cttcgcggac     360
tccgtaatgg tggcctcctc ggccggtgtc cacgacggcg gtgccatgct cagcgcggcc     420
gccgctaacg gtgtcgctgg cgctgccagt gccaacggcg gcggcatcgg gctgtccatg     480
atcaagaact ggctgcggag ccaaccggcg cccatgcagc cgagggcggc ggcggctgag     540
ggcgcgcagg ggctctcttt gtccatgaac atggcgggga cgacccaagg cgctgctggc     600
atgccacttc tcgctggaga gcgcgcacgg gcgcccgaga gtgtatcgac gtcagcacag     660
ggtggtgccg tcgtcgtcac ggcgccgaag gaggatagcg gtggcagcgg tgttgccggt     720
gctctagtag ccgtgagcac ggacacgggt ggcagcggcg gcgcgtcggc tgacaacacg     780
gcaaggaaga cggtggacac gttcgggcag cgcacgtcga tttaccgtgg cgtgacaagg     840
taaggggtg atgaatcaa gtaatcatga aattttgaaa agccattggt aatccaagga     900
actgtcatga tagatttgat tgcatctaga catagttccg atcgaatcaa atgagtaggc     960
caatgtttag cctttgggga tctcgctgat tattaggagt accattgtat tgggcatggt    1020
tgtggtatag tagtagacaa ttaacaaaaa agctaccact tttcaattat tttaggcata    1080
gatggactgg gagatatgag gcacatcttt gggataacag ttgcagaagg gaaggacaaa    1140
ctcgtaaggg tcgtcaaggt atacaaatat aatgcaacat actgtcatta aatatgcttt    1200
ttctgtaagt tttatatttc accaatgatg ttgttattgt taactgacat tgcttcacac    1260
tatcaatttt ggattcggcg caatgatttg tgggattgaa atcaaatctt aaatctacag    1320
tctatttagg tacgcgattt ctctccaact acttaatgca gttcgtttct ccctataacc    1380
atattctttt tcatctcaaa tctcactcga ctctttttt ttatcttgta ccattgatag    1440
gtggctatga taaagaggag aaagctgcta gggcttatga tcttgctgct ctgaagtact    1500
ggggtcccac aacaacaaca aatttcccag tatgtatatg tagcatccag ttttacttta    1560
ctgaagttca tatctcgtta tgggctataa atatgtatca aatgatgtcc attagctagt    1620
gatctggagt gaaggttcta tagtaaagta aacgctgtgt gcggagtgca gtagcgggag    1680
gtctctcttc tattttctaa gaaaatgga cattgctgaa attgtactta aagtcgttta    1740
ttttatttt ttgtatttcc aggtgagtaa ctacgaaaag gagctcgagg acatgaagca    1800
catgacaagc caggagtttg tagcgtctct gagaaggtcg gtctaacagc attgattaat    1860
cagtaccacc tctactgaat aaaatctgct gctatttgtt aaattttgag cgaggtcaac    1920
tgcatatttg atcttattag accactgtat atgaatgcag aagagcagt ggtttctcca    1980
gaggtgcatc catttacagg ggagtgacta ggtatgaatt catatagcta agaacttaac    2040
atcaacaaaa acacacatac acttgggttg atgtggcaga tgcatgcatg gattgaaaat    2100
gtgtgcatgt tgttttactt gaactcgatc tctgtattta taggcatcac caacatggaa    2160
gatggcaagc acggattgga cgagttgcag ggaacaagga tctttacttg gcacccttca    2220
gtaagtagca acaaatatg ttttgcatt gtatatagag tacccttgaa tatataaatt    2280
caccacatat acaagcaagt tacagtcaac taacacaatc tcaacgcaac gagaaagcaa    2340
```

```
gtgttccagc tgatagtaca catttgtaga ccagccgcat atggttgttt tgtatgcatg    2400
atgactatta aaaatgtgac catcgcatta agtcatgcaa agttgcattg cagtagtaca    2460
ttgcttagtg catgctcctc aagtggcttt tttcaaacct gatcccatgt ctggtgctat    2520
tgttgtctcc cattcacccg tgcatcaggt caaaatagta ccatgcctga ataagaaaaa    2580
caaaacgagc atgcactggc agcagcagac taataaacaa agttccagca tttactaata    2640
aactaattag ctacagcat ccaaaagatt cttccaatta agccacaact gttcatgcat     2700
acatgggtat gccacccagg ataccatgca tgcaccgtgc acgacgaaag cgaaacgctc    2760
gttctcggaa tattagaact gacgaagccg agtgcaacct tctgtcgtgg atgcaggcac    2820
ccaggaggag gcagcggagg cgtacgacat cgcggcgatc aagttccgcg gcctaaacgc    2880
cgtcaccaac ttcgacatga ccgctacga cgtgaagagc atcctggaca gcagcgccct    2940
ccccatcggc agcgccgcca agcgcctcaa ggaggccgag gccgcagcgt ccgcgcagca    3000
ccaccacgcc ggcgtggtga gttacgacgt cggccgcatc gcctcgcagc tcggcgacgg    3060
cggagccctg gcggcggcgt acggcgcgca ctaccacggc gccgctggc cgaccatcgc     3120 gttccagccg ggcgccgcca ccacaggcct gtaccacccg tacgcgcagc agccaatgcg    3180
cggcggcggg tggtgcaagc aggagcagga ccacgcggtg atcgcggccg cgcacagcct    3240
gcaggacctc caccacctga acctgggcgc ggccggcgcg cacgactttt tctcggcagg    3300
gcagcaggcc gccgccgctg cgatgcacgg cctgggtagc atcgacagtg cgtcgctcga    3360
gcacagcacc ggctccaact ccgtcgtcta caacggcggg gtcggcgaca gcaacggcgc    3420
cagcgccgtc ggcggcagtg gcggtggcta catgatgccg atgagcgctg ccggagcaac    3480
cactacatcg gcaatggtga gccacgagca ggtgcatgca cgggcctacg acgaagccaa    3540
gcaggctgct cagatggggt acgagagcta cctggtgaac gcggagaaca atggtggcgg    3600
aaggatgtct gcatggggga ctgtcgtgtc tgcagccgcg gcggcagcag caagcagcaa    3660
cgacaacatg gccgccgacg tcggccatgg cggcgcgcag ctcttcagtg tctggaacga    3720
cacttaa                                                              3727

<210> SEQ ID NO 117
<211> LENGTH: 4325
<212> TYPE: DNA
<213> ORGANISM: Oryza sativa

<400> SEQUENCE: 117
atgcatatct atcttatata aatatctacc agtgatactg ttgcttagtg ctccaaacct     60
ctcttgacct cttcttcttc ttctcagtta gcttagctta agcttcccct aaccttgagc    120
tcaccacaac aatggcgact tgatctaaca gagcttaacc aagtagcaaa tcatacatat    180
aaccatagct taattcgcat tgaatcttgt cttgttcagt gtgaatcatc aaccatggcc    240
accatgaaca actggctggc cttctcccte tccccgcagg atcagctccc gccgtctcag    300
accaactcca ctctcatctc cgccgccgcc accaccacca ccgccggcga ctcctccacc    360
ggcgacgtct gcttcaacat cccccaaggt aattaagctc accaatcgat gcatgcattc    420
atgagctaga tatagctagt gttggttggg atttgaagag acatgcatgt ttgattgatt    480
gatttgatgt gcagattgga gcatgagggg atcggagctc tcggcgctcg tcgccgagcc    540
gaagctggag gacttcctcg gcggcatctc cttctcggag cagcagcatc atcacggcgg    600
caagggcggc gtgatcccga gcagcgccgc cgcttgctac gcgagctccg gcagcagcgt    660
cggctacctg taccctcctc caagctcatc ctcgctccag ttcgccgact ccgtcatggt    720
```

-continued

```
ggccacctcc tcgcccgtcg tcgcccacga cggcgtcagc ggcggcggca tggtgagcgc    780
cgccgccgcc gcggcggcca gtggcaacgg cggcattggc ctgtccatga tcaagaactg    840
gctccggagc cagccggcgc cgcagccggc gcaggcgctg tctctgtcca tgaacatggc    900
ggggacgacg acgcgcaggg gcggcggcgc catggcgctc ctcgccggcg caggggagcg    960
aggccggacg acgcccgcgt cagagagcct gtccacgtcg gcgcacggag cgacgacggc   1020
gacgatggct ggtggtcgca aggagattaa cgaggaaggc agcggcagcg ccggcgccgt   1080
ggttgccgtc ggctcggagt caggcggcag cggcgccgtg gtggaggccg gcgcggcggc   1140
ggcggcggcg aggaagtccg tcgacacgtt cggccagaga acatcgatct accgcggcgt   1200
gacaaggtat ttagggtgca attaattaat catctatcta tattttgctc aaaaaagttc   1260
atctactagc tagcttagca caaatcatca tcagtgtaat catatatatt ctttgatgat   1320
ttaactgtgt tgcatgaatt cattcctatt tgatgtttgt gatttggatc ccatttttcta  1380 ggatagctat ataggtgata gattgatcat tagatttgta ggatttatca ttatgtcatt   1440
attatgtggg acatgattgt tgtgattaac aaagttgtaa tatcttttgg tttggttata   1500
ggcatagatg gacagggagg tatgaggctc atctttggga caacagctgc agaagagagg   1560
gccaaactcg caagggtcgt caaggtaggc taactagtgc catttaaatc gattaattgt   1620 tttttttatgc tccaatggcg attgatactg atcttgtttc tttttctaat gatcatttcg  1680
ggatcgaatg atcttcctct gtttgatcga acttggcttt tgaatctaca gtctatctag   1740
gtgagtgaga ttccttgaac ctagatgttc tgtttgcgat gcatgtatat attcggtaga   1800
ttgaattatt tgctgatctt tgcttttcttg aagtttaatg atcttataaa ttgtaatgct  1860
gataggtggt tatgacaaag aggaaaaagc tgctagagct tatgatttgg ctgctctcaa   1920
atactggggc ccgacgacga cgacaaattt tccggtgtgt ttataattaa tatacagatt   1980
gtgtcacatt gttatttttct cactcttttta tttgatactg atctagtgta atgatgatta  2040
ctaaaactgt acttaaaggc aatggtttct gtattttttca ggtaaataac tatgaaaagg   2100
agctggagga gatgaagcac atgacaaggc aggagttcgt agcctctttg agaaggttgg   2160
tctctacaat caagatatcc atactatact aattaatttc cttttagatt tatagtaatt   2220
tatctatcgc attgaagtta attaattatc tgatgcttac tgatactaac aaatactgtt   2280
ccttatatgt gcaggaagag cagtggtttc tccagaggtg catccattta ccgtggagta   2340
actaggtaca tatatatatg catcattgta caattaattt tttttaatttt tttagggtaa   2400 aaaatgaaga ctgtgatata gatccattaa tttgatcttg tgtacttgta aatataggca   2460
tcaccagcat gggagatggc aagcaaggat aggaagagtt gcagggaaca aggacctcta   2520
cttgggcacc ttcagtaagt acaaatattc atatttatac tgcaaaacca tataaatcca   2580
tattaataag tatgtccttt ctcattgagt atacaaaata tcatattttc ttggcaagta   2640
caatttattc attcagggca aaatagtagt agtaagaaag aggggtgact cttcaaagaa   2700
cacagagctt acttaagcct gtaactaatt aattaaacta aaaatgtgat ctgcaagtca   2760
tgtcaagttg cattacacca ctaatatata tactctgtgc atgcttgcat gctctcctca   2820
tgtggctagc tacctttttca aaccttccat gtctggtgct actcctgtct ccattcacca   2880
ctgcacctgg tcaagatcct cactaattaa gaaacaataa tgcattattt gcagtaaata   2940
atttaactag tgttaatcac attctttgca acacaaacta atcaccaatt aagctagcta   3000
gctagccaaa atgataatct tgcttgcatg cgctaatggt gtgtgtgatg atggtggtgt   3060
```

| | |
|---|---|
| cacgcatgca ggcacgcagg aggaggcggc ggaggcgtac gacatcgcgg cgatcaagtt | 3120 |
| ccggggctc aacgccgtca ccaacttcga catgagccgc tacgacgtca agagcatcct | 3180 |
| cgacagcgct gccctccccg tcggcaccgc cgccaagcgc ctcaaggacg ccgaggccgc | 3240 |
| cgccgcctac gacgtcggcc gcatcgcctc gcacctcggc ggcgacggcg cctacgccgc | 3300 |
| gcattacggc caccaccacc actcggccgc cgccgcctgg ccgaccatcg cgttccaggc | 3360 |
| ggcggcggcg ccgccgccgc acgccgccgg gctttaccac ccgtacgcgc agccgctgcg | 3420 |
| tgggtggtgc aagcaggagc aggaccacgc cgtgatcgcg gcggcgcaca gcctgcagga | 3480 |
| tctccaccac ctcaacctcg cgccgccgc cgccgcgcat gacttcttct cgcaggcgat | 3540 |
| gcagcagcag cacggcctcg gcagcatcga caacgcgtcg ctcgagcaca gcaccggctc | 3600 |
| caactccgtc gtctacaacg cgacaatgg cggcggaggc ggcggctaca tcatggcgcc | 3660 |
| gatgagcgcc gtgtcggcca cggccaccgc ggtggcgagc agccacgatc acggcggcga | 3720 |
| cggcgggaag caggtgcaga tggggtacga cagctacctc gtcggcgcag acgcctacgg | 3780 |
| cggcggcggc gccgggagga tgccatcctg gcgatgacg ccggcgtcgg cgccggccgc | 3840 |
| cacgagcagc agcgacatga ccggagtctg ccatggcgca cagctcttca gcgtctggaa | 3900 |
| cgacacataa aaaaaaact aggttagcca gcttaattag cagggtaaac cactgacaca | 3960 |
| attaagccat acttaaatta gggttcatga gatgaccatt aagcaggtta ttatcattaa | 4020 |
| tgatgtttaa tttctcaatt agtacttagc tcaaaaggag gggatttctt ctgaaggatg | 4080 |
| gtgatggctt gtgaaattga acctggtgtt cttgccatga tttttttttc acaagctgcc | 4140 |
| attttgggt tcaggttcag aaggatcctg attattata accagccata tatataga | 4200 |
| agggtagaaa tggaggtatc ctgcttgtaa attggggcaa tggtagctag agttgatgca | 4260 |
| atgaccatgc ttcatgtgat gagaactaat tgtcttcctc tgatcaaatt aagcaggaag | 4320 |
| attaa | 4325 |

<210> SEQ ID NO 118
<211> LENGTH: 2079
<212> TYPE: DNA
<213> ORGANISM: Oryza sativa
<220> FEATURE:
<221> NAME/KEY: CDS
<222> LOCATION: (1)...(2079)

<400> SEQUENCE: 118

| | |
|---|---|
| atg gcc act atg aac aac tgg ctc gcc ttc tcg ctc tcg ccg cag gac<br>Met Ala Thr Met Asn Asn Trp Leu Ala Phe Ser Leu Ser Pro Gln Asp<br>1               5                   10                  15 | 48 |
| caa ctc cca ccg tcg cag acc aat agc act ctc atc tcc gct gct gca<br>Gln Leu Pro Pro Ser Gln Thr Asn Ser Thr Leu Ile Ser Ala Ala Ala<br>            20                  25                  30 | 96 |
| acc acc aca acc gca ggc gat tcg tca acg ggc gac gtc tgc ttc aac<br>Thr Thr Thr Thr Ala Gly Asp Ser Ser Thr Gly Asp Val Cys Phe Asn<br>        35                  40                  45 | 144 |
| atc cct caa gac tgg tcc atg cgc gga agc gag ctt agc gct ctc gtc<br>Ile Pro Gln Asp Trp Ser Met Arg Gly Ser Glu Leu Ser Ala Leu Val<br>    50                  55                  60 | 192 |
| gcg gag ccc aag ttg gag gat ttc ttg gga ggc atc tcc ttc tcg gag<br>Ala Glu Pro Lys Leu Glu Asp Phe Leu Gly Gly Ile Ser Phe Ser Glu<br>65                  70                  75                  80 | 240 |
| caa cag cat cat cac ggc gga aag ggc ggt gtt atc cca agc tct gct<br>Gln Gln His His His Gly Gly Lys Gly Gly Val Ile Pro Ser Ser Ala<br>                85                  90                  95 | 288 |

| | | |
|---|---|---|
| gcc gca tgc tat gca agc tcc ggc tcc agc gtg ggc tac ctc tac cct<br>Ala Ala Cys Tyr Ala Ser Ser Gly Ser Ser Val Gly Tyr Leu Tyr Pro<br>100 105 110 | 336 | |
| ccg cct tca tcc tcg tca ctt cag ttt gca gac agc gtg atg gtc gca<br>Pro Pro Ser Ser Ser Ser Leu Gln Phe Ala Asp Ser Val Met Val Ala<br>115 120 125 | 384 | |
| acc tca tct cca gtg gtt gcg cac gat ggc gtg agc ggt ggc ggt atg<br>Thr Ser Ser Pro Val Val Ala His Asp Gly Val Ser Gly Gly Gly Met<br>130 135 140 | 432 | |
| gtc tca gca gca gcg gct gca gca gct tcg ggt aat ggc ggg att ggc<br>Val Ser Ala Ala Ala Ala Ala Ala Ala Ser Gly Asn Gly Gly Ile Gly<br>145 150 155 160 | 480 | |
| ctc tcc atg atc aag aac tgg ctc agg agc caa ccg gct ccg caa cct<br>Leu Ser Met Ile Lys Asn Trp Leu Arg Ser Gln Pro Ala Pro Gln Pro<br>165 170 175 | 528 | |
| gcg caa gca ctc agc ctg tcg atg aac atg gct ggt act act acc gct<br>Ala Gln Ala Leu Ser Leu Ser Met Asn Met Ala Gly Thr Thr Thr Ala<br>180 185 190 | 576 | |
| caa ggt gga ggc gca atg gca ctt ctc gca ggc gct ggc gaa aga gga<br>Gln Gly Gly Gly Ala Met Ala Leu Leu Ala Gly Ala Gly Glu Arg Gly<br>195 200 205 | 624 | |
| agg acc aca cca gca tcc gag agc ctc tct act tcc gcg cac gga gcc<br>Arg Thr Thr Pro Ala Ser Glu Ser Leu Ser Thr Ser Ala His Gly Ala<br>210 215 220 | 672 | |
| acc acg gct aca atg gct ggc ggg agg aaa gag atc aac gag gaa gga<br>Thr Thr Ala Thr Met Ala Gly Gly Arg Lys Glu Ile Asn Glu Glu Gly<br>225 230 235 240 | 720 | |
| tct gga tcc gct ggt gcc gtg gtt gca gtt ggc tca gaa tca ggt gga<br>Ser Gly Ser Ala Gly Ala Val Val Ala Val Gly Ser Glu Ser Gly Gly<br>245 250 255 | 768 | |
| tcc ggc gct gtt gtt gaa gct ggt gcc gct gcg gca gcg gct cgg aag<br>Ser Gly Ala Val Val Glu Ala Gly Ala Ala Ala Ala Ala Arg Lys<br>260 265 270 | 816 | |
| agc gtt gat act ttc ggc caa aga acg agc atc tac aga ggc gtt act<br>Ser Val Asp Thr Phe Gly Gln Arg Thr Ser Ile Tyr Arg Gly Val Thr<br>275 280 285 | 864 | |
| cgg cac cgc tgg acc ggc agg tac gag gca cac ttg tgg gac aac agc<br>Arg His Arg Trp Thr Gly Arg Tyr Glu Ala His Leu Trp Asp Asn Ser<br>290 295 300 | 912 | |
| tgt cgc cgc gag ggc caa act agg aag gga aga cag gga gga tat gac<br>Cys Arg Arg Glu Gly Gln Thr Arg Lys Gly Arg Gln Gly Gly Tyr Asp<br>305 310 315 320 | 960 | |
| aaa gag gag aag gct gcc aga gcg tac gac ctg gcc gcg ttg aag tac<br>Lys Glu Glu Lys Ala Ala Arg Ala Tyr Asp Leu Ala Ala Leu Lys Tyr<br>325 330 335 | 1008 | |
| tgg ggt cca aca acg acg acc aac ttc ccg gtg aac aac tac gag aag<br>Trp Gly Pro Thr Thr Thr Thr Asn Phe Pro Val Asn Asn Tyr Glu Lys<br>340 345 350 | 1056 | |
| gag ctg gaa gag atg aag cac atg acg cgg cag gag ttc gtc gct tct<br>Glu Leu Glu Glu Met Lys His Met Thr Arg Gln Glu Phe Val Ala Ser<br>355 360 365 | 1104 | |
| ctc agg cgc aag tca tct ggt ttc tcc aga ggt gcg tcg atc tat aga<br>Leu Arg Arg Lys Ser Ser Gly Phe Ser Arg Gly Ala Ser Ile Tyr Arg<br>370 375 380 | 1152 | |
| gga gtt acc cgc cac cac cag cac gga agg tgg cag gca aga atc ggg<br>Gly Val Thr Arg His His Gln His Gly Arg Trp Gln Ala Arg Ile Gly<br>385 390 395 400 | 1200 | |
| aga gtc gcc ggt aac aag gac ctg tac ttg gga acc ttc tcg act cag<br>Arg Val Ala Gly Asn Lys Asp Leu Tyr Leu Gly Thr Phe Ser Thr Gln<br>405 410 415 | 1248 | |

```
gag gag gca gcg gaa gcg tat gac att gcg gcg atc aag ttc cgc ggt      1296
Glu Glu Ala Ala Glu Ala Tyr Asp Ile Ala Ala Ile Lys Phe Arg Gly
            420                 425                 430 ctc aat gcc gtg acc aac ttc gac atg tca cgc tat gat gtc aag tcg      1344
Leu Asn Ala Val Thr Asn Phe Asp Met Ser Arg Tyr Asp Val Lys Ser
        435                 440                 445 att ctg gat agc gct gcg ttg cct gtg gga acc gct gcc aaa cgc ctc      1392
Ile Leu Asp Ser Ala Ala Leu Pro Val Gly Thr Ala Ala Lys Arg Leu
    450                 455                 460 aag gac gcg gaa gca gct gcc gcg tac gat gtt ggc agg att gcc tca      1440
Lys Asp Ala Glu Ala Ala Ala Ala Tyr Asp Val Gly Arg Ile Ala Ser
465                 470                 475                 480 cat ctc ggt gga gat gga gct tac gct gcc cac tac ggg cat cat cac      1488
His Leu Gly Gly Asp Gly Ala Tyr Ala Ala His Tyr Gly His His His
                485                 490                 495 cac tct gca gcc gca gct tgg cct aca ata gca ttc caa gcg gca gcg      1536
His Ser Ala Ala Ala Ala Trp Pro Thr Ile Ala Phe Gln Ala Ala Ala
            500                 505                 510 gct cct cct cca cac gct gct ggt ctt tac cat ccg tac gcg caa cct      1584
Ala Pro Pro Pro His Ala Ala Gly Leu Tyr His Pro Tyr Ala Gln Pro
        515                 520                 525 ctc cgc ggt tgg tgt aag cag gaa caa gat cat gcg gtg att gcg gct      1632
Leu Arg Gly Trp Cys Lys Gln Glu Gln Asp His Ala Val Ile Ala Ala
    530                 535                 540 gca cac agc ttg caa gat ctg cat cac ctc aat ctg gga gcc gca gca      1680
Ala His Ser Leu Gln Asp Leu His His Leu Asn Leu Gly Ala Ala Ala
545                 550                 555                 560 gct gcc cat gac ttc ttc tca caa gcc atg cag cag cag cat ggc ctg      1728
Ala Ala His Asp Phe Phe Ser Gln Ala Met Gln Gln Gln His Gly Leu
                565                 570                 575 ggc agc ata gac aat gcg tct ctg gag cac tcc acc gga tcg aac tcg      1776
Gly Ser Ile Asp Asn Ala Ser Leu Glu His Ser Thr Gly Ser Asn Ser
            580                 585                 590 gtg gtg tac aat gga gac aac ggc gga gga ggt gga ggt tac atc atg      1824
Val Val Tyr Asn Gly Asp Asn Gly Gly Gly Gly Gly Gly Tyr Ile Met
        595                 600                 605 gca cct atg tca gcg gtc tct gct acc gct acg gcg gtg gcc tca tcc      1872
Ala Pro Met Ser Ala Val Ser Ala Thr Ala Thr Ala Val Ala Ser Ser
    610                 615                 620 cac gac cac ggt gga gac ggc ggc aag cag gtc caa atg ggc tac gac      1920
His Asp His Gly Gly Asp Gly Gly Lys Gln Val Gln Met Gly Tyr Asp
625                 630                 635                 640 tcc tac ctt gtg gga gct gac gct tac ggc gga gga gga gct ggt cgc      1968
Ser Tyr Leu Val Gly Ala Asp Ala Tyr Gly Gly Gly Gly Ala Gly Arg
                645                 650                 655 atg cct agc tgg gcc atg acg cct gct tct gct cct gcg gct acg agc      2016
Met Pro Ser Trp Ala Met Thr Pro Ala Ser Ala Pro Ala Ala Thr Ser
            660                 665                 670 tcg tcg gat atg aca gga gtg tgt cat ggc gcc caa ctg ttc tcg gtg      2064
Ser Ser Asp Met Thr Gly Val Cys His Gly Ala Gln Leu Phe Ser Val
        675                 680                 685 tgg aat gat aca tag                                                   2079
Trp Asn Asp Thr
    690

<210> SEQ ID NO 119
<211> LENGTH: 692
<212> TYPE: PRT
<213> ORGANISM: Oryza sativa
```

```
<400> SEQUENCE: 119

Met Ala Thr Met Asn Asn Trp Leu Ala Phe Ser Leu Ser Pro Gln Asp
 1               5                  10                  15

Gln Leu Pro Pro Ser Gln Thr Asn Ser Thr Leu Ile Ser Ala Ala Ala
             20                  25                  30

Thr Thr Thr Thr Ala Gly Asp Ser Ser Thr Gly Asp Val Cys Phe Asn
         35                  40                  45

Ile Pro Gln Asp Trp Ser Met Arg Gly Ser Glu Leu Ser Ala Leu Val
 50                  55                  60

Ala Glu Pro Lys Leu Glu Asp Phe Leu Gly Gly Ile Ser Phe Ser Glu
 65                  70                  75                  80

Gln Gln His His His Gly Gly Lys Gly Gly Val Ile Pro Ser Ser Ala
                 85                  90                  95

Ala Ala Cys Tyr Ala Ser Ser Gly Ser Ser Val Gly Tyr Leu Tyr Pro
            100                 105                 110

Pro Pro Ser Ser Ser Ser Leu Gln Phe Ala Asp Ser Val Met Val Ala
            115                 120                 125

Thr Ser Ser Pro Val Val Ala His Asp Gly Val Ser Gly Gly Gly Met
        130                 135                 140

Val Ser Ala Ala Ala Ala Ala Ala Ser Gly Asn Gly Gly Ile Gly
145                 150                 155                 160

Leu Ser Met Ile Lys Asn Trp Leu Arg Ser Gln Pro Ala Pro Gln Pro
                165                 170                 175

Ala Gln Ala Leu Ser Leu Ser Met Asn Met Ala Gly Thr Thr Thr Ala
            180                 185                 190

Gln Gly Gly Gly Ala Met Ala Leu Leu Ala Gly Ala Gly Glu Arg Gly
        195                 200                 205

Arg Thr Thr Pro Ala Ser Glu Ser Leu Ser Thr Ser Ala His Gly Ala
210                 215                 220

Thr Thr Ala Thr Met Ala Gly Gly Arg Lys Glu Ile Asn Glu Glu Gly
225                 230                 235                 240

Ser Gly Ser Ala Gly Ala Val Val Ala Val Gly Ser Glu Ser Gly Gly
                245                 250                 255

Ser Gly Ala Val Val Glu Ala Gly Ala Ala Ala Ala Ala Arg Lys
            260                 265                 270

Ser Val Asp Thr Phe Gly Gln Arg Thr Ser Ile Tyr Arg Gly Val Thr
            275                 280                 285

Arg His Arg Trp Thr Gly Arg Tyr Glu Ala His Leu Trp Asp Asn Ser
        290                 295                 300

Cys Arg Arg Glu Gly Gln Thr Arg Lys Gly Arg Gln Gly Gly Tyr Asp
305                 310                 315                 320

Lys Glu Glu Lys Ala Ala Arg Ala Tyr Asp Leu Ala Ala Leu Lys Tyr
                325                 330                 335

Trp Gly Pro Thr Thr Thr Thr Asn Phe Pro Val Asn Asn Tyr Glu Lys
            340                 345                 350

Glu Leu Glu Glu Met Lys His Met Thr Arg Gln Glu Phe Val Ala Ser
        355                 360                 365

Leu Arg Arg Lys Ser Ser Gly Phe Ser Arg Gly Ala Ser Ile Tyr Arg
370                 375                 380

Gly Val Thr Arg His His Gln His Gly Arg Trp Gln Ala Arg Ile Gly
385                 390                 395                 400

Arg Val Ala Gly Asn Lys Asp Leu Tyr Leu Gly Thr Phe Ser Thr Gln
                405                 410                 415
```

```
Glu Glu Ala Ala Glu Ala Tyr Asp Ile Ala Ala Ile Lys Phe Arg Gly
            420                 425                 430
Leu Asn Ala Val Thr Asn Phe Asp Met Ser Arg Tyr Asp Val Lys Ser
        435                 440                 445
Ile Leu Asp Ser Ala Ala Leu Pro Val Gly Thr Ala Ala Lys Arg Leu
    450                 455                 460
Lys Asp Ala Glu Ala Ala Ala Tyr Asp Val Gly Arg Ile Ala Ser
465                 470                 475                 480
His Leu Gly Gly Asp Gly Ala Tyr Ala Ala His Tyr Gly His His His
                485                 490                 495
His Ser Ala Ala Ala Trp Pro Thr Ile Ala Phe Gln Ala Ala
            500                 505                 510
Ala Pro Pro Pro His Ala Ala Gly Leu Tyr His Pro Tyr Ala Gln Pro
        515                 520                 525
Leu Arg Gly Trp Cys Lys Gln Glu Gln Asp His Ala Val Ile Ala Ala
    530                 535                 540
Ala His Ser Leu Gln Asp Leu His His Leu Asn Leu Gly Ala Ala Ala
545                 550                 555                 560
Ala Ala His Asp Phe Phe Ser Gln Ala Met Gln Gln Gln His Gly Leu
                565                 570                 575
Gly Ser Ile Asp Asn Ala Ser Leu Glu His Ser Thr Gly Ser Asn Ser
            580                 585                 590
Val Val Tyr Asn Gly Asp Asn Gly Gly Gly Gly Gly Tyr Ile Met
        595                 600                 605
Ala Pro Met Ser Ala Val Ser Ala Thr Ala Thr Ala Val Ala Ser Ser
    610                 615                 620
His Asp His Gly Gly Asp Gly Gly Lys Gln Val Gln Met Gly Tyr Asp
625                 630                 635                 640
Ser Tyr Leu Val Gly Ala Asp Ala Tyr Gly Gly Gly Ala Gly Arg
                645                 650                 655
Met Pro Ser Trp Ala Met Thr Pro Ala Ser Ala Pro Ala Ala Thr Ser
            660                 665                 670
Ser Ser Asp Met Thr Gly Val Cys His Gly Ala Gln Leu Phe Ser Val
        675                 680                 685
Trp Asn Asp Thr
    690

<210> SEQ ID NO 120
<211> LENGTH: 2088
<212> TYPE: DNA
<213> ORGANISM: Oryza sativa
<220> FEATURE:
<221> NAME/KEY: CDS
<222> LOCATION: (1)...(2088)

<400> SEQUENCE: 120 atg gcc act atg aac aac tgg ctc gcc ttc tcg ctc tcg ccg cag gac    48
Met Ala Thr Met Asn Asn Trp Leu Ala Phe Ser Leu Ser Pro Gln Asp
  1               5                  10                  15 caa ctc cca ccg tcg cag acc aat agc act ctc atc tcc gct gct gca    96
Gln Leu Pro Pro Ser Gln Thr Asn Ser Thr Leu Ile Ser Ala Ala Ala
             20                  25                  30 acc aca aca acc gca ggc gat tcg tca acg ggc gac gtc tgc ttc aac   144
Thr Thr Thr Thr Ala Gly Asp Ser Ser Thr Gly Asp Val Cys Phe Asn
         35                  40                  45 atc cct caa gac tgg tcc atg cgc gga agc gag ctt agc gct ctc gtc   192
Ile Pro Gln Asp Trp Ser Met Arg Gly Ser Glu Leu Ser Ala Leu Val
```

```
                Ile Pro Gln Asp Trp Ser Met Arg Gly Ser Glu Leu Ser Ala Leu Val
                     50                  55                  60 gcg gag ccc aag ttg gag gat ttc ttg gga ggc atc tcc ttc tcg gag           240
Ala Glu Pro Lys Leu Glu Asp Phe Leu Gly Gly Ile Ser Phe Ser Glu
 65                  70                  75                  80 caa cag cat cat cac ggc gga aag ggc ggt gtt atc cca agc tct gct           288
Gln Gln His His His Gly Gly Lys Gly Gly Val Ile Pro Ser Ser Ala
                     85                  90                  95 gcc gca tgc tat gca agc tcc ggc tcc agc gtg ggc tac ctc tac cct           336
Ala Ala Cys Tyr Ala Ser Ser Gly Ser Ser Val Gly Tyr Leu Tyr Pro
                100                 105                 110 ccg cct tca tcc tcg tca ctt cag ttt gca gac agc gtg atg gtc gca           384
Pro Pro Ser Ser Ser Ser Leu Gln Phe Ala Asp Ser Val Met Val Ala
            115                 120                 125 acc tca tct cca gtg gtt gcg cac gat ggc gtg agc ggt ggc ggt atg           432
Thr Ser Ser Pro Val Val Ala His Asp Gly Val Ser Gly Gly Gly Met
    130                 135                 140 gtc tca gca gca gcg gct gca gca gct tcg ggt aat ggc ggg att ggc           480
Val Ser Ala Ala Ala Ala Ala Ala Ala Ser Gly Asn Gly Gly Ile Gly
145                 150                 155                 160 ctc tcc atg atc aag aac tgg ctc agg agc caa ccg gct ccg caa cct           528
Leu Ser Met Ile Lys Asn Trp Leu Arg Ser Gln Pro Ala Pro Gln Pro
                165                 170                 175 gcg caa gca ctc agc ctg tcg atg aac atg gct ggt act act acc gct           576
Ala Gln Ala Leu Ser Leu Ser Met Asn Met Ala Gly Thr Thr Thr Ala
            180                 185                 190 caa ggt gga ggc gca atg gca ctt ctc gca ggc gct ggc gaa aga gga           624
Gln Gly Gly Gly Ala Met Ala Leu Leu Ala Gly Ala Gly Glu Arg Gly
        195                 200                 205 agg acc aca cca gca tcc gag agc ctc tct act tcc gcg cac gga gcc           672
Arg Thr Thr Pro Ala Ser Glu Ser Leu Ser Thr Ser Ala His Gly Ala
    210                 215                 220 acc acg gct aca atg gct ggc ggg agg aaa gag atc aac gag gaa gga           720
Thr Thr Ala Thr Met Ala Gly Gly Arg Lys Glu Ile Asn Glu Glu Gly
225                 230                 235                 240 tct gga tcc gct ggt gcc gtg gtt gca gtt ggc tca gaa tca ggt gga           768
Ser Gly Ser Ala Gly Ala Val Val Ala Val Gly Ser Glu Ser Gly Gly
                245                 250                 255 tcc ggc gct gtt gtt gaa gct ggt gcc gct gcg gca gcg gct cgg aag           816
Ser Gly Ala Val Val Glu Ala Gly Ala Ala Ala Ala Ala Ala Arg Lys
            260                 265                 270 agc gtt gat act ttc ggc caa aga acg agc atc tac aga ggc gtt act           864
Ser Val Asp Thr Phe Gly Gln Arg Thr Ser Ile Tyr Arg Gly Val Thr
        275                 280                 285 cgg cac cgc tgg acc ggc agg tac gag gca cac ttg tgg gac aac agc           912
Arg His Arg Trp Thr Gly Arg Tyr Glu Ala His Leu Trp Asp Asn Ser
    290                 295                 300 tgt cgc cgc gag ggc caa act agg aag gga aga cag gtc tat cta gga           960
Cys Arg Arg Glu Gly Gln Thr Arg Lys Gly Arg Gln Val Tyr Leu Gly
305                 310                 315                 320 gga tat gac aaa gag gag aag gct gcc aga gcg tac gac ctg gcc gcg          1008
Gly Tyr Asp Lys Glu Glu Lys Ala Ala Arg Ala Tyr Asp Leu Ala Ala
                325                 330                 335 ttg aag tac tgg ggt cca aca acg acg acc aac ttc ccg gtg aac aac          1056
Leu Lys Tyr Trp Gly Pro Thr Thr Thr Thr Asn Phe Pro Val Asn Asn
            340                 345                 350 tac gag aag gag ctg gaa gag atg aag cac atg acg cgg cag gag ttc          1104
Tyr Glu Lys Glu Leu Glu Glu Met Lys His Met Thr Arg Gln Glu Phe
        355                 360                 365
```

```
gtc gct tct ctc agg cgc aag tca tct ggt ttc tcc aga ggt gcg tcg      1152
Val Ala Ser Leu Arg Arg Lys Ser Ser Gly Phe Ser Arg Gly Ala Ser
        370             375             380 atc tat aga gga gtt acc cgc cac cac cag cac gga agg tgg cag gca      1200
Ile Tyr Arg Gly Val Thr Arg His His Gln His Gly Arg Trp Gln Ala
385             390             395             400 aga atc ggg aga gtc gcc ggt aac aag gac ctg tac ttg gga acc ttc      1248
Arg Ile Gly Arg Val Ala Gly Asn Lys Asp Leu Tyr Leu Gly Thr Phe
        405             410             415 tcg act cag gag gag gca gcg gaa gcg tat gac att gcg gcg atc aag      1296
Ser Thr Gln Glu Glu Ala Ala Glu Ala Tyr Asp Ile Ala Ala Ile Lys
            420             425             430 ttc cgc ggt ctc aat gcc gtg acc aac ttc gac atg tca cgc tat gat      1344
Phe Arg Gly Leu Asn Ala Val Thr Asn Phe Asp Met Ser Arg Tyr Asp
        435             440             445 gtc aag tcg att ctg gat agc gct gcg ttg cct gtg gga acc gct gcc      1392
Val Lys Ser Ile Leu Asp Ser Ala Ala Leu Pro Val Gly Thr Ala Ala
    450             455             460 aaa cgc ctc aag gac gcg gaa gca gct gcc gcg tac gat gtt ggc agg      1440
Lys Arg Leu Lys Asp Ala Glu Ala Ala Ala Ala Tyr Asp Val Gly Arg
465             470             475             480 att gcc tca cat ctc ggt gga gat gga gct tac gct gcc cac tac ggg      1488
Ile Ala Ser His Leu Gly Gly Asp Gly Ala Tyr Ala Ala His Tyr Gly
            485             490             495 cat cat cac cac tct gca gcc gca gct tgg cct aca ata gca ttc caa      1536
His His His His Ser Ala Ala Ala Ala Trp Pro Thr Ile Ala Phe Gln
        500             505             510 gcg gca gcg gct cct cct cca cac gct gct ggt ctt tac cat ccg tac      1584
Ala Ala Ala Ala Pro Pro Pro His Ala Ala Gly Leu Tyr His Pro Tyr
    515             520             525 gcg caa cct ctc cgc ggt tgg tgt aag cag gaa caa gat cat gcg gtg      1632
Ala Gln Pro Leu Arg Gly Trp Cys Lys Gln Glu Gln Asp His Ala Val
530             535             540 att gcg gct gca cac agc ttg caa gat ctg cat cac ctc aat ctg gga      1680
Ile Ala Ala Ala His Ser Leu Gln Asp Leu His His Leu Asn Leu Gly
545             550             555             560 gcc gca gca gct gcc cat gac ttc ttc tca caa gcc atg cag cag cag      1728
Ala Ala Ala Ala Ala His Asp Phe Phe Ser Gln Ala Met Gln Gln Gln
            565             570             575 cat ggc ctg ggc agc ata gac aat gcg tct ctg gag cac tcc acc gga      1776
His Gly Leu Gly Ser Ile Asp Asn Ala Ser Leu Glu His Ser Thr Gly
        580             585             590 tcg aac tcg gtg gtg tac aat gga gac aac ggc gga gga ggt gga ggt      1824
Ser Asn Ser Val Val Tyr Asn Gly Asp Asn Gly Gly Gly Gly Gly Gly
    595             600             605 tac atc atg gca cct atg tca gcg gtc tct gct acc gct acg gcg gtg      1872
Tyr Ile Met Ala Pro Met Ser Ala Val Ser Ala Thr Ala Thr Ala Val
610             615             620 gcc tca tcc cac gac cac ggt gga gac ggc ggc aag cag gtc caa atg      1920
Ala Ser Ser His Asp His Gly Gly Asp Gly Gly Lys Gln Val Gln Met
625             630             635             640 ggc tac gac tcc tac ctt gtg gga gct gac gct tac ggc gga gga gga      1968
Gly Tyr Asp Ser Tyr Leu Val Gly Ala Asp Ala Tyr Gly Gly Gly Gly
            645             650             655 gct ggt cgc atg cct agc tgg gcc atg acg cct gct tct gct cct gcg      2016
Ala Gly Arg Met Pro Ser Trp Ala Met Thr Pro Ala Ser Ala Pro Ala
        660             665             670 gct acg agc tcg tcg gat atg aca gga gtg tgt cat ggc gcc caa ctg      2064
Ala Thr Ser Ser Ser Asp Met Thr Gly Val Cys His Gly Ala Gln Leu
    675             680             685
```

```
ttc tcg gtg tgg aat gat aca tag                                      2088
Phe Ser Val Trp Asn Asp Thr
    690                 695

<210> SEQ ID NO 121
<211> LENGTH: 2133
<212> TYPE: DNA
<213> ORGANISM: Zea mays
<220> FEATURE:
<221> NAME/KEY: CDS
<222> LOCATION: (1)...(2133)

<400> SEQUENCE: 121 atg gcc act gtg aac aac tgg ctc gct ttc tcc ctc tcc ccg cag gag     48
Met Ala Thr Val Asn Asn Trp Leu Ala Phe Ser Leu Ser Pro Gln Glu
 1               5                  10                  15 ctg ccg ccc tcc cag acg acg gac tcc aca ctc atc tcg gcc gcc acc     96
Leu Pro Pro Ser Gln Thr Thr Asp Ser Thr Leu Ile Ser Ala Ala Thr
             20                  25                  30 gcc gac cat gtc tcc ggc gat gtc tgc ttc aac atc ccc caa gat tgg    144
Ala Asp His Val Ser Gly Asp Val Cys Phe Asn Ile Pro Gln Asp Trp
         35                  40                  45 agc atg agg gga tca gag ctt tcg gcg ctc gtc gcg gag ccg aag ctg    192
Ser Met Arg Gly Ser Glu Leu Ser Ala Leu Val Ala Glu Pro Lys Leu
     50                  55                  60 gag gac ttc ctc ggc ggc atc tcc ttc tcc gag cag cat cac aag gcc    240
Glu Asp Phe Leu Gly Gly Ile Ser Phe Ser Glu Gln His His Lys Ala
 65                  70                  75                  80 aac tgc aac atg ata ccc agc act agc agc aca gtt tgc tac gcg agc    288
Asn Cys Asn Met Ile Pro Ser Thr Ser Ser Thr Val Cys Tyr Ala Ser
                 85                  90                  95 tca ggt gct agc acc ggc tac cat cac cag ctg tac cac cag ccc acc    336
Ser Gly Ala Ser Thr Gly Tyr His His Gln Leu Tyr His Gln Pro Thr
            100                 105                 110 agc tca gcg ctc cac ttc gcg gac tcc gta atg gtg gcc tcc tcg gcc    384
Ser Ser Ala Leu His Phe Ala Asp Ser Val Met Val Ala Ser Ser Ala
        115                 120                 125 ggt gtc cac gac ggc ggt gcc atg ctc agc gcg gcc gcc gct aac ggt    432
Gly Val His Asp Gly Gly Ala Met Leu Ser Ala Ala Ala Ala Asn Gly
    130                 135                 140 gtc gct ggc gct gcc agt gcc aac ggc ggc ggc atc ggg ctg tcc atg    480
Val Ala Gly Ala Ala Ser Ala Asn Gly Gly Gly Ile Gly Leu Ser Met
145                 150                 155                 160 att aag aac tgg ctg cgg agc caa ccg gcg ccc atg cag ccg agg gtg    528
Ile Lys Asn Trp Leu Arg Ser Gln Pro Ala Pro Met Gln Pro Arg Val
                165                 170                 175 gcg gcg gct gag ggc gcg cag ggg ctc tct ttg tcc atg aac atg gcg    576
Ala Ala Ala Glu Gly Ala Gln Gly Leu Ser Leu Ser Met Asn Met Ala
            180                 185                 190 ggg acg acc caa ggc gct gct ggc atg cca ctt ctc gct gga gag cgc    624
Gly Thr Thr Gln Gly Ala Ala Gly Met Pro Leu Leu Ala Gly Glu Arg
        195                 200                 205 gca cgg gcg ccc gag agt gta tcg acg tca gca cag ggt gga gcc gtc    672
Ala Arg Ala Pro Glu Ser Val Ser Thr Ser Ala Gln Gly Gly Ala Val
    210                 215                 220 gtc gtc acg gcg ccg aag gag gat agc ggt ggc agc ggt gtt gcc ggc    720
Val Val Thr Ala Pro Lys Glu Asp Ser Gly Gly Ser Gly Val Ala Gly
225                 230                 235                 240 gct cta gta gcc gtg agc acg gac acg ggt ggc agc ggc ggc gcg tcg    768
Ala Leu Val Ala Val Ser Thr Asp Thr Gly Gly Ser Gly Gly Ala Ser
                245                 250                 255
```

```
gct gac aac acg gca agg aag acg gtg gac acg ttc ggg cag cgc acg      816
Ala Asp Asn Thr Ala Arg Lys Thr Val Asp Thr Phe Gly Gln Arg Thr
            260                 265                 270 tcg att tac cgt ggc gtg aca agg cat aga tgg act ggg aga tat gag      864
Ser Ile Tyr Arg Gly Val Thr Arg His Arg Trp Thr Gly Arg Tyr Glu
        275                 280                 285 gca cat ctt tgg gat aac agt tgc aga agg gaa ggg caa act cgt aag      912
Ala His Leu Trp Asp Asn Ser Cys Arg Arg Glu Gly Gln Thr Arg Lys
    290                 295                 300 ggt cgt caa gtc tat tta ggt ggc tat gat aaa gag gag aaa gct gct      960
Gly Arg Gln Val Tyr Leu Gly Gly Tyr Asp Lys Glu Glu Lys Ala Ala
305                 310                 315                 320 agg gct tat gat ctt gct gct ctg aag tac tgg ggt gcc aca aca aca     1008
Arg Ala Tyr Asp Leu Ala Ala Leu Lys Tyr Trp Gly Ala Thr Thr Thr
                325                 330                 335 aca aat ttt cca gtg agt aac tac gaa aag gag ctc gag gac atg aag     1056
Thr Asn Phe Pro Val Ser Asn Tyr Glu Lys Glu Leu Glu Asp Met Lys
            340                 345                 350 cac atg aca agg cag gag ttt gta gcg tct ctg aga agg aag agc agt     1104
His Met Thr Arg Gln Glu Phe Val Ala Ser Leu Arg Arg Lys Ser Ser
        355                 360                 365 ggt ttc tcc aga ggt gca tcc att tac agg gga gtg act agg cat cac     1152
Gly Phe Ser Arg Gly Ala Ser Ile Tyr Arg Gly Val Thr Arg His His
    370                 375                 380 caa cat gga aga tgg caa gca cgg att gga cga gtt gca ggg aac aag     1200
Gln His Gly Arg Trp Gln Ala Arg Ile Gly Arg Val Ala Gly Asn Lys
385                 390                 395                 400 gat ctt tac ttg ggc acc ttc agc acc cag gag gag gca gcg gag gcg     1248
Asp Leu Tyr Leu Gly Thr Phe Ser Thr Gln Glu Glu Ala Ala Glu Ala
                405                 410                 415 tac gac atc gcg gcg atc aag ttc cgc ggc ctc aac gcc gtc acc aac     1296
Tyr Asp Ile Ala Ala Ile Lys Phe Arg Gly Leu Asn Ala Val Thr Asn
            420                 425                 430 ttc gac atg agc cgc tac gac gtg aag agc atc ctg gac agc agc gcc     1344
Phe Asp Met Ser Arg Tyr Asp Val Lys Ser Ile Leu Asp Ser Ser Ala
        435                 440                 445 ctc ccc atc ggc agc gcc gcc aag cgc ctc aag gag gcc gag gcc gca     1392
Leu Pro Ile Gly Ser Ala Ala Lys Arg Leu Lys Glu Ala Glu Ala Ala
    450                 455                 460 gcg tcc gcg cag cac cac cac gcc ggc gtg gtg agc tac gac gtc ggc     1440
Ala Ser Ala Gln His His His Ala Gly Val Val Ser Tyr Asp Val Gly
465                 470                 475                 480 cgc atc gcc tcg cag ctc ggc gac ggc gga gcc ctg gcg gcg gcg tac     1488
Arg Ile Ala Ser Gln Leu Gly Asp Gly Gly Ala Leu Ala Ala Ala Tyr
                485                 490                 495 ggc gcg cac tac cac ggc gcc gcc tgg ccg acc atc gcg ttc cag ccg     1536
Gly Ala His Tyr His Gly Ala Ala Trp Pro Thr Ile Ala Phe Gln Pro
            500                 505                 510 ggc gcc gcc agc aca ggc ctg tac cac ccg tac gcg cag cag cca atg     1584
Gly Ala Ala Ser Thr Gly Leu Tyr His Pro Tyr Ala Gln Gln Pro Met
        515                 520                 525 cgc ggc ggc ggg tgg tgc aag cag gag cag gac cac gcg gtg atc gcg     1632
Arg Gly Gly Gly Trp Cys Lys Gln Glu Gln Asp His Ala Val Ile Ala
    530                 535                 540 gcc gcg cac agc ctg cag gac ctc cac cac ctg aac ctg ggc gcg gcc     1680
Ala Ala His Ser Leu Gln Asp Leu His His Leu Asn Leu Gly Ala Ala
545                 550                 555                 560 ggc gcg cac gac ttt ttc tcg gca ggg cag cag gcc gcc gcc gct gcg     1728
Gly Ala His Asp Phe Phe Ser Ala Gly Gln Gln Ala Ala Ala Ala Ala
```

|  |  |  |  |  |  |  |  |  |  |  |  |  |  |  |  |
|---|---|---|---|---|---|---|---|---|---|---|---|---|---|---|---|
|  |  |  |  | 565 |  |  |  |  | 570 |  |  |  |  | 575 |  |

```
atg cac ggc ctg ggt agc atc gac agt gcg tcg ctc gag cac agc acc      1776
Met His Gly Leu Gly Ser Ile Asp Ser Ala Ser Leu Glu His Ser Thr
            580                 585                 590 ggc tcc aac tcc gtc gtc tac aac ggg gtc ggc gac agc aac ggc          1824
Gly Ser Asn Ser Val Val Tyr Asn Gly Val Gly Asp Ser Asn Gly
        595                 600                 605 gcc agc gcc gtc ggc ggc agt ggc ggt ggc tac atg atg ccg atg agc      1872
Ala Ser Ala Val Gly Gly Ser Gly Gly Gly Tyr Met Met Pro Met Ser
610                 615                 620 gct gcc gga gca acc act aca tcg gca atg gtg agc cac gag cag gtg      1920
Ala Ala Gly Ala Thr Thr Thr Ser Ala Met Val Ser His Glu Gln Val
625                 630                 635                 640 cat gca cgg gcc tac gac gaa gcc aag cag gct gct cag atg ggg tac      1968
His Ala Arg Ala Tyr Asp Glu Ala Lys Gln Ala Ala Gln Met Gly Tyr
                645                 650                 655 gag agc tac ctg gtg aac gcg gag aac aat ggt ggc gga agg atg tct      2016
Glu Ser Tyr Leu Val Asn Ala Glu Asn Asn Gly Gly Gly Arg Met Ser
            660                 665                 670 gca tgg ggg act gtc gtg tct gca gcc gcg gca gca agc agc              2064
Ala Trp Gly Thr Val Val Ser Ala Ala Ala Ala Ala Ser Ser
        675                 680                 685 aac gac aac atg gcc gcc gac gtc ggc cat ggc ggc gcg cag ctc ttc      2112
Asn Asp Asn Met Ala Ala Asp Val Gly His Gly Gly Ala Gln Leu Phe
690                 695                 700 agt gtc tgg aac gac act taa                                          2133
Ser Val Trp Asn Asp Thr
705                 710

<210> SEQ ID NO 122
<211> LENGTH: 710
<212> TYPE: PRT
<213> ORGANISM: Zea mays

<400> SEQUENCE: 122

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                85                  90                  95

Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Asn Gly
    130                 135                 140

Val Ala Gly Ala Ala Ser Ala Asn Gly Gly Gly Ile Gly Leu Ser Met
145                 150                 155                 160

Ile Lys Asn Trp Leu Arg Ser Gln Pro Ala Pro Met Gln Pro Arg Val
                165                 170                 175
```

```
Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Ser Gly Val Ala Gly
225                 230                 235                 240

Ala Leu Val Ala Val Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Gly Ala Leu Ala Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525

Arg Gly Gly Gly Trp Cys Lys Gln Glu Gln Asp His Ala Val Ile Ala
    530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Gln Ala Ala Ala Ala Ala
                565                 570                 575

Met His Gly Leu Gly Ser Ile Asp Ser Ala Ser Leu Glu His Ser Thr
            580                 585                 590

Gly Ser Asn Ser Val Val Tyr Asn Gly Gly Val Gly Asp Ser Asn Gly
```

```
                    595                 600                 605
Ala Ser Ala Val Gly Ser Gly Gly Gly Tyr Met Met Pro Met Ser
    610                 615                 620

Ala Ala Gly Ala Thr Thr Ser Ala Met Val Ser His Glu Gln Val
625                 630                 635                 640

His Ala Arg Ala Tyr Asp Glu Ala Lys Gln Ala Ala Gln Met Gly Tyr
                    645                 650                 655

Glu Ser Tyr Leu Val Asn Ala Glu Asn Asn Gly Gly Gly Arg Met Ser
    660                 665                 670

Ala Trp Gly Thr Val Val Ser Ala Ala Ala Ala Ala Ala Ser Ser
    675                 680                 685

Asn Asp Asn Met Ala Ala Asp Val Gly His Gly Gly Ala Gln Leu Phe
    690                 695                 700

Ser Val Trp Asn Asp Thr
705                 710

<210> SEQ ID NO 123
<211> LENGTH: 25
<212> TYPE: DNA
<213> ORGANISM: Artificial Sequence
<220> FEATURE:
<223> OTHER INFORMATION: Plasmid linker sequence

<400> SEQUENCE: 123
tcgaaggaga tagaaccgat ccacc                                             25

<210> SEQ ID NO 124
<211> LENGTH: 8
<212> TYPE: DNA
<213> ORGANISM: Artificial Sequence
<220> FEATURE:
<223> OTHER INFORMATION: Plasmid linker sequence

<400> SEQUENCE: 124 tgagctag                                                                 8

<210> SEQ ID NO 125
<211> LENGTH: 508
<212> TYPE: DNA
<213> ORGANISM: Zea mays

<400> SEQUENCE: 125
ctatagtatt ttaaaattgc attaacaaac atgtcctaat tggtactcct gagatactat       60
accctcctgt tttaaaatag ttggcattat cgaattatca ttttactttt taatgttttc      120
tcttctttta atatatttta tgaatttttaa tgtatttttaa aatgttatgc agttcgctct    180 ggactttttct cgtgcgccta cacttgggtg tactgggcct aaattcagcc tgaccgaccg     240
cctgcattga ataatggatg agcaccggta aaatccgcgt acccaacttt cgagaagaac     300
cgagacgtgg cgggccgggc caccgacgca cggcaccagc gactgcacac gtcccgccgg     360
cgtacgtgta cgtgctgttc cctcactggc cgcccaatcc actcatgcat gcccacgtac     420
acccctgccg tggcgcgccc agatcctaat cctttcgccg ttctgcactt ctgctgccta    480
taaatggcgg catcgaccgt cacctgct                                         508

<210> SEQ ID NO 126
<211> LENGTH: 558
<212> TYPE: DNA
<213> ORGANISM: Zea mays
```

```
<400> SEQUENCE: 126
gtactgtaat atttatatta tatataatta taaactataa tatttcaaaa ctatagtatt      60
ttaaaattgc attaacaaac atgtcctaat tggtactcct gagatactat accctcctgt     120
tttaaaatag ttggcattat cgaattatca ttttactttt taatgttttc tcttcttttta    180 atatatttta tgaattttaa tgtattttaa aatgttatgc agttcgctct ggacttttct     240
cgtgcgccta cacttgggtg tactgggcct aaattcagcc tgaccgaccg cctgcattga     300
ataatggatg agcaccggta aaatccgcgt acccaacttt cgagaagaac cgagacgtgg     360
cgggccgggc caccgacgca cggcaccagc gactgcacac gtcccgccgg cgtacgtgta     420
cgtgctgttc cctcactggc cgcccaatcc actcatgcat gcccacgtac acccctgccg     480
tggcgcgccc agatcctaat cctttcgccg ttctgcactt ctgctgccta taaatggcgg     540
catcgaccgt cacctgct                                                  558
```